US012551734B2

(12) United States Patent
Ciaramella et al.

(10) Patent No.: US 12,551,734 B2
(45) **Date of Patent: *Feb. 17, 2026**

(54) BETACORONAVIRUS mRNA VACCINES

(71) Applicant: ModernaTX, Inc., Cambridge, MA (US)

(72) Inventors: Giuseppe Ciaramella, Sudbury, MA (US); Sunny Himansu, Winchester, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/000,377

(22) Filed: Dec. 23, 2024

(65) Prior Publication Data

US 2025/0121220 A1 Apr. 17, 2025

Related U.S. Application Data

(63) Continuation of application No. 18/762,372, filed on Jul. 2, 2024, now Pat. No. 12,208,288, and a continuation of application No. 18/762,296, filed on Jul. 2, 2024, now Pat. No. 12,409,347, and a continuation of application No. 18/762,384, filed on Jul. 2, 2024, which is a continuation of application No. 18/528,323, filed on Dec. 4, 2023, now Pat. No. 12,403,335, said application No. 18/762,296 is a continuation of application No. 18/528,323, filed on Dec. 4, 2023, now Pat. No. 12,403,335, which is a continuation of application No. 16/897,734, filed on Jun. 10, 2020, now Pat. No. 11,872,278, which is a continuation of application No. 16/368,270, filed on Mar. 28, 2019, now Pat. No. 10,702,599, which is a continuation of application No. 16/040,981, filed on Jul. 20, 2018, now Pat. No. 10,272,150, which is a continuation of application No. 15/674,599, filed on Aug. 11, 2017, now Pat. No. 10,064,934, which is a continuation of application No. PCT/US2016/058327, filed on Oct. 21, 2016.

(60) Provisional application No. 62/247,362, filed on Oct. 28, 2015, provisional application No. 62/247,394, filed on Oct. 28, 2015, provisional application No. 62/247,297, filed on Oct. 28, 2015, provisional application No. 62/247,483, filed on Oct. 28, 2015, provisional application No. 62/244,802, filed on Oct. 22, 2015, provisional application No. 62/245,031, filed on Oct. 22, 2015, provisional application No. 62/244,946, filed on Oct. 22, 2015, provisional application No. 62/244,813, filed on Oct. 22, 2015, provisional application No. 62/244,837, filed on Oct. 22, 2015.

(51) Int. Cl.

| | |
|---|---|
| ***A61P 31/14*** | (2006.01) |
| ***A61K 39/12*** | (2006.01) |
| ***A61K 39/155*** | (2006.01) |
| ***A61K 39/215*** | (2006.01) |
| ***A61P 11/00*** | (2006.01) |
| ***C07K 16/10*** | (2006.01) |
| *A61K 39/00* | (2006.01) |

(52) U.S. Cl.

CPC ............ *A61K 39/12* (2013.01); *A61K 39/155* (2013.01); *A61K 39/215* (2013.01); *A61P 11/00* (2018.01); *A61P 31/14* (2018.01); *C07K 16/10* (2013.01); *C07K 16/1002* (2023.08); *C07K 16/1027* (2013.01); *A61K 2039/53* (2013.01); *A61K 2039/55511* (2013.01); *A61K 2039/55555* (2013.01); *A61K 2039/6018* (2013.01); *A61K 2039/70* (2013.01); *C07K 2317/76* (2013.01); *C12N 2760/18034* (2013.01); *C12N 2760/18334* (2013.01); *C12N 2760/18434* (2013.01); *C12N 2760/18534* (2013.01); *C12N 2760/18634* (2013.01); *C12N 2770/20034* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 3,906,092 | A | 9/1975 | Hilleman et al. |
| 4,790,987 | A | 12/1988 | Compans et al. |
| 5,169,628 | A | 12/1992 | Wathen |
| 5,427,782 | A | 6/1995 | Compans et al. |
| 6,225,091 | B1 | 5/2001 | Klein et al. |
| 6,500,419 | B1 | 12/2002 | Hone et al. |
| 6,514,948 | B1 | 2/2003 | Raz et al. |
| 7,001,890 | B1 | 2/2006 | Wagner et al. |
| 7,208,161 | B1 | 4/2007 | Murphy et al. |
| 7,449,324 | B2 | 11/2008 | Fouchier et al. |
| 7,531,342 | B2 | 5/2009 | Fouchier et al. |

(Continued)

FOREIGN PATENT DOCUMENTS

| | | |
|---|---|---|
| AU | 2015210364 A1 | 3/2017 |
| CA | 2473135 | 6/2003 |

(Continued)

OTHER PUBLICATIONS

[IPR-2023-01358] Institution Decision in IPR2023-01358 dated Mar. 19, 2024.

(Continued)

*Primary Examiner* — Nicole Kinsey White

(74) *Attorney, Agent, or Firm* — Foley & Lardner LLP

(57) ABSTRACT

The disclosure relates to ribonucleic acid (RNA) vaccines and combination vaccines, as well as methods of using the vaccines and compositions comprising the vaccines. Specific embodiments relate to RNA betacoronavirus vaccines formulated in a lipid nanoparticle.

8 Claims, 24 Drawing Sheets

Specification includes a Sequence Listing.

(56) References Cited

U.S. PATENT DOCUMENTS

| | | | |
|---|---|---|---|
| 7,671,186 | B2 | 3/2010 | Klein et al. |
| 7,704,720 | B2 | 4/2010 | Tang et al. |
| 8,217,016 | B2 | 7/2012 | Hoerr et al. |
| 8,252,289 | B2 | 8/2012 | Eleouët et al. |
| 8,691,966 | B2 | 4/2014 | Kariko et al. |
| 8,710,200 | B2 | 4/2014 | Schrum et al. |
| 8,722,341 | B2 | 5/2014 | Fouchier et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,841,433 | B2 | 9/2014 | Fouchier et al. |
| 8,889,146 | B2 | 11/2014 | Blais et al. |
| 8,927,206 | B2 | 1/2015 | De Jong et al. |
| 8,980,864 | B2 | 3/2015 | Hoge et al. |
| 8,999,380 | B2 | 4/2015 | Bancel et al. |
| 9,192,651 | B2 | 11/2015 | Chakraborty et al. |
| 9,192,661 | B2 | 11/2015 | Jain et al. |
| 9,221,891 | B2 | 12/2015 | Bancel et al. |
| 9,271,996 | B2 | 3/2016 | De Fougerolles et al. |
| 9,283,287 | B2 | 3/2016 | Bancel et al. |
| 9,295,689 | B2 | 3/2016 | De Fougerolles et al. |
| 9,303,079 | B2 | 4/2016 | Bancel et al. |
| 9,376,726 | B2 | 6/2016 | Fouchier et al. |
| 9,464,124 | B2 | 10/2016 | Bancel et al. |
| 9,512,456 | B2 | 12/2016 | Wang et al. |
| 9,533,047 | B2 | 1/2017 | de Fougerolles et al. |
| 9,567,653 | B2 | 2/2017 | Fouchier et al. |
| 9,572,896 | B2 | 2/2017 | Bancel et al. |
| 9,597,380 | B2 | 3/2017 | Chakraborty et al. |
| 9,623,095 | B2 | 4/2017 | Kallen et al. |
| 9,669,089 | B2 | 6/2017 | Thess et al. |
| 9,675,668 | B2 | 6/2017 | Bancel et al. |
| 9,790,531 | B2 | 10/2017 | Wang et al. |
| 9,803,199 | B2 | 10/2017 | Koizumi et al. |
| 9,868,691 | B2 | 1/2018 | Benenato et al. |
| 9,872,900 | B2 | 1/2018 | Ciaramella et al. |
| 9,937,196 | B2 | 4/2018 | Jain et al. |
| 10,023,626 | B2 | 7/2018 | Bolen et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,232,055 | B2 | 3/2019 | Kariko et al. |
| 10,272,150 | B2 | 4/2019 | Ciaramella et al. |
| 10,273,269 | B2 | 4/2019 | Ciaramella |
| 10,286,086 | B2 | 5/2019 | Roy et al. |
| 10,323,076 | B2 | 6/2019 | Ellsworth et al. |
| 10,385,088 | B2 | 8/2019 | Fraley et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,543,269 | B2 | 1/2020 | Ciaramella et al. |
| 10,653,712 | B2 | 5/2020 | Hoge |
| 10,653,767 | B2 | 5/2020 | Ciaramella et al. |
| 10,695,419 | B2 | 6/2020 | Ciaramella et al. |
| 10,702,599 | B2 | 7/2020 | Ciaramella et al. |
| 10,702,600 | B1 | 7/2020 | Ciaramella et al. |
| 10,857,105 | B2 | 12/2020 | Benenato et al. |
| 10,906,944 | B2 | 2/2021 | He et al. |
| 10,912,826 | B2 | 2/2021 | Thess et al. |
| 10,925,958 | B2 | 2/2021 | Ciaramella |
| 10,960,070 | B2 | 3/2021 | Graham et al. |
| 11,027,025 | B2 | 6/2021 | Hoge et al. |
| 11,045,540 | B2 | 6/2021 | Ciaramella |
| 11,103,578 | B2 | 8/2021 | Ciaramella et al. |
| 11,266,735 | B2 | 3/2022 | Kallen et al. |
| 11,351,242 | B1 | 6/2022 | Lori et al. |
| 11,384,352 | B2 | 7/2022 | Miracco |
| 11,406,703 | B2 | 8/2022 | Kramarczyk et al. |
| 11,464,848 | B2 | 10/2022 | Ciaramella et al. |
| 11,485,960 | B2 | 11/2022 | Dousis et al. |
| 11,497,807 | B2 | 11/2022 | Ciaramella et al. |
| 11,564,893 | B2 | 1/2023 | Smith |
| 11,576,961 | B2 | 2/2023 | Ciaramella et al. |
| 11,638,693 | B2 | 5/2023 | Geall |
| 11,638,694 | B2 | 5/2023 | Geall |
| 11,643,441 | B1 | 5/2023 | Ciaramella et al. |
| 11,666,534 | B2 | 6/2023 | Geall |
| 11,696,946 | B2 | 7/2023 | Ciaramella |
| 11,752,206 | B2 | 9/2023 | Ciaramella et al. |
| 11,766,401 | B2 | 9/2023 | Geall |
| 11,786,467 | B2 | 10/2023 | Geall |
| 11,786,607 | B2 | 10/2023 | Hoge et al. |
| 11,851,694 | B1 | 12/2023 | Mauger et al. |
| 11,866,696 | B2 | 1/2024 | Issa et al. |
| 11,872,278 | B2 | 1/2024 | Ciaramella et al. |
| 11,905,525 | B2 | 2/2024 | Brito et al. |
| 11,911,453 | B2 | 2/2024 | Ciaramella et al. |
| 11,912,982 | B2 | 2/2024 | Issa et al. |
| 2003/0092653 | A1 | 5/2003 | Kisich et al. |
| 2003/0232061 | A1 | 12/2003 | Fouchier et al. |
| 2004/0005545 | A1 | 1/2004 | Fouchier et al. |
| 2004/0096451 | A1 | 5/2004 | Young et al. |
| 2005/0032730 | A1 | 2/2005 | Von Der Mulbe et al. |
| 2005/0059624 | A1 | 3/2005 | Hoerr et al. |
| 2005/0250723 | A1 | 11/2005 | Hoerr et al. |
| 2006/0002958 | A1 | 1/2006 | Naylor et al. |
| 2006/0172003 | A1 | 8/2006 | Meers et al. |
| 2006/0228367 | A1 | 10/2006 | Ulbrandt et al. |
| 2007/0280929 | A1 | 12/2007 | Hoerr et al. |
| 2008/0025944 | A1 | 1/2008 | Hoerr et al. |
| 2008/0171079 | A1 | 7/2008 | Hanon et al. |
| 2008/0171711 | A1 | 7/2008 | Hoerr et al. |
| 2009/0123529 | A1 | 5/2009 | Xiaomao |
| 2009/0162395 | A1 | 6/2009 | Crowe et al. |
| 2010/0203076 | A1 | 8/2010 | Fotin-Mleczek et al. |
| 2010/0239608 | A1 | 9/2010 | Von Der Mulbe et al. |
| 2010/0272747 | A1 | 10/2010 | Chow et al. |
| 2010/0291156 | A1 | 11/2010 | Barner et al. |
| 2010/0305196 | A1 | 12/2010 | Probst et al. |
| 2011/0135645 | A1 | 6/2011 | Williamson et al. |
| 2011/0250225 | A1 | 10/2011 | Fotin-Mleczek et al. |
| 2011/0269950 | A1 | 11/2011 | Mulbe et al. |
| 2012/0009221 | A1 | 1/2012 | Hoerr et al. |
| 2012/0045471 | A1 | 2/2012 | Haller et al. |
| 2012/0101148 | A1 | 4/2012 | Aking et al. |
| 2012/0177701 | A1 | 7/2012 | Ilyinskii et al. |
| 2012/0213812 | A1 | 8/2012 | Lipford et al. |
| 2012/0219573 | A1 | 8/2012 | Baumhof et al. |
| 2012/0276209 | A1 | 11/2012 | Cullis et al. |
| 2013/0022538 | A1 | 1/2013 | Rossi |
| 2013/0078281 | A1 | 3/2013 | He et al. |
| 2013/0102034 | A1 | 4/2013 | Schrum et al. |
| 2013/0121988 | A1 | 5/2013 | Hoerr et al. |
| 2013/0142818 | A1 | 6/2013 | Baumhof et al. |
| 2013/0183355 | A1 | 7/2013 | Jain et al. |
| 2013/0195867 | A1 | 8/2013 | Hoerr et al. |
| 2013/0195967 | A1 | 8/2013 | Guild et al. |
| 2013/0195969 | A1 | 8/2013 | Geall et al. |
| 2013/0202684 | A1 | 8/2013 | Geall et al. |
| 2013/0236974 | A1 | 9/2013 | De Fougerolles |
| 2013/0243848 | A1 | 9/2013 | Lobovkina et al. |
| 2013/0245103 | A1 | 9/2013 | de Fougerolles et al. |
| 2013/0259923 | A1 | 10/2013 | Bancel et al. |
| 2013/0266640 | A1 | 10/2013 | De Fougerolles et al. |
| 2013/0295043 | A1 | 11/2013 | Kallen et al. |
| 2013/0336998 | A1 | 12/2013 | Kallen et al. |
| 2014/0024076 | A1 | 1/2014 | Tang et al. |
| 2014/0037660 | A1 | 2/2014 | Folin-Mleczek et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0255472 | A1 | 9/2014 | Geall et al. |
| 2014/0271829 | A1 | 9/2014 | Lilja et al. |
| 2014/0308304 | A1 | 10/2014 | Manoharan et al. |
| 2014/0370497 | A1 | 12/2014 | Fouchier et al. |
| 2014/0378538 | A1 | 12/2014 | Bancel |
| 2015/0051268 | A1 | 2/2015 | Bancel et al. |
| 2015/0056253 | A1 | 2/2015 | Bancel et al. |
| 2015/0093413 | A1 | 4/2015 | Thess et al. |
| 2015/0126589 | A1 | 5/2015 | Geiger et al. |
| 2015/0141499 | A1 | 5/2015 | Bancel et al. |

(56) References Cited

U.S. PATENT DOCUMENTS

| | | | |
|---|---|---|---|
| 2015/0307542 | A1 | 10/2015 | Roy et al. |
| 2015/0315541 | A1 | 11/2015 | Bancel et al. |
| 2015/0335728 | A1 | 11/2015 | Wong et al. |
| 2016/0022580 | A1 | 1/2016 | Ramsay et al. |
| 2016/0024140 | A1 | 1/2016 | Issa et al. |
| 2016/0024141 | A1 | 1/2016 | Issa et al. |
| 2016/0032273 | A1 | 2/2016 | Shahrokh et al. |
| 2016/0038612 | A1 | 2/2016 | Hoge et al. |
| 2016/0039884 | A1 | 2/2016 | Li et al. |
| 2016/0046675 | A1 | 2/2016 | Kwong et al. |
| 2016/0151474 | A1 | 6/2016 | Kallen et al. |
| 2016/0194368 | A1 | 7/2016 | Hoge et al. |
| 2016/0194625 | A1 | 7/2016 | Hoge et al. |
| 2016/0243221 | A1 | 8/2016 | Hoge et al. |
| 2016/0271272 | A1 | 9/2016 | Bancel et al. |
| 2016/0317647 | A1 | 11/2016 | Ciaramella et al. |
| 2016/0331828 | A1 | 11/2016 | Ciaramella et al. |
| 2016/0361411 | A1 | 12/2016 | Gindy et al. |
| 2017/0043037 | A1 | 2/2017 | Kariko et al. |
| 2017/0065675 | A1 | 3/2017 | Bancel et al. |
| 2017/0130255 | A1 | 5/2017 | Wang et al. |
| 2017/0202979 | A1 | 7/2017 | Chakraborty et al. |
| 2017/0204152 | A1 | 7/2017 | Nelson et al. |
| 2017/0340724 | A1 | 11/2017 | Ciaramella et al. |
| 2018/0000953 | A1 | 1/2018 | Almarsson et al. |
| 2018/0002393 | A1 | 1/2018 | Bancel et al. |
| 2018/0008694 | A1 | 1/2018 | Ciaramella et al. |
| 2018/0028645 | A1 | 2/2018 | Ciaramella et al. |
| 2018/0028664 | A1 | 2/2018 | Besin et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0280496 | A1 | 10/2018 | Ciaramella et al. |
| 2018/0289792 | A1 | 10/2018 | Ciaramella et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0318409 | A1 | 11/2018 | Valiante et al. |
| 2018/0326039 | A1 | 11/2018 | Haruta |
| 2018/0363019 | A1 | 12/2018 | Hoge |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0085368 | A1 | 3/2019 | Bancel et al. |
| 2019/0099481 | A1 | 4/2019 | Ciaramella et al. |
| 2019/0125839 | A1 | 5/2019 | Frederick et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0240317 | A1 | 8/2019 | Ciaramella et al. |
| 2019/0241633 | A1 | 8/2019 | Fotin-Mleczek et al. |
| 2019/0275170 | A1 | 9/2019 | Benenato et al. |
| 2019/0298657 | A1 | 10/2019 | Martini et al. |
| 2019/0298658 | A1 | 10/2019 | Benenato |
| 2019/0300906 | A1 | 10/2019 | Martini et al. |
| 2019/0314292 | A1 | 10/2019 | Benenato et al. |
| 2019/0314493 | A1 | 10/2019 | Ciaramella et al. |
| 2019/0336452 | A1 | 11/2019 | Brader |
| 2019/0336595 | A1 | 11/2019 | Ciaramella |
| 2019/0351040 | A1 | 11/2019 | Valiante et al. |
| 2019/0351047 | A1 | 11/2019 | Jasny et al. |
| 2019/0382774 | A1 | 12/2019 | Hoge et al. |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0061185 | A1 | 2/2020 | Graham et al. |
| 2020/0069599 | A1 | 3/2020 | Smith et al. |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129445 | A1 | 4/2020 | Patel et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282046 | A1 | 9/2020 | Ciaramella et al. |
| 2020/0282047 | A1 | 9/2020 | Ciaramella et al. |
| 2020/0297634 | A1 | 9/2020 | Karmali et al. |
| 2020/0306191 | A1 | 10/2020 | Schariter et al. |
| 2020/0338004 | A1 | 10/2020 | Hansson et al. |
| 2020/0368162 | A1 | 11/2020 | Martini |
| 2020/0399322 | A1 | 12/2020 | Baumhof et al. |
| 2020/0407402 | A1 | 12/2020 | He et al. |
| 2021/0023199 | A1 | 1/2021 | Kallen et al. |
| 2021/0030866 | A1 | 2/2021 | Kallen et al. |
| 2021/0046173 | A1 | 2/2021 | Ciaramella et al. |
| 2021/0060175 | A1 | 3/2021 | Baumhof et al. |
| 2021/0087135 | A1 | 3/2021 | Benenato et al. |
| 2021/0128716 | A1 | 5/2021 | Probst et al. |
| 2021/0139543 | A1 | 5/2021 | He et al. |
| 2021/0145982 | A1 | 5/2021 | Hoge et al. |
| 2021/0162037 | A1 | 6/2021 | Jasny et al. |
| 2021/0163919 | A1 | 6/2021 | Issa et al. |
| 2021/0187097 | A1 | 6/2021 | Ciaramella et al. |
| 2021/0206818 | A1 | 7/2021 | Huang et al. |
| 2021/0217484 | A1 | 7/2021 | Giessel et al. |
| 2021/0228707 | A1 | 7/2021 | Mektar et al. |
| 2021/0228708 | A1 | 7/2021 | Smith et al. |
| 2021/0268086 | A1 | 9/2021 | Zhong et al. |
| 2021/0309976 | A1 | 10/2021 | Dousis et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0142529 | A1 | 5/2023 | White et al. |
| 2023/0173060 | A1 | 6/2023 | Benmohamed |
| 2023/0181481 | A1 | 6/2023 | White et al. |
| 2023/0190761 | A1 | 6/2023 | Brader et al. |
| 2023/0212645 | A1 | 7/2023 | Marquardt et al. |
| 2023/0287437 | A1 | 9/2023 | Smith et al. |
| 2023/0338506 | A1 | 10/2023 | Shaw et al. |
| 2023/0338512 | A1 | 10/2023 | Muik et al. |
| 2023/0346914 | A1 | 11/2023 | Stewart-Jones et al. |
| 2023/0355743 | A1 | 11/2023 | Stewart-Jones et al. |
| 2024/0100145 | A1 | 3/2024 | Bollman et al. |
| 2024/0100151 | A1 | 3/2024 | Carfi et al. |
| 2024/0139309 | A1 | 5/2024 | Carfi et al. |
| 2024/0173400 | A1 | 5/2024 | Ciaramella et al. |
| 2024/0181030 | A1 | 6/2024 | Himansu et al. |
| 2025/0121221 | A1 | 4/2025 | Ciaramella et al. |

FOREIGN PATENT DOCUMENTS

| | | | |
|---|---|---|---|
| CA | 3194325 | A1 | 5/2022 |
| CN | 110951756 | A | 4/2020 |
| CN | 110974950 | A | 4/2020 |
| CN | 110974954 | A | 4/2020 |
| CN | 111088283 | A | 5/2020 |
| CN | 111218458 | A | 6/2020 |
| CN | 111218459 | A | 6/2020 |
| CN | 111303254 | A | 6/2020 |
| CN | 111518175 | A | 8/2020 |
| CN | 111592602 | A | 8/2020 |

(56) References Cited

FOREIGN PATENT DOCUMENTS

| | | | |
|---|---|---|---|
| CN | 111848753 | A | 10/2020 |
| CN | 111939250 | A | 11/2020 |
| CN | 111978377 | A | 11/2020 |
| CN | 112023035 | A | 12/2020 |
| CN | 112028976 | A | 12/2020 |
| CN | 112043825 | A | 12/2020 |
| CN | 112048005 | A | 12/2020 |
| CN | 112094327 | A | 12/2020 |
| CN | 112220920 | A | 1/2021 |
| CN | 112226445 | A | 1/2021 |
| CN | 112266411 | A | 1/2021 |
| CN | 112321688 | A | 2/2021 |
| CN | 112358533 | A | 2/2021 |
| CN | 112480217 | A | 3/2021 |
| CN | 112546211 | A | 3/2021 |
| CN | 112626089 | A | 4/2021 |
| CN | 112794884 | A | 5/2021 |
| EP | 1026253 | | 8/2000 |
| EP | 1083232 | | 2/2005 |
| EP | 1905844 | A2 | 2/2008 |
| EP | 2548960 | A1 | 1/2013 |
| EP | 3608308 | A | 2/2020 |
| JP | 2015-518472 | A | 7/2015 |
| JP | 2016-515815 | A | 6/2016 |
| WO | WO 1987/005326 | A1 | 9/1987 |
| WO | WO 1990/011092 | | 10/1990 |
| WO | WO 1993/014778 | | 8/1993 |
| WO | WO 1995/024485 | | 9/1995 |
| WO | WO 1995/026204 | | 10/1995 |
| WO | WO 1995/033835 | | 12/1995 |
| WO | WO 1996/040945 | A2 | 12/1996 |
| WO | WO 1998/058956 | | 12/1998 |
| WO | WO 1999/33982 | | 7/1999 |
| WO | WO 1999/033982 | | 7/1999 |
| WO | WO 2003/072720 | A2 | 9/2003 |
| WO | WO 2004/076645 | A1 | 9/2004 |
| WO | WO 2005/009346 | | 2/2005 |
| WO | WO 2005/027963 | A2 | 3/2005 |
| WO | WO 2005/118813 | A2 | 12/2005 |
| WO | WO 2006/056027 | A1 | 6/2006 |
| WO | WO 2006/071903 | | 7/2006 |
| WO | WO 2006/095259 | | 9/2006 |
| WO | WO 2007/024708 | A2 | 3/2007 |
| WO | WO 2007/038862 | A1 | 4/2007 |
| WO | WO 2007/094854 | A2 | 8/2007 |
| WO | WO 2007/095976 | A2 | 8/2007 |
| WO | WO 2008/052770 | A2 | 5/2008 |
| WO | WO 2009/030254 | A1 | 3/2009 |
| WO | WO 2009/030481 | A1 | 3/2009 |
| WO | WO 2009/095226 | | 8/2009 |
| WO | WO 2009/127230 | A1 | 10/2009 |
| WO | WO 2010/037408 | A1 | 4/2010 |
| WO | WO 2010/037539 | A1 | 4/2010 |
| WO | WO 2010/042877 | A1 | 4/2010 |
| WO | WO 2010/054401 | A1 | 5/2010 |
| WO | WO 2010/054406 | A1 | 5/2010 |
| WO | WO 2010/088927 | A1 | 8/2010 |
| WO | WO 2010/129709 | A1 | 11/2010 |
| WO | WO 2010/144740 | A1 | 12/2010 |
| WO | WO 2010/149743 | A2 | 12/2010 |
| WO | WO 2011/005799 | A2 | 1/2011 |
| WO | WO 2011/026641 | A9 | 3/2011 |
| WO | WO 2011/068810 | A1 | 6/2011 |
| WO | WO 2011/069529 | A1 | 6/2011 |
| WO | WO 2011/069586 | A1 | 6/2011 |
| WO | WO 2011/140627 | A1 | 11/2011 |
| WO | WO 2011/144358 | A1 | 11/2011 |
| WO | WO 2012/006369 | A2 | 1/2012 |
| WO | WO 2012/006372 | A1 | 1/2012 |
| WO | WO 2012/006377 | A2 | 1/2012 |
| WO | WO-2012/006378 | A1 | 1/2012 |
| WO | WO 2012/019630 | A1 | 2/2012 |
| WO | WO 2012/019780 | A1 | 2/2012 |
| WO | WO 2012/030901 | A1 | 3/2012 |
| WO | WO 2012/031043 | A1 | 3/2012 |
| WO | WO 2012/031046 | A2 | 3/2012 |
| WO | WO 2012/045082 | A2 | 4/2012 |
| WO | WO-2012/068295 | A1 | 5/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2012/045075 | A1 | 4/2013 |
| WO | WO 2013/052523 | A1 | 4/2013 |
| WO | WO 2013/055905 | A1 | 4/2013 |
| WO | WO 2013/090186 | A1 | 6/2013 |
| WO | WO 2013/090648 | A1 | 6/2013 |
| WO | WO 2013/102203 | A1 | 7/2013 |
| WO | WO 2013/120628 | A1 | 8/2013 |
| WO | WO 2013/120629 | A1 | 8/2013 |
| WO | WO 2013/185069 | A1 | 12/2013 |
| WO | WO 2014/089239 | A1 | 6/2014 |
| WO | WO 2014/089486 | A1 | 6/2014 |
| WO | WO 2014/144196 | A1 | 9/2014 |
| WO | WO 2014/144711 | A1 | 9/2014 |
| WO | WO 2014/152027 | A1 | 9/2014 |
| WO | WO 2014/152030 | A1 | 9/2014 |
| WO | WO 2014/152200 | A1 | 9/2014 |
| WO | WO 2014/152774 | A1 | 9/2014 |
| WO | WO 2014/152940 | A1 | 9/2014 |
| WO | WO 2014/159813 | A1 | 10/2014 |
| WO | WO 2014/160243 | A1 | 10/2014 |
| WO | WO 2015/005253 | A1 | 1/2015 |
| WO | WO 2015/024668 | A2 | 2/2015 |
| WO | WO-2015/081155 | A1 | 6/2015 |
| WO | WO 2015/085318 | A2 | 6/2015 |
| WO | WO 2015/095340 | A1 | 6/2015 |
| WO | WO 2015/095346 | A1 | 6/2015 |
| WO | WO 2015/101414 | A2 | 7/2015 |
| WO | WO 2015/101415 | A1 | 7/2015 |
| WO | WO 2015/130584 | A2 | 9/2015 |
| WO | WO 2015/143335 | A1 | 9/2015 |
| WO | WO 2016/103238 | | 6/2016 |
| WO | WO 2016/123864 | A1 | 8/2016 |
| WO | WO 2016/138160 | A1 | 9/2016 |
| WO | WO 2016/164762 | A1 | 10/2016 |
| WO | WO 2016/201377 | A1 | 12/2016 |
| WO | WO 2017/011773 | A2 | 1/2017 |
| WO | WO 2017/015457 | A1 | 1/2017 |
| WO | WO 2017/015463 | A1 | 1/2017 |
| WO | WO 2017/019935 | A1 | 2/2017 |
| WO | WO 2017/020026 | A1 | 2/2017 |
| WO | WO 2017/062513 | A1 | 4/2017 |
| WO | WO 2017/066789 | A1 | 4/2017 |
| WO | WO 2017/070601 | A1 | 4/2017 |
| WO | WO 2017/070616 | A1 | 4/2017 |
| WO | WO 2017/070618 | A1 | 4/2017 |
| WO | WO 2017/070620 | A1 | 4/2017 |
| WO | WO 2017/070622 | A1 | 4/2017 |
| WO | WO 2017/070623 | A1 | 4/2017 |
| WO | WO 2017/070626 | A1 | 4/2017 |
| WO | WO 2017/075038 | A1 | 5/2017 |
| WO | WO 2017/075531 | A1 | 5/2017 |
| WO | WO 2017/081082 | A1 | 5/2017 |
| WO | WO 2017/112865 | A1 | 6/2017 |
| WO | WO 2017/127750 | A1 | 7/2017 |
| WO | WO 2017/174564 | A1 | 10/2017 |
| WO | WO 2017/201333 | A1 | 11/2017 |
| WO | WO 2017/201340 | A1 | 11/2017 |
| WO | WO 2017/201342 | A1 | 11/2017 |
| WO | WO 2017/201347 | A1 | 11/2017 |
| WO | WO 2017/201349 | A1 | 11/2017 |
| WO | WO 2018/006052 | A1 | 1/2018 |
| WO | WO 2018/053209 | A1 | 3/2018 |
| WO | WO 2018/075980 | A1 | 4/2018 |
| WO | WO 2018/081459 | A1 | 5/2018 |
| WO | WO 2018/081462 | A1 | 5/2018 |
| WO | WO 2018/089851 | A1 | 5/2018 |
| WO | WO 2018/107088 | A1 | 6/2018 |
| WO | WO 2018/111967 | A1 | 6/2018 |
| WO | WO 2018/144082 | A1 | 8/2018 |
| WO | WO 2018/144778 | A1 | 8/2018 |
| WO | WO 2018/151816 | A1 | 8/2018 |
| WO | WO 2018/157009 | A1 | 8/2018 |

(56) References Cited

FOREIGN PATENT DOCUMENTS

WO WO 2018/170245 A1 9/2018
WO WO 2018/170256 A1 9/2018
WO WO 2018/170260 A1 9/2018
WO WO 2018/170270 A1 9/2018
WO WO 2018/170347 A1 9/2018
WO WO 2018/175783 A1 9/2018
WO WO 2018/187590 A2 10/2018
WO WO 2018/200737 A1 11/2018
WO WO 2018/232355 A1 12/2018
WO WO 2018/232357 A1 12/2018
WO WO 2019/036670 A1 2/2019
WO WO 2019/036682 A1 2/2019
WO WO 2019/036683 A1 2/2019
WO WO 2019/036685 A1 2/2019
WO WO 2019/103993 A1 5/2019
WO WO 2019/148101 A1 8/2019
WO WO 2019/202035 A1 10/2019
WO WO 2020/006242 A1 1/2020
WO WO 2020/056370 A1 3/2020
WO WO 2020/061284 A1 3/2020
WO WO 2020/061295 A1 3/2020
WO WO 2020/061367 A1 3/2020
WO WO 2020/097291 A1 5/2020
WO WO 2020/172239 A1 8/2020
WO WO 2020/185811 A1 9/2020
WO WO 2020/190750 A1 9/2020
WO WO 2020/243561 A1 12/2020
WO WO 2021/030533 A1 2/2021
WO WO 2021/050864 A1 3/2021
WO WO 2021/055811 A1 3/2021
WO WO 2021/155243 A1 8/2021
WO WO 2021/155274 A1 8/2021
WO WO 2021/159040 A2 8/2021
WO WO 2021/159130 A2 8/2021
WO WO 2021/160346 A1 8/2021
WO WO 2021/163365 A1 8/2021
WO WO 2021/204175 A1 10/2021
WO WO 2021/211343 A1 10/2021
WO WO 2021/213945 A1 10/2021
WO WO 2021/222304 A1 11/2021
WO WO 2021/226436 A1 11/2021
WO WO 2021/231901 A1 11/2021
WO WO 2021/231929 A1 11/2021
WO WO 2021/231963 A1 11/2021
WO WO 2021/237084 A1 11/2021
WO WO 2021/247817 A1 12/2021
WO WO 2022/032154 A2 2/2022
WO WO 2022/043551 A2 3/2022
WO WO 2022/067010 A1 3/2022
WO WO 2022/076562 A1 4/2022
WO WO 2022/099003 A1 5/2022
WO WO 2022/101469 A1 5/2022
WO WO 2022/104265 A1 5/2022
WO WO 2022/137133 A1 6/2022
WO WO 2022/150717 A1 7/2022
WO WO 2022/155524 A1 7/2022
WO WO 2022/155530 A1 7/2022
WO WO 2022/187698 A1 9/2022
WO WO 2022/197624 A1 9/2022
WO WO 2022/204491 A1 9/2022
WO WO 2022/212191 A1 10/2022
WO WO 2022/212442 A1 10/2022
WO WO 2022/212711 A2 10/2022
WO WO 2022/221335 A1 10/2022
WO WO 2022/221336 A1 10/2022
WO WO 2022/221359 A1 10/2022
WO WO 2022/221440 A1 10/2022
WO WO 2022/226277 A1 10/2022
WO WO 2022/226318 A1 10/2022
WO WO 2022/232585 A1 11/2022
WO WO 2022/241103 A1 11/2022
WO WO 2022/245888 A1 11/2022
WO WO 2022/266010 A1 12/2022
WO WO 2022/266012 A1 12/2022
WO WO 2022/266389 A1 12/2022
WO WO 2023/283642 A2 1/2023
WO WO 2023/283645 A1 1/2023
WO WO 2023/283651 A1 1/2023
WO WO 2023/014649 A1 2/2023
WO WO 2023/018773 A1 2/2023
WO WO 2023/018923 A1 2/2023
WO WO 2023/019181 A1 2/2023
WO WO 2023/056401 A1 4/2023
WO WO 2023/069625 A1 4/2023
WO WO 2023/069895 A1 4/2023
WO WO 2023/069900 A1 4/2023
WO WO 2023/076658 A1 5/2023
WO WO 2023/081311 A1 5/2023
WO WO 2023/092069 A1 5/2023
WO WO 2023/094713 A2 6/2023
WO WO 2023/107999 A2 6/2023
WO WO 2023/114307 A1 6/2023
WO WO 2023/132885 A1 7/2023
WO WO 2023/135333 A1 7/2023
WO WO 2023/137149 A1 7/2023
WO WO 2023/147091 A1 8/2023
WO WO 2023/150256 A1 8/2023
WO WO 2023/154818 A1 8/2023
WO WO 2023/196914 A1 10/2023
WO WO 2023/201204 A1 10/2023
WO WO 2023/201294 A1 10/2023
WO WO 2023/201296 A1 10/2023
WO WO 2023/212696 A1 11/2023
WO WO 2023/225524 A1 11/2023
WO WO 2023/250119 A1 12/2023
WO WO 2024/010993 A1 1/2024
WO WO 2024/015890 A1 1/2024
WO WO 2024/026005 A1 2/2024
WO WO 2024/030369 A1 2/2024
WO WO 2024/050483 A1 3/2024
WO WO 2024/097874 A1 5/2024

OTHER PUBLICATIONS

[IPR-2023-01358] Patent Owner's Preliminary Response in IPR2023-01358 dated Dec. 8, 2023.

[IPR-2023-01358] Patent Owner's Preliminary Statement Regarding Petitioner's Inconsistent Positions in IPR2023-01358 dated Jan. 16, 2024.

[IPR-2023-01358] Patent Owner's Response in IPR2023-01358 dated May 31, 2024.

[IPR-2023-01358] Patent Owner's Sur-Reply in IPR2023-01358 dated Oct. 16, 2024.

[IPR-2023-01358] Patent Owner's Sur-Reply in Support of Preliminary Response in IPR2023-01358 dated Jan. 25, 2024.

[IPR-2023-01358] Petitioner's Preliminary Statement Regarding Patent Owner's Inconsistent Positions in IPR-2023-01358 dated Jan. 23, 2024.

[IPR-2023-01358] Petitioner's Reply to Patent Owner's Preliminary Response in IPR2023-01358 dated Jan. 12, 2024.

[IPR-2023-01358] Petitioner's Reply to Patent Owner's Response in IPR2023-01358 dated Aug. 30, 2024.

[IPR2023-01359] Institution Decision dated Mar. 19, 2024 in IPR2023-01359.

[IPR2023-01359] Patent Owner's Preliminary Response in IPR2023-01359 dated Dec. 7, 2023.

[IPR2023-01359] Patent Owner's Preliminary Statement Regarding Alleged Inconsistent Positions in IPR2023-01359 dated Jan. 16, 2024.

[IPR2023-01359] Patent Owner's Response in IPR2023-01359 dated May 31, 2024.

[IPR2023-01359] Patent Owner's Sur-Reply in IPR2023-01359 dated Oct. 16, 2024.

[IPR2023-01359] Patent Owner's Sur-Reply in Support of Preliminary Response in IPR2023-01359 dated Jan. 25, 2024.

[IPR2023-01359] Petitioner's Reply to Patent Owner's Preliminary Response in IPR2024-01359 dated Jan. 12, 2024.

[IPR2023-01359] Petitioner's Reply to Patent Owner's Response in IPR2023-01359 dated Aug. 30, 2024.

(56) References Cited

OTHER PUBLICATIONS

Agnihothram, S., Review Committee Chair, Summary Basis for Regulatory Action, 2022, STN 125752/0 (30 Pages).
Ahmed et al., Biochemistry, Lipids, Statpearls Publishing (2023) (available at https://www.ncbi.nlm.nih.gov/books/NBK525952/).
Akinc et al., "Targeted Delivery of RNAi Therapeutics With Endogenous and Exogenous Ligand-Based Mechanisms," 2010, vol. 18, Issue 7, Molecular Therapy (8 pages).
Allen et al., "Liposomal drug delivery systems: From concept to clinical applications," 2013, Adv. Drug Deliv. Rev., pp. 36-48.
Atkins et al., "The molecular pathogenesis of Semliki Forest virus: a model virus made useful?," Journal of General Virology 2287, 1999 (11 Pages).
Bahl et al., "Preclinical and Clinical Demonstration of Immunogenicity by mRNA Vaccines against H10N8 and H7N9 Influenza Viruses," 2017, vol. 25, Issue 6, Mol Ther.
Bisht et al., "Severe acute respiratory syndrome coronavirus spike protein expressed by attenuated vaccinia virus protectively immunizes mice," 2004, Biological Sciences (6 Pages).
Brito et al., "A Cationic Nanoemulsion for the Delivery of Next-generation RNA Vaccines," 2014, The American Society of Gene & Cell Therapy (12 Pages).
Buchholz et al., "Contributions of the structural proteins of severe acute respiratory syndrome coronavirus to protective immunity," 2004, vol. 101, Issue 26, Biological Sciences.
Buschmann et al., "Chitosans for Delivery of Nucleic Acids," 2013, Advanced Drug Delivery Reviews, pp. 1234-1270.
Cassimeris et al., "Lewin&#x2019s Cells," 2011, Jones and Bartlett Publishers, vol. 2 (109 Pages).
Center for Drug Evaluation and Research Approval Package for New Drug Application No. 50-718/S-50 for Doxil (97 Pages).
Chalkias et al., "Safety, immunogenicity and antibody persistence of a bivalent Beta-containing booster vaccine against COVID-19: a phase 2/3 trial," 2022, Nature Medicine, pp. 2388-2397.
Chang et al., Recent Insights into the Developments of Therapeutics Against Coronavirus Disease by Targeting N Protein, 2016, Drug Discovery Today, No. 4, pp. 562-572.
Cherry et al., "SARS: The First Pandemic of the 21st Century," 2004, Pediatric Research, vol. 56, Issue 1, pp. 1-5.
Coelho et al., "Safety and Efficacy of RNAi Therapy for Transthyretin Amyloidosis," 2013, vol. 369, Issue 9, New England J. Med. (11 Pages).
Curriculum Vitae of Daniel O. Griffin, M.D., Ph.D.
Curriculum Vitae of James J. Moon, Ph.D.
Curriculum Vitae of Deborah Fuller (Deposition Exhibit).
Declaration of Amy K. Wigmore in IPR2023-01358 dated Apr. 16, 2024.
Declaration of Amy K. Wigmore in IPR2023-01359 dated Apr. 16, 2024.
Declaration of Andrew J. Danford in IPR2023-01358 dated Jul. 1, 2024.
Declaration of Daniel O. Griffin, M.D., Ph.D. in IPR2023-01358 dated Aug. 27, 2023.
Declaration of Daniel O. Griffin, M.D., Ph.D. in IPR2023-01359 dated Aug. 27, 2023.
Declaration of Deborah H. Fuller, Ph.D., in IPR2023-01358 dated May 30, 2024 (public redacted version of Ex. 2199).
Declaration of Deborah H. Fuller, Ph.D., in IPR2023-01359 dated May 30, 2024. (public redacted version of Ex. 2199).
Declaration of Douglas L. Sawyer in IPR2023-01358 dated Jul. 17, 2024.
Declaration of Douglas L. Sawyer in IPR2023-01359 dated Jul. 17, 2024.
Declaration of Gabrielle Landes in IPR2023-01358 dated Apr. 25, 2024.
Declaration of Gabrielle Landes in IPR2023-01359 dated Apr. 25, 2024.
Declaration of James E. Malackowski in IPR2023-01358 dated May 29, 2024.
Declaration of James E. Malackowski in IPR2023-01359 dated May 29, 2024.
Declaration of James J. Moon, Ph.D. in IPR2023-01358 dated Apr. 25, 2023.
Declaration of James J. Moon, Ph.D. in IPR2023-01359 dated Apr. 25, 2023.
Declaration of Joshua L. Stern in IPR2023-01358 dated Apr. 17, 2024.
Declaration of Joshua L. Stern in IPR2023-01359 dated Apr. 17, 2024.
Declaration of Kathryn S. Kayali in IPR2023-01358 dated Apr. 16, 2024.
Declaration of Kathryn S. Kayali in IPR2023-01359 dated Apr. 26, 2024.
Declaration of Kevin S. Prussia in IPR2023-01358 dated Apr. 17, 2024.
Declaration of Kevin S. Prussia in IPR2023-01359 dated Apr. 17, 2024.
Declaration of L. Ross Pierce in IPR2023-01358 dated Aug. 30, 2024 (Redacted public version).
Declaration of L. Ross Pierce in IPR2023-01359 dated Aug. 30, 2024. (Redacted public version).
Declaration of M. Ryan Meuth in IPR2023-01358 dated Apr. 25, 2024.
Declaration of M. Ryan Meuth in IPR2023-01359 dated Apr. 25, 2024.
Declaration of Philp Krause, M.D., in IPR2023-01359 dated May 28, 2024. (public redacted version of Ex. 2200).
Declaration of Philp Krause, M.D., in IPR2023-01358 dated May 28, 2024. (public redacted version of Ex. 2200).
Declaration of Thomas H. L. Selby in IPR2023-01358 dated Apr. 26, 2024.
Declaration of Thomas H. L. Selby in IPR2023-01359 dated Apr. 26, 2024.
Declaration of W. Christopher Bakewell in IPR2023-01358 dated Aug. 30, 2024.
Declaration of W. Christopher Bakewell in IPR2023-01359 dated Aug. 30, 2024.
Declaration of Warren C.W. Chan, Ph.D. in IPR2023-01358 dated May 29, 2024.
Declaration of Warren C.W. Chan, Ph.D. in IPR2023-01359 dated May 29, 2024.
Defendants' Supplemental Patent-Related Disclosures, Exhibit C—Invalidity Contentions of U.S. Pat. No. 10,702,600 (Jun. 27, 2023)(Excerpts).
Defendants' Patent-Related Disclosures, Exhibit D—Invalidity Contentions of U.S. Pat. No. 10,933,127, 2023, pp. 1-5 (Excerpts).
Defendants' Patent-Related Disclosures, Exhibit C—Invalidity Contentions of U.S. Pat. No. 10,702,600 (Mar. 31, 2023) (Excerpts).
Defendants' Supplemental Patent-Related Disclosures, Exhibit D—Invalidity Contentions of U.S. Pat. No. 10,933,127, 2023, pp. 1-110 (Excerpts).
Deming et al., "Vaccine Efficacy in Senescent Mice Challenged with Recombinant SARS-CoV Bearing Epidemic and Zoonotic Spike Variants," 2006, vol. 3, Issue 12, Plos Medicine.
Deposition of Daniel O. Griffin, M.D., Ph.D. (May 22, 2024), in *BioNTech SE and Pfizer Inc.* v. *Moderna TX, Inc.*, in IPR2023-01358 and -01359.
Deposition of Daniel O. Griffin, M.D., Ph.D. (Sep. 20, 2024) in *BioNTech SE and Pfizer Inc.* v. *Moderna TX, Inc.*, in IPR2023-01358 and -01359.
Deposition of Deborah Fuller, Ph.D., dated Aug. 2, 2024.
Deposition of James E. Malackowski dated Jul. 22, 2024 and Errata Sheet dated Aug. 27, 2024.
Deposition of James J. Moon, Ph.D. (May 10, 2024), in *BioNTech SE and Pfizer Inc.* v. *Moderna TX, Inc.*, in IPR2023-01358 and -01359.
Deposition of James J. Moon, Ph.D. (Sep. 13, 2024) in *BioNTech SE and Pfizer Inc.* v. *Moderna TX, Inc.*, in IPR2023-01358 and -01359.
Deposition of L. Ross Pierce, M.D., (Oct. 4, 2024) in *BioNTech SE and Pfizer Inc.* v. *Moderna TX, Inc.*, in IPR2023-01358. (redacted version of Ex. 2256).

(56) References Cited

OTHER PUBLICATIONS

Deposition of L. Ross Pierce, M.D., (Oct. 4, 2024) in *BioNTech SE and Pfizer Inc.* v. *Moderna TX, Inc.*, in IPR2023-01359. (redacted version of Ex. 2256).
Deposition of Philip Krause, M.D., dated Aug. 14, 2024 (redacted).
Deposition of W. Christopher Bakewell (Oct. 3, 2024) in *BioNTech SE and Pfizer Inc.* v. *Moderna TX, Inc.*, in IPR2023-01358 and -01359.
Deposition of Warren C.W. Chan Ph.D., dated Jul. 30, 2024.
Division of Microbiology and Infectious Diseases (DMID) Protocol, Phase 1, Open-Label, Dose-Ranging Study of the Safety and Immunogenicity of 2019-nCoV Vaccine (mRNA-1273) in Healthy Adults, 2020, pp. 1-10 (Excerpts).
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults," 2020, pp. 1-12 (Excerpts).
Division of Microbiology and Infectious Diseases (DMID) Protocol (Feb. 14, 2020); MOD_000477491-MOD_000477561 at MOD_000477491-MOD_000477498; MOD_000477504-MOD_000477509 (Excerpts).
Division of Microbiology and Infectious Diseases (DMID) Protocol (Mar. 30, 2020); MOD_000477134-MOD_000477212 at MOD_000477134-MOD_000477139, MOD_000477148-MOD_000477154 (Excerpts).
Division of Microbiology and Infectious Diseases (DMID) Protocol (May 20, 2020); MOD_000471975-MOD_000472059 at MOD_000471975-MOD_000471983; MOD_000471990-MOD_000471992; MOD_000471994-MOD_000471997 (Excerpts).
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults," 2020, pp. 1-8 (Excerpts).
Drummond et al., "The Evolutionary Consequences of Erroneous Protein Synthesis," 2009, Nature Reviews Genetics (10 Pages).
European Medicines Agency Assessment Report for COVID-19 Vaccine Moderna, 2021, pp. 1-169.
European Medicines Agency, Assessment Report for Spikevax (Sep. 14, 2023).
European Medicines Agency, Nuvaxovid (available at https://www.ema.europa.eu/en/medicines/human/EPAR/nuvaxovid).
FDA, E6(R2) Good Clinical Practice: Integrated Addendum to ICH E6(R1) (Mar. 2018).
FDA, Guidance for Industry E6 Good Clinical Practice: Consolidated Guidance (Apr. 1996).
Felgner et al., "Lipofection: A highly efficient, lipid-mediated DNA-transfection procedure," 1987, 84 Proc. Natl. Acad. Sci. USA (5 Pages).
Fuller, Deborah, The Conversation, "How mRNA and DNA vaccines could soon treat cancers, HIV, autoimmune disorders and genetic diseases," 2022, pp. 1-5.
Gandhi et al., "Immunization of HIV-1-Infected Persons with Autologous Dendritic Cells Transfected with mRNA Encoding HIV-1 Gag and Nef: Results of a Randomized, Placebo-Controlled Clinical Trial, 71 J," 2016, Acquired Immune Deficiency Syndrome, Basic Translational Science.
Gao et al., "Nonviral gene delivery: What we know and what is next," 2007, The AAPS Journal (13 Pages).
Gilleron et al., "Image-Based Analysis of Lipid Nanoparticle-Mediated siRNA Delivery, Intracellular Trafficking and Endosomal Escape," 2013, Nature Biotech. 638.
Ginn et al., "Gene Therapy Clinical Trials Worldwide to 2017: An Update," 2018, 20 J, Gene Med, Article e3015.
Gorbalenya, A., E., "The Species Severe Acute Respiratory Syndrome-related Coronavirus: Classifying 2019-nCoV and Naming it SARS-CoV-2, 5," 2020, Nature Microbiology, pp. 536-544.
Griffin et al., "Co-infection with Hepatitis C Virus Increases Mortality in HIV-1 Infected Patients Through Increased Liver-Related Deaths Rather Than By Increasing Malignancy Related Deaths," 2016, vol. 7, Issue 4, J. Aids and Clin. Res. (3 Pages).
Griffin et al., "Cytokine storm of a different flavour: the different cytokine signature of SARS-CoV-2 the cause of COVID-19 from the original SARS outbreak," Journal of Global Antimicrobial Resistance, pp. 1-3.
Griffin et al., "Human B1 cells in umbilical cord and adult peripheral blood express the novel phenotype CD20 CD27 CD43 CD70-," 2011, vol. 208, Issue 1, J. Exp. Med. (14 Pages).
Griffin et al., A small CD11b human B1 cell subpopulation stimulates T cells and is expanded in lupus, 2011, vol. 208, Issue 13, J. Exp. Med (8 Pages).
Hattinger, E., et al. "Prophylactic mRNA Vaccination against Allergy Confers Long-Term Memory Responses and Persistent Protection in Mice," 2015, Journal of Immunology Research 2015, Article 797421.
Hekele et al., "Rapidly produced SAM? vaccine against H7N9 influenza is immunogenic in mice," 2013, vol. 2, Issue 8, Emerging Microbes and Infections (7 Pages).
Heyes et al., "Cationic lipid saturation influences intracellular delivery of encapsulated nucleic acids," 2005, 107 J.. Controlled Release, pp. 276-287.
Hoerr et al., "In vivo application of RNA leads to induction of specific cytotoxic T lymphocytes and antibodies," 2000, 30 Eur. J. Immunol.
Holtkamp et al., "Modification of antigen-encoding RNA increases stability, translational efficacy, and T-cell stimulatory capacity of dendritic cells," 2006, vol. 108, Issue 13, Gene Therapy.
Hu et al., "Cytosolic delivery mediated via electrostatic surface binding of protein, virus, or siRNA cargos to pH-responsive core-shell gel particles," 2009, vol. 10, Issue 4, Biomacromolecules (10 Pages).
Huang, "In Vivo Delivery of RNAi with Lipid-Based Nanoparticles," 2011, 13 Ann. Rev. Biomed. Eng'g.
International Publication No. WO 2012/006378 A1 (Asserted in *GlaxoSmithKline Biologicals SA et al* v. *Pfizer Inc. et al*, C.A. No. 24-512 (GBW) (D. Del.)).
Japanese Package Insert for Spikevax Intramuscular Injection (Monovalent: Omicron XBB.1.5).
Jaume et al., "Anti-Severe Acute Respiratory Syndrome Coronavirus Spike Antibodies Trigger Infection of Human Immune Cells via a pH- and Cysteine Protease-Independent FcγR Pathway," 2011, Journal of Virology, pp. 10582-10597.
Jeffs et al., "A Scalable, Extrusion-Free Method for Efficient Liposomal Encapsulation of Plasmid DNA," 2005, 22 Pharmaceutical Research (11 Pages).
Jesse H. Erasmus et al., "An Alphavirus-derived replicon RNA vaccine induces SARS-CoV-2 neutralizing antibody and T cell responses in mice and nonhuman primates," 2020, Sci. Transl. Med. (11 Pages).
Johansson et al., "Intradermal Electroporation of Naked Replicon RNA Elicits Strong Immune Responses, " 2012, PLoSONE, Article e29732.
Kam et al., "Antibodies against trimeric S glycoprotein protect hamsters against SARS-CoV challenge despite their capacity to mediate Fc?RII-dependent entry into B cells in vitro," 2007, Vaccine (13 Pages).
Kariko et al., "Modified Uridines Are the Key to a Successful Message," 2021, Nature Reviews Immunology (2 Pages).
Kariko et al., "Naturally occurring nucleoside modifications suppress the immunostimulatory activity of RNA: Implication for therapeutic RNA development," Curr. Opin. Drug Discov. Devel., pp. 523-532.
Kariko et al., "Suppression of RNA recognition by Toll-like receptors: The impact of nucleoside modification and the evolutionary origin of RNA," 2005, Immunity (8 Pages).
Kariko et al., Increased eythropoiesis in mice injected with submicrogram quantities of pseudouridine-containing mRNA encoding erythropoietin, 20 Molecular Therapy 948 (2012) (Ex. 1028).
Kim et al., "Generation and Characterization of DNA Vaccines Targeting the Nucleocapsid Protein of Severe Acute Respiratory Syndrome Coronavirus," 2004, vol. 78 J, Issue 9, Virology, pp. 4638-4645.
King et al., "Virus Taxonomy: Classification and Nomenclature of Viruses," 2012, Elsevier Academic Press (50 Pages).

(56) References Cited

OTHER PUBLICATIONS

Kranz et al., "Systemic RNA Delivery to Dendritic Cells Exploits Antiviral Defense for Cancer Immunotherapy," 2016, Nature, vol. 534, pp. 396-411.
Kreiter et al., "Intranodal Vaccination with Naked Antigen-Encoding RNA Elicits Potent Prophylactic and Therapeutic Antitumoral Immunity," 2010, Cancer Research, pp. 9301-9040.
Kutzler et al., "DNA Vaccines: Ready for Prime Time?," 2008, Nature Reviews Genetics, vol. 9, pp. 776-788.
Langer, R., "New methods of drug delivery," 1990, Science, 1527-1533.
Leal et al., "Phase I clinical trial of an intranodally administered mRNA-based therapeutic vaccine against HIV-1 infection," 2018, AIDS, vol. 32, Issue 17, Pages.
Leung et al., "Chapter Four—Lipid nanoparticles for short interfering RNA delivery," 2014, in Advances in Genetic, vol. 88 (40 Pages).
Liang et al., "Efficient Targeting and Activation of Antigen-Presenting Cells In Vivo after Modified mRNA Vaccine Administration in Rhesus Macaques," 2017, 25 Mol Therapy, pp. 2635-2647.
Lingshu Wang et al., "Evaluation of candidate vaccine approaches for MERS-CoV," 2015, Nature Communications (11 Pages).
Liu et al., "The Membrane Protein of Severe Acute Respiratory Syndrome Coronavirus Acts as a Dominant Immunogen Revealed by a Clustering Region of Novel Functionally and Structurally Defined Cytotoxic T-Lymphocyte Epitopes," 2010, vol. 202 J, Infectious Diseases, pp. 1171-1180.
Lu et al., "Immunogenicity of DNA Vaccines Expressing Human Immunodeficiency Virus Type 1 Envelope Glycoprotein With and Without Deletions in the V1/2 and V3 Regions," AIDS Research & Human Retroviruses, pp. 151-155.
Marshall et al., "Ch. 79: Regulation and Testing of Vaccines," 2018, Plotkin's Vaccines, 7th edition, pp. 1547-1565.
Martin et al., "A SARS DNA Vaccine Induces Neutralizing Antibody and Cellular Immune Responses in Healthy Adults in a Phase I Clinical Trial," 2008, Vaccine (6 Pages).
Matthew G. Stanton & Kerry E. Murphy-Benenato, "Messenger RNA as a Novel Therapeutic Approach," 2017, Topics in Medicinal Chemistry RNA Therapeutics, pp. 1-2 (Excerpts).
Moderna Form 10-K for the fiscal year ended Dec. 31, 2018.
Moderna Form 10-K for the fiscal year ended Dec. 31, 2022.
Moderna Form 10-Q for the quarterly period ended Jun. 30, 2024.
Moderna Form 8-K, Mar. 16, 2020.
Moderna, Inc. 2020 Form 10-K.
Moderna, Inc. 2023 Form 10-K.
Moderna, Inc., Patents, https://www.modernatx.com/patents (3 Pages).
Moderna, Science & Technology Day dated May 17, 2022.
Moderna, Vaccines and Related Biological Products Advisory Committee Presentation: Moderna COVID-19 Variant Vaccines (Jun. 15, 2023); MOD_000767652-MOD_000767686.
Nakayama et al., "Comparison of Current Regulatory Status for Gene-Based Vaccines in the U.S., Europe and Japan," 2015, Vaccines, pp. 186-202.
National Human Genome Research Institute, "Double Helix," 2023, NIH, https://www.genome.gov/geneticsglossary/Double-Helix (2 Pages).
National Human Genome Research Institute, Central Dogma, 2023, NIH, https://www.genome.gov/geneticsglossary/Central-Dogma (4 Pages).
Onpattro Prescribing Label (available at https://www.accessdata.fda.gov/drugsatfda_docs/label/2018/210922s000lbl.pdf).
Openshaw et al., "Immune Responses and Disease Enhancement During Respiratory Syncytial Virus Infection," 2005, Clinical Microbiology Reviews, vol. 18, Issue 13, pp. 541-555.
Package Insert for Spikevax (COVID-19 Vaccine, mRNA) &#x2013 2023-2024 Formula (45 Pages).
Package Insert for Spikevax (COVID-19 Vaccine, mRNA) &#x2013 2023-2024 Formula (Apr. 2024).
Paoletti, E., "Applications of Pox Virus Vectors to Vaccination: An Update," 1996, Proceedings of the Natl. Acad. of Sci., pp. 11349-11353.
Paramasivam et al., "Endosomal Escape of Delivered mRNA from Endosomal Recycling Tubules Visualized at the Nanoscale," 221 J. Cell Biology e202110137.
Park et al., "Non-Viral COVID-19 Vaccine Delivery Systems," Advanced Drug Delivery Reviews, pp. 137-151.
Pascolo, S., "Vaccination with Messenger RNA (mRNA)," 2008, Handbook of Experimental Pharmacology, pp. 221-235.
Patent Sublicense Agreement Between Cellscript, LLC and ModernaTx, Inc.
Plotkin, S., A., "Vaccines: Past, Present and Future, 11 Nature Medicine Supplement 55," 2005, Historical Perspective, Nature Medicine, pp. S5-S11.
Regla-Nava et al., "Severe Acute Respiratory Syndrome Coronaviruses with Mutations in the E Protein Are Attenuated and Promising Vaccine Candidates," 2015, vol. 89, Journal of Virology (18 Pages).
Reply Declaration of Daniel Griffin in IPR2023-01358 dated Aug. 30, 2024. (Redacted public version).
Reply Declaration of Daniel Griffin in IPR2023-01359 dated Aug. 30, 2024. (Redacted public version).
Reply Declaration of James Moon in IPR2023-01358 dated Aug. 30, 2024. (Redacted public version).
Reply Declaration of James Moon in IPR2023-01359 dated Aug. 30, 2024. (Redacted public version).
Sahdev et al., Biomaterials for Nanoparticle Vaccine Delivery Systems, Pharmaceutical Research, 2014, pp. 2563-2582.
Sahin et al., "mRNA-based therapeutics Developing a new class of drugs," 2014, Nature Reviews Drug Discovery.
Semple et al., "Efficient encapsulation of antisense oligonucleotides in lipid vesicles using ionizable aminolipids: Formation of novel small multilamellar vesicle structures," 2001, Biochimica et Biophysica Acta, pp. 152-166.
Semple et al., "Rational design of cationic lipids for siRNA delivery," 2010, Nature Biotechnology, pp. 172-178.
Shaw et al., "The Path to an RSV Vaccine," 2013, Current Opinion in Virology, pp. 332-342.
Slimko et al., "Codon optimization of Caenorhabditis elegans GluCl ion channel genes for mammalian cells dramatically improves expression levels," 2003, Journal of Neuroscience Methods.
Song et al., "Middle East Respiratory Syndrome Coronavirus Spike Protein Delivered by Modified Vaccinia Virus Ankara Efficiently Induces Virus-Neutralizing Antibodies," 2013, 87 J. of Virology, pp. 1-5.
Steitz et al., "Effective Induction of Anti-Melanoma Immunity Following Genetic Vaccination with Synthetic mRNA Coding for the Fusion Protein EGFP.TRP2," 2006, Cancer Immunology, pp. 246-253.
Stenler et al., "Safety and efficacy of DNA vaccines: Plasmids vs. minicircles," 2014, vol. 10, Issue 5, Human Vaccines & Immunotherapeutics.
Tenchov et al., "Lipid nanoparticles 2014 From liposomes to mRNA vaccine delivery, a landscape of research diversity and advancement," 2021, ACS Nano (34 Pages).
Updated Curriculum Vitae of Daniel O. Griffin, Ph.D.
Vennema et al., "Early Death After Feline Infectious Peritonitis Virus Challenge due to Recombinant Vaccinia Virus Immunization," 1990, Journal of Virology, pp. 1407-1409.
Vergati et al., "Strategies for Cancer Vaccine Development," 2010, Journal of Biomedicine and Biotechnology, (13 Pages).
Wan et al., "Comparison of Immunogenicity Between Codon Optimized HIV-1 Thailand Subtype B gp140 and gp145 Vaccines," 2007, Vaccine, vol. 25, pp. 4949-4959.
Weide et al., "Direct Injection of Protamine-protected mRNA: Results of a Phase 1/2 Vaccination Trial in Metastatic Melanoma Patients," 2009, Immunotherapy (11 Pages).
Weide et al., "Results of the First Phase I/II Clinical Vaccination Trial with Direct Injection of mRNA," 2008, J. Immunotherapy, pp. 180-188.

(56) References Cited

OTHER PUBLICATIONS

Withoff et al., "Replication-defective Recombinant Semliki Forest Virus Encoding GM-CSF as a Vector System for Rapid and Facile Generation of Autologous Human Tumor Cell Vaccines," 2001, Gene Therapy, pp. 1515-1523.
Wolff et al., Direct gene transfer into mouse muscle in vivo, 247 Science 1465 (1990) (Ex. 1013).
Yang et al., "Evasion of Antibody Neutralization in Emerging Severe Acute Respiratory Syndrome Coronaviruses," 2005, PNAS, vol. 102, Issue 3, pp. 797-801.
Yoo et al., Synthesis and Processing of the Haemagglutinin-Esterase Glycoprotein of Bovine Coronavirus Encoded in the E3 Region of Adenovirus, vol. 73, J. Gen. Virology, pp. 2591-2600.
Zhou et al., "Current RNA-Based Therapeutics in Clinical Trials," 2019, Current Gene Therapy, pp. 172-196.
International Search Report and Written Opinion for Application No. PCT/US2016/058327 mailed Jun. 29, 2017.
[No Author Listed], "Messenger RNA", Internet: Wikipedia. Jun. 19, 2013, XP002699196, Retrieved from the Internet: URL: http://en.wikipedia.org/wiki/Messenger RNA.
[No Author Listed], Clinical trial NCT04528719: A Dose Escalation Study to Evaluate Safety, Reactogenicity, and Immunogenicity of mRNA-1345 in Healthy Adults and in Children Who Are Respiratory Syncytial Virus Seropositive (ModernaTX, Inc.) First Posted Aug. 27, 2020. Retrieved online on Mar. 15, 2021 at https://www.clinicaltrials.gov/ct2/show/NCT04528719?term=NCT04528719&draw=2&rank=1.
[No Author Listed], Geneseq Accession No. BC153556. First entry: Jan. 14, 2016. 3 pages.
[No Author Listed], Geneseq Accession No. BGP67180. First entry: Sep. 19, 2019. 3 pages.
[No Author Listed], Katalin Karikó and Drew Weissman awarded Horwitz Prize for pioneering research on COVID-19 vaccines, Columbia University Irving Medical Center, Aug. 16, 2021, https://www.cuimc.columbia.edu/news/horwitz-prize-2021 (last accessed Aug. 24, 2023). 12 pages.
[No Author Listed], List of past and pending litigations. Prepared Oct. 24, 2023. 1 page.
Agrawal et al., Immunization with inactivated Middle East Respiratory Syndrome coronavirus vaccine leads to lung immunopathology on challenge with live virus. Hum Vaccin Immunother. Sep. 2016;12(9):2351-6. doi:10.1080/21645515.2016.1177688. Epub Jun. 7, 2016.
Aliprantis et al., A phase 1, randomized, placebo-controlled study to evaluate the safety and immunogenicity of an mRNA-based RSV prefusion F protein vaccine in healthy younger and older adults. Hum Vaccin Immunother. May 4, 2021;17(5):1248-1261. doi: 10.1080/21645515.2020.1829899. Epub Oct. 29, 2020.
*Alnylam Pharmaceuticals, Inc.* v. *Moderna, Inc.* (Fed. Circ. 2023-2357) D.I. 8—Docketing Statement, Sep. 21, 2023. 2 pages.
*Alnylam Pharmaceuticals, Inc.* v. *Moderna, Inc. et al* (D. Del. 23-cv-580-CFC) D.I. 1—Complaint for Patent Infringement, May 26, 2023. 28 pages.
*Alnylam Pharmaceuticals, Inc.* v. *Moderna, Inc. et al* (D. Del. 23-cv-580-CFC) D.I. 12—Answer to the Complaint, Jul. 17, 2023. 37 pages.
*Alnylam Pharmaceuticals, Inc.* v. *Moderna, Inc. et al.* (D. Del. 22-cv-335-CFC) D.I. 1—Complaint for Patent Infringement, Mar. 17, 2022. 14 pages.
*Alnylam Pharmaceuticals, Inc.* v. *Moderna, Inc. et al.* (D. Del. 22-cv-335-CFC) D.I. 128—Final Judgement, Aug. 30, 2023. 2 pages.
*Alnylam Pharmaceuticals, Inc.* v. *Moderna, Inc. et al.* (D. Del. 22-cv-335-CFC) D.I. 130—Notice of Appeal to the U.S. Court of Appeals for the Federal Circuit, Aug. 31, 2023. 3 pages.
*Alnylam Pharmaceuticals, Inc.* v. *Moderna, Inc. et al.* (D. Del. 22-cv-335-CFC) D.I. 87—Answer to the Complaint, May 10, 2023. 44 pages.
*Arbutus BioPharma Corp. et al.* v. *Moderna, Inc. et al.* (D. Del. 22-cv-252-MSG) D.I. 1—Complaint for Patent Infringement, Feb. 28, 2022. 51 pages.
*Arbutus BioPharma Corp. et al.* v. *Moderna, Inc. et al.* (D. Del. 22-cv-252-MSG) D.I. 31—District Court Memorandum, Nov. 2, 2022. 16 pages.
*Arbutus BioPharma Corp. et al.* v. *Moderna, Inc. et al.* (D. Del. 22-cv-252-MSG) D.I. 35—Answer to the Complaint, Nov. 30, 2022. 83 pages.
*Arbutus BioPharma Corp. et al.* v. *Moderna, Inc. et al.* (D. Del. 22-cv-252-MSG) D.I. 64—District Court Memorandum, Mar. 10, 2023. 4 pages.
Archer, S.J., Induction of a T-cell specific antigen on bone marrow lymphocytes with thymus RNA. Immunology. Jan. 1978;34(1): 123-9.
Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.
Austin et al., Split-Dose Administration Enhances Immune Responses Elicited by a mRNA/Lipid Nanoparticle Vaccine Expressing Respiratory Syncytial Virus F Protein. Mol Pharm. Jan. 2, 2023;20(1):279-289. doi: 10.1021/acs.molpharmaceut.2c00635. Epub Oct. 17, 2022.
Barbier et al., The clinical progress of mRNA vaccines and immunotherapies. Nat Biotechnol. Jun. 2022;40(6):840-854. doi: 10.1038/s41587-022-01294-2. Epub May 9, 2022.
Bettinger, T. et al., Peptide-mediated RNA delivery: a novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Bose, S. et al., Role of nucleolin in human parainfluenza virus type 3 infection of human lung epithelial cells. J Viral. Aug. 2004;78(15):8146-58.
Byoung-Shik et al., Intranasal immunization with plasmid DNA encoding spike protein of SARS-coronavirus/polyethylenimine nanoparticles elicits antigen-specific humoral and cellular immune responses. BMC Immunol. Dec. 31, 2010;11:65. doi: 10.1186/1471-2172-11-65.
Chaudhary et al., mRNA vaccines for infectious diseases: principles, delivery and clinical translation. Nature Reviews Drug Discovery vol. 20, pp. 817-838 (2021).
Clancy et al., Translation: DNA to mRNA to Protein. Nature Education 2008;1(1):101.
Cobb et al., Who discovered messenger RNA? Curr Biol. Jun. 29, 2015;25(13):R526-32. doi:10.1016/j.cub.2015.05.032.
Conry, R.M. et al., Characterization of a messenger RNA polynucleotide vaccine vector. Cancer Res. Apr. 1, 1995 ;55 (7):1397-1400.
Cross, Without these lipid shells, there would be No. mRNA vaccines for COVID-19. Chem Eng News. Mar. 6, 2021; 99(8). 8 pages.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Dahlman, James E. et al., In vivo endothelial siRNA delivery using polymeric nanoparticles with low molecular weight, Nature Nanotechnology, 2014, No. vol. #, pp. 1-8.
Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014.
Degroot et al., Part II—The Positive Sense Single Stranded RNA Viruses, Family Coronaviridae, in Virus Taxonomy: Ninth Report of the International Committee on Taxonomy of Viruses 806 (2012). 25 pages.

(56) References Cited

OTHER PUBLICATIONS

Del Pozo-Rodriguez et al., Lipid nanoparticles as vehicles for macromolecules: nucleic acids and peptides. Recent Pat Drug Deliv Formul. Sep. 2011;5(3):214-26. doi: 10.2174/187221111797200515.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Du et al., Recombinant adeno-associated virus expressing the receptor-binding domain of severe acute respiratory syndrome coronavirus S protein elicits neutralizing antibodies: Implication for developing SARS vaccines. Virology. Sep. 15, 2006;353(1):6-16. doi: 10.1016/j.virol.2006.03.049. Epub Jun. 21, 2006.
Du et al., The spike protein of SARS-CoV—a target for vaccine and therapeutic development. Nat Rev Microbiol. Mar. 2009;7(3):226-36. doi: 10.1038/nrmicro2090. Epub Feb. 9, 2009.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Furuichi, Caps on Eukaryotic mRNAs. eLS. John Wiley & Sons. Jul. 2014. 1-12.
Geall et al., Nonviral delivery of self-amplifying RNA vaccines. Proc Natl Acad Sci U S A. Sep. 4, 2012;109(36):14604-9. doi: 10.1073/pnas.1209367109. Epub Aug. 20, 2012.
Geall et al., RNA: the new revolution in nucleic acid vaccines. Semin Immunol. Apr. 2013;25(2):152-9. doi: 10.1016/j.smim.2013.05.001. Epub Jun. 2, 2013.
GenBank Accession No. AHX22069. First seen on NCBI on May 14, 2014.
Gilboa, E. et al., Cancer immunotherapy with mRNA-transfected dendritic cells. Immunol Rev. Jun. 2004;199:251-63.
Glenn et al., Safety and immunogenicity of a Sf9 insect cell-derived respiratory syncytial virus fusion protein nanoparticle vaccine. Vaccine. Jan. 7, 2013;31(3):524-32. doi: 10.1016/j.vaccine.2012.11.009.
Graham et al., Novel antigens for RSV vaccines. Curr Opin Immunol. Aug. 2015;35:30-8. doi: 10.1016/j.coi.2015.04.005. Epub Jun. 10, 2015.
Graham et al., Novel Vaccine Technologies: Essential Components of an Adequate Response to Emerging Viral Diseases. JAMA. Apr. 10, 2018;319(14):1431-1432. doi: 10.1001/jama.2018.0345.
Greer et al., Long-term protection in hamsters against human parainfluenza virus type 3 following mucosal or combinations of mucosal and systemic immunizations with chimeric alphavirus-based replicon particles. Scand J Immunol. Dec. 2007;66(6):645-53. Epub Oct. 17, 2007.
Hartmann et al., Handbook of RNA Biochemistry, Second Edition, "Part I RNA Synthesis and Detection." 2014. p. 1-27.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heiser, A. et al., Induction of polyclonal prostate cancer-specific CTL using dendritic cells transfected with amplified tumor Rna. J Immunol. Mar. 1, 2001; 166(5):2953-60.
Heyes et al., Cationic lipid saturation influences intracellular delivery of encapsulated nucleic acids. J Control Release. Oct. 3, 2005;107(2):276-87.
Hoerr, I. et al., In vivo application of RNA leads to induction of specific cytotoxic T lymphocytes and antibodies. EurJ Immunol. Jan. 2000;30(1):1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp, S. et al., Modification of antigen-encoding RNA increases stability, translational efficacy, and T-cell stimulatory capacity of dendritic cells. Blood. Dec. 15, 2006;108(13):4009-17.
Hörr, RNA vaccine for the induction of specific cytotoxic T lymphocytes (CTL) and antibodies. Eberhard Karls University of Tübingen. Dissertation. English-Language Translation. 1999. 138 Pages.
Hou et al., Lipid nanoparticles for mRNA delivery. Nature Reviews Materials vol. 6, pp. 1078-1094 (2021).
Human Metapneumovirus (HM PV) Clinical Features, CDC Website, https://www.cdc.gov/surveillance/nrevss/hmpv/clinical.html, Sep. 5, 2019. (Year: 2019).
Jirikowski, G.F., et al., Reversal of diabetes insipidus in Brattleboro Rats: Intrahypothalamic injection of vasopressin mRNA. Science. Feb. 1992; 255(5047): 996-998.
Jorquera et al., Nanoparticle vaccines encompassing the respiratory syncytial virus (RSV) G protein CX3C chemokine motif induce robust immunity protecting from challenge and disease. PLoS One. Sep. 10, 2013;8(9):e74905. doi: 10.1371/journal.pone.0074905. eCollection 2013.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kalra et al., Virosomes: As a Drug Delivery Carrier. American Journal of Advanced Drug Delivery. 2013;1:29-35.
Kanapathipillai, et al., Nanoparticle targeting of anti-cancer drugs that alter intracellular signaling or influence the tumor microenvironment, Adv. Drug Deliv. Rev. (2014), , pp. 1-12.
Kariko et al., Incorporation of pseudouridine into mRNA yields superior nonimmunogenic vector with increased translational capacity and biological stability. Mol Ther. Nov. 2008; 16(11):1833-40. Epub Sep. 16, 2008.
Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Keshwara et al., Rabies-based vaccine induces potent immune responses against Nipah virus. NPJ Vaccines. Apr. 15, 2019;4:15. Erratum in: NPJ Vaccines. May 13, 2019;4:18.
Kisich et al., Antimycobacterial agent based on mRNA encoding human beta-defensin 2 enables primary macrophages to restrict growth of *Mycobacterium tuberculosis*.Infect Immun. Apr. 2001;69(4):2692-9.
Kozielski et al., Bioreducible cationic polymer-based nanoparticles for efficient and environmentally triggered cytoplasmic siRNA delivery to primary human brain cancer cells. ACS Nano. Apr. 22, 2014;8(4):3232-41. doi: 10.1021/nn500704t. Epub Apr. 3, 2014.
Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.
Kreiter, S., et al., Intranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in Immun. Jun. 2011; 23(3): 399-406.
Kresge, The messenger RNA pioneers everyone ignored. Bloomberg, Nov. 23, 2021, https://www.bloomberg.com/news/newsletters/2021-11-23/themessenger-rna-pioneers-everyone-ignored (last accessed Aug. 24, 2023). 8 pages.
Kuhn, A.N., et al., mRNA as a versatile tool for exogenous protein expression. Current Gene Therapy. Oct. 2012; 12 (5): 347-361.

(56) References Cited

OTHER PUBLICATIONS

Leitner, W.W. et al., DNA and RNA-based vaccines: principles, progress and prospects. Vaccine. Dec. 10, 1999;18 (9-10):765-77.
Li et al., Effects of local structural transformation of lipid-like compounds on delivery of messenger RNA. Sci Rep. Feb. 26, 2016;6:22137. doi: 10.1038/srep22137.
Li et al., Lipid-based nanoparticles for nucleic acid delivery. Pharm Res. Mar. 2007;24(3):438-49. doi: 10.1007/s11095-006-9180-5.
Li, L. et al., Overcoming obstacles to develop effective and safe siRNA therapeutics. Expert Opin Biol Ther. May 2009; 9(5): 609-19.
Liang et al., Enhanced Neutralizing Antibody Response Induced by Respiratory Syncytial Virus Prefusion F Protein Expressed by a Vaccine Candidate. J Virol. Sep. 2015;89(18):9499-510. doi: 10.1128/JVI.01373-15. Epub Jul. 8, 2015.
Lin et al., Progress and challenges of mRNA vaccines. Interdisc Med. Dec. 22, 2022;1(1):e20220008. doi: 10.1002/INMD.20220008.
Lorenzi, J.C., et al., Intranasal vaccination with messenger RNA as a new approach in gene therapy: Use against tuberculosis. BMC Biotechnol. Oct. 2010; 10(77): 1-11.
Lu et al., Bat-to-human: spike features determining 'host jump' of coronaviruses SARS-CoV, MERS-CoV, and beyond. Trends Microbiol. Aug. 2015;23(8):468-78. doi: 10.1016/j.tim.2015.06.003. Epub Jul. 21, 2015.
Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.
Martinon, F. et al., Induction of virus-specific cytotoxic T lymphocytes in vivo by liposome-entrapped mRNA. EurJ Immunol. Jul. 1993;23(7):1719-22.
Mas et al., Engineering, Structure and Immunogenicity of the Human Metapneumovirus F Protein in the Postfusion Conformation. PLoS Pathog. Sep. 9, 2016;12(9):e1005859. doi: 10.1371/journal.ppat.1005859. eCollection Sep. 2016.
McDonnell et al. DNA vaccines. N Engl J Med. Jan. 4, 1996;334(1):42-5. doi: 10.1056/NEJM199601043340110.
McLellan et al., Structure of respiratory syncytial virus fusion glycoprotein in the postfusion conformation reveals preservation of neutralizing epitopes. J Virol. Aug. 2011;85(15):7788-96. doi: 10.1128/JVI.00555-11. Epub May 25, 2011.
McLellan et al., Structure-based design of a fusion glycoprotein vaccine for respiratory syncytial virus. Science. Nov. 1, 2013;342(6158):592-8. doi: 10.1126/science.1243283.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell, Da et al., RNA transfected dendritic cells as cancer vaccines. Curr Opin Mal Ther. Apr. 2000;2(2):176-81.
Mitchell, Da et al., RNA-transfected dendritic cells in cancer immunotherapy. J Clin Invest. Nov. 2000;106 (9):1065-9.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
*ModernaTX, Inc. et al* v. *Pfizer Inc.et al*. (D. Mass. 22-11378-RGS) D.I. 105—District Court Memorandum and Order on Claim Construction, Aug. 1, 2023. 15 pages.
*ModernaTX, Inc. et al*.v. *Pfizer Inc.et al*. (D. Mass. 22-11378-RGS) D.I. 1—Complaint for Patent Infringement, Aug. 26, 2022. 39 pages.
*ModernaTX, Inc. et al*.v. *Pfizer Inc.et al*. (D. Mass. 22-11378-RGS) D.I. 45—Answer to the Complaint, Dec. 5, 2022. 81 pages.
Mok et al., An Alphavirus Replicon-Based Human Metapneumovirus Vaccine Is Immunogenic and Protective in Mice and Cotton Rats. J Virol. Nov. 2008; 82(22): 11410-11418.
Muller, M.R. et al., Transfection of dendritic cells with RNA induces CD4- and COB-mediated T cell immunity against breast carcinomas and reveals the immunodominance of presented T cell epitopes. J Immunol. Jun. 15, 2003;170(12):5892-6.
Narayanan et al., Interplay between viruses and host mRNA degradation. Biochim Biophys Acta. Jun.-Jul. 2013;1829(6-7):732-41. doi: 10.1016/j.bbagrm.2012.12.003. Epub Dec. 26, 2012.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Pascolo, S. Vaccination with messenger RNA (mRNA). Handb Exp Pharmacol. 2008; 183:221-235.
Petition for Inter Partes Review of U.S. Pat. No. 10,702,600. *BioNTech SE and Pfizer Inc.* (Petitioners) v. *ModernaTX, Inc.* (Patent Owner). Filed Aug. 28, 2023. 87 pages.
Petition for Inter Partes Review of U.S. Pat. No. 10,933,127. *BioNTech SE and Pfizer Inc.* (Petitioners) v. *ModernaTX, Inc.* (Patent Owner). Filed Aug. 28, 2023. 89 pages.
Petition for Inter Partes Review of U.S. Pat. No. 8,058,069 (IPR2019-00554). *Moderna Therapeutics, Inc.* (Petitioner) v. *Arbutus Biopharma Corporation* (Patent Owner). Filed Nov. 15, 2011. 81 pages.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Mesenger RNA (mRNA) nanoparticle tumour vaccination. Nanoscale. Jul. 22, 2014;6(14):7715-29. dsoi: 10.1039/c4nr01346h. Review.
*Promosome, LLC* v. *Moderna, Inc.* (S.D. Cal. 23-cv-1047-JES-DDL) D.I. 1—Complaint for Patent Infringement, Jun. 6, 2023. 51 pages.
*Promosome, LLC* v. *Moderna, Inc.* (S.D. Cal. 23-cv-1047-JES-DDL) D.I. 30—Notice of Dismissal, Sep. 19, 2023. 4 pages.
Pulford, B., et al., Liposome-siRNA-peptide complexes cross the blood-brain barrier and significantly decrease PrP'C on neuronal cells and PrP'RES in infected cell cultures. PLoS One. 201 O; 5(6): e11085.
Rabinovich, P.M., et al., Synthetic messenger RNA as a tool for gene therapy. Hum. Gene Ther. Oct. 2006; 17: 1027-1035.
Ramamoorth et al., Nonviral vectors in gene therapy- an overview. J Clin Diagn Res. Jan. 2015; 9(1): GE01-GE06.
Reichmuth et al., mRNA Vaccine Delivery Using Lipid Nanoparticles. Ther Deliv. 2016;7(5):319-34. doi: 10.4155/tde-2016-0006.
Ren et al., Recent vaccine development for human metapneumovirus. J Gen Virol. Jul. 2015;96(Pt 7):1515-20. doi: 10.1099/vir.0.000083. Epub Feb. 9, 2015.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Schlake et al., Developing mRNA-vaccine technologies. RNA Biol. Nov. 2012;9(11):1319-30. doi: 10.4161/rna.22269. Epub Oct. 12, 2012.
Schmitt, W.E. et al., In vitro induction of a bladder cancer-specific T-cell response by mRNA-transfected dendritic cells. J Cancer Res Clin Oncol. 2001 ;127(3):203-6.
Schott, J.W., et al., Viral and non-viral approaches for transient delivery of mRNA and proteins. Current Gene Ther. 2011; 11 (5): 382-398.
Segura, J., et al., Monitoring gene therapy by external imaging of mRNA: Pilot study on murine erythropoietin. Ther Drug Monit. Oct. 2007; 29(5): 612-8.
Shin et al., Recent Advances in RNA Therapeutics and RNA Delivery Systems Based on Nanoparticles. Adv. Therap., Nov. 2018;1(7):1800065. Review.

(56) References Cited

OTHER PUBLICATIONS

Smits, E., et al., RNA-based gene transfer for adult stem cells and T cells. Leukemia. 2004; 18:1898-1902.
Sohn, R.L., et al., In-vivo particle mediated delivery of mRNA to mammalian tissues: ballistic and biological effects. Wound Rep and Regen. Jul.-Aug. 2001; 287-296.
Strong, V.T. et al., Incorporation of beta-globin untranslated regions into a Sindbis virus vector for augmentation of heterologous mRNA expression. Gene Ther. Jun. 1997;4(6):624-7.
Sullenger, BA et al., Emerging clinical applications of RNA. Nature. Jul. 11, 2002;418(6894):252-8.
Tam et al., Advances in Lipid Nanoparticles for siRNA Delivery. Pharmaceutics. Sep. 18, 2013;5(3):498-507. doi: 10.3390/pharmaceutics5030498.
Tavernier, G., et al., mRNA as gene therapeutic: How to control protein expression. J. of Controlled Release. Mar. 2011; 150(3): 238-247.
Tenchov et al., Lipid Nanoparticles—From Liposomes to mRNA Vaccine Delivery, a Landscape of Research Diversity and Advancement. ACS Nano. Nov. 23, 2021;15(11):16982-17015. doi: 10.1021/acsnano.1c04996. Epub Jun. 28, 2021.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
To et al., An overview of rational design of mRNA-based therapeutics and vaccines. Expert Opin Drug Discov. Nov. 2021; 16(11):1307-1317. doi: 10.1080/17460441.2021.1935859. Epub Jul. 19, 2021.
Ulmer et al., RNA-based vaccines. Vaccine. Jun. 22, 2012;30(30):4414-8. doi: 10.1016/j.vaccine.2012.04.060. Epub Apr. 28, 2012.
Wang et al., Delivery of oligonucleotides with lipid nanoparticles. Adv Drug Deliv Rev. Jun. 29, 2015;87:68-80. doi: 10.1016/j.addr.2015.02.007. Epub Feb. 27, 2015.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weissman, mRNA transcript therapy. Expert Rev Vaccines. Feb. 2015;14(2):265-81. doi: 10.1586/14760584.2015.973859. Epub Oct. 31, 2014.
Wen et al., New Approaches for Immunization and Therapy against Human Metapneumovirus. Clin Vaccine Immunol. Aug. 2015;22(8):858-66. doi: 10.1128/CVI.00230-15. Epub Jun. 10, 2015.
Williams et al., Human metapneumovirus isolate TN/92-4 fusion protein gene, complete eds. GenBank: EF051124.1. Nov. 29, 2007.
Wong et al., An mRNA vaccine for influenza. Nat Biotechnol. Dec. 2012;30(12):1202-4. doi: 10.1038/nbt.2439.
Yamamoto et al., Current prospects for mRNA gene delivery, European Journal of Pharmaceutics and Biopharmaceutics 71 (2009) 484-489.
Youn et al., Modified mRNA as an alternative to plasmid DNA (pDNA) for transcript replacement and vaccination therapy. Expert Opin Biol Ther. 2015;15(9):1337-48. doi: 10.1517/14712598.2015.1057563. Epub Jun. 30, 2015.
Yuan et al., Cryo-EM structures of MERS-CoV and SARS-CoV spike glycoproteins reveal the dynamic receptor binding domains. Nat Commun. Apr. 10, 2017;8:15092. doi: 10.1038/ncomms15092.
Zeng et al., Formulation and Delivery Technologies for mRNA Vaccines. Curr Top Microbiol Immunol. Jun. 2, 2020;10.1007/82_2020_217. doi: 10.1007/82_2020_217.
Zhao et al., Chapter Two: Lipid Nanoparticles for Gene Delivery. Book: Advances in Genetics. Elsevier, 2014. 24 pages.
Zhao et al., Nanoparticle vaccines. Vaccine. Jan. 9, 2014;32(3):327-37. doi: 10.1016/j.vaccine.2013.11.069. Epub Dec. 2, 2013.
Zhou, W.Z. et al., RNA melanoma vaccine: induction of antitumor immunity by human glycoprotein 100 mRNA immunization. Hum Gene Ther. Nov. 1, 1999;10(16):2719-24.
Zumla et al., Middle East respiratory syndrome. Lancet. Sep. 5, 2015;386(9997):995-1007. doi: 10.1016/S0140-6736(15)60454-8. Epub Jun. 3, 2015.
[No Author Listed] fusion glycoprotein F0 [Human respirovirus 3]. GenBank Accession No. AHX22069. First seen on NCBI on May 14, 2014. 2 pages.
[No Author Listed] Lineage list. Last accessed Oct. 17, 2023 at https://cov-lineages.org/lineage_list.html. 77 pages.
[No Author Listed], "Messenger RNA" definition. Collins Dictionary of Science. 2005:514.
[No Author Listed], "Messenger RNA" definition. The Penguin Dictionary of Science. 2009: 3 pages.
[No Author Listed], "Messenger RNA" definition. Webster's New World Medical Dictionary. 2008;3:271.
[No Author Listed], 1st International mRNA Health Conference Programme. Universitat Tubingen. Oct. 23-24, 2013: 32 pages.
[No Author Listed], 2022 Breakthrough Prize in Life Sciences Awarded to Penn Medicine mRNA Pioneers Drew Weissman and Katalin Kariko. Press Release. Sep. 9, 2021: 3 pages.
[No Author Listed], 3rd International mRNA Health Conference Program. mRNA Conference. Nov. 11, 2015: 28 pages.
[No Author Listed], A Phase 3, Randomized, Stratified, Observer-Blind, Placebo-Controlled Study to Evaluate the Efficacy, Safety, and Immunogenicity of mRNA-1273 SARS- CoV-2 Vaccine in Adults Aged 18 Years and Older. ModernaTX, Inc. Protocol mRNA-1273-P301, Amendment 3. Aug. 20, 2020. 135 pages.
[No Author Listed], An Audience with Moncef Slaoui. Nat Rev Drug Discov Jul. 1, 2015;14:452-453. https://doi.org/10.1038/nrd4669.
[No Author Listed], Background document on the mRNA-1273 vaccine (Moderna) against COVID-19. World Health Organization. Feb. 3, 2021. Accessed from <https://www.who.int/publications/i/item/background-document-on-the-mrna-1273-vaccine-(moderna)-against-covid-19>. 41 pages.
[No Author Listed], BioNTech Expands Clinical Oncology Portfolio with First Patient Dosed in Phase 2 Trial of mRNA-based Individualized Immunotherapy BNT122 in Colorectal Cancer Patients. Press Release. BioNTech. Oct. 1, 2021: 2 pages.
[No Author Listed], BioNTech Fourth Quarter and Full-Year 2019 Results. BioNTech. Mar. 3, 20201: 15 pages.
[No Author Listed], BioNTech SE Annual Report (Form 20-F) 179, F-12. United States Securities and Exchange Commission. Mar. 30, 2021: 739 pages.
[No Author Listed], BioNTech SE Annual Report (Form 20-F) 81. United States Securities and Exchange Commission. Mar. 30, 2022: 700 pages.
[No Author Listed], BioNTech Signs Collaboration Agreement with Pfizer to Develop mRNA-based Vaccines for Prevention of Influenza. Press Release. Aug. 16, 2018: 3 pages.
[No Author Listed], BNT162 COVID-19 Vaccine Program Update. BioNTech. Apr. 23, 2020: 15 pages.
[No Author Listed], Canada Exercises Increased Option for 20 Million Doses of mRNA Vaccine Against COVID-19 (mRNA-1273). Moderna Press Release. Sep. 22, 2020. 2 pages.
[No Author Listed], Cdc. SARS-CoV-2 Variant Classifications and Definitions. https://www.cdc.gov/coronavirus/2019-ncov/variants/variant-classifications.html. Updated Sep. 1, 2023. 5 pages.
[No Author Listed], Center for Drug Evaluation and Research Approval Package for New Drug Application No. 50-718/S-50 for Doxil®. Approved Dec. 28, 2015. 97 pages.
[No Author Listed], Comirnaty (mRNA-1273) EMA SmPC (summary of product characteristics);. Published Dec. 1, 2021. 276 pages.
[No. Author Listed], Comirnaty Dosing Schedule for People 12 Years of Age & Older (2023-2024 Formula). Oct. 2023: 2 pages.
[No. Author Listed], Comirnaty Prescribing Information. Jul. 2022: 27 pages.

(56) References Cited

OTHER PUBLICATIONS

[No. Author Listed], Comirnaty Prescribing Information. COMIRNATY. Oct. 2023: 36 pages.
[No. Author Listed], Coronavirus (COVID-19) Update: FDA Authorizes Changes to Simplify Use of Bivalent mRNA COVID-19 Vaccines. FDA News Release. Apr. 1, 20238: 3 pages.
[No. Author Listed], Coronavirus (COVID-19) Update: FDA Issues Policies to Guide Medical Product Developers Addressing Virus Variants. FDA News Release. Feb. 22, 2021. 5 pages.
[No. Author Listed], Could COVID-19 vaccines be tweaked to cover new coronavirus variants? I Gavi, the Vaccine Alliance. Published Jan. 14, 2021. URL:https://www.gavi.org/vaccineswork/could-covid-19-vaccines-be-tweaked-cover-new-c oronavirus-variants: Last accessed Apr. 26, 2022. 5 Pages.
[No. Author Listed], COVID-19 Vaccine Development Program. Pfizer. Jul. 1, 2020: 18 pages.
[No. Author Listed], Darpa Awards Moderna Therapeutics a Grant for up to $25 Million to Develop Messenger RNA Therapeutics. News Release. Moderna. Oct. 2, 2013: 1 page.
[No. Author Listed], Delivery means to avoid degradation of RNA preparations: Lipid nanoparticles (LNPs) for RNA delivery. CosmoBio. English-Language Machine Translation. Retrieved from the Internet: https://www.cosmobio.co.jp/product/detail/lipid-nanoparticles-for- rna-delivery-ecl.asp?entry_id=43081. Last Accessed: Oct. 23, 2023. 10 pages.
[No. Author Listed], Dosing Schedule for Ages 12 Years of Age and Older with Pfizer- BioNTech COVID-19 Vaccine, Bivalent (Original and Omicron BA.4/BA.5). Apr. 2023:7-9.
[No. Author Listed], European Commission Authorizes COVID 19 Vaccine Moderna in Europe. Jan. 6, 2021. Accessed from <https://www.drugs.com/clinical_trials/european- commission-authorizes-covid-19-vaccine-moderna-europe-19152.html>. 4 pages.
[No. Author Listed], Experimental COVID-19 Vaccine Protects Upper and Lower Airways in Nonhuman Primates. NIH News Release. Jul. 28, 2020. 4 pages.
[No. Author Listed], Experimental COVID-19 Vaccine Safe, Generates Immune Response. NIH News Release. Jul. 14, 2020. 4 pages.
[No. Author Listed], Fact Sheet for Healthcare Providers Administering Vaccine: Emergency Use Authorization of Pfizer-BioNTech COVID-19 Vaccine (2023-2024 Formula) for 6 Months through 11 Years of Age. Pfizer-BioNTech. 2023 Sept: 59 pages.
[No. Author Listed], Goldman Sachs Virtual 41st Annual Global Healthcare Conference. Pfizer Inc. Jun. 9, 2020: 13 pages.
[No Author Listed], History of Changes for Study: NCT04283461, Safety and Immunogenicity Study of 2019-nCoV Vaccine (mRNA-1273) for Prophylaxis of SARS-CoV-2 Infection (COVID-19). Version submitted Dec. 8, 2022. 8 pages.
[No Author Listed], History of Changes for Study: NCT04283461, Safety and Immunogenicity Study of 2019-nCoV Vaccine (mRNA-1273) for Prophylaxis of SARS-CoV-2 Infection (COVID-19). Version submitted Mar. 11, 2021. 10 pages.
[No Author Listed], History of Changes for Study: NCT04405076, Dose-Confirmation Study to Evaluate the Safety, Reactogenicity, and Immunogenicity of mRNA-1273 COVID-19 Vaccine in Adults Aged 18 Years and Older. Version submitted Dec. 6, 2022. 6 pages.
[No Author Listed], Increase in Manufacturing Capacity for COVID-19 Vaccines from Janssen, Moderna, and BioNTech/Pfizer. European Medicines Agency. Dec. 16, 2021: 4 pages.
[No Author Listed], Influenza A virus A/Jiangxi/IPB13/2013(H10N8) hemagglutinin protein. UniProtKB Accession: A0A059T4A1. Sep. 3, 2014. 1 page.
[No Author Listed], Katalin Kariko and Drew Weissman Awarded Horwitz Prize for Pioneering Research on COVID-19 Vaccines. Columbia University. Aug. 16, 2021: 12 pages.
[No Author Listed], Katalin Kariko Laureate de la Grande Medaille 2021 de L'Academie des Sciences. Press Release. De L'Academie des Sciences. Sep. 28, 2021: 2 pages.
[No Author Listed], Messenger RNA Pioneer Katalin Kariko Receives European Inventor Award 2022 for Lifetime Achievement. Press Release. European Patent Office. Jun. 21, 2022: 4 pages.
[No Author Listed], Moderna Advances Late-Stage Development of its Vaccine (mRNA-1273) Against COVID-19. Moderna Press Release. Jun. 11, 2020. 3 pages.
[No Author Listed], Moderna and Lonza Announce Worldwide Strategic Collaboration to Manufacture Moderna's Vaccine (mRNA-1273) Against Novel Coronavirus. Moderna Press Release. May 1, 2020. 3 pages.
[No Author Listed], Moderna Announces Award from U.S. Government Agency BARDA for up to $483 Million to Accelerate Development of mRNA Vaccine (mRNA-1273) Against Novel Coronavirus. Moderna Press Release. Apr. 16, 2020. 3 pages.
[No Author Listed], Moderna Announces Expansion of BARDA Agreement to Support Larger Phase 3 Program forVaccine (mRNA-1273) Against COVID-19. Moderna Press Release. Jul. 26, 2020. 3 pages.
[No Author Listed], Moderna Announces FDA Authorization of Moderna COVID 19 Vaccine in U.S. Press Release. Dec. 19, 2020. 3 pages.
[No Author Listed], Moderna Announces First Participant Dosed in NIH-led Phase 1 Study of mRNA Vaccine (mRNA-1273) Against Novel Coronavirus. Moderna Press Release. Mar. 16, 2020. 2 pages.
[No Author Listed], Moderna Announces First Participant Dosed in Phase 2 Study of Omicron-Specific Booster Candidate and Publication of Data on Booster Durability Against Omicron Variant. News Release. Moderna. Jan. 26, 2022: 4 pages.
[No Author Listed], Moderna Announces First Participant Dosed in Phase 2 Study of Omicron-Specific Booster Candidate. News Release. Mar. 10, 2022: 3 pages.
[No Author Listed], Moderna Announces First Participants in Each Age Cohort Dosed in Phase 2 Study of mRNA Vaccine (mRNA-1273) Against Novel Coronavirus. Moderna Press Release. May 29, 2020. 2 pages.
[No Author Listed], Moderna Announces Funding Award from CEPI to Accelerate Development of Messenger RNA (mRNA) Vaccine Against Novel Coronavirus. News Release, Moderna. Jan. 23, 2020: 2 pages.
[No Author Listed], Moderna Announces IND Submitted to U.S. FDA for Phase 2 Study of mRNA Vaccine (mRNA-1273) Against Novel Coronavirus. Moderna Press Release. Apr. 27, 2020. 3 pages.
[No Author Listed], Moderna Announces it has Shipped Variant-Specific Vaccine Candidate, mRNA-1273.351, to NIH for Clinical Study. Moderna Press Release. Feb. 24, 2021. 3 pages.
[No Author Listed], Moderna Announces Phase 3 COVE Study of mRNA Vaccine Against COVID-19 (mRNA-1273) Begins. Moderna Press Release. Jul. 27, 2020. 3 pages.
[No Author Listed], Moderna Announces Positive Interim Phase 1 Data for its mRNA Vaccine (mRNA-1273) Against Novel Coronavirus. Moderna Press Release. May 18, 2020. 3 pages.
[No Author Listed], Moderna Announces Progress Across Broad Portfolio and all Three Clinical Stage Therapeutic Areas at 2020 R&D Day. Moderna Press Release. Sep. 17, 2020. 4 pages.
[No Author Listed], Moderna Announces Publication in The New England Journal of Medicine of Interim Results From Phase 1 Study of Its mRNA Vaccine Against COVID-19 (mRNA-1273). Moderna Press Release. Jul. 14, 2020. 5 pages.
[No Author Listed], Moderna Announces Publication in The New England Journal of Medicine of Non-Human Primate Preclinical Viral Challenge Study of its mRNA Vaccine Against COVID-19 (mRNA-1273). Moderna Press Release. Jul. 28, 2020. 3 pages.
[No Author Listed], Moderna Announces Strategy to Address Omicron (B.1.1.529) SARS-CoV-2 Variant. Press Release. Moderna. Nov. 26, 2021: 2 pages.
[No Author Listed], Moderna Announces Supply Agreement with U.S. Government for Initial 100 Million Doses of mRNA Vaccine Against COVID-19 (mRNA-1273). Moderna Press Release. Aug. 11, 2020. 3 pages.
[No Author Listed], Moderna Completes Enrollment of Phase 2 Study of its mRNA Vaccine Against COVID-19 (mRNA-1273). Moderna Press Release. Jul. 8, 2020. 2 pages.

(56) References Cited

OTHER PUBLICATIONS

[No Author Listed], Moderna Confirms Advanced Discussions with European Commission to Supply Europe with 80 Million Doses of mRNA Vaccine Against COVID-19 (mRNA-1273). Moderna Press Release. Aug. 24, 2020. 3 pages.
[No Author Listed], Moderna Confirms Discussions with the Ministry of Health, Labour and Welfare to Supply Japan with 40 Million Doses of mRNA Vaccine Against COVID-19 (mRNA-1273). Moderna Press Release. Aug. 28, 2020. 2 pages.
[No Author Listed], Moderna has No. plans to share its COVID-19 vaccine recipe. Associated Press. Oct. 11, 2021:8 pages.
[No Author Listed], Moderna Inc to Discuss Updates on Respiratory Syncytial Virus (RSV) Vaccine Program Call. Edited Transcript. Refinitiv. Oct. 8, 2020: 14 pages.
[No Author Listed], Moderna Patents. https://www.modernatx.com/en-US/patents [last accessed Jul. 1, 2024].
[No Author Listed], Moderna Provides Business Update and Announces Three New Development Programs in Infectious Disease Vaccines. Press Release. Jan. 11, 2021. 5 pages.
[No Author Listed], Moderna Receives FDA Authorization for Emergency Use of Omicron-Targeting Bivalent COVID-19 Booster Vaccine for Adults 18 Years and Older. News Release. Moderna. Aug. 31, 2022: 5 pages.
[No Author Listed], Moderna Receives FDA Fast Track Designation for mRNA Vaccine (mRNA-1273) Against Novel Coronavirus. Moderna Press Release. May 12, 2020. 2 pages.
[No Author Listed], Moderna Reports Fourth Quarter and Fiscal Year 2020 Financial Results and Provides Business Updates. Press Release. Feb. 25, 2021. 9 pages.
[No Author Listed], Moderna Ships mRNA Vaccine Against Novel Coronavirus (mRNA-1273) for Phase 1 Study. Moderna Press Release. Feb. 24, 2020. 2 pages.
[No Author Listed], Moderna's COVID-19 Vaccine Candidate Meets its Primary Efficacy Endpoint in the First Interim Analysis of the Phase 3 COVE Study. Press Release. Nov. 16, 2020. 3 pages.
[No Author Listed], Moderna's Update Patent Pledge. Press Release. Moderna. Mar. 7, 2022: 2 pages.
[No Author Listed], Modified mRNA Vaccines. 2021 Lasker-DeBakey Clinical Medicial Research Award. 17 pages.
[No Author Listed], NIH Clinical Trial of Investigational Vaccine for COVID-19 begins. NIH News Release. Mar. 16, 2020. 3 pages.
[No Author Listed], NIH-Moderna Investigational COVID-19 Vaccine Shows Promise in Mouse Studies. NIH News Release. Aug. 5, 2020. 4 pages.
[No Author Listed], Penn mRNA Scientists Drew Weissman and Katalin Kariko Receive 2021 Lasker Award, America's Top Biomedical Research Prize. Penn News Release. Sep. 24, 2021: 6 pages.
[No Author Listed], Pfizer and BioNTech Announce Early Positive Data from an Ongoing Phase 1/2 Study of mRNA-based Vaccine Candidate against SARS-CoV-2. Press Release. Jul. 1, 2020: 8 pages.
[No Author Listed], Pfizer and BioNTech Announce Early Positive Update from German Phase 1/2 Study of COVID-19 Vaccine Study, Including First T Cell Response Data. Press Release. Jul. 20, 2020: 6 pages.
[No Author Listed], Pfizer and BioNTech Announce Phase 3 Trial Data Showing High Efficacy of a Booster Dose of Their COVID-19 Vaccine. Press Release. Pfizer. Oct. 21, 2021: 10 pages.
[No Author Listed], Pfizer and BioNTech Choose Lead mRNA Vaccine Candidate Against COVID-19 and Commence Pivotal Phase 2/3 Global Study. Press Release. Jul. 27, 2020: 7 pages.
[No Author Listed], Pfizer and BioNTech Granted FDA Emergency Use Authorization of Omicron BA.4/BA.5-Adapted Bivalent COVID-19 Vaccine Booster for Ages 12 Years and Older. Pfizer. Aug. 31, 2022: 12 pages.
[No Author Listed], Pfizer and BioNTech Receive Expanded U.S. Emergency Use Authorization for an Additional COVID-19 Vaccine Booster in Individuals Aged 50 Years and Older. Press Release. Pfizer. Mar. 29, 2022: 12 pages.
[No Author Listed], Pfizer and BioNTech Submit Applications to U.S. FDA for Omicron XBB.1.5-Adapted Monovalent COVID-19 Vaccine. Pfizer. Jun. 23, 2023: 8 pages.
[No Author Listed], Pfizer and BioNTech Submit Supplemental Biologics License Application for U.S. FDA Approval of Omicron BA.4/BA.5-Adapted Bivalent COVID-19 Vaccine for Ages 12 Years and Older as Primary Series or Booster. Pfizer. Feb. 24, 2023: 12 pages.
[No Author Listed], Pfizer Inc to discuss data from an ongoing phase 1/2 study of mRNA-based vaccine candidate against SARS_CoV-2 Call. Edited Transcript. Thomson Reuters. Jul. 1, 2020: 15 pages.
[No Author Listed], Pfizer reports fourth-quarter and full-year 2021 results. Pfizer. Feb. 8, 2022: 41 pages.
[No Author Listed], Pfizer-BioNTech COVID-19 Vaccine Information Sheet. 3 pages.
[No Author Listed], Phase 3 Clinical Trial of Investigational Vaccine for COVID-19 Begins. NIH News Release. Jul. 27, 2020. 3 pages.
[No Author Listed], Pioneering Scientists Awarded the Albany Prize, America's Most Distinguished Prize in Medicine, for Research Leading to Covid-19 Vaccines. The Albany Prize. Aug. 26, 2021: 4 pages.
[No Author Listed], Press release, Moderna, "Moderna Announces Publication in The New England Journal of Medicine of Interim Results From Older Adult Age Cohorts in Phase 1 Study of its mRNA Vaccine Against COVID-19 (mRNA-1273)", Sep. 29, 2020. 7 pages.
[No Author Listed], Programme of the 1st International mRNA Health Conference held in Germany, Oct. 2013, 32 pages.
[No Author Listed], Q2 2020 Earnings Call. BioNTech SE. Aug. 11, 2020:26 pages.
[No Author Listed], RBC capital Markets Global Healthcare Conference. Pfizer Inc. May 19, 2020: 9 pages.
[No Author Listed], Remarks by President Trump and Members of the Coronavirus Task Force in Meeting with Pharmaceutical Companies. The White House. Mar. 2, 2022: 31 pages.
[No Author Listed], SARS-CoV-2 variants of concern as of May 4, 2023. European Centre for Disease Prevention and Control. Last accessed May 16, 2023 at https://www.ecdc.europa.eu/en/covid-19/variants-concern. 7 pages.
[No Author Listed], Severe acute respiratory syndrome coronavirus 2 isolate Wuhan-Hu-1, complete genome. GenBank Accession No. 045512, published on Jul. 18, 2020. 15 pages.
[No Author Listed], Severe acute respiratory syndrome coronavirus 2 isolate Wuhan-Hu-1, complete genome. Genbank Accession No. MN908947.3. Jan. 13, 2020. 15 pages.
[No Author Listed], spike glycoprotein [Middle East respiratory syndrome coronavirus]. GenBank Accession No. AGN52936.1. Published Jun. 10, 2013. 2 pages.
[No Author Listed], Spike_Cvhsa. UniProt KB Accession No. P59594. Published Oct. 14, 2015. 1 page.
[No Author Listed], Spikevax (mRNA-1273) EMA SmPC (summary of product characteristics). Published Jan. 20, 2021. 137 pages.
[No Author Listed], Statement by Moderna on Intellectual Property Matters during the COVID-19 Pandemic. Press Release. Moderna. Oct. 8, 2020: 1 page.
[No Author Listed], Statement from NIH and BARDA on the FDA Emergency Use Authorization of the Moderna COVID-19 Vaccines. COVID.gov. Dec. 18, 2020: 3 pages.
[No Author Listed], Two Pioneering RNA Scientists Win the 2021 Dr. Paul Janssen Award for Biomedical Research. Press Release. Johnson & Johnson. Sep. 28, 2021: 2 pages.
[No Author Listed], Vaccine information fact sheet for recipients and caregivers about Comirnaty (COVID-19 Vaccine, mRNA) and the Pfizer-BioNTech COVID-19 vaccine to prevent coronavirus disease 2019 (COVID-19) for use in individuals 12 years of age and older. Jul. 8, 2022: 9 pages.
[No Author Listed], WHO Drug Information, vol. 35, No. 2, 2021, 341 pages.
[No Author Listed], WHO Drug Information. 2021;35(2):578-9.

(56) References Cited

OTHER PUBLICATIONS

[No Author Listed], World Health Organization. 2021. Classification of Omicron(B.1.1.529): SARS-CoV-2Variant of Concern. Nov. 26, 2021. 3 pages.
[No Author Listed]. Reflection paper on the regulatory requirements for vaccines intended to provide protection against variant strain(s) of SARS-CoV-2. European Medicines Agency. EMA/117973/2021. Feb. 23, 2021. 7 pages.
Abbasi, COVID-19 and mRNA Vaccines-First Large Test for a New Approach. JAMA. Sep. 22, 2020;324(12):1125-1127. doi: 10.1001/jama.2020.16866.
Adney et al., Efficacy of an Adjuvanted Middle East Respiratory Syndrome Coronavirus Spike Protein Vaccine in Dromedary Camels and Alpacas. Viruses. Mar. 2, 2019;11(3). pii: E212. doi: 10.3390/v11030212.
Ahmad et al., New multivalent cationic lipids reveal bell curve for transfection efficiency versus membrane charge density: lipid-DNA complexes for gene delivery. J Gene Med. Jun. 2005;7(6):739-48. doi: 10.1002/jgm.717.
Ahmed et al., Biochemistry, Lipids, Statpearls Publishing (2023) (https://www.ncbi.nlm.nih.gov/books/NBK525952/ [last accessed Aug. 24, 2023]: 5 pages.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Al Kahlout et al., Comparative Serological Study for the Prevalence of Anti-MERS Coronavirus Antibodies in High- and Low-Risk Groups in Qatar. J Immunol Res. Feb. 18, 2019;2019:1386740. doi: 10.1155/2019/1386740. eCollection 2019.
Altieri et al., The influence of 4-thiouridine labeling on pre-mRNA splicing outcomes. PLoS One. Dec. 13, 2021;16(12):e0257503. doi: 10.1371/journal.pone.0257503. eCollection 2021.
Anderson et al., Safety and Immunogenicity of SARS-CoV-2 mRNA-1273 Vaccine in Older Adults. N Engl J Med. Sep. 29, 2020;NEJMoa2028436: 1-12. doi: 10.1056/NEJMoa2028436.
Andries et al., N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44. doi: 10.1016/j.jconrel.2015.08.051. Epub Sep. 3, 2015.
Arthur, Pfizer predicts $54bn in 2022 revenue from Comirnaty and Paxlovid. BioPharmaReporter. Feb. 8, 2022: 2 pages.
Atsmon et al., Safety and immunogenicity of multimeric-001—a novel universal influenza vaccine. J Clin Immunol. Jun. 2012;32(3):595-603. doi: 10.1007/s10875-011-9632-5. Epub Feb. 9, 2012.
Baden et al., Efficacy and Safety of the mRNA-1273 SARS-CoV-2 Vaccine. N Engl J Med. Feb. 4, 2021;384(5):403-416. doi: 10.1056/NEJMoa2035389. Epub Dec. 30, 2020.
Bancel, Our Global Commitment to Vaccine Access. Moderna. Oct. 8, 2021: 1 page.
Bangham et al., Diffusion of univalent ions across the lamellae of swollen phospholipids. J Mol Biol. Aug. 1965; 13(1):238-52. doi: 10.1016/s0022-2836(65)80093-6.
Bear, Gene expression and regulation. In: Lewin's Cells. 2011. Cassimeris et al., Eds. Chapter 4:105-68.
Bennett et al., Cholesterol enhances cationic liposome-mediated DNA transfection of human respiratory epithelial cells. Biosci Rep. Feb. 1995;15(1):47-53. doi: 10.1007/BF01200214.
Bermudez, We decided not to enforce our patent during the pandemic: Noubar Afeyan, co-founder of Moderna. BBC News World. May 6, 2021: 11 pages.
Bharali et al., Nanoparticles and cancer therapy: a concise review with emphasis on dendrimers. Int J Nanomedicine. 2009;4:1-7. Epub Apr. 1, 2009.
Bhavana et al., COVID-19: Pathophysiology, treatment options, nanotechnology approaches, and research agenda to combating the SARS-CoV2 pandemic. Life Sci. Nov. 15, 2020;261:118336. doi: 10.1016/j.lfs.2020.118336. Epub Aug. 23, 2020.
Bourla, An Open Letter from Pfizer Chairman and CEO to Colleagues. Pfizer. May 7, 2021: 3 pages.
Bruxvoort et al., Real-world effectiveness of the mRNA-1273 vaccine against COVID-19: Interim results from a prospective observational cohort study. Lancet Reg Health Am. Feb. 2022:6:100134. doi: 10.1016/j.lana.2021.100134. Epub Nov. 25, 2021.
Buschmann et al, Nanomaterial Delivery Systems for mRNA Vaccines. Vaccines (Basel). Jan. 19, 2021;9(1):65. doi: 10.3390/vaccines9010065.
Callaway, Omicron likely to weaken COVID vaccine protection. Nature. Dec. 2021:600(7889):367-368. doi: 10.1038/d41586-021-03672-3.
Carvalho et al., The first 12 months of COVID-19: a timeline of immunological insights. Nat Rev Immunol. Apr. 2021;21(4):245-256. doi: 10.1038/s41577-021-00522-1. Epub Mar. 15, 2021.
Cele et al., SARS-CoV-2 Omicron has extensive but incomplete escape of Pfizer BNT162b2 elicited neutralization and requires ACE2 for infection. medRxiv. 2021 doi: 10.1101/2021.12.08.21267417. 2021.12.08.21267417. 15 pages.
Cerutti et al., Potent SARS-CoV-2 neutralizing antibodies directed against spike N-terminal domain target a single supersite. Cell Host Microbe. May 12, 2021;29(5):819-833.e7. doi: 10.1016/j.chom.2021.03.005. Epub Mar. 12, 2021.
Chan et al., Genomic characterization of the 2019 novel human-pathogenic coronavirus isolated from a patient with atypical pneumonia after visiting Wuhan. Emerg Microbes Infect. Jan. 28, 2020;9(1):221-236. doi: 10.1080/22221751.2020.1719902. eCollection 2020.
Chen et al., A novel neutralizing monoclonal antibody targeting the N-terminal domain of the MERS-CoV spike protein. Emerg Microbes Infect. Jun. 28, 2017;6(6):e60. doi: 10.1038/emi.2017.50. Erratum for: Emerg Microbes Infect. May 24, 2017;6(5):e37.
Chen et al., Emerging coronaviruses: Genome structure, replication, and pathogenesis. J Med Virol. Apr. 2020;92(4):418-423. doi: 10.1002/jmv.25681. Epub Feb. 7, 2020. Erratum in: J Med Virol. Oct. 2020;92(10):2249.
Chen et al., Vaccine design of hemagglutinin glycoprotein against influenza. Trends Biotechnol. Sep. 2011;29(9):426-34. doi: 10.1016/j.tibtech.2011.04.007.
Cheng et al., Selective ORgan Targeting (SORT) nanoparticles for tissue specific mRNA delivery and CRISPR/Cas gene editing. Nat Nanotechnol. Apr. 2020; 15(4): 313-320.
Chi et al., A neutralizing human antibody binds to the N-terminal domain of the Spike protein of SARS-CoV-2. Science. Aug. 7, 2020;369(6504):650-655. doi: 10.1126/science.abc6952. Epub Jun. 22, 2020.
Choi et al., 2'-O-methylation in mRNA disrupts IRNA decoding during translation elongation. Nat Struct Mol Biol. Mar. 2018;25(3):208-216. doi: 10.1038/s41594-018-0030-z. Epub Feb. 19, 2018.
Choi et al., Safety and immunogenicity of SARS-CoV-2 variant mRNA vaccine boosters in healthy adults: an interim analysis. Nat Med. Nov. 2021:27(11):2025-2031. doi: 10.1038/s41591-021-01527-y. Epub Sep. 15, 2021.
Choi et al., Serum Neutralizing Activity of mRNA-1273 against SARS-CoV-2 Variants, J Virol. Nov. 9, 2021;95(23):e0131321. doi: 10.1128/JVI.01313-21. Epub Sep. 22, 2021.
Chu et al., Immune Memory Response After a Booster Injection of mRNA-1273 for Severe Acute Respiratory Syndrome Coronavirus-2 (SARS-CoV-2). 2021 MedRxiv doi: https://doi.org/10.1101/2021.09.29.21264089. 52 pages.
Cohen, New crop of mRNA vaccines aim for accessibility. Science. Apr. 8, 2022;376(6589):120-121. doi: 10.1126/science.abq3935. Epub Apr. 7, 2022.
Cohen, Scientists are moving at record speed to create new coronavirus vaccines—but they may come too late. Science Insider. Jan. 27, 2020. 6 pages.
Cohen, Scientists question Moderna invention claim in COVID-19 vaccine dispute. Science Insider. Aug. 29, 2022: 3 pages.
Cooper et al., Chapters 1, 7, and 8 in The Cell: A Molecular Approach, 5th Ed. (2009), 163 pages.
Corbett et al., Evaluation of the mRNA-1273 Vaccine against SARS-CoV-2 in Nonhuman Primates. N Engl J Med 2020; 383:1544-55. doi: 10.1056/NEJMoa2024671.

(56) References Cited

OTHER PUBLICATIONS

Corbett et al., SARS-CoV-2 mRNA vaccine design enabled by prototype pathogen preparedness. Nature. Oct. 2020;586(7830):567-571. doi: 10.1038/s41586-020-2622-0. Epub Aug. 5, 2020.
Cox et al., FluBlok, a recombinant hemagglutinin influenza vaccine. Influenza Other Respir Viruses. Nov. 2008; 2(6): 211-219.
Dai et al., Viral targets for vaccines against COVID-19. Nat Rev Immunol. Feb. 2021;21(2):73-82. doi: 10.1038/s41577-020-00480-0. Epub Dec. 18, 2020.
Defrancesco, The 'anti-hype' vaccine. Nat Biotechnol. Mar. 2017;35(3):193-197. doi: 10.1038/nbt.3812. Epub Feb. 27, 2017.
Dejnirattisai et al., Reduced neutralisation of SARS-CoV-2 omicron B.1.1.529 variant by post-immunisation serum. Lancet. Jan. 15, 2022;399(10321):234-236. doi: 10.1016/S0140-6736(21)02844-0. Epub Dec. 20, 2021.
Dimitriadis et al., Translation of rabbit globin mRNA introduced by liposomes into mouse lymphocytes. Nature. Aug. 31, 1978;274(5674):923-4. doi: 10.1038/274923a0.
Dolgin, Business: The billion-dollar biotech. Nature. Jun. 4, 2015;522(7554):26-8. doi: 10.1038/522026a.
Dormitzer, Synthetic Vaccinology at Novartis, Presentation at The National Academy of Sciences Forum on Synthetic Biology. Oct. 21, 2013, The Keck Center, Washington, DC. 12 pages.
Dufourc, Sterols and membrane dynamics. J Chem Biol. Nov. 2008;1(1-4):63-77. doi: 10.1007/s12154-008-0010-6. Epub Sep. 23, 2008.
El Sahly et al., Efficacy of the mRNA-1273 SARS-CoV-2 Vaccine at Completion of Blinded Phase. N Engl J Med. Nov. 4, 2021; 385:1774-1785.
Ellebedy et al., Influenza Vaccines. Vaccine. Nov. 5, 2009; 27(Suppl 4): D65-D68.
Engler et al., Half- vs full-dose trivalent inactivated influenza vaccine (2004-2005): age, dose, and sex effects on immune responses. Arch Intern Med. Dec. 8, 2008;168(22):2405-14. doi: 10.1001/archinternmed.2008.513.
Erasmus et al., A Nanostructured Lipid Carrier for Delivery of a Replicating Viral RNA Provides Single, Low-Dose Protection against Zika. Mol Ther. Oct. 3, 2018;26(10):2507-2522. doi: 10.1016/j.ymthe.2018.07.010. Epub Aug. 2, 2018.
Escriou et al., Protection from SARS coronavirus conferred by live measles vaccine expressing the spike glycoprotein. Virology. Mar. 2014;452-453:32-41. doi: 10.1016/j.virol.2014.01.002. Epub Jan. 28, 2014.
Fauquet, Taxonomy, Classification and Nomenclature of Viruses. Encyclopedia of Virology. 2008:9-23. doi: 10.1016/B978-012374410-4.00509-4. Epub Jul. 30, 2008.
Fujimori, How this Once Little-Known Molecule is Disrupting Medicine. Pfizer. Jun. 2022: 7 pages.
Furuichi et al., Viral and cellular mRNA capping: past and prospects. Adv Virus Res. 2000;55:135-84. doi: 10.1016/s0065-3527(00)55003-9.
Gallie, D.R., The cap and poly(A) tail function synergistically to regulate mRNA translational efficiency. Genes Dev. Nov. 1991;5(11):2108-16.
Garde et al., The story of mRNA: How a once-dismissed idea became a leading technology in the Covid vaccine race. STAT News. Nov. 10, 2020: 23 pages.
Geall et al., Using self-amplifying mRNA vaccines to facilitate a rapid response to pandemic influenza. Eur Pharm Rev. Jul. 3, 2014; 3. 5 pages.
Guevara et al., Advances in Lipid Nanoparticles for mRNA-Based Cancer Immunotherapy. Front Chem. 2020; 8: 589959.
Guo et al., An Engineered Receptor-Binding Domain Improves the Immunogenicity of Multivalent SARS-CoV-2 Vaccines. mBio. May-Jun. 2021; 12(3): e00930-21.
Guo et al., Nanoparticles escaping RES and endosome: Challenges for siRNA delivery for cancer therapy. J Nanomat. Jan. 2011;742895:1-12.
Hashiba et al., The use of design of experiments with multiple responses to determine optimal formulations for in vivo hepatic mRNA delivery. J Control Release. Nov. 10, 2020;327:467-476. doi: 10.1016/j.jconrel.2020.08.031. Epub Aug. 25, 2020.
Hatziantoniou et al., Anaphylactic reactions to mRNA COVID-19 vaccines: A call for further study. Vaccine. May 6, 2021;39(19):2605-2607. doi: 10.1016/j.vaccine.2021.03.073. Epub Apr. 6, 2021. PMID: 33846043; PMCID: PMC8023205.
He et al., Receptor-binding domain of SARS-CoV spike protein induces highly potent neutralizing antibodies: implication for developing subunit vaccine. Biochem Biophys Res Commun. Nov. 12, 2004;324(2):773-81. doi: 10.1016/j.bbrc.2004.09.106.
He et al., Single-component, self-assembling, protein nanoparticles presenting the receptor binding domain and stabilized spike as SARS-CoV-2 vaccine candidates. Sci Adv. Mar. 19, 2021;7(12):eabf1591. doi: 10.1126/sciadv.abf1591. Print Mar. 2021.
Heinz et al., Distinguishing features of current COVID-19 vaccines: knowns and unknowns of antigen presentation and modes of action. NPJ Vaccines. Aug. 16, 2021;6(1):104. doi: 10.1038/s41541-021-00369-6.
Hemmer et al., Minimal peptide length requirements for CD4(+) T cell clones—implications for molecular mimicry and T cell survival. Int Immunol. Mar. 2000;12(3):375-83. doi: 10.1093/intimm/12.3.375.
Hoernes et al., Nucleotide modifications within bacterial messenger RNAs regulate their translation and are able to rewire the genetic code. Nucleic Acids Res. Jan. 29, 2016; 44(2): 852-862.
Hope et al., Reduction of Liposome Size and Preparation of Unilamellar Vesicles by Extrusion Techniques. In: Liposome Technology. 1993. Gregoriadis et al., Ed. vol. 1:123.
Houser et al., Influenza Vaccines: Challenges and Solutions. Cell Host Microbe. Mar. 11, 2015; 17(3): 295-300. doi: 10.1016/j.chom.2015.02.012.
Hsieh et al., Structure-based design of prefusion-stabilized SARS-CoV-2 spikes. Science. Sep. 18, 2020;369(6510):1501-1505. doi: 10.1126/science.abd0826. Epub Jul. 23, 2020.
Huang et al., Asymmetric 1-alkyl-2-acyl phosphatidylcholine: a helper lipid for enhanced non-viral gene delivery. Int J Pharm. May 1, 2012;427(1):64-70. doi: 10.1016/j.ijpharm.2011.06.022. Epub Jun. 21, 2011.
Huang et al., Clinical features of patients infected with 2019 novel coronavirus in Wuhan, China. Lancet. Jan. 24, 2020;395(10223)497-506.
Huang et al., Construction and biological characterisation of recombinant porcine circovirus type 2 expressing the V5 epitope tag. Virus Res. Nov. 2011;161(2):115-23. doi: 10.1016/j.virusres.2011.05.015. Epub May 27, 2011.
Jackson et al., An mRNA Vaccine against SARS-CoV-2—Preliminary Report. N Engl J Med. Jul. 14, 2020; NEJMoa2022483. doi: 10.1056/NEJMoa2022483. Online ahead of print.
Javier et al., Phylogenetic Analysis and Structural Modeling of SARS-CoV-2 Spike Protein Reveals an Evolutionary Distinct and Proteolytically Sensitive Activation Loop. J Mol Biol. May 1, 2020;432(10):3309-3325. doi: 10.1016/j.jmb.2020.04.009. Epub Apr. 19, 2020.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263.
Jiaming et al., The recombinant N-terminal domain of spike proteins is a potential vaccine against Middle East respiratory syndrome coronavirus (MERS-CoV) infection. Vaccine. Jan. 3, 2017;35(1):10-18. doi: 10.1016/j.vaccine.2016.11.064. Epub Nov. 26, 2016.
Jiang et al., The Variation of SARS-CoV-2 and Advanced Research on Current Vaccines. Front Med (Lausanne). Jan. 18, 2022:8:806641. doi: 10.3389/fmed.2021.806641. eCollection 2021.
Johanning et al., A Sindbis virus mRNA polynucleotide vector achieves prolonged and high level heterologous gene expression in vivo. Nucleic Acids Res. May 11, 1995; 23(9): 1495-1501.
Kanasty et al., Delivery materials for siRNA therapeutics. Nat Mater. Nov. 2013;12(11):967-77. doi: 10.1038/nmat3765.
Kariko et al., Generating the optimal mRNA for therapy: HPLC purification eliminates immune activation and improves translation of nucleoside-modified, protein-encoding mRNA. Nucleic Acids Res. Nov. 2011;39(21):e142. doi: 10.1093/nar/gkr695. Epub Sep. 2, 2011.

(56) References Cited

OTHER PUBLICATIONS

Kariko et al., Suppression of RNA recognition by Toll-like receptors: the impact of nucleoside modification and the evolutionary origin of RNA. Immunity. Aug. 2005:23(2):165-75. doi: 10.1016/j.immuni.2005.06.008.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Keegan, The Lasker Awards: A History of "America's Nobels". Cell Mentor. Sep. 11, 2018: 7 pages.
Khoury et al., Neutralizing antibody levels are highly predictive of immune protection from symptomatic SARS-CoV-2 infection. Nat Med. Jul. 2021;27(7):1205-1211. doi: 10.1038/s41591-021-01377-8. Epub May 17, 2021.
King et al., Virus Taxonomy: Classification and Nomenclature of Viruses. Ninth Report of the International Committee on Taxonomy of Viruses. Int Union of Microbiol Soc. 2012: 50 pages.
Kirchdoerfer et al., Stabilized coronavirus spikes are resistant to conformational changes induced by receptor recognition or protseolysis. Sci Rep. Oct. 24, 2018;8(1):15701. doi: 10.1038/s41598-018-34171-7.
Kolata, Kati Kariko Helped Shield the World from the Coronavirus. New York Times. Sep. 24, 2021: 5 pages.
Koyama et al., Analysis on Genie reveals novel recurrent variants that affect molecular diagnosis of sizable number of cancer patients. BMC Cancer. Feb. 1, 2019;19(1):114. doi: 10.1186/s12885-019-5313-1.
Koyama et al., Emergence of Drift Variants That May Affect COVID-19 Vaccine Development and Antibody Treatment. Pathogens. Apr. 26, 2020;9(5):324. doi: 10.3390/pathogens9050324.
Krammer et al., Chimeric hemagglutinin influenza virus vaccine constructs elicit broadly protective stalk-specific antibodies. J Virol. Jun. 2013;87(12):6542-50. doi: 10.1128/JVI.00641-13. Epub Apr. 10, 2013.
Kresge, The Messenger RNA Pioneers Everyone Ignored. Bloomberg. Nov. 2, 20213: 4 pages.
Kurimoto et al., PEG-OligoRNA Hybridization of mRNA for Developing Sterically Stable Lipid Nanoparticles toward In Vivo Administration. Molecules. Apr. 3, 2019;24(7): 1303.
Leung et al., Lipid nanoparticles for short interfering RNA delivery. Adv Genet. 2014;88:71-110. doi: 10.1016/B978-0-12-800148-6.00004-3.
Leuschner et al., Therapeutic siRNA silencing in inflammatory monocytes in mice. Nat Biotechnol. Oct. 9, 2011;29(11):1005-10. doi: 10.1038/nbt.1989.
Li et al., Application of ultra-high performance liquid chromatography for chemical characterization of liposome-based therapeutic small-interfering RNA, 13 American Pharmaceutical Review 102 (2010). 13 pages.
Li et al., Cell Attachment Domains of the Porcine Epidemic Diarrhea Virus Spike Protein Are Key Targets of Neutralizing Antibodies. J Virol. May 26, 2017;91(12):e00273-17. doi: 10.1128/JVI.00273-17. Print Jun. 15, 2017.
Li, Receptor recognition mechanisms of coronaviruses: a decade of structural studies. J Virol. Feb. 2015;89(4):1954-64. doi: 10.1128/JVI.02615-14. Epub Nov. 26, 2014.
Li, Structure, Function, and Evolution of Coronavirus Spike Proteins. Annu Rev Virol. Sep. 29, 2016;3(1):237-261. doi: 10.1146/annurev-virology-110615-042301. Epub Aug. 25, 2016.
Lin et al., Glycan Masking of Epitopes in the NTD and RBD of the Spike Protein Elicits Broadly Neutralizing Antibodies Against SARS-CoV-2 Variants. Front Immunol. Dec. 2, 2021:12:795741. doi: 10.3389/fimmu.2021.795741. eCollection 2021.
Lin et al., Three-dimensional imaging of lipid gene-carriers: membrane charge density controls universal transfection behavior in lamellar cationic liposome-DNA complexes. Biophys J. May 2003;84(5):3307-16. doi: 10.1016/S0006-3495(03)70055-1.
Liu et al., Chimeric severe acute respiratory syndrome coronavirus (Sars-CoV) S glycoprotein and influenza matrix 1 efficiently form virus-like particles (VLPs) that protect mice against challenge with SARS-CoV. Vaccine. Sep. 2, 2011;29(38):6606-13. doi: 10.1016/j.vaccine.2011.06.111. Epub Jul. 14, 2011.
Liu et al., Influence of polyethylene glycol density and surface lipid on pharmacokinetics and biodistribution of lipid-calcium-phosphate nanoparticles. Biomaterials. Mar. 2014;35(9):3027-34. doi: 10.1016/j.biomaterials.2013.12.022. Epub Jan. 2, 2014.
Liu et al., Potent neutralizing antibodies against multiple epitopes on SARS-CoV-2 spike. Nature. Aug. 2020:584(7821):450-456. doi: 10.1038/s41586-020-2571-7. Epub Jul. 22, 2020.
Loftus, Moderna Signals It May Enforce Covid-19 Vaccine Patents in Wealthy Nations. Wall Street Journal. Mar. 7, 2022. https://www.wsj.com/articles/moderna-signals-it-may-enforce-covid-19-vaccine-patents-in-wealthy-nations-11646699609 [last accessed Jul. 1, 2024].
Lu et al., Genomic characterisation and epidemiology of 2019 novel coronavirus: implications for virus origins and receptor binding. Lancet. Feb. 22, 2020;395(10224):565-574. doi: 10.1016/S0140-6736(20)30251-8. Epub Jan. 30, 2020.
Lutz et al., Unmodified mRNA in LNPs constitutes a competitive technology for prophylactic vaccines. NPJ Vaccines. Oct. 19, 2017:2:29. doi: 10.1038/s41541-017-0032-6. eCollection 2017.
Ma et al., Intranasal vaccination with recombinant receptor-binding domain of MERS-CoV spike protein induces much stronger local mucosal immune responses than subcutaneous immunization: Implication for designing novel mucosal MERS vaccines. Vaccine. Apr. 11, 2014;32(18):2100-8. doi: 10.1016/j.vaccine.2014.02.004. Epub Feb. 18, 2014.
Mandal et al., Reprogramming human fibroblasts to pluripotency using modified mRNA. Nat Protoc. Mar. 2013;8(3):568-82. doi: 10.1038/nprot.2013.019. Epub Feb. 21, 2013.
Martinez-Flores et al., SARS-CoV-2 Vaccines Based on the Spike Glycoprotein and Implications of New Viral Variants. Front Immunol. Jul. 12, 2021;12:701501. doi: 10.3389/fimmu.2021.701501. eCollection 2021.
Mccallum et al., N-terminal domain antigenic mapping reveals a site of vulnerability for SARS-CoV-2. Cell. Apr. 29, 2021; 184(9): 2332-2347.e16.
Mckay et al., Self-amplifying Rna SARS-CoV-2 lipid nanoparticle vaccine candidate induces high neutralizing antibody titers in mice. Nat Commun. Jul. 9, 2020;11(1):3523. doi: 10.1038/s41467-020-17409-9.
Mclellan et al., Structure and function of respiratory syncytial virus surface glycoproteins. Curr Top Microbiol Immunol. 2013;372:83-104. doi: 10.1007/978-3-642-38919-1_4.
Mendonca et al., Design of lipid-based nanoparticles for delivery of therapeutic nucleic acids. Drug Discov Today. Mar. 2023;28(3):103505. doi: 10.1016/j.drudis.2023.103505. Epub Jan. 25, 2023.
Miao et al., Delivery of mRNA vaccines with heterocyclic lipids increases anti-tumor efficacy by STING-mediated immune cell activation. Nat Biotechnol 37, 1174-1185 (2019). https://doi.org/10.1038/s41587-019-0247-3.
Modjarrad., Mers-CoV vaccine candidates in development: The current landscape. Vaccine. Jun. 3, 2016;34(26):2982-2987. doi: 10.1016/j.vaccine.2016.03.104. Epub Apr. 12, 2016.
Mullard, COVID-19 vaccine success enables a bolder vision for mRNA cancer vaccines, says BioNTech CEO. Nat Rev Drug Discov. Jul. 2021;20(7):500-501. doi: 10.1038/d41573-021-00110-x.
Mulligan et al., Phase I/II study of COVID-19 RNA vaccine BNT162b1 in adults. Nature. Oct. 2020;586(7830):589-593. doi: 10.1038/s41586-020-2639-4. Epub Aug. 12, 2020.
Murphy, Excerpts from Janeway's Immunobiology, 8th Ed. (2012). 250 pages.
Muthumani et al., A synthetic consensus anti-spike protein DNA vaccine induces protective immunity against Middle East respiratory syndrome coronavirus in nonhuman primates. Sci Transl Med. Aug. 19, 2015;7(301):301ra132. doi: 10.1126/scitranslmed.aac7462.
Nance et al.,Modifications in an Emergency: The Role of N1-Methylpseudouridine in COVID-19 Vaccines. ACS Cent Sci. May 26, 2021;7(5):748-756. doi: 10.1021/acscentsci.1c00197. Epub Apr. 6, 2021.
Oostvogels et al., Phase 1 Assessment of the Safety and Immunogenicity of an mRNA-Lipid Nanoparticle Vaccine Candidate Against

(56) References Cited

OTHER PUBLICATIONS

SARS-CoV-2 in Human Volunteers. medRxiv Nov. 9, 2020. 20228551;1-38. doi: https://doi.org/10.1101/2020.11.09.20228551.
Opposition against European Patent No. 3324979 B1, filed by BioNTech SE (Opponent) against Moderna TX, Inc. (Patentee) on Jul. 10, 2023. 86 pages.
Ostro et al., Evidence for translation of rabbit globin mRNA after liposome-mediated insertion into a human cell line. Nature. Aug. 31, 1978;274(5674):921-3. doi: 10.1038/274921a0.
Pallesen et al., Immunogenicity and structures of a rationally designed prefusion MERS-CoV spike antigen. Proc Natl Acad Sci U S A. Aug. 29, 2017;114(35):E7348-E7357. doi: 10.1073/pnas.1707304114. Epub Aug. 14, 2017.
Pardi et al., Nucleoside-modified mRNA vaccines induce potent T follicular helper and germinal center B cell responses. J Exp Med. Jun. 4, 2018;215(6):1571-1588. doi: 10.1084/jem.20171450. Epub May 8, 2018.
Pardi et al., Zika virus protection by a single low-dose nucleoside-modified mRNA vaccination. Nature. Mar. 9, 2017;543(7644):248-251. doi: 10.1038/nature21428. Epub Feb. 2, 2017.
Park et al., The Miracle Workers. Heroes of the Year. TIME Magazine. 2021: 17 pages.
Pascolo., Messenger RNA-based vaccines. Expert Opin Biol Ther. Aug. 2004;4(8):1285-94. doi: 10.1517/14712598.4.8.1285.
Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.
Pathak et al., Intra-host variability in global SARS-CoV-2 genomes as signatures of RNA editing: implications in viral and host response outcomes. bioRxiv Dec. 9, 2020; 2020.12.09.417519; doi: https://doi.org/10.1101/2020.12.09.417519. 32 pages.
Peabody et al., Termination-reinitiation occurs in the translation of mammalian cell mRNAs. Mol Cell Biol. Jul. 1986;6(7):2695-703. doi: 10.1128/mcb.6.7.2695-2703.1986.
Peek et al., Nanotechnology in vaccine delivery. Adv Drug Deliv Rev. May 22, 2008;60(8):915-28. doi: 10.1016/j.addr.2007.05.017. Epub Feb. 7, 2008.
Pegu et al., Durability of mRNA-1273 vaccine-induced antibodies against SARS-CoV-2 variants. Science. Sep. 17, 2021:373(6561):1372-1377. doi: 10.1126/science.abj4176. Epub Aug. 13, 2021.
Probst et al., Characterization of the ribonuclease activity on the skin surface. Genet Vaccines Ther. May 29, 2006;4:4. doi: 10.1186/1479-0556-4-4.
Pulliam et al., Increased risk of SARS-CoV-2 reinfection associated with emergence of the Omicron variant in South Africa. medRxiv 2021. doi:10.1101/2021.11.11.21266068:2021.11.11.21266068. 42 pages.
Raj et al., Dipeptidyl peptidase 4 is a functional receptor for the emerging human coronavirus—EMC. Nature. Mar. 14, 2013;495(7440):251-4. doi: 10.1038/nature12005.
Regalado, Don't panic about the latest coronavirus mutations say drug companies. MIT Technology Review. Dec. 23, 2020. 5 pages.
Regalado, Moderna believes it could update its coronavirus vaccine without a big new trial. MIT Technology Review. Jan. 13, 2021. 4 pages.
Robbins et al., Moderna Backs down in its Vaccine Patent Fight with the NIH. New York Times. Dec. 17, 2021: 1 page.
Rodriguez-Gascon et al., Development of nucleic acid vaccines: use of self-amplifying RNA in lipid nanoparticles. Int J Nanomedicine. 2014; 9: 1833-1843.
Rossi et al., IRES-based Venezuelan equine encephalitis vaccine candidate elicits protective immunity in mice. Virology. Mar. 15, 2013;437(2):81-8. doi: 10.1016/j.virol.2012.11.013. Epub Jan. 22, 2013.
Sahin et al., Personalized RNA mutanome vaccines mobilize poly-specific therapeutic immunity against cancer. Nature. Jul. 13, 2017;547(7662):222-226. doi: 10.1038/nature23003. Epub Jul. 5, 2017.
Salomon et al., A liposomal RNA vaccine inducing neoantigen-specific CD4+ T cells augments the antitumor activity of local radiotherapy in mice. Oncoimmunology. Jun. 22, 2020;9(1):1771925. doi: 10.1080/2162402X.2020.1771925.
Santoro et al., An efficient system for the evolution of aminoacyl-tRNA synthetase specificity. Nat Biotechnol. Oct. 2002;20(10):1044-8. doi: 10.1038/nbt742. Epub Sep. 16, 2002.
Sarkar et al., S glycoprotein diversity of the Omicron variant. medRxiv 2021. doi:10.1101/2021.12.04.21267284:2021.12.04.21267284. 30 pages.
Schoenmaker et al., mRNA-lipid nanoparticle COVID-19 vaccines: Structure and stability. Int J Pharm. May 15, 2021:601:120586. doi: 10.1016/j.ijpharm.2021.120586. Epub Apr. 9, 2021.
Schumann et al., Multiple links between 5-methylcytosine content of mRNA and translation. BMC Biol. Apr. 15, 2020;18(1):40. doi: 10.1186/s12915-020-00769-5.
Schuurhuis et al., Ins and outs of dendritic cells. Int Arch Allergy Immunol. 2006;140(1):53-72. doi: 10.1159/000092002. Epub Mar. 13, 2006.
Shidhadye et al., Solid lipid nanoparticles and nanostructured lipid carriers—innovative generations of solid lipid carriers. Curr Drug Deliv. Oct. 2008;5(4):324-31. doi: 10.2174/156720108785915087.
Shim et al. Intranasal immunization with plasmid DNA encoding spike protein of SARS-coronavirus/polyethylenimine nanoparticles elicits antigen-specific humoral and cellular immune responses. BMC Immunol. Dec. 31, 2010;11:65. doi: 10.1186/1471-2172-11-65.
Skidmore et al., Genomic Sequencing of SARS-CoV-2 E484K Variant B.1.243.1, Arizona, USA. Emerg Infect Dis. Oct. 2021;27(10):2718-2720. doi: 10.3201/eid2710.211189.
Stephenson et al., Cross-reactivity to highly pathogenic avian influenza H5N1 viruses after vaccination with nonadjuvanted and MF59-adjuvanted influenza A/Duck/Singapore/97 (H5N3) vaccine: a potential priming strategy. J Infect Dis. Apr. 15, 2005;191(8):1210-5. doi: 10.1086/428948. Epub Mar. 14, 2005.
Tegally et al., Emergence and rapid spread of a new severe acute respiratory syndrome-related coronavirus 2 (SARS-CoV-2) lineage with multiple spike mutations in South Africa. medRxIV. Dec. 22, 2020; Preprint: 19 pages. doi: 10.1101/2020.12.21.20248640. Epub Dec. 22, 2020.
Tews et al., Chapter 2: Self-Replicating RNA. RNA Vaccines. 2017; 1499: 15-35. Published online Jun. 11, 2016. doi: 10.1007/978-1-4939-6481-9_2.
Thery et al., The cell biology of antigen presentation in dendritic cells. Curr Opin Immunol. Feb. 2001; 13(1):45-51. doi: 10.1016/s0952-7915(00)00180-1.
Van Boheemen et al., Genomic characterization of a newly discovered coronavirus associated with acute respiratory distress syndrome in humans. mBio. Nov. 20, 2012;3(6):e00473-12. doi: 10.1128/mBio.00473-12.
Vardi et al., Moderna's Mysterious Medicines. Forbes. Dec. 14, 2016: 5 pages.
Vardi, Moderna's Mysterious Coronavirus Vaccine Delivery System. Forbes. Jul. 29, 2020: 9 pages.
Verma et al., Double-headed nucleosides: Synthesis and applications. Beilstein J Org Chem. Jun. 8, 2021;17:1392-1439. doi: 10.3762/bjoc.17.98. eCollection 2021.
Vogel et al., BNT162b vaccines protect rhesus macaques from SARS-CoV-2. Nature. Apr. 2021;592(7853):283-289. doi: 10.1038/s41586-021-03275-y. Epub Feb. 1, 2021.
Von Niessen et al., Improving mRNA-Based Therapeutic Gene Delivery by Expression-Augmenting 3' UTRs Identified by Cellular Library Screening. Mol Ther. Apr. 10, 2019;27(4):824-836. doi: 10.1016/j.ymthe.2018.12.011. Epub Dec. 18, 2018.
Walls et al., Crucial steps in the structure determination of a coronavirus spike glycoprotein using cryo-electron microscopy. Protein Sci. Jan. 2017;26(1):113-121. doi: 10.1002/pro.3048. Epub Oct. 18, 2016.
Walls et al., Tectonic conformational changes of a coronavirus spike glycoprotein promote membrane fusion. Proc Natl Acad Sci U S A. Oct. 17, 2017;114(42):11157-11162. doi: 10.1073/pnas.1708727114. Epub Oct. 3, 2017.

(56) References Cited

OTHER PUBLICATIONS

Walsh et al., Safety and Immunogenicity of Two RNA-Based Covid-19 Vaccine Candidates. N Engl J Med. Oct. 14, 2020;NEJMoa2027906: 1-13. doi: 10.1056/NEJMoa2027906. Online ahead of print.
Wang et al., An Evidence Based Perspective on mRNA-SARS-CoV-2 Vaccine Development. Med Sci Monit. May 5, 2020;26: e924700. doi: 10.12659/MSM.924700.
Wang et al., Antibody Resistance of SARS-CoV-2 Variants B.1.351 and B.1.1.7. bioRxiv [Preprint]. Feb. 12, 2021:2021.01.25.428137. doi: 10.1101/2021.01.25.428137. 24 pages. Update in: Nature. May 2021;593(7857):130-135.
Wang et al., Chapter 3: Lipid Nanoparticles for the Delivery of Nucleic Acids. Book: Nanoparticulate Drug Delivery Systems: Strategies, Technologies, and Applications. 2013. 29 pages.
Wang et al., Increased Resistance of SARS-CoV-2 Variants B.1.351 and B.1.1.7 to Antibody Neutralization. bioRxiv. Jan. 26, 2021; 23 pages. doi: 10.1101 /2021.01.25.428137. Preprint.
Wang et al., mRNA vaccine-elicited antibodies to SARS-CoV-2 and circulating variants. Nature. Apr. 2021;592(7855):616-622. doi: 10.1038/s41586-021-03324-6. Epub Feb. 10, 2021. PMID: 33567448; PMCID: PMC8503938.
Wang et al., Structural Definition of a Neutralization-sensitive Epitope on the Mers-CoV S1-NTD. Cell Rep. Sep. 24, 2019;28(13):3395-3405.e6. doi: 10.1016/j.celrep.2019.08.052.
Whitehead et al., Knocking down barriers: advances in siRNA delivery. Nat Rev Drug Discov. Feb. 2009;8(2):129-38. doi: 10.1038/nrd2742.
Whitt, Generation of VSV pseudotypes using recombinant ΔG-VSV for studies on virus entry, identification of entry inhibitors, and immune responses to vaccines. J Virol Methods. Nov. 2010;169(2):365-74. doi: 10.1016/j.jviromet.2010.08.006. Epub Aug. 13, 2010.
Wilhelm et al., Reduced Neutralization of SARS-CoV-2 Omicron Variant by Vaccine Sera and Monoclonal Antibodies. medRxiv. 2021. doi: 10.1101/2021.12.07.21267432:2021.12.07.21267432. 9 pages.
Wrapp et al., Cryo-EM structure of the 2019-nCoV spike in the prefusion conformation. Science. Feb. 19, 2020. pii: eabb2507. doi: 10.1126/science.abb2507.
Wu et al., A new coronavirus associated with human respiratory disease in China. Nature. Mar. 2020;579(7798):265-269. doi: 10.1038/s41586-020-2008-3. Epub Feb. 3, 2020.
Wu et al., mRNA-1273 vaccine induces neutralizing antibodies against spike mutants from global SARS-CoV-2 variants. bioRxiv preprint. Jan. 25, 2021. doi: 10.1101/2021.01.25.427948. 20 pages.
Wu et al., Serum Neutralizing Activity Elicited by mRNA-1273 Vaccine. N Engl J Med. Apr. 15, 2021;384(15):1468-1470. doi: 10.1056/NEJMc2102179. Epub Mar. 17, 2021.
Wu et al., Variant SARS-CoV-2 mRNA vaccines confer broad neutralization as primary or booster series in mice. Vaccine. Dec. 17, 2021;39(51):7394-7400.
Xia, Detailed Dissection and Critical Evaluation of the Pfizer/BioNTech and Moderna mRNA Vaccines. Vaccines (Basel). Jul. 3, 2021;9(7):734. doi: 10.3390/vaccines9070734.
Yang et al., A DNA vaccine induces SARS coronavirus neutralization and protective immunity in mice. Nature. Apr. 1, 2004;428(6982):561-4. doi: 10.1038/nature02463.
Yang et al., The structure and functions of coronavirus genomic 3' and 5' ends. Virus Res. Aug. 3, 2015;206:120-33. doi: 10.1016/j.virusres.2015.02.025. Epub Feb. 28, 2015.
Ye et al., Rational development of a combined mRNA vaccine against COVID-19 and influenza. NPJ Vaccines. Jul. 26, 2022;7(1):84. doi: 10.1038/s41541-022-00478-w.
Yin et al., Immunogenicity and protective efficacy of recombinant fusion proteins containing spike protein of infectious bronchitis virus and hemagglutinin of H3N2 influenza virus in chickens. Virus Res. Sep. 2, 2016;223:206-12. doi: 10.1016/j.virusres.2016.07.010. Epub Aug. 3, 2016.
Yin et al., Non-viral vectors for gene-based therapy. Nat Rev Genet. Aug. 2014;15(8):541-55. doi: 10.1038/nrg3763. Epub Jul. 15, 2014.
Zangi et al., Modified mRNA directs the fate of heart progenitor cells and induces vascular regeneration after myocardial infarction. Nat Biotechnol. Oct. 2013;31(10):898-907. doi: 10.1038/nbt.2682. Epub Sep. 8, 2013.
Zhang et al., A Thermostable mRNA Vaccine against COVID-19. Cell. Sep. 3, 2020;182(5):1271-1283.e16. doi: 10.1016/j.cell.2020.07.024. Epub Jul. 23, 2020.
Zhang et al., Delivery of mRNA vaccine with a lipid-like material potentiates antitumor efficacy through Toll-like receptor 4 signaling. Proc Natl Acad Sci U S A. Feb. 9, 2021;118(6):e2005191118. doi: 10.1073/pnas.2005191118.
Zhang et al., Prefusion spike protein stabilization through computational mutagenesis. Proteins. Apr. 2021:89(4):399-408. doi: 10.1002/prot.26025. Epub Dec. 4, 2020.
Zhao et al., Key Aspects of Coronavirus Avian Infectious Bronchitis Virus. Pathogens. May 11, 2023;12(5):698. doi: 10.3390/pathogens12050698.
Zhou et al., Evidence of escape of SARS-CoV-2 variant B.1.351 from natural and vaccine- induced sera. Cell. Apr. 29, 2021; 184(9): 2348-2361.e6.
Zhukovsky et al., Heterogeneity of early intermediates in cell-liposome fusion mediated by influenza hemagglutinin. Biophys J. Nov. 1, 2006;91(9):3349-58. doi: 10.1529/biophysj.106.088005. Epub Aug. 11, 2006.
Ziganshina et al., Antibody-Dependent Enhancement with a Focus on SARS-CoV-2 and Anti-Glycan Antibodies. Viruses. Jul. 20, 2023;15(7):1584. doi: 10.3390/v15071584.
"Final Written Decision" IPR2023-01358 dated Mar. 5, 2025.
"Final Written Decision" IPR2023-01359 dated Mar. 5, 2025.
'Heroes of Chemistry' recognized for contributions to health, medicine and more, American Chemical Society, pp. 1-2.
Alberer et al., "Safety and Immunogenicity of a mRNA Rabies Vaccine in Healthy Adults: an Open-label, Nonrandomised, Prospective, First-in-human Phase 1 Clinical Trial," 2017, The Lancet, pp. 1-10.
Berkeley Lovelace Jr. & Noah Higgins-Dunn, Dr. Anthony Fauci says chance of coronavirus vaccine being highly effective is 'not great', CNBC.com (last updated Aug. 8, 2020), https://www.cnbc.com/2020/08/07/coronavirus-vaccine-dr-fauci-says-chances-of-it-being-highly-effective-is-not-great.html.
Ernsting et al., "Factors controlling the pharmacokinetics, biodistribution and intratumoral penetration of nanoparticles. J Control Release," Dec. 28, 2013; 172(3):782-94. doi: 10.1016/j.jconrel.2013.09.013. Epub Sep. 25, 2013.
Fraiser Kansteiner, It's the end of the line for J&J's COVID shot in the US, CDC says, Fiercepharma (May 16, 2023).
Liu, Agnus, AstraZeneca withdraws US COVID vaccine application, shifts focus to antibody treatments, Fierce Pharma (Nov. 10, 2022).
Monika Kumari et al., A critical overview of current progress for COVID-19: development of vaccines, antiviral drugs, and therapeutic antibodies, J. Biomed Sci 29(68) (2022).
Prescribing Information for Comirnaty (Pfizer).
Prescribing Information for Spikevax (Moderna).
Press Release, Novavax, U.S. FDA Grants Emergency Use Authorization for Novavax COVID-19 Vaccine, Adjuvanted for Individuals Aged 18 and Over (Jul. 13, 2022).
Szebeni et al., "Activation of complement by therapeutic liposomes and other lipid excipient-based therapeutic products: prediction and prevention," 2011, Adv Drug Deliv Rev., Sep. 16;63(12):1020-30. doi: 10.1016/j.addr.2011.06.017. Epub Jul. 14, 2011.
Szebeni et al., "Complement activation as a bioequivalence issue relevant to the development of generic liposomes and other nanoparticulate drugs," Biochem Biophys Res Commun. Dec. 18, 2015;468(3):490-7. doi: 10.1016/j.bbrc.2015.06.177. Epub Jul. 14, 2015. PMID: 26182876.
Szebeni J. Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Walter et al., "Evaluation of the BNT162b2 COVID-19 Vaccine in Children 5 to 11 Years of Age," New England J. Med., 2022; 386: 35-46 (published online Nov. 9, 2021).

Day 0 serum titration
A450
Dilution Factor
PBS
10ug
2ug

Day 14 serum titration
A450
Dilution Factor
PBS
10ug
2ug

Day 35 serum titration
A450
Dilution Factor
PBS
10ug
2ug

Mouse IgG2a - hMPV F specific
A450
2.0
1.5
1.0
0.5
0.0
Day 0
Day 14
Day 28
Day 35
2ug Dose
10ug Dose
PBS Mouse IgG1 - hMPV F specific
A450
2.0
1.5
1.0
0.5
0.0
Day 0
Day 14
Day 28
Day 35
2ug Dose
10ug Dose
PBS IgG2a/IgG1
IgG2a/Th1
IgG1/Th2
>1.0
0.0
0.5
1.0
1.5
2.0
10ug Dose
2ug Dose IL10
pg/mL
800
600
400
200
0
PBS
10ug Dose
2ug Dose TNF-α
pg/mL
500
400
300
200
100
0
PBS
10ug Dose
2ug Dose
Media only
HMPV virus
Con-A IL4
pg/mL
400
300
200
100
0
PBS
10ug Dose
2ug Dose IL5
pg/mL
500
400
300
200
100
0
PBS
10ug Dose
2ug Dose IL6
pg/mL
6000
4000
2000
0
PBS
10ug Dose
2ug Dose

SEQUENCE LISTING

```
Sequence total quantity: 147
SEQ ID NO: 1            moltype = DNA  length = 1620
FEATURE                 Location/Qualifiers
source                  1..1620
                        mol_type = genomic DNA
                        organism = Human metapneumovirus
SEQUENCE: 1
atgagctgga aggtggtgat tatcttcagc ctgctgatta cacctcaaca cggcctgaag  60
gagagctacc tggaagagag ctgctccacc atcaccgagg gctacctgag cgtgctgcgg  120
accggctggt acaccaacgt gttcaccctg gaggtgggcg acgtggagaa cctgacctgc  180
agcgacggcc ctagcctgat caagaccgag ctggacctga ccaagagcgc tctgagagag  240
ctgaagaccg tgtccgccga ccagctggcc agagaggaac agatcgagaa ccctcggcag  300
agcagattcg tgctgggcgc catcgctctg ggagtcgccg ctgccgctgc agtgacagct  360
ggagtggcca ttgctaagac catcagactg gaaagcgagg tgacagccat caacaatgcc  420
ctgaagaaga ccaacgaggc cgtgagcacc ctgggcaatg gagtgagagt gctggccaca  480
gccgtgcggg agctgaagga cttcgtgagc aagaacctga ccagagccat caacaagaac  540
aagtgcgaca tcgatgacct gaagatggcc gtgagcttct cccagttcaa cagacggttc  600
ctgaacgtgg tgagacagtt ctccgacaac gctggaatca cacctgccat tagcctggac  660
ctgatgaccg acgccgagct ggctagagcc gtgcccaaca tgcccaccag cgctggccag  720
atcaagctga tgctggagaa cagagccatg gtgcggagaa agggcttcgg catcctgatt  780
ggggtgtatg gaagctccgt gatctacatg gtgcagctgc ccatcttcgg cgtgatcgac  840
acaccctgct ggatcgtgaa ggccgctcct agctgctccg agaagaaagg aaactatgcc  900
tgtctgctga gagaggacca gggctggtac tgccagaacg ccggaagcac agtgtactat  960
cccaacgaga aggactgcga gaccagaggc gaccacgtgt tctgcgacac cgctgccgga  1020
atcaacgtgg ccgagcagag caaggagtgc aacatcaaca tcagcacaac caactacccc  1080
tgcaaggtga gcaccggacg gcaccccatc agcatggtgg ctctgagccc tctgggcgct  1140
ctggtggcct gctataaggg cgtgtcctgt agcatcggca gcaatcgggt gggcatcatc  1200
aagcagctga acaagggatg ctcctacatc accaaccagg acgccgacac cgtgaccatc  1260
gacaacaccg tgtaccagct gagcaaggtg gagggcgagc agcacgtgat caagggcaga  1320
cccgtgagct ccagcttcga ccccatcaag ttccctgagg accagttcaa cgtggccctg  1380
gaccaggtgt ttgagaacat cgagaacagc caggccctgg tggaccagag caacagaatc  1440
ctgtccagcg ctgagaaggg caacaccggc ttcatcattg tgatcattct gatcgccgtg  1500
ctgggcagct ccatgatcct ggtgagcatc ttcatcatta tcaagaagac caagaaaccc  1560
accggagccc ctcctgagct gagcggcgtg accaacaatg gcttcattcc ccacaactga  1620

SEQ ID NO: 2            moltype = DNA  length = 1620
FEATURE                 Location/Qualifiers
source                  1..1620
                        mol_type = genomic DNA
                        organism = Human metapneumovirus
SEQUENCE: 2
atgtcttgga aagtgatgat catcatttcg ttactcataa caccccagca cgggctaaag  60
gagagttatt tggaagaatc atgtagtact ataactgagg gatacctcag tgttttaaga  120
acaggctggt acactaatgt cttcacatta gaagttggtg atgttgaaaa tcttacatgt  180
actgatggac ctagcttaat caaaacagaa cttgatctaa caaaaagtgc tttaagggaa  240
ctcaaaacag tctctgctga tcagttggcg agagaggagc aaattgaaaa tcccagacaa  300
tcaagatttg tcttaggtgc gatagctctc ggagttgcta cagcagcagc agtcacagca  360
ggcattgcaa tagccaaaac cataaggctt gagagtgagg tgaatgcaat taaaggtgct  420
ctcaaacaaa ctaatgaagc agtatccaca ttagggaatg gtgtgcgggt cctagccact  480
gcagtgagag agctaaaaga atttgtgagc aaaaacctga ctagtgcaat caacaggaac  540
aaatgtgaca ttgctgatct gaagatggct gtcagcttca gtcaattcaa cagaagattt  600
ctaaatgttg tgcggcagtt ttcagacaat gcagggataa caccagcaat atcattggac  660
ctgatgactg atgctgagtt ggccagagct gtatcataca tgccaacatc tgcagggcag  720
ataaaactga tgttggagaa ccgcgcaatg gtaaggagaa aaggatttgg aatcctgata  780
ggggtctacg gaagctctgt gatttacatg gttcaattgc cgatctttgg tgtcatagat  840
acaccttgtt ggatcatcaa ggcagctccc tcttgctcag aaaaaaacgg gaattatgct  900
tgcctcctaa gagaggatca agggtggtat tgtaaaaatg caggatctac tgtttactac  960
ccaaatgaaa aagactgcga aacaagaggt gatcatgttt tttgtgacac agcagcaggg  1020
atcaatgttg ctgagcaatc aagagaatgc aacatcaaca tatctactac caactaccca  1080
```

```
tgcaaagtca gcacaggaag acaccctata agcatggttg cactatcacc tctcggtgct  1140
ttggtggctt gctataaagg ggtaagctgc tcgattggca gcaattgggt tggaatcatc  1200
aaacaattac ccaaaggctg ctcatacata accaaccagg atgcagacac tgtaacaatt  1260
gacaataccg tgtatcaact aagcaaagtt gaaggtgaac agcatgtaat aaaagggaga  1320
ccagtttcaa gcagttttga tccaatcaag tttcctgagg atcagttcaa tgttgcgctt  1380
gatcaagtct tcgaaagcat tgagaacagt caggcactag tggaccagtc aaacaaaatt  1440
ctaaacagtg cagaaaaagg aaacactggt ttcattatcg tagtaatttt ggttgctgtt  1500
cttggtctaa ccatgatttc agtgagcatc atcatcataa tcaagaaaac aaggaagccc  1560
acaggagcac ctccagagct gaatggtgtc accaacggcg gtttcatacc acatagttag  1620

SEQ ID NO: 3           moltype = DNA  length = 1620
FEATURE                Location/Qualifiers
source                 1..1620
                       mol_type = genomic DNA
                       organism = Human metapneumovirus
SEQUENCE: 3
atgtcttgga aagtgatgat tatcatttcg ttactcataa cacctcagca tggactaaaa  60
gaaagttatt tagaagaatc atgtagtact ataactgaag gatatctcag tgttttaaga  120
acaggttggt acaccaatgt ctttacatta gaagttggtg atgttgaaaa tcttacatgt  180
actgatggac ctagcttaat caaaacagaa cttgacctaa ccaaaagtgc tttaagagaa  240
ctcaaaacag tttctgctga tcagttagcg agagaagaac aaattgaaaa tcccagacaa  300
tcaaggtttg tcctaggtgc aatagctctt ggagttgcca cagcagcagc agtcacagca  360
ggcattgcaa tagccaaaac tataaggctt gagagtgaag tgaatgcaat caaaggtgct  420
ctcaaaacaa ccaatgaggc agtatcaaca ctaggaaatg gagtgcgggt cctagccact  480
gcagtaagag agctgaaaga atttgtgagc aaaaacctga ctagtgcgat caacaagaac  540
aagtgtgaca ttgctgattt gaagatggct gtcagcttca gtcagttcaa cagaagattc  600
ctaaatgttg tgcggcagtt ttcagacaat gcagggataa caccagcaat atcattggac  660
ctgatgaatg atgctgagct ggccagagct gtatcataca tgccaacatc tgcaggacag  720
ataaaactaa tgttagagaa ccgtgcaatg gtgaggagaa aaggatttgg aatcttgata  780
ggggtctacg gaagctctgt gatttacatg gtccagctgc cgatctttgg tgtcataaat  840
acaccttgtt ggataatcaa ggcagctccc tcttgttcag aaaaagatgg aaattatgct  900
tgcctcctaa gagaggatca agggtggtat tgtaaaaatg caggatccac tgtttactac  960
ccaaatgaaa aagactgcga aacaagaggt gatcatgttt tttgtgacac agcagcaggg  1020
atcaatgttg ctgagcaatc aagagaatgc aacatcaaca tatctaccac caactaccca  1080
tgcaaagtca gcacaggaag acaccctatc agcatggttg cactatcacc tctcggtgct  1140
ttggtagctt gctacaaagg ggttagctgc tcgactggca gtaatcaggt tggaataatc  1200
aaacaactac ctaaaggctg ctcatacata actaaccagg acgcagacac tgtaacaatt  1260
gacaacactg tgtatcaact aagcaaagtt gagggtgaac agcatgtaat aaaagggaga  1320
ccagtttcaa gcagttttga tccaatcagg tttcctgagg atcagttcaa tgttgcgctt  1380
gatcaagtct ttgaaagcat tgaaaacagt caagcactag tggaccagtc aaacaaaatt  1440
ctgaacagtg cagaaaaagg aaacactggt ttcattattg taataatttt gattgctgtt  1500
cttgggttaa ccatgatttc agtgagcatc atcatcataa tcaaaaaaac aaggaagccc  1560
acaggggcac ctccggagct gaatggtgtt accaacggcg gtttcatacc gcatagttag  1620

SEQ ID NO: 4           moltype = DNA  length = 1725
FEATURE                Location/Qualifiers
source                 1..1725
                       mol_type = genomic DNA
                       note = Human respiratory syncytial virus
                       organism = unidentified
SEQUENCE: 4
atggagttgc caatcctcaa aacaaatgca attaccacaa tccttgctgc agtcacactc  60
tgtttcgctt ccagtcaaaa catcactgaa gaattttatc aatcaacatg cagtgcagtt  120
agcaaaggct atcttagtgc tctaagaact ggttggtata ctagtgttat aactatagaa  180
ttaagtaata tcaaggaaaa taagtgtaat ggaacagatg ctaaggtaaa attgataaaa  240
caagaattag ataaatataa aaatgctgta acagaattgc agttgctcat gcaaagcaca  300
ccagcagcca acaatcgagc cagaagagaa ctaccaaggt ttatgaatta tacactcaat  360
aataccaaaa ataccaatgt aacattaagc aagaaaagga aaagaagatt tcttggcttt  420
ttgttaggtg ttggatctgc aatcgccagt ggcattgctg tatctaaggt cctgcaccta  480
gaaggggaag tgaacaaaat caaaagtgct ctactatcca caaacaaggc tgtagtcagc  540
ttatcaaatg gagttagtgt cttaaccagc aaagtgttag acctcaaaaa ctatatagat  600
aaacagttgt tacctattgt gaacaagcaa agctgcagca tatcaaacat tgaaactgtg  660
atagagttcc aacaaaagaa caacagacta ctagagatta ccagggaatt tagtgttaat  720
gcaggtgtaa ctacacctgt aagcacttat atgttaacta atagtgaatt attatcatta  780
atcaatgata tgcctataac aaatgatcag aaaaagttaa tgtccaacaa tgttcaaata  840
gttagacagc aaagttactc tatcatgtcc ataataaagg aggaagtctt agcatatgta  900
gtacaattac cactatatgg tgtaatagat acaccctgtt ggaaactgca cacatcccct  960
ctatgtacaa ccaacacaaa ggaagggtcc aacatctgct taacaagaac cgacagagga  1020
tggtattgtg acaatgcagg atcagtatct ttcttcccac aagctgaaac atgtaaagtt  1080
caatcgaatc gggtattttg tgacacaatg aacagtttaa cattaccaag tgaagtaaat  1140
ctctgcaaca ttgacatatt caaccccaaa tatgattgca aaattatgac ttcaaaaaca  1200
gatgtaagca gctccgttat cacatctcta ggagccattg tgtcatgcta tggcaaaact  1260
aaatgtacag catccaataa aaatcgtggg atcataaaga cattttctaa cgggtgtgat  1320
tatgtatcaa ataagggggt ggatactgtg tctgtaggta atacattata ttatgtaaat  1380
aagcaagaag gcaaaagtct ctatgtaaaa ggtgaaccaa taataaattt ctatgaccca  1440
ttagtgttcc cctctgatga atttgatgca tcaatatctc aagtcaatga gaagattaac  1500
cagagcctag catttattcg taaatccgat gaattattac ataatgtaaa tgctggtaaa  1560
tccaccacaa atatcatgat aactactata attatagtga ttatagtaat attgttatca  1620
ttaattgcag ttggactgct cctatactgc aaggccagaa gcacaccagt cacactaagt  1680
```

```
aaggatcaac tgagtggtat aaataatatt gcatttagta actga                1725

SEQ ID NO: 5            moltype = AA  length = 539
FEATURE                 Location/Qualifiers
source                  1..539
                        mol_type = protein
                        note = Human metapneumovirus isolate
                        organism = unidentified
SEQUENCE: 5
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPRQ SRFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFNVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 6            moltype = AA  length = 539
FEATURE                 Location/Qualifiers
source                  1..539
                        mol_type = protein
                        organism = Human metapneumovirus
SEQUENCE: 6
MSWKVMIIIS LLITPQHGLK ESYLEESCST ITEGYLSVLR TGWYTNVFTL EVGDVENLTC  60
TDGPSLIKTE LDLTKSALRE LKTVSADQLA REEQIENPRQ SRFVLGAIAL GVATAAAVTA  120
GIAIAKTIRL ESEVNAIKGA LKQTNEAVST LGNGVRVLAT AVRELKEFVS KNLTSAINRN  180
KCDIADLKMA VSFSQFNRRF LNVVRQFSDN AGITPAISLD LMTDAELARA VSYMPTSAGQ  240
IKLMLENRAM VRRKGFGILI GVYGSSVIYM VQLPIFGVID TPCWIIKAAP SCSEKNGNYA  300
CLLREDQGWY CKNAGSTVYY PNEKDCETRG DHVFCDTAAG INVAEQSREC NINISTTNYP  360
CKVSTGRHPI SMVALSPLGA LVACYKGVSC SIGSNWVGII KQLPKGCSYI TNQDADTVTI  420
DNTVYQLSKV EGEQHVIKGR PVSSSFDPIK FPEDQFNVAL DQVFESIENS QALVDQSNKI  480
LNSAEKGNTG FIIVVILVAV LGLTMISVSI IIIIKKTRKP TGAPPELNGV TNGGFIPHS   539

SEQ ID NO: 7            moltype = AA  length = 539
FEATURE                 Location/Qualifiers
source                  1..539
                        mol_type = protein
                        organism = Human metapneumovirus
SEQUENCE: 7
MSWKVMIIIS LLITPQHGLK ESYLEESCST ITEGYLSVLR TGWYTNVFTL EVGDVENLTC  60
TDGPSLIKTE LDLTKSALRE LKTVSADQLA REEQIENPRQ SRFVLGAIAL GVATAAAVTA  120
GIAIAKTIRL ESEVNAIKGA LKTTNEAVST LGNGVRVLAT AVRELKEFVS KNLTSAINKN  180
KCDIADLKMA VSFSQFNRRF LNVVRQFSDN AGITPAISLD LMNDAELARA VSYMPTSAGQ  240
IKLMLENRAM VRRKGFGILI GVYGSSVIYM VQLPIFGVIN TPCWIIKAAP SCSEKDGNYA  300
CLLREDQGWY CKNAGSTVYY PNEKDCETRG DHVFCDTAAG INVAEQSREC NINISTTNYP  360
CKVSTGRHPI SMVALSPLGA LVACYKGVSC STGSNQVGII KQLPKGCSYI TNQDADTVTI  420
DNTVYQLSKV EGEQHVIKGR PVSSSFDPIR FPEDQFNVAL DQVFESIENS QALVDQSNKI  480
LNSAEKGNTG FIIVIILIAV LGLTMISVSI IIIIKKTRKP TGAPPELNGV TNGGFIPHS   539

SEQ ID NO: 8            moltype = AA  length = 574
FEATURE                 Location/Qualifiers
source                  1..574
                        mol_type = protein
                        note = Human respiratory syncytial virus
                        organism = unidentified
SEQUENCE: 8
MELPILKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 9            moltype = DNA  length = 1617
FEATURE                 Location/Qualifiers
source                  1..1617
                        mol_type = genomic DNA
                        note = Human parainfluenza virus 3
                        organism = unidentified
SEQUENCE: 9
atgccaattt caatactgtt aattattaca accatgatca tggcatcaca ctgccaaata  60
gacatcacaa aactacagca tgtaggtgta ttggtcaaca gtcccaaagg gatgaagata  120
tcacaaaact tcgaaacaag atatctaatc ctgagtctca taccaaaaat agaagattct  180
```

```
aactcttgtg gtgaccaaca gatcaagcaa tacaagaggt tattggatag actgatcatt  240
cctttatatg atggactaag attacagaag gatgtgatag tgactaatca agaatccaat  300
gaaaacactg atcccagaac agaacgattc tttggagggg taattggaac tattgctcta  360
ggagtagcaa cctcagcaca aattacagca gcagttgctc tggttgaagc caagcaggca  420
agatcagaca ttgaaaaact caaggaagca atcagggaca caaataaagc agtgcagtca  480
gttcagagct ctgtaggaaa tttgatagta gcaattaaat cagtccagga ttatgtcaac  540
aaagaaatcg tgccatcgat tgcgagacta ggttgtgaag cagcaggact tcagttaggg  600
attgcattaa cacagcatta ctcagaatta acaaatatat ttggtgataa cataggatcg  660
ttacaagaaa aaggaataaa attacaaggt atagcatcat tataccgtac aaatatcaca  720
gaaatattca caacatcaac agttgacaaa tatgatattt atgatctatt atttacagaa  780
tcaataaagg tgagagttat agatgttgat ttgaatgatt actcaataac cctccaagtc  840
agactccctt tattgaccag actgctgaac actcaaatct acaaagtaga ttccatatca  900
tacaatatcc aaaatagaga atggtatatc cctcttccca gccatatcat gacgaaaggg  960
gcatttctag gtggagcaga tgtcaaagaa tgcatagaag cattcagcag ttatatatgc  1020
ccttctgatc caggatttgt actaaaccat gaaatggaga gctgtctatc aggaaacata  1080
tcccaatgtc caagaaccac agtcacatca gacatagttc ctaggtatgc atttgtcaat  1140
ggaggagtgg ttgcgaattg tataacaact acatgtacat gcaatggtat cggtaataga  1200
atcaaccaac cacctgatca aggagtcaaa attataacac ataaagaatg taatacaata  1260
ggtatcaacg gaatgctatt caacacaaac aaagaaggaa ctcttgcatt ctacacacca  1320
gacgacataa cattaaacaa ttctgttgca cttgatccga ttgacatatc aatcgagctc  1380
aacaaggcca aatcagatct tgaggaatca aaagaatgga taagaaggtc aaatcaaaag  1440
ctagattcta ttggaagttg gcatcaatct agcactacaa tcatagttat tttgataatg  1500
atgattatat tgtttataat taatataaca ataattacaa ttgcaattaa gtattacaga  1560
attcaaaaga gaaatcgagt ggatcaaaat gataagccgt atgtattaac aaacaag     1617
```

```
SEQ ID NO: 10          moltype = DNA  length = 1716
FEATURE                Location/Qualifiers
source                 1..1716
                       mol_type = genomic DNA
                       note = Human parainfluenza virus 3
                       organism = unidentified
SEQUENCE: 10
atggaatact ggaagcacac caaccacgga aaggatgctg gtaatgagct ggagacatcc  60
acagccactc atggcaacaa gctcaccaac aagataacat atatattgtg gacgataacc  120
ctggtgttat tatcaatagt cttcatcata gtgctaacta attccatcaa aagtgaaaag  180
gcccgcgaat cattgctaca agacataaat aatgagttta tggaagttac agaaaagatc  240
caagtggcat cggataatac taatgatcta atacagtcag gagtgaatac aaggcttctt  300
acaattcaga gtcatgtcca gaattatata ccaatatcat tgacacaaca aatatcggat  360
cttaggaaat tcattagtga aattacaatt agaaatgata atcaagaagt gccaccacaa  420
agaataacac atgatgtggg tataaaacct ttaaatccag atgatttctg gagatgcacg  480
tctggtcttc catctttgat gaaaactcca aaaataagat taatgccggg accaggatta  540
ttagctatgc caacgactgt tgatggctgt gtcagaaccc cgtccttagt gataaatgat  600
ctgatttatg cttacacctc aaatctaatt actcgaggtt gccaggatat agggaaatca  660
tatcaagtat tacagatagg gataataact gtaaactcag acttggtacc tgacttaaat  720
cctaggatct ctcatacctt caacataaat gacaatagaa agtcatgttc tctagcactc  780
ctaaatacag atgtatatca actgtgttca accccaaaag ttgatgaaag atcagattat  840
gcatcatcag gcatagaaga tattgtactt gatattgtca attatgatgg ctcaatctcg  900
acaacaagat ttaagaataa taatataagt tttgatcaac catatgcggc attataccca  960
tctgttggac cagggatata ctacaaaggc aaaataatat ttctcgggta tggaggtctt  1020
gaacatccaa taaatgagaa tgcaatctgc aacacaactg ggtgtcctgg gaaaacacag  1080
agagactgta atcaagcatc tcatagtcca tggttttcag atagaaggat ggtcaactct  1140
ataattgttg ttgacaaggg cttgaactca gttccaaaat tgaaggtatg gacgatatct  1200
atgagacaaa attactgggg gtcagaagga agattacttc tactaggtaa caagatctac  1260
atatacacaa gatctacaag ttggcacagc aagttacaat taggaataat tgacattact  1320
gactacagtg atataaggat aaaatggaca tggcataatg tgctatcaag accaggaaac  1380
aatgaatgtc catggggaca ttcatgtccg gatggatgta taacgggagt atataccgat  1440
gcatatccac tcaatcccac aggaagcatt gtatcatctg tcatattgga ctcacaaaaa  1500
tcgagagtca acccagtcat aacttactca acagcaaccg aaagggtaaa cgagctggct  1560
atccgaaaca aaacactctc agctgggtac acaacaacaa gctgcattac acactataac  1620
aaagggtatt gttttcatat agtagaaata aatcataaaa gcttaaacac atttcaaccc  1680
atgttgttca aaacagagat tccaaaaagc tgcagt                           1716
```

```
SEQ ID NO: 11          moltype = DNA  length = 1716
FEATURE                Location/Qualifiers
misc_feature           1..1716
                       note = Synthetic Polynucleotide
source                 1..1716
                       mol_type = other DNA
                       organism = synthetic construct
SEQUENCE: 11
atggaatact ggaagcacac caaccacggc aaggacgccg gcaacgagct ggaaaccagc  60
acagccacac acggcaacaa gctgaccaac aagatcacct acatcctgtg gaccatcacc  120
ctggtgctgc tgagcatcgt gttcatcatc gtgctgacca atagcatcaa gagcgagaag  180
gccagagaga gcctgctgca ggacatcaac aacgagttca tggaagtgac cgagaagatc  240
caggtggcca gcgacaacac caacgacctg atccagagcg gcgtgaacac ccggctgctg  300
accatccaga gccacgtgca gaactacatc cccatcagcc tgacccagca gatcagcgac  360
ctgcggaagt tcatcagcga gatcaccatc cggaacgaca accaggaagt gcccccccag  420
agaatcaccc acgacgtggg catcaagccc ctgaaccccg acgatttctg gcggtgtaca  480
agcggcctgc ccagcctgat gaagaccccc aagatccggc tgatgcctgg ccctggactg  540
```

-continued

```
ctggccatgc ctaccacagt ggatggctgt gtgcggaccc ccagcctcgt gatcaacgat  600
ctgatctacg cctacaccag caacctgatc acccggggct gccaggatat cggcaagagc  660
taccaggtgc tgcagatcgg catcatcacc gtgaactccg acctggtgcc cgacctgaac  720
cctcggatca gccacacctt caacatcaac gacaacagaa agagctgcag cctggctctg  780
ctgaacaccg acgtgtacca gctgtgcagc acccccaagg tggacgagag aagcgactac  840
gccagcagcg gcatcgagga tatcgtgctg gacatcgtga actacgacgg cagcatcagc  900
accacccggt tcaagaacaa caacatcagc ttcgaccagc cctacgccgc cctgtaccct  960
tctgtgggcc ctggcatcta ctacaagggc aagatcatct tcctgggcta cggcggcctg  1020
gaacacccca tcaacgagaa cgccatctgc aacaccaccg gctgccctgg caagacccag  1080
agagactgca atcaggccag ccacagcccc tggttcagcg accgcagaat ggtcaactct  1140
atcatcgtgg tggacaaggg cctgaacagc gtgcccaagc tgaaagtgtg gacaatcagc  1200
atgcgccaga actactgggg cagcgagggc agacttctgc tgctgggaaa caagatctac  1260
atctacaccc ggtccaccag ctggcacagc aaactgcagc tgggaatcat cgacatcacc  1320
gactacagcg acatccggat caagtggacc tggcacaacg tgctgagcag acccggcaac  1380
aatgagtgcc cttggggcca cagctgcccc gatggatgta tcaccggcgt gtacaccgac  1440
gcctaccccc tgaatcctac cggctccatc gtgtccagcg tgatcctgga cagccagaaa  1500
agcagagtga accccgtgat cacatacagc accgccaccg agagagtgaa cgaactggcc  1560
atcagaaaca agaccctgag cgccggctac accaccacaa gctgcatcac acactacaac  1620
aagggctact gcttccacat cgtggaaatc aaccacaagt ccctgaacac cttccagccc  1680
atgctgttca agaccgagat ccccaagagc tgctcc                           1716

SEQ ID NO: 12          moltype = DNA  length = 1617
FEATURE                Location/Qualifiers
misc_feature           1..1617
                       note = Synthetic Polynucleotide
source                 1..1617
                       mol_type = other DNA
                       organism = synthetic construct
SEQUENCE: 12
atgcccatca gcatcctgct gatcatcacc acaatgatca tggccagcca ctgccagatc  60
gacatcacca agctgcagca cgtgggcgtg ctcgtgaaca gccccaaggg catgaagatc  120
agccagaact tcgagacacg ctacctgatc ctgagcctga tccccaagat cgaggacagc  180
aacagctgcg gcgaccagca gatcaagcag tacaagcggc tgctggacag actgatcatc  240
cccctgtacg acggcctgcg gctgcagaaa gacgtgatcg tgaccaacca ggaaagcaac  300
gagaacaccg acccccggac cgagagattc ttcggcggcg tgatcggcac aatcgccctg  360
ggagtggcca caagcgccca gattacagcc gctgtggccc tggtggaagc caagcaggcc  420
agaagcgaca tcgagaagct gaaagaggcc atccgggaca ccaacaaggc cgtgcagagc  480
gtgcagtcca gcgtgggcaa tctgatcgtg gccatcaagt ccgtgcagga ctacgtgaac  540
aaagaaatcg tgccctctat cgcccggctg ggctgtgaag ctgccggact gcagctgggc  600
attgccctga cacagcacta cagcgagctg accaacatct tcggcgacaa catcggcagc  660
ctgcaggaaa agggcattaa gctgcaggga atcgccagcc tgtaccgcac caacatcacc  720
gagatcttca ccaccagcac cgtggataag tacgacatct acgacctgct gttcaccgag  780
agcatcaaag tgcgcgtgat cgacgtggac ctgaacgact acagcatcac cctgcaagtg  840
cggctgcccc tgctgaccag actgctgaac acccagatct acaaggtgga cagcatctcc  900
tacaacatcc agaaccgcga gtggtacatc cctctgccca gccacattat gaccaagggc  960
gcctttctgg gcggagccga cgtgaaagag tgcatcgagg ccttcagcag ctacatctgc  1020
cccagcgacc ctggcttcgt gctgaaccac gagatggaaa gctgcctgag cggcaacatc  1080
agccagtgcc ccagaaccac cgtgacctcc gacatcgtgc ccagatacgc cttcgtgaat  1140
ggcggcgtgg tggccaactg catcaccacc acctgtacct gcaacggcat cggcaaccgg  1200
atcaaccagc ctcccgatca gggcgtgaag attatcaccc acaaagagtg taacaccatc  1260
ggcatcaacg gcatgctgtt caataccaac aaagagggca ccctggcctt ctacaccccc  1320
gacgatatca ccctgaacaa ctccgtggct ctggacccca tcgacatctc catcgagctg  1380
aacaaggcca agagcgacct ggaagagtcc aaagagtgga tccggcggag caaccagaag  1440
ctggactcta tcggcagctg gcaccagagc agcaccacca tcatcgtgat cctgattatg  1500
atgattatcc tgttcatcat caacattacc atcatcacta tcgccattaa gtactaccgg  1560
atccagaaac ggaaccgggt ggaccagaat gacaagccct acgtgctgac aaacaag     1617

SEQ ID NO: 13          moltype = AA  length = 539
FEATURE                Location/Qualifiers
source                 1..539
                       mol_type = protein
                       note = Human parainfluenza virus 3
                       organism = unidentified
SEQUENCE: 13
MPISILLIIT TMIMASHCQI DITKLQHVGV LVNSPKGMKI SQNFETRYLI LSLIPKIEDS  60
NSCGDQQIKQ YKRLLDRLII PLYDGLRLQK DVIVTNQESN ENTDPRTERF FGGVIGTIAL  120
GVATSAQITA AVALVEAKQA RSDIEKLKEA IRDTNKAVQS VQSSVGNLIV AIKSVQDYVN  180
KEIVPSIARL GCEAAGLQLG IALTQHYSEL TNIFGDNIGS LQEKGIKLQG IASLYRTNIT  240
EIFTTSTVDK YDIYDLLFTE SIKVRVIDVD LNDYSITLQV RLPLLTRLLN TQIYKVDSIS  300
YNIQNREWYI PLPSHIMTKG AFLGGADVKE CIEAFSSYIC PSDPGFVLNH EMESCLSGNI  360
SQCPRTTVTS DIVPRYAFVN GGVVANCITT TCTCNGIGNR INQPPDQGVK IITHKECNTI  420
GINGMLFNTN KEGTLAFYTP DDITLNNSVA LDPIDISIEL NKAKSDLEES KEWIRRSNQK  480
LDSIGSWHQS STTIIVILIM MIILFIINIT IITIAIKYYR IQKRNRVDQN DKPYVLTNK   539

SEQ ID NO: 14          moltype = AA  length = 572
FEATURE                Location/Qualifiers
source                 1..572
                       mol_type = protein
                       note = Human parainfluenza virus 3
```

```
                         organism = unidentified
SEQUENCE: 14
MEYWKHTNHG KDAGNELETS TATHGNKLTN KITYILWTIT LVLLSIVFII VLTNSIKSEK  60
ARESLLQDIN NEFMEVTEKI QVASDNTNDL IQSGVNTRLL TIQSHVQNYI PISLTQQISD  120
LRKFISEITI RNDNQEVPPQ RITHDVGIKP LNPDDFWRCT SGLPSLMKTP KIRLMPGPGL  180
LAMPTTVDGC VRTPSLVIND LIYAYTSNLI TRGCQDIGKS YQVLQIGIIT VNSDLVPDLN  240
PRISHTFNIN DNRKSCSLAL LNTDVYQLCS TPKVDERSDY ASSGIEDIVL DIVNYDGSIS  300
TTRFKNNNIS FDQPYAALYP SVGPGIYYKG KIIFLGYGGL EHPINENAIC NTTGCPGKTQ  360
RDCNQASHSP WFSDRRMVNS IIVVDKGLNS VPKLKVWTIS MRQNYWGSEG RLLLLGNKIY  420
IYTRSTSWHS KLQLGIIDIT DYSDIRIKWT WHNVLSRPGN NECPWGHSCP DGCITGVYTD  480
AYPLNPTGSI VSSVILDSQK SRVNPVITYS TATERVNELA IRNKTLSAGY TTTSCITHYN  540
KGYCFHIVEI NHKSLNTFQP MLFKTEIPKS CS                                572

SEQ ID NO: 15            moltype = AA  length = 20
FEATURE                  Location/Qualifiers
REGION                   1..20
                         note = Synthetic Polypeptide
source                   1..20
                         mol_type = protein
                         organism = synthetic construct
SEQUENCE: 15
METPAQLLFL LLLWLPDTTG                                              20

SEQ ID NO: 16            moltype = AA  length = 18
FEATURE                  Location/Qualifiers
REGION                   1..18
                         note = Synthetic Polypeptide
source                   1..18
                         mol_type = protein
                         organism = synthetic construct
SEQUENCE: 16
MDWTWILFLV AAATRVHS                                                18

SEQ ID NO: 17            moltype = AA  length = 24
FEATURE                  Location/Qualifiers
REGION                   1..24
                         note = Synthetic Polypeptide
source                   1..24
                         mol_type = protein
                         organism = synthetic construct
SEQUENCE: 17
MLGSNSGQRV VFTILLLLVA PAYS                                         24

SEQ ID NO: 18            moltype = AA  length = 17
FEATURE                  Location/Qualifiers
REGION                   1..17
                         note = Synthetic Polypeptide
source                   1..17
                         mol_type = protein
                         organism = synthetic construct
SEQUENCE: 18
MKCLLYLAFL FIGVNCA                                                 17

SEQ ID NO: 19            moltype = AA  length = 15
FEATURE                  Location/Qualifiers
REGION                   1..15
                         note = Synthetic Polypeptide
source                   1..15
                         mol_type = protein
                         organism = synthetic construct
SEQUENCE: 19
MWLVSLAIVT ACAGA                                                   15

SEQ ID NO: 20            moltype = DNA  length = 4062
FEATURE                  Location/Qualifiers
source                   1..4062
                         mol_type = genomic DNA
                         note = Middle East respiratory syndrome coronavirus
                         organism = unidentified
SEQUENCE: 20
atgatacact cagtgtttct actgatgttc ttgttaacac ctacagaaag ttacgttgat  60
gtagggccag attctgttaa gtctgcttgt attgaggttg atatacaaca gaccttcttt  120
gataaaactt ggcctaggcc aattgatgtt tctaaggctg acggtattat ataccctcaa  180
ggccgtacat attctaacat aactatcact tatcaaggtc tttttcccta tcagggagac  240
catggtgata tgtatgttta ctctgcagga catgctacag gcacaactcc acaaaagttg  300
tttgtagcta actattctca ggacgtcaaa cagtttgcta atgggtttgt cgtccgtata  360
ggagcagctg ccaattccac tggcactgtt attattagcc catctaccag cgctactata  420
cgaaaaattt accctgcttt tatgctgggt tcttcagttg gtaatttctc agatggtaaa  480
atgggccgct tcttcaatca tactctagtt cttttgcccg atggatgtgg cactttactt  540
```

-continued

```
agagctttttt attgtattct agagcctcgc tctggaaatc attgtcctgc tggcaattcc  600
tatacttctt ttgccactta tcacactcct gcaacagatt gttctgatgg caattacaat  660
cgtaatgcca gtctgaactc ttttaaggag tattttaatt tacgtaactg cacctttatg  720
tacacttata acattaccga agatgagatt ttagagtggt ttggcattac acaaactgct  780
caaggtgttc acctcttctc atctcggtat gttgatttgt acggcggcaa tatgtttcaa  840
tttgccacct tgcctgttta tgatactatt aagtattatt ctatcattcc tcacagtatt  900
cgttctatcc aaagtgatag aaaagcttgg gctgccttct acgtatataa acttcaaccg  960
ttaactttcc tgttggattt ttctgttgat ggttatatac gcagagctat agactgtggt  1020
tttaatgatt tgtcacaact ccactgctca tatgaatcct tcgatgttga atctggagtt  1080
tattcagttt cgtctttcga agcaaaacct tctggctcag ttgtggaaca ggctgaaggt  1140
gttgaatgtg atttttcacc tcttctgtct ggcacacctc ctcaggttta taatttcaag  1200
cgtttggttt ttaccaattg caattataat cttaccaaat tgctttcact tttttctgtg  1260
aatgatttta cttgtagtca aatatctcca gcagcaattg ctagcaactg ttattcttca  1320
ctgattttgg attatttttc atacccactt agtatgaaat ccgatctcag tgttagttct  1380
gctggtccaa tatcccagtt taattataaa cagtcctttt ctaatcccac atgtttgatc  1440
ttagcgactg ttcctcataa ccttactact attactaagc ctcttaagta cagctatatt  1500
aacaagtgct ctcgtcttct ttctgatgat cgtactgaag tacctcagtt agtgaacgct  1560
aatcaatact caccctgtgt atccattgtc ccatccactg tgtgggaaga cggtgattat  1620
tataggaaac aactatctcc acttgaaggt ggtggctggc ttgttgctag tggctcaact  1680
gttgccatga ctgagcaatt acagatgggc tttggtatta cagttcaata tggtacagac  1740
accaatagtg tttgccccaa gcttgaattt gctaatgaca caaaaaattgc ctctcaatta  1800
ggcaattgcg tggaatattc cctctatggt gtttcgggcc gtggtgtttt tcagaattgc  1860
acagctgtag gtgttcgaca gcagcgcttt gtttatgatg cgtaccagaa tttagttggc  1920
tattattctg atgatggcaa ctactactgt ctgcgtgctt gtgttagtgt tcctgtttct  1980
gtcatctatg ataaagaaac taaaacccac gctactctat ttggtagtgt tgcatgtgaa  2040
cacatttctt ctaccatgtc tcaatactcc cgttctacgc gatcaatgct taaacggcga  2100
gattctacat atggccccct tcagacacct gttggttgtg tcctaggact tgttaattcc  2160
tctttgttcg tagaggactg caagttgcct ctcggtcaat ctctctgtgc tcttcctgac  2220
acacctagta ctctcacacc tcgcagtgtg cgctctgtgc caggtgaaat gcgcttggca  2280
tccattgctt ttaatcatcc cattcaggtt gatcaactta atagtagtta ttttaaatta  2340
agtataccca ctaattttc ctttggtgtg actcaggagt acattcagac aaccattcag  2400
aaagttactg ttgattgtaa acagtacgtt tgcaatggtt tccagaagtg tgagcaatta  2460
ctgcgcgagt atggccagtt ttgttccaaa ataaaccagg ctctccatgg tgccaattta  2520
cgccaggatg attctgtacg taatttgttt gcgagcgtga aagctctca atcatctcct  2580
atcataccag gttttggagg tgactttaat ttgacacttc tagaacctgt ttctatatct  2640
actggcagtc gtagtgcacg tagtgctatt gaggatttgc tatttgacaa agtcactata  2700
gctgatcctg gttatatgca aggttacgat gattgtatgc agcaaggtcc agcatcagct  2760
cgtgatctta tttgtgctca atatgtggct ggttataaag tattacctcc tcttatggat  2820
gttaatatgg aagccgcgta tacttcatct ttgcttggca gcatagcagg tgttggctgg  2880
actgctggct tatcctcctt tgctgctatt ccatttgcac agagtatytt ttataggtta  2940
aacggtgttg gcattactca acaggttctt tcagagaacc aaaagcttat tgccaataag  3000
tttaatcagg ctctgggagc tatgcaaaca ggcttcacta caactaatga agcttttcgg  3060
aaggttcagg atgctgtgaa caacaatgca caggctctat ccaaattagc tagcgagcta  3120
tctaatactt ttggtgctat ttccgcctct attggagaca tcatacaacg tcttgatgtt  3180
ctcgaacagg acgcccaaat agacagactt attaatggcc gtttgacaac actaaatgct  3240
tttgttgcac agcagcttgt tcgttccgaa tcagctgctc tttccgctca attggctaaa  3300
gataaagtca atgagtgtgt caaggcacaa tccaagcgtt ctggattttg cggtcaaggc  3360
acacatatag tgtcctttgt tgtaaatgcc cctaatggcc tttactttat gcatgttggt  3420
tattacccta gcaaccacat tgaggttgtt tctgcttatg gtctttgcga tgcagctaac  3480
cctactaatt gtatagcccc tgttaatggc tactttatta aaactaataa cactaggatt  3540
gttgatgagt ggtcatatac tggctcgtcc ttctatgcac ctgagcccat cacctctctt  3600
aatactaagt atgttgcacc acaggtgaca taccaaaaca tttctactaa cctccctcct  3660
cctcttctcg gcaattccac cgggattgac ttccaagatg agttggatga gtttttcaaa  3720
aatgttagca ccagtatacc taattttggt tctctaacac agattaatac tacattactc  3780
gatcttacct acgagatgtt gtctcttcaa caagttgtta aagcccttaa tgagtcttac  3840
atagacctta aagagcttgg caattatact tattacaaca aatggccgtg gtacatttgg  3900
cttggtttca ttgctgggct tgttgcctta gctctatgcg tcttcttcat actgtgctgc  3960
actggttgtg gcacaaactg tatgggaaaa cttaagtgta atcgttgttg tgatagatac  4020
gaggaatacg acctcgagcc gcataaggtt catgttcact aa                    4062
```

```
SEQ ID NO: 21          moltype = DNA  length = 4062
FEATURE                Location/Qualifiers
misc_feature           1..4062
                       note = Synthetic Polynucleotide
source                 1..4062
                       mol_type = other DNA
                       organism = synthetic construct
SEQUENCE: 21
atgatacact cagtgtttct actgatgttc ttgttaacac ctacagaaag ttacgttgat  60
gtagggccag attctgttaa gtctgcttgt attgaggttg atatacaaca gactttcttt  120
gataaaactt ggcctaggcc aattgatgtt tctaaggctg acggtattat ataccctcaa  180
ggccgtacat attctaacat aactatcact tatcaaggtc tttttcccta tcagggagac  240
catggtgata tgtatgttta ctctgcagga catgctacag gcacaactcc acaaaagttg  300
tttgtagcta actattctca ggacgtcaaa cagtttgcta atgggtttgt cgtccgtata  360
ggagcagctg ccaattccac tggcactgtt attattagcc catctaccag cgctactata  420
cgaaaaattt accctgcttt tatgctgggt tcttcagttg gtaatttctc agatggtaaa  480
atgggccgct tcttcaatca tactctagtt cttttgcccg atggatgtgg cactttactt  540
agagcttttt attgtattct ggagcctcgc tctggaaatc attgtcctgc tggcaattcc  600
tatacttctt ttgccactta tcacactcct gcaacagatt gttctgatgg caattacaat  660
```

```
cgtaatgcca gtctgaactc ttttaaggag tattttaatt tacgtaactg cacctttatg  720
tacacttata acattaccga agatgagatt ttagagtggt ttggcattac acaaactgct  780
caaggtgttc acctcttctc atctcggtat gttgatttgt acggcggcaa tatgtttcaa  840
tttgccacct tgcctgttta tgatactatt aagtattatt ctatcattcc tcacagtatt  900
cgttctatcc aaagtgatag aaaagcttgg gctgccttct acgtatataa acttcaaccg  960
ttaactttcc tgttggattt ttctgttgat ggttatatac gcagagctat agactgtggt  1020
tttaatgatt tgtcacaact ccactgctca tatgaatcct tcgatgttga atctggagtt  1080
tattcagttt cgtctttcga agcaaaacct tctggctcag ttgtggaaca ggctgaaggt  1140
gttgaatgtg atttttcacc tcttctgtct ggcacacctc ctcaggttta taatttcaag  1200
cgtttggttt ttaccaattg caattataat cttaccaaat tgctttcact tttttctgtg  1260
aatgatttta cttgtagtca aatatctcca gcagcaattg ctagcaactg ttattcttca  1320
ctgattttgg attacttttc atacccactt agtatgaaat ccgatctcag tgttagttct  1380
gctggtccaa tatcccagtt taattataaa cagtcctttt ctaatcccac atgtttgatt  1440
ttagcgactg ttcctcataa ccttactact attactaagc ctcttaagta cagctatatt  1500
aacaagtgct ctcgtcttct ttctgatgat cgtactgaag tacctcagtt agtgaacgct  1560
aatcaatact caccctgtgt atccattgtc ccatccactg tgtgggaaga cggtgattat  1620
tataggaaac aactatctcc acttgaaggt ggtggctggc ttgttgctag tggctcaact  1680
gttgccatga ctgagcaatt acagatgggc tttggtatta cagttcaata tggtacagac  1740
accaatagtg tttgccccaa gcttgaattt gctaatgaca caaaaattgc ctctcaatta  1800
ggcaattgcg tggaatattc cctctatggt gtttcgggcc gtggtgtttt tcagaattgc  1860
acagctgtag gtgttcgaca gcagcgcttt gtttatgatg cgtaccagaa tttagttggc  1920
tattattctg atgatggcaa ctactactgt ttgcgtgctt gtgttagtgt tcctgtttct  1980
gtcatctatg ataaagaaac taaaacccac gctactctat ttggtagtgt tgcatgtgaa  2040
cacatttctt ctaccatgtc tcaatactcc cgttctacgc gatcaatgct taaacggcga  2100
gattctacat atggccccct tcagacacct gttggttgtg tcctaggact tgttaattcc  2160
tctttgttcg tagaggactg caagttgcct cttggtcaat ctctctgtgc tcttcctgac  2220
acacctagta ctctcacacc tcgcagtgtg cgctctgttc caggtgaaat gcgcttggca  2280
tccattgctt ttaatcatcc tattcaggtt gatcaactta atagtagtta ttttaaatta  2340
agtataccca ctaatttttc ctttggtgtg actcaggagt acattcagac aaccattcag  2400
aaagttactg ttgattgtaa acagtacgtt tgcaatggtt tccagaagtg tgagcaatta  2460
ctgcgcgagt atggccagtt ttgttccaaa ataaaccagg ctctccatgg tgccaattta  2520
cgccaggatg attctgtacg taatttgttt gcgagcgtga aagctctca atcatctcct  2580
atcataccag gttttggagg tgactttaat ttgacacttc tggaacctgt ttctatatct  2640
actggcagtc gtagtgcacg tagtgctatt gaggatttgc tatttgacaa agtcactata  2700
gctgatcctg gttatatgca aggttacgat gattgcatgc agcaaggtcc agcatcagct  2760
cgtgatctta tttgtgctca atatgtggct ggttacaaag tattacctcc tcttatggat  2820
gttaatatgg aagccgcgta tacttcatct ttgcttggca gcatagcagg tgttggctgg  2880
actgctggct tatcctcctt tgctgctatt ccatttgcac agagtatctt ttataggtta  2940
aacggtgttg gcattactca acaggttctt tcagagaacc aaaagcttat tgccaataag  3000
tttaatcagg ctctgggagc tatgcaaaca ggcttcacta caactaatga agcttttcag  3060
aaggttcagg atgctgtgaa caacaatgca caggctctat ccaaattagc tagcgagcta  3120
tctaatactt ttggtgctat ttccgcctct attggagaca tcatacaacg tcttgatgtt  3180
ctcgaacagg acgcccaaat agacagactt attaatggcc gtttgacaac actaaatgct  3240
tttgttgcac agcagcttgt tcgttccgaa tcagctgctc tttccgctca attggctaaa  3300
gataaagtca atgagtgtgt caaggcacaa tccaagcgtt ctggattttg cggtcaaggc  3360
acacatatag tgtcctttgt tgtaaatgcc cctaatggcc tttacttcat gcatgttggt  3420
tattacccta gcaaccacat tgaggttgtt tctgcttatg gtctttgcga tgcagctaac  3480
cctactaatt gtatagcccc tgttaatggc tactttatta aaactaataa cactaggatt  3540
gttgatgagt ggtcatatac tggctcgtcc ttctatgcac ctgagcccat tacctccctt  3600
aatactaagt atgttgcacc acaggtgaca taccaaaaca tttctactaa cctccctcct  3660
cctcttctcg gcaattccac cggattgac ttccaagatg agttggatga gtttttcaaa  3720
aatgttagca ccagtatacc taattttggt tccctaacac agattaatac tacattactc  3780
gatcttacct acgagatgtt gtctcttcaa caagttgtta aagcccttaa tgagtcttac  3840
atagacctta aagagcttgg caattatact tattacaaca aatggccgtg gtacatttgg  3900
cttggtttca ttgctgggct tgttgcctta gctctatgcg tcttcttcat actgtgctgc  3960
actggttgtg gcacaaactg tatgggaaaa cttaagtgta atcgttgttg tgatagatac  4020
gaggaatacg acctcgagcc gcataaggtt catgttcact aa                    4062
```

```
SEQ ID NO: 22          moltype = DNA  length = 1845
FEATURE                Location/Qualifiers
misc_feature           1..1845
                       note = Synthetic Polynucleotide
source                 1..1845
                       mol_type = other DNA
                       organism = synthetic construct
SEQUENCE: 22
atgatccact ccgtgttcct cctcatgttc ctgttgaccc ccactgagtc agactgcaag  60
ctcccgctgg gacagtccct gtgtgcgctg cctgacactc ctagcactct gaccccacgc  120
tccgtgcggt cggtgcctgg cgaaatgcgg ctggcctcca tcgccttcaa tcacccaatc  180
caagtggatc agctgaatag ctcgtatttc aagctgtcca tccccacgaa cttctcgttc  240
ggggtcaccc aggagtacat ccagaccaca attcagaagg tcaccgtcga ttgcaagcaa  300
tacgtgtgca acggcttcca gaagtgcgag cagctgctga gagaatacgg gcagttttgc  360
agcaagatca accaggcgct gcatggagct aacttgcgcc aggacgactc cgtgcgcaac  420
ctctttgcct ctgtgaagtc atcccagtcc tccccaatca tcccgggatt cggaggggac  480
ttcaacctga ccctcctgga gcccgtgtcg atcagcaccg gtagcagatc ggcgcgctca  540
gccattgaag atcttctgtt cgacaaggtc accatcgccg atccgggcta catgcaggga  600
tacgacgact gtatgcagca gggaccagcc tccgcgaggg acctcatctg cgcgcaatac  660
gtggccgggt acaaagtgct gcctcctctg atggatgtga acatggaggc cgcttatact  720
tcgtccctgc tcggctctat cgccggcgtg gggtggaccg ccggcctgtc ctccttcgcc  780
```

-continued gctatcccct ttgcacaatc cattttctac cggctcaacg gcgtgggcat tactcaacaa 840
gtcctgtcgg agaaccagaa gttgatcgca aacaagttca atcaggccct gggggccatg 900
cagactggat tcactacgac taacgaagcg ttccagaagg tccaggacgc tgtgaacaac 960
aacgcccagg cgctctcaaa gctggcctcc gaactcagca acaccttcgg agccatcagc 1020
gcatcgatcg gtgacataat tcagcggctg gacgtgctgg agcaggacgc ccagatcgac 1080
cgcctcatca acggacggct gaccaccttg aatgccttcg tggcacaaca gctggtccgg 1140
agcgaatcag cggcactttc cgcccaactc gccaaggaca aagtcaacga atgcgtgaag 1200
gcccagtcca agaggtccgg tttctgcggt caaggaaccc atattgtgtc cttcgtcgtg 1260
aacgcgccca acggtctgta ctttatgcac gtcggctact acccgagcaa tcatatcgaa 1320
gtggtgtccg cctacggcct gtgcgatgcc gctaacccca ctaactgtat tgcccctgtg 1380
aacggatatt ttattaagac caacaacacc cgcattgtgg acgaatggtc atacaccggt 1440
tcgtccttct acgcgcccga gcccatcact tcactgaaca ccaaatacgt ggctccgcaa 1500
gtgacctacc agaacatctc caccaatttg ccgccgccgc tgctcggaaa cagcaccgga 1560
attgatttcc aagatgaact ggacgaattc ttcaagaacg tgtccacttc cattcccaac 1620
ttcggaagcc tgacacagat caacaccacc cttctcgacc tgacctacga gatgctgagc 1680
cttcaacaag tggtcaaggc cctgaacgag agctacatcg acctgaagga gctgggcaac 1740
tatacctact acaacaagtg gccggacaag attgaggaga ttctgtcgaa aatctaccac 1800
attgaaaacg agatcgccag aatcaagaag cttatcggcg aagcc 1845

SEQ ID NO: 23 moltype = DNA length = 4071
FEATURE Location/Qualifiers
misc_feature 1..4071
note = Synthetic Polynucleotide
source 1..4071
mol_type = other DNA
organism = synthetic construct
SEQUENCE: 23
atggaaaccc ctgcccagct gctgttcctg ctgctgctgt ggctgcctga taccaccggc 60
agctatgtgg acgtgggccc cgatagcgtg aagtccgcct gtatcgaagt ggacatccag 120
cagacctttt tcgacaagac ctggcccaga cccatcgacg tgtccaaggc cgacggcatc 180
atctatccac aaggccggac ctacagcaac atcaccatta cctaccaggg cctgttccca 240
tatcaaggcg accacggcga tatgtacgtg tactctgccg gccacgccac cggcaccaca 300
ccccagaaac tgttcgtggc caactacagc caggacgtga agcagttcgc caacggcttc 360
gtcgtgcgga ttggcgccgc tgccaatagc accggcacag tgatcatcag ccccagcacc 420
agcgccacca tccggaagat ctaccccgcc ttcatgctgg gcagctccgt gggcaatttc 480
agcgacggca agatgggccg gttcttcaac cacaccctgg tgctgctgcc cgatggctgt 540
ggcacactgc tgagagcctt ctactgcatc ctggaaccca gaagcggcaa ccactgccct 600
gccggcaata gctacaccag cttcgccacc taccacacac ccgccaccga ttgctccgac 660
ggcaactaca accggaacgc cagcctgaac agcttcaaag agtacttcaa cctgcggaac 720
tgcaccttca tgtacaccta caatatcacc gaggacgaga tcctggaatg gttcggcatc 780
acccagaccg cccagggcgt gcacctgttc agcagcagat acgtggacct gtacggcggc 840
aacatgttcc agtttgccac cctgcccgtg tacgacacca tcaagtacta cagcatcatc 900
ccccacagca tccggtccat ccagagcgac agaaaagcct gggccgcctt ctacgtgtac 960
aagctgcagc ccctgacctt cctgctggac ttcagcgtgg acggctacat cagacgggcc 1020
atcgactgcg gcttcaacga cctgagccag ctgcactgct cctacgagag cttcgacgtg 1080
gaaagcggcg tgtacagcgt gtccagcttc gaggccaagc ctagcggcag cgtggtggaa 1140
caggctgagg gcgtggaatg cgacttcagc cctctgctga gcggcacccc tccccaggtg 1200
tacaacttca agcggctggt gttcaccaac tgcaattaca acctgaccaa gctgctgagc 1260
ctgttctccg tgaacgactt cacctgtagc cagatcagcc ctgccgccat tgccagcaac 1320
tgctacagca gcctgatcct ggactacttc agctaccccc tgagcatgaa gtccgatctg 1380
agcgtgtcct ccgccggacc catcagccag ttcaactaca agcagagctt cagcaaccct 1440
acctgcctga ttctggccac cgtgccccac aatctgacca ccatcaccaa gcccctgaag 1500
tacagctaca tcaacaagtg cagcagactg ctgtccgacg accggaccga agtgccccag 1560
ctcgtgaacg ccaaccagta cagcccctgc gtgtccatcg tgcccagcac cgtgtgggag 1620
gacggcgact actacagaaa gcagctgagc cccctggaag gcggcggatg gctggtggct 1680
tctggaagca cagtggccat gaccgagcag ctgcagatgg gctttggcat caccgtgcag 1740
tacggcaccg acaccaacag cgtgtgcccc aagctggaat tcgccaatga caccaagatc 1800
gccagccagc tgggaaactg cgtggaatac tccctgtatg gcgtgtccgg acggggcgtg 1860
ttccagaatt gcacagcagt gggagtgcgg cagcagagat tcgtgtacga tgcctaccag 1920
aacctcgtgg gctactacag cgacgacggc aattactact gcctgcgggc ctgtgtgtcc 1980
gtgcccgtgt ccgtgatcta cgacaaagag acaaagaccc acgccacact gttcggctcc 2040
gtggcctgcg agcacatcag ctccaccatg agccagtact cccgctccac ccggtccatg 2100
ctgaagcgga gagatagcac ctacggcccc ctgcagacac ctgtgggatg tgtgctgggc 2160
ctcgtgaaca gctccctgtt tgtggaagat tgcaagctgc ccctgggcca gagcctgtgt 2220
gccctgccag ataccoctag caccctgacc cctagaagcg tgcgctctgt gcccggcgaa 2280
atgcggctgg cctctatcgc cttcaatcac cccatccagg tggaccagct gaactccagc 2340
tacttcaagc tgagcatccc caccaacttc agcttcggcg tgacccagga gtacatccag 2400
accacaatcc agaaagtgac cgtggactgc aagcagtacg tgtgcaacgg ctttcagaag 2460
tgcgaacagc tgctgcgcga gtacggccag ttctgcagca agatcaacca ggccctgcac 2520
ggcgccaacc tgagacagga tgacagcgtg cggaacctgt tcgccagcgt gaaaagcagc 2580
cagtccagcc ccatcatccc tggcttcggc ggcgacttta acctgaccct gctggaacct 2640
gtgtccatca gcaccggctc cagaagcgcc agatccgcca tcgaggacct gctgttcgac 2700
aaagtgacca ttgccgaccc cggctacatg cagggctacg acgattgcat gcagcagggc 2760
ccagccagcg ccagggatct gatctgtgcc cagtatgtgg ccggctacaa ggtgctgccc 2820
cccctgatgg acgtgaacat ggaagccgcc tacacctcca gcctgctggg ctctattgct 2880
ggcgtgggat ggacagccgg cctgtctagc tttgccgcca tccctttcgc ccagagcatc 2940
ttctaccggc tgaacggcgt gggcatcaca caacaggtgc tgagcgagaa ccagaagctg 3000
atcgccaaca agtttaacca ggcactgggc gccatgcaga ccggcttcac caccaccaac 3060
gaggccttca gaaaggtgca ggacgccgtg aacaacaacg cccaggctct gagcaagctg 3120

-continued

```
gcctccgagc tgagcaatac cttcggcgcc atcagcgcct ccatcggcga catcatccag  3180
cggctggacg tgctggaaca ggacgcccag atcgaccggc tgatcaacgg cagactgacc  3240
accctgaacg ccttcgtggc acagcagctc gtgcggagcg aatctgccgc tctgtctgct  3300
cagctggcca aggacaaagt gaacgagtgc gtgaaggccc agtccaagcg gagcggcttt  3360
tgtggccagg gcacccacat cgtgtccttc gtcgtgaatg cccccaacgg cctgtacttt  3420
atgcacgtgg gctattaccc cagcaaccac atcgaggtgg tgtccgccta tggcctgtgc  3480
gacgccgcca atcctaccaa ctgtatcgcc cccgtgaacg gctacttcat caagaccaac  3540
aacacccgga tcgtggacga gtggtcctac acaggcagca gcttctacgc ccccgagccc  3600
atcacctccc tgaacaccaa atacgtggcc ccccaagtga cataccagaa catctccacc  3660
aacctgcccc ctccactgct gggaaattcc accggcatcg acttccagga cgagctggac  3720
gagttcttca agaacgtgtc cacctccatc cccaacttcg gcagcctgac ccagatcaac  3780
accactctgc tggacctgac ctacgagatg ctgtccctgc aacaggtcgt gaaagccctg  3840
aacgagagct acatcgacct gaaagagctg ggaactaca cctactacaa caagtggcct  3900
tggtacattt ggctgggctt tatcgccggc ctggtggccc tggccctgtg cgtgttcttc  3960
atcctgtgct gcaccggctg cggcaccaat tgcatgggca agctgaaatg caaccggtgc  4020
tgcgacagat acgaggaata cgacctggaa cctcacaaag tgcatgtgca c           4071

SEQ ID NO: 24          moltype = AA  length = 1353
FEATURE                Location/Qualifiers
source                 1..1353
                       mol_type = protein
                       note = Middle East respiratory syndrome coronavirus
                       organism = unidentified
SEQUENCE: 24
MIHSVFLLMF LLTPTESYVD VGPDSVKSAC IEVDIQQTFF DKTWPRPIDV SKADGIIYPQ  60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRLLSDD RTEVPQLVNA NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQYVA GYKVLPPLMD VNMEAAYTSS LLGSIAGVGW  960
TAGLSSFAAI PFAQSIFYRL NGVGITQQVL SENQKLIANK FNQALGAMQT GFTTTNEAFR  1020
KVQDAVNNNA QALSKLASEL SNTFGAISAS IGDIIQRLDV LEQDAQIDRL INGRLTTLNA  1080
FVAQQLVRSE SAALSAQLAK DKVNECVKAQ SKRSGFCGQG THIVSFVVNA PNGLYFMHVG  1140
YYPSNHIEVV SAYGLCDAAN PTNCIAPVNG YFIKTNNTRI VDEWSYTGSS FYAPEPITSL  1200
NTKYVAPQVT YQNISTNLPP PLLGNSTGID FQDELDEFFK NVSTSIPNFG SLTQINTTLL  1260
DLTYEMLSLQ QVVKALNESY IDLKELGNYT YYNKWPWYIW LGFIAGLVAL ALCVFFILCC  1320
TGCGTNCMGK LKCNRCCDRY EEYDLEPHKV HVH                                1353

SEQ ID NO: 25          moltype = AA  length = 1353
FEATURE                Location/Qualifiers
REGION                 1..1353
                       note = Synthetic Polypeptide
source                 1..1353
                       mol_type = protein
                       organism = synthetic construct
SEQUENCE: 25
MIHSVFLLMF LLTPTESYVD VGPDSVKSAC IEVDIQQTFF DKTWPRPIDV SKADGIIYPQ  60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRLLSDD RTEVPQLVNA NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQYVA GYKVLPPLMD VNMEAAYTSS LLGSIAGVGW  960
TAGLSSFAAI PFAQSIFYRL NGVGITQQVL SENQKLIANK FNQALGAMQT GFTTTNEAFQ  1020
KVQDAVNNNA QALSKLASEL SNTFGAISAS IGDIIQRLDV LEQDAQIDRL INGRLTTLNA  1080
FVAQQLVRSE SAALSAQLAK DKVNECVKAQ SKRSGFCGQG THIVSFVVNA PNGLYFMHVG  1140
YYPSNHIEVV SAYGLCDAAN PTNCIAPVNG YFIKTNNTRI VDEWSYTGSS FYAPEPITSL  1200
NTKYVAPQVT YQNISTNLPP PLLGNSTGID FQDELDEFFK NVSTSIPNFG SLTQINTTLL  1260
DLTYEMLSLQ QVVKALNESY IDLKELGNYT YYNKWPWYIW LGFIAGLVAL ALCVFFILCC  1320
TGCGTNCMGK LKCNRCCDRY EEYDLEPHKV HVH                                1353
```

```
SEQ ID NO: 26          moltype = AA  length = 615
FEATURE                Location/Qualifiers
REGION                 1..615
                       note = Synthetic Polypeptide
source                 1..615
                       mol_type = protein
                       organism = synthetic construct
SEQUENCE: 26
MIHSVFLLMF LLTPTESDCK LPLGQSLCAL PDTPSTLTPR SVRSVPGEMR LASIAFNHPI  60
QVDQLNSSYF KLSIPTNFSF GVTQEYIQTT IQKVTVDCKQ YVCNGFQKCE QLLREYGQFC  120
SKINQALHGA NLRQDDSVRN LFASVKSSQS SPIIPGFGGD FNLTLLEPVS ISTGSRSARS  180
AIEDLLFDKV TIADPGYMQG YDDCMQQGPA SARDLICAQY VAGYKVLPPL MDVNMEAAYT  240
SSLLGSIAGV GWTAGLSSFA AIPFAQSIFY RLNGVGITQQ VLSENQKLIA NKFNQALGAM  300
QTGFTTTNEA FQKVQDAVNN NAQALSKLAS ELSNTFGAIS ASIGDIIQRL DVLEQDAQID  360
RLINGRLTTL NAFVAQQLVR SESAALSAQL AKDKVNECVK AQSKRSGFCG QGTHIVSFVV  420
NAPNGLYFMH VGYYPSNHIE VVSAYGLCDA ANPTNCIAPV NGYFIKTNNT RIVDEWSYTG  480
SSFYAPEPIT SLNTKYVAPQ VTYQNISTNL PPPLLGNSTG IDFQDELDEF FKNVSTSIPN  540
FGSLTQINTT LLDLTYEMLS LQQVVKALNE SYIDLKELGN YTYYNKWPDK IEEILSKIYH  600
IENEIARIKK LIGEA                                                  615

SEQ ID NO: 27          moltype = AA  length = 1353
FEATURE                Location/Qualifiers
source                 1..1353
                       mol_type = protein
                       note = Middle East respiratory syndrome coronavirus
                       organism = unidentified
SEQUENCE: 27
MIHSVFLLMF LLTPTESYVD VGPDSVKSAC IEVDIQQTFF DKTWPRPIDV SKADGIIYPQ  60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRLLSDD RTEVPQLVNA NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQYVA GYKVLPPLMD VNMEAAYTSS LLGSIAGVGW  960
TAGLSSFAAI PFAQSIFYRL NGVGITQQVL SENQKLIANK FNQALGAMQT GFTTTNEAFR  1020
KVQDAVNNNA QALSKLASEL SNTFGAISAS IGDIIQRLDV LEQDAQIDRL INGRLTTLNA  1080
FVAQQLVRSE SAALSAQLAK DKVNECVKAQ SKRSGFCGQG THIVSFVVNA PNGLYFMHVG  1140
YYPSNHIEVV SAYGLCDAAN PTNCIAPVNG YFIKTNNTRI VDEWSYTGSS FYAPEPITSL  1200
NTKYVAPHVT YQNISTNLPP PLLGNSTGID FQDELDEFFK NVSTSIPNFG SLTQINTTLL  1260
DLTYEMLSLQ QVVKALNESY IDLKELGNYT YYNKWPWYIW LGFIAGLVAL ALCVFFILCC  1320
TGCGTNCMGK LKCNRCCDRY EEYDLEPHKV HVH                               1353

SEQ ID NO: 28          moltype = AA  length = 1353
FEATURE                Location/Qualifiers
source                 1..1353
                       mol_type = protein
                       note = Middle East respiratory syndrome coronavirus
                       organism = unidentified
SEQUENCE: 28
MIHSVFLLMF LLTPTESYVD VGPDSVKSAC IEVDIQQTFF DKTWPRPIDV SKADGIIYPQ  60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRLLSDD RTEVPQLVNA NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQYVA GYKVLPPLMD VNMEAAYTSS LLGSIAGVGW  960
TAGLSSFAAI PFAQSIFYRL NGVGITQQVL SENQKLIANK FNQALGAMQT GFTTTNEAFR  1020
KVQDAVNNNA QALSKLASEL SNTFGAISAS IGDIIQRLDV LEQDAQIDRL INGRLTTLNA  1080
FVAQQLVRSE SAALSAQLAK DKVNECVKAQ SKRSGFCGQG THIVSFVVNA PNGLYFMHVG  1140
YYPSNHIEVV SAYGLCDAAN PTNCIAPVNG YFIKTNNTRI VDEWSYTGSS FYAPEPITSL  1200
```

-continued

```
NTKYVAPHVT YQNISTNLPP PLLGNSTGID FQDELDEFFK NVSTSIPNFG SLTQINTTLL  1260
DLTYEMLSLQ QVVKALNESY IDLKELGNYT YYNKWPWYIW LGFIAGLVAL ALCVFFILCC  1320
TGCGTNCMGK LKCNRCCDRY EEYDLEPHKV HVH                               1353

SEQ ID NO: 29          moltype = AA  length = 1255
FEATURE                Location/Qualifiers
source                 1..1255
                       mol_type = protein
                       note = Human SARS coronavirus
                       organism = unidentified
SEQUENCE: 29
MFIFLLFLTL TSGSDLDRCT TFDDVQAPNY TQHTSSMRGV YYPDEIFRSD TLYLTQDLFL  60
PFYSNVTGFH TINHTFGNPV IPFKDGIYFA ATEKSNVVRG WVFGSTMNNK SQSVIIINNS  120
TNVVIRACNF ELCDNPFFAV SKPMGTQTHT MIFDNAFNCT FEYISDAFSL DVSEKSGNFK  180
HLREFVFKNK DGFLYVYKGY QPIDVVRDLP SGFNTLKPIF KLPLGINITN FRAILTAFSP  240
AQDIWGTSAA AYFVGYLKPT TFMLKYDENG TITDAVDCSQ NPLAELKCSV KSFEIDKGIY  300
QTSNFRVVPS GDVVRFPNIT NLCPFGEVFN ATKFPSVYAW ERKKISNCVA DYSVLYNSTF  360
FSTFKCYGVS ATKLNDLCFS NVYADSFVVK GDDVRQIAPG QTGVIADYNY KLPDDFMGCV  420
LAWNTRNIDA TSTGNYNYKY RYLRHGKLRP FERDISNVPF SPDGKPCTPP ALNCYWPLND  480
YGFYTTTGIG YQPYRVVVLS FELLNAPATV CGPKLSTDLI KNQCVNFNFN GLTGTGVLTP  540
SSKRFQPFQQ FGRDVSDFTD SVRDPKTSEI LDISPCSFGG VSVITPGTNA SSEVAVLYQD  600
VNCTDVSTAI HADQLTPAWR IYSTGNNVFQ TQAGCLIGAE HVDTSYECDI PIGAGICASY  660
HTVSLLRSTS QKSIVAYTMS LGADSSIAYS NNTIAIPTNF SISITTEVMP VSMAKTSVDC  720
NMYICGDSTE CANLLLQYGS FCTQLNRALS GIAAEQDRNT REVFAQVKQM YKTPTLKYFG  780
GFNFSQILPD PLKPTKRSFI EDLLFNKVTL ADAGFMKQYG ECLGDINARD LICAQKFNGL  840
TVLPPLLTDD MIAAYTAALV SGTATAGWTF GAGAALQIPF AMQMAYRFNG IGVTQNVLYE  900
NQKQIANQFN KAISQIQESL TTTSTALGKL QDVVNQNAQA LNTLVKQLSS NFGAISSVLN  960
DILSRLDKVE AEVQIDRLIT GRLQSLQTYV TQQLIRAAEI RASANLAATK MSECVLGQSK  1020
RVDFCGKGYH LMSFPQAAPH GVVFLHVTYV PSQERNFTTA PAICHEGKAY FPREGVFVFN  1080
GTSWFITQRN FFSPQIITTD NTFVSGNCDV VIGIINNTVY DPLQPELDSF KEELDKYFKN  1140
HTSPDVDLGD ISGINASVVN IQKEIDRLNE VAKNLNESLI DLQELGKYEQ YIKWPWYVWL  1200
GFIAGLIAIV MVTILLCCMT SCCSCLKGAC SCGSCCKFDE DDSEPVLKGV KLHYT        1255

SEQ ID NO: 30          moltype = AA  length = 1353
FEATURE                Location/Qualifiers
source                 1..1353
                       mol_type = protein
                       note = Human coronavirus
                       organism = unidentified
SEQUENCE: 30
MFLILLISLP TAFAVIGDLK CTSDNINDKD TGPPPISTDT VDVTNGLGTY YVLDRVYLNT  60
TLFLNGYYPT SGSTYRNMAL KGSVLLSRLW FKPPFLSDFI NGIFAKVKNT KVIKDRVMYS  120
EFPAITIGST FVNTSYSVVV QPRTINSTQD GDNKLQGLLE VSVCQYNMCE YPQTICHPNL  180
GNHRKELWHL DTGVVSCLYK RNFTYDVNAD YLYFHFYQEG GTFYAYFTDT GVVTKFLFNV  240
YLGMALSHYY VMPLTCNSKL TLEYWVTPLT SRQYLLAFNQ DGIIFNAEDC MSDFMSEIKC  300
KTQSIAPPTG VYELNGYTVQ PIADVYRRKP NLPNCNIEAW LNDKSVPSPL NWERKTFSNC  360
NFNMSSLMSF IQADSFTCNN IDAAKIYGMC FSSITIDKFA IPNGRKVDLQ LGNLGYLQSF  420
NYRIDTTATS CQLYYNLPAA NVSVSRFNPS TWNKRFGFIE DSVFKPRPAG VLTNHDVVYA  480
QHCFKAPKNF CPCKLNGSCV GSGPGKNNGI GTCPAGTNYL TCDNLCTPDP ITFTGTYKCP  540
QTKSLVGIGE HCSGLAVKSD YCGGNSCTCR PQAFLGWSAD SCLQGDKCNI FANFILHDVN  600
SGLTCSTDLQ KANTDIILGV CVNYDLYGIL GQGIFVEVNA TYYNSWQNLL YDSNGNLYGF  660
RDYIINRTFM IRSCYSGRVS AAFHANSSEP ALLFRNIKCN YVFNNSLTRQ LQPINYFDSY  720
LGCVVNAYNS TAISVQTCDL TVGSGYCVDY SKNRRSRGAI TTGYRFTNFE PFTVNSVNDS  780
LEPVGGLYEI QIPSEFTIGN MVEFIQTSSP KVTIDCAAFV CGDYAACKSQ LVEYGSFCDN  840
INAILTEVNE LLDTTQLQVA NSLMNGVTLS TKLKDGVNFN VDDINFSPVL GCLGSECSKA  900
SSRSAIEDLL FDKVKLSDVG FVEAYNNCTG GAEIRDLICV QSYKGIKVLP PLLSENQISG  960
YTLAATSASL FPPWTAAAGV PFYLNVQYRI NGLGVTMDVL SQNQKLIANA FNNALYAIQE  1020
GFDATNSALV KIQAVVNANA EALNNLLQQL SNRFGAISAS LQEILSRLDA LEAEAQIDRL  1080
INGRLTALNA YVSQQLSDST LVKFSAAQAM EKVNECVKSQ SSRINFCGNG NHIISLVQNA  1140
PYGLYFIHFS YVPTKYVTAR VSPGLCIAGD RGIAPKSGYF VNVNNTWMYT GSGYYYPEPI  1200
TENNVVVMST CAVNYTKAPY VMLNTSIPNL PDFKEELDQW FKNQTSVAPD LSLDYINVTF  1260
LDLQVEMNRL QEAIKVLNQS YINLKDIGTY EYYVKWPWYV WLLICLAGVA MLVLLFFICC  1320
CTGCGTSCFK KCGGCCDDYT GYQELVIKTS HDD                               1353

SEQ ID NO: 31          moltype = AA  length = 1351
FEATURE                Location/Qualifiers
source                 1..1351
                       mol_type = protein
                       note = Human coronavirus
                       organism = unidentified
SEQUENCE: 31
MFLIIFILPT TLAVIGDFNC TNSFINDYNK TIPRISEDVV DVSLGLGTYY VLNRVYLNTT  60
LLFTGYFPKS GANFRDLALK GSIYLSTLWY KPPFLSDFNN GIFSKVKNTK LYVNNTLYSE  120
FSTIVIGSVF VNTSYTIVVQ PHNGILEITA CQYTMCEYPH TVCKSKGSIR NESWHIDSSE  180
PLCLFKKNFT YNVSADWLYF HFYQERGVFY AYYADVGMPT TFLFSLYLGT ILSHYYVMPL  240
TCNAISSNTD NETLEYWVTP LSRRQYLLNF DEHGVITNAV DCSSSFLSEI QCKTQSFAPN  300
TGVYDLSGFT VKPVATVYRR IPNLPDCDID NWLNNVSVPS PLNWERRIFS NCNFNLSTLL  360
RLVHVDSFSC NNLDKSKIFG SCFNSITVDK FAIPNRRRDD LQLGSSGFLQ SSNYKIDISS  420
SSCQLYYSLP LVNVTINNFN PSSWNRRYGF GSFNLSSYDV VYSDHCFSVN SDFCPCADPS  480
```

```
VVNSCAKSKP PSAICPAGTK YRHCDLDTTL YVKNWCRCSC LPDPISTYSP NTCPQKKVVV  540
GIGEHCPGLG INEEKCGTQL NHSSCFCSPD AFLGWSFDSC ISNNRCNIFS NFIFNGINSG  600
TTCSNDLLYS NTEISTGVCV NYDLYGITGQ GIFKEVSAAY YNNWQNLLYD SNGNIIGFKD  660
FLTNKTYTIL PCYSGRVSAA FYQNSSSPAL LYRNLKCSYV LNNISFISQP FYFDSYLGCV  720
LNAVNLTSYS VSSCDLRMGS GFCIDYALPS SRRKRRGISS PYRFVTFEPF NVSFVNDSVE  780
TVGGLFEIQI PTNFTIAGHE EFIQTSSPKV TIDCSAFVCS NYAACHDLLS EYGTFCDNIN  840
SILNEVNDLL DITQLQVANA LMQGVTLSSN LNTNLHSDVD NIDFKSLLGC LGSQCGSSSR  900
SLLEDLLFNK VKLSDVGFVE AYNNCTGGSE IRDLLCVQSF NGIKVLPPIL SETQISGYTT  960
AATVAAMFPP WSAAAGVPFS LNVQYRINGL GVTMDVLNKN QKLIANAFNK ALLSIQNGFT  1020
ATNSALAKIQ SVVNANAQAL NSLLQQLFNK FGAISSSLQE ILSRLDNLEA QVQIDRLING  1080
RLTALNAYVS QQLSDITLIK AGASRAIEKV NECVKSQSPR INFCGNGNHI LSLVQNAPYG  1140
LLFIHFSYKP TSFKTVLVSP GLCLSGDRGI APKQGYFIKQ NDSWMFTGSS YYYPEPISDK  1200
NVVFMNSCSV NFTKAPFIYL NNSIPNLSDF EAELSLWFKN HTSIAPNLTF NSHINATFLD  1260
LYYEMNVIQE SIKSLNSSFI NLKEIGTYEM YVKWPWYIWL LIVILFIIFL MILFFICCCT  1320
GCGSACFSKC HNCCDEYGGH NDFVIKASHD D                                 1351

SEQ ID NO: 32          moltype = AA  length = 526
FEATURE                Location/Qualifiers
REGION                 1..526
                       note = Synthetic Polypeptide
source                 1..526
                       mol_type = protein
                       organism = synthetic construct
SEQUENCE: 32
MFIFLLFLTL TSGSDLDRAL SGIAAEQDRN TREVFAQVKQ MYKTPTLKYF GGFNFSQILP  60
DPLKPTKRSF IEDLLFNKVT LADAGFMKQY GECLGDINAR DLICAQKFNG LTVLPPLLTD  120
DMIAAYTAAL VSGTATAGWT FGAGAALQIP FAMQMAYRFN GIGVTQNVLY ENQKQIANQF  180
NKAISQIQES LTTTSTALGK LQDVVNQNAQ ALNTLVKQLS SNFGAISSVL NDILSRLDKV  240
EAEVQIDRLI TGRLQSLQTY VTQQLIRAAE IRASANLAAT KMSECVLGQS KRVDFCGKGY  300
HLMSFPQAAP HGVVFLHVTY VPSQERNFTT APAICHEGKA YFPREGVFVF NGTSWFITQR  360
NFFSPQIITT DNTFVSGNCD VVIGIINNTV YDPLQPELDS FKEELDKYFK NHTSPDVDLG  420
DISGINASVV NIQKEIDRLN EVAKNLNESL IDLQELGKYE QYIKWPWYVW LGFIAGLIAI  480
VMVTILLCCM TSCCSCLKGA CSCGSCCKFD EDDSEPVLKG VKLHYT                 526

SEQ ID NO: 33          moltype = AA  length = 588
FEATURE                Location/Qualifiers
REGION                 1..588
                       note = Synthetic Polypeptide
source                 1..588
                       mol_type = protein
                       organism = synthetic construct
SEQUENCE: 33
MIHSVFLLMF LLTPTESDCK LPLGQSLCAL PDTPSTLTPR SVRSVPGEMR LASIAFNHPI  60
QVDQLNSSYF KLSIPTNFSF GVTQEYIQTT IQKVTVDCKQ YVCNGFQKCE QLLREYGQFC  120
SKINQALHGA NLRQDDSVRN LFASVKSSQS SPIIPGFGGD FNLTLLEPVS ISTGSRSARS  180
AIEDLLFDKV TIADPGYMQG YDDCMQQGPA SARDLICAQY VAGYKVLPPL MDVNMEAAYT  240
SSLLGSIAGV GWTAGLSSFA AIPFAQSIFY RLNGVGITQQ VLSENQKLIA NKFNQALGAM  300
QTGFTTTNEA FQKVQDAVNN NAQALSKLAS ELSNTFGAIS ASIGDIIQRL DVLEQDAQID  360
RLINGRLTTL NAFVAQQLVR SESAALSAQL AKDKVNECVK AQSKRSGFCG QGTHIVSFVV  420
NAPNGLYFMH VGYYPSNHIE VVSAYGLCDA ANPTNCIAPV NGYFIKTNNT RIVDEWSYTG  480
SSFYAPEPIT SLNTKYVAPQ VTYQNISTNL PPPLLGNSTG IDFQDELDEF FKNVSTSIPN  540
FGSLTQINTT LLDLTYEMLS LQQVVKALNE SYIDLKELGN YTYYNKWP               588

SEQ ID NO: 34          moltype = AA  length = 526
FEATURE                Location/Qualifiers
REGION                 1..526
                       note = Synthetic Polypeptide
source                 1..526
                       mol_type = protein
                       organism = synthetic construct
SEQUENCE: 34
MFIFLLFLTL TSGSDLDRAL SGIAAEQDRN TREVFAQVKQ MYKTPTLKYF GGFNFSQILP  60
DPLKPTKRSF IEDLLFNKVT LADAGFMKQY GECLGDINAR DLICAQKFNG LTVLPPLLTD  120
DMIAAYTAAL VSGTATAGWT FGAGAALQIP FAMQMAYRFN GIGVTQNVLY ENQKQIANQF  180
NKAISQIQES LTTTSTALGK LQDVVNQNAQ ALNTLVKQLS SNFGAISSVL NDILSRLDKV  240
EAEVQIDRLI TGRLQSLQTY VTQQLIRAAE IRASANLAAT KMSECVLGQS KRVDFCGKGY  300
HLMSFPQAAP HGVVFLHVTY VPSQERNFTT APAICHEGKA YFPREGVFVF NGTSWFITQR  360
NFFSPQIITT DNTFVSGNCD VVIGIINNTV YDPLQPELDS FKEELDKYFK NHTSPDVDLG  420
DISGINASVV NIQKEIDRLN EVAKNLNESL IDLQELGKYE QYIKWPWYVW LGFIAGLIAI  480
VMVTILLCCM TSCCSCLKGA CSCGSCCKFD EDDSEPVLKG VKLHYT                 526

SEQ ID NO: 35          moltype = DNA  length = 1864
FEATURE                Location/Qualifiers
misc_feature           1..1864
                       note = Synthetic Polynucleotide
source                 1..1864
                       mol_type = other DNA
                       organism = synthetic construct
SEQUENCE: 35
```

-continued

```
tcaagctttt ggaccctcgt acagaagcta atacgactca ctatagggaa ataagagaga  60
aaagaagagt aagaagaaat ataagagcca ccatgggtct caaggtgaac gtctctgccg  120
tattcatggc agtactgtta actctccaaa cacccgccgg tcaaattcat tggggcaatc  180
tctctaagat aggggtagta ggaataggaa gtgcaagcta caaagttatg actcgttcca  240
gccatcaatc attagtcata aaattaatgc ccaatataac tctcctcaat aactgcacga  300
gggtagagat tgcagaatac aggagactac taagaacagt tttggaacca attagggatg  360
cacttaatgc aatgacccag aacataaggc cggttcagag cgtagcttca agtaggagac  420
acaagagatt tgcgggagta gtcctggcag gtgcggccct aggtgttgcc acagctgctc  480
agataacagc cggcattgca cttcaccggt ccatgctgaa ctctcaggcc atcgacaatc  540
tgagagcgag cctggaaact actaatcagg caattgaggc aatcagacaa gcagggcagg  600
agatgatatt ggctgttcag ggtgtccaag actacatcaa taatgagctg ataccgtcta  660
tgaaccagct atcttgtgat ctaatcggtc agaagctcgg gctcaaattg cttagatact  720
atacagaaat cctgtcatta tttggcccca gcctacggga ccccatatct gcggagatat  780
ctatccaggc tttgagttat gcacttggag gagatatcaa taaggtgtta gaaaagctcg  840
gatacagtgg aggcgattta ctaggcatct tagagagcag aggaataaag gctcggataa  900
ctcacgtcga cacagagtcc tacttcatag tcctcagtat agcctatccg acgctgtccg  960
agattaaggg ggtgattgtc caccggctag agggggtctc gtacaacata ggctctcaag  1020
agtggtatac cactgtgccc aagtatgttg caacccaagg gtaccttatc tcgaattttg  1080
atgagtcatc atgtactttc atgccagagg ggactgtgtg cagccaaaat gccttgtacc  1140
cgatgagtcc tctgctccaa gaatgcctcc gggggtccac caagtcctgt gctcgtacac  1200
tcgtatccgg gtcttttggg aaccggttca ttttatcaca agggaaccta atagccaatt  1260
gtgcatcaat tctttgtaag tgttacacaa caggtacgat tattaatcaa gaccctgaca  1320
agatcctaac atacattgct gccgatcgct gcccggtagt cgaggtgaac ggcgtgacca  1380
tccaagtcgg gagcaggagg tatccagacg ctgtgtactt gcacagaatt gacctcggtc  1440
ctcccatatc attggagagg ttggacgtag ggacaaatct ggggaatgca attgccaaat  1500
tggaggatgc caaggaattg ttggaatcat cggaccagat attgagaagt atgaaaggtt  1560
tatcgagcac tagcatagtc tacatcctga ttgcagtgtg tcttggaggg ttgataggga  1620
tccccacttt aatatgttgc tgcagggggc gttgtaacaa aaagggagaa caagttggta  1680
tgtcaagacc aggcctaaag cctgacctta caggaacatc aaaatcctat gtaagatcgc  1740
tttgatgata ataggctgga gcctcggtgg ccaagcttct tgccccttgg gcctcccccc  1800
agcccctcct ccccttcctg cacccgtacc cccgtggtct ttgaataaag tctgagtggg  1860
cggc                                                              1864
```

```
SEQ ID NO: 36          moltype = DNA  length = 1653
FEATURE                Location/Qualifiers
misc_feature           1..1653
                       note = Synthetic Polynucleotide
source                 1..1653
                       mol_type = other DNA
                       organism = synthetic construct
SEQUENCE: 36
atgggtctca aggtgaacgt ctctgccgta ttcatggcag tactgttaac tctccaaaca  60
cccgccggtc aaattcattg gggcaatctc tctaagatag gggtagtagg aataggaagt  120
gcaagctaca aagttatgac tcgttccagc catcaatcat tagtcataaa attaatgccc  180
aatataactc tcctcaataa ctgcacgagg gtagagattg cagaatacag gagactacta  240
agaacagttt tggaaccaat tagggatgca cttaatgcaa tgacccagaa cataaggccg  300
gttcagagcg tagcttcaag taggagacac aagagatttg cgggagtagt cctggcaggt  360
gcggccctag gtgttgccac agctgctcag ataacagccg gcattgcact tcaccggtcc  420
atgctgaact ctcaggccat cgacaatctg agagcgagcc tggaaactac taatcaggca  480
attgaggcaa tcagacaagc agggcaggag atgatattgg ctgttcaggg tgtccaagac  540
tacatcaata atgagctgat accgtctatg aaccagctat cttgtgatct aatcggtcag  600
aagctcgggc tcaaattgct tagatactat acagaaatcc tgtcattatt tggccccagc  660
ctacgggacc ccatatctgc ggagatatct atccaggctt tgagttatgc acttggagga  720
gatatcaata aggtgttaga aaagctcgga tacagtggag gcgatttact aggcatctta  780
gagagcagag gaataaaggc tcggataact cacgtcgaca cagagtccta cttcatagtc  840
ctcagtatag cctatccgac gctgtccgag attaaggggg tgattgtcca ccggctagag  900
ggggtctcgt acaacatagg ctctcaagag tggtatacca ctgtgcccaa gtatgttgca  960
acccaagggt accttatctc gaattttgat gagtcatcat gtactttcat gccagagggg  1020
actgtgtgca gccaaaatgc cttgtacccg atgagtcctc tgctccaaga atgcctccgg  1080
gggtccacca agtcctgtgc tcgtacactc gtatccgggt cttttgggaa ccggttcatt  1140
ttatcacaag ggaacctaat agccaattgt gcatcaattc tttgtaagtg ttacacaaca  1200
ggtacgatta ttaatcaaga ccctgacaag atcctaacat acattgctgc cgatcgctgc  1260
ccggtagtcg aggtgaacgg cgtgaccatc caagtcggga gcaggaggta tccagacgct  1320
gtgtacttgc acagaattga cctcggtcct cccatatcat tggagaggtt ggacgtaggg  1380
acaaatctgg ggaatgcaat tgccaaattg gaggatgcca aggaattgtt ggaatcatcg  1440
gaccagatat tgagaagtat gaaaggttta tcgagcacta gcatagtcta catcctgatt  1500
gcagtgtgtc ttggagggtt gatagggatc cccactttaa tatgttgctg caggggggcgt  1560
tgtaacaaaa agggagaaca agttggtatg tcaagaccag gcctaaagcc tgaccttaca  1620
ggaacatcaa aatcctatgt aagatcgctt tga                              1653
```

```
SEQ ID NO: 37          moltype = DNA  length = 1925
FEATURE                Location/Qualifiers
misc_feature           1..1925
                       note = Synthetic Polynucleotide
source                 1..1925
                       mol_type = other DNA
                       organism = synthetic construct
SEQUENCE: 37
ggggaaataa gagagaaaag aagagtaaga agaaatataa gagccaccat gggtctcaag  60
```

-continued

```
gtgaacgtct ctgccgtatt catggcagta ctgttaactc tccaaacacc cgccggtcaa  120
attcattggg gcaatctctc taagataggg gtagtaggaa taggaagtgc aagctacaaa  180
gttatgactc gttccagcca tcaatcatta gtcataaaat taatgcccaa tataactctc  240
ctcaataact gcacgagggt agagattgca gaatacagga gactactaag aacagttttg  300
gaaccaatta gggatgcact taatgcaatg acccagaaca taaggccggt tcagagcgta  360
gcttcaagta ggagacacaa gagatttgcg ggagtagtcc tggcaggtgc ggccctaggt  420
gttgccacag ctgctcagat aacagccggc attgcacttc accggtccat gctgaactct  480
caggccatcg acaatctgag agcgagcctg gaaactacta atcaggcaat tgaggcaatc  540
agacaagcag ggcaggagat gatattggct gttcagggtg tccaagacta catcaataat  600
gagctgatac cgtctatgaa ccagctatct tgtgatctaa tcggtcagaa gctcgggctc  660
aaattgctta gatactatac agaaatcctg tcattatttg gccccagcct acgggacccc  720
atatctgcgg agatatctat ccaggctttg agttatgcac ttggaggaga tatcaataag  780
gtgttagaaa agctcggata cagtggaggc gatttactag gcatcttaga gagcagagga  840
ataaaggctc ggataactca cgtcgacaca gagtcctact tcatagtcct cagtatagcc  900
tatccgacgc tgtccgagat taagggggtg attgtccacc ggctagaggg ggtctcgtac  960
aacataggct ctcaagagtg gtataccact gtgcccaagt atgttgcaac ccaagggtac  1020
cttatctcga attttgatga gtcatcatgt actttcatgc cagaggggac tgtgtgcagc  1080
caaaatgcct tgtacccgat gagtcctctg ctccaagaat gcctccgggg gtccaccaag  1140
tcctgtgctc gtacactcgt atccgggtct tttgggaacc ggttcatttt atcacaaggg  1200
aacctaatag ccaattgtgc atcaattctt tgtaagtgtt acacaacagg tacgattatt  1260
aatcaagacc ctgacaagat cctaacatac attgctgccg atcgctgccc ggtagtcgag  1320
gtgaacggcg tgaccatcca agtcgggagc aggaggtatc cagacgctgt gtacttgcac  1380
agaattgacc tcggtcctcc catatcattg gagaggttgg acgtagggac aaatctgggg  1440
aatgcaattg ccaaattgga ggatgccaag gaattgttgg aatcatcgga ccagatattg  1500
agaagtatga aaggtttatc gagcactagc atagtctaca tcctgattgc agtgtgtctt  1560
ggagggttga tagggatccc cactttaata tgttgctgca gggggcgttg taacaaaaag  1620
ggagaacaag ttggtatgtc aagaccaggc ctaaagcctg accttacagg aacatcaaaa  1680
tcctatgtaa gatcgctttg atgataatag gctggagcct cggtggccaa gcttcttgcc  1740
ccttgggcct ccccccagcc cctcctcccc ttcctgcacc cgtacccccg tggtctttga  1800
ataaagtctg agtgggcggc aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
tctag                                                              1925
```

```
SEQ ID NO: 38          moltype = DNA  length = 1864
FEATURE                Location/Qualifiers
misc_feature           1..1864
                       note = Synthetic Polynucleotide
source                 1..1864
                       mol_type = other DNA
                       organism = synthetic construct
SEQUENCE: 38
tcaagctttt ggaccctcgt acagaagcta atacgactca ctatagggaa ataagagaga  60
aaagaagagt aagaagaaat ataagagcca ccatgggtct caaggtgaac gtctctgtca  120
tattcatggc agtactgtta actcttcaaa cacccaccgg tcaaatccat tggggcaatc  180
tctctaagat aggggtggta ggggtaggaa gtgcaagcta caaagttatg actcgttcca  240
gccatcaatc attagtcata aagttaatgc ccaatataac tctcctcaac aattgcacga  300
gggtagggat tgcagaatac aggagactac tgagaacagt tctggaacca attagagatg  360
cacttaatgc aatgacccag aatataagac cggttcagag tgtagcttca agtaggagac  420
acaagagatt tgcgggagtt gtcctggcag gtgcggccct aggcgttgcc acagctgctc  480
aaataacagc cggtattgca cttcaccagt ccatgctgaa ctctcaagcc atcgacaatc  540
tgagagcgag cctagaaact actaatcagg caattgaggc aatcagacaa gcagggcagg  600
agatgatatt ggctgttcag ggtgtccaag actacatcaa taatgagctg ataccgtcta  660
tgaatcaact atcttgtgat ttaatcggcc agaagctagg gctcaaattg ctcagatact  720
atacagaaat cctgtcatta tttggcccca gcttacggga ccccatatct gcggagatat  780
ctatccaggc tttgagctat gcgcttggag gagatatcaa taaggtgttg gaaaagctcg  840
gatacagtgg aggtgatcta ctgggcatct tagagagcag aggaataaag gcccggataa  900
ctcacgtcga cacagagtcc tacttcattg tactcagtat agcctatccg acgctatccg  960
agattaaggg ggtgattgtc caccggctag agggggtctc gtacaacata ggctctcaag  1020
agtggtatac cactgtgccc aagtatgttg caacccaagg gtaccttatc tcgaattttg  1080
atgagtcatc atgcactttc atgccagagg ggactgtgtg cagccagaat gccttgtacc  1140
cgatgagtcc tctgctccaa gaatgcctcc gggggtccac taagtcctgt gctcgtacac  1200
tcgtatccgg gtctttcggg aaccggttca ttttatcaca ggggaaccta atagccaatt  1260
gtgcatcaat cctttgcaag tgttacacaa caggaacaat cattaatcaa gaccctgaca  1320
agatcctaac atacattgct gccgatcact gcccggtggt cgaggtgaat ggcgtgacca  1380
tccaagtcgg gagcaggagg tatccggacg ctgtgtactt gcacaggatt gacctcggtc  1440
ctcccatatc tttggagagg ttggacgtag ggacaaatct ggggaatgca attgctaagt  1500
tggaggatgc caaggaattg ttggagtcat cggaccagat attgaggagt atgaaaggtt  1560
tatcgagcac tagtatagtt tacatcctga ttgcagtgtg tcttggagga ttgataggga  1620
tccccgcttt aatatgttgc tgcagggggc gttgtaacaa gaagggagaa caagttggta  1680
tgtcaagacc aggcctaaag cctgatctta caggaacatc aaaatcctat gtaaggtcac  1740
tctgatgata ataggctgga gcctcggtgg ccaagcttct tgccccttgg gcctcccccc  1800
agcccctcct ccccttcctg cacccgtacc cccgtggtct ttgaataaag tctgagtggg  1860
cggc                                                               1864
```

```
SEQ ID NO: 39          moltype = DNA  length = 1653
FEATURE                Location/Qualifiers
misc_feature           1..1653
                       note = Synthetic Polynucleotide
source                 1..1653
```

```
                        mol_type = other DNA
                        organism = synthetic construct
SEQUENCE: 39
atgggtctca aggtgaacgt ctctgtcata ttcatggcag tactgttaac tcttcaaaca  60
cccaccggtc aaatccattg gggcaatctc tctaagatag gggtggtagg ggtaggaagt  120
gcaagctaca aagttatgac tcgttccagc catcaatcat tagtcataaa gttaatgccc  180
aatataactc tcctcaacaa ttgcacgagg gtagggattg cagaatacag gagactactg  240
agaacagttc tggaaccaat tagagatgca cttaatgcaa tgacccagaa tataagaccg  300
gttcagagtg tagcttcaag taggagacac aagagatttg cgggagttgt cctggcaggt  360
gcggccctag gcgttgccac agctgctcaa ataacagccg gtattgcact tcaccagtcc  420
atgctgaact ctcaagccat cgacaatctg agagcgagcc tagaaactac taatcaggca  480
attgaggcaa tcagacaagc agggcaggag atgatattgg ctgttcaggg tgtccaagac  540
tacatcaata atgagctgat accgtctatg aatcaactat cttgtgattt aatcggccag  600
aagctagggc tcaaattgct cagatactat acagaaatcc tgtcattatt tggccccagc  660
ttacgggacc ccatatctgc ggagatatct atccaggctt tgagctatgc gcttggagga  720
gatatcaata aggtgttgga aaagctcgga tacagtggag gtgatctact gggcatctta  780
gagagcagag gaataaaggc ccggataact cacgtcgaca cagagtccta cttcattgta  840
ctcagtatag cctatccgac gctatccgag attaaggggg tgattgtcca ccggctagag  900
ggggtctcgt acaacatagg ctctcaagag tggtatacca ctgtgcccaa gtatgttgca  960
acccaagggt accttatctc gaattttgat gagtcatcat gcactttcat gccagagggg  1020
actgtgtgca gccagaatgc cttgtacccg atgagtcctc tgctccaaga atgcctccgg  1080
gggtccacta agtcctgtgc tcgtacactc gtatccgggt ctttcgggaa ccggttcatt  1140
ttatcacagg ggaacctaat agccaattgt gcatcaatcc tttgcaagtg ttacacaaca  1200
ggaacaatca ttaatcaaga ccctgacaag atcctaacat acattgctgc cgatcactgc  1260
ccggtggtcg aggtgaatgg cgtgaccatc caagtcggga gcaggaggta tccggacgct  1320
gtgtacttgc acaggattga cctcggtcct cccatatctt tggagaggtt ggacgtaggg  1380
acaaatctgg ggaatgcaat tgctaagttg gaggatgcca aggaattgtt ggagtcatcg  1440
gaccagatat tgaggagtat gaaaggttta tcgagcacta gtatagttta catcctgatt  1500
gcagtgtgtc ttggaggatt gatagggatc cccgctttaa tatgttgctg caggggggcgt  1560
tgtaacaaga agggagaaca agttggtatg tcaagaccag gcctaaagcc tgatcttaca  1620
ggaacatcaa aatcctatgt aaggtcactc tga                              1653

SEQ ID NO: 40           moltype = DNA  length = 1925
FEATURE                 Location/Qualifiers
misc_feature            1..1925
                        note = Synthetic Polynucleotide
source                  1..1925
                        mol_type = other DNA
                        organism = synthetic construct
SEQUENCE: 40
ggggaaataa gagagaaaag aagagtaaga agaaatataa gagccaccat gggtctcaag  60
gtgaacgtct ctgtcatatt catggcagta ctgttaactc ttcaaacacc caccggtcaa  120
atccattggg gcaatctctc taagataggg gtggtagggg taggaagtgc aagctacaaa  180
gttatgactc gttccagcca tcaatcatta gtcataaagt taatgcccaa tataactctc  240
ctcaacaatt gcacgagggt agggattgca gaatacagga gactactgag aacagttctg  300
gaaccaatta gagatgcact taatgcaatg acccagaata taagaccggt tcagagtgta  360
gcttcaagta ggagacacaa gagatttgcg ggagttgtcc tggcaggtgc ggccctaggc  420
gttgccacag ctgctcaaat aacagccggt attgcacttc accagtccat gctgaactct  480
caagccatcg acaatctgag agcgagccta gaaactacta atcaggcaat tgaggcaatc  540
agacaagcag ggcaggagat gatattggct gttcagggtg tccaagacta catcaataat  600
gagctgatac cgtctatgaa tcaactatct tgtgatttaa tcggccagaa gctagggctc  660
aaattgctca gatactatac agaaatcctg tcattatttg gccccagctt acgggacccc  720
atatctgcgg agatatctat ccaggctttg agctatgcgc ttggaggaga tatcaataag  780
gtgttggaaa agctcggata cagtggaggt gatctactgg gcatcttaga gagcagagga  840
ataaaggccc ggataactca cgtcgacaca gagtcctact tcattgtact cagtatagcc  900
tatccgacgc tatccgagat taagggggtg attgtccacc ggctagaggg ggtctcgtac  960
aacataggct ctcaagagtg gtataccact gtgcccaagt atgttgcaac ccaagggtac  1020
cttatctcga attttgatga gtcatcatgc actttcatgc cagaggggac tgtgtgcagc  1080
cagaatgcct tgtacccgat gagtcctctg ctccaagaat gcctccgggg gtccactaag  1140
tcctgtgctc gtacactcgt atccgggtct ttcgggaacc ggttcatttt atcacagggg  1200
aacctaatag ccaattgtgc atcaatcctt tgcaagtgtt acacaacagg aacaatcatt  1260
aatcaagacc ctgacaagat cctaacatac attgctgccg atcactgccc ggtggtcgag  1320
gtgaatggcg tgaccatcca agtcgggagc aggaggtatc cggacgctgt gtacttgcac  1380
aggattgacc tcggtcctcc catatctttg gagaggttgg acgtagggac aaatctgggg  1440
aatgcaattg ctaagttgga ggatgccaag gaattgttgg agtcatcgga ccagatattg  1500
aggagtatga aaggtttatc gagcactagt atagtttaca tcctgattgc agtgtgtctt  1560
ggaggattga tagggatccc cgctttaata tgttgctgca gggggcgttg taacaagaag  1620
ggagaacaag ttggtatgtc aagaccaggc ctaaagcctg atcttacagg aacatcaaaa  1680
tcctatgtaa ggtcactctg atgataatag gctggagcct cggtggccaa gcttcttgcc  1740
ccttgggcct ccccccagcc cctcctcccc ttcctgcacc cgtacccccg tggtctttga  1800
ataaagtctg agtgggcggc aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
tctag                                                             1925

SEQ ID NO: 41           moltype = DNA  length = 2065
FEATURE                 Location/Qualifiers
misc_feature            1..2065
                        note = Synthetic Polynucleotide
source                  1..2065
```

```
                        mol_type = other DNA
                        organism = synthetic construct
SEQUENCE: 41
tcaagctttt ggaccctcgt acagaagcta atacgactca ctatagggaa ataagagaga  60
aaagaagagt aagaagaaat ataagagcca ccatgtcacc gcaacgagac cggataaatg  120
ccttctacaa agataaccct tatcccaagg gaagtaggat agttattaac agagaacatc  180
ttatgattga cagaccctat gttctgctgg ctgttctgtt cgtcatgttt ctgagcttga  240
tcggattgct ggcaattgca ggcattagac ttcatcgggc agccatctac accgcggaga  300
tccataaaag cctcagtacc aatctggatg tgactaactc catcgagcat caggtcaagg  360
acgtgctgac accactcttt aaaatcatcg gggatgaagt gggcctgaga acacctcaga  420
gattcactga cctagtgaaa ttcatctcgg acaagattaa attccttaat ccggataggg  480
agtacgactt cagagatctc acttggtgca tcaacccgcc agagaggatc aaactagatt  540
atgatcaata ctgtgcagat gtggctgctg aagagctcat gaatgcattg gtgaactcaa  600
ctctactgga gaccagaaca accactcagt tcctagctgt ctcaaaggga aactgctcag  660
ggcccactac aatcagaggt caattctcaa acatgtcgct gtccttgttg gacttgtact  720
taggtcgagg ttacaatgtg tcatctatag tcactatgac atcccaggga atgtatgggg  780
gaacctacct agttgaaaag cctaatctga acagcaaagg gtcagagttg tcacaactga  840
gcatgtaccg agtgtttgaa gtaggtgtga tcagaaaccc gggtttgggg gctccggtgt  900
tccatatgac aaactatttt gagcaaccag tcagtaatgg tctcggcaac tgtatggtgg  960
ctttggggga gctcaaactc gcagcccttt gtcacgggga cgattctatc ataattccct  1020
atcagggatc agggaaaggt gtcagcttcc agctcgtcaa gctgggtgtc tggaaatccc  1080
caaccgacat gcaatcctgg gtccccttat caacggatga tccagtggta gacaggcttt  1140
acctctcatc tcacagaggt gtcatcgctg acaatcaagc aaaatgggct gtcccgacaa  1200
cacgaacaga tgacaagttg cgaatggaga catgcttcca gcaggcgtgt aaaggtaaaa  1260
tccaagcact ctgcgagaat cccgagtggg taccattgaa ggataacagg attccttcat  1320
acggggtcct gtctgttgat ctgagtctga cggttgagct taaaatcaaa attgcttcgg  1380
gattcgggcc attgatcaca cacggctcag ggatggacct atacaaatcc aactgcaaca  1440
atgtgtattg gctgactatt ccgccaatga gaaatctagc cttaggcgta atcaacacat  1500
tggagtggat accgagattc aaggttagtc ccaacctctt cactgtccca attaaggaag  1560
caggcgaaga ctgccatgcc ccaacatacc tacctgcgga ggtggacggt gatgtcaaac  1620
tcagttccaa cctggtgatt ctacctggtc aagatctcca atatgttttg gcaacctacg  1680
atacctccag ggttgagcat gctgtggttt attacgttta cagcccaagc cgctcatttt  1740
cttactttta tccttttagg ttgcctataa agggggtccc aatcgaacta caagtggaat  1800
gcttcacatg ggatcaaaaa ctctggtgcc gtcacttctg tgtgcttgcg gactcagaat  1860
ccggtggact tatcactcac tctgggatgg tgggcatggg agtcagctgc acagctaccc  1920
gggaagatgg aaccaatcgc agataatgat aataggctgg agcctcggtg gccaagcttc  1980
ttgccccttg ggcctccccc cagcccctcc tccccttcct gcacccgtac ccccgtggtc  2040
tttgaataaa gtctgagtgg gcggc                                        2065

SEQ ID NO: 42           moltype = DNA  length = 1854
FEATURE                 Location/Qualifiers
misc_feature            1..1854
                        note = Synthetic Polynucleotide
source                  1..1854
                        mol_type = other DNA
                        organism = synthetic construct
SEQUENCE: 42
atgtcaccgc aacgagaccg gataaatgcc ttctacaaag ataaccctta tcccaaggga  60
agtaggatag ttattaacag agaacatctt atgattgaca gaccctatgt tctgctggct  120
gttctgttcg tcatgtttct gagcttgatc ggattgctgg caattgcagg cattagactt  180
catcgggcag ccatctacac cgcggagatc cataaaagcc tcagtaccaa tctggatgtg  240
actaactcca tcgagcatca ggtcaaggac gtgctgacac cactctttaa aatcatcggg  300
gatgaagtgg gcctgagaac acctcagaga ttcactgacc tagtgaaatt catctcggac  360
aagattaaat tccttaatcc ggatagggag tacgacttca gagatctcac ttggtgcatc  420
aacccgccag agaggatcaa actagattat gatcaatact gtgcagatgt ggctgctgaa  480
gagctcatga atgcattggt gaactcaact ctactggaga ccagaacaac cactcagttc  540
ctagctgtct caaagggaaa ctgctcaggg cccactacaa tcagaggtca attctcaaac  600
atgtcgctgt ccttgttgga cttgtactta ggtcgaggtt acaatgtgtc atctatagtc  660
actatgacat cccagggaat gtatgggga acctacctag ttgaaaagcc taatctgaac  720
agcaaagggt cagagttgtc acaactgagc atgtaccgag tgtttgaagt aggtgtgatc  780
agaaacccgg gtttgggggc tccggtgttc catatgacaa actattttga gcaaccagtc  840
agtaatggtc tcggcaactg tatggtggct ttgggggagc tcaaactcgc agccctttgt  900
cacggggacg attctatcat aattccctat cagggatcag ggaaaggtgt cagcttccag  960
ctcgtcaagc tgggtgtctg gaaatcccca accgacatgc aatcctgggt ccccttatca  1020
acggatgatc cagtggtaga caggctttac ctctcatctc acagaggtgt catcgctgac  1080
aatcaagcaa aatgggctgt cccgacaaca cgaacagatg acaagttgcg aatggagaca  1140
tgcttccagc aggcgtgtaa aggtaaaatc caagcactct gcgagaatcc cgagtgggta  1200
ccattgaagg ataacaggat tccttcatac ggggtcctgt ctgttgatct gagtctgacg  1260
gttgagctta aaatcaaaat tgcttcggga ttcgggccat tgatcacaca cggctcaggg  1320
atggacctat acaaatccaa ctgcaacaat gtgtattggc tgactattcc gccaatgaga  1380
aatctagcct taggcgtaat caacacattg gagtggatac cgagattcaa ggttagtccc  1440
aacctcttca ctgtcccaat taaggaagca ggcgaagact gccatgcccc aacataccta  1500
cctgcggagg tggacggtga tgtcaaactc agttccaacc tggtgattct acctggtcaa  1560
gatctccaat atgttttggc aacctacgat acctccaggg ttgagcatgc tgtggtttat  1620
tacgtttaca gcccaagccg ctcatttttct tacttttatc cttttaggtt gcctataaag  1680
ggggtcccaa tcgaactaca agtggaatgc ttcacatggg atcaaaaact ctggtgccgt  1740
cacttctgtg tgcttgcgga ctcagaatcc ggtggactta tcactcactc tgggatggtg  1800
ggcatgggag tcagctgcac agctacccgg gaagatggaa ccaatcgcag ataa        1854
```

```
SEQ ID NO: 43           moltype = DNA  length = 2126
FEATURE                 Location/Qualifiers
misc_feature            1..2126
                        note = Synthetic Polynucleotide
source                  1..2126
                        mol_type = other DNA
                        organism = synthetic construct
SEQUENCE: 43
ggggaaataa gagagaaaag aagagtaaga agaaatataa gagccaccat gtcaccgcaa  60
cgagaccgga taaatgcctt ctacaaagat aacccttatc ccaagggaag taggatagtt  120
attaacagag aacatcttat gattgacaga ccctatgttc tgctggctgt tctgttcgtc  180
atgtttctga gcttgatcgg attgctggca attgcaggca ttagacttca tcgggcagcc  240
atctacaccg cggagatcca taaaagcctc agtaccaatc tggatgtgac taactccatc  300
gagcatcagg tcaaggacgt gctgacacca ctctttaaaa tcatcgggga tgaagtgggc  360
ctgagaacac ctcagagatt cactgaccta gtgaaattca tctcggacaa gattaaattc  420
cttaatccgg atagggagta cgacttcaga gatctcactt ggtgcatcaa cccgccagag  480
aggatcaaac tagattatga tcaatactgt gcagatgtgg ctgctgaaga gctcatgaat  540
gcattggtga actcaactct actggagacc agaacaacca ctcagttcct agctgtctca  600
aagggaaact gctcagggcc cactacaatc agaggtcaat tctcaaacat gtcgctgtcc  660
ttgttggact tgtacttagg tcgaggttac aatgtgtcat ctatagtcac tatgacatcc  720
cagggaatgt atgggggaac ctacctagtt gaaaagccta atctgaacag caaagggtca  780
gagttgtcac aactgagcat gtaccgagtg tttgaagtag gtgtgatcag aaacccgggt  840
ttgggggctc cggtgttcca tatgacaaac tattttgagc aaccagtcag taatggtctc  900
ggcaactgta tggtggcttt gggggagctc aaactcgcag ccctttgtca cggggacgat  960
tctatcataa ttccctatca gggatcaggg aaaggtgtca gcttccagct cgtcaagctg  1020
ggtgtctgga aatccccaac cgacatgcaa tcctgggtcc ccttatcaac ggatgatcca  1080
gtggtagaca ggctttacct ctcatctcac agaggtgtca tcgctgacaa tcaagcaaaa  1140
tgggctgtcc cgacaacacg aacagatgac aagttgcgaa tggagacatg cttccagcag  1200
gcgtgtaaag gtaaaatcca agcactctgc gagaatcccg agtgggtacc attgaaggat  1260
aacaggattc cttcatacgg ggtcctgtct gttgatctga gtctgacggt tgagcttaaa  1320
atcaaaattg cttcgggatt cgggccattg atcacacacg gctcagggat ggacctatac  1380
aaatccaact gcaacaatgt gtattggctg actattccgc caatgagaaa tctagcctta  1440
ggcgtaatca acacattgga gtggataccg agattcaagg ttagtcccaa cctcttcact  1500
gtcccaatta aggaagcagg cgaagactgc catgccccaa catacctacc tgcggaggtg  1560
gacggtgatg tcaaactcag ttccaacctg gtgattctac ctggtcaaga tctccaatat  1620
gttttggcaa cctacgatac ctccagggtt gagcatgctg tggtttatta cgtttacagc  1680
ccaagccgct cattttctta cttttatcct tttaggttgc ctataaaggg ggtcccaatc  1740
gaactacaag tggaatgctt cacatgggat caaaaactct ggtgccgtca cttctgtgtg  1800
cttgcggact cagaatccgg tggacttatc actcactctg ggatggtggg catgggagtc  1860
agctgcacag ctacccggga agatggaacc aatcgcagat aatgataata ggctggagcc  1920
tcggtggcca agcttcttgc cccttgggcc tccccccagc ccctcctccc cttcctgcac  1980
ccgtaccccc gtggtctttg aataaagtct gagtgggcgg caaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa atctag                                       2126

SEQ ID NO: 44           moltype = DNA  length = 2065
FEATURE                 Location/Qualifiers
misc_feature            1..2065
                        note = Synthetic Polynucleotide
source                  1..2065
                        mol_type = other DNA
                        organism = synthetic construct
SEQUENCE: 44
tcaagctttt ggaccctcgt acagaagcta atacgactca ctatagggaa ataagagaga  60
aaagaagagt aagaagaaat ataagagcca ccatgtcacc acaacgagac cggataaatg  120
ccttctacaa agacaacccc catcctaagg gaagtaggat agttattaac agagaacatc  180
ttatgattga tagaccttat gttttgctgg ctgttctatt cgtcatgttt ctgagcttga  240
tcgggttgct agccattgca ggcattagac ttcatcgggc agccatctac accgcagaga  300
tccataaaag cctcagcacc aatctggatg taactaactc aatcgagcat caggttaagg  360
acgtgctgac accactcttc aagatcatcg gtgatgaagt gggcttgagg acacctcaga  420
gattcactga cctagtgaag ttcatctctg acaagattaa attccttaat ccggacaggg  480
aatacgactt cagagatctc acttggtgta tcaacccgcc agagagaatc aaattggatt  540
atgatcaata ctgtgcagat gtggctgctg aagaactcat gaatgcattg gtgaactcaa  600
ctctactgga gaccagggca accaatcagt tcctagctgt ctcaaaggga aactgctcag  660
ggcccactac aatcagaggc caattctcaa acatgtcgct gtccctgttg gacttgtatt  720
taagtcgagg ttacaatgtg tcatctatag tcactatgac atcccaggga atgtacgggg  780
gaacttacct agtggaaaag cctaatctga gcagcaaagg gtcagagttg tcacaactga  840
gcatgcaccg agtgtttgaa gtaggtgtta tcagaaatcc gggtttgggg gctccggtat  900
tccatatgac aaactatctt gagcaaccag tcagtaatga tttcagcaac tgcatggtgg  960
ctttggggga gctcaagttc gcagccctct gtcacaggga agattctatc acaattccct  1020
atcagggatc agggaaaggt gtcagcttcc agcttgtcaa gctaggtgtc tggaaatccc  1080
caaccgacat gcaatcctgg gtccccctat caacggatga tccagtgata gacaggcttt  1140
acctctcatc tcacagaggc gttatcgctg acaatcaagc aaaatgggct gtcccgacaa  1200
cacggacaga tgacaagttg cgaatggaga catgcttcca gcaggcgtgt aagggtaaaa  1260
tccaagcact ttgcgagaat cccgagtgga caccattgaa ggataacagg attccttcat  1320
acggggtctt gtctgttgat ctgagtctga cagttgagct taaaatcaaa attgtttcag  1380
gattcgggcc attgatcaca cacggttcag ggatggacct atacaaatcc aaccacaaca  1440
atatgtattg gctgactatc ccgccaatga agaacctggc cttaggtgta atcaacacat  1500
tggagtggat accgagattc aaggttagtc ccaacctctt cactgttcca attaaggaag  1560
```

```
caggcgagga ctgccatgcc ccaacatacc tacctgcgga ggtggatggt gatgtcaaac  1620
tcagttccaa tctggtgatt ctacctggtc aagatctcca atatgttctg gcaacctacg  1680
atacttccag agttgaacat gctgtagttt attacgttta cagcccaagc cgctcatttt  1740
cttactttta tccttttagg ttgcctgtaa ggggggtccc cattgaatta caagtggaat  1800
gcttcacatg ggaccaaaaa ctctggtgcc gtcacttctg tgtgcttgcg gactcagaat  1860
ctggtggaca tatcactcac tctgggatgg tgggcatggg agtcagctgc acagccactc  1920
gggaagatgg aaccagccgc agatagtgat aataggctgg agcctcggtg gccaagcttc  1980
ttgccccttg ggcctccccc cagcccctcc tccccttcct gcacccgtac cccgtggtc   2040
tttgaataaa gtctgagtgg gcggc                                        2065
```

```
SEQ ID NO: 45          moltype = DNA  length = 1854
FEATURE                Location/Qualifiers
misc_feature           1..1854
                       note = Synthetic Polynucleotide
source                 1..1854
                       mol_type = other DNA
                       organism = synthetic construct
SEQUENCE: 45
atgtcaccac aacgagaccg gataaatgcc ttctacaaag acaacccccca tcctaaggga  60
agtaggatag ttattaacag agaacatctt atgattgata gaccttatgt tttgctggct  120
gttctattcg tcatgtttct gagcttgatc gggttgctag ccattgcagg cattagactt  180
catcgggcag ccatctacac cgcagagatc cataaaagcc tcagcaccaa tctggatgta  240
actaactcaa tcgagcatca ggttaaggac gtgctgacac cactcttcaa gatcatcggt  300
gatgaagtgg gcttgaggac acctcagaga ttcactgacc tagtgaagtt catctctgac  360
aagattaaat tccttaatcc ggacagggaa tacgacttca gagatctcac ttggtgtatc  420
aacccgccag agagaatcaa attggattat gatcaatact gtgcagatgt ggctgctgaa  480
gaactcatga atgcattggt gaactcaact ctactggaga ccagggcaac caatcagttc  540
ctagctgtct caaagggaaa ctgctcaggg cccactacaa tcagaggcca attctcaaac  600
atgtcgctgt ccctgttgga cttgtattta agtcgaggtt acaatgtgtc atctatagtc  660
actatgacat cccagggaat gtacgggggga acttacctag tggaaaagcc taatctgagc  720
agcaaagggt cagagttgtc acaactgagc atgcaccgag tgtttgaagt aggtgttatc  780
agaaatccgg gtttgggggc tccggtattc catatgacaa actatcttga gcaaccagtc  840
agtaatgatt tcagcaactg catggtggct ttgggggagc tcaagttcgc agccctctgt  900
cacagggaag attctatcac aattccctat cagggatcag ggaaaggtgt cagcttccag  960
cttgtcaagc taggtgtctg gaaatcccca accgacatgc aatcctgggt cccccctatca  1020
acggatgatc cagtgataga caggctttac ctctcatctc acagaggcgt tatcgctgac  1080
aatcaagcaa aatgggctgt cccgacaaca cggacagatg acaagttgcg aatggagaca  1140
tgcttccagc aggcgtgtaa gggtaaaatc caagcacttt gcgagaatcc cgagtggaca  1200
ccattgaagg ataacaggat tccttcatac ggggtcttgt ctgttgatct gagtctgaca  1260
gttgagctta aaatcaaaat tgtttcagga ttcgggccat tgatcacaca cggttcaggg  1320
atggacctat acaaatccaa ccacaacaat atgtattggc tgactatccc gccaatgaag  1380
aacctggcct taggtgtaat caacacattg gagtggatac cgagattcaa ggttagtccc  1440
aacctcttca ctgttccaat taaggaagca ggcgaggact gccatgcccc aacataccta  1500
cctgcggagg tggatggtga tgtcaaactc agttccaatc tggtgattct acctggtcaa  1560
gatctccaat atgttctggc aacctacgat acttccagag ttgaacatgc tgtagtttat  1620
tacgtttaca gcccaagccg ctcattttct tacttttatc cttttaggtt gcctgtaagg  1680
ggggtcccca ttgaattaca agtggaatgc ttcacatggg accaaaaact ctggtgccgt  1740
cacttctgtg tgcttgcgga ctcagaatct ggtggacata tcactcactc tgggatggtg  1800
ggcatgggag tcagctgcac agccactcgg gaagatggaa ccagccgcag atag        1854
```

```
SEQ ID NO: 46          moltype = DNA  length = 2126
FEATURE                Location/Qualifiers
misc_feature           1..2126
                       note = Synthetic Polynucleotide
source                 1..2126
                       mol_type = other DNA
                       organism = synthetic construct
SEQUENCE: 46
ggggaaataa gagagaaaag aagagtaaga agaaatataa gagccaccat gtcaccacaa  60
cgagaccgga taaatgcctt ctacaaagac aacccccatc ctaagggaag taggatagtt  120
attaacagag aacatcttat gattgataga ccttatgttt tgctggctgt tctattcgtc  180
atgtttctga gcttgatcgg gttgctagcc attgcaggca ttagacttca tcgggcagcc  240
atctacaccg cagagatcca taaaagcctc agcaccaatc tggatgtaac taactcaatc  300
gagcatcagg ttaaggacgt gctgacacca ctcttcaaga tcatcggtga tgaagtgggc  360
ttgaggacac ctcagagatt cactgaccta gtgaagttca tctctgacaa gattaaattc  420
cttaatccgg acagggaata cgacttcaga gatctcactt ggtgtatcaa cccgccagag  480
agaatcaaat tggattatga tcaatactgt gcagatgtgg ctgctgaaga actcatgaat  540
gcattggtga actcaactct actggagacc agggcaacca atcagttcct agctgtctca  600
aagggaaact gctcagggcc cactacaatc agaggccaat tctcaaacat gtcgctgtcc  660
ctgttggact tgtatttaag tcgaggttac aatgtgtcat ctatagtcac tatgacatcc  720
cagggaatgt acgggggaac ttacctagtg gaaaagccta atctgagcag caaagggtca  780
gagttgtcac aactgagcat gcaccgagtg tttgaagtag gtgttatcag aaatccgggt  840
ttgggggctc cggtattcca tatgacaaac tatcttgagc aaccagtcag taatgatttc  900
agcaactgca tggtggcttt gggggagctc aagttcgcag ccctctgtca cagggaagat  960
tctatcacaa ttccctatca gggatcaggg aaaggtgtca gcttccagct tgtcaagcta  1020
ggtgtctgga aatccccaac cgacatgcaa tcctgggtcc ccctatcaac ggatgatcca  1080
gtgatagaca ggctttacct ctcatctcac agaggcgtta tcgctgacaa tcaagcaaaa  1140
tgggctgtcc cgacaacacg gacagatgac aagttgcgaa tggagacatg cttccagcag  1200
gcgtgtaagg gtaaaatcca agcactttgc gagaatcccg agtggacacc attgaaggat  1260
```

-continued

```
aacaggattc cttcatacgg ggtcttgtct gttgatctga gtctgacagt tgagcttaaa  1320
atcaaaattg tttcaggatt cgggccattg atcacacacg gttcagggat ggacctatac  1380
aaatccaacc acaacaatat gtattggctg actatcccgc caatgaagaa cctggcctta  1440
ggtgtaatca acacattgga gtggataccg agattcaagg ttagtcccaa cctcttcact  1500
gttccaatta aggaagcagg cgaggactgc catgccccaa catacctacc tgcggaggtg  1560
gatggtgatg tcaaactcag ttccaatctg gtgattctac ctggtcaaga tctccaatat  1620
gttctggcaa cctacgatac ttccagagtt gaacatgctg tagtttatta cgtttacagc  1680
ccaagccgct cattttctta cttttatcct tttaggttgc ctgtaagggg ggtccccatt  1740
gaattacaag tggaatgctt cacatgggac caaaaactct ggtgccgtca cttctgtgtg  1800
cttgcggact cagaatctgg tggacatatc actcactctg ggatggtggg catgggagtc  1860
agctgcacag ccactcggga agatggaacc agccgcagat agtgataata ggctggagcc  1920
tcggtggcca agcttcttgc cccttgggcc tccccccagc ccctcctccc cttcctgcac  1980
ccgtaccccc gtggtctttg aataaagtct gagtgggcgg caaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa atctag                                       2126

SEQ ID NO: 47          moltype = AA  length = 550
FEATURE                Location/Qualifiers
REGION                 1..550
                       note = Synthetic Polypeptide
source                 1..550
                       mol_type = protein
                       organism = synthetic construct
SEQUENCE: 47
MGLKVNVSAV FMAVLLTLQT PAGQIHWGNL SKIGVVGIGS ASYKVMTRSS HQSLVIKLMP  60
NITLLNNCTR VEIAEYRRLL RTVLEPIRDA LNAMTQNIRP VQSVASSRRH KRFAGVVLAG  120
AALGVATAAQ ITAGIALHRS MLNSQAIDNL RASLETTNQA IEAIRQAGQE MILAVQGVQD  180
YINNELIPSM NQLSCDLIGQ KLGLKLLRYY TEILSLFGPS LRDPISAEIS IQALSYALGG  240
DINKVLEKLG YSGGDLLGIL ESRGIKARIT HVDTESYFIV LSIAYPTLSE IKGVIVHRLE  300
GVSYNIGSQE WYTTVPKYVA TQGYLISNFD ESSCTFMPEG TVCSQNALYP MSPLLQECLR  360
GSTKSCARTL VSGSFGNRFI LSQGNLIANC ASILCKCYTT GTIINQDPDK ILTYIAADRC  420
PVVEVNGVTI QVGSRRYPDA VYLHRIDLGP PISLERLDVG TNLGNAIAKL EDAKELLESS  480
DQILRSMKGL SSTSIVYILI AVCLGGLIGI PTLICCCRGR CNKKGEQVGM SRPGLKPDLT  540
GTSKSYVRSL                                                         550

SEQ ID NO: 48          moltype = AA  length = 550
FEATURE                Location/Qualifiers
REGION                 1..550
                       note = Synthetic Polypeptide
source                 1..550
                       mol_type = protein
                       organism = synthetic construct
SEQUENCE: 48
MGLKVNVSVI FMAVLLTLQT PTGQIHWGNL SKIGVVGVGS ASYKVMTRSS HQSLVIKLMP  60
NITLLNNCTR VGIAEYRRLL RTVLEPIRDA LNAMTQNIRP VQSVASSRRH KRFAGVVLAG  120
AALGVATAAQ ITAGIALHQS MLNSQAIDNL RASLETTNQA IEAIRQAGQE MILAVQGVQD  180
YINNELIPSM NQLSCDLIGQ KLGLKLLRYY TEILSLFGPS LRDPISAEIS IQALSYALGG  240
DINKVLEKLG YSGGDLLGIL ESRGIKARIT HVDTESYFIV LSIAYPTLSE IKGVIVHRLE  300
GVSYNIGSQE WYTTVPKYVA TQGYLISNFD ESSCTFMPEG TVCSQNALYP MSPLLQECLR  360
GSTKSCARTL VSGSFGNRFI LSQGNLIANC ASILCKCYTT GTIINQDPDK ILTYIAADHC  420
PVVEVNGVTI QVGSRRYPDA VYLHRIDLGP PISLERLDVG TNLGNAIAKL EDAKELLESS  480
DQILRSMKGL SSTSIVYILI AVCLGGLIGI PALICCCRGR CNKKGEQVGM SRPGLKPDLT  540
GTSKSYVRSL                                                         550

SEQ ID NO: 49          moltype = AA  length = 617
FEATURE                Location/Qualifiers
REGION                 1..617
                       note = Synthetic Polypeptide
source                 1..617
                       mol_type = protein
                       organism = synthetic construct
SEQUENCE: 49
MSPQRDRINA FYKDNPYPKG SRIVINREHL MIDRPYVLLA VLFVMFLSLI GLLAIAGIRL  60
HRAAIYTAEI HKSLSTNLDV TNSIEHQVKD VLTPLFKIIG DEVGLRTPQR FTDLVKFISD  120
KIKFLNPDRE YDFRDLTWCI NPPERIKLDY DQYCADVAAE ELMNALVNST LLETRTTTQF  180
LAVSKGNCSG PTTIRGQFSN MSLSLLDLYL GRGYNVSSIV TMTSQGMYGG TYLVEKPNLN  240
SKGSELSQLS MYRVFEVGVI RNPGLGAPVF HMTNYFEQPV SNGLGNCMVA LGELKLAALC  300
HGDDSIIIPY QGSGKGVSFQ LVKLGVWKSP TDMQSWVPLS TDDPVVDRLY LSSHRGVIAD  360
NQAKWAVPTT RTDDKLRMET CFQQACKGKI QALCENPEWV PLKDNRIPSY GVLSVDLSLT  420
VELKIKIASG FGPLITHGSG MDLYKSNCNN VYWLTIPPMR NLALGVINTL EWIPRFKVSP  480
NLFTVPIKEA GEDCHAPTYL PAEVDGDVKL SSNLVILPGQ DLQYVLATYD TSRVEHAVVY  540
YVYSPSRSFS YFYPFRLPIK GVPIELQVEC FTWDQKLWCR HFCVLADSES GGLITHSGMV  600
GMGVSCTATR EDGTNRR                                                 617

SEQ ID NO: 50          moltype = AA  length = 617
FEATURE                Location/Qualifiers
REGION                 1..617
                       note = Synthetic Polypeptide
source                 1..617
```

```
                          mol_type = protein
                          organism = synthetic construct
SEQUENCE: 50
MSPQRDRINA FYKDNPHPKG SRIVINREHL MIDRPYVLLA VLFVMFLSLI GLLAIAGIRL  60
HRAAIYTAEI HKSLSTNLDV TNSIEHQVKD VLTPLFKIIG DEVGLRTPQR FTDLVKFISD  120
KIKFLNPDRE YDFRDLTWCI NPPERIKLDY DQYCADVAAE ELMNALVNST LLETRATNQF  180
LAVSKGNCSG PTTIRGQFSN MSLSLLDLYL SRGYNVSSIV TMTSQGMYGG TYLVEKPNLS  240
SKGSELSQLS MHRVFEVGVI RNPGLGAPVF HMTNYLEQPV SNDFSNCMVA LGELKFAALC  300
HREDSITIPY QGSGKGVSFQ LVKLGVWKSP TDMQSWVPLS TDDPVIDRLY LSSHRGVIAD  360
NQAKWAVPTT RTDDKLRMET CFQQACKGKI QALCENPEWT PLKDNRIPSY GVLSVDLSLT  420
VELKIKIVSG FGPLITHGSG MDLYKSNHNN MYWLTIPPMK NLALGVINTL EWIPRFKVSP  480
NLFTVPIKEA GEDCHAPTYL PAEVDGDVKL SSNLVILPGQ DLQYVLATYD TSRVEHAVVY  540
YVYSPSRSFS YFYPFRLPVR GVPIELQVEC FTWDQKLWCR HFCVLADSES GGHITHSGMV  600
GMGVSCTATR EDGTSRR                                                  617

SEQ ID NO: 51             moltype = DNA  length = 1729
FEATURE                   Location/Qualifiers
misc_feature              1..1729
                          note = Synthetic Polynucleotide
source                    1..1729
                          mol_type = other DNA
                          organism = synthetic construct
SEQUENCE: 51
tcaagctttt ggaccctcgt acagaagcta atacgactca ctatagggaa ataagagaga  60
aaagaagagt aagaagaaat ataagagcca ccatggcaca agtcattaat acaaacagcc  120
tgtcgctgtt gacccagaat aacctgaaca aatcccagtc cgcactgggc actgctatcg  180
agcgtttgtc ttccggtctg cgtatcaaca gcgcgaaaga cgatgcggca ggacaggcga  240
ttgctaaccg ttttaccgcg aacatcaaag gtctgactca ggcttcccgt aacgctaacg  300
acggtatctc cattgcgcag accactgaag gcgcgctgaa cgaaatcaac aacaacctgc  360
agcgtgtgcg tgaactggcg gttcagtctg cgaatggtac taactcccag tctgacctcg  420
actccatcca ggctgaaatc acccagcgcc tgaacgaaat cgaccgtgta tccggccaga  480
ctcagttcaa cggcgtgaaa gtcctggcgc aggacaacac cctgaccatc caggttggtg  540
ccaacgacgg tgaaactatc gatattgatt taaaagaaat cagctctaaa acactgggac  600
ttgataagct taatgtccaa gatgcctaca ccccgaaaga aactgctgta accgttgata  660
aaactaccta taaaaatggt acagatccta ttacagccca gagcaatact gatatccaaa  720
ctgcaattgg cggtggtgca acgggggtta ctggggctga tatcaaattt aaagatggtc  780
aatactattt agatgttaaa ggcggtgctt ctgctggtgt ttataaagcc acttatgatg  840
aaactacaaa gaaagttaat attgatacga ctgataaaac tccgttggca actgcggaag  900
ctacagctat tcggggaacg gccactataa cccacaacca aattgctgaa gtaacaaaag  960
agggtgttga tacgaccaca gttgcggctc aacttgctgc agcaggggtt actggcgccg  1020
ataaggacaa tactagcctt gtaaaactat cgtttgagga taaaaacggt aaggttattg  1080
atggtggcta tgcagtgaaa atgggcgacg atttctatgc cgctacatat gatgagaaaa  1140
caggtgcaat tactgctaaa accactactt atacagatgg tactggcgtt gctcaaactg  1200
gagctgtgaa atttggtggc gcaaatggta aatctgaagt tgttactgct accgatggta  1260
agacttactt agcaagcgac cttgacaaac ataacttcag aacaggcggt gagcttaaag  1320
aggttaatac agataagact gaaaacccac tgcagaaaat tgatgctgcc ttggcacagg  1380
ttgatacact tcgttctgac ctgggtgcgg ttcagaaccg tttcaactcc gctatcacca  1440
acctgggcaa taccgtaaat aacctgtctt ctgcccgtag ccgtatcgaa gattccgact  1500
acgcaaccga agtctccaac atgtctcgcg cgcagattct gcagcaggcc ggtacctccg  1560
ttctggcgca ggcgaaccag gttccgcaaa acgtcctctc tttactgcgt tgataatagg  1620
ctggagcctc ggtggccatg cttcttgccc cttgggcctc cccccagccc ctcctcccct  1680
tcctgcaccc gtacccccgt ggtctttgaa taaagtctga gtgggcggc             1729

SEQ ID NO: 52             moltype = DNA  length = 1518
FEATURE                   Location/Qualifiers
misc_feature              1..1518
                          note = Synthetic Polynucleotide
source                    1..1518
                          mol_type = other DNA
                          organism = synthetic construct
SEQUENCE: 52
atggcacaag tcattaatac aaacagcctg tcgctgttga cccagaataa cctgaacaaa  60
tcccagtccg cactgggcac tgctatcgag cgtttgtctt ccggtctgcg tatcaacagc  120
gcgaaagacg atgcggcagg acaggcgatt gctaaccgtt ttaccgcgaa catcaaaggt  180
ctgactcagg cttcccgtaa cgctaacgac ggtatctcca ttgcgcagac cactgaaggc  240
gcgctgaacg aaatcaacaa caacctgcag cgtgtgcgtg aactggcggt tcagtctgcg  300
aatggtacta actcccagtc tgacctcgac tccatccagg ctgaaatcac ccagcgcctg  360
aacgaaatcg accgtgtatc cggccagact cagttcaacg gcgtgaaagt cctggcgcag  420
gacaacaccc tgaccatcca ggttggtgcc aacgacggtg aaactatcga tattgattta  480
aaagaaatca gctctaaaac actgggactt gataagctta atgtccaaga tgcctacacc  540
ccgaaagaaa ctgctgtaac cgttgataaa actacctata aaaatggtac agatcctatt  600
acagcccaga gcaatactga tatccaaact gcaattggcg gtggtgcaac gggggttact  660
ggggctgata tcaaatttaa agatggtcaa tactatttag atgttaaagg cggtgcttct  720
gctggtgttt ataaagccac ttatgatgaa actacaaaga aagttaatat tgatacgact  780
gataaaactc cgttggcaac tgcggaagct acagctattc ggggaacggc cactataacc  840
cacaaccaaa ttgctgaagt aacaaaagag ggtgttgata cgaccacagt tgcggctcaa  900
cttgctgcag caggggttac tggcgccgat aaggacaata ctagccttgt aaaactatcg  960
tttgaggata aaaacggtaa ggttattgat ggtggctatg cagtgaaaat gggcgacgat  1020
ttctatgccg ctacatatga tgagaaaaca ggtgcaatta ctgctaaaac cactacttat  1080
```

-continued

```
acagatggta ctggcgttgc tcaaactgga gctgtgaaat ttggtggcgc aaatggtaaa  1140
tctgaagttg ttactgctac cgatggtaag acttacttag caagcgacct tgacaaacat  1200
aacttcagaa caggcggtga gcttaaagag gttaatacag ataagactga aaacccactg  1260
cagaaaattg atgctgcctt ggcacaggtt gatacacttc gttctgacct gggtgcggtt  1320
cagaaccgtt tcaactccgc tatcaccaac ctgggcaata ccgtaaataa cctgtcttct  1380
gcccgtagcc gtatcgaaga ttccgactac gcaaccgaag tctccaacat gtctcgcgcg  1440
cagattctgc agcaggccgg tacctccgtt ctggcgcagg cgaaccaggt tccgcaaaac  1500
gtcctctctt tactgcgt                                                1518

SEQ ID NO: 53          moltype = RNA  length = 1790
FEATURE                Location/Qualifiers
misc_feature           1..1790
                       note = Synthetic Polynucleotide
source                 1..1790
                       mol_type = other RNA
                       organism = synthetic construct
SEQUENCE: 53
ggggaaataa gagagaaaag aagagtaaga agaaatataa gagccaccat ggcacaagtc  60
attaatacaa acagcctgtc gctgttgacc cagaataacc tgaacaaatc ccagtccgca  120
ctgggcactg ctatcgagcg tttgtcttcc ggtctgcgta tcaacagcgc gaaagacgat  180
gcggcaggac aggcgattgc taaccgtttt accgcgaaca tcaaaggtct gactcaggct  240
tcccgtaacg ctaacgacgg tatctccatt gcgcagacca ctgaaggcgc gctgaacgaa  300
atcaacaaca acctgcagcg tgtgcgtgaa ctggcggttc agtctgcgaa tggtactaac  360
tcccagtctg acctcgactc catccaggct gaaatcaccc agcgcctgaa cgaaatcgac  420
cgtgtatccg gccagactca gttcaacggc gtgaaagtcc tggcgcagga caacaccctg  480
accatccagg ttggtgccaa cgacggtgaa actatcgata ttgatttaaa agaaatcagc  540
tctaaaacac tgggacttga taagcttaat gtccaagatg cctacacccc gaaagaaact  600
gctgtaaccg ttgataaaac tacctataaa aatggtacag atcctattac agcccagagc  660
aatactgata tccaaactgc aattggcggt ggtgcaacgg gggttactgg ggctgatatc  720
aaatttaaag atggtcaata ctatttagat gttaaaggcg gtgcttctgc tggtgtttat  780
aaagccactt atgatgaaac tacaaagaaa gttaatattg atacgactga taaaactccg  840
ttggcaactg cggaagctac agctattcgg ggaacggcca ctataaccca caaccaaatt  900
gctgaagtaa caaaagaggg tgttgatacg accacagttg cggctcaact tgctgcagca  960
ggggttactg gcgccgataa ggacaatact agccttgtaa aactatcgtt tgaggataaa  1020
aacggtaagg ttattgatgg tggctatgca gtgaaaatgg gcgacgattt ctatgccgct  1080
acatatgatg agaaaacagg tgcaattact gctaaaacca ctacttatac agatggtact  1140
ggcgttgctc aaactggagc tgtgaaattt ggtggcgcaa atggtaaatc tgaagttgtt  1200
actgctaccg atggtaagac ttacttagca agcgaccttg acaaacataa cttcagaaca  1260
ggcggtgagc ttaaagaggt taatacagat aagactgaaa acccactgca gaaaattgat  1320
gctgccttgg cacaggttga tacacttcgt tctgacctgg gtgcggttca gaaccgtttc  1380
aactccgcta tcaccaacct gggcaatacc gtaaataacc tgtcttctgc ccgtagccgt  1440
atcgaagatt ccgactacgc aaccgaagtc tccaacatgt ctcgcgcgca gattctgcag  1500
caggccggta cctccgttct ggcgcaggcg aaccaggttc cgcaaaacgt cctctcttta  1560
ctgcgttgat aataggctgg agcctcggtg gccatgcttc ttgccccttg ggcctccccc  1620
cagcccctcc tccccttcct gcacccgtac ccccgtggtc tttgaataaa gtctgagtgg  1680
gcggcaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaatctag             1790

SEQ ID NO: 54          moltype = AA  length = 506
FEATURE                Location/Qualifiers
REGION                 1..506
                       note = Synthetic Polypeptide
source                 1..506
                       mol_type = protein
                       organism = synthetic construct
SEQUENCE: 54
MAQVINTNSL SLLTQNNLNK SQSALGTAIE RLSSGLRINS AKDDAAGQAI ANRFTANIKG  60
LTQASRNAND GISIAQTTEG ALNEINNNLQ RVRELAVQSA NGTNSQSDLD SIQAEITQRL  120
NEIDRVSGQT QFNGVKVLAQ DNTLTIQVGA NDGETIDIDL KEISSKTLGL DKLNVQDAYT  180
PKETAVTVDK TTYKNGTDPI TAQSNTDIQT AIGGGATGVT GADIKFKDGQ YYLDVKGGAS  240
AGVYKATYDE TTKKVNIDTT DKTPLATAEA TAIRGTATIT HNQIAEVTKE GVDTTTVAAQ  300
LAAAGVTGAD KDNTSLVKLS FEDKNGKVID GGYAVKMGDD FYAATYDEKT GAITAKTTTY  360
TDGTGVAQTG AVKFGGANGK SEVVTATDGK TYLASDLDKH NFRTGGELKE VNTDKTENPL  420
QKIDAALAQV DTLRSDLGAV QNRFNSAITN LGNTVNNLSS ARSRIEDSDY ATEVSNMSRA  480
QILQQAGTSV LAQANQVPQN VLSLLR                                       506

SEQ ID NO: 55          moltype = AA  length = 698
FEATURE                Location/Qualifiers
REGION                 1..698
                       note = Synthetic Polypeptide
source                 1..698
                       mol_type = protein
                       organism = synthetic construct
SEQUENCE: 55
MAQVINTNSL SLLTQNNLNK SQSALGTAIE RLSSGLRINS AKDDAAGQAI ANRFTANIKG  60
LTQASRNAND GISIAQTTEG ALNEINNNLQ RVRELAVQSA NSTNSQSDLD SIQAEITQRL  120
NEIDRVSGQT QFNGVKVLAQ DNTLTIQVGA NDGETIDIDL KQINSQTLGL DTLNVQQKYK  180
VSDTAATVTG YADTTIALDN STFKASATGL GGTDQKIDGD LKFDDTTGKY YAKVTVTGGT  240
GKDGYYEVSV DKTNGEVTLA GGATSPLTGG LPATATEDVK NVQVANADLT EAKAALTAAG  300
```

```
VTGTASVVKM SYTDNNGKTI DGGLAVKVGD DYYSATQNKD GSISINTTKY TADDGTSKTA  360
LNKLGGADGK TEVVSIGGKT YAASKAEGHN FKAQPDLAEA AATTENPLQ  KIDAALAQVD  420
TLRSDLGAVQ NRFNSAITNL GNTVNNLTSA RSRIEDSDYA TEVSNMSRAQ ILQQAGTSVL  480
AQANQVPQNV LSLLRGGGGS GGGGSMMAPD PNANPNANPN ANPNANPNAN PNANPNANPN  540
ANPNANPNAN PNANPNANPN ANPNANPNAN PNANPNANPN ANPNANPNKN NQGNGQGHNM  600
PNDPNRNVDE NANANNAVKN NNNEEPSDKH IEQYLKKIKN SISTEWSPCS VTCGNGIQVR  660
IKPGSANKPK DELDYENDIE KKICKMEKCS SVFNVVNS                          698

SEQ ID NO: 56          moltype = AA  length = 692
FEATURE                Location/Qualifiers
REGION                 1..692
                       note = Synthetic Polypeptide
source                 1..692
                       mol_type = protein
                       organism = synthetic construct
SEQUENCE: 56
MMAPDPNANP NANPNANPNA NPNANPNANP NANPNANPNA NPNANPNANP NANPNANPNA  60
NPNANPNANP NANPNANPNA NPNKNNQGNG QGHNMPNDPN RNVDENANAN NAVKNNNNEE  120
PSDKHIEQYL KKIKNSISTE WSPCSVTCGN GIQVRIKPGS ANKPKDELDY ENDIEKKICK  180
MEKCSSVFNV VNSRPVTMAQ VINTNSLSLL TQNNLNKSQS ALGTAIERLS SGLRINSAKD  240
DAAGQAIANR FTANIKGLTQ ASRNANDGIS IAQTTEGALN EINNNLQRVR ELAVQSANST  300
NSQSDLDSIQ AEITQRLNEI DRVSGQTQFN GVKVLAQDNT LTIQVGANDG ETIDIDLKQI  360
NSQTLGLDTL NVQQKYKVSD TAATVTGYAD TTIALDNSTF KASATGLGGT DQKIDGDLKF  420
DDTTGKYYAK VTVTGGTGKD GYYEVSVDKT NGEVTLAGGA TSPLTGGLPA TATEDVKNVQ  480
VANADLTEAK AALTAAGVTG TASVVKMSYT DNNGKTIDGG LAVKVGDDYY SATQNKDGSI  540
SINTTKYTAD DGTSKTALNK LGGADGKTEV VSIGGKTYAA SKAEGHNFKA QPDLAEAAAT  600
TTENPLQKID AALAQVDTLR SDLGAVQNRF NSAITNLGNT VNNLTSARSR IEDSDYATEV  660
SNMSRAQILQ QAGTSVLAQA NQVPQNVLSL LR                                692

SEQ ID NO: 57          moltype = RNA  length = 1620
FEATURE                Location/Qualifiers
source                 1..1620
                       mol_type = genomic RNA
                       organism = Human metapneumovirus
SEQUENCE: 57
atgagctgga aggtggtgat tatcttcagc ctgctgatta cacctcaaca cggcctgaag  60
gagagctacc tggaagagag ctgctccacc atcaccgagg gctacctgag cgtgctgcgg  120
accggctggt acaccaacgt gttcaccctg gaggtgggcg acgtggagaa cctgacctgc  180
agcgacggcc ctagcctgat caagaccgag ctggacctga ccaagagcgc tctgagagag  240
ctgaagaccg tgtccgccga ccagctggcc agagaggaac agatcgagaa ccctcggcag  300
agcagattcg tgctgggcgc catcgctctg ggagtcgccg ctgccgctgc agtgacagct  360
ggagtggcca ttgctaagac catcagactg gaaagcgagg tgacagccat caacaatgcc  420
ctgaagaaga ccaacgaggc cgtgagcacc ctgggcaatg gagtgagagt gctggccaca  480
gccgtgcggg agctgaagga cttcgtgagc aagaacctga ccagagccat caacaagaac  540
aagtgcgaca tcgatgacct gaagatggcc gtgagcttct cccagttcaa cagacggttc  600
ctgaacgtgg tgagacagtt ctccgacaac gctggaatca cacctgccat tagcctggac  660
ctgatgaccg acgccgagct ggctagagcc gtgcccaaca tgcccaccag cgctggccag  720
atcaagctga tgctggagaa cagagccatg gtgcggagaa agggcttcgg catcctgatt  780
ggggtgtatg gaagctccgt gatctacatg gtgcagctgc ccatcttcgg cgtgatcgac  840
acaccctgct ggatcgtgaa ggccgctcct agctgctccg agaagaaagg aaactatgcc  900
tgtctgctga gagaggacca gggctggtac tgccagaacg ccggaagcac agtgtactat  960
cccaacgaga aggactgcga gaccagaggc gaccacgtgt tctgcgacac cgctgccgga  1020
atcaacgtgg ccgagcagag caaggagtgc aacatcaaca tcagcacaac caactacccc  1080
tgcaaggtga gcaccggacg gcaccccatc agcatggtgg ctctgagccc tctgggcgct  1140
ctggtggcct gctataaggg cgtgtcctgt agcatcggca gcaatcgggt gggcatcatc  1200
aagcagctga acaagggatg ctcctacatc accaaccagg acgccgacac cgtgaccatc  1260
gacaacaccg tgtaccagct gagcaaggtg gagggcgagc agcacgtgat caagggcaga  1320
cccgtgagct ccagcttcga ccccatcaag ttccctgagg accagttcaa cgtggccctg  1380
gaccaggtgt ttgagaacat cgagaacagc caggccctgg tggaccagag caacagaatc  1440
ctgtccagcg ctgagaaggg caacaccggc ttcatcattg tgatcattct gatcgccgtg  1500
ctgggcagct ccatgatcct ggtgagcatc ttcatcatta tcaagaagac caagaaaccc  1560
accggagccc ctcctgagct gagcggcgtg accaacaatg gcttcattcc ccacaactga  1620

SEQ ID NO: 58          moltype = RNA  length = 1620
FEATURE                Location/Qualifiers
source                 1..1620
                       mol_type = genomic RNA
                       organism = Human metapneumovirus
SEQUENCE: 58
atgtcttgga aagtgatgat catcatttcg ttactcataa caccccagca cgggctaaag  60
gagagttatt tggaagaatc atgtagtact ataactgagg gatacctcag tgttttaaga  120
acaggctggt acactaatgt cttcacatta gaagttggtg atgttgaaaa tcttacatgt  180
actgatggac ctagcttaat caaaacagaa cttgatctaa caaaaaagtgc tttaagggaa  240
ctcaaaacag tctctgctga tcagttggcg agagaggagc aaattgaaaa tcccagacaa  300
tcaagatttg tcttaggtgc gatagctctc ggagttgcta cagcagcagc agtcacagca  360
ggcattgcaa tagccaaaac cataaggctt gagagtgagg tgaatgcaat taaaggtgct  420
ctcaaacaaa ctaatgaagc agtatccaca ttagggaatg gtgtgcgggt cctagccact  480
gcagtgagag agctaaaaga atttgtgagc aaaaacctga ctagtgcaat caacaggaac  540
aaatgtgaca ttgctgatct gaagatggct gtcagcttca gtcaattcaa cagaagattt  600
```

```
ctaaatgttg tgcggcagtt ttcagacaat gcagggataa caccagcaat atcattggac  660
ctgatgactg atgctgagtt ggccagagct gtatcataca tgccaacatc tgcagggcag  720
ataaaactga tgttggagaa ccgcgcaatg gtaaggagaa aaggatttgg aatcctgata  780
ggggtctacg gaagctctgt gatttacatg gttcaattgc cgatctttgg tgtcatagat  840
acaccttgtt ggatcatcaa ggcagctccc tcttgctcag aaaaaaacgg gaattatgct  900
tgcctcctaa gagaggatca agggtggtat tgtaaaaatg caggatctac tgtttactac  960
ccaaatgaaa aagactgcga aacaagaggt gatcatgttt tttgtgacac agcagcaggg  1020
atcaatgttg ctgagcaatc aagagaatgc aacatcaaca tatctactac caactaccca  1080
tgcaaagtca gcacaggaag acaccctata agcatggttg cactatcacc tctcggtgct  1140
ttggtggctt gctataaagg ggtaagctgc tcgattggca gcaattgggt tggaatcatc  1200
aaacaattac ccaaaggctg ctcatacata accaaccagg atgcagacac tgtaacaatt  1260
gacaataccg tgtatcaact aagcaaagtt gaaggtgaac agcatgtaat aaaagggaga  1320
ccagtttcaa gcagttttga tccaatcaag tttcctgagg atcagttcaa tgttgcgctt  1380
gatcaagtct tcgaaagcat tgagaacagt caggcactag tggaccagtc aaacaaaatt  1440
ctaaacagtg cagaaaaagg aaacactggt ttcattatcg tagtaatttt ggttgctgtt  1500
cttggtctaa ccatgatttc agtgagcatc atcatcataa tcaagaaaac aaggaagccc  1560
acaggagcac ctccagagct gaatggtgtc accaacggcg gtttcatacc acatagttag  1620

SEQ ID NO: 59          moltype = RNA  length = 1620
FEATURE                Location/Qualifiers
source                 1..1620
                       mol_type = genomic RNA
                       organism = Human metapneumovirus
SEQUENCE: 59
atgtcttgga aagtgatgat tatcatttcg ttactcataa cacctcagca tggactaaaa  60
gaaagttatt tagaagaatc atgtagtact ataactgaag gatatctcag tgttttaaga  120
acaggttggt acaccaatgt ctttacatta gaagttggtg atgttgaaaa tcttacatgt  180
actgatggac ctagcttaat caaaacagaa cttgacctaa ccaaaagtgc tttaagagaa  240
ctcaaaacag tttctgctga tcagttagcg agagaagaac aaattgaaaa tcccagacaa  300
tcaaggtttg tcctaggtgc aatagctctt ggagttgcca cagcagcagc agtcacagca  360
ggcattgcaa tagccaaaac tataaggctt gagagtgaag tgaatgcaat caaaggtgct  420
ctcaaaacaa ccaatgaggc agtatcaaca ctaggaaatg gagtgcgggt cctagccact  480
gcagtaagag agctgaaaga atttgtgagc aaaaacctga ctagtgcgat caacaagaac  540
aagtgtgaca ttgctgattt gaagatggct gtcagcttca gtcagttcaa cagaagattc  600
ctaaatgttg tgcggcagtt ttcagacaat gcagggataa caccagcaat atcattggac  660
ctgatgaatg atgctgagct ggccagagct gtatcataca tgccaacatc tgcaggacag  720
ataaaactaa tgttagagaa ccgtgcaatg gtgaggagaa aaggatttgg aatcttgata  780
ggggtctacg gaagctctgt gatttacatg gtccagctgc cgatctttgg tgtcataaat  840
acaccttgtt ggataatcaa ggcagctccc tcttgttcag aaaaagatgg aaattatgct  900
tgcctcctaa gagaggatca agggtggtat tgtaaaaatg caggatccac tgtttactac  960
ccaaatgaaa aagactgcga aacaagaggt gatcatgttt tttgtgacac agcagcaggg  1020
atcaatgttg ctgagcaatc aagagaatgc aacatcaaca tatctaccac caactaccca  1080
tgcaaagtca gcacaggaag acaccctatc agcatggttg cactatcacc tctcggtgct  1140
ttggtagctt gctacaaagg ggttagctgc tcgactggca gtaatcaggt tggaataatc  1200
aaacaactac ctaaaggctg ctcatacata actaaccagg acgcagacac tgtaacaatt  1260
gacaacactg tgtatcaact aagcaaagtt gagggtgaac agcatgtaat aaaagggaga  1320
ccagtttcaa gcagttttga tccaatcagg tttcctgagg atcagttcaa tgttgcgctt  1380
gatcaagtct ttgaaagcat tgaaaacagt caagcactag tggaccagtc aaacaaaatt  1440
ctgaacagtg cagaaaaagg aaacactggt ttcattattg taataatttt gattgctgtt  1500
cttgggttaa ccatgatttc agtgagcatc atcatcataa tcaaaaaaac aaggaagccc  1560
acaggggcac ctccggagct gaatggtgtt accaacggcg gtttcatacc gcatagttag  1620

SEQ ID NO: 60          moltype = RNA  length = 1725
FEATURE                Location/Qualifiers
source                 1..1725
                       mol_type = genomic RNA
                       note = Human respiratory syncytial virus
                       organism = unidentified
SEQUENCE: 60
atggagttgc caatcctcaa aacaaatgca attaccacaa tccttgctgc agtcacactc  60
tgtttcgctt ccagtcaaaa catcactgaa gaattttatc aatcaacatg cagtgcagtt  120
agcaaaggct atcttagtgc tctaagaact ggttggtata ctagtgttat aactatagaa  180
ttaagtaata tcaaggaaaa taagtgtaat ggaacagatg ctaaggtaaa attgataaaa  240
caagaattag ataaatataa aaatgctgta acagaattgc agttgctcat gcaaagcaca  300
ccagcagcca acaatcgagc cagaagagaa ctaccaaggt ttatgaatta tacactcaat  360
aataccaaaa ataccaatgt aacattaagc aagaaaagga aaagaagatt tcttggcttt  420
ttgttaggtg ttggatctgc aatcgccagt ggcattgctg tatctaaggt cctgcaccta  480
gaaggggaag tgaacaaaat caaaagtgct ctactatcca caaacaaggc tgtagtcagc  540
ttatcaaatg gagttagtgt cttaaccagc aaagtgttag acctcaaaaa ctatatagat  600
aaacagttgt tacctattgt gaacaagcaa agctgcagca tatcaaacat tgaaactgtg  660
atagagttcc aacaaaagaa caacagacta ctagagatta ccagggaatt tagtgttaat  720
gcaggtgtaa ctacacctgt aagcacttat atgttaacta atagtgaatt attatcatta  780
atcaatgata tgcctataac aaatgatcag aaaaagttaa tgtccaacaa tgttcaaata  840
gttagacagc aaagttactc tatcatgtcc ataataaagg aggaagtctt agcatatgta  900
gtacaattac cactatatgg tgtaatagat acaccctgtt ggaaactgca cacatcccct  960
ctatgtacaa ccaacacaaa ggaagggtcc aacatctgct taacaagaac cgacagagga  1020
tggtattgtg acaatgcagg atcagtatct ttcttcccac aagctgaaac atgtaaagtt  1080
caatcgaatc gggtattttg tgacacaatg aacagtttaa cattaccaag tgaagtaaat  1140
ctctgcaaca ttgacatatt caaccccaaa tatgattgca aaattatgac ttcaaaaaca  1200
```

```
gatgtaagca gctccgttat cacatctcta ggagccattg tgtcatgcta tggcaaaact  1260
aaatgtacag catccaataa aaatcgtggg atcataaaga cattttctaa cgggtgtgat  1320
tatgtatcaa ataagggggt ggatactgtg tctgtaggta atacattata ttatgtaaat  1380
aagcaagaag gcaaaagtct ctatgtaaaa ggtgaaccaa taataaattt ctatgaccca  1440
ttagtgttcc cctctgatga atttgatgca tcaatatctc aagtcaatga gaagattaac  1500
cagagcctag catttattcg taaatccgat gaattattac ataatgtaaa tgctggtaaa  1560
tccaccacaa atatcatgat aactactata attatagtga ttatagtaat attgttatca  1620
ttaattgcag ttggactgct cctatactgc aaggccagaa gcacaccagt cacactaagt  1680
aaggatcaac tgagtggtat aaataatatt gcatttagta actga                  1725

SEQ ID NO: 61           moltype = RNA  length = 1617
FEATURE                 Location/Qualifiers
source                  1..1617
                        mol_type = genomic RNA
                        note = Human parainfluenza virus
                        organism = unidentified
SEQUENCE: 61
atgccaattt caatactgtt aattattaca accatgatca tggcatcaca ctgccaaata  60
gacatcacaa aactacagca tgtaggtgta ttggtcaaca gtcccaaagg gatgaagata  120
tcacaaaact tcgaaacaag atatctaatc ctgagtctca taccaaaaat agaagattct  180
aactcttgtg gtgaccaaca gatcaagcaa tacaagaggt tattggatag actgatcatt  240
cctttatatg atggactaag attacagaag gatgtgatag tgactaatca agaatccaat  300
gaaaacactg atcccagaac agaacgattc tttggagggg taattggaac tattgctcta  360
ggagtagcaa cctcagcaca aattacagca gcagttgctc tggttgaagc caagcaggca  420
agatcagaca ttgaaaaact caaggaagca atcagggaca caaataaagc agtgcagtca  480
gttcagagct ctgtaggaaa tttgatagta gcaattaaat cagtccagga ttatgtcaac  540
aaagaaatcg tgccatcgat tgcgagacta ggttgtgaag cagcaggact tcagttaggg  600
attgcattaa cacagcatta ctcagaatta acaaatatat ttggtgataa catagaatcg  660
ttacaagaaa aaggaataaa attacaaggt atagcatcat tataccgtac aaatatcaca  720
gaaatattca caacatcaac agttgacaaa tatgatattt atgatctatt atttacagaa  780
tcaataaagg tgagagttat agatgttgat ttgaatgatt actcaataac cctccaagtc  840
agactccctt tattgaccag actgctgaac actcaaatct acaaagtaga ttccatatca  900
tacaatatcc aaaatagaga atggtatatc cctcttccca gccatatcat gacgaaaggg  960
gcatttctag gtggagcaga tgtcaaagaa tgcatagaag cattcagcag ttatatatgc  1020
ccttctgatc caggatttgt actaaaccat gaaatggaga gctgtctatc aggaaacata  1080
tcccaatgtc caagaaccac agtcacatca gacatagttc ctaggtatgc atttgtcaat  1140
ggaggagtgg ttgcgaattg tataacaact acatgtacat gcaatggtat cggtaataga  1200
atcaaccaac cacctgatca aggagtcaaa attataacac ataaagaatg taatacaata  1260
ggtatcaacg gaatgctatt caacacaaac aaagaaggaa ctcttgcatt ctacacacca  1320
gacgacataa cattaaacaa ttctgttgca cttgatccga ttgacatatc aatcgagctc  1380
aacaaggcca aatcagatct tgaggaatca aaagaatgga taagaaggtc aaatcaaaag  1440
ctagattcta ttggaagttg gcatcaatct agcactacaa tcatagttat tttgataatg  1500
atgattatat tgtttataat taatataaca ataattacaa ttgcaattaa gtattacaga  1560
attcaaaaga gaaatcgagt ggatcaaaat gataagccgt atgtattaac aaacaag     1617

SEQ ID NO: 62           moltype = RNA  length = 1716
FEATURE                 Location/Qualifiers
source                  1..1716
                        mol_type = genomic RNA
                        note = Human parainfluenza virus 3
                        organism = unidentified
SEQUENCE: 62
atggaatact ggaagcacac caaccacgga aaggatgctg gtaatgagct ggagacatcc  60
acagccactc atggcaacaa gctcaccaac aagataacat atatattgtg gacgataacc  120
ctggtgttat tatcaatagt cttcatcata gtgctaacta attccatcaa aagtgaaaag  180
gcccgcgaat cattgctaca agacataaat aatgagttta tggaagttac agaaaagatc  240
caagtggcat cggataatac taatgatcta atacagtcag gagtgaatac aaggcttctt  300
acaattcaga gtcatgtcca gaattatata ccaatatcat tgacacaaca aatatcggat  360
cttaggaaat tcattagtga aattacaatt agaaatgata atcaagaagt gccaccacaa  420
agaataacac atgatgtggg tataaaacct ttaaatccag atgatttctg gagatgcacg  480
tctggtcttc catctttgat gaaaactcca aaaataagat taatgccggg accaggatta  540
ttagctatgc caacgactgt tgatggctgt gtcagaaccc cgtccttagt gataaatgat  600
ctgatttatg cttacacctc aaatctaatt actcgaggtt gccaggatat agggaaatca  660
tatcaagtat tacagatagg gataataact gtaaactcag acttggtacc tgacttaaat  720
cctaggatct ctcatacctt caacataaat gacaatagaa agtcatgttc tctagcactc  780
ctaaatacag atgtatatca actgtgttca accccaaaag ttgatgaaag atcagattat  840
gcatcatcag gcatagaaga tattgtactt gatattgtca attatgatgg ctcaatctcg  900
acaacaagat ttaagaataa taatataagt tttgatcaac catatgcggc attataccca  960
tctgttggac cagggatata ctacaaaggc aaaataatat ttctcgggta tggaggtctt  1020
gaacatccaa taaatgagaa tgcaatctgc aacacaactg ggtgtcctgg gaaaacacag  1080
agagactgta atcaagcatc tcatagtcca tggttttcag atagaaggat ggtcaactct  1140
ataattgttg ttgacaaggg cttgaactca gttccaaaat tgaaggtatg gacgatatct  1200
atgagacaaa attactgggg gtcagaagga agattacttc tactaggtaa caagatctac  1260
atatacacaa gatctacaag ttggcacagc aagttacaat taggaataat tgacattact  1320
gactacagtg atataaggat aaaatggaca tggcataatg tgctatcaag accaggaaac  1380
aatgaatgtc catggggaca ttcatgtccg gatggatgta taacgggagt atataccgat  1440
gcatatccac tcaatcccac aggaagcatt gtatcatctg tcatattgga ctcacaaaaa  1500
tcgagagtca acccagtcat aacttactca acagcaaccg aaagggtaaa cgagctggct  1560
atccgaaaca aaacactctc agctgggtac acaacaacaa gctgcattac acactataac  1620
```

-continued

```
aaagggtatt gttttcatat agtagaaata aatcataaaa gcttaaacac atttcaaccc  1680
atgttgttca aaacagagat tccaaaaagc tgcagt                            1716

SEQ ID NO: 63           moltype = RNA  length = 1716
FEATURE                 Location/Qualifiers
misc_feature            1..1716
                        note = Synthetic Polynucleotide
source                  1..1716
                        mol_type = other RNA
                        organism = synthetic construct
SEQUENCE: 63
atggaatact ggaagcacac caaccacggc aaggacgccg gcaacgagct ggaaaccagc  60
acagccacac acggcaacaa gctgaccaac aagatcacct acatcctgtg gaccatcacc  120
ctggtgctgc tgagcatcgt gttcatcatc gtgctgacca atagcatcaa gagcgagaag  180
gccagagaga gcctgctgca ggacatcaac aacgagttca tggaagtgac cgagaagatc  240
caggtggcca gcgacaacac caacgacctg atccagagcg gcgtgaacac ccggctgctg  300
accatccaga gccacgtgca gaactacatc cccatcagcc tgacccagca gatcagcgac  360
ctgcggaagt tcatcagcga gatcaccatc cggaacgaca accaggaagt gcccccccag  420
agaatcaccc acgacgtggg catcaagccc ctgaaccccg acgatttctg gcggtgtaca  480
agcggcctgc ccagcctgat gaagaccccc aagatccggc tgatgcctgg ccctggactg  540
ctggccatgc ctaccacagt ggatggctgt gtgcggaccc ccagcctcgt gatcaacgat  600
ctgatctacg cctacaccag caacctgatc acccggggct gccaggatat cggcaagagc  660
taccaggtgc tgcagatcgg catcatcacc gtgaactccg acctggtgcc cgacctgaac  720
cctcggatca gccacacctt caacatcaac gacaacagaa agagctgcag cctggctctg  780
ctgaacaccg acgtgtacca gctgtgcagc acccccaagg tggacgagag aagcgactac  840
gccagcagcg gcatcgagga tatcgtgctg gacatcgtga actacgacgg cagcatcagc  900
accacccggt tcaagaacaa caacatcagc ttcgaccagc cctacgccgc cctgtaccct  960
tctgtgggcc ctggcatcta ctacaagggc aagatcatct tcctgggcta cggcggcctg  1020
gaacacccca tcaacgagaa cgccatctgc aacaccaccg gctgccctgg caagacccag  1080
agagactgca atcaggccag ccacagcccc tggttcagcg accgcagaat ggtcaactct  1140
atcatcgtgg tggacaaggg cctgaacagc gtgcccaagc tgaaagtgtg gacaatcagc  1200
atgcgccaga actactgggg cagcgagggc agacttctgc tgctgggaaa caagatctac  1260
atctacaccc ggtccaccag ctggcacagc aaactgcagc tgggaatcat cgacatcacc  1320
gactacagcg acatccggat caagtggacc tggcacaacg tgctgagcag acccggcaac  1380
aatgagtgcc cttggggcca cagctgcccc gatggatgta tcaccggcgt gtacaccgac  1440
gcctaccccc tgaatcctac cggctccatc gtgtccagcg tgatcctgga cagccagaaa  1500
agcagagtga accccgtgat cacatacagc accgccaccg agagagtgaa cgaactggcc  1560
atcagaaaca agaccctgag cgccggctac accaccacaa gctgcatcac acactacaac  1620
aagggctact gcttccacat cgtggaaatc aaccacaagt ccctgaacac cttccagccc  1680
atgctgttca agaccgagat ccccaagagc tgctcc                            1716

SEQ ID NO: 64           moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 64
atgcccatca gcatcctgct gatcatcacc acaatgatca tggccagcca ctgccagatc  60
gacatcacca agctgcagca cgtgggcgtg ctcgtgaaca gccccaaggg catgaagatc  120
agccagaact tcgagacacg ctacctgatc ctgagcctga tccccaagat cgaggacagc  180
aacagctgcg gcgaccagca gatcaagcag tacaagcggc tgctggacag actgatcatc  240
cccctgtacg acggcctgcg gctgcagaaa gacgtgatcg tgaccaacca ggaaagcaac  300
gagaacaccg acccccggac cgagagattc ttcggcggcg tgatcggcac aatcgccctg  360
ggagtggcca caagcgccca gattacagcc gctgtggccc tggtggaagc caagcaggcc  420
agaagcgaca tcgagaagct gaaagaggcc atccgggaca ccaacaaggc cgtgcagagc  480
gtgcagtcca gcgtgggcaa tctgatcgtg gccatcaagt ccgtgcagga ctacgtgaac  540
aaagaaatcg tgccctctat cgcccggctg ggctgtgaag ctgccggact gcagctgggc  600
attgccctga cacagcacta cagcgagctg accaacatct tcggcgacaa catcggcagc  660
ctgcaggaaa agggcattaa gctgcaggga atcgccagcc tgtaccgcac caacatcacc  720
gagatcttca ccaccagcac cgtggataag tacgacatct acgacctgct gttcaccgag  780
agcatcaaag tgcgcgtgat cgacgtggac ctgaacgact acagcatcac cctgcaagtg  840
cggctgcccc tgctgaccag actgctgaac acccagatct acaaggtgga cagcatctcc  900
tacaacatcc agaaccgcga gtggtacatc cctctgccca gccacattat gaccaagggc  960
gcctttctgg gcggagccga cgtgaaagag tgcatcgagg ccttcagcag ctacatctgc  1020
cccagcgacc ctggcttcgt gctgaaccac gagatggaaa gctgcctgag cggcaacatc  1080
agccagtgcc ccagaaccac cgtgacctcc gacatcgtgc ccagatacgc cttcgtgaat  1140
ggcggcgtgg tggccaactg catcaccacc acctgtacct gcaacggcat cggcaaccgg  1200
atcaaccagc ctcccgatca gggcgtgaag attatcaccc acaaagagtg taacaccatc  1260
ggcatcaacg gcatgctgtt caataccaac aaagagggca ccctggcctt ctacaccccc  1320
gacgatatca ccctgaacaa ctccgtggct ctggacccca tcgacatctc catcgagctg  1380
aacaaggcca agagcgacct ggaagagtcc aaagagtgga tccggcggag caaccagaag  1440
ctggactcta tcggcagctg gcaccagagc agcaccacca tcatcgtgat cctgattatg  1500
atgattatcc tgttcatcat caacattacc atcatcacta tcgccattaa gtactaccgg  1560
atccagaaac ggaaccgggt ggaccagaat gacaagccct acgtgctgac aaacaag     1617

SEQ ID NO: 65           moltype = RNA  length = 4062
FEATURE                 Location/Qualifiers
```

```
source                  1..4062
                        mol_type = genomic RNA
                        note = Middle East respiratory syndrome coronavirus
                        organism = unidentified
SEQUENCE: 65
atgatacact cagtgtttct actgatgttc ttgttaacac ctacagaaag ttacgttgat  60
gtagggccag attctgttaa gtctgcttgt attgaggttg atatacaaca gaccttcttt  120
gataaaactt ggcctaggcc aattgatgtt tctaaggctg acggtattat ataccctcaa  180
ggccgtacat attctaacat aactatcact tatcaaggtc tttttcccta tcagggagac  240
catggtgata tgtatgttta ctctgcagga catgctacag gcacaactcc acaaaagttg  300
tttgtagcta actattctca ggacgtcaaa cagtttgcta atgggtttgt cgtccgtata  360
ggagcagctg ccaattccac tggcactgtt attattagcc catctaccag cgctactata  420
cgaaaaattt accctgcttt tatgctgggt tcttcagttg gtaatttctc agatggtaaa  480
atgggccgct tcttcaatca tactctagtt cttttgcccg atggatgtgg cactttactt  540
agagcttttt attgtattct agagcctcgc tctggaaatc attgtcctgc tggcaattcc  600
tatacttctt ttgccactta tcacactcct gcaacagatt gttctgatgg caattacaat  660
cgtaatgcca gtctgaactc ttttaaggag tattttaatt tacgtaactg cacctttatg  720
tacacttata acattaccga agatgagatt ttagagtggt ttggcattac acaaactgct  780
caaggtgttc acctcttctc atctcggtat gttgatttgt acggcggcaa tatgtttcaa  840
tttgccacct tgcctgttta tgatactatt aagtattatt ctatcattcc tcacagtatt  900
cgttctatcc aaagtgatag aaaagcttgg gctgccttct acgtatataa acttcaaccg  960
ttaactttcc tgttggattt ttctgttgat ggttatatac gcagagctat agactgtggt  1020
tttaatgatt tgtcacaact ccactgctca tatgaatcct tcgatgttga atctggagtt  1080
tattcagttt cgtctttcga agcaaaacct tctggctcag ttgtggaaca ggctgaaggt  1140
gttgaatgtg atttttcacc tcttctgtct ggcacacctc ctcaggttta taatttcaag  1200
cgtttggttt ttaccaattg caattataat cttaccaaat tgctttcact tttttctgtg  1260
aatgatttta cttgtagtca aatatctcca gcagcaattg ctagcaactg ttattcttca  1320
ctgattttgg attatttttc atacccactt agtatgaaat ccgatctcag tgttagttct  1380
gctggtccaa tatcccagtt taattataaa cagtcctttt ctaatcccac atgtttgatc  1440
ttagcgactg ttcctcataa ccttactact attactaagc ctcttaagta cagctatatt  1500
aacaagtgct ctcgtcttct ttctgatgat cgtactgaag tacctcagtt agtgaacgct  1560
aatcaatact caccctgtgt atccattgtc ccatccactg tgtgggaaga cggtgattat  1620
tataggaaac aactatctcc acttgaaggt ggtggctggc ttgttgctag tggctcaact  1680
gttgccatga ctgagcaatt acagatgggc tttggtatta cagttcaata tggtacagac  1740
accaatagtg tttgccccaa gcttgaattt gctaatgaca caaaaattgc ctctcaatta  1800
ggcaattgcg tggaatattc cctctatggt gtttcgggcc gtggtgtttt tcagaattgc  1860
acagctgtag gtgttcgaca gcagcgcttt gtttatgatg cgtaccagaa tttagttggc  1920
tattattctg atgatggcaa ctactactgt ctgcgtgctt gtgttagtgt tcctgtttct  1980
gtcatctatg ataaagaaac taaaacccac gctactctat ttggtagtgt tgcatgtgaa  2040
cacatttctt ctaccatgtc tcaatactcc cgttctacgc gatcaatgct taaacggcga  2100
gattctacat atggcccccct tcagacacct gttggttgtg tcctaggact tgttaattcc  2160
tctttgttcg tagaggactg caagttgcct ctcggtcaat ctctctgtgc tcttcctgac  2220
acacctagta ctctcacacc tcgcagtgtg cgctctgtgc caggtgaaat gcgcttggca  2280
tccattgctt ttaatcatcc cattcaggtt gatcaactta atagtagtta ttttaaatta  2340
agtataccca ctaattttc ctttggtgtg actcaggagt acattcagac aaccattcag  2400
aaagttactg ttgattgtaa acagtacgtt tgcaatggtt tccagaagtg tgagcaatta  2460
ctgcgcgagt atggccagtt ttgttccaaa ataaaccagg ctctccatgg tgccaattta  2520
cgccaggatg attctgtacg taatttgttt gcgagcgtga aagctctca atcatctcct  2580
atcataccag gttttggagg tgactttaat ttgacacttc tagaacctgt ttctatatct  2640
actggcagtc gtagtgcacg tagtgctatt gaggatttgc tatttgacaa agtcactata  2700
gctgatcctg gttatatgca aggttacgat gattgtatgc agcaaggtcc agcatcagct  2760
cgtgatctta tttgtgctca atatgtggct ggttataaag tattacctcc tcttatggat  2820
gttaatatgg aagccgcgta tacttcatct ttgcttggca gcatagcagg tgttggctgg  2880
actgctggct tatcctcctt tgctgctatt ccatttgcac agagtatytt ttataggtta  2940
aacggtgttg gcattactca acaggttctt tcagagaacc aaaagcttat tgccaataag  3000
tttaatcagg ctctgggagc tatgcaaaca ggcttcacta caactaatga agcttttcgg  3060
aaggttcagg atgctgtgaa caacaatgca caggctctat ccaaattagc tagcgagcta  3120
tctaatactt ttggtgctat ttccgcctct attggagaca tcatacaacg tcttgatgtt  3180
ctcgaacagg acgcccaaat agacagactt attaatggcc gtttgacaac actaaatgct  3240
tttgttgcac agcagcttgt tcgttccgaa tcagctgctc tttccgctca attggctaaa  3300
gataaagtca atgagtgtgt caaggcacaa tccaagcgtt ctggattttg cggtcaaggc  3360
acacatatag tgtcctttgt tgtaaatgcc cctaatggcc tttactttat gcatgttggt  3420
tattaccct a gcaaccacat tgaggttgtt tctgcttatg gtctttgcga tgcagctaac  3480
cctactaatt gtatagcccc tgttaatggc tactttatta aaactaataa cactaggatt  3540
gttgatgagt ggtcatatac tggctcgtcc ttctatgcac ctgagcccat cacctctctt  3600
aatactaagt atgttgcacc acaggtgaca taccaaaaca tttctactaa cctccctcct  3660
cctcttctcg gcaattccac cgggattgac ttccaagatg agttggatga gtttttcaaa  3720
aatgttagca ccagtatacc taattttggt tctctaacac agattaatac tacattactc  3780
gatcttacct acgagatgtt gtctcttcaa caagttgtta aagcccttaa tgagtcttac  3840
atagacctta aagagcttgg caattatact tattacaaca aatggccgtg gtacatttgg  3900
cttggtttca ttgctgggct tgttgcctta gctctatgcg tcttcttcat actgtgctgc  3960
actggttgtg gcacaaactg tatgggaaaa cttaagtgta atcgttgttg tgatagatac  4020
gaggaatacg acctcgagcc gcataaggtt catgttcact aa                    4062

SEQ ID NO: 66           moltype = RNA  length = 4062
FEATURE                 Location/Qualifiers
misc_feature            1..4062
                        note = Synthetic Polynucleotide
source                  1..4062
```

mol_type = other RNA
organism = synthetic construct
SEQUENCE: 66
atgatacact cagtgtttct actgatgttc ttgttaacac ctacagaaag ttacgttgat 60
gtagggccag attctgttaa gtctgcttgt attgaggttg atatacaaca gactttcttt 120
gataaaactt ggcctaggcc aattgatgtt tctaaggctg acggtattat ataccctcaa 180
ggccgtacat attctaacat aactatcact tatcaaggtc tttttcccta tcagggagac 240
catggtgata tgtatgttta ctctgcagga catgctacag gcacaactcc acaaaagttg 300
tttgtagcta actattctca ggacgtcaaa cagtttgcta atgggtttgt cgtccgtata 360
ggagcagctg ccaattccac tggcactgtt attattagcc catctaccag cgctactata 420
cgaaaaattt accctgcttt tatgctgggt tcttcagttg gtaatttctc agatggtaaa 480
atgggccgct tcttcaatca tactctagtt cttttgcccg atggatgtgg cactttactt 540
agagcttttt attgtattct ggagcctcgc tctggaaatc attgtcctgc tggcaattcc 600
tatacttctt ttgccactta tcacactcct gcaacagatt gttctgatgg caattacaat 660
cgtaatgcca gtctgaactc ttttaaggag tattttaatt tacgtaactg cacctttatg 720
tacacttata acattaccga agatgagatt ttagagtggt ttggcattac acaaactgct 780
caaggtgttc acctcttctc atctcggtat gttgatttgt acggcggcaa tatgtttcaa 840
tttgccacct tgcctgttta tgatactatt aagtattatt ctatcattcc tcacagtatt 900
cgttctatcc aaagtgatag aaaagcttgg gctgccttct acgtatataa acttcaaccg 960
ttaactttcc tgttggattt ttctgttgat ggttatatac gcagagctat agactgtggt 1020
tttaatgatt tgtcacaact ccactgctca tatgaatcct tcgatgttga atctggagtt 1080
tattcagttt cgtctttcga agcaaaacct tctggctcag ttgtggaaca ggctgaaggt 1140
gttgaatgtg atttttcacc tcttctgtct ggcacacctc ctcaggttta taatttcaag 1200
cgtttggttt ttaccaattg caattataat cttaccaaat tgctttcact tttttctgtg 1260
aatgatttta cttgtagtca aatatctcca gcagcaattg ctagcaactg ttattcttca 1320
ctgattttgg attacttttc atacccactt agtatgaaat ccgatctcag tgttagttct 1380
gctggtccaa tatcccagtt taattataaa cagtcctttt ctaatcccac atgtttgatt 1440
ttagcgactg ttcctcataa ccttactact attactaagc ctcttaagta cagctatatt 1500
aacaagtgct ctcgtcttct ttctgatgat cgtactgaag tacctcagtt agtgaacgct 1560
aatcaatact caccctgtgt atccattgtc ccatccactg tgtgggaaga cggtgattat 1620
tataggaaac aactatctcc acttgaaggt ggtggctggc ttgttgctag tggctcaact 1680
gttgccatga ctgagcaatt acagatgggc tttggtatta cagttcaata tggtacagac 1740
accaatagtg tttgccccaa gcttgaattt gctaatgaca caaaaattgc ctctcaatta 1800
ggcaattgcg tggaatattc cctctatggt gtttcgggcc gtggtgtttt tcagaattgc 1860
acagctgtag gtgttcgaca gcagcgcttt gtttatgatg cgtaccagaa tttagttggc 1920
tattattctg atgatggcaa ctactactgt ttgcgtgctt gtgttagtgt tcctgtttct 1980
gtcatctatg ataaagaaac taaaacccac gctactctat ttggtagtgt tgcatgtgaa 2040
cacatttctt ctaccatgtc tcaatactcc cgttctacgc gatcaatgct taaacggcga 2100
gattctacat atggcccccct tcagacacct gttggttgtg tcctaggact tgttaattcc 2160
tctttgttcg tagaggactg caagttgcct cttggtcaat ctctctgtgc tcttcctgac 2220
acacctagta ctctcacacc tcgcagtgtg cgctctgttc caggtgaaat gcgcttggca 2280
tccattgctt ttaatcatcc tattcaggtt gatcaactta atagtagtta ttttaaatta 2340
agtataccca ctaatttttc ctttggtgtg actcaggagt acattcagac aaccattcag 2400
aaagttactg ttgattgtaa acagtacgtt tgcaatggtt tccagaagtg tgagcaatta 2460
ctgcgcgagt atggccagtt ttgttccaaa ataaaccagg ctctccatgg tgccaattta 2520
cgccaggatg attctgtacg taatttgttt gcgagcgtga aagctctca atcatctcct 2580
atcataccag gttttggagg tgactttaat ttgacacttc tggaacctgt ttctatatct 2640
actggcagtc gtagtgcacg tagtgctatt gaggatttgc tatttgacaa agtcactata 2700
gctgatcctg gttatatgca aggttacgat gattgcatgc agcaaggtcc agcatcagct 2760
cgtgatctta tttgtgctca atatgtggct ggttacaaag tattacctcc tcttatggat 2820
gttaatatgg aagccgcgta tacttcatct ttgcttggca gcatagcagg tgttggctgg 2880
actgctggct tatcctcctt tgctgctatt ccatttgcac agagtatctt ttataggtta 2940
aacggtgttg gcattactca acaggttctt tcagagaacc aaaagcttat tgccaataag 3000
tttaatcagg ctctgggagc tatgcaaaca ggcttcacta caactaatga agcttttcag 3060
aaggttcagg atgctgtgaa caacaatgca caggctctat ccaaattagc tagcgagcta 3120
tctaatactt ttggtgctat ttccgcctct attggagaca tcatacaacg tcttgatgtt 3180
ctcgaacagg acgcccaaat agacagactt attaatggcc gtttgacaac actaaatgct 3240
tttgttgcac agcagcttgt tcgttccgaa tcagctgctc tttccgctca attggctaaa 3300
gataaagtca atgagtgtgt caaggcacaa tccaagcgtt ctggattttg cggtcaaggc 3360
acacatatag tgtcctttgt tgtaaatgcc cctaatggcc tttacttcat gcatgttggt 3420
tattacccta gcaaccacat tgaggttgtt tctgcttatg gtctttgcga tgcagctaac 3480
cctactaatt gtatagcccc tgttaatggc tactttatta aaactaataa cactaggatt 3540
gttgatgagt ggtcatatac tggctcgtcc ttctatgcac ctgagcccat tacctccctt 3600
aatactaagt atgttgcacc acaggtgaca taccaaaaca tttctactaa cctccctcct 3660
cctcttctcg gcaattccac cgggattgac ttccaagatg agttggatga gtttttcaaa 3720
aatgttagca ccagtatacc taattttggt tccctaacac agattaatac tacattactc 3780
gatcttacct acgagatgtt gtctcttcaa caagttgtta aagcccttaa tgagtcttac 3840
atagacctta aagagcttgg caattatact tattacaaca aatggccgtg gtacatttgg 3900
cttggtttca ttgctgggct tgttgcctta gctctatgcg tcttcttcat actgtgctgc 3960
actggttgtg gcacaaactg tatgggaaaa cttaagtgta atcgttgttg tgatagatac 4020
gaggaatacg acctcgagcc gcataaggtt catgttcact aa 4062

SEQ ID NO: 67 moltype = RNA length = 1845
FEATURE Location/Qualifiers
misc_feature 1..1845
note = Synthetic Polynucleotide
source 1..1845
mol_type = other RNA
organism = synthetic construct SEQUENCE: 67
atgatccact ccgtgttcct cctcatgttc ctgttgaccc ccactgagtc agactgcaag 60
ctcccgctgg gacagtccct gtgtgcgctg cctgacactc ctagcactct gaccccacgc 120
tccgtgcggt cggtgcctgg cgaaatgcgg ctggcctcca tcgccttcaa tcacccaatc 180
caagtggatc agctgaatag ctcgtatttc aagctgtcca tccccacgaa cttctcgttc 240
ggggtcaccc aggagtacat ccagaccaca attcagaagg tcaccgtcga ttgcaagcaa 300
tacgtgtgca acggcttcca gaagtgcgag cagctgctga gagaatacgg gcagttttgc 360
agcaagatca accaggcgct gcatggagct aacttgcgcc aggacgactc cgtgcgcaac 420
ctctttgcct ctgtgaagtc atcccagtcc tccccaatca tcccgggatt cggaggggac 480
ttcaacctga ccctcctgga gcccgtgtcg atcagcaccg gtagcagatc ggcgcgctca 540
gccattgaag atcttctgtt cgacaaggtc accatcgccg atccgggcta catgcaggga 600
tacgacgact gtatgcagca gggaccagcc tccgcgaggg acctcatctg cgcgcaatac 660
gtggccgggt acaaagtgct gcctcctctg atggatgtga acatggaggc cgcttatact 720
tcgtccctgc tcggctctat cgccggcgtg gggtggaccg ccggcctgtc ctccttcgcc 780
gctatcccct ttgcacaatc cattttctac cggctcaacg gcgtgggcat tactcaacaa 840
gtcctgtcgg agaaccagaa gttgatcgca aacaagttca atcaggccct gggggccatg 900
cagactggat tcactacgac taacgaagcg ttccagaagg tccaggacgc tgtgaacaac 960
aacgcccagg cgctctcaaa gctggcctcc gaactcagca acaccttcgg agccatcagc 1020
gcatcgatcg gtgacataat tcagcggctg gacgtgctgg agcaggacgc ccagatcgac 1080
cgcctcatca acggacggct gaccaccttg aatgccttcg tggcacaaca gctggtccgg 1140
agcgaatcag cggcactttc cgcccaactc gccaaggaca aagtcaacga atgcgtgaag 1200
gcccagtcca agaggtccgg tttctgcggt caaggaaccc atattgtgtc cttcgtcgtg 1260
aacgcgccca acggtctgta ctttatgcac gtcggctact acccgagcaa tcatatcgaa 1320
gtggtgtccg cctacggcct gtgcgatgcc gctaacccca ctaactgtat tgcccctgtg 1380
aacggatatt ttattaagac caacaacacc cgcattgtgg acgaatggtc atacaccggt 1440
tcgtccttct acgcgcccga gcccatcact tcactgaaca ccaaatacgt ggctccgcaa 1500
gtgacctacc agaacatctc caccaatttg ccgccgccgc tgctcggaaa cagcaccgga 1560
attgatttcc aagatgaact ggacgaattc ttcaagaacg tgtccacttc cattcccaac 1620
ttcggaagcc tgacacagat caacaccacc cttctcgacc tgacctacga gatgctgagc 1680
cttcaacaag tggtcaaggc cctgaacgag agctacatcg acctgaagga gctgggcaac 1740
tatacctact acaacaagtg gccggacaag attgaggaga ttctgtcgaa aatctaccac 1800
attgaaaacg agatcgccag aatcaagaag cttatcggcg aagcc 1845

SEQ ID NO: 68 moltype = RNA length = 4071
FEATURE Location/Qualifiers
misc_feature 1..4071
note = Synthetic Polynucleotide
source 1..4071
mol_type = other RNA
organism = synthetic construct
SEQUENCE: 68
atggaaaccc ctgcccagct gctgttcctg ctgctgctgt ggctgcctga taccaccggc 60
agctatgtgg acgtgggccc cgatagcgtg aagtccgcct gtatcgaagt ggacatccag 120
cagacctttt tcgacaagac ctggcccaga cccatcgacg tgtccaaggc cgacggcatc 180
atctatccac aaggccggac ctacagcaac atcaccatta cctaccaggg cctgttccca 240
tatcaaggcg accacggcga tatgtacgtg tactctgccg gccacgccac cggcaccaca 300
ccccagaaac tgttcgtggc caactacagc caggacgtga agcagttcgc caacggcttc 360
gtcgtgcgga ttggcgccgc tgccaatagc accggcacag tgatcatcag ccccagcacc 420
agcgccacca tccggaagat ctacccccgcc ttcatgctgg gcagctccgt gggcaatttc 480
agcgacggca agatgggccg gttcttcaac cacaccctgg tgctgctgcc cgatggctgt 540
ggcacactgc tgagagcctt ctactgcatc ctggaaccca gaagcggcaa ccactgccct 600
gccggcaata gctacaccag cttcgccacc taccacacac ccgccaccga ttgctccgac 660
ggcaactaca accggaacgc cagcctgaac agcttcaaag agtacttcaa cctgcggaac 720
tgcaccttca tgtacaccta caatatcacc gaggacgaga tcctggaatg gttcggcatc 780
acccagaccg cccagggcgt gcacctgttc agcagcagat acgtggacct gtacggcggc 840
aacatgttcc agtttgccac cctgcccgtg tacgacacca tcaagtacta cagcatcatc 900
ccccacagca tccggtccat ccagagcgac agaaaagcct gggccgcctt ctacgtgtac 960
aagctgcagc ccctgacctt cctgctggac ttcagcgtgg acggctacat cagacgggcc 1020
atcgactgcg gcttcaacga cctgagccag ctgcactgct cctacgagag cttcgacgtg 1080
gaaagcggcg tgtacagcgt gtccagcttc gaggccaagc ctagcggcag cgtggtggaa 1140
caggctgagg gcgtggaatg cgacttcagc cctctgctga gcggcacccc tccccaggtg 1200
tacaacttca agcggctggt gttcaccaac tgcaattaca acctgaccaa gctgctgagc 1260
ctgttctccg tgaacgactt cacctgtagc cagatcagcc ctgccgccat tgccagcaac 1320
tgctacagca gcctgatcct ggactacttc agctaccccc tgagcatgaa gtccgatctg 1380
agcgtgtcct ccgccggacc catcagccag ttcaactaca agcagagctt cagcaaccct 1440
acctgcctga ttctggccac cgtgccccac aatctgacca ccatcaccaa gcccctgaag 1500
tacagctaca tcaacaagtg cagcagactg ctgtccgacg accggaccga agtgccccag 1560
ctcgtgaacg ccaaccagta cagcccctgc gtgtccatcg tgcccagcac cgtgtgggag 1620
gacggcgact actacagaaa gcagctgagc cccctggaag gcggcggatg gctggtggct 1680
tctggaagca cagtggccat gaccgagcag ctgcagatgg gctttggcat caccgtgcag 1740
tacggcaccg acaccaacag cgtgtgcccc aagctggaat tcgccaatga caccaagatc 1800
gccagccagc tgggaaactg cgtggaatac tccctgtatg gcgtgtccgg acggggcgtg 1860
ttccagaatt gcacagcagt gggagtgcgg cagcagagat tcgtgtacga tgcctaccag 1920
aacctcgtgg gctactacag cgacgacggc aattactact gcctgcgggc ctgtgtgtcc 1980
gtgcccgtgt ccgtgatcta cgacaaagag acaaagaccc acgccacact gttcggctcc 2040
gtggcctgcg agcacatcag ctccaccatg agccagtact cccgctccac ccggtccatg 2100
ctgaagcgga gagatagcac ctacggcccc ctgcagacac ctgtgggatg tgtgctgggc 2160
ctcgtgaaca gctccctgtt tgtggaagat tgcaagctgc ccctgggcca gagcctgtgt 2220
gccctgccag ataccccctag caccctgacc cctagaagcg tgcgctctgt gcccggcgaa 2280

-continued

```
atgcggctgg cctctatcgc cttcaatcac cccatccagg tggaccagct gaactccagc  2340
tacttcaagc tgagcatccc caccaacttc agcttcggcg tgacccagga gtacatccag  2400
accacaatcc agaaagtgac cgtggactgc aagcagtacg tgtgcaacgg ctttcagaag  2460
tgcgaacagc tgctgcgcga gtacggccag ttctgcagca agatcaacca ggccctgcac  2520
ggcgccaacc tgagacagga tgacagcgtg cggaacctgt tcgccagcgt gaaaagcagc  2580
cagtccagcc ccatcatccc tggcttcggc ggcgacttta acctgaccct gctggaacct  2640
gtgtccatca gcaccggctc cagaagcgcc agatccgcca tcgaggacct gctgttcgac  2700
aaagtgacca ttgccgaccc cggctacatg cagggctacg acgattgcat gcagcagggc  2760
ccagccagcg ccagggatct gatctgtgcc cagtatgtgg ccggctacaa ggtgctgccc  2820
cccctgatgg acgtgaacat ggaagccgcc tacacctcca gcctgctggg ctctattgct  2880
ggcgtgggat ggacagccgg cctgtctagc tttgccgcca tccctttcgc ccagagcatc  2940
ttctaccggc tgaacggcgt gggcatcaca caacaggtgc tgagcgagaa ccagaagctg  3000
atcgccaaca agtttaacca ggcactgggc gccatgcaga ccggcttcac caccaccaac  3060
gaggccttca gaaaggtgca ggacgccgtg aacaacaacg cccaggctct gagcaagctg  3120
gcctccgagc tgagcaatac cttcggcgcc atcagcgcct ccatcggcga catcatccag  3180
cggctggacg tgctggaaca ggacgcccag atcgaccggc tgatcaacgg cagactgacc  3240
accctgaacg ccttcgtggc acagcagctc gtgcggagcg aatctgccgc tctgtctgct  3300
cagctggcca aggacaaagt gaacgagtgc gtgaaggccc agtccaagcg gagcggcttt  3360
tgtggccagg gcacccacat cgtgtccttc gtcgtgaatg cccccaacgg cctgtacttt  3420
atgcacgtgg gctattaccc cagcaaccac atcgaggtgg tgtccgccta tggcctgtgc  3480
gacgccgcca atcctaccaa ctgtatcgcc cccgtgaacg gctacttcat caagaccaac  3540
aacacccgga tcgtggacga gtggtcctac acaggcagca gcttctacgc ccccgagccc  3600
atcacctccc tgaacaccaa atacgtggcc ccccaagtga cataccagaa catctccacc  3660
aacctgcccc ctccactgct gggaaattcc accggcatcg acttccagga cgagctggac  3720
gagttcttca agaacgtgtc cacctccatc cccaacttcg gcagcctgac ccagatcaac  3780
accactctgc tggacctgac ctacgagatg ctgtccctgc aacaggtcgt gaaagccctg  3840
aacgagagct acatcgacct gaaagagctg ggaactaca cctactacaa caagtggcct  3900
tggtacattt ggctgggctt tatcgccggc ctggtggccc tggccctgtg cgtgttcttc  3960
atcctgtgct gcaccggctg cggcaccaat tgcatgggca agctgaaatg caaccggtgc  4020
tgcgacagat acgaggaata cgacctggaa cctcacaaag tgcatgtgca c           4071
```

```
SEQ ID NO: 69            moltype = RNA  length = 1864
FEATURE                  Location/Qualifiers
misc_feature             1..1864
                         note = Synthetic Polynucleotide
source                   1..1864
                         mol_type = other RNA
                         organism = synthetic construct
SEQUENCE: 69
tcaagctttt ggaccctcgt acagaagcta atacgactca ctatagggaa ataagagaga  60
aaagaagagt aagaagaaat ataagagcca ccatgggtct caaggtgaac gtctctgccg  120
tattcatggc agtactgtta actctccaaa cacccgccgg tcaaattcat tggggcaatc  180
tctctaagat aggggtagta ggaataggaa gtgcaagcta caaagttatg actcgttcca  240
gccatcaatc attagtcata aaattaatgc ccaatataac tctcctcaat aactgcacga  300
gggtagagat tgcagaatac aggagactac taagaacagt tttggaacca attagggatg  360
cacttaatgc aatgacccag aacataaggc cggttcagag cgtagcttca agtaggagac  420
acaagagatt tgcgggagta gtcctggcag gtgcggccct aggtgttgcc acagctgctc  480
agataacagc cggcattgca cttcaccggt ccatgctgaa ctctcaggcc atcgacaatc  540
tgagagcgag cctggaaact actaatcagg caattgaggc aatcagacaa gcagggcagg  600
agatgatatt ggctgttcag ggtgtccaag actacatcaa taatgagctg ataccgtcta  660
tgaaccagct atcttgtgat ctaatcggtc agaagctcgg gctcaaattg cttagatact  720
atacagaaat cctgtcatta tttggcccca gcctacggga ccccatatct gcggagatat  780
ctatccaggc tttgagttat gcacttggag gagatatcaa taaggtgtta gaaaagctcg  840
gatacagtgg aggcgattta ctaggcatct tagagagcag aggaataaag gctcggataa  900
ctcacgtcga cacagagtcc tacttcatag tcctcagtat agcctatccg acgctgtccg  960
agattaaggg ggtgattgtc caccggctag agggggtctc gtacaacata ggctctcaag  1020
agtggtatac cactgtgccc aagtatgttg caacccaagg gtaccttatc tcgaattttg  1080
atgagtcatc atgtactttc atgccagagg ggactgtgtg cagccaaaat gccttgtacc  1140
cgatgagtcc tctgctccaa gaatgcctcc gggggtccac caagtcctgt gctcgtacac  1200
tcgtatccgg gtcttttggg aaccggttca ttttatcaca agggaaccta atagccaatt  1260
gtgcatcaat tctttgtaag tgttacacaa caggtacgat tattaatcaa gaccctgaca  1320
agatcctaac atacattgct gccgatcgct gcccggtagt cgaggtgaac ggcgtgacca  1380
tccaagtcgg gagcaggagg tatccagacg ctgtgtactt gcacagaatt gacctcggtc  1440
ctcccatatc attggagagg ttggacgtag ggacaaatct ggggaatgca attgccaaat  1500
tggaggatgc caaggaattg ttggaatcat cggaccagat attgagaagt atgaaaggtt  1560
tatcgagcac tagcatagtc tacatcctga ttgcagtgtg tcttggaggg ttgataggga  1620
tccccacttt aatatgttgc tgcagggggc gttgtaacaa aaagggagaa caagttggta  1680
tgtcaagacc aggcctaaag cctgacctta caggaacatc aaaatcctat gtaagatcgc  1740
tttgatgata ataggctgga gcctcggtgg ccaagcttct tgccccttgg gcctcccccc  1800
agcccctcct ccccttcctg cacccgtacc cccgtggtct ttgaataaag tctgagtggg  1860
cggc                                                               1864
```

```
SEQ ID NO: 70            moltype = RNA  length = 1653
FEATURE                  Location/Qualifiers
misc_feature             1..1653
                         note = Synthetic Polynucleotide
source                   1..1653
                         mol_type = other RNA
                         organism = synthetic construct
```

```
SEQUENCE: 70
atgggtctca aggtgaacgt ctctgccgta ttcatggcag tactgttaac tctccaaaca  60
cccgccggtc aaattcattg gggcaatctc tctaagatag gggtagtagg aataggaagt  120
gcaagctaca aagttatgac tcgttccagc catcaatcat tagtcataaa attaatgccc  180
aatataactc tcctcaataa ctgcacgagg gtagagattg cagaatacag gagactacta  240
agaacagttt tggaaccaat tagggatgca cttaatgcaa tgacccagaa cataaggccg  300
gttcagagcg tagcttcaag taggagacac aagagatttg cgggagtagt cctggcaggt  360
gcggccctag gtgttgccac agctgctcag ataacagccg gcattgcact tcaccggtcc  420
atgctgaact ctcaggccat cgacaatctg agagcgagcc tggaaactac taatcaggca  480
attgaggcaa tcagacaagc agggcaggag atgatattgg ctgttcaggg tgtccaagac  540
tacatcaata atgagctgat accgtctatg aaccagctat cttgtgatct aatcggtcag  600
aagctcgggc tcaaattgct tagatactat acagaaatcc tgtcattatt tggccccagc  660
ctacgggacc ccatatctgc ggagatatct atccaggctt tgagttatgc acttggagga  720
gatatcaata aggtgttaga aaagctcgga tacagtggag gcgatttact aggcatctta  780
gagagcagag gaataaaggc tcggataact cacgtcgaca cagagtccta cttcatagtc  840
ctcagtatag cctatccgac gctgtccgag attaaggggg tgattgtcca ccggctagag  900
ggggtctcgt acaacatagg ctctcaagag tggtatacca ctgtgcccaa gtatgttgca  960
acccaagggt accttatctc gaattttgat gagtcatcat gtactttcat gccagagggg  1020
actgtgtgca gccaaaatgc cttgtacccg atgagtcctc tgctccaaga atgcctccgg  1080
gggtccacca agtcctgtgc tcgtacactc gtatccgggt cttttgggaa ccggttcatt  1140
ttatcacaag ggaacctaat agccaattgt gcatcaattc tttgtaagtg ttacacaaca  1200
ggtacgatta ttaatcaaga ccctgacaag atcctaacat acattgctgc cgatcgctgc  1260
ccggtagtcg aggtgaacgg cgtgaccatc caagtcggga gcaggaggta tccagacgct  1320
gtgtacttgc acagaattga cctcggtcct cccatatcat tggagaggtt ggacgtaggg  1380
acaaatctgg ggaatgcaat tgccaaattg gaggatgcca aggaattgtt ggaatcatcg  1440
gaccagatat tgagaagtat gaaaggttta tcgagcacta gcatagtcta catcctgatt  1500
gcagtgtgtc ttggagggtt gatagggatc cccactttaa tatgttgctg caggggggcgt  1560
tgtaacaaaa agggagaaca agttggtatg tcaagaccag gcctaaagcc tgaccttaca  1620
ggaacatcaa aatcctatgt aagatcgctt tga                              1653

SEQ ID NO: 71          moltype = RNA  length = 1925
FEATURE                Location/Qualifiers
misc_feature           1..1925
                       note = Synthetic Polynucleotide
source                 1..1925
                       mol_type = other RNA
                       organism = synthetic construct
SEQUENCE: 71
ggggaaataa gagagaaaag aagagtaaga agaaatataa gagccaccat gggtctcaag  60
gtgaacgtct ctgccgtatt catggcagta ctgttaactc tccaaacacc cgccggtcaa  120
attcattggg gcaatctctc taagataggg gtagtaggaa taggaagtgc aagctacaaa  180
gttatgactc gttccagcca tcaatcatta gtcataaaat taatgcccaa tataactctc  240
ctcaataact gcacgagggt agagattgca gaatacagga gactactaag aacagttttg  300
gaaccaatta gggatgcact taatgcaatg acccagaaca taaggccggt tcagagcgta  360
gcttcaagta ggagacacaa gagatttgcg ggagtagtcc tggcaggtgc ggccctaggt  420
gttgccacag ctgctcagat aacagccggc attgcacttc accggtccat gctgaactct  480
caggccatcg acaatctgag agcgagcctg gaaactacta atcaggcaat tgaggcaatc  540
agacaagcag ggcaggagat gatattggct gttcagggtg tccaagacta catcaataat  600
gagctgatac cgtctatgaa ccagctatct tgtgatctaa tcggtcagaa gctcgggctc  660
aaattgctta gatactatac agaaatcctg tcattatttg gccccagcct acgggacccc  720
atatctgcgg agatatctat ccaggctttg agttatgcac ttggaggaga tatcaataag  780
gtgttagaaa agctcggata cagtggaggc gatttactag gcatcttaga gagcagagga  840
ataaaggctc ggataactca cgtcgacaca gagtcctact tcatagtcct cagtatagcc  900
tatccgacgc tgtccgagat taagggggtg attgtccacc ggctagaggg ggtctcgtac  960
aacataggct ctcaagagtg gtataccact gtgcccaagt atgttgcaac ccaagggtac  1020
cttatctcga attttgatga gtcatcatgt actttcatgc cagaggggac tgtgtgcagc  1080
caaaatgcct tgtacccgat gagtcctctg ctccaagaat gcctccgggg gtccaccaag  1140
tcctgtgctc gtacactcgt atccgggtct tttgggaacc ggttcatttt atcacaaggg  1200
aacctaatag ccaattgtgc atcaattctt tgtaagtgtt acacaacagg tacgattatt  1260
aatcaagacc ctgacaagat cctaacatac attgctgccg atcgctgccc ggtagtcgag  1320
gtgaacggcg tgaccatcca agtcgggagc aggaggtatc cagacgctgt gtacttgcac  1380
agaattgacc tcggtcctcc catatcattg gagaggttgg acgtagggac aaatctgggg  1440
aatgcaattg ccaaattgga ggatgccaag gaattgttgg aatcatcgga ccagatattg  1500
agaagtatga aaggtttatc gagcactagc atagtctaca tcctgattgc agtgtgtctt  1560
ggagggttga tagggatccc cactttaata tgttgctgca gggggcgttg taacaaaaag  1620
ggagaacaag ttggtatgtc aagaccaggc ctaaagcctg accttacagg aacatcaaaa  1680
tcctatgtaa gatcgctttg atgataatag gctggagcct cggtggccaa gcttcttgcc  1740
ccttgggcct ccccccagcc cctcctcccc ttcctgcacc cgtacccccg tggtctttga  1800
ataaagtctg agtgggcggc aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
tctag                                                              1925

SEQ ID NO: 72          moltype = RNA  length = 1864
FEATURE                Location/Qualifiers
misc_feature           1..1864
                       note = Synthetic Polynucleotide
source                 1..1864
                       mol_type = other RNA
                       organism = synthetic construct
```

SEQUENCE: 72
tcaagctttt ggaccctcgt acagaagcta atacgactca ctatagggaa ataagagaga 60
aaagaagagt aagaagaaat ataagagcca ccatgggtct caaggtgaac gtctctgtca 120
tattcatggc agtactgtta actcttcaaa cacccaccgg tcaaatccat tggggcaatc 180
tctctaagat aggggtggta ggggtaggaa gtgcaagcta caaagttatg actcgttcca 240
gccatcaatc attagtcata aagttaatgc ccaatataac tctcctcaac aattgcacga 300
gggtagggat tgcagaatac aggagactac tgagaacagt tctggaacca attagagatg 360
cacttaatgc aatgacccag aatataagac cggttcagag tgtagcttca agtaggagac 420
acaagagatt tgcgggagtt gtcctggcag gtgcggccct aggcgttgcc acagctgctc 480
aaataacagc cggtattgca cttcaccagt ccatgctgaa ctctcaagcc atcgacaatc 540
tgagagcgag cctagaaact actaatcagg caattgaggc aatcagacaa gcagggcagg 600
agatgatatt ggctgttcag ggtgtccaag actacatcaa taatgagctg ataccgtcta 660
tgaatcaact atcttgtgat ttaatcggcc agaagctagg gctcaaattg ctcagatact 720
atacagaaat cctgtcatta tttggcccca gcttacggga ccccatatct gcggagatat 780
ctatccaggc tttgagctat gcgcttggag gagatatcaa taaggtgttg gaaaagctcg 840
gatacagtgg aggtgatcta ctgggcatct tagagagcag aggaataaag gcccggataa 900
ctcacgtcga cacagagtcc tacttcattg tactcagtat agcctatccg acgctatccg 960
agattaaggg ggtgattgtc caccggctag agggggtctc gtacaacata ggctctcaag 1020
agtggtatac cactgtgccc aagtatgttg caacccaagg gtaccttatc tcgaattttg 1080
atgagtcatc atgcactttc atgccagagg ggactgtgtg cagccagaat gccttgtacc 1140
cgatgagtcc tctgctccaa gaatgcctcc gggggtccac taagtcctgt gctcgtacac 1200
tcgtatccgg gtctttcggg aaccggttca ttttatcaca ggggaaccta atagccaatt 1260
gtgcatcaat cctttgcaag tgttacacaa caggaacaat cattaatcaa gaccctgaca 1320
agatcctaac atacattgct gccgatcact gcccggtggt cgaggtgaat ggcgtgacca 1380
tccaagtcgg gagcaggagg tatccggacg ctgtgtactt gcacaggatt gacctcggtc 1440
ctcccatatc tttggagagg ttggacgtag ggacaaatct ggggaatgca attgctaagt 1500
tggaggatgc caaggaattg ttggagtcat cggaccagat attgaggagt atgaaaggtt 1560
tatcgagcac tagtatagtt tacatcctga ttgcagtgtg tcttggagga ttgataggga 1620
tccccgcttt aatatgttgc tgcagggggc gttgtaacaa gaagggagaa caagttggta 1680
tgtcaagacc aggcctaaag cctgatctta caggaacatc aaaatcctat gtaaggtcac 1740
tctgatgata ataggctgga gcctcggtgg ccaagcttct tgccccttgg gcctcccccc 1800
agcccctcct ccccttcctg cacccgtacc cccgtggtct ttgaataaag tctgagtggg 1860
cggc 1864

SEQ ID NO: 73 moltype = RNA length = 1653
FEATURE Location/Qualifiers
misc_feature 1..1653
note = Synthetic Polynucleotide
source 1..1653
mol_type = other RNA
organism = synthetic construct
SEQUENCE: 73
atgggtctca aggtgaacgt ctctgtcata ttcatggcag tactgttaac tcttcaaaca 60
cccaccggtc aaatccattg gggcaatctc tctaagatag gggtggtagg ggtaggaagt 120
gcaagctaca aagttatgac tcgttccagc catcaatcat tagtcataaa gttaatgccc 180
aatataactc tcctcaacaa ttgcacgagg gtagggattg cagaatacag gagactactg 240
agaacagttc tggaaccaat tagagatgca cttaatgcaa tgacccagaa tataagaccg 300
gttcagagtg tagcttcaag taggagacac aagagatttg cgggagttgt cctggcaggt 360
gcggccctag gcgttgccac agctgctcaa ataacagccg gtattgcact tcaccagtcc 420
atgctgaact ctcaagccat cgacaatctg agagcgagcc tagaaactac taatcaggca 480
attgaggcaa tcagacaagc agggcaggag atgatattgg ctgttcaggg tgtccaagac 540
tacatcaata atgagctgat accgtctatg aatcaactat cttgtgattt aatcggccag 600
aagctagggc tcaaattgct cagatactat acagaaatcc tgtcattatt tggccccagc 660
ttacgggacc ccatatctgc ggagatatct atccaggctt tgagctatgc gcttggagga 720
gatatcaata aggtgttgga aaagctcgga tacagtggag gtgatctact gggcatctta 780
gagagcagag gaataaaggc ccggataact cacgtcgaca cagagtccta cttcattgta 840
ctcagtatag cctatccgac gctatccgag attaaggggg tgattgtcca ccggctagag 900
ggggtctcgt acaacatagg ctctcaagag tggtatacca ctgtgcccaa gtatgttgca 960
acccaagggt accttatctc gaattttgat gagtcatcat gcactttcat gccagagggg 1020
actgtgtgca gccagaatgc cttgtacccg atgagtcctc tgctccaaga atgcctccgg 1080
gggtccacta agtcctgtgc tcgtacactc gtatccgggt ctttcgggaa ccggttcatt 1140
ttatcacagg ggaacctaat agccaattgt gcatcaatcc tttgcaagtg ttacacaaca 1200
ggaacaatca ttaatcaaga ccctgacaag atcctaacat acattgctgc cgatcactgc 1260
ccggtggtcg aggtgaatgg cgtgaccatc caagtcggga gcaggaggta tccggacgct 1320
gtgtacttgc acaggattga cctcggtcct cccatatctt tggagaggtt ggacgtaggg 1380
acaaatctgg ggaatgcaat tgctaagttg gaggatgcca aggaattgtt ggagtcatcg 1440
gaccagatat tgaggagtat gaaaggttta tcgagcacta gtatagttta catcctgatt 1500
gcagtgtgtc ttggaggatt gatagggatc cccgctttaa tatgttgctg caggggggcgt 1560
tgtaacaaga agggagaaca agttggtatg tcaagaccag gcctaaagcc tgatcttaca 1620
ggaacatcaa aatcctatgt aaggtcactc tga 1653

SEQ ID NO: 74 moltype = RNA length = 1925
FEATURE Location/Qualifiers
misc_feature 1..1925
note = Synthetic Polynucleotide
source 1..1925
mol_type = other RNA
organism = synthetic construct
SEQUENCE: 74

-continued

```
ggggaaataa gagagaaaag aagagtaaga agaaatataa gagccaccat gggtctcaag  60
gtgaacgtct ctgtcatatt catggcagta ctgttaactc ttcaaacacc caccggtcaa  120
atccattggg gcaatctctc taagataggg gtggtagggg taggaagtgc aagctacaaa  180
gttatgactc gttccagcca tcaatcatta gtcataaagt taatgcccaa tataactctc  240
ctcaacaatt gcacgagggt agggattgca gaatacagga gactactgag aacagttctg  300
gaaccaatta gagatgcact taatgcaatg acccagaata taagaccggt tcagagtgta  360
gcttcaagta ggagacacaa gagatttgcg ggagttgtcc tggcaggtgc ggccctaggc  420
gttgccacag ctgctcaaat aacagccggt attgcacttc accagtccat gctgaactct  480
caagccatcg acaatctgag agcgagccta gaaactacta atcaggcaat tgaggcaatc  540
agacaagcag ggcaggagat gatattggct gttcagggtg tccaagacta catcaataat  600
gagctgatac cgtctatgaa tcaactatct tgtgatttaa tcggccagaa gctagggctc  660
aaattgctca gatactatac agaaatcctg tcattatttg gccccagctt acgggacccc  720
atatctgcgg agatatctat ccaggctttg agctatgcgc ttggaggaga tatcaataag  780
gtgttggaaa agctcggata cagtggaggt gatctactgg gcatcttaga gagcagagga  840
ataaaggccc ggataactca cgtcgacaca gagtcctact tcattgtact cagtatagcc  900
tatccgacgc tatccgagat taagggggtg attgtccacc ggctagaggg ggtctcgtac  960
aacataggct ctcaagagtg gtataccact gtgcccaagt atgttgcaac ccaagggtac  1020
cttatctcga attttgatga gtcatcatgc actttcatgc cagaggggac tgtgtgcagc  1080
cagaatgcct tgtacccgat gagtcctctg ctccaagaat gcctccgggg gtccactaag  1140
tcctgtgctc gtacactcgt atccgggtct ttcgggaacc ggttcatttt atcacagggg  1200
aacctaatag ccaattgtgc atcaatcctt tgcaagtgtt acacaacagg aacaatcatt  1260
aatcaagacc ctgacaagat cctaacatac attgctgccg atcactgccc ggtggtcgag  1320
gtgaatggcg tgaccatcca agtcgggagc aggaggtatc cggacgctgt gtacttgcac  1380
aggattgacc tcggtcctcc catatctttg gagaggttgg acgtagggac aaatctgggg  1440
aatgcaattg ctaagttgga ggatgccaag gaattgttgg agtcatcgga ccagatattg  1500
aggagtatga aaggtttatc gagcactagt atagtttaca tcctgattgc agtgtgtctt  1560
ggaggattga tagggatccc cgctttaata tgttgctgca gggggcgttg taacaagaag  1620
ggagaacaag ttggtatgtc aagaccaggc ctaaagcctg atcttacagg aacatcaaaa  1680
tcctatgtaa ggtcactctg atgataatag gctggagcct cggtggccaa gcttcttgcc  1740
ccttgggcct ccccccagcc cctcctcccc ttcctgcacc cgtacccccg tggtctttga  1800
ataaagtctg agtgggcggc aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
tctag                                                              1925
```

```
SEQ ID NO: 75          moltype = RNA  length = 2065
FEATURE                Location/Qualifiers
misc_feature           1..2065
                       note = Synthetic Polynucleotide
source                 1..2065
                       mol_type = other RNA
                       organism = synthetic construct
SEQUENCE: 75
tcaagctttt ggaccctcgt acagaagcta atacgactca ctatagggaa ataagagaga  60
aaagaagagt aagaagaaat ataagagcca ccatgtcacc gcaacgagac cggataaatg  120
ccttctacaa agataaccct tatcccaagg gaagtaggat agttattaac agagaacatc  180
ttatgattga cagaccctat gttctgctgg ctgttctgtt cgtcatgttt ctgagcttga  240
tcggattgct ggcaattgca ggcattagac ttcatcgggc agccatctac accgcggaga  300
tccataaaag cctcagtacc aatctggatg tgactaactc catcgagcat caggtcaagg  360
acgtgctgac accactcttt aaaatcatcg gggatgaagt gggcctgaga acacctcaga  420
gattcactga cctagtgaaa ttcatctcgg acaagattaa attccttaat ccggataggg  480
agtacgactt cagagatctc acttggtgca tcaacccgcc agagaggatc aaactagatt  540
atgatcaata ctgtgcagat gtggctgctg aagagctcat gaatgcattg gtgaactcaa  600
ctctactgga gaccagaaca accactcagt tcctagctgt ctcaaaggga aactgctcag  660
ggcccactac aatcagaggt caattctcaa acatgtcgct gtccttgttg gacttgtact  720
taggtcgagg ttacaatgtg tcatctatag tcactatgac atcccaggga atgtatgggg  780
gaacctacct agttgaaaag cctaatctga acagcaaagg gtcagagttg tcacaactga  840
gcatgtaccg agtgtttgaa gtaggtgtga tcagaaaccc gggtttgggg gctccggtgt  900
tccatatgac aaactatttt gagcaaccag tcagtaatgg tctcggcaac tgtatggtgg  960
ctttggggga gctcaaactc gcagcccttt gtcacgggga cgattctatc ataattccct  1020
atcagggatc agggaaaggt gtcagcttcc agctcgtcaa gctgggtgtc tggaaatccc  1080
caaccgacat gcaatcctgg gtccccttat caacggatga tccagtggta gacaggcttt  1140
acctctcatc tcacagaggt gtcatcgctg acaatcaagc aaaatgggct gtcccgacaa  1200
cacgaacaga tgacaagttg cgaatggaga catgcttcca gcaggcgtgt aaaggtaaaa  1260
tccaagcact ctgcgagaat cccgagtggg taccattgaa ggataacagg attccttcat  1320
acggggtcct gtctgttgat ctgagtctga cggttgagct taaaatcaaa attgcttcgg  1380
gattcgggcc attgatcaca cacggctcag ggatggacct atacaaatcc aactgcaaca  1440
atgtgtattg gctgactatt ccgccaatga gaaatctagc cttaggcgta atcaacacat  1500
tggagtggat accgagattc aaggttagtc ccaacctctt cactgtccca attaaggaag  1560
caggcgaaga ctgccatgcc ccaacatacc tacctgcgga ggtggacggt gatgtcaaac  1620
tcagttccaa cctggtgatt ctacctggtc aagatctcca atatgttttg gcaacctacg  1680
atacctccag ggttgagcat gctgtggttt attacgttta cagcccaagc cgctcatttt  1740
cttactttta tccttttagg ttgcctataa agggggtccc aatcgaacta caagtggaat  1800
gcttcacatg ggatcaaaaa ctctggtgcc gtcacttctg tgtgcttgcg gactcagaat  1860
ccggtggact tatcactcac tctgggatgg tgggcatggg agtcagctgc acagctaccc  1920
gggaagatgg aaccaatcgc agataatgat aataggctgg agcctcggtg gccaagcttc  1980
ttgccccttg ggcctccccc cagcccctcc tccccttcct gcacccgtac cccgtggtc  2040
tttgaataaa gtctgagtgg gcggc                                        2065
```

```
SEQ ID NO: 76          moltype = RNA  length = 1854
```

-continued

```
FEATURE                 Location/Qualifiers
misc_feature            1..1854
                        note = Synthetic Polynucleotide
source                  1..1854
                        mol_type = other RNA
                        organism = synthetic construct
SEQUENCE: 76
atgtcaccgc aacgagaccg gataaatgcc ttctacaaag ataaccctta tcccaaggga  60
agtaggatag ttattaacag agaacatctt atgattgaca gaccctatgt tctgctggct  120
gttctgttcg tcatgtttct gagcttgatc ggattgctgg caattgcagg cattagactt  180
catcgggcag ccatctacac cgcggagatc cataaaagcc tcagtaccaa tctggatgtg  240
actaactcca tcgagcatca ggtcaaggac gtgctgacac cactctttaa aatcatcggg  300
gatgaagtgg gcctgagaac acctcagaga ttcactgacc tagtgaaatt catctcggac  360
aagattaaat tccttaatcc ggatagggag tacgacttca gagatctcac ttggtgcatc  420
aacccgccag agaggatcaa actagattat gatcaatact gtgcagatgt ggctgctgaa  480
gagctcatga atgcattggt gaactcaact ctactggaga ccagaacaac cactcagttc  540
ctagctgtct caaagggaaa ctgctcaggg cccactacaa tcagaggtca attctcaaac  600
atgtcgctgt ccttgttgga cttgtactta ggtcgaggtt acaatgtgtc atctatagtc  660
actatgacat cccagggaat gtatgggggga acctacctag ttgaaaagcc taatctgaac  720
agcaaagggt cagagttgtc acaactgagc atgtaccgag tgtttgaagt aggtgtgatc  780
agaaacccgg gtttgggggc tccggtgttc catatgacaa actattttga gcaaccagtc  840
agtaatggtc tcggcaactg tatggtggct ttgggggagc tcaaactcgc agccctttgt  900
cacggggacg attctatcat aattccctat cagggatcag ggaaaggtgt cagcttccag  960
ctcgtcaagc tgggtgtctg gaaatcccca accgacatgc aatcctgggt ccccttatca  1020
acggatgatc cagtggtaga caggctttac ctctcatctc acagaggtgt catcgctgac  1080
aatcaagcaa aatgggctgt cccgacaaca cgaacagatg acaagttgcg aatggagaca  1140
tgcttccagc aggcgtgtaa aggtaaaatc caagcactct gcgagaatcc cgagtgggta  1200
ccattgaagg ataacaggat tccttcatac ggggtcctgt ctgttgatct gagtctgacg  1260
gttgagctta aaatcaaaat tgcttcggga ttcgggccat tgatcacaca cggctcaggg  1320
atggacctat acaaatccaa ctgcaacaat gtgtattggc tgactattcc gccaatgaga  1380
aatctagcct taggcgtaat caacacattg gagtggatac cgagattcaa ggttagtccc  1440
aacctcttca ctgtcccaat taaggaagca ggcgaagact gccatgcccc aacataccta  1500
cctgcggagg tggacggtga tgtcaaactc agttccaacc tggtgattct acctggtcaa  1560
gatctccaat atgttttggc aacctacgat acctccaggg ttgagcatgc tgtggtttat  1620
tacgtttaca gcccaagccg ctcattttct tacttttatc cttttaggtt gcctataaag  1680
ggggtcccaa tcgaactaca agtggaatgc ttcacatggg atcaaaaact ctggtgccgt  1740
cacttctgtg tgcttgcgga ctcagaatcc ggtggactta tcactcactc tgggatggtg  1800
ggcatgggag tcagctgcac agctacccgg gaagatggaa ccaatcgcag ataa        1854

SEQ ID NO: 77           moltype = RNA  length = 2126
FEATURE                 Location/Qualifiers
misc_feature            1..2126
                        note = Synthetic Polynucleotide
source                  1..2126
                        mol_type = other RNA
                        organism = synthetic construct
SEQUENCE: 77
ggggaaataa gagagaaaag aagagtaaga agaaatataa gagccaccat gtcaccgcaa  60
cgagaccgga taaatgcctt ctacaaagat aacccttatc ccaagggaag taggatagtt  120
attaacagag aacatcttat gattgacaga ccctatgttc tgctggctgt tctgttcgtc  180
atgtttctga gcttgatcgg attgctggca attgcaggca ttagacttca tcgggcagcc  240
atctacaccg cggagatcca taaaagcctc agtaccaatc tggatgtgac taactccatc  300
gagcatcagg tcaaggacgt gctgacacca ctctttaaaa tcatcgggga tgaagtgggc  360
ctgagaacac ctcagagatt cactgaccta gtgaaattca tctcggacaa gattaaattc  420
cttaatccgg atagggagta cgacttcaga gatctcactt ggtgcatcaa cccgccagag  480
aggatcaaac tagattatga tcaatactgt gcagatgtgg ctgctgaaga gctcatgaat  540
gcattggtga actcaactct actggagacc agaacaacca ctcagttcct agctgtctca  600
aagggaaact gctcagggcc cactacaatc agaggtcaat tctcaaacat gtcgctgtcc  660
ttgttggact tgtacttagg tcgaggttac aatgtgtcat ctatagtcac tatgacatcc  720
cagggaatgt atggggggaac ctacctagtt gaaaagccta atctgaacag caaagggtca  780
gagttgtcac aactgagcat gtaccgagtg tttgaagtag gtgtgatcag aaacccgggt  840
ttgggggctc cggtgttcca tatgacaaac tattttgagc aaccagtcag taatggtctc  900
ggcaactgta tggtggcttt gggggagctc aaactcgcag ccctttgtca cggggacgat  960
tctatcataa ttccctatca gggatcaggg aaaggtgtca gcttccagct cgtcaagctg  1020
ggtgtctgga aatccccaac cgacatgcaa tcctgggtcc ccttatcaac ggatgatcca  1080
gtggtagaca ggctttacct ctcatctcac agaggtgtca tcgctgacaa tcaagcaaaa  1140
tgggctgtcc cgacaacacg aacagatgac aagttgcgaa tggagacatg cttccagcag  1200
gcgtgtaaag gtaaaatcca agcactctgc gagaatcccg agtgggtacc attgaaggat  1260
aacaggattc cttcatacgg ggtcctgtct gttgatctga gtctgacggt tgagcttaaa  1320
atcaaaattg cttcgggatt cgggccattg atcacacacg gctcagggat ggacctatac  1380
aaatccaact gcaacaatgt gtattggctg actattccgc caatgagaaa tctagcctta  1440
ggcgtaatca acacattgga gtggataccg agattcaagg ttagtcccaa cctcttcact  1500
gtcccaatta aggaagcagg cgaagactgc catgccccaa catacctacc tgcggaggtg  1560
gacggtgatg tcaaactcag ttccaacctg gtgattctac ctggtcaaga tctccaatat  1620
gttttggcaa cctacgatac ctccagggtt gagcatgctg tggtttatta cgtttacagc  1680
ccaagccgct cattttctta cttttatcct tttaggttgc ctataaaggg ggtcccaatc  1740
gaactacaag tggaatgctt cacatgggat caaaaactct ggtgccgtca cttctgtgtg  1800
cttgcggact cagaatccgg tggacttatc actcactctg ggatggtggg catgggagtc  1860
agctgcacag ctacccggga agatggaacc aatcgcagat aatgataata ggctggagcc  1920
```

-continued

```
tcggtggcca agcttcttgc cccttgggcc tccccccagc ccctcctccc cttcctgcac  1980
ccgtaccccc gtggtctttg aataaagtct gagtgggcgg caaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa atctag                                        2126

SEQ ID NO: 78           moltype = RNA  length = 2065
FEATURE                 Location/Qualifiers
misc_feature            1..2065
                        note = Synthetic Polynucleotide
source                  1..2065
                        mol_type = other RNA
                        organism = synthetic construct
SEQUENCE: 78
tcaagctttt ggaccctcgt acagaagcta atacgactca ctatagggaa ataagagaga  60
aaagaagagt aagaagaaat ataagagcca ccatgtcacc acaacgagac cggataaatg  120
ccttctacaa agacaacccc catcctaagg gaagtaggat agttattaac agagaacatc  180
ttatgattga tagaccttat gttttgctgg ctgttctatt cgtcatgttt ctgagcttga  240
tcgggttgct agccattgca ggcattagac ttcatcgggc agccatctac accgcagaga  300
tccataaaag cctcagcacc aatctggatg taactaactc aatcgagcat caggttaagg  360
acgtgctgac accactcttc aagatcatcg gtgatgaagt gggcttgagg acacctcaga  420
gattcactga cctagtgaag ttcatctctg acaagattaa attccttaat ccggacaggg  480
aatacgactt cagagatctc acttggtgta tcaacccgcc agagagaatc aaattggatt  540
atgatcaata ctgtgcagat gtggctgctg aagaactcat gaatgcattg gtgaactcaa  600
ctctactgga gaccagggca accaatcagt tcctagctgt ctcaaaggga aactgctcag  660
ggcccactac aatcagaggc caattctcaa acatgtcgct gtccctgttg gacttgtatt  720
taagtcgagg ttacaatgtg tcatctatag tcactatgac atcccaggga atgtacgggg  780
gaacttacct agtggaaaag cctaatctga gcagcaaagg gtcagagttg tcacaactga  840
gcatgcaccg agtgtttgaa gtaggtgtta tcagaaatcc gggtttgggg gctccggtat  900
tccatatgac aaactatctt gagcaaccag tcagtaatga tttcagcaac tgcatggtgg  960
ctttgggggga gctcaagttc gcagccctct gtcacaggga agattctatc acaattccct  1020
atcagggatc agggaaaggt gtcagcttcc agcttgtcaa gctaggtgtc tggaaatccc  1080
caaccgacat gcaatcctgg gtccccctat caacggatga tccagtgata gacaggcttt  1140
acctctcatc tcacagaggc gttatcgctg acaatcaagc aaaatgggct gtcccgacaa  1200
cacggacaga tgacaagttg cgaatggaga catgcttcca gcaggcgtgt aagggtaaaa  1260
tccaagcact ttgcgagaat cccgagtgga caccattgaa ggataacagg attccttcat  1320
acggggtctt gtctgttgat ctgagtctga cagttgagct taaaatcaaa attgtttcag  1380
gattcgggcc attgatcaca cacggttcag ggatggacct atacaaatcc aaccacaaca  1440
atatgtattg gctgactatc ccgccaatga agaacctggc cttaggtgta atcaacacat  1500
tggagtggat accgagattc aaggttagtc ccaacctctt cactgttcca attaaggaag  1560
caggcgagga ctgccatgcc ccaacatacc tacctgcgga ggtggatggt gatgtcaaac  1620
tcagttccaa tctggtgatt ctacctggtc aagatctcca atatgttctg gcaacctacg  1680
atacttccag agttgaacat gctgtagttt attacgttta cagcccaagc cgctcatttt  1740
cttactttta tccttttagg ttgcctgtaa ggggggtccc cattgaatta caagtggaat  1800
gcttcacatg ggaccaaaaa ctctggtgcc gtcacttctg tgtgcttgcg gactcagaat  1860
ctggtggaca tatcactcac tctgggatgg tgggcatggg agtcagctgc acagccactc  1920
gggaagatgg aaccagccgc agatagtgat aataggctgg agcctcggtg gccaagcttc  1980
ttgccccttg ggcctccccc cagcccctcc tccccttcct gcacccgtac cccgtggtc  2040
tttgaataaa gtctgagtgg gcggc                                         2065

SEQ ID NO: 79           moltype = RNA  length = 1854
FEATURE                 Location/Qualifiers
misc_feature            1..1854
                        note = Synthetic Polynucleotide
source                  1..1854
                        mol_type = other RNA
                        organism = synthetic construct
SEQUENCE: 79
atgtcaccac aacgagaccg gataaatgcc ttctacaaag acaacccccca tcctaaggga  60
agtaggatag ttattaacag agaacatctt atgattgata gaccttatgt tttgctggct  120
gttctattcg tcatgtttct gagcttgatc gggttgctag ccattgcagg cattagactt  180
catcgggcag ccatctacac cgcagagatc cataaaagcc tcagcaccaa tctggatgta  240
actaactcaa tcgagcatca ggttaaggac gtgctgacac cactcttcaa gatcatcggt  300
gatgaagtgg gcttgaggac acctcagaga ttcactgacc tagtgaagtt catctctgac  360
aagattaaat tccttaatcc ggacagggaa tacgacttca gagatctcac ttggtgtatc  420
aacccgccag agagaatcaa attggattat gatcaatact gtgcagatgt ggctgctgaa  480
gaactcatga atgcattggt gaactcaact ctactggaga ccagggcaac caatcagttc  540
ctagctgtct caaagggaaa ctgctcaggg cccactacaa tcagaggcca attctcaaac  600
atgtcgctgt ccctgttgga cttgtattta agtcgaggtt acaatgtgtc atctatagtc  660
actatgacat cccagggaat gtacggggga acttacctag tggaaaagcc taatctgagc  720
agcaaagggt cagagttgtc acaactgagc atgcaccgag tgtttgaagt aggtgttatc  780
agaaatccgg gtttgggggc tccggtattc catatgacaa actatcttga gcaaccagtc  840
agtaatgatt tcagcaactg catggtggct ttgggggagc tcaagttcgc agccctctgt  900
cacagggaag attctatcac aattccctat cagggatcag ggaaaggtgt cagcttccag  960
cttgtcaagc taggtgtctg gaaatcccca accgacatgc aatcctgggt ccccctatca  1020
acggatgatc cagtgataga caggctttac ctctcatctc acagaggcgt tatcgctgac  1080
aatcaagcaa aatgggctgt cccgacaaca cggacagatg acaagttgcg aatggagaca  1140
tgcttccagc aggcgtgtaa gggtaaaatc caagcacttt gcgagaatcc cgagtggaca  1200
ccattgaagg ataacaggat tccttcatac ggggtcttgt ctgttgatct gagtctgaca  1260
gttgagctta aaatcaaaat tgtttcagga ttcgggccat tgatcacaca cggttcaggg  1320
```

-continued

```
atggacctat acaaatccaa ccacaacaat atgtattggc tgactatccc gccaatgaag  1380
aacctggcct taggtgtaat caacacattg gagtggatac cgagattcaa ggttagtccc  1440
aacctcttca ctgttccaat taaggaagca ggcgaggact gccatgcccc aacataccta  1500
cctgcggagg tggatggtga tgtcaaactc agttccaatc tggtgattct acctggtcaa  1560
gatctccaat atgttctggc aacctacgat acttccagag ttgaacatgc tgtagtttat  1620
tacgtttaca gcccaagccg ctcattttct tacttttatc cttttaggtt gcctgtaagg  1680
ggggtcccca ttgaattaca agtggaatgc ttcacatggg accaaaaact ctggtgccgt  1740
cacttctgtg tgcttgcgga ctcagaatct ggtggacata tcactcactc tgggatggtg  1800
ggcatgggag tcagctgcac agccactcgg gaagatggaa ccagccgcag atag        1854

SEQ ID NO: 80          moltype = RNA  length = 2126
FEATURE                Location/Qualifiers
misc_feature           1..2126
                       note = Synthetic Polynucleotide
source                 1..2126
                       mol_type = other RNA
                       organism = synthetic construct
SEQUENCE: 80
ggggaaataa gagagaaaag aagagtaaga agaaatataa gagccaccat gtcaccacaa  60
cgagaccgga taaatgcctt ctacaaagac aaccccccatc ctaagggaag taggatagtt  120
attaacagag aacatcttat gattgataga ccttatgttt tgctggctgt tctattcgtc  180
atgtttctga gcttgatcgg gttgctagcc attgcaggca ttagacttca tcgggcagcc  240
atctacaccg cagagatcca taaaagcctc agcaccaatc tggatgtaac taactcaatc  300
gagcatcagg ttaaggacgt gctgacacca ctcttcaaga tcatcggtga tgaagtgggc  360
ttgaggacac ctcagagatt cactgaccta gtgaagttca tctctgacaa gattaaattc  420
cttaatccgg acagggaata cgacttcaga gatctcactt ggtgtatcaa cccgccagag  480
agaatcaaat tggattatga tcaatactgt gcagatgtgg ctgctgaaga actcatgaat  540
gcattggtga actcaactct actggagacc agggcaacca atcagttcct agctgtctca  600
aagggaaact gctcagggcc cactacaatc agaggccaat tctcaaacat gtcgctgtcc  660
ctgttggact tgtatttaag tcgaggttac aatgtgtcat ctatagtcac tatgacatcc  720
cagggaatgt acgggggaac ttacctagtg gaaaagccta atctgagcag caaagggtca  780
gagttgtcac aactgagcat gcaccgagtg tttgaagtag gtgttatcag aaatccgggt  840
ttgggggctc cggtattcca tatgacaaac tatcttgagc aaccagtcag taatgatttc  900
agcaactgca tggtggcttt gggggagctc aagttcgcag ccctctgtca cagggaagat  960
tctatcacaa ttccctatca gggatcaggg aaaggtgtca gcttccagct tgtcaagcta  1020
ggtgtctgga aatccccaac cgacatgcaa tcctgggtcc ccctatcaac ggatgatcca  1080
gtgatagaca ggctttacct ctcatctcac agaggcgtta tcgctgacaa tcaagcaaaa  1140
tgggctgtcc cgacaacacg gacagatgac aagttgcgaa tggagacatg cttccagcag  1200
gcgtgtaagg gtaaaatcca agcactttgc gagaatcccg agtggacacc attgaaggat  1260
aacaggattc cttcatacgg ggtcttgtct gttgatctga gtctgacagt tgagcttaaa  1320
atcaaaattg tttcaggatt cgggccattg atcacacacg gttcagggat ggacctatac  1380
aaatccaacc acaacaatat gtattggctg actatcccgc caatgaagaa cctggcctta  1440
ggtgtaatca acacattgga gtggataccg agattcaagg ttagtcccaa cctcttcact  1500
gttccaatta aggaagcagg cgaggactgc catgccccaa catacctacc tgcggaggtg  1560
gatggtgatg tcaaactcag ttccaatctg gtgattctac ctggtcaaga tctccaatat  1620
gttctggcaa cctacgatac ttccagagtt gaacatgctg tagtttatta cgtttacagc  1680
ccaagccgct cattttctta cttttatcct tttaggttgc ctgtaagggg ggtccccatt  1740
gaattacaag tggaatgctt cacatgggac caaaaactct ggtgccgtca cttctgtgtg  1800
cttgcggact cagaatctgg tggacatatc actcactctg ggatggtggg catgggagtc  1860
agctgcacag ccactcggga agatggaacc agccgcagat agtgataata ggctggagcc  1920
tcggtggcca agcttcttgc cccttgggcc tccccccagc ccctcctccc cttcctgcac  1980
ccgtaccccc gtggtctttg aataaagtct gagtgggcgg caaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa atctag                                      2126

SEQ ID NO: 81          moltype = RNA  length = 1729
FEATURE                Location/Qualifiers
misc_feature           1..1729
                       note = Synthetic Polynucleotide
source                 1..1729
                       mol_type = other RNA
                       organism = synthetic construct
SEQUENCE: 81
tcaagctttt ggaccctcgt acagaagcta atacgactca ctatagggaa ataagagaga  60
aaagaagagt aagaagaaat ataagagcca ccatggcaca agtcattaat acaaacagcc  120
tgtcgctgtt gacccagaat aacctgaaca aatcccagtc cgcactgggc actgctatcg  180
agcgtttgtc ttccggtctg cgtatcaaca gcgcgaaaga cgatgcggca ggacaggcga  240
ttgctaaccg ttttaccgcg aacatcaaag gtctgactca ggcttcccgt aacgctaacg  300
acggtatctc cattgcgcag accactgaag gcgcgctgaa cgaaatcaac aacaacctgc  360
agcgtgtgcg tgaactggcg gttcagtctg cgaatggtac taactcccag tctgacctcg  420
actccatcca ggctgaaatc acccagcgcc tgaacgaaat cgaccgtgta tccggccaga  480
ctcagttcaa cggcgtgaaa gtcctggcgc aggacaacac cctgaccatc caggttggtg  540
ccaacgacgg tgaaactatc gatattgatt taaaagaaat cagctctaaa acactgggac  600
ttgataagct taatgtccaa gatgcctaca ccccgaaaga aactgctgta accgttgata  660
aaactaccta taaaaatggt acagatccta ttacagccca gagcaatact gatatccaaa  720
ctgcaattgg cggtggtgca acgggggtta ctggggctga tatcaaattt aaagatggtc  780
aatactattt agatgttaaa ggcggtgctt ctgctggtgt ttataaagcc acttatgatg  840
aaactacaaa gaaagttaat attgatacga ctgataaaac tccgttggca actgcggaag  900
ctacagctat tcggggaacg gccactataa cccacaacca aattgctgaa gtaacaaaag  960
```

```
agggtgttga tacgaccaca gttgcggctc aacttgctgc agcaggggtt actggcgccg  1020
ataaggacaa tactagcctt gtaaaactat cgtttgagga taaaaacggt aaggttattg  1080
atggtggcta tgcagtgaaa atgggcgacg atttctatgc cgctacatat gatgagaaaa  1140
caggtgcaat tactgctaaa accactactt atacagatgg tactggcgtt gctcaaactg  1200
gagctgtgaa atttggtggc gcaaatggta aatctgaagt tgttactgct accgatggta  1260
agacttactt agcaagcgac cttgacaaac ataacttcag aacaggcggt gagcttaaag  1320
aggttaatac agataagact gaaaacccac tgcagaaaat tgatgctgcc ttggcacagg  1380
ttgatacact tcgttctgac ctgggtgcgg ttcagaaccg tttcaactcc gctatcacca  1440
acctgggcaa taccgtaaat aacctgtctt ctgcccgtag ccgtatcgaa gattccgact  1500
acgcaaccga agtctccaac atgtctcgcg cgcagattct gcagcaggcc ggtacctccg  1560
ttctggcgca ggcgaaccag gttccgcaaa acgtcctctc tttactgcgt tgataatagg  1620
ctggagcctc ggtggccatg cttcttgccc cttgggcctc cccccagccc ctcctcccct  1680
tcctgcaccc gtacccccgt ggtctttgaa taaagtctga gtgggcggc             1729
```

```
SEQ ID NO: 82           moltype = RNA  length = 1518
FEATURE                 Location/Qualifiers
misc_feature            1..1518
                        note = Synthetic Polynucleotide
source                  1..1518
                        mol_type = other RNA
                        organism = synthetic construct
SEQUENCE: 82
atggcacaag tcattaatac aaacagcctg tcgctgttga cccagaataa cctgaacaaa  60
tcccagtccg cactgggcac tgctatcgag cgtttgtctt ccggtctgcg tatcaacagc  120
gcgaaagacg atgcggcagg acaggcgatt gctaaccgtt ttaccgcgaa catcaaaggt  180
ctgactcagg cttcccgtaa cgctaacgac ggtatctcca ttgcgcagac cactgaaggc  240
gcgctgaacg aaatcaacaa caacctgcag cgtgtgcgtg aactggcggt tcagtctgcg  300
aatggtacta actcccagtc tgacctcgac tccatccagg ctgaaatcac ccagcgcctg  360
aacgaaatcg accgtgtatc cggccagact cagttcaacg gcgtgaaagt cctggcgcag  420
gacaacaccc tgaccatcca ggttggtgcc aacgacggtg aaactatcga tattgattta  480
aaagaaatca gctctaaaac actgggactt gataagctta atgtccaaga tgcctacacc  540
ccgaaagaaa ctgctgtaac cgttgataaa actacctata aaaatggtac agatcctatt  600
acagcccaga gcaatactga tatccaaact gcaattggcg gtggtgcaac ggggggttact  660
ggggctgata tcaaatttaa agatggtcaa tactatttag atgttaaagg cggtgcttct  720
gctggtgttt ataaagccac ttatgatgaa actacaaaga aagttaatat tgatacgact  780
gataaaactc cgttggcaac tgcggaagct acagctattc ggggaacggc cactataacc  840
cacaaccaaa ttgctgaagt aacaaaagag ggtgttgata cgaccacagt tgcggctcaa  900
cttgctgcag caggggttac tggcgccgat aaggacaata ctagccttgt aaaactatcg  960
tttgaggata aaaacggtaa ggttattgat ggtggctatg cagtgaaaat gggcgacgat  1020
ttctatgccg ctacatatga tgagaaaaca ggtgcaatta ctgctaaaac cactacttat  1080
acagatggta ctggcgttgc tcaaactgga gctgtgaaat ttggtggcgc aaatggtaaa  1140
tctgaagttg ttactgctac cgatggtaag acttacttag caagcgacct tgacaaacat  1200
aacttcagaa caggcggtga gcttaaagag gttaatacag ataagactga aaacccactg  1260
cagaaaattg atgctgcctt ggcacaggtt gatacacttc gttctgacct gggtgcggtt  1320
cagaaccgtt tcaactccgc tatcaccaac ctgggcaata ccgtaaataa cctgtcttct  1380
gcccgtagcc gtatcgaaga ttccgactac gcaaccgaag tctccaacat gtctcgcgcg  1440
cagattctgc agcaggccgg tacctccgtt ctggcgcagg cgaaccaggt tccgcaaaac  1500
gtcctctctt tactgcgt                                                1518
```

```
SEQ ID NO: 83           moltype = RNA  length = 1790
FEATURE                 Location/Qualifiers
misc_feature            1..1790
                        note = Synthetic Polynucleotide
source                  1..1790
                        mol_type = other RNA
                        organism = synthetic construct
SEQUENCE: 83
ggggaaataa gagagaaaag aagagtaaga agaaatataa gagccaccat ggcacaagtc  60
attaatacaa acagcctgtc gctgttgacc cagaataacc tgaacaaatc ccagtccgca  120
ctgggcactg ctatcgagcg tttgtcttcc ggtctgcgta tcaacagcgc gaaagacgat  180
gcggcaggac aggcgattgc taaccgtttt accgcgaaca tcaaaggtct gactcaggct  240
tcccgtaacg ctaacgacgg tatctccatt gcgcagacca ctgaaggcgc gctgaacgaa  300
atcaacaaca acctgcagcg tgtgcgtgaa ctggcggttc agtctgcgaa tggtactaac  360
tcccagtctg acctcgactc catccaggct gaaatcaccc agcgcctgaa cgaaatcgac  420
cgtgtatccg gccagactca gttcaacggc gtgaaagtcc tggcgcagga caacaccctg  480
accatccagg ttggtgccaa cgacggtgaa actatcgata ttgatttaaa agaaatcagc  540
tctaaaacac tgggacttga taagcttaat gtccaagatg cctacacccc gaaagaaact  600
gctgtaaccg ttgataaaac tacctataaa aatggtacag atcctattac agcccagagc  660
aatactgata tccaaactgc aattggcggt ggtgcaacgg gggttactgg ggctgatatc  720
aaatttaaag atggtcaata ctatttagat gttaaaggcg gtgcttctgc tggtgtttat  780
aaagccactt atgatgaaac tacaaagaaa gttaatattg atacgactga taaaactccg  840
ttggcaactg cggaagctac agctattcgg ggaacggcca ctataaccca caaccaaatt  900
gctgaagtaa caaaagaggg tgttgatacg accacagttg cggctcaact tgctgcagca  960
ggggttactg gcgccgataa ggacaatact agccttgtaa aactatcgtt tgaggataaa  1020
aacggtaagg ttattgatgg tggctatgca gtgaaaatgg gcgacgattt ctatgccgct  1080
acatatgatg agaaaacagg tgcaattact gctaaaacca ctacttatac agatggtact  1140
ggcgttgctc aaactggagc tgtgaaattt ggtggcgcaa atggtaaatc tgaagttgtt  1200
actgctaccg atggtaagac ttacttagca agcgaccttg acaaacataa cttcagaaca  1260
ggcggtgagc ttaaagaggt taatacagat aagactgaaa acccactgca gaaaattgat  1320
```

-continued

```
gctgccttgg cacaggttga tacacttcgt tctgacctgg gtgcggttca gaaccgtttc  1380
aactccgcta tcaccaacct gggcaatacc gtaaataacc tgtcttctgc ccgtagccgt  1440
atcgaagatt ccgactacgc aaccgaagtc tccaacatgt ctcgcgcgca gattctgcag  1500
caggccggta cctccgttct ggcgcaggcg aaccaggttc cgcaaaacgt cctctcttta  1560
ctgcgttgat aataggctgg agcctcggtg gccatgcttc ttgccccttg ggcctccccc  1620
cagcccctcc tccccttcct gcacccgtac ccccgtggtc tttgaataaa gtctgagtgg  1680
gcggcaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaatctag             1790

SEQ ID NO: 84          moltype = AA  length = 13
FEATURE                Location/Qualifiers
source                 1..13
                       mol_type = protein
                       note = Salmonella typhimurium
                       organism = unidentified
SEQUENCE: 84
LQRVRELAVQ SAN                                                     13

SEQ ID NO: 85          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 85
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAICKTIRL ESEVTAINNA LKKTNEAVST LGNGVRVLAF AVRELKDFVS KNLTRALNKN  180
KCDIDDLKMA VSFSQFNRRF LNVVRQFSDN AGITPAISLD LMTDAELARA VPNMPTSAGQ  240
IKLMLENRAM VRRKGFGILC GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFNVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 86          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 86
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAICKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILC GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEHQWHVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 87          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 87
MSWKVVIIFS LLITPQHGLK ESYLEESCST ITEGYLSVLR TGWYTNVFTL EVGDVENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIPDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 88          moltype = AA  length = 539
FEATURE                Location/Qualifiers
REGION                 1..539
                       note = Synthetic Polypeptide
source                 1..539
                       mol_type = protein
                       organism = synthetic construct
```

```
SEQUENCE: 88
MSWKVVIIFS LLITPQHGLK ESYLEESCST ITEGYLSVLR TGWYTNVFTL EVGDVENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIPDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPENQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 89          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 89
MSWKVVIIFS LLITPQHGLK ESYLEESCST ITEGYLSVLR TGWYTNVFTL EVGDVENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVL KNLTRAINKN  180
KCDIPDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 90          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 90
MSWKVVIIFS LLITPQHGLK ESYLEESCST ITEGYLSVLR TGWYTNVFTL EVGDVENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVL KNLTRAINKN  180
KCDIPDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPENQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 91          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 91
MSWKVVIIFS LLITPQHGLK ESYLEESCST ITEGYLSVLR TGWYTNVFTL PVGDVENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 92          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 92
MSWKVVIIFS LLITPQHGLK ESYLEESCST ITEGYLSVLR TGWYTNVFTL PVGDVENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
```

```
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPENQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 93          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 93
MSWKVVIIFS LLITPQHGLK ESYLEESCST ITEGYLSVLR TGWYTNVFTL EVGDVENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 94          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 94
MSWKVVIIFS LLITPQHGLK ESYLEESCST ITEGYLSVLR TGWYTNVFTL EVGDLENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 95          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 95
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVL KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 96          moltype = AA  length = 539
FEATURE                Location/Qualifiers
REGION                 1..539
                       note = Synthetic Polypeptide
source                 1..539
                       mol_type = protein
                       organism = synthetic construct
SEQUENCE: 96
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLWRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 97          moltype = AA  length = 539
FEATURE                Location/Qualifiers
REGION                 1..539
```

```
                        note = Synthetic Polypeptide
source                  1..539
                        mol_type = protein
                        organism = synthetic construct
SEQUENCE: 97
MSWKVVIIFS LLITPQHGLK ESYLEESCST ITEGYLSVLR TGWYTNVFTL EVGDLENLTC  60
SDGPSLIKTE LDLLKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVL KNLWRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 98           moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 98
MSWKVVIIFS LLITPQHGLK ESYLEESCST ITEGYLSVLR TGWYTNVFTL PVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 99           moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 99
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIPDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 100          moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 100
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCPIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 101          moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 101
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
```

-continued

```
GVAIAKTIRL PSEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 102          moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 102
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFPPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 103          moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 103
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPENQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 104          moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 104
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQFNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPQDQFQVAL DQVFENIENS QALVDQSNRI  480
LSSAEKGNTG FIIVIILIAV LGSSMILVSI FIIIKKTKKP TGAPPELSGV TNNGFIPHN   539

SEQ ID NO: 105          moltype = AA  length = 539
FEATURE                 Location/Qualifiers
REGION                  1..539
                        note = Synthetic Polypeptide
source                  1..539
                        mol_type = protein
                        organism = synthetic construct
SEQUENCE: 105
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPGS GSFVLGAIAL GVAAAAAVTA  120
GVAIAKTIRL ESEVTAINNA LKKTNEAVST LGNGVRVLAT AVRELKDFVS KNLTRAINKN  180
KCDIDDLKMA VSFSQWNRRF LNVVRQFSDN AGITPAISLD LMTDAELARA VPNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFQVAL DQVFENIENS QALVDQSNRI  480
LSSAEKGNTG FIIVIILIAV LGSSMILVSI FIIIKKTKKP TGAPPELSGV TNNGFIPHN   539
```

```
SEQ ID NO: 106          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 106
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tctgcaagac catcagactg gaaagcgaag tgaccgccat caacaacgcc  420
ctgaagaaga caaacgaggc cgtcagcaca ctcggcaatg gcgttagagt gctggccttt  480
gccgtgcgcg agctgaagga cttcgtgtcc aagaacctga cacgggccct gaacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgtgt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcaa cgtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 107          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 107
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tctgcaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgtgt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagc accagtggca tgtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 108          moltype = DNA  length = 1617
FEATURE                 Location/Qualifiers
misc_feature            1..1617
                        note = Synthetic Polynucleotide
source                  1..1617
                        mol_type = other DNA
```

organism = synthetic construct
SEQUENCE: 108
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tccctgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgagg atcagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

SEQ ID NO: 109 moltype = DNA length = 1617
FEATURE Location/Qualifiers
misc_feature 1..1617
note = Synthetic Polynucleotide
source 1..1617
mol_type = other DNA
organism = synthetic construct
SEQUENCE: 109
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300
ggcagctttg tgctgggagc cattgctctt ggagtggctg ctgctgcagc tgttacagca 360
ggcgtggcca tcgctaagac catcagactg gaaagcgaag tgaccgccat caacaacgcc 420
ctgaagaaga caaacgaggc cgtcagcaca ctcggcaatg gcgttagagt gctggccaca 480
gccgtgcgcg agctgaagga cttcgtgtcc aagaacctga cacgggccat taacaagaac 540
aagtgcgaca tccctgacct gaagatggcc gtgtccttta gccagttcaa ccggcggttt 600
ctgaacgtcg tgcggcagtt tagcgacaac gccggaatca caccagccat cagcctggac 660
ctgatgacag atgctgagct ggctagagcc gtgcctaaca tgcctacatc tgccggccag 720
atcaagctga tgctcgagaa tagagccatg gtccgacgga aaggcttcgg cattctgatt 780
ggcgtgtacg gcagcagcgt gatctatatg gtgcagctgc ctatcttcgg cgtgatcgac 840
acaccctgct ggattgtgaa ggccgctcct agctgtagcg agaagaaggg caattacgcc 900
tgcctgctga gagaggacca aggctggtat tgtcagaacg ccggcagcac cgtgtactac 960
cctaacgaga aggactgcga gacaagaggc gaccacgtgt tctgtgatac cgccgctgga 1020
atcaatgtgg ccgagcagag caaagagtgc aacatcaaca tcagcaccac caactatccc 1080
tgcaaggtgt ccaccggcag gcaccctatt tctatggtgg ctctgtctcc tctgggagcc 1140
ctggtggctt gttataaggg cgtgtcctgt agcatcggca gcaacagagt gggcatcatc 1200
aagcagctga acaagggctg cagctacatc accaaccagg acgccgatac cgtgaccatc 1260
gacaacaccg tgtatcagct gagcaaggtg gaaggcgaac agcacgtgat caagggcaga 1320
cctgtgtcca gcagcttcga ccctatcaag ttccctgaga accagttcca ggtggccctg 1380
gaccaggtgt tcgagaacat cgagaattcc caggctctgg tggaccagtc caacagaatc 1440
ctgtctagcg ccgagaaggg aaacaccggc ttcatcatcg tgatcatcct gatcgccgtg 1500
ctgggcagct ccatgatcct ggtgtccatc ttcatcatta tcaagaagac caagaagccc 1560
accggcgctc ctccagaact gagcggagtg accaacaatg gcttcatccc tcacaac 1617

SEQ ID NO: 110 moltype = DNA length = 1617
FEATURE Location/Qualifiers
misc_feature 1..1617
note = Synthetic Polynucleotide
source 1..1617
mol_type = other DNA
organism = synthetic construct
SEQUENCE: 110
atgagctgga aggtggtcat catcttcagc ctgctgatca cacctcagca cggcctgaaa 60
gagagctacc tggaagagtc ctgcagcacc atcacagagg gctacctgtc tgtgctgaga 120
accggctggt acaccaacgt gttcacactg gaagtgggcg acgtcgagaa tctgacatgc 180
tctgatggcc ctagcctgat caagaccgag ctggatctgc tcaagagcgc cctgagagaa 240
ctcaagaccg tgtctgccga tcagctggcc agagaggaac agatcgagaa tcctggcagc 300

```
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 111          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 111
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgaga accagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 112          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 112
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg cctgtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
```

```
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 113          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 113
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg cctgtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgaga accagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 114          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 114
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
```

```
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 115          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 115
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acctcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 116          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 116
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
```

```
accggcgctc ctccagaact gagcggagtg accaacaatg gcttcatccc tcacaac     1617

SEQ ID NO: 117         moltype = DNA  length = 1617
FEATURE                Location/Qualifiers
misc_feature           1..1617
                       note = Synthetic Polynucleotide
source                 1..1617
                       mol_type = other DNA
                       organism = synthetic construct
SEQUENCE: 117
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctgt ggcgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 118         moltype = DNA  length = 1617
FEATURE                Location/Qualifiers
misc_feature           1..1617
                       note = Synthetic Polynucleotide
source                 1..1617
                       mol_type = other DNA
                       organism = synthetic construct
SEQUENCE: 118
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acctcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctgt ggcgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 119         moltype = DNA  length = 1617
FEATURE                Location/Qualifiers
misc_feature           1..1617
                       note = Synthetic Polynucleotide
source                 1..1617
```

```
                       mol_type = other DNA
                       organism = synthetic construct
SEQUENCE: 119
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg cctgtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 120         moltype = DNA  length = 1617
FEATURE                Location/Qualifiers
misc_feature           1..1617
                       note = Synthetic Polynucleotide
source                 1..1617
                       mol_type = other DNA
                       organism = synthetic construct
SEQUENCE: 120
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 121         moltype = DNA  length = 1617
FEATURE                Location/Qualifiers
misc_feature           1..1617
                       note = Synthetic Polynucleotide
source                 1..1617
                       mol_type = other DNA
                       organism = synthetic construct
SEQUENCE: 121
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
```

-continued

```
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcccta tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 122          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 122
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg cctagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 123          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 123
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
```

```
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttccc acctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 124          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 124
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgaga accagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 125          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 125
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
```

-continued

```
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctcagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 126          moltype = DNA  length = 1617
FEATURE                 Location/Qualifiers
misc_feature            1..1617
                        note = Synthetic Polynucleotide
source                  1..1617
                        mol_type = other DNA
                        organism = synthetic construct
SEQUENCE: 126
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagtggaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 127          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 127
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tctgcaagac catcagactg gaaagcgaag tgaccgccat caacaacgcc  420
ctgaagaaga caaacgaggc cgtcagcaca ctcggcaatg gcgttagagt gctggccttt  480
gccgtgcgcg agctgaagga cttcgtgtcc aagaacctga cacgggccct gaacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgtgt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcaa cgtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
```

-continued

```
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 128          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 128
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tctgcaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgtgt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagc accagtggca tgtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 129          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 129
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 130          moltype = RNA  length = 1617
FEATURE                 Location/Qualifiers
misc_feature            1..1617
                        note = Synthetic Polynucleotide
```

-continued

```
source                  1..1617
                        mol_type = other RNA
                        organism = synthetic construct
SEQUENCE: 130
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgaga accagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 131          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 131
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 132          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 132
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
```

```
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgaga accagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 133          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 133
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg cctgtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 134          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 134
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg cctgtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
```

```
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgaga accagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 135         moltype = RNA  length = 1617
FEATURE                Location/Qualifiers
misc_feature           1..1617
                       note = Synthetic Polynucleotide
source                 1..1617
                       mol_type = other RNA
                       organism = synthetic construct
SEQUENCE: 135
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 136         moltype = RNA  length = 1617
FEATURE                Location/Qualifiers
misc_feature           1..1617
                       note = Synthetic Polynucleotide
source                 1..1617
                       mol_type = other RNA
                       organism = synthetic construct
SEQUENCE: 136
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acctcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
```

```
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 137          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 137
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 138          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 138
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctgt ggcgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
```

```
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 139         moltype = RNA  length = 1617
FEATURE                Location/Qualifiers
misc_feature           1..1617
                       note = Synthetic Polynucleotide
source                 1..1617
                       mol_type = other RNA
                       organism = synthetic construct
SEQUENCE: 139
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acctcgagaa tctgacatgc  180
tctgatggcc ctagcctgat caagaccgag ctggatctgc tcaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgctt aagaacctgt ggcgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 140         moltype = RNA  length = 1617
FEATURE                Location/Qualifiers
misc_feature           1..1617
                       note = Synthetic Polynucleotide
source                 1..1617
                       mol_type = other RNA
                       organism = synthetic construct
SEQUENCE: 140
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg cctgtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 141         moltype = RNA  length = 1617
FEATURE                Location/Qualifiers
misc_feature           1..1617
```

```
                        note = Synthetic Polynucleotide
source                  1..1617
                        mol_type = other RNA
                        organism = synthetic construct
SEQUENCE: 141
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tccctgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 142          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 142
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcccta tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617

SEQ ID NO: 143          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 143
atgagctgga aggtggtcat catcttcagc ctgctgatca cacctcagca cggcctgaaa  60
gagagctacc tggaagagtc ctgcagcacc atcacagagg gctacctgtc tgtgctgaga  120
```

```
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg cctagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 144          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 144
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttccc acctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 145          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 145
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
```

-continued

```
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgaga accagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 146          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 146
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagttcaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctcagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

```
SEQ ID NO: 147          moltype = RNA  length = 1617
FEATURE                 Location/Qualifiers
misc_feature            1..1617
                        note = Synthetic Polynucleotide
source                  1..1617
                        mol_type = other RNA
                        organism = synthetic construct
SEQUENCE: 147
atgagctgga aggtggtcat catcttcagc ctgctgatca cacctcagca cggcctgaaa  60
gagagctacc tggaagagtc ctgcagcacc atcacagagg gctacctgtc tgtgctgaga  120
accggctggt acaccaacgt gttcacactg gaagtgggcg acgtcgagaa tctgacatgc  180
tctgatggcc ctagcctgat caagaccgag ctggatctga ccaagagcgc cctgagagaa  240
ctcaagaccg tgtctgccga tcagctggcc agagaggaac agatcgagaa tcctggcagc  300
ggcagctttg tgctgggagc cattgctctt ggagtggctg ctgctgcagc tgttacagca  360
ggcgtggcca tcgctaagac catcagactg gaaagcgaag tgaccgccat caacaacgcc  420
ctgaagaaga caaacgaggc cgtcagcaca ctcggcaatg gcgttagagt gctggccaca  480
gccgtgcgcg agctgaagga cttcgtgtcc aagaacctga cacgggccat taacaagaac  540
aagtgcgaca tcgacgacct gaagatggcc gtgtccttta gccagtggaa ccggcggttt  600
ctgaacgtcg tgcggcagtt tagcgacaac gccggaatca caccagccat cagcctggac  660
ctgatgacag atgctgagct ggctagagcc gtgcctaaca tgcctacatc tgccggccag  720
atcaagctga tgctcgagaa tagagccatg gtccgacgga aaggcttcgg cattctgatt  780
ggcgtgtacg gcagcagcgt gatctatatg gtgcagctgc ctatcttcgg cgtgatcgac  840
acaccctgct ggattgtgaa ggccgctcct agctgtagcg agaagaaggg caattacgcc  900
tgcctgctga gagaggacca aggctggtat tgtcagaacg ccggcagcac cgtgtactac  960
```

-continued

```
cctaacgaga aggactgcga gacaagaggc gaccacgtgt tctgtgatac cgccgctgga  1020
atcaatgtgg ccgagcagag caaagagtgc aacatcaaca tcagcaccac caactatccc  1080
tgcaaggtgt ccaccggcag gcaccctatt tctatggtgg ctctgtctcc tctgggagcc  1140
ctggtggctt gttataaggg cgtgtcctgt agcatcggca gcaacagagt gggcatcatc  1200
aagcagctga acaagggctg cagctacatc accaaccagg acgccgatac cgtgaccatc  1260
gacaacaccg tgtatcagct gagcaaggtg gaaggcgaac agcacgtgat caagggcaga  1320
cctgtgtcca gcagcttcga ccctatcaag ttccctgagg atcagttcca ggtggccctg  1380
gaccaggtgt tcgagaacat cgagaattcc caggctctgg tggaccagtc caacagaatc  1440
ctgtctagcg ccgagaaggg aaacaccggc ttcatcatcg tgatcatcct gatcgccgtg  1500
ctgggcagct ccatgatcct ggtgtccatc ttcatcatta tcaagaagac caagaagccc  1560
accggcgctc ctccagaact gagcggagtg accaacaatg gcttcatccc tcacaac     1617
```

BETACORONAVIRUS mRNA VACCINES

RELATED APPLICATIONS

This application is a continuation of U.S. application Ser. No. 18/762,384, U.S. application Ser. No. 18/762,372 (now U.S. Pat. No. 12,208,288) and U.S. application Ser. No. 18/762,296, each filed Jul. 2, 2024, and which each are a continuation of U.S. application Ser. No. 18/528,323 filed Dec. 4, 2023, which is a continuation of U.S. application Ser. No. 16/897,734 (now U.S. Pat. No. 11,872,278), filed Jun. 10, 2020, which is a continuation of U.S. application Ser. No. 16/368,270 (now U.S. Pat. No. 10,702,599), filed Mar. 28, 2019, which is a continuation of U.S. application Ser. No. 16/040,981 (now U.S. Pat. No. 10,272,150), filed Jul. 20, 2018, which is a continuation of U.S. application Ser. No. 15/674,599 (now U.S. Pat. No. 10,064,934), filed Aug. 11, 2017, which is a continuation of international application number PCT/US2016/058327, filed Oct. 21, 2016, which claims the benefit under 35 U.S.C. § 119(e) of U.S. provisional application No. 62/244,802, filed Oct. 22, 2015, U.S. provisional application No. 62/247,297, filed Oct. 28, 2015, U.S. provisional application No. 62/244,946, filed Oct. 22, 2015, U.S. provisional application No. 62/247,362, filed Oct. 28, 2015, U.S. provisional application No. 62/244,813, filed Oct. 22, 2015, U.S. provisional application No. 62/247,394, filed Oct. 28, 2015, U.S. provisional application No. 62/244,837, filed Oct. 22, 2015, U.S. provisional application No. 62/247,483, filed Oct. 28, 2015, and U.S. provisional application No. 62/245,031, filed Oct. 22, 2015, each of which is incorporated by reference herein in its entirety.

REFERENCE TO AN ELECTRONIC SEQUENCE LISTING

The contents of the electronic sequence listing (M137870053US1 1-SEQ-JXV.xml; Size: 387,115 bytes; and Date of Creation: Nov. 29, 2023) is herein incorporated by reference in its entirety.

BACKGROUND

Respiratory disease is a medical term that encompasses pathological conditions affecting the organs and tissues that make gas exchange possible in higher organisms, and includes conditions of the upper respiratory tract, trachea, bronchi, bronchioles, alveoli, pleura and pleural cavity, and the nerves and muscles of breathing. Respiratory diseases range from mild and self-limiting, such as the common cold, to life-threatening entities like bacterial pneumonia, pulmonary embolism, acute asthma and lung cancer. Respiratory disease is a common and significant cause of illness and death around the world. In the US, approximately 1 billion "common colds" occur each year. Respiratory conditions are among the most frequent reasons for hospital stays among children.

The human metapneumovirus (hMPV) is a negative-sense, single-stranded RNA virus of the genus Pneumovirinae and of the family Paramyxoviridae and is closely related to the avian metapneumovirus (AMPV) subgroup C. It was isolated for the first time in 2001 in the Netherlands by using the RAP-PCR (RNA arbitrarily primed PCR) technique for identification of unknown viruses growing in cultured cells. hPMV is second only to RSV as an important cause of viral lower respiratory tract illness (LRI) in young children. The seasonal epidemiology of hMPV appears to be similar to that of RSV, but the incidence of infection and illness appears to be substantially lower.

Parainfluenza virus type 3 (PIV3), like hMPV, is also a negative-sense, single-stranded sense RNA virus of the genus Pneumovirinae and of the family Paramyxoviridae and is a major cause of ubiquitous acute respiratory infections of infancy and early childhood. Its incidence peaks around 4-12 months of age, and the virus is responsible for 3-10% of hospitalizations, mainly for bronchiolitis and pneumonia. PIV3 can be fatal, and in some instances is associated with neurologic diseases, such as febrile seizures. It can also result in airway remodeling, a significant cause of morbidity. In developing regions of the world, infants and young children are at the highest risk of mortality, either from primary PIV3 viral infection or a secondary consequences, such as bacterial infections. Human parainfluenza viruses (hPIV) types 1, 2 and 3 (hPIV1, hPIV2 and hPIV3, respectively), also like hMPV, are second only to RSV as important causes of viral LRI in young children.

RSV, too, is a negative-sense, single-stranded RNA virus of the genus Pneumovirinae and of the family Paramyxoviridae. Symptoms in adults typically resemble a sinus infection or the common cold, although the infection may be asymptomatic. In older adults (e.g., >60 years), RSV infection may progress to bronchiolitis or pneumonia. Symptoms in children are often more severe, including bronchiolitis and pneumonia. It is estimated that in the United States, most children are infected with RSV by the age of three. The RSV virion consists of an internal nucleocapsid comprised of the viral RNA bound to nucleoprotein (N), phosphoprotein (P), and large polymerase protein (L). The nucleocapsid is surrounded by matrix protein (M) and is encapsulated by a lipid bilayer into which the viral fusion (F) and attachment (G) proteins as well as the small hydrophobic protein (SH) are incorporated. The viral genome also encodes two non-structural proteins (NS1 and NS2), which inhibit type I interferon activity as well as the M-2 protein.

The continuing health problems associated with hMPV, PIV3 and RSV are of concern internationally, reinforcing the importance of developing effective and safe vaccine candidates against these virus.

Despite decades of research, no vaccines currently exist (Sato and Wright, *Pediatr. Infect. Dis. J.* 2008: 27 (10 Suppl): S123-5). Recombinant technology, however, has been used to target the formation of vaccines for hPIV-1, 2 and 3 serotypes, for example, and has taken the form of several live-attenuated intranasal vaccines. Two vaccines in particular were found to be immunogenic and well tolerated against hPIV-3 in phase I trials. hPIV1 and hPIV2 vaccine candidates remain less advanced (Durbin and Karron, Clinical infectious diseases: an official publication of the Infectious Diseases Society of America 2003; 37 (12): 1668-77).

Measles virus (MeV), like hMPV, PIV3 and RSV, is a negative-sense, single-stranded RNA virus that is the cause of measles, an infection of the respiratory system. MeV is of the genus Morbillivirus within the family Paramyxoviridae. Humans are the natural hosts of the virus; no animal reservoirs are known to exist. Symptoms of measles include fever, cough, runny nose, red eyes and a generalized, maculopapular, erythematous rash. The virus is highly contagious and is spread by coughing In additional to hMPV, PIV, RSV and MeV, betacoronaviruses are known to cause respiratory illnesses. Betacoronaviruses (BetaCoVs) are one of four genera of coronaviruses of the subfamily Coronavirinae in the family Coronaviridae, of the order Nidovirales. They are enveloped, positive-sense, single-stranded RNA viruses of zoonotic origin. The coronavirus genera are each composed of varying viral lineages, with the betacoronavirus genus containing four such lineages. The BetaCoVs of the greatest clinical importance concerning humans are OC43 and HKU1 of the A lineage, SARS-CoV of the B lineage, and MERS-CoV of the C lineage. MERS-CoV is the first betacoronavirus belonging to lineage C that is known to infect humans.

The Middle East respiratory syndrome coronavirus (MERS-CoV), or EMC/2012 (HCoV-EMC/2012), initially referred to as novel coronavirus 2012 or simply novel coronavirus, was first reported in 2012 after genome sequencing of a virus isolated from sputum samples from a person who fell ill during a 2012 outbreak of a new flu. As of July 2015, MERS-CoV cases have been reported in over 21 countries. The outbreaks of MERS-CoV have raised serious concerns world-wide, reinforcing the importance of developing effective and safe vaccine candidates against MERS-CoV.

Severe acute respiratory syndrome (SARS) emerged in China in 2002 and spread to other countries before brought under control. Because of a concern for reemergence or a deliberate release of the SARS coronavirus, vaccine development was initiated.

Deoxyribonucleic acid (DNA) vaccination is one technique used to stimulate humoral and cellular immune responses to foreign antigens, such as hMPV antigens and/or PIV antigens and/or RSV antigens. The direct injection of genetically engineered DNA (e.g., naked plasmid DNA) into a living host results in a small number of its cells directly producing an antigen, resulting in a protective immunological response. With this technique, however, comes potential problems, including the possibility of insertional mutagenesis, which could lead to the activation of oncogenes or the inhibition of tumor suppressor genes.

SUMMARY

Provided herein are ribonucleic acid (RNA) vaccines that build on the knowledge that RNA (e.g., messenger RNA (mRNA)) can safely direct the body's cellular machinery to produce nearly any protein of interest, from native proteins to antibodies and other entirely novel protein constructs that can have therapeutic activity inside and outside of cells. The RNA (e.g., mRNA) vaccines of the present disclosure may be used to induce a balanced immune response against hMPV, PIV, RSV, MeV, and/or BetaCoV (e.g., MERS-CoV, SARS-CoV, HCoV-OC43, HCoV-229E, HCoV-NL63, HCoV-NL, HCoV-NH and/or HCoV-HKU1), or any combination of two or more of the foregoing viruses, comprising both cellular and humoral immunity, without risking the possibility of insertional mutagenesis, for example. hMPV, PIV, RSV, MeV, BetaCoV (e.g., MERS-CoV, SARS-CoV, HCoV-OC43, HCoV-229E, HCoV-NL63, HCoV-NL, HCoV-NH and HCoV-HKU1) and combinations thereof are referred to herein as "respiratory viruses." Thus, the term "respiratory virus RNA vaccines" encompasses hMPV RNA vaccines, PIV RNA vaccines, RSV RNA vaccines, MeV RNA vaccines, BetaCoV RNA vaccines, and any combination of two or more of hMPV RNA vaccines, PIV RNA vaccines, RSV RNA vaccines, MeV RNA vaccines, and BetaCoV RNA vaccines.

The RNA (e.g., mRNA) vaccines may be utilized in various settings depending on the prevalence of the infection or the degree or level of unmet medical need. The RNA (e.g. mRNA) vaccines may be utilized to treat and/or prevent a hMPV, PIV, RSV, MeV, a BetaCoV (e.g., MERS-CoV, SARS-CoV, HCoV-OC43, HCoV-229E, HCoV-NL63, HCoV-NL, HCoV-NH, HCoV-HKU1), or any combination of two or more of the foregoing viruses, of various genotypes, strains, and isolates. The RNA (e.g., mRNA) vaccines have superior properties in that they produce much larger antibody titers and produce responses earlier than commercially available anti-viral therapeutic treatments. While not wishing to be bound by theory, it is believed that the RNA (e.g., mRNA) vaccines, as mRNA polynucleotides, are better designed to produce the appropriate protein conformation upon translation as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

In some aspects the invention is a respiratory virus vaccine, comprising at least one RNA polynucleotide having an open reading frame encoding at least one respiratory virus antigenic polypeptide, formulated in a cationic lipid nanoparticle.

Surprisingly, in some aspects, it has also been shown that efficacy of mRNA vaccines can be significantly enhanced when combined with a flagellin adjuvant, in particular, when one or more antigen-encoding mRNAs is combined with an mRNA encoding flagellin.

RNA (e.g., mRNA) vaccines combined with the flagellin adjuvant (e.g., mRNA-encoded flagellin adjuvant) have superior properties in that they may produce much larger antibody titers and produce responses earlier than commercially available vaccine formulations. While not wishing to be bound by theory, it is believed that the RNA (e.g., mRNA) vaccines, for example, as mRNA polynucleotides, are better designed to produce the appropriate protein conformation upon translation, for both the antigen and the adjuvant, as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Some embodiments of the present disclosure provide RNA (e.g., mRNA) vaccines that include at least one RNA (e.g., mRNA) polynucleotide having an open reading frame encoding at least one antigenic polypeptide or an immunogenic fragment thereof (e.g., an immunogenic fragment capable of inducing an immune response to the antigenic polypeptide) and at least one RNA (e.g., mRNA polynucleotide) having an open reading frame encoding a flagellin adjuvant.

In some embodiments, at least one flagellin polypeptide (e.g., encoded flagellin polypeptide) is a flagellin protein. In some embodiments, at least one flagellin polypeptide (e.g., encoded flagellin polypeptide) is an immunogenic flagellin fragment. In some embodiments, at least one flagellin polypeptide and at least one antigenic polypeptide are encoded by a single RNA (e.g., mRNA) polynucleotide. In other embodiments, at least one flagellin polypeptide and at least one antigenic polypeptide are each encoded by a different 30 RNA polynucleotide.

In some embodiments at least one flagellin polypeptide has at least 80%, at least 85%, at least 90%, or at least 95% identity to a flagellin polypeptide having a sequence identified by any one of SEQ ID NO: 54-56.

Provided herein, in some embodiments, is a ribonucleic acid (RNA) (e.g., mRNA) vaccine, comprising at least one (e.g., at least 2, 3, 4 or 5) RNA (e.g., mRNA) polynucleotide having an open reading frame encoding at least one (e.g., at least 2, 3, 4 or 5) hMPV, PIV, RSV. MeV, or a BetaCoV (e.g., MERS-CoV, SARS-CoV, HCoV-OC43, HCoV-229E, HCoV-NL63, HCoV-NL, HCoV-NH, HCoV-HKU1) antigenic polypeptide, or any combination of two or more of the foregoing antigenic polypeptides. Herein, use of the term "antigenic polypeptide" encompasses immunogenic fragments of the antigenic polypeptide (an immunogenic fragment that is induces (or is capable of inducing) an immune response to hMPV, PIV, RSV, MeV, or a BetaCoV), unless otherwise stated.

Also provided herein, in some embodiments, is a RNA (e.g., mRNA) vaccine comprising at least one (e.g., at least 2, 3, 4 or 5) RNA polynucleotide having an open reading frame encoding at least one (e.g., at least 2, 3, 4 or 5) hMPV, PIV, RSV, MeV, and/or a BetaCoV (e.g., MERS-CoV, SARS-CoV, HCoV-OC43, HCoV-229E, HCoV-NL63, HCoV-NL, HCoV-NH, HCoV-HKU1) antigenic polypeptide or an immunogenic fragment thereof, linked to a signal peptide.

Further provided herein, in some embodiments, is a nucleic acid (e.g., DNA) encoding at least one (e.g., at least 2, 3, 4 or 5) hMPV, PIV, RSV, MeV, and/or a BetaCoV (e.g., MERS-CoV, SARS-CoV, HCoV-OC43, HCoV-229E, HCoV-NL63, HCoV-NL, HCoV-NH, HCoV-HKU1) RNA (e.g., mRNA) polynucleotide.

Further still, provided herein, in some embodiments, is a method of inducing an immune response in a subject, the method comprising administering to the subject a vaccine comprising at least one (e.g., at least 2, 3, 4 or 5) RNA (e.g., mRNA) polynucleotide having an open reading frame encoding at least one (e.g., at least 2, 3, 4 or 5) hMPV, PIV, RSV, MeV, and/or a BetaCoV (e.g., MERS-CoV, SARS-CoV, HCoV-OC43, HCoV-229E, HCoV-NL63, HCoV-NL, HCoV-NH, HCoV-HKU1) antigenic polypeptide, or any combination of two or more of the foregoing antigenic polypeptides.

hMPV/PIV3/RSV

In some embodiments, a RNA (e.g., mRNA) vaccine comprises at least one RNA (e.g., mRNA) polynucleotide having an open reading frame encoding at least one hMPV, PIV3 or RSV antigenic polypeptide. In some embodiments, at least one antigenic polypeptide is a hMPV, PIV3 or RSV polyprotein. In some embodiments, at least one antigenic polypeptide is major surface glycoprotein G or an immunogenic fragment thereof. In some embodiments, at least one antigenic polypeptide is Fusion (F) glycoprotein (e.g., Fusion glycoprotein F0, F1 or F2) or an immunogenic fragment thereof. In some embodiments, at least one antigenic polypeptide is major surface glycoprotein G or an immunogenic fragment thereof and F glycoprotein or an immunogenic fragment thereof. In some embodiments, the antigenic polypeptide is nucleoprotein (N) or an immunogenic fragment thereof, phosphoprotein (P) or an immunogenic fragment thereof, large polymerase protein (L) or an immunogenic fragment thereof, matrix protein (M) or an immunogenic fragment thereof, small hydrophobic protein (SH) or an immunogenic fragment thereof nonstructural protein 1 (NS1) or an immunogenic fragment thereof, or nonstructural protein 2 (NS2) and an immunogenic fragment thereof.

In some embodiments, at least one hMPV antigenic polypeptide comprises an amino acid sequence identified by any one of SEQ ID NO: 5-8 (Table 3; see also amino acid sequences of Table 4). In some embodiments, the amino acid sequence of the hMPV antigenic polypeptide is, or is a fragment of, or is a homolog or variant having at least 80% (e.g., 85%, 90%, 95%, 98%, 99%) identity to, the amino acid sequence identified by any one of SEQ ID NO: 5-8 (Table 3; see also amino acid sequences of Table 4).

In some embodiments, at least one hMPV antigenic polypeptide is encoded by a nucleic acid sequence identified by any one of SEQ ID NO: 1-4 (Table 2).

In some embodiments, at least one hMPV RNA (e.g., mRNA) polynucleotide is encoded by a nucleic acid sequence, or a fragment of a nucleotide sequence, identified by any one of SEQ ID NO: 1-4 (Table 2). In some embodiments, at least one hMPV RNA (e.g., mRNA) polynucleotide comprises a nucleic acid sequence, or a fragment of a nucleotide sequence, identified by any one of SEQ ID NO: 57-60 (Table 2).

In some embodiments, at least one antigenic polypeptide is obtained from hMPV strain CAN98-75 (CAN75) or the hMPV strain CAN97-83 (CAN83).

In some embodiments, at least one PIV3 antigenic polypeptide comprises hemagglutinin-neuraminidase, Fusion (F) glycoprotein, matrix protein (M), nucleocapsid protein (N), viral replicase (L), non-structural V protein, or an immunogenic fragment thereof.

In some embodiments, at least one PIV3 antigenic polypeptide comprises an amino acid sequence identified by any one of SEQ ID NO: 12-13 (Table 6; see also amino acid sequences of Table 7). In some embodiments, the amino acid sequence of the PIV3 antigenic polypeptide is, or is a fragment of, or is a homolog or variant having at least 80% (e.g., 85%, 90%, 95%, 98%, 99%) identity to, the amino acid sequence identified by any one of SEQ ID NO: 12-13 (Table 6; see also amino acid sequences of Table 7).

In some embodiments, at least one PIV3 antigenic polypeptide is encoded by a nucleic acid sequence identified by any one of SEQ ID NO: 9-12 (Table 5; see also nucleic acid sequences of Table 7).

In some embodiments, at least one PIV3 RNA (e.g., mRNA) polynucleotide is encoded by a nucleic acid sequence, or a fragment of a nucleotide sequence, identified by any one of SEQ ID NO: 9-12 (Table 5; see also nucleic acid sequences of Table 7). In some embodiments, at least one PIV3 RNA (e.g., mRNA) polynucleotide comprises a nucleic acid sequence, or a fragment of a nucleotide sequence, identified by any one of SEQ ID NO: 61-64 (Table 5).

In some embodiments, at least one antigenic polypeptide is obtained from PIV3 strain HPIV3/*Homo sapiens*/PER/FLA4815/2008.

In some embodiments, at least one RSV antigenic polypeptide comprises at least one antigenic polypeptide that comprises glycoprotein G, glycoprotein F, or an immunogenic fragment thereof. In some embodiments, at least one RSV antigenic polypeptide comprises at least one antigenic polypeptide that comprises glycoprotein F and at least one or at least two antigenic polypeptide selected from G, M, N, P, L, SH, M2, NS1 and NS2.

MeV

In some embodiments, a RNA (e.g., mRNA) vaccine comprises at least one RNA (e.g., mRNA) polynucleotide having an open reading frame encoding at least one MeV antigenic polypeptide. In some embodiments, at least one antigenic polypeptide is a hemagglutinin (HA) protein or an immunogenic fragment thereof. The HA protein may be from MeV strain D3 or B8, for example. In some embodiments, at least one antigenic polypeptide is a Fusion (F) protein or an immunogenic fragment thereof. The F protein may be from MeV strain D3 or B8, for example. In some embodiments, a MeV RNA (e.g., mRNA) vaccines comprises a least one RNA polynucleotide encoding a HA protein and a F protein. The HA and F proteins may be from MeV strain D3 or B8, for example.

In some embodiments, at least one MeV antigenic polypeptide comprises an amino acid sequence identified by any one of SEQ ID NO: 47-50 (Table 14). In some embodiments, the amino acid sequence of the MeV antigenic polypeptide is, or is a fragment of, or is a homolog or variant having at least 80% (e.g., 85%, 90%, 95%, 98%, 99%) identity to, the amino acid sequence identified by any one of SEQ ID NO: 47-50 (Table 14).

In some embodiments, at least one MeV antigenic polypeptide is encoded by a nucleic acid sequence of SEQ ID NO: 35-46 (Table 13).

In some embodiments, at least one MeV RNA (e.g., mRNA) polynucleotide is encoded by a nucleic acid sequence, or a fragment of a nucleotide sequence, identified by any one of SEQ ID NO: 35-46 (Table 13). In some embodiments, at least one MeV RNA (e.g., mRNA) polynucleotide comprises a nucleic acid sequence, or a fragment of a nucleotide sequence, identified by any one of SEQ ID NO: 69-80 (Table 13).

In some embodiments, at least one antigenic polypeptide is obtained from MeV strain B3/B3.1, C2, D4, D6, D7, D8, G3, H1, Moraten, Rubeovax, MVi/New Jersey.USA/45.05, MVi/Texas.USA/4.07, AIK-C, MVi/New York.USA/26.09/3, MVi/California. USA/16.03, MVi/Virginia.USA/15.09, MVi/California.USA/8.04, or MVi/Pennsylvania.USA/20.09.

BetaCoV

In some embodiments, a RNA (e.g., mRNA) vaccine comprises at least one RNA (e.g., mRNA) polynucleotide having an open reading frame encoding at least one BetaCoV antigenic polypeptide. In some embodiments, the BetaCoV is MERS-CoV. In some embodiments, the BetaCoV is SARS-CoV. In some embodiments, the BetaCoV is HCoV-OC43. In some embodiments, the BetaCoV is HCoV-229E. In some embodiments, the BetaCoV is HCoV-NL63. In some embodiments, the BetaCoV is HCoV-HKU1. In some embodiments, at least one antigenic polypeptide is a betacoronavirus structural protein. For example, a betacoronavirus structural protein may be spike protein(S), envelope protein (E), nucleocapsid protein (N), membrane protein (M) or an immunogenic fragment thereof. In some embodiments, a betacoronavirus structural protein is a spike protein (S). In some embodiments, a betacoronavirus structural protein is a S1 subunit or a S2 subunit of spike protein(S) or an immunogenic fragment thereof.

BetaCoV RNA (e.g., mRNA) polynucleotides of the vaccines provided herein may encode viral protein components of betacoronaviruses, for example, accessory proteins, replicase proteins and the like are encompassed by the present disclosure. RNA (e.g., mRNA) vaccines may include RNA polynucleotides encoding at least one accessory protein (e.g., protein 3, protein 4a, protein 4b, protein 5), at least one replicase protein (e.g., protein 1a, protein 1b), or a combination of at least one accessory protein and at least one replicase protein. The present disclosure also encompasses RNA (e.g., mRNA) vaccines comprising RNA (e.g., mRNA) polynucleotides encoding an accessory protein and/or a replicase protein in combination with at least one structural protein. Due to their surface expression properties, vaccines featuring RNA polynucleotides encoding structural proteins are believed to have preferred immunogenic activity and, hence, may be most suitable for use in the vaccines of the present disclosure.

Some embodiments of the present disclosure provide betacoronavirus (e.g., MERS-CoV, SARS-CoV, HCoV-OC43, HCoV-229E, HCoV-NL63, HCoV-NL, HCoV-NH, HCoV-HKU1 or a combination thereof) vaccines that include at least one RNA (e.g., mRNA) polynucleotide having an open reading frame encoding at least one betacoronavirus (e.g., MERS-CoV, SARS-CoV, HCoV-OC43, HCoV-229E, HCoV-NL63, HCoV-NL, HCoV-NH, HCoV-HKU1) antigenic polypeptide. Also provided herein are pan-betacoronavirus vaccines. Thus, a betacoronavirus vaccine comprising a RNA (e.g., mRNA) polynucleotide having an open reading frame encoding any one, two, three or four of MERS-CoV, SARS-CoV, HCoV-OC43, HCoV-229E, HCoV-NL63, and HCoV-HKU1, for example, may be effective against any one of, any combination of, or all of, MERS-CoV, SARS-CoV, HCoV-OC43, HCoV-229E, HCoV-NL63, HCoV-NL, HCoV-NH and HCoV-HKU1. Other betacoronaviruses are encompassed by the present disclosure.

In some embodiments, at least one antigenic polypeptide is a MERS-CoV structural protein. For example, a MERS-CoV structural protein may be spike protein(S), envelope protein (E), nucleocapsid protein (N), membrane protein (M) or an immunogenic fragment thereof. In some embodiments, the MERS-CoV structural protein is a spike protein (S) (see, e.g., Coleman C M et al. *Vaccine* 2014; 32:3169-74, incorporated herein by reference). In some embodiments, the MERS-CoV structural protein is a S1 subunit or a S2 subunit of spike protein(S) or an immunogenic fragment thereof (Li J et al. *Viral Immunol* 2013; 26 (2): 126-32; He Y et al. *Biochem Biophys Res Commun* 2004; 324 (2): 773-81, each of which is incorporated herein by reference).

In some embodiments, at least one MERS-CoV antigenic polypeptide comprises an amino acid sequence identified by any one of SEQ ID NO: 24-28 or 33 (Table 11). In some embodiments, the amino acid sequence of the MERS-CoV antigenic polypeptide is, or is a fragment of, or is a homolog or variant having at least 80% (e.g., 85%, 90%, 95%, 98%, 99%) identity to, the amino acid sequence identified by any one of SEQ ID NO: 24-28 or 33 (Table 11).

In some embodiments, at least one MERS-CoV antigenic polypeptide is encoded by a nucleic acid sequence identified by any one of SEQ ID NO: 20-23 (Table 10).

In some embodiments, at least one MERS-CoV RNA (e.g., mRNA) polynucleotide is encoded by a nucleic acid sequence, or a fragment of a nucleotide sequence, identified by any one of SEQ ID NO: 20-23 (Table 10). In some embodiments, at least one MERS-CoV RNA (e.g., mRNA) polynucleotide comprises a nucleic acid sequence, or a fragment of a nucleotide sequence, identified by any one of SEQ ID NO: 65-68 (Table 10).

In some embodiments, at least one antigenic polypeptide is obtained from MERS-CoV strain Riyadh_14_2013, 2cEMC/2012, or Hasa_1_2013.

In some embodiments, at least one antigenic polypeptide is a SARS-CoV structural protein. For example, a SARS-CoV structural protein may be spike protein(S), envelope protein (E), nucleocapsid protein (N), membrane protein (M) or an immunogenic fragment thereof. In some embodiments, the SARS-CoV structural protein is a spike protein (S). In some embodiments, the SARS-CoV structural protein is a S1 subunit or a S2 subunit of spike protein(S) or an immunogenic fragment thereof.

In some embodiments, at least one SARS-CoV antigenic polypeptide comprises an amino acid sequence identified by any one of SEQ ID NO: 29, 32 or 34 (Table 11). In some embodiments, the amino acid sequence of the SARS-CoV antigenic polypeptide is, or is a fragment of, or is a homolog or variant having at least 80% (e.g., 85%, 90%, 95%, 98%, 99%) identity to, the amino acid sequence identified by any one of SEQ ID NO: 29, 32 or 34 (Table 11).

In some embodiments, at least one antigenic polypeptide is a HCoV-OC43 structural protein. For example, a HCoV-OC43 structural protein may be spike protein(S), envelope protein (E), nucleocapsid protein (N), membrane protein (M) or an immunogenic fragment thereof. In some embodiments, the HCoV-OC43 structural protein is a spike protein (S). In some embodiments, the HCoV-OC43 structural protein is a S1 subunit or a S2 subunit of spike protein(S) or an immunogenic fragment thereof.

In some embodiments, at least one HCoV-OC43 antigenic polypeptide comprises an amino acid sequence identified by any one of SEQ ID NO: 30 (Table 11). In some embodiments, the amino acid sequence of the HCoV-OC43 antigenic polypeptide is, or is a fragment of, or is a homolog or variant having at least 80% (e.g., 85%, 90%, 95%, 98%, 99%) identity to, the amino acid sequence identified by any one of SEQ ID NO: 30 (Table 11).

In some embodiments, an antigenic polypeptide is a HCoV-HKU1 structural protein. For example, a HCoV-HKU1 structural protein may be spike protein(S), envelope protein (E), nucleocapsid protein (N), membrane protein (M) or an immunogenic fragment thereof. In some embodiments, the HCoV-HKU1 structural protein is a spike protein (S). In some embodiments, the HCoV-HKU1 structural protein is a S1 subunit or a S2 subunit of spike protein(S) or an immunogenic fragment thereof.

In some embodiments, at least one HCoV-HKU1 antigenic polypeptide comprises an amino acid sequence identified by any one of SEQ ID NO: 31 (Table 11). In some embodiments, the amino acid sequence of the HCoV-HKU1 antigenic polypeptide is, or is a fragment of, or is a homolog or variant having at least 80% (e.g., 85%, 90%, 95%, 98%, 99%) identity to, the amino acid sequence identified by any one of SEQ ID NO: 31 (Table 11).

In some embodiments, an open reading frame of a RNA (e.g., mRNA) vaccine is codon-optimized. In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and is codon optimized mRNA.

In some embodiments, a RNA (e.g., mRNA) vaccine further comprising an adjuvant.

Tables 4, 7, 12 and 15 provide National Center for Biotechnology Information (NCBI) accession numbers of interest. It should be understood that the phrase "an amino acid sequence of Tables 4, 7, 12 and 15" refers to an amino acid sequence identified by one or more NCBI accession numbers listed in Tables 4, 7, 12 and 15. Each of the amino acid sequences, and variants having greater than 95% identity or greater than 98% identity to each of the amino acid sequences encompassed by the accession numbers of Tables 4, 7, 12 and 15 are included within the constructs (polynucleotides/polypeptides) of the present disclosure.

In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 80% identity to wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 75%, 85% or 95% identity to a wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 50-80%, 60-80%, 40-80%, 30-80%, 70-80%, 75-80% or 78-80% identity to wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 40-85%, 50-85%, 60-85%, 30-85%, 70-85%, 75-85% or 80-85% identity to wild-type mRNA sequence. In some embodiments, at least one mRNA polynucleotide is encoded by a nucleic acid having a sequence identified by any one of SEQ ID NO: 1-4, 9-12, 20-23, or 35-46 (Tables 2, 5, 10 and 13; see also nucleic acid sequences of Table 7) and having less than 40-90%, 50-90%, 60-90%, 30-90%, 70-90%, 75-90%, 80-90%, or 85-90% identity to wild-type mRNA sequence.

In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and having at least 80% (e.g., 85%, 90%, 95%, 98%, 99%) identity to wild-type mRNA sequence, but does not include wild-type mRNA sequence.

In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and has less than 95%, 90%, 85%, 80% or 75% identity to wild-type mRNA sequence. In some embodiments, at least one RNA polynucleotide encodes at least one antigenic polypeptide having an amino acid sequence identified by any one of SEQ ID NO: 5-8, 12-13, 24-34, or 47-50 (Tables 3, 6, 11 and 14; see also amino acid sequences of Tables 4, 7, 12 and 15) and has 30-80%, 40-80%, 50-80%, 60-80%, 70-80%, 75-80% or 78-80%, 30-85%, 40-85%, 50-805%, 60-85%, 70-85%, 75-85% or 78-85%, 30-90%, 40-90%, 50-90%, 60-90%, 70-90%, 75-90%, 80-90% or 85-90% identity to wild-type mRNA sequence.

In some embodiments, at least one RNA polynucleotide encodes at least one antigenic polypeptide having at least 90%, at least 95%, at least 96%, at least 97%, at least 98%, or at least 99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15). In some embodiments, at least one RNA polynucleotide encodes at least one antigenic polypeptide having 95%-99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15).

In some embodiments, at least one RNA polynucleotide encodes at least one antigenic polypeptide having at least 90%, at least 95%, at least 96%, at least 97%, at least 98%, or at least 99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15) and having membrane fusion activity. In some embodiments, at least one RNA polynucleotide encodes at least one antigenic polypeptide having 95%-99% identity to an amino acid sequence identified by any one of SEQ ID NO: 5-8, 12-13, 24-34, or 47-50 (Tables 3, 6, 11 and 14; see also amino acid sequences of Tables 4, 7, 12 and 15) and having membrane fusion activity.

In some embodiments, at least one RNA polynucleotide encodes at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) that attaches to cell receptors.

In some embodiments, at least one RNA polynucleotide encodes at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) that causes fusion of viral and cellular membranes.

In some embodiments, at least one RNA polynucleotide encodes at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) that is responsible for binding of the virus to a cell being infected.

Some embodiments of the present disclosure provide a vaccine that includes at least one ribonucleic acid (RNA) (e.g., mRNA) polynucleotide having an open reading frame encoding at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides), at least one 5' terminal cap and at least one chemical modification, formulated within a lipid nanoparticle.

In some embodiments, a 5' terminal cap is 7mG(5')ppp (5')NlmpNp.

In some embodiments, at least one chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, the chemical modification is in the 5-position of the uracil. In some embodiments, the chemical modification is a N1-methylpseudouridine. In some embodiments, the chemical modification is a N1-ethylpseudouridine.

In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino) butanoyl)oxy)heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530).

In some embodiments, the lipid is (L608)

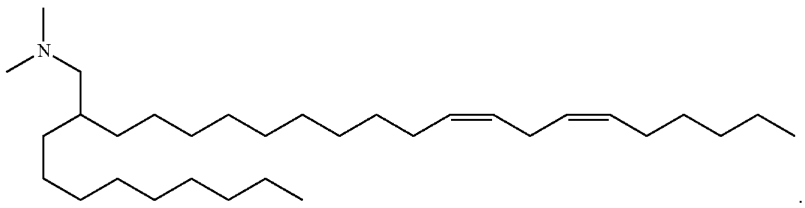

In some embodiments, the lipid is (L530)

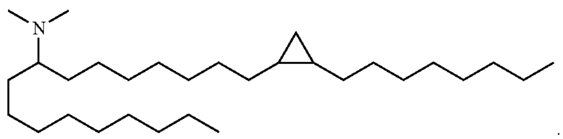

In some embodiments, a lipid nanoparticle comprises compounds of Formula (I) and/or Formula (II), discussed below.

In some embodiments, a respiratory virus RNA (e.g., mRNA) vaccine is formulated in a lipid nanoparticle that comprises a compound selected from Compounds 3, 18, 20, 25, 26, 29, 30, 60, 108-112 and 122, described below.

Some embodiments of the present disclosure provide a vaccine that includes at least one RNA (e.g., mRNA) polynucleotide having an open reading frame encoding at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides), wherein at least 80% (e.g., 85%, 90%, 95%, 98%, 99%) of the uracil in the open reading frame have a chemical modification, optionally wherein the vaccine is formulated in a lipid nanoparticle (e.g., a lipid nanoparticle comprises a cationic lipid, a PEG-modified lipid, a sterol and a non-cationic lipid).

In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, 100% of the uracil in the open reading frame have a N1-methyl pseudouridine in the 5-position of the uracil.

In some embodiments, an open reading frame of a RNA (e.g., mRNA) polynucleotide encodes at least two antigenic polypeptides (e.g., at least two hMPV antigenic polypeptides, at least two PIV3 antigenic polypeptides, at least two RSV antigenic polypeptides, at least two MeV antigenic polypeptides, or at least two BetaCoV antigenic polypeptides, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides). In some embodiments, the open reading frame encodes at least five or at least ten antigenic polypeptides. In some embodiments, the open reading frame encodes at least 100 antigenic polypeptides. In some embodiments, the open reading frame encodes 2-100 antigenic polypeptides.

In some embodiments, a vaccine comprises at least two RNA (e.g., mRNA) polynucleotides, each having an open reading frame encoding at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides). In some embodiments, the vaccine comprises at least five or at least ten RNA (e.g., mRNA) polynucleotides, each having an open reading frame encoding at least one antigenic polypeptide or an immunogenic fragment thereof. In some embodiments, the vaccine comprises at least 100 RNA (e.g., mRNA) polynucleotides, each having an open reading frame encoding at least one antigenic polypeptide. In some embodiments, the vaccine comprises 2-100 RNA (e.g., mRNA) polynucleotides, each having an open reading frame encoding at least one antigenic polypeptide.

In some embodiments, at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) is fused to a signal peptide. In some embodiments, the signal peptide is selected from: a HuIgGk signal peptide (METPAQLLFLLLLWLPDTTG; SEQ ID NO: 15); IgE heavy chain epsilon-1 signal peptide (MDWTWILFLVAAATRVHS; SEQ ID NO: 16); Japanese encephalitis PRM signal sequence (MLGSNSGQRVVFTILLLLVAPAYS; SEQ ID NO: 17), VSVg protein signal sequence (MKCLLYLAFLFIGVNCA; SEQ ID NO: 18) and Japanese encephalitis JEV signal sequence (MWLVSLAIVTACAGA; SEQ ID NO: 19).

In some embodiments, the signal peptide is fused to the N-terminus of at least one antigenic polypeptide. In some embodiments, a signal peptide is fused to the C-terminus of at least one antigenic polypeptide.

In some embodiments, at least one antigenic polypeptide (e.g., at least one hMPV antigenic polypeptide, at least one PIV3 antigenic polypeptide, at least one RSV antigenic polypeptide, at least one MeV antigenic polypeptide, or at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides) comprises a mutated N-linked glycosylation site.

Also provided herein is a RNA (e.g., mRNA) vaccine of any one of the foregoing paragraphs (e.g., a hMPV vaccine, a PIV3 vaccine, a RSV vaccine, a MeV vaccine, or a BetaCoV vaccine, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing vaccines), formulated in a nanoparticle (e.g., a lipid nanoparticle).

In some embodiments, the nanoparticle has a mean diameter of 50-200 nm. In some embodiments, the nanoparticle is a lipid nanoparticle. In some embodiments, the lipid nanoparticle comprises a cationic lipid, a PEG-modified lipid, a sterol and a non-cationic lipid. In some embodiments, the lipid nanoparticle comprises a molar ratio of about 20-60% cationic lipid, 0.5-15% PEG-modified lipid, 25-55% sterol, and 25% non-cationic lipid. In some embodiments, the cationic lipid is an ionizable cationic lipid and the non-cationic lipid is a neutral lipid, and the sterol is a cholesterol. In some embodiments, the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319).

In some embodiments, a lipid nanoparticle comprises compounds of Formula (I) and/or Formula (II), as discussed below.

In some embodiments, a lipid nanoparticle comprises Compounds 3, 18, 20, 25, 26, 29, 30, 60, 108-112, or 122, as discussed below.

In some embodiments, the nanoparticle has a polydispersity value of less than 0.4 (e.g., less than 0.3, 0.2 or 0.1).

In some embodiments, the nanoparticle has a net neutral charge at a neutral pH value.

In some embodiments, the respiratory virus vaccine is multivalent.

Some embodiments of the present disclosure provide methods of inducing an antigen specific immune response in a subject, comprising administering to the subject any of the RNA (e.g., mRNA) vaccine as provided herein in an amount effective to produce an antigen-specific immune response. In some embodiments, the RNA (e.g., mRNA) vaccine is a hMPV vaccine, a PIV3 vaccine, a RSV vaccine, a MeV vaccine, or a BetaCoV vaccine, e.g., selected from MERS-CoV, SARS-CoV, HCoV-OC43, HCoV-229E, HCoV-NL63, HCoV-NL, HCoV-NH and HCoV-HKU1 vaccines. In some embodiments, the RNA (e.g., mRNA) vaccine is a combination vaccine comprising a combination of any two or more of the foregoing vaccines.

In some embodiments, an antigen-specific immune response comprises a T cell response or a B cell response.

In some embodiments, a method of producing an antigen-specific immune response comprises administering to a subject a single dose (no booster dose) of a RNA (e.g., mRNA) vaccine of the present disclosure. In some embodiments, the RNA (e.g., mRNA) vaccine is a hMPV vaccine, a PIV3 vaccine, a RSV vaccine, a MeV vaccine, or a BetaCoV vaccine, e.g., selected from MERS-CoV, SARS-CoV, HCoV-OC43, HCoV-229E, HCoV-NL63, HCoV-NL, HCoV-NH and HCoV-HKU1 vaccines. In some embodiments, the RNA (e.g., mRNA) vaccine is a combination vaccine comprising a combination of any two or more of the foregoing vaccines.

In some embodiments, a method further comprises administering to the subject a second (booster) dose of a RNA (e.g., mRNA) vaccine. Additional doses of a RNA (e.g., mRNA) vaccine may be administered.

In some embodiments, the subjects exhibit a seroconversion rate of at least 80% (e.g., at least 85%, at least 90%, or at least 95%) following the first dose or the second (booster) dose of the vaccine. Seroconversion is the time period during which a specific antibody develops and becomes detectable in the blood. After seroconversion has occurred, a virus can be detected in blood tests for the antibody. During an infection or immunization, antigens enter the blood, and the immune system begins to produce antibodies in response. Before seroconversion, the antigen itself may or may not be detectable, but antibodies are considered absent. During seroconversion, antibodies are present but not yet detectable. Any time after seroconversion, the antibodies can be detected in the blood, indicating a prior or current infection.

In some embodiments, a RNA (e.g., mRNA) vaccine is administered to a subject by intradermal or intramuscular injection.

Some embodiments, of the present disclosure provide methods of inducing an antigen specific immune response in a subject, including administering to a subject a RNA (e.g., mRNA) vaccine in an effective amount to produce an antigen specific immune response in a subject. Antigen-specific immune responses in a subject may be determined, in some embodiments, by assaying for antibody titer (for titer of an antibody that binds to a hMPV, PIV3, RSV, MeV and/or BetaCoV antigenic polypeptide) following administration to the subject of any of the RNA (e.g., mRNA) vaccines of the present disclosure. In some embodiments, the anti-antigenic polypeptide antibody titer produced in the subject is increased by at least 1 log relative to a control. In some embodiments, the anti-antigenic polypeptide antibody titer produced in the subject is increased by 1-3 log relative to a control. In some embodiments, the anti-antigenic polypeptide antibody titer produced in a subject is increased at least 2 times relative to a control. In some embodiments, the anti-antigenic polypeptide antibody titer produced in the subject is increased at least 5 times relative to a control. In some embodiments, the anti-antigenic polypeptide antibody titer produced in the subject is increased at least 10 times relative to a control. In some embodiments, the anti-antigenic polypeptide antibody titer produced in the subject is increased 2-10 times relative to a control.

In some embodiments, the control is an anti-antigenic polypeptide antibody titer produced in a subject who has not been administered a RNA (e.g., mRNA) vaccine of the present disclosure. In some embodiments, the control is an anti-antigenic polypeptide antibody titer produced in a subject who has been administered a live attenuated or inactivated hMPV, PIV3, RSV, MeV and/or BetaCoV vaccine (see, e.g., Ren J. et al. *J of Gen. Virol.* 2015; 96:1515-1520), or wherein the control is an anti-antigenic polypeptide antibody titer produced in a subject who has been administered a recombinant or purified hMPV, PIV3, RSV, MeV and/or BetaCoV protein vaccine. In some embodiments, the control is an anti-antigenic polypeptide antibody titer produced in a subject who has been administered a hMPV, PIV3, RSV, MeV and/or BetaCoV virus-like particle (VLP) vaccine (see, e.g., Cox R G et al., *J Virol.* 2014 June; 88 (11): 6368-6379).

A RNA (e.g., mRNA) vaccine of the present disclosure is administered to a subject in an effective amount (an amount effective to induce an immune response). In some embodiments, the effective amount is a dose equivalent to an at least 2-fold, at least 4-fold, at least 10-fold, at least 100-fold, at least 1000-fold reduction in the standard of care dose of a recombinant hMPV, PIV3, RSV, MeV and/or BetaCoV protein vaccine, wherein the anti-antigenic polypeptide antibody titer produced in the subject is equivalent to an anti-antigenic polypeptide antibody titer produced in a control subject administered the standard of care dose of a recombinant hMPV, PIV3, RSV, MeV and/or BetaCoV protein vaccine, a purified hMPV, PIV3, RSV, MeV and/or BetaCoV protein vaccine, a live attenuated hMPV, PIV3, RSV, MeV and/or BetaCoV vaccine, an inactivated hMPV, PIV3, RSV, MeV and/or BetaCoV vaccine, or a hMPV, PIV3, RSV, MeV and/or BetaCoV VLP vaccine. In some embodiments, the effective amount is a dose equivalent to 2-1000-fold reduction in the standard of care dose of a recombinant hMPV, PIV3, RSV, MeV and/or BetaCoV protein vaccine, wherein the anti-antigenic polypeptide antibody titer produced in the subject is equivalent to an anti-antigenic polypeptide antibody titer produced in a control subject administered the standard of care dose of a recombinant hMPV, PIV3, RSV, MeV and/or BetaCoV protein vaccine, a purified hMPV, PIV3, RSV, MeV and/or BetaCoV protein vaccine, a live attenuated hMPV, PIV3, RSV, MeV and/or BetaCoV vaccine, an inactivated hMPV, PIV3, RSV, MeV and/or BetaCoV vaccine, or a hMPV, PIV3, RSV, MeV and/or BetaCoV VLP vaccine.

In some embodiments, the control is an anti-antigenic polypeptide antibody titer produced in a subject who has been administered a virus-like particle (VLP) vaccine comprising structural proteins of hMPV, PIV3, RSV, MeV and/or BetaCoV.

In some embodiments, the RNA (e.g., mRNA) vaccine is formulated in an effective amount to produce an antigen specific immune response in a subject.

In some embodiments, the effective amount is a total dose of 25 μg to 1000 μg, or 50 μg to 1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments, the efficacy (or effectiveness) of a RNA (e.g., mRNA) vaccine is greater than 60%. In some embodiments, the RNA (e.g., mRNA) polynucleotide of the vaccine at least one hMPV antigenic polypeptide, at least one PIV3 antigenic polypeptide, at least one RSV antigenic polypeptide, at least one MeV antigenic polypeptide, at least one BetaCoV antigenic polypeptide, e.g., selected from MERS-CoV, SARS-CoV, HCoV-OC43, HCoV-229E, HCoV-NL63, HCoV-NL, HCoV-NH and HCoV-HKU1, or any combination of two or more of the foregoing antigenic polypeptides.

Vaccine efficacy may be assessed using standard analyses (see, e.g., Weinberg et al., *J Infect Dis.* 2010 Jun. 1; 201 (11):

1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy} = (ARU - ARV)/ARU \times 100; \text{ and}$$

$$\text{Efficacy} = (1 - RR) \times 100.$$

Likewise, vaccine effectiveness may be assessed using standard analyses (see, e.g., Weinberg et al., *J Infect Dis.* 2010 Jun. 1; 201 (11): 1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness} = (1 - OR) \times 100.$$

In some embodiments, the efficacy (or effectiveness) of a RNA (e.g., mRNA) vaccine is at least 65%, at least 70%, at least 75%, at least 80%, at least 85%, or at least 90%.

In some embodiments, the vaccine immunizes the subject against hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses for up to 2 years. In some embodiments, the vaccine immunizes the subject against hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses for more than 2 years, more than 3 years, more than 4 years, or for 5-10 years.

In some embodiments, the subject is about 5 years old or younger. For example, the subject may be between the ages of about 1 year and about 5 years (e.g., about 1, 2, 3, 5 or 5 years), or between the ages of about 6 months and about 1 year (e.g., about 6, 7, 8, 9, 10, 11 or 12 months). In some embodiments, the subject is about 12 months or younger (e.g., 12, 11, 10, 9, 8, 7, 6, 5, 4, 3, 2 months or 1 month). In some embodiments, the subject is about 6 months or younger.

In some embodiments, the subject was born full term (e.g., about 37-42 weeks). In some embodiments, the subject was born prematurely, for example, at about 36 weeks of gestation or earlier (e.g., about 36, 35, 34, 33, 32, 31, 30, 29, 28, 27, 26 or 25 weeks). For example, the subject may have been born at about 32 weeks of gestation or earlier. In some embodiments, the subject was born prematurely between about 32 weeks and about 36 weeks of gestation. In such subjects, a RNA (e.g., mRNA) vaccine may be administered later in life, for example, at the age of about 6 months to about 5 years, or older.

In some embodiments, the subject is pregnant (e.g., in the first, second or third trimester) when administered an RNA (e.g., mRNA) vaccine. Viruses such as hMPV, PIV3 and RSV causes infections of the lower respiratory tract, mainly in infants and young children. One-third of RSV related deaths, for example, occur in the first year of life, with 99 percent of these deaths occurring in low-resource countries. It's so widespread in the United States that nearly all children become infected with the virus before their second birthdays. Thus, the present disclosure provides RNA (e.g., mRNA) vaccines for maternal immunization to improve mother-to-child transmission of protection against the virus.

In some embodiments, the subject is a young adult between the ages of about 20 years and about 50 years (e.g., about 20, 25, 30, 35, 40, 45 or 50 years old).

In some embodiments, the subject is an elderly subject about 60 years old, about 70 years old, or older (e.g., about 60, 65, 70, 75, 80, 85 or 90 years old).

In some embodiments, the subject is has a chronic pulmonary disease (e.g., chronic obstructive pulmonary disease (COPD) or asthma). Two forms of COPD include chronic bronchitis, which involves a long-term cough with mucus, and emphysema, which involves damage to the lungs over time. Thus, a subject administered a RNA (e.g., mRNA) vaccine may have chronic bronchitis or emphysema.

In some embodiments, the subject has been exposed to hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses; the subject is infected with hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses; or subject is at risk of infection by hMPV, PIV3, RSV, MeV, BetaCoV (e.g., selected from MERS-CoV, SARS-CoV, HCoV-OC43, HCoV-229E, HCoV-NL63, HCoV-NL, HCoV-NH and HCoV-HKU1), or any combination of two or more of the foregoing viruses.

In some embodiments, the subject is immunocompromised (has an impaired immune system, e.g., has an immune disorder or autoimmune disorder).

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first respiratory virus antigenic polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 μg/kg and 400 μg/kg of the nucleic acid vaccine is administered to the subject. In some embodiments the dosage of the RNA polynucleotide is 1-5 μg, 5-10 μg, 10-15

μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no nucleotide modification, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 μg and 400 μg of one or more RNA polynucleotides having an open reading frame comprising at least one chemical modification or optionally no nucleotide modification, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a respiratory virus strain in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. Both chemically modified and unmodified RNA vaccines are useful according to the invention. Surprisingly, in contrast to prior art reports that it was preferable to use chemically unmodified mRNA formulated in a carrier for the production of vaccines, it is described herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding a respiratory virus antigenic polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding a respiratory virus antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding a respiratory virus antigenic polypeptide in an effective amount to vaccinate the subject.

In some aspects the invention is a method of vaccinating a subject with a combination vaccine including at least two nucleic acid sequences encoding respiratory antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

The RNA polynucleotide is one of SEQ ID NO: 1-4, 9-12, 20-23, 35-46, 57-61, and 64-80 and includes at least one chemical modification. In other embodiments the RNA polynucleotide is one of SEQ ID NO: 1-4, 9-12, 20-23, 35-46, 57-61, and 64-80 and does not include any nucleotide modifications, or is unmodified. In yet other embodiments the at least one RNA polynucleotide encodes an antigenic protein of any of SEQ ID NO: 5-8, 12-13, 24-34, and 47-50 and includes at least one chemical modification. In other embodiments the RNA polynucleotide encodes an antigenic protein of any of SEQ ID NO: 5-8, 12-13, 24-34, and 47-50 and does not include any nucleotide modifications, or is unmodified.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

The details of various embodiments of the disclosure are set forth in the description below. Other features, objects, and advantages of the disclosure will be apparent from the description and from the claims.

BRIEF DESCRIPTION OF THE DRAWINGS

The foregoing and other objects, features and advantages will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of various embodiments of the disclosure.

FIG. 3C shows that hMPV fusion protein mRNA vaccine induced a mixed Th1/Th2 cytokine response with a Th1 bias.

FIG. 19A shows that two doses of MERS-CoV mRNA vaccine resulted in a 3 log reduction of viral load in the nose and led to complete protection in the throat of the New Zealand white rabbits. FIG. 19B shows that two doses of MERS-CoV mRNA vaccine resulted in a 4 log reduction of viral load in the BAL of the New Zealand white rabbits. FIG. 19C show one dose of MERS-CoV mRNA vaccine resulted in a 2 log reduction of viral load, while two doses of MERS-CoV mRNA vaccine resulted in an over 4 log reduction of viral load in the lungs of the New Zealand white rabbits.

FIG. 20A shows that two doses of 20 μg a MERS-CoV mRNA vaccine reduced over 99% (2 log) of viruses in the lungs of New Zealand white rabbits. FIG. 20B shows that the group of New Zealand white rabbits that received 2 doses of 20 μg MERS-CoV mRNA vaccine did not have any detectable replicating MERS-CoV virus in their lungs.

DETAILED DESCRIPTION

Figure 1:
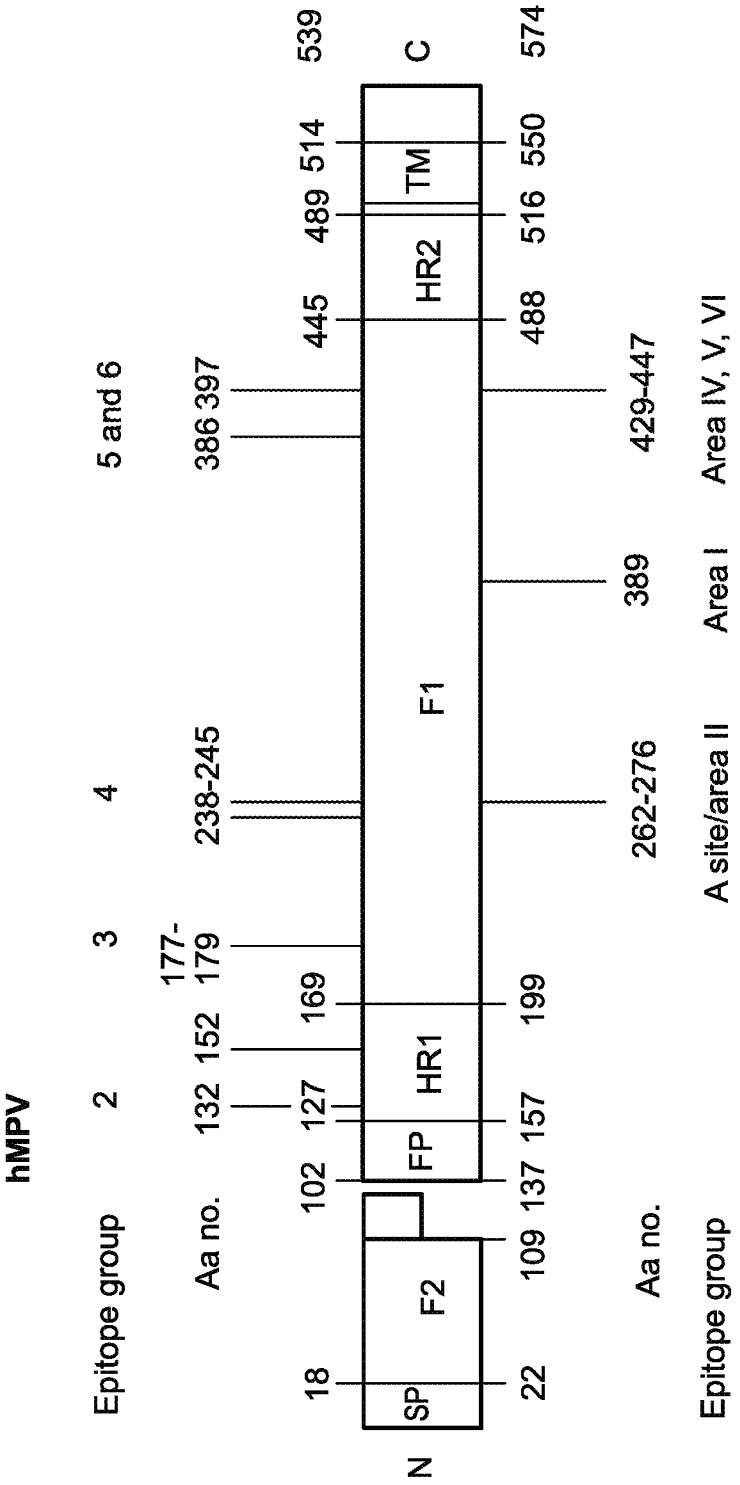
FIG. 1 shows a schematic of one example of a RNA (e.g. mRNA) vaccine construct of the present disclosure. The construct depicts a human metapneumovirus and human respiratory syncytial virus full length fusion protein obtained from wild-type strains (*The Journal of General Virology*. 2008; 89 (Pt 12): 3113-3118, incorporated herein by reference).

The present disclosure provides, in some embodiments, vaccines that comprise RNA (e.g., mRNA) polynucleotides encoding a human metapneumovirus (hMPV) antigenic polypeptide, a parainfluenza virus type 3 (PIV3) antigenic polypeptide, a respiratory syncytial virus (RSV) antigenic polypeptide, a measles virus (MeV) antigenic polypeptide, or a betacoronavirus antigenic polypeptide (e.g., Middle East respiratory syndrome coronavirus (MERS-CoV), SARS-CoV, human coronavirus (HCoV)—OC43, HCoV-229E, HCoV-NL63, HCoV-NL, HCoV-NH (New Haven) and HCoV-HKU1) (see, e.g., Esper F. et al. *Emerging Infectious Diseases,* 12 (5), 2006; and Pyrc K. et al. *Journal of Virology,* 81 (7): 3051-57, 2007, the contents of each of which is here incorporated by reference in their entirety). The present disclosure also provides, in some embodiments, combination vaccines that comprise at least one RNA (e.g., mRNA) polynucleotide encoding at least two antigenic polypeptides selected from hMPV antigenic polypeptides, PIV3 antigenic polypeptides, RSV antigenic polypeptides, MeV antigenic polypeptides and BetaCoV antigenic polypeptides. Also provided herein are methods of administering the RNA (e.g., mRNA) vaccines, methods of producing the RNA (e.g., mRNA) vaccines, compositions (e.g., pharmaceutical compositions) comprising the RNA (e.g., mRNA) vaccines, and nucleic acids (e.g., DNA) encoding the RNA (e.g., mRNA) vaccines. In some embodiments, a RNA (e.g., mRNA) vaccine comprises an adjuvant, such as a flagellin adjuvant, as provided herein.

The RNA (e.g., mRNA) vaccines (e.g., hMPV, PIV3, RSV, MeV, BetaCoV RNA vaccines and combinations thereof), in some embodiments, may be used to induce a balanced immune response, comprising both cellular and humoral immunity, without many of the risks associated with DNA vaccination.

The entire contents of International Application No. PCT/US2015/02740 is incorporated herein by reference.

Human Metapneumovirus (hMPV)

hMPV shares substantial homology with respiratory syncytial virus (RSV) in its surface glycoproteins. hMPV fusion protein (F) is related to other paramyxovirus fusion proteins and appears to have homologous regions that may have similar functions. The hMPV fusion protein amino acid sequence contains features characteristic of other paramyxovirus F proteins, including a putative cleavage site and potential N-linked glycosylation sites. Paramyxovirus fusion proteins are synthesized as inactive precursors (F0) that are cleaved by host cell proteases into the biologically fusion-active F1 and F2 domains (see, e.g., Cseke G. et al. *Journal of Virology* 2007; 81 (2): 698-707, incorporated herein by reference). hMPV has one putative cleavage site, in contrast to the two sites established for RSV F, and only shares 34% amino acid sequence identity with RSV F. F2 is extracellular and disulfide linked to F1. Fusion proteins are type I glycoproteins existing as trimers, with two 4-3 heptad repeat domains at the N- and C-terminal regions of the protein (HR1 and HR2), which form coiled-coil alpha-helices. These coiled coils become apposed in an antiparallel fashion when the protein undergoes a conformational change into the fusogenic state. There is a hydrophobic fusion peptide N proximal to the N-terminal heptad repeat, which is thought to insert into the target cell membrane, while the association of the heptad repeats brings the transmembrane domain into close proximity, inducing membrane fusion (see, e.g., Baker, K A et al. *Mol. Cell* 1999; 3:309-319). This mechanism has been proposed for a number of different viruses, including RSV, influenza virus, and human immunodeficiency virus. Fusion proteins are major antigenic determinants for all known paramyxoviruses and for other viruses that possess similar fusion proteins such as human immunodeficiency virus, influenza virus, and Ebola virus.

In some embodiments, a hMPV vaccine of the present disclosure comprises a RNA (e.g., mRNA) polynucleotide encoding hMPV fusion protein (F). In some embodiments, a hMPV vaccine of the present disclosure comprises a RNA (e.g., mRNA) polynucleotide encoding a F1 or F2 subunit of a hMPV F protein. In some embodiments, a hMPV vaccine of the present disclosure comprises a RNA (e.g., mRNA)

polynucleotide encoding hMPV glycoprotein (G). In some embodiments, a hMPV vaccine of the present disclosure comprises a RNA (e.g., mRNA) polynucleotide encoding hMPV matrix protein (M). In some embodiments, a hMPV vaccine of the present disclosure comprises a RNA (e.g., mRNA) polynucleotide encoding hMPV phosphoprotein (P). In some embodiments, a hMPV vaccine of the present disclosure comprises a RNA (e.g., mRNA) polynucleotide encoding hMPV nucleoprotein (N). In some embodiments, a hMPV vaccine of the present disclosure comprises a RNA (e.g., mRNA) polynucleotide encoding hMPV SH protein (SH).

In some embodiments, a hMPV vaccine of the present disclosure comprises a RNA (e.g., mRNA) polynucleotide encoding F protein, G protein, M protein, P protein, N protein and SH protein.

In some embodiments, a hMPV vaccine of the present disclosure comprises a RNA (e.g., mRNA) polynucleotide encoding F protein and G protein. In some embodiments, a hMPV vaccine of the present disclosure comprises a RNA (e.g., mRNA) polynucleotide encoding F protein and M protein. In some embodiments, a hMPV vaccine of the present disclosure comprises a RNA (e.g., mRNA) polynucleotide encoding F protein and P protein. In some embodiments, a hMPV vaccine of the present disclosure comprises a RNA (e.g., mRNA) polynucleotide encoding F protein and N protein. In some embodiments, a hMPV vaccine of the present disclosure comprises a RNA (e.g., mRNA) polynucleotide encoding F protein and SH protein.

In some embodiments, a hMPV vaccine of the present disclosure comprises a RNA (e.g., mRNA) polynucleotide encoding G protein and M protein. In some embodiments, a hMPV vaccine of the present disclosure comprises a RNA (e.g., mRNA) polynucleotide encoding G protein and P protein. In some embodiments, a hMPV vaccine of the present disclosure comprises a RNA (e.g., mRNA) polynucleotide encoding G protein and N protein. In some embodiments, a hMPV vaccine of the present disclosure comprises a RNA (e.g., mRNA) polynucleotide encoding G protein and SH protein.

In some embodiments, a hMPV vaccine of the present disclosure comprises a RNA (e.g., mRNA) polynucleotide encoding F protein, G protein and M protein. In some embodiments, a hMPV vaccine of the present disclosure comprises a RNA (e.g., mRNA) polynucleotide encoding F protein, G protein and P protein. In some embodiments, a hMPV vaccine of the present disclosure comprises a RNA (e.g., mRNA) polynucleotide encoding F protein, G protein and N protein. In some embodiments, a hMPV vaccine of the present disclosure comprises a RNA (e.g., mRNA) polynucleotide encoding F protein, G protein and SH protein.

A hMPV vaccine may comprise, for example, at least one RNA (e.g., mRNA) polynucleotide having an open reading frame encoding at least one hMPV antigenic polypeptide identified by any one of SEQ ID NO: 5-8 (Table 3; see also amino acid sequences of Table 4).

A hMPV vaccine may comprise, for example, at least one RNA (e.g., mRNA) polynucleotide encoded by a nucleic acid (e.g., DNA) identified by any one of SEQ ID NO: 1-4 (Table 2).

The present disclosure is not limited by a particular strain of hMPV. The strain of hMPV used in a vaccine may be any strain of hMPV. Non-limiting examples of strains of hMPV for use as provide herein include the CAN98-75 (CAN75) and the CAN97-83 (CAN83) hMPV strains (Skiadopoulos M H et al. *J Virol.* 20014; 78 (13) 6927-37, incorporated herein by reference), a hMPV A1, A2, B1 or B2 strain (see, e.g., de Graaf M et al. *The Journal of General Virology* 2008; 89:975-83; Peret T C T et al. *The Journal of Infectious Disease* 2002; 185:1660-63, incorporated herein by reference), a hMPV isolate TN/92-4 (e.g., SEQ ID NO: 1 and 5), a hMPV isolate NL/1/99 (e.g., SEQ ID NO: 2 and 6), or a hMPV isolate PER/CFI0497/2010/B (e.g., SEQ ID NO: 3 and 7).

In some embodiments, at least one hMPV antigenic polypeptide is obtained from a hMPV A1, A2, B1 or B2 strain (see, e.g., de Graaf M et al. *The Journal of General Virology* 2008; 89:975-83; Peret T C T et al. *The Journal of Infectious Disease* 2002; 185:1660-63, incorporated herein by reference). In some embodiments, at least one antigenic polypeptide is obtained from the CAN98-75 (CAN75) hMPV strain. In some embodiments, at least one antigenic polypeptide is obtained from the CAN97-83 (CAN83) hMPV strain. In some embodiments, at least one antigenic polypeptide is obtained from hMPV isolate TN/92-4 (e.g., SEQ ID NO: 1 and 5). In some embodiments, at least one antigenie polypeptide is obtained from hMPV isolate NL/1/99 (e.g., SEQ ID NO: 2 and 6). In some embodiments, at least one antigenic polypeptide is obtained from hMPV isolate PER/CFI0497/2010/B (e.g., SEQ ID NO: 3 and 7).

In some embodiments, hMPV vaccines comprise RNA (e.g., mRNA) polynucleotides encoding a hMPV antigenic polypeptides having at least 95%, at least 96%, at least 97%, at least 98% or at least 99% identity with hMPV F protein and having F protein activity.

A protein is considered to have F protein activity if, for example, the protein acts to fuse the viral envelope and host cell plasma membrane, mediates viral entry into a host cell via an interaction with arginine-glycine-aspartate RGD-binding integrins, or a combination thereof (see, e.g., Cox R G et al. *J Virol.* 2012; 88 (22): 12148-60, incorporated herein by reference).

In some embodiments, hMPV vaccines comprise RNA (e.g., mRNA) polynucleotides encoding hMPV antigenic polypeptides having at least 95%, at least 96%, at least 97%, at least 98% or at least 99% identity with hMPV G protein and having G protein activity.

A protein is considered to have G protein activity if, for example, the protein acts to modulate (e.g., inhibit) hMPV-induced cellular (immune) responses (see, e.g., Bao X et al. *PLOS Pathog.* 2008; 4 (5): e1000077, incorporated herein by reference).

Human Parainfluenza Virus Type 3 (PIV3)

Parainfluenza viruses belong to the family Paramyxoviridae. These are enveloped viruses with a negative-sense single-stranded RNA genome. Parainfluenza viruses belong to the subfamily Paramyxoviridae, which is subdivided into three genera: Respirovirus (PIV-1, PIV-3, and Sendai virus (SeV)), Rubulavirus (PIV-2, PIV-4 and mumps virus) and Morbillivirus (measles virus, rinderpest virus and canine distemper virus (CDV)). Their genome, a ~15 500 nucleotide-long negative-sense RNA molecule, encodes two envelope glycoproteins, the hemagglutinin-neuraminidase (HN), the fusion protein (F or F0), which is cleaved into F1 and F2 subunits, a matrix protein (M), a nucleocapsid protein (N) and several nonstructural proteins including the viral replicase (L). All parainfluenza viruses, except for PIV-1, express a non-structural V protein that blocks IFN signaling in the infected cell and acts therefore as a virulence factor (see, e.g., Nishio M et al. *J Virol.* 2008; 82 (13): 6130-38).

PIV3 hemagglutinin-neuraminidase (HN), a structural protein, is found on the viral envelope, where it is necessary for attachment and cell entry. It recognizes and binds to sialic acid-containing receptors on the host cell's surface. As a neuroaminidase, HN removes sialic acid from virus particles, preventing self-aggregation of the virus, and promoting the efficient spread of the virus. Furthermore, HN promotes the activity of the fusion (F or F0) protein, contributing to the penetration of the host cell's surface.

PIV3 fusion protein (PIV3 F) is located on the viral envelope, where it facilitates the viral fusion and cell entry. The F protein is initially inactive, but proteolytic cleavage leads to its active forms, F1 and F2, which are linked by disulfide bonds. This occurs when the HN protein binds its receptor on the host cell's surface. During early phases of infection, the F glycoprotein mediates penetration of the host cell by fusion of the viral envelope to the plasma membrane. In later stages of the infection, the F protein facilitates the fusion of the infected cells with neighboring uninfected cells, which leads to the formation of a syncytium and spread of the infection.

PIV3 matrix protein (M) is found within the viral envelope and assists with viral assembly. It interacts with the nucleocapsid and envelope glycoproteins, where it facilitates the budding of progeny viruses through its interactions with specific sites on the cytoplasmic tail of the viral glycoproteins and nucleocapsid. It also plays a role in transporting viral components to the budding site.

PIV3 phosphoprotein (P) and PIV3 large polymerase protein (L) are found in the nucleocapsid where they form part of the RNA polymerase complex. The L protein, a viral RNA-dependent RNA polymerase, facilitates genomic transcription, while the host cell's ribosomes translate the viral mRNA into viral proteins.

PIV3 V is a non-structural protein that blocks IFN signaling in the infected cell, therefore acting as a virulence factor.

PIV3 nucleoprotein (N) encapsidates the genome in a ratio of 1 N per 6 ribonucleotides, protecting it from nucleases. The nucleocapsid (NC) has a helical structure. The encapsidated genomic RNA is termed the NC and serves as template for transcription and replication. During replication, encapsidation by PIV3 N is coupled to RNA synthesis and all replicative products are resistant to nucleases. PIV3 N homo-multimerizes to form the nucleocapsid and binds to viral genomic RNA. PIV3 N binds the P protein and thereby positions the polymerase on the template.

In some embodiments, a PIV3 vaccine of the present disclosure comprises a RNA (e.g., mRNA) polynucleotide encoding PIV3 fusion protein (F). In some embodiments, a PIV3 vaccine of the present disclosure comprises a RNA (e.g., mRNA) polynucleotide encoding a F1 or F2 subunit of a PIV3 F protein. In some embodiments, a PIV3 vaccine of the present disclosure comprises a RNA (e.g., mRNA) polynucleotide encoding PIV3 hemagglutinin-neuraminidase (HN) (see, e.g., van Wyke Coelingh K L et al. *J Virol.* 1987; 61 (5): 1473-77, incorporated herein by reference). In some embodiments, a PIV3 vaccine of the present disclosure comprises a RNA (e.g., mRNA) polynucleotide encoding PIV3 matrix protein (M). In some embodiments, a PIV3 vaccine of the present disclosure comprises a RNA (e.g., mRNA) polynucleotide encoding PIV3 phosphoprotein (P). In some embodiments, a PIV3 vaccine of the present disclosure comprises a RNA (e.g., mRNA) polynucleotide encoding PIV3 nucleoprotein (N).

In some embodiments, a PIV3 vaccine of the present disclosure comprises a RNA (e.g., mRNA) polynucleotide encoding F protein, HN protein, M protein, P protein, and N protein.

In some embodiments, a PIV3 vaccine of the present disclosure comprises a RNA (e.g., mRNA) polynucleotide encoding F protein and HN protein. In some embodiments, a PIV3 vaccine of the present disclosure comprises a RNA (e.g., mRNA) polynucleotide encoding F protein and M protein. In some embodiments, a PIV3 vaccine of the present disclosure comprises a RNA (e.g., mRNA) polynucleotide encoding F protein and P protein. In some embodiments, a PIV3 vaccine of the present disclosure comprises a RNA (e.g., mRNA) polynucleotide encoding F protein and N protein.

In some embodiments, a PIV3 vaccine of the present disclosure comprises a RNA (e.g., mRNA) polynucleotide encoding HN protein and M protein. In some embodiments, a PIV3 vaccine of the present disclosure comprises a RNA (e.g., mRNA) polynucleotide encoding HN protein and P protein. In some embodiments, a PIV3 vaccine of the present disclosure comprises a RNA (e.g., mRNA) polynucleotide encoding HN protein and N protein.

In some embodiments, a PIV3 vaccine of the present disclosure comprises a RNA (e.g., mRNA) polynucleotide encoding F protein, HN protein and M protein. In some embodiments, a PIV3 vaccine of the present disclosure comprises a RNA (e.g., mRNA) polynucleotide encoding F protein, HN protein and P protein. In some embodiments, a PIV3 vaccine of the present disclosure comprises a RNA (e.g., mRNA) polynucleotide encoding F protein, HN protein and N protein.

A PIV3 vaccine may comprise, for example, at least one RNA (e.g., mRNA) polynucleotide having an open reading frame encoding at least one PIV3 antigenic polypeptide identified by any one of SEQ ID NO: 12-13 (Table 6; see also amino acid sequences of Table 7).

A PIV3 vaccine may comprise, for example, at least one RNA (e.g., mRNA) polynucleotide encoded by a nucleic acid (e.g., DNA) identified by any one of SEQ ID NO: 9-12 (Table 5; see also nucleic acid sequences of Table 7).

The present disclosure is not limited by a particular strain of PIV3. The strain of PIV3 used in a vaccine may be any strain of PIV3. A non-limiting example of a strain of PIV3 for use as provide herein includes HPIV3/*Homo sapiens*/PER/FLA4815/2008.

In some embodiments, PIV3 vaccines comprise RNA (e.g., mRNA) polynucleotides encoding a PIV3 antigenic polypeptides having at least 95%, at least 96%, at least 97%, at least 98% or at least 99% identity with PIV3 F protein and having F protein activity.

In some embodiments, PIV3 vaccines comprise RNA (e.g., mRNA) polynucleotides encoding PIV3 antigenic polypeptides having at least 95%, at least 96%, at least 97%, at least 98% or at least 99% identity with PIV3 hemagglutinin-neuraminidase (HN) and having hemagglutinin-neuraminidase activity.

A protein is considered to have hemagglutinin-neuraminidase activity if, for example, it is capable of both receptor binding and receptor cleaving. Such proteins are major surface glycoproteins that have functional sites for cell attachment and for neuraminidase activity. They are able to cause red blood cells to agglutinate and to cleave the glycosidic linkages of neuraminic acids, so they have the potential to both bind a potential host cell and then release the cell if necessary, for example, to prevent self-aggregation of the virus.

In some embodiments, PIV3 vaccines comprise RNA (e.g., mRNA) polynucleotides encoding PIV3 antigenic polypeptides having at least 95%, at least 96%, at least 97%, at least 98% or at least 99% identity with PIV3 HN, F (e.g., F, F1 or F2), M, N, L or V and having HN, F (e.g., F, F1 or F2), M, N, L or V activity, respectively.

Respiratory Syncytial Virus (RSV)

RSV is a negative-sense, single-stranded RNA virus of the genus Pneumovirinae. The virus is present in at least two antigenic subgroups, known as Group A and Group B, primarily resulting from differences in the surface G glycoproteins. Two RSV surface glycoproteins-G and F-mediate attachment with and attachment to cells of the respiratory epithelium. F surface glycoproteins mediate coalescence of neighboring cells. This results in the formation of syncytial cells. RSV is the most common cause of bronchiolitis. Most infected adults develop mild cold-like symptoms such as congestion, low-grade fever, and wheezing. Infants and small children may suffer more severe symptoms such as bronchiolitis and pneumonia. The disease may be transmitted among humans via contact with respiratory secretions.

The genome of RSV encodes at least three surface glycoproteins, including F, G, and SH, four nucleocapsid proteins, including L, P, N, and M2, and one matrix protein, M. Glycoprotein F directs viral penetration by fusion between the virion and the host membrane. Glycoprotein G is a type II transmembrane glycoprotein and is the major attachment protein. SH is a short integral membrane protein. Matrix protein M is found in the inner layer of the lipid bilayer and assists virion formation. Nucleocapsid proteins L, P, N, and M2 modulate replication and transcription of the RSV genome. It is thought that glycoprotein G tethers and stabilizes the virus particle at the surface of bronchial epithelial cells, while glycoprotein F interacts with cellular glycosaminoglycans to mediate fusion and delivery of the RSV virion contents into the host cell (Krzyzaniak M A et al. *PLOS Pathog* 2013; 9 (4)).

In some embodiments, a RSV vaccine of the present disclosure comprises a RNA (e.g., mRNA) polynucleotide encoding F protein. In some embodiments, a PIV3 vaccine of the present disclosure comprises a RNA (e.g., mRNA) polynucleotide encoding G protein. In some embodiments, a PIV3 vaccine of the present disclosure comprises a RNA (e.g., mRNA) polynucleotide encoding L protein. In some embodiments, a PIV3 vaccine of the present disclosure comprises a RNA (e.g., mRNA) polynucleotide encoding P protein. In some embodiments, a PIV3 vaccine of the present disclosure comprises a RNA (e.g., mRNA) polynucleotide encoding N protein. In some embodiments, a PIV3 vaccine of the present disclosure comprises a RNA (e.g., mRNA) polynucleotide encoding M2 protein. In some embodiments, a PIV3 vaccine of the present disclosure comprises a RNA (e.g., mRNA) polynucleotide encoding M protein.

In some embodiments, a RSV vaccine of the present disclosure comprises a RNA (e.g., mRNA) polynucleotide encoding F protein, G protein, L protein, P protein, N protein, M2 protein and M protein.

In some embodiments, a RSV vaccine of the present disclosure comprises a RNA (e.g., mRNA) polynucleotide encoding F protein and G protein. In some embodiments, a RSV vaccine of the present disclosure comprises a RNA (e.g., mRNA) polynucleotide encoding F protein and L protein. In some embodiments, a RSV vaccine of the present disclosure comprises a RNA (e.g., mRNA) polynucleotide encoding F protein and P protein. In some embodiments, a RSV vaccine of the present disclosure comprises a RNA (e.g., mRNA) polynucleotide encoding F protein and N protein. In some embodiments, a RSV vaccine of the present disclosure comprises a RNA (e.g., mRNA) polynucleotide encoding F protein and M2 protein. In some embodiments, a RSV vaccine of the present disclosure comprises a RNA (e.g., mRNA) polynucleotide encoding F protein and M protein.

In some embodiments, a RSV vaccine of the present disclosure comprises a RNA (e.g., mRNA) polynucleotide encoding G protein and L protein. In some embodiments, a RSV vaccine of the present disclosure comprises a RNA (e.g., mRNA) polynucleotide encoding G protein and P protein. In some embodiments, a RSV vaccine of the present disclosure comprises a RNA (e.g., mRNA) polynucleotide encoding G protein and N protein. In some embodiments, a RSV vaccine of the present disclosure comprises a RNA (e.g., mRNA) polynucleotide encoding G protein and M2 protein. In some embodiments, a RSV vaccine of the present disclosure comprises a RNA (e.g., mRNA) polynucleotide encoding G protein and M protein.

In some embodiments, a RSV vaccine of the present disclosure comprises a RNA (e.g., mRNA) polynucleotide encoding F protein, G protein and L protein. In some embodiments, a RSV vaccine of the present disclosure comprises a RNA (e.g., mRNA) polynucleotide encoding F protein, G protein and P protein. In some embodiments, a RSV vaccine of the present disclosure comprises a RNA (e.g., mRNA) polynucleotide encoding F protein, G protein and N protein. In some embodiments, a RSV vaccine of the present disclosure comprises a RNA (e.g., mRNA) polynucleotide encoding F protein, G protein and M2 protein. In some embodiments, a RSV vaccine of the present disclosure comprises a RNA (e.g., mRNA) polynucleotide encoding F protein, G protein and M protein.

The present disclosure is not limited by a particular strain of RSV. The strain of RSV used in a vaccine may be any strain of RSV.

In some embodiments, RSV vaccines comprise RNA (e.g., mRNA) polynucleotides encoding a RSV antigenic polypeptides having at least 95%, at least 96%, at least 97%, at least 98% or at least 99% identity with RSV F protein and having F protein activity.

In some embodiments, RSV vaccines comprise RNA (e.g., mRNA) polynucleotides encoding RSV antigenic polypeptides having at least 95%, at least 96%, at least 97%, at least 98% or at least 99% identity with RSV G protein and having G protein activity.

A protein is considered to have G protein activity if, for example, the protein acts to modulate (e.g., inhibit) hMPV-induced cellular (immune) responses (see, e.g., Bao X et al. *PLOS Pathog.* 2008; 4 (5): e1000077, incorporated herein by reference).

Measles Virus (MeV)

Molecular epidemiologic investigations and virologic surveillance contribute notably to the control and prevention of measles. Nearly half of measles-related deaths worldwide occur in India, yet virologic surveillance data are incomplete for many regions of the country. Previous studies have documented the presence of measles virus genotypes D4, D7, and D8 in India, and genotypes D5, D9, D11, H1, and G3 have been detected in neighboring countries. Recently, MeV genotype B3 was detected in India (Kuttiatt V S et al. *Emerg Infect Dis.* 2014; 20 (10): 1764-66).

The glycoprotein complex of paramyxoviruses mediates receptor binding and membrane fusion. In particular, the MeV fusion (F) protein executes membrane fusion, after receptor binding by the hemagglutinin (HA) protein (Muhlebach M D et al. *Journal of Virology* 2008; 82 (22): 11437-45). The MeV P gene codes for three proteins: P, an essential polymerase cofactor, and V and C, which have multiple functions but are not strictly required for viral propagation in cultured cells. V shares the amino-terminal domain with P but has a zinc-binding carboxyl-terminal domain, whereas C is translated from an overlapping reading frame. The MeV C protein is an infectivity factor. During replication, the P protein binds incoming monomeric nucleocapsid (N) proteins with its amino-terminal domain and positions them for assembly into the nascent ribonucleocapsid. The P protein amino-terminal domain is natively unfolded (Deveaux P et al. *Journal of Virology* 2004; 78 (21): 11632-40).

In some embodiments, a MeV vaccine of the present disclosure comprises a RNA (e.g., mRNA) polynucleotide encoding HA protein. In some embodiments, a MeV vaccine of the present disclosure comprises a RNA (e.g., mRNA) polynucleotide encoding F protein. In some embodiments, a MeV vaccine of the present disclosure comprises a RNA (e.g., mRNA) polynucleotide encoding P protein. In some embodiments, a MeV vaccine of the present disclosure comprises a RNA (e.g., mRNA) polynucleotide encoding V protein. In some embodiments, a MeV vaccine of the present disclosure comprises a RNA (e.g., mRNA) polynucleotide encoding C protein.

In some embodiments, a MeV vaccine of the present disclosure comprises a RNA (e.g., mRNA) polynucleotide encoding HA protein, F protein, P protein, V protein and C protein.

In some embodiments, a MeV vaccine of the present disclosure comprises a RNA (e.g., mRNA) polynucleotide encoding HA protein and F protein. In some embodiments, a MeV vaccine of the present disclosure comprises a RNA (e.g., mRNA) polynucleotide encoding HA protein and P protein. In some embodiments, a MeV vaccine of the present disclosure comprises a RNA (e.g., mRNA) polynucleotide encoding HA protein and V protein. In some embodiments, a MeV vaccine of the present disclosure comprises a RNA (e.g., mRNA) polynucleotide encoding HA protein and C protein.

some embodiments, a MeV vaccine of the present disclosure comprises a RNA (e.g., mRNA) polynucleotide encoding F protein and P protein. In some embodiments, a MeV vaccine of the present disclosure comprises a RNA (e.g., mRNA) polynucleotide encoding F protein and V protein. In some embodiments, a MeV vaccine of the present disclosure comprises a RNA (e.g., mRNA) polynucleotide encoding F protein and C protein.

In some embodiments, a MeV vaccine of the present disclosure comprises a RNA (e.g., mRNA) polynucleotide encoding HA protein, F protein and P protein. In some embodiments, a MeV vaccine of the present disclosure comprises a RNA (e.g., mRNA) polynucleotide encoding HA protein, F protein and V protein. In some embodiments, a MeV vaccine of the present disclosure comprises a RNA (e.g., mRNA) polynucleotide encoding HA protein, F protein and C protein.

In some embodiments, MeV vaccines comprise RNA (e.g., mRNA) encoding a MeV antigenic polypeptide having at least 95%, at least 96%, at least 97%, at least 98% or at least 99% identity with MeV HA protein and having MeV HA protein activity.

In some embodiments, MeV vaccines comprise RNA (e.g., mRNA) encoding a MeV antigenic polypeptide having at least 95%, at least 96%, at least 97%, at least 98% or at least 99% identity with MeV F protein and having MeV F protein activity.

A protein is considered to have HA protein activity if the protein mediates receptor binding and/or membrane fusion. MeV F protein executes membrane fusion, after receptor binding by the MeV HA protein.

A MeV vaccine may comprise, for example, at least one RNA (e.g., mRNA) polynucleotide having an open reading frame encoding at least one MeV antigenic polypeptide identified by any one of SEQ ID NO: 47-50 (Table 14; see also amino acid sequences of Table 15).

A MeV vaccine may comprise, for example, at least one RNA (e.g., mRNA) polynucleotide identified by any one of SEQ ID NO: 37, 40, 43, 46 (Table 13).

A MeV vaccine may comprise, for example, at least one RNA (e.g., mRNA) polynucleotide encoded by a nucleic acid (e.g., DNA) identified by any one of SEQ ID NO: 35, 36, 38, 39, 41, 42, 44 and 45 (Table 13).

The present disclosure is not limited by a particular strain of MeV. The strain of MeV used in a vaccine may be any strain of MeV. Non-limiting examples of strains of MeV for use as provide herein include B3/B3.1, C2, D4, D6, D7, D8, G3, H1, Moraten, Rubeovax, MVi/New Jersey.USA/45.05, MVi/Texas.USA/4.07, AIK-C, MVi/New York.USA/26.09/3, MVi/California.USA/16.03, MVi/Virginia.USA/15.09, MVi/California.USA/8.04, and MVi/Pennsylvania.USA/20.09.

MeV proteins may be from MeV genotype D4, D5, D7, D8, D9, D11, H1, G3 or B3. In some embodiments, a MeV HA protein or a MeV F protein is from MeV genotype D8. In some embodiments, a MeV HA protein or a MeV F protein is from MeV genotype B3.

Betacoronaviruses (BetaCoV)

MERS-CoV. MERS-CoV is a positive-sense, single-stranded RNA virus of the genus Betacoronavirus. The genomes are phylogenetically classified into two clades, clade A and clade B. It has a strong tropism for non-ciliated bronchial epithelial cells, evades the innate immune response and antagonizes interferon (IFN) production in infected cells. Dipeptyl peptidase 4 (DDP4, also known as CD26) has been identified as a functional cellular receptor for MERS-CoV. Its enzymatic activity is not required for infection, although its amino acid sequence is highly conserved across species and is expressed in the human bronchial epithelium and kidneys. Most infected individuals develop severe acute respiratory illnesses, including fever, cough, and shortness of breath, and the virus can be fatal. The disease may be transmitted among humans, generally among those in close contact.

The genome of MERS-CoV encodes at least four unique accessory proteins, such as 3, 4a, 4b and 5, two replicase proteins (open reading frame 1a and 1b), and four major structural proteins, including spike(S), envelope (E), nucleocapsid (N), and membrane (M) proteins (Almazan F et al. *MBio* 2013; 4 (5): e00650-13). The accessory proteins play nonessential roles in MERS-CoV replication, but they are likely structural proteins or interferon antagonists, modulating in vivo replication efficiency and/or pathogenesis, as in the case of SARS-CoV (Almazan F et al. *MBio* 2013; 4 (5): e00650-13; Totura A L et al. *Curr Opin Virol* 2012; 2 (3): 264-75; Scobey T et al. *Proc Natl Acad Sci USA* 2013; 110 (40): 16157-62). The other proteins of MERS-CoV maintain different functions in virus replication. The E protein, for example, involves in virulence, and deleting the E-coding gene results in replication-competent and propagation-defective viruses or attenuated viruses (Almazan F et al. *MBio* 2013; 4 (5): e00650-13). The S protein is particularly essential in mediating virus binding to cells expressing receptor dipeptidyl peptidase-4 (DPP4) through receptor-binding domain (RBD) in the S1 subunit, whereas the S2 subunit subsequently mediates virus entry via fusion of the virus and target cell membranes (Li F. *J Virol* 2015; 89 (4): 1954-64; Raj V S et al. *Nature* 2013; 495 (7440): 251-4).

In some embodiments, a MERS-CoV vaccine of the present disclosure comprises a RNA (e.g., mRNA) polynucleotide encoding S protein. In some embodiments, a MERS-CoV vaccine of the present disclosure comprises a RNA (e.g., mRNA) polynucleotide encoding the S1 subunit of the S protein. In some embodiments, a MERS-CoV vaccine of the present disclosure comprises a RNA (e.g., mRNA) polynucleotide encoding the S2 subunit of the S protein. In some embodiments, a MERS-CoV vaccine of the present disclosure comprises a RNA (e.g., mRNA) polynucleotide encoding E protein. In some embodiments, a MERS-CoV vaccine of the present disclosure comprises a RNA (e.g., mRNA) polynucleotide encoding N protein. In some embodiments, a MERS-CoV vaccine of the present disclosure comprises a RNA (e.g., mRNA) polynucleotide encoding M protein.

In some embodiments, a MERS-CoV vaccine of the present disclosure comprises a RNA (e.g., mRNA) polynucleotide encoding S protein (S, S1 and/or S2), E protein, N protein and M protein.

In some embodiments, a MERS-CoV vaccine of the present disclosure comprises a RNA (e.g., mRNA) polynucleotide encoding S protein (S, S1 and/or S2) and E protein. In some embodiments, a MERS-CoV vaccine of the present disclosure comprises a RNA (e.g., mRNA) polynucleotide encoding S protein (S, S1 and/or S2) and N protein. In some embodiments, a MERS-CoV vaccine of the present disclosure comprises a RNA (e.g., mRNA) polynucleotide encoding S protein (S, S1 and/or S2) and M protein.

In some embodiments, a MERS-CoV vaccine of the present disclosure comprises a RNA (e.g., mRNA) polynucleotide encoding S protein (S, S1 and/or S2), E protein and M protein. In some embodiments, a MERS-CoV vaccine of the present disclosure comprises a RNA (e.g., mRNA) polynucleotide encoding S protein (S, S1 and/or S2), E protein and N protein. In some embodiments, a MERS-CoV vaccine of the present disclosure comprises a RNA (e.g., mRNA) polynucleotide encoding S protein (S, S1 and/or S2), M protein and N protein. In some embodiments, a MERS-CoV vaccine of the present disclosure comprises a RNA (e.g., mRNA) polynucleotide encoding E protein, M protein and N protein.

A MERS-CoV vaccine may comprise, for example, at least one RNA (e.g., mRNA) polynucleotide having an open reading frame encoding at least one MERS-CoV antigenic polypeptide identified by any one of SEQ ID NO: 24-38 or 33 (Table 11; see also amino acid sequences of Table 12).

A MERS-CoV vaccine may comprise, for example, at least one RNA (e.g., mRNA) polynucleotide encoded by a nucleic acid (e.g., DNA) identified by any one of SEQ ID NO: 20-23 (Table 10).

The present disclosure is not limited by a particular strain of MERS-CoV. The strain of MERS-CoV used in a vaccine may be any strain of MERS-CoV. Non-limiting examples of strains of MERS-CoV for use as provide herein include Riyadh_14_2013, and 2cEMC/2012, Hasa_1_2013.

SARS-CoV. The genome of SARS-CoV includes of a single, positive-strand RNA that is approximately 29,700 nucleotides long. The overall genome organization of SARS-CoV is similar to that of other coronaviruses. The reference genome includes 13 genes, which encode at least 14 proteins. Two large overlapping reading frames (ORFs) encompass 71% of the genome. The remainder has 12 potential ORFs, including genes for structural proteins S (spike), E (small envelope), M (membrane), and N (nucleocapsid). Other potential ORFs code for unique putative SARS-CoV-specific polypeptides that lack obvious sequence similarity to known proteins. A detailed analysis of the SARS-CoV genome has been published in *J Mol Biol* 2003; 331:991-1004.

In some embodiments, a SARS-CoV vaccine of the present disclosure comprises a RNA (e.g., mRNA) polynucleotide encoding S protein (S, S1 and/or S2), E protein, N protein and M protein.

In some embodiments, a SARS-CoV vaccine of the present disclosure comprises a RNA (e.g., mRNA) polynucleotide encoding S protein (S, S1 and/or S2) and E protein. In some embodiments, a SARS-CoV vaccine of the present disclosure comprises a RNA (e.g., mRNA) polynucleotide encoding S protein (S, S1 and/or S2) and N protein. In some embodiments, a SARS-CoV vaccine of the present disclosure comprises a RNA (e.g., mRNA) polynucleotide encoding S protein (S, S1 and/or S2) and M protein.

In some embodiments, a SARS-CoV vaccine of the present disclosure comprises a RNA (e.g., mRNA) polynucleotide encoding S protein (S, S1 and/or S2), E protein and M protein. In some embodiments, a SARS-CoV vaccine of the present disclosure comprises a RNA (e.g., mRNA) polynucleotide encoding S protein (S, S1 and/or S2), E protein and N protein. In some embodiments, a SARS-CoV vaccine of the present disclosure comprises a RNA (e.g., mRNA) polynucleotide encoding S protein (S, S1 and/or S2), M protein and N protein. In some embodiments, a SARS-CoV vaccine of the present disclosure comprises a RNA (e.g., mRNA) polynucleotide encoding E protein, M protein and N protein.

A SARS-CoV vaccine may comprise, for example, at least one RNA (e.g., mRNA) polynucleotide having an open reading frame encoding at least one SARS-CoV antigenic polypeptide identified by any one of SEQ ID NO: 29, 32 or 34 (Table 11; see also amino acid sequences of Table 12).

The present disclosure is not limited by a particular strain of SARS-CoV. The strain of SARS-CoV used in a vaccine may be any strain of SARS-CoV.

HCoV-OC43. Human coronavirus OC43 is an enveloped, positive-sense, single-stranded RNA virus in the species Betacoronavirus-1 (genus Betacoronavirus, subfamily Coronavirinae, family Coronaviridae, order Nidovirales). Four HCoV-OC43 genotypes (A to D), have been identified with genotype D most likely arising from recombination. The complete genome sequencing of two genotype C and D strains and bootscan analysis shows recombination events between genotypes B and C in the generation of genotype D. Of 29 strains identified, none belong to the more ancient genotype A. Along with HCoV-229E, a species in the Alphacoronavirus genus, HCoV-OC43 are among the known viruses that cause the common cold. Both viruses can cause severe lower respiratory tract infections, including pneumonia in infants, the elderly, and immunocompromised individuals such as those undergoing chemotherapy and those with HIV-AIDS.

HCoV-HKU1. Human coronavirus HKU1 (HCoV-HKU1) is a positive-sense, single-stranded RNA virus with the HE gene, which distinguishes it as a group 2, or betacoronavirus. It was discovered in January 2005 in two patients in Hong Kong. The genome of HCoV-HKU1 is a 29,926-nucleotide, polyadenylated RNA. The GC content is 32%, the lowest among all known coronaviruses. The genome organization is the same as that of other group II coronaviruses, with the characteristic gene order 1a, 1b, HE, S, E, M, and N. Furthermore, accessory protein genes are present between the S and E genes (ORF4) and at the position of the N gene (ORF8). The TRS is presumably located within the AAUCUAAAC sequence, which precedes each ORF except E. As in sialodacryoadenitis virus and mouse hepatitis virus (MHV), translation of the E protein possibly occurs via an internal ribosomal entry site. The 3' untranslated region contains a predicted stem-loop structure immediately downstream of the N ORF (nucleotide position 29647 to 29711). Further downstream, a pseudoknot structure is present at nucleotide position 29708 to 29760. Both RNA structures are conserved in group II coronaviruses and are critical for virus replication.

HCoV-NL63. The RNA genome of human coronavirus NL63 (HCoV-NL63) is 27,553 nucleotides, with a poly(A) tail (FIG. 1). With a GC content of 34%, HCoV-NL63 has one of the lowest GC contents of the coronaviruses, for which GC content ranges from 32 to 42%. Untranslated regions of 286 and 287 nucleotides are present at the 5' and 3' termini, respectively. Genes predicted to encode the S, E, M, and N proteins are found in the 3' part of the HCoV-NL63 genome. The HE gene, which is present in some group II coronaviruses, is absent, and there is only a single, monocistronic accessory protein ORF (ORF3) located between the S and E genes. Subgenomic mRNAs are generated for all ORFs (S, ORF3, E, M, and N), and the core sequence of the TRS of HCoV-NL63 is defined as AACUAAA. This sequence is situated upstream of every ORF except for the E ORF, which contains the suboptimal core sequence AACUAUA. Interestingly, a 13-nucleotide sequence with perfect homology to the leader sequence is situated upstream of the suboptimal E TRS. Annealing of this 13-nucleotide sequence to the leader sequence may act as a compensatory mechanism for the disturbed leader-TRS/body-TRS interaction.

HCoV-229E. Human coronavirus 229E (HCoV-229E) is a single-stranded, positive-sense, RNA virus species in the Alphacoronavirus genus of the subfamily Coronavirinae, in the family Coronaviridae, of the order Nidovirales. Along with Human coronavirus OC43, it is responsible for the common cold. HCoV-NL63 and HCoV-229E are two of the four human coronaviruses that circulate worldwide. These two viruses are unique in their relationship towards each other. Phylogenetically, the viruses are more closely related to each other than to any other human coronavirus, yet they only share 65% sequence identity. Moreover, the viruses use different receptors to enter their target cell. HCoV-NL63 is associated with croup in children, whereas all signs suggest that the virus probably causes the common cold in healthy adults. HCoV-229E is a proven common cold virus in healthy adults, so it is probable that both viruses induce comparable symptoms in adults, even though their mode of infection differs (HCoV-NL63 and HCoV-229E are two of the four human coronaviruses that circulate worldwide. These two viruses are unique in their relationship towards each other. Phylogenetically, the viruses are more closely related to each other than to any other human coronavirus, yet they only share 65% sequence identity. Moreover, the viruses use different receptors to enter their target cell. HCoV-NL63 is associated with croup in children, whereas all signs suggest that the virus probably causes the common cold in healthy adults. HCoV-229E is a proven common cold virus in healthy adults, so it is probable that both viruses induce comparable symptoms in adults, even though their mode of infection differs (Dijkman R. et al. *J Formos Med Assoc.* 2009 April; 108 (4): 270-9, the contents of which is incorporated herein by reference in their entirety).

Combination Vaccines

Embodiments of the present disclosure also provide combination RNA (e.g., mRNA) vaccines. A "combination RNA (e.g., mRNA) vaccine" of the present disclosure refers to a vaccine comprising at least one (e.g., at least 2, 3, 4, or 5) RNA (e.g., mRNA) polynucleotide having an open reading frame encoding a combination of any two or more (or all of) antigenic polypeptides selected from hMPV antigenic polypeptides, PIV3 antigenic polypeptides, RSV antigenic polypeptides, MeV antigenic polypeptides, and BetaCoV antigenic polypeptides (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide, a RSV antigenic polypeptide, a MeV antigenic polypeptide, and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide and a PIV3 antigenic polypeptide.

In some embodiments, a combination RNA (e.g., mRNA) vaccine comprises a RNA (e.g., mRNA) polynucleotide encoding a hMPV antigenic polypeptide and a RSV antigenic polypeptide.

In some embodiments, a combination RNA (e.g., mRNA) vaccine comprises a RNA (e.g., mRNA) polynucleotide encoding a hMPV antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide and a BetaCoV antigenic polypeptide.

In some embodiments, a combination RNA (e.g., mRNA) vaccine comprises a RNA (e.g., mRNA) polynucleotide encoding a PIV3 antigenic polypeptide and a RSV antigenic polypeptide.

In some embodiments, a combination RNA (e.g., mRNA) vaccine comprises a RNA (e.g., mRNA) polynucleotide encoding a PIV3 antigenic polypeptide and a MeV antigenic polypeptide.

In some embodiments, a combination RNA (e.g., mRNA) vaccine comprises a RNA (e.g., mRNA) polynucleotide encoding a PIV3 antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a RSV antigenic polypeptide and a MeV antigenic polypeptide.

In some embodiments, a combination RNA (e.g., mRNA) vaccine comprises a RNA (e.g., mRNA) polynucleotide encoding a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide, a RSV antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide, a PIV3 antigenic polypeptide, a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a RSV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a PIV3 antigenic polypeptide, a RSV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a PIV3 antigenic polypeptide and a RSV antigenic polypeptide.

In some embodiments, a combination RNA (e.g., mRNA) vaccine comprises a RNA (e.g., mRNA) polynucleotide encoding a hMPV antigenic polypeptide, a PIV3 antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide, a PIV3 antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a RSV antigenic polypeptide and a MeV antigenic polypeptide.

In some embodiments, a combination RNA (e.g., mRNA) vaccine comprises a RNA (e.g., mRNA) polynucleotide encoding a hMPV antigenic polypeptide, a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a hMPV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a PIV3 antigenic polypeptide, a RSV antigenic polypeptide and a MeV antigenic polypeptide.

In some embodiments, a combination RNA (e.g., mRNA) vaccine comprises a RNA (e.g., mRNA) polynucleotide encoding a PIV3 antigenic polypeptide, a RSV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

In some embodiments, a combination RNA (e.g., mRNA) vaccine comprises a RNA (e.g., mRNA) polynucleotide encoding a RSV antigenic polypeptide, a MeV antigenic polypeptide and a BetaCoV antigenic polypeptide (e.g., selected from MERS-CoV, SARS-CoV, HCoV-OC43, HCoV-229E, HCoV-NL63, HCoV-NL, HCoV-NH and HCoV-HKU1).

Other combination respiratory virus RNA (e.g., mRNA) vaccines are encompassed by the present disclosure.

It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the invention generate a more rapid immune response with fewer doses of antigen than other vaccines tested. The mRNA-LNP formulations of the invention also produce quantitatively and qualitatively better immune responses than vaccines formulated in a different carriers.

The data described herein demonstrate that the formulations of the invention produced significant unexpected improvements over existing antigen vaccines. Additionally, the mRNA-LNP formulations of the invention are superior to other vaccines even when the dose of mRNA is lower than other vaccines. Mice immunized with either 10 μg or 2 μg doses of an hMPV fusion protein mRNA LNP vaccine or a PIV3 mRNA LNP vaccine produced neutralizing antibodies which for instance, successfully neutralized the hMPV B2 virus. A 10 μg dose of mRNA vaccine protected 100% of mice from lethal challenge and drastically reduced the viral titer after challenge (~2 log reduction).

Two 20 μg doses of MERS-CoV mRNA LNP vaccine significantly reduced viral load and induced significant amount of neutralizing antibodies against MERS-CoV ($EC_{50}$ between 500-1000). The MERS-CoV mRNA vaccine induced antibody titer was 3-5 fold better than any other vaccines tested in the same model.

The LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Nucleic Acids/Polynucleotides

Respiratory virus vaccines, as provided herein, comprise at least one (one or more) ribonucleic acid (RNA) (e.g., mRNA) polynucleotide having an open reading frame encoding at least one antigenic polypeptide selected from hMPV, PIV3, RSV, MeV and BetaCoV (e.g., selected from MERS-CoV, SARS-CoV, HCoV-OC43, HCoV-229E, HCoV-NL63, HCoV-NL, HCoV-NH and HCoV-HKU1) antigenic polypeptides. The term "nucleic acid" includes any compound and/or substance that comprises a polymer of nucleotides (nucleotide monomer). These polymers are referred to as polynucleotides. Thus, the terms "nucleic acid" and "polynucleotide" are used interchangeably.

Nucleic acids may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The skilled artisan will appreciate that, except where otherwise noted, polynucleotide sequences set forth in the instant application will recite "T"s in a representative DNA sequence but where the sequence represents RNA (e.g., mRNA), the "T"'s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U."

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features, which serve to overcome existing problems of effective polypeptide expression using nucleic-acid based therapeutics.

In some embodiments, a RNA polynucleotide of an RNA (e.g., mRNA) vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA (e.g., mRNA) polynucleotide of a respiratory virus vaccine encodes at least 10, 20, 30, 40, 50, 60, 70, 80, 90 or 100 antigenic polypeptides. In some embodiments, a RNA (e.g., mRNA) polynucleotide of a respiratory virus vaccine encodes at least 100 or at least 200 antigenic polypeptides. In some embodiments, a RNA polynucleotide of an respiratory virus vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity, less than 90% sequence identity, less than 85% sequence identity, less than 80% sequence identity, or les than 75% sequence identity to a naturally-occurring or wild-type sequence (e.g., a naturally-occurring or wild-type mRNA sequence encoding a polypeptide or protein of interest (e.g., an antigenic protein or antigenic polypeptide)).

In some embodiments, a codon-optimized sequence shares between 65% and 85% (e.g., between about 67% and about 85%, or between about 67% and about 80%) sequence identity to a naturally-occurring sequence or a wild-type sequence (e.g., a naturally-occurring or wild-type mRNA sequence encoding a polypeptide or protein of interest (e.g., an antigenic protein or polypeptide)). In some embodiments, a codon-optimized sequence shares between 65% and 75%, or about 80% sequence identity to a naturally-occurring sequence or wild-type sequence (e.g., a naturally-occurring or wild-type mRNA sequence encoding a polypeptide or protein of interest (e.g., an antigenic protein or polypeptide)).

In some embodiments a codon-optimized RNA (e.g., mRNA) may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Antigens/Antigenic Polypeptides

In some embodiments, an antigenic polypeptide (e.g., a hMPV, PIV3, RSV, MeV or BetaCoV antigenic polypeptide) is longer than 25 amino acids and shorter than 50 amino acids. Polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain polypeptides or multichain polypeptides, such as antibodies or insulin, and may be associated or linked to each other. Most commonly, disulfide linkages are found in multichain polypeptides. The term "polypeptide" may also apply to amino acid polymers in which at least one amino acid residue is an artificial chemical analogue of a corresponding naturally-occurring amino acid.

A "polypeptide variant" is a molecule that differs in its amino acid sequence relative to a native sequence or a reference sequence. Amino acid sequence variants may possess substitutions, deletions, insertions, or a combination of any two or three of the foregoing, at certain positions within the amino acid sequence, as compared to a native sequence or a reference sequence. Ordinarily, variants possess at least 50% identity to a native sequence or a reference sequence. In some embodiments, variants share at least 80% identity or at least 90% identity with a native sequence or a reference sequence.

In some embodiments "variant mimics" are provided. A "variant mimic" contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic. For example, phenylalanine may act as an inactivating substitution for tyrosine, or alanine may act as an inactivating substitution for serine.

"Orthologs" refers to genes in different species that evolved from a common ancestral gene by speciation. Normally, orthologs retain the same function in the course of evolution. Identification of orthologs is important for reliable prediction of gene function in newly sequenced genomes.

"Analogs" is meant to include polypeptide variants that differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more (e.g., 3, 4 or 5) amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini and any combination(s) thereof.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide-based or polynucleotide-based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity," as known in the art, refers to a relationship between the sequences of two or more polypeptides or polynucleotides, as determined by comparing the sequences. In the art, identity also means the degree of sequence relatedness between two sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. Identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al. (1997). "Gapped BLAST and PSI-BLAST: a new generation of protein database search programs," *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM *J Applied Math.,* 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12 (1), 387 (1984)), BLASTP, BLASTN, and FASTA Altschul, S. F. et al., *J. Molec. Biol.,* 215, 403 (1990)).

Multiprotein and Multicomponent Vaccines

The present disclosure encompasses respiratory virus vaccines comprising multiple RNA (e.g., mRNA) polynucleotides, each encoding a single antigenic polypeptide, as well as respiratory virus vaccines comprising a single RNA polynucleotide encoding more than one antigenic polypeptide (e.g., as a fusion polypeptide). Thus, a vaccine composition comprising a RNA (e.g., mRNA) polynucleotide having an open reading frame encoding a first antigenic polypeptide and a RNA (e.g., mRNA) polynucleotide having an open reading frame encoding a second antigenic polypeptide encompasses (a) vaccines that comprise a first RNA polynucleotide encoding a first antigenic polypeptide and a second RNA polynucleotide encoding a second antigenic polypeptide, and (b) vaccines that comprise a single RNA polynucleotide encoding a first and second antigenic polypeptide (e.g., as a fusion polypeptide). RNA (e.g., mRNA) vaccines of the present disclosure, in some embodiments, comprise 2-10 (e.g., 2, 3, 4, 5, 6, 7, 8, 9 or 10), or more, RNA polynucleotides having an open reading frame, each of which encodes a different antigenic polypeptide (or a single RNA polynucleotide encoding 2-10, or more, different antigenic polypeptides). The antigenic polypeptides may be selected from hMPV, PIV3, RSV, MEV and BetaCoV (e.g., selected from MERS-CoV, SARS-CoV, HCoV-OC43, HCoV-229E, HCoV-NL63, HCoV-NL, HCoV-NH and HCoV-HKU1) antigenic polypeptides.

In some embodiments, a respiratory virus vaccine comprises a RNA (e.g., mRNA) polynucleotide having an open reading frame encoding a viral capsid protein, a RNA (e.g., mRNA) polynucleotide having an open reading frame encoding a viral premembrane/membrane protein, and a RNA (e.g., mRNA) polynucleotide having an open reading frame encoding a viral envelope protein. In some embodiments, a respiratory virus vaccine comprises a RNA (e.g., mRNA) polynucleotide having an open reading frame encoding a viral fusion (F) protein and a RNA polynucleotide having an open reading frame encoding a viral major surface glycoprotein (G protein). In some embodiments, a vaccine comprises a RNA (e.g., mRNA) polynucleotide having an open reading frame encoding a viral F protein. In some embodiments, a vaccine comprises a RNA (e.g., mRNA) polynucleotide having an open reading frame encoding a viral G protein. In some embodiments, a vaccine comprises a RNA (e.g., mRNA) polynucleotide having an open reading frame encoding a HN protein.

In some embodiments, a multicomponent vaccine comprises at least one RNA (e.g., mRNA) polynucleotide encoding at least one antigenic polypeptide fused to a signal peptide (e.g., any one of SEQ ID NO: 15-19). The signal peptide may be fused at the N-terminus or the C-terminus of an antigenic polypeptide. An antigenic polypeptide fused to a signal peptide may be selected from hMPV, PIV3, RSV, MEV and BetaCoV (e.g., selected from MERS-CoV, SARS- CoV, HCoV-OC43, HCoV-229E, HCoV-NL63, HCoV-NL, HCoV-NH and HCoV-HKU1) antigenic polypeptides.

Signal Peptides

In some embodiments, antigenic polypeptides encoded by respiratory virus RNA (e.g., mRNA) polynucleotides comprise a signal peptide. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. Signal peptides generally include three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane. The signal peptide, however, is not responsible for the final destination of the mature protein. Secretory proteins devoid of additional address tags in their sequence are by default secreted to the external environment. During recent years, a more advanced view of signal peptides has evolved, showing that the functions and immunodominance of certain signal peptides are much more versatile than previously anticipated.

Respiratory virus vaccines of the present disclosure may comprise, for example, RNA (e.g., mRNA) polynucleotides encoding an artificial signal peptide, wherein the signal peptide coding sequence is operably linked to and is in frame with the coding sequence of the antigenic polypeptide. Thus, respiratory virus vaccines of the present disclosure, in some embodiments, produce an antigenic polypeptide comprising an antigenic polypeptide (e.g., hMPV, PIV3, RSV, MeV or BetaCoV) fused to a signal peptide. In some embodiments, a signal peptide is fused to the N-terminus of the antigenic polypeptide. In some embodiments, a signal peptide is fused to the C-terminus of the antigenic polypeptide.

In some embodiments, the signal peptide fused to the antigenic polypeptide is an artificial signal peptide. In some embodiments, an artificial signal peptide fused to the antigenic polypeptide encoded by the RNA (e.g., mRNA) vaccine is obtained from an immunoglobulin protein, e.g., an IgE signal peptide or an IgG signal peptide. In some embodiments, a signal peptide fused to the antigenic polypeptide encoded by a RNA (e.g., mRNA) vaccine is an Ig heavy chain epsilon-1 signal peptide (IgE HC SP) having the sequence of: MDWTWILFLVAAATRVHS (SEQ ID NO: 16). In some embodiments, a signal peptide fused to the antigenic polypeptide encoded by the (e.g., mRNA) RNA (e.g., mRNA) vaccine is an IgGk chain V-III region HAH signal peptide (IgGk SP) having the sequence of METPAQLLFLLLLWLPDTTG (SEQ ID NO: 15). In some embodiments, the signal peptide is selected from: Japanese encephalitis PRM signal sequence (MLGSNSGQRVVFTILLLLVAPAYS; SEQ ID NO: 17), VSVg protein signal sequence (MKCLLYLAFLFIGVNCA; SEQ ID NO: 18) and Japanese encephalitis JEV signal sequence (MWLVSLAIVTACAGA; SEQ ID NO: 19).

In some embodiments, the antigenic polypeptide encoded by a RNA (e.g., mRNA) vaccine comprises an amino acid sequence identified by any one of SEQ ID NO: 5-8, 12-13, 24-34, 47-50 or 54-56 (Tables 3, 6, 11, 14 or 17; see also amino acid sequences of Tables 4, 7, 12 or 15) fused to a signal peptide identified by any one of SEQ ID NO: 15-19 (Table 8). The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature antigenic polypeptide produce by a respiratory virus RNA (e.g., mRNA) vaccine of the present disclosure typically does not comprise a signal peptide.

Chemical Modifications

Respiratory virus vaccines of the present disclosure, in some embodiments, comprise at least RNA (e.g. mRNA) polynucleotide having an open reading frame encoding at least one antigenic polypeptide that comprises at least one chemical modification.

The terms “chemical modification” and “chemically modified” refer to modification with respect to adenosine (A), guanosine (G), uridine (U), thymidine (T) or cytidine (C) ribonucleosides or deoxyribnucleosides in at least one of their position, pattern, percent or population. Generally, these terms do not refer to the ribonucleotide modifications in naturally occurring 5'-terminal mRNA cap moieties. With respect to a polypeptide, the term “modification” refers to a modification relative to the canonical set 20 amino acids. Polypeptides, as provided herein, are also considered “modified” of they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Modifications of polynucleotides include, without limitation, those described herein. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphdioester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides) that are useful in the vaccines of the present disclosure include, but are not limited to the following: 2-methylthio-N6-(cis-hydroxyisopentenyl) adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl) adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl) adenine; N6-cis-hydroxy-isopentenyl-adenosine; α-thio-adenosine; 2 (amino) adenine; 2 (aminopropyl) adenine; 2 (methylthio) N6 (isopentenyl) adenine; 2-(alkyl) adenine; 2-(aminoalkyl) adenine; 2-(aminopropyl) adenine; 2-(halo) adenine; 2-(halo) adenine; 2-(propyl) adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl) adenine; 6 (methyl) adenine; 6-(alkyl) adenine; 6-(methyl) adenine; 7 (deaza) adenine; 8 (alkenyl) adenine; 8 (alkynyl) adenine; 8 (amino) adenine; 8 (thioalkyl) adenine; 8-(alkenyl) adenine; 8-(alkyl) adenine; 8-(alkynyl) adenine; 8-(amino) adenine; 8-(halo) adenine; 8-(hydroxyl) adenine; 8-(thioalkyl) adenine; 8-(thiol) adenine; 8-azido-adenosine; aza adenine; deaza adenine; N6 (methyl) adenine; N6-(isopentyl) adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio) cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza) cytosine; 3 (methyl) cytosine; 3-(alkyl) cytosine; 3-(deaza) 5 (aza) cytosine; 3-(methyl) cytidine; 4,2'-O-dimethylcytidine; 5 (halo) cytosine; 5 (methyl) cytosine; 5 (propynyl) cytosine; 5 (trifluoromethyl) cytosine; 5-(alkyl) cytosine; 5-(alkynyl) cytosine; 5-(halo) cytosine; 5-(propynyl) cytosine; 5-(trifluoromethyl) cytosine; 5-bromo-cytidine; 5-iodo-cytidine; 5-propynyl cytosine; 6-(azo) cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl) cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl) cytidine TP; 3'-Ethynylcytidine TP; 4'-Azidocytidine TP; 4'-Carbocyclic cytidine TP; 4'-Ethynylcytidine TP; 5-(1-Propynyl) ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl) guanine; 2-(alkyl) guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl) guanine; 6-(alkyl) guanine; 6-(methyl) guanine; 6-methyl-guanosine; 7 (alkyl) guanine; 7 (deaza) guanine; 7 (methyl) guanine; 7-(alkyl) guanine; 7-(deaza) guanine; 7-(methyl) guanine; 8 (alkyl) guanine; 8 (alkynyl) guanine; 8 (halo) guanine; 8 (thioalkyl) guanine; 8-(alkenyl) guanine; 8-(alkyl) guanine; 8-(alkynyl) guanine; 8-(amino) guanine; 8-(halo) guanine; 8-(hydroxyl) guanine; 8-(thioalkyl) guanine; 8-(thiol) guanine; aza guanine; deaza guanine; N (methyl) guanine; N-(methyl) guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl) uridine; 1-methyl-3-(3-amino-5-carboxypropyl) pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl) uridine; 3,2'-O-dimethyluridine; 3-Methyl-pseudo-Uridine TP; 4-thiouridine; 5-(carboxyhydroxymethyl) uridine; 5-(carboxyhydroxymethyl) uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl) uridine TP; 5-propynyl uracil; α-thio-uridine; 1 (aminoalkylamino-carbonylethylenyl)-2 (thio)-pseudouracil; 1 (aminoalkylaminocarbonylethylenyl)-2,4-(dithio) pseudouracil; 1 (aminoalkylaminocarbonylethylenyl)-4 (thio) pseudouracil; 1 (aminoalkylaminocarbonylethylenyl)-pseudouracil; 1 (aminocarbonylethylenyl)-2 (thio)-pseudouracil; 1 (aminocarbonylethylenyl)-2,4-(dithio) pseudouracil; 1 (aminocarbonylethylenyl)-4 (thio) pseudouracil; 1 (aminocarbonylethylenyl)-pseudouracil; 1 substituted 2 (thio)-pseudouracil; 1 substituted 2,4-(dithio) pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 2 (thio) pseudouracil; 2' deoxy uridine; 2' fluorouridine; 2-(thio) uracil; 2,4-(dithio) psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio) pseudouracil; 4-(thio) pseudouracil; 4-(thio) uracil; 4-thiouracil; 5 (1,3-diazole-1-alkyl) uracil; 5 (2-aminopropyl) uracil; 5 (aminoalkyl) uracil; 5 (dimethylaminoalkyl) uracil; 5 (guanidiniumalkyl) uracil; 5 (methoxycarbonylmethyl)-2-(thio) uracil; 5 (methoxycarbonyl-methyl) uracil; 5 (methyl) 2 (thio) uracil; 5 (methyl) 2,4 (dithio) uracil; 5 (methyl) 4 (thio) uracil; 5 (methylaminomethyl)-2 (thio) uracil; 5 (methylaminomethyl)-2,4 (dithio) uracil; 5 (methylaminomethyl)-4 (thio) uracil; 5 (propynyl) uracil; 5 (trifluoromethyl) uracil; 5-(2-aminopropyl) uracil; 5-(alkyl)-2-(thio) pseudouracil; 5-(alkyl)-2,4 (dithio) pseudouracil; 5-(alkyl)-4 (thio) pseudouracil; 5-(alkyl) pseudouracil; 5-(alkyl) uracil; 5-(alkynyl) uracil; 5-(allylamino) uracil; 5-(cyanoalkyl) uracil; 5-(dialkylaminoalkyl) uracil; 5-(dimethylaminoalkyl) uracil; 5-(guanidiniumalkyl) uracil; 5-(halo) uracil; 5-(1,3-diazole-1-alkyl) uracil; 5-(methoxy) uracil; 5-(methoxycarbonylmethyl)-2-(thio) uracil; 5-(methoxycarbonyl-methyl) uracil; 5-(methyl) 2 (thio) uracil; 5-(methyl) 2,4 (dithio) uracil; 5-(methyl) 4 (thio) uracil; 5-(methyl)-2-(thio) pseudouracil; 5-(methyl)-2,4 (dithio) pseudouracil; 5-(methyl)-4 (thio) pseudouracil; 5-(methyl) pseudouracil; 5-(methylaminomethyl)-2 (thio) uracil; 5-(methylaminomethyl)-2,4 (dithio) uracil; 5-(methylaminomethyl)-4-(thio) uracil; 5-(propynyl) uracil; 5-(trifluoromethyl) uracil; 5-aminoallyl-uridine; 5-bromo-uridine; 5-iodo-uridine; 5-uracil; 6 (azo) uracil; 6-(azo) uracil; 6-aza-uridine; allyamino-uracil; aza uracil; deaza uracil; N3 (methyl) uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (+) 1-(2-Hydroxypropyl) pseudouridine TP; (2R)-1-(2-Hydroxypropyl) pseudouridine TP; (2S)-1-(2-Hydroxypropyl) pseudouridine TP; (E)-5-(2-Bromo-vinyl) ara-uridine TP; (E)-5-(2-Bromo-vinyl) uridine TP; (Z)-5-(2-Bromo-vinyl) ara-uridine TP; (Z)-5-(2-Bromo-vinyl) uridine TP; 1-(2,2,2-Trifluoroethyl)-pseudo-UTP; 1-(2,2,3,3,3-Pentafluoropropyl) pseudouridine TP; 1-(2,2-Diethoxyethyl) pseudouridine TP; 1-(2,4,6-Trimethylbenzyl) pseudouridine TP; 1-(2,4,6-Trimethyl-benzyl) pseudo-UTP; 1-(2,4,6-Trimethyl-phenyl) pseudo-UTP; 1-(2-Amino-2-carboxyethyl) pseudo-UTP; 1-(2-Amino-ethyl) pseudo-UTP; 1-(2-Hydroxyethyl) pseudouridine TP; 1-(2-Methoxyethyl) pseudouridine TP; 1-(3,4-Bis-trifluoromethoxybenzyl) pseudouridine TP; 1-(3,4-Dimethoxybenzyl) pseudouridine TP; 1-(3-Amino-3-carboxypropyl) pseudo-UTP; 1-(3-Amino-propyl) pseudo-UTP; 1-(3-Cyclopropyl-prop-2-ynyl) pseudouridine TP; 1-(4-Amino-4-carboxybutyl) pseudo-UTP; 1-(4-Amino-benzyl) pseudo-UTP; 1-(4-Amino-butyl) pseudo-UTP; 1-(4-Amino-phenyl) pseudo-UTP; 1-(4-Azidobenzyl) pseudouridine TP; 1-(4-Bromobenzyl) pseudouridine TP; 1-(4-Chlorobenzyl) pseudouridine TP; 1-(4-Fluorobenzyl) pseudouridine TP; 1-(4-Iodobenzyl) pseudouridine TP; 1-(4-Methanesulfonylbenzyl) pseudouridine TP; 1-(4-Methoxybenzyl) pseudouridine TP; 1-(4-Methoxy-benzyl) pseudo-UTP; 1-(4-Methoxy-phenyl) pseudo-UTP; 1-(4-Methylbenzyl) pseudouridine TP; 1-(4-Methyl-benzyl) pseudo-UTP; 1-(4-Nitrobenzyl) pseudouridine TP; 1-(4-Nitro-benzyl) pseudo-UTP; 1 (4-Nitro-phenyl) pseudo-UTP; 1-(4-Thiomethoxybenzyl) pseudouridine TP; 1-(4-Trifluoromethoxybenzyl) pseudouridine TP; 1-(4-Trifluoromethyl-benzyl) pseudouridine TP; 1-(5-Amino-pentyl) pseudo-UTP; 1-(6-Amino-hexyl) pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl) pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl) uridine TP; 3-Alkyl-pseudo-UTP; 4'-Azidouridine TP; 4'-Carbocyclic uridine TP; 4'-Ethynyluridine TP; 5-(1-Propynyl) ara-uridine TP; 5-(2-Furanyl) uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2

(2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino) purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino) purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl) isocarbostyrilyl; 4-(fluoro)-6-(methyl)benzimidazole; 4-(methyl)benzimidazole; 4-(methyl) indolyl; 4,6-(dimethyl) indolyl; 5 nitroindole; 5 substituted pyrimidines; 5-(methyl) isocarbostyrilyl; 5-nitroindole; 6-(aza)pyrimidine; 6-(azo) thymine; 6-(methyl)-7-(aza) indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza) indolyl; 7-(guanidiniumalkylhydroxy)-1-(aza)-2-(thio)-3-(aza)-phenoxazin-1-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl) isocarbostyrilyl; 7-(propynyl) isocarbostyrilyl, propynyl-7-(aza) indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza) indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl) uridine TP; and N6-(19-Amino-pentaoxanonadecyl) adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), N1-methylpseudouridine ($m^1ψ$), N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine ($m^1ψ$), 5-methoxy-uridine ($mo^5U$), 5-methyl-cytidine ($m^5C$), pseudouridine (ψ), α-thio-guanosine and α-thio-adenosine. In some embodiments, polynucleotides includes a combination of at least two (e.g., 2, 3, 4 or more) of the aforementioned modified nucleobases.

In some embodiments, polynucleotides (e.g., RNA polynucleotides, such as mRNA polynucleotides) comprise pseudouridine (ψ) and 5-methyl-cytidine ($m^5C$). In some embodiments, polynucleotides (e.g., RNA polynucleotides, such as mRNA polynucleotides) comprise 1-methyl-pseudouridine ($m^1ψ$). In some embodiments, polynucleotides (e.g., RNA polynucleotides, such as mRNA polynucleotides) comprise 1-methyl-pseudouridine ($m^1ψ$) and 5-methyl-cytidine ($m^5C$). In some embodiments, polynucleotides (e.g., RNA polynucleotides, such as mRNA polynucleotides) comprise 2-thiouridine ($s^2U$). In some embodiments, polynucleotides (e.g., RNA polynucleotides, such as mRNA polynucleotides) comprise 2-thiouridine and 5-methyl-cytidine ($m^5C$). In some embodiments, polynucleotides (e.g., RNA polynucleotides, such as mRNA polynucleotides) comprise methoxy-uridine ($mo^5U$). In some embodiments, polynucleotides (e.g., RNA polynucleotides, such as mRNA polynucleotides) comprise 5-methoxy-uridine ($mo^5U$) and 5-methyl-cytidine ($m^5C$). In some embodiments, polynucleotides (e.g., RNA polynucleotides, such as mRNA polynucleotides) comprise 2'-O-methyl uridine. In some embodiments polynucleotides (e.g., RNA polynucleotides, such as mRNA polynucleotides) comprise 2'-O-methyl uridine and 5-methyl-cytidine ($m^5C$). In some embodiments, polynucleotides (e.g., RNA polynucleotides, such as mRNA polynucleotides) comprise N6-methyl-adenosine ($m^6A$). In some embodiments, polynucleotides (e.g., RNA polynucleotides, such as mRNA polynucleotides) comprise N6-methyl-adenosine ($m^6A$) and 5-methyl-cytidine ($m^5C$).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 5-methyl-cytidine ($m^5C$), meaning that all cytosine residues in the mRNA sequence are replaced with 5-methyl-cytidine ($m^5C$). Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and In some embodiments, a modified nucleobase is a modified cytosine. nucleosides having a modified uridine include 5-cyano uridine, and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the disclosure, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). Any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). n some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Thus, in some embodiments, the RNA (e.g., mRNA) vaccines comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s2U), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine ($\tau m^5s^2U$), 1-taurinomethyl-4-thio-pseudouridine, 5-methyl-uridine ($m^5U$, i.e., having the nucleobase deoxythymine), 1-methyl-pseudouridine ($m^1\psi$), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine ($acp^3U$), 1-methyl-3-(3-amino-3-carboxypropyl) pseudouridine ($acp^3\psi$), 5-(isopentenylaminomethyl) uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^3Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2m^6A$), N6-isopentenyl-adenosine ($i^6A$), 2-methylthio-N6-isopentenyl-adenosine ($ms^2i^6A$), N6-(cis-hydroxyisopentenyl) adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6$ $t^6A$), 2-methylthio-N6-threonylcarbamoyl-adenosine ($ms^2g^6A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2_2G$), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, 06-methyl-guanosine, 2'-F-ara-guanosine, and 2'-F-guanosine.

N-Linked Glycosylation Site Mutants

N-linked glycans of viral proteins play important roles in modulating the immune response. Glycans can be important for maintaining the appropriate antigenic conformations, shielding potential neutralization epitopes, and may alter the proteolytic susceptibility of proteins. Some viruses have putative N-linked glycosylation sites. Deletion or modification of an N-linked glycosylation site may enhance the immune response. Thus, the present disclosure provides, in some embodiments, RNA (e.g., mRNA) vaccines comprising nucleic acids (e.g., mRNA) encoding antigenic polypeptides that comprise a deletion or modification at one or more N-linked glycosylation sites.

In Vitro Transcription of RNA (e.g., mRNA)

Respiratory virus vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (5'UTR) refers to a region of an mRNA that is directly upstream (i.e., 5') from the start codon (i.e., the first codon of an mRNA transcript translated by a ribosome) that does not encode a polypeptide.

A "3' untranslated region" (3'UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. typhimurium, H. pylori, V. cholera, S. marcesens, S. flexneri, T. Pallidum, L. pneumophila, B. burgdorferei, C. difficile, R. meliloti, A. tumefaciens, R. lupini, B. clarridgeiae, P. mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identify to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8), and SEQ ID NO: 54-56 (Table 17). In some embodiments, the flagellin polypeptide has at least 60%, 70%, 75%, 80%, 90%, 95%, 97%, 98%, or 99% sequence identify to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains DO through D3. DO and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 (in *Salmonella typhimurium* FliC flagellin. Within the 13 amino acids in the 88-100 region, at least 6 substitutions are permitted between *Salmonella* flagellin and other flagellins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 84).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides and the other encoding the flagellin polypeptide. The at least two RNA polynucleotides may be co-formulated in a carrier such as a lipid nanoparticle.

Broad Spectrum RNA (e.g., mRNA) Vaccines

There may be situations where persons are at risk for infection with more than one strain of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1), a combination vaccine can be administered that includes RNA (e.g., mRNA) encoding at least one antigenic polypeptide protein (or antigenic portion thereof) of a first respiratory virus and further includes RNA encoding at least one antigenic polypeptide protein (or antigenic portion thereof) of a second respiratory virus. RNA (e.g., mRNA)

can be co-formulated, for example, in a single lipid nanoparticle (LNP) or can be formulated in separate LNPs for co-administration.

Methods of Treatment

Provided herein are compositions (e.g., pharmaceutical compositions), methods, kits and reagents for prevention and/or treatment of respiratory diseases/infections in humans and other mammals. Respiratory virus RNA (e.g. mRNA) vaccines can be used as therapeutic or prophylactic agents, alone or in combination with other vaccine(s). They may be used in medicine to prevent and/or treat respiratory disease/infection. In exemplary aspects, the RNA (e.g., mRNA) vaccines of the present disclosure are used to provide prophylactic protection from hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). Prophylactic protection from hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) can be achieved following administration of a RNA (e.g., mRNA) vaccine of the present disclosure. Respiratory virus RNA (e.g., mRNA) vaccines of the present disclosure may be used to treat or prevent viral "co-infections" containing two or more respiratory infections. Vaccines can be administered once, twice, three times, four times or more, but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) is provided in aspects of the present disclosure. The method involves administering to the subject a respiratory virus RNA (e.g., mRNA) vaccine comprising at least one RNA (e.g., mRNA) polynucleotide having an open reading frame encoding at least one hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide thereof, thereby inducing in the subject an immune response specific to hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide or an immunogenic fragment thereof, wherein anti-antigenic polypeptide antibody titer in the subject is increased following vaccination relative to anti-antigenic polypeptide antibody titer in a subject vaccinated with a prophylactically effective dose of a traditional vaccine against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). An "anti-antigenic polypeptide antibody" is a serum antibody the binds specifically to the antigenic polypeptide.

In some embodiments, a RNA (e.g., mRNA) vaccine (e.g., a hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1 RNA vaccine) capable of eliciting an immune response is administered intramuscularly via a composition including a compound according to Formula (I), (IA), (II), (IIa), (IIb), (IIc), (IId) or (IIe) (e.g., Compound 3, 18, 20, 25, 26, 29, 30, 60, 108-112, or 122).

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the RNA (e.g., mRNA) vaccines of the present disclosure. For instance, a traditional vaccine includes but is not limited to live/attenuated microorganism vaccines, killed/inactivated microorganism vaccines, subunit vaccines, protein antigen vaccines, DNA vaccines, VLP vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1).

In some embodiments the anti-antigenic polypeptide antibody titer in the subject is increased 1 log, 2 log, 3 log, 5 log or 10 log following vaccination relative to anti-antigenic polypeptide antibody titer in a subject vaccinated with a prophylactically effective dose of a traditional vaccine against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1).

A method of eliciting an immune response in a subject against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) is provided in other aspects of the disclosure. The method involves administering to the subject a respiratory virus RNA (e.g., mRNA) vaccine comprising at least one RNA (e.g., mRNA) polynucleotide having an open reading frame encoding at least one hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide or an immunogenic fragment thereof, thereby inducing in the subject an immune response specific to hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide or an immunogenic fragment thereof, wherein the immune response in the subject is equivalent to an immune response in a subject vaccinated with a traditional vaccine against the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) at 2 times to 100 times the dosage level relative to the RNA (e.g., mRNA) vaccine.

In some embodiments, the immune response in the subject is equivalent to an immune response in a subject vaccinated with a traditional vaccine at 2, 3, 4, 5, 10, 50, 100 times the dosage level relative to the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) RNA (e.g., mRNA) vaccine.

In some embodiments the immune response in the subject is equivalent to an immune response in a subject vaccinated with a traditional vaccine at 10-100 times, or 100-1000 times, the dosage level relative to the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) RNA (e.g., mRNA) vaccine.

In some embodiments the immune response is assessed by determining [protein] antibody titer in the subject.

Some aspects of the present disclosure provide a method of eliciting an immune response in a subject against a In some embodiments the immune response in the subject is equivalent to an immune response in a subject vaccinated with a traditional vaccine at 2, 3, 4, 5, 10, 50, 100 times the dosage level relative to the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) RNA (e.g., mRNA) vaccine by administering to the subject a respiratory virus RNA (e.g., mRNA) vaccine comprising at least one RNA (e.g., mRNA) polynucleotide having an open reading frame encoding at least one hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) antigenic polypeptide, thereby inducing in the subject an immune response specific to the antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1). In some embodiments, the immune response in the subject is induced in a subject vaccinated with a prophylactically effective dose of a traditional vaccine at 2 times to 100 times the dosage level relative to the RNA (e.g., mRNA) vaccine.

In some embodiments, the immune response in the subject is induced 2 days earlier, or 3 days earlier, relative to an immune response induced in a subject vaccinated with a prophylactically effective dose of a traditional vaccine.

In some embodiments the immune response in the subject is induced 1 week, 2 weeks, 3 weeks, 5 weeks, or 10 weeks earlier relative to an immune response induced in a subject vaccinated with a prophylactically effective dose of a traditional vaccine.

Also provided herein is a method of eliciting an immune response in a subject against hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) by administering to the subject a respiratory virus RNA (e.g., mRNA) vaccine having an open reading frame encoding a first antigenic polypeptide, wherein the RNA polynucleotide does not include a stabilization element, and wherein an adjuvant is not co-formulated or co-administered with the vaccine.

Therapeutic and Prophylactic Compositions

Provided herein are compositions (e.g., pharmaceutical compositions), methods, kits and reagents for prevention, treatment or diagnosis of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1) in humans and other mammals, for example. Respiratory virus RNA (e.g. mRNA) vaccines can be used as therapeutic or prophylactic agents. They may be used in medicine to prevent and/or treat infectious disease. In some embodiments, the respiratory RNA (e.g., mRNA) vaccines of the present disclosure are used fin the priming of immune effector cells, for example, to activate peripheral blood mononuclear cells (PBMCs) ex vivo, which are then infused (re-infused) into a subject.

In some embodiments, respiratory virus vaccine containing RNA (e.g., mRNA) polynucleotides as described herein can be administered to a subject (e.g., a mammalian subject, such as a human subject), and the RNA (e.g., mRNA) polynucleotides are translated in vivo to produce an antigenic polypeptide.

The respiratory virus RNA (e.g., mRNA) vaccines may be induced for translation of a polypeptide (e.g., antigen or immunogen) in a cell, tissue or organism. In some embodiments, such translation occurs in vivo, although such translation may occur ex vivo, in culture or in vitro. In some embodiments, the cell, tissue or organism is contacted with an effective amount of a composition containing a respiratory virus RNA (e.g., mRNA) vaccine that contains a polynucleotide that has at least one a translatable region encoding an antigenic polypeptide.

An “effective amount” of an respiratory virus RNA (e.g. mRNA) vaccine is provided based, at least in part, on the target tissue, target cell type, means of administration, physical characteristics of the polynucleotide (e.g., size, and extent of modified nucleosides) and other components of the vaccine, and other determinants. In general, an effective amount of the respiratory virus RNA (e.g., mRNA) vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA, e.g., mRNA, vaccine), increased protein translation from the polynucleotide, decreased nucleic acid degradation (as demonstrated, for example, by increased duration of protein translation from a modified polynucleotide), or altered antigen specific immune response of the host cell.

In some embodiments, RNA (e.g. mRNA) vaccines (including polynucleotides their encoded polypeptides) in accordance with the present disclosure may be used for treatment of hMPV, PIV3, RSV, MeV and/or BetaCoV (including MERS-CoV, SARS-CoV, HCoV-OC43, HCoV-229E, HCoV-NL63, HCoV-NL, HCoV-NH and/or HCoV-HKU1).

Respiratory RNA (e.g. mRNA) vaccines may be administered prophylactically or therapeutically as part of an active immunization scheme to healthy individuals or early in infection during the incubation phase or during active infection after onset of symptoms. In some embodiments, the amount of RNA (e.g., mRNA) vaccine of the present disclosure provided to a cell, a tissue or a subject may be an amount effective for immune prophylaxis.

Respiratory virus RNA (e.g. mRNA) vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term “booster” refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In some embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, respiratory virus RNA (e.g. mRNA) vaccines may be administered intramuscularly or intradermally, similarly to the administration of inactivated vaccines known in the art.

Respiratory virus RNA (e.g. mRNA) vaccines may be utilized in various settings depending on the prevalence of the infection or the degree or level of unmet medical need. As a non-limiting example, the RNA (e.g., mRNA) vaccines may be utilized to treat and/or prevent a variety of respiratory infections. RNA (e.g., mRNA) vaccines have superior properties in that they produce much larger antibody titers and produce responses early than commercially available anti-viral agents/compositions.

Provided herein are pharmaceutical compositions including respiratory virus RNA (e.g. mRNA) vaccines and RNA (e.g. mRNA) vaccine compositions and/or complexes optionally in combination with one or more pharmaceutically acceptable excipients.

Respiratory virus RNA (e.g. mRNA) vaccines may be formulated or administered alone or in conjunction with one or more other components. For instance, hMPV/PIV3/RSV RNA (e.g., mRNA) vaccines (vaccine compositions) may comprise other components including, but not limited to, adjuvants.

In some embodiments, respiratory virus (e.g. mRNA) vaccines do not include an adjuvant (they are adjuvant free).

Respiratory virus RNA (e.g. mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, respiratory virus RNA (e.g. mRNA) vaccines are administered to humans, human patients or subjects. For the purposes of the present disclosure, the phrase "active ingredient" generally refers to the RNA (e.g., mRNA) vaccines or the polynucleotides contained therein, for example, RNA polynucleotides (e.g., mRNA polynucleotides) encoding antigenic polypeptides.

Formulations of the respiratory virus vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Respiratory virus RNA (e.g. mRNA) vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with respiratory virus RNA (e.g. mRNA) vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA (e.g., mRNA) vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA (e.g., mRNA) vaccines include a coding region, at least one histone stem-loop, and optionally, a poly(A) sequence or polyadenylation signal.

The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine: guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA (e.g., mRNA) vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA (e.g., mRNA) vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, including (e.g., consisting of) a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA (e.g., mRNA) vaccine may have one or more AU-rich sequences removed. These sequences, sometimes referred to as AURES are destabilizing sequences found in the 3'UTR. The AURES may be removed from the RNA (e.g., mRNA) vaccines. Alternatively the AURES may remain in the RNA (e.g., mRNA) vaccine.

Nanoparticle Formulations

In some embodiments, respiratory virus RNA (e.g. mRNA) vaccines are formulated in a nanoparticle. In some embodiments, respiratory virus RNA (e.g. mRNA) vaccines are formulated in a lipid nanoparticle. In some embodiments, respiratory virus RNA (e.g. mRNA) vaccines are formulated in a lipid-polycation complex, referred to as a cationic lipid nanoparticle. As a non-limiting example, the polycation may include a cationic peptide or a polypeptide such as, but not limited to, polylysine, polyornithine and/or polyarginine. In some embodiments, respiratory virus RNA (e.g., mRNA) vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (*Nature Biotech.* 2010 28:172-176), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. *Mol Ther.* 2011 19:2186-2200).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol) 2000) carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, an respiratory virus RNA (e.g. mRNA) vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids.

The amino alcohol cationic lipid may be the lipids described in and/or made by the methods described in U.S. Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy) heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-CDMA, in a molar ratio of 20-60% cationic lipid: 5-25% neutral lipid: 25-55% sterol; 0.5-15% PEG-lipid.

In some embodiments, a lipid nanoparticle formulation includes 25% to 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), e.g., 35 to 65%, 45 to 65%, 60%, 57.5%, 50% or 40% on a molar basis. In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), PEG-CDMA (further discussed in Reyes et al. *J. Controlled Release,* 107, 276-287 (2005) the contents of which are herein incorporated by reference in their entirety).

In some embodiments, lipid nanoparticle formulations include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 7.5% of the neutral lipid, 31% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 10% of the neutral lipid, 38.5% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 15% of the neutral lipid, 40% of the sterol, and 5% of the PEG or PEG-modified lipid on a molar basis.

In some embodiments, lipid nanoparticle formulations include 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-CDMA (PEG-CDMA is further discussed in Reyes et al. (J. Controlled Release, 107, 276-287 (2005), the contents of which are herein incorporated by reference in their entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid: 5-45% neutral lipid: 20-55% cholesterol: 0.5-15% PEG-modified lipid. In some embodiments, lipid nanoparticle formulations consists essentially of a lipid mixture in a molar ratio of 20-60% cationic lipid: 5-25% neutral lipid: 25-55% cholesterol: 0.5-15% PEG-modified lipid.

In some embodiments, the molar lipid ratio is 50/10/38.5/1.5 (mol % cationic lipid/neutral lipid, e.g., DSPC/Chol/

PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51:8529-8533; and Maier et al. (2013) *Molecular Therapy* 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid L319, 10% of the non-cationic lipid DSPC, 2.5% of the PEG lipid PEG-DMG and 32.5% of the structural lipid cholesterol.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the respiratory virus RNA (e.g. mRNA) vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding H10N8 hMPV), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Liposomes, Lipoplexes, and Lipid Nanoparticles

The RNA (e.g., mRNA) vaccines of the disclosure can be formulated using one or more liposomes, lipoplexes, or lipid nanoparticles. In some embodiments, pharmaceutical compositions of RNA (e.g., mRNA) vaccines include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In some embodiments, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, WA), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, PA).

In some embodiments, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations may comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In some embodiments, formulations may comprise a percentage of cholesterol selected from the group consisting of 28.5%, 31.5%, 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In some embodiments, the RNA (e.g., mRNA) vaccine pharmaceutical compositions may be formulated in liposomes such as, but not limited to, DiLa2 liposomes (Marina Biotech, Bothell, WA), SMARTICLES® (Marina Biotech, Bothell, WA), neutral DOPC (1,2-dioleoyl-sn-glycero-3-phosphocholine) based liposomes (e.g., siRNA delivery for ovarian cancer (Landen et al. Cancer Biology & Therapy 2006 5 (12) 1708-1713); herein incorporated by reference in its entirety) and hyaluronan-coated liposomes (Quiet Therapeutics, Israel).

In some embodiments, the cationic lipid may be a low molecular weight cationic lipid such as those described in U.S. patent application No. 20130090372, the contents of which are herein incorporated by reference in their entirety.

In some embodiments, the RNA (e.g., mRNA) vaccines may be formulated in a lipid vesicle, which may have crosslinks between functionalized lipid bilayers.

In some embodiments, the RNA (e.g., mRNA) vaccines may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine. In some embodiments, the RNA (e.g., mRNA) vaccines may be formulated in a lipid-polycation complex, which may further include a non-cationic lipid such as, but not limited to, cholesterol or dioleoyl phosphatidylethanolamine (DOPE).

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol) 2000) carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, the RNA (e.g., mRNA) vaccines may be formulated in a lipid nanoparticle.

In some embodiments, the RNA (e.g., mRNA) vaccine formulation comprising the polynucleotide is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in U.S. Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy) heptadecanedioate (L319), and further comprise a neutral lipid, a sterol and a molecule capable of reducing particle aggregation, for example a PEG or PEG-modified lipid.

In some embodiments, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid.

In some embodiments, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), e.g., from about 35 to about 65%, from about 45 to about 65%, about 60%, about 57.5%, about 50% or about 40% on a molar basis.

In some embodiments, the formulation includes from about 0.5% to about 15% on a molar basis of the neutral lipid e.g., from about 3 to about 12%, from about 5 to about 10% or about 15%, about 10%, or about 7.5% on a molar basis. Examples of neutral lipids include, but are not limited to, DSPC, POPC, DPPC, DOPE and SM. In some embodiments, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In some embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In some embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Examples of PEG-modified lipids include, but are not limited to, PEG-distearoyl glycerol (PEG-DMG) (also referred herein as PEG-C14 or C14-PEG), PEG-CDMA (further discussed in Reyes et al. *J. Controlled Release,* 107, 276-287 (2005) the contents of which are herein incorporated by reference in their entirety)

In some embodiments, the formulations of the present disclosure include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 0.5-15% of the neutral lipid, 5-50% of the sterol, and 0.5-20% of the PEG or PEG-modified lipid on a molar basis.

In some embodiments, the formulations of the present disclosure include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 3-12% of the neutral lipid, 15-45% of the sterol, and 0.5-10% of the PEG or PEG-modified lipid on a molar basis.

In some embodiments, the formulations of the present disclosure include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), 5-10% of the neutral lipid, 25-40% of the sterol, and 0.5-10% of the PEG or PEG-modified lipid on a molar basis.

In some embodiments, the formulations of the present disclosure include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 7.5% of the neutral lipid, about 31% of the sterol, and about 1.5% of the PEG or PEG-modified lipid on a molar basis.

In some embodiments, the formulations of the present disclosure include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 10% of the neutral lipid, about 38.5% of the sterol, and about 1.5% of the PEG or PEG-modified lipid on a molar basis.

In some embodiments, the formulations of the present disclosure include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 10% of the neutral lipid, about 35% of the sterol, about 4.5% or about 5% of the PEG or PEG-modified lipid, and about 0.5% of the targeting lipid on a molar basis.

In some embodiments, the formulations of the present disclosure include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 15% of the neutral lipid, about 40% of the sterol, and about 5% of the PEG or PEG-modified lipid on a molar basis.

In some embodiments, the formulations of the present disclosure include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319), about 7.1% of the neutral lipid, about 34.3% of the sterol, and about 1.4% of the PEG or PEG-modified lipid on a molar basis.

In some embodiments, the formulations of the present disclosure include about 57.5% of a cationic lipid selected from the PEG lipid is PEG-CDMA (PEG-CDMA is further discussed in Reyes et al. (J. Controlled Release, 107, 276-287 (2005), the contents of which are herein incorporated by reference in their entirety), about 7.5% of the neutral lipid, about 31.5% of the sterol, and about 3.5% of the PEG or PEG-modified lipid on a molar basis.

In some embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid: 5-25% neutral lipid: 25-55% cholesterol: 0.5-15% PEG-modified lipid.

In some embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Examples of lipid nanoparticle compositions and methods of making same are described, for example, in Semple et al. (2010) *Nat. Biotechnol.* 28:172-176; Jayarama et al. (2012), *Angew. Chem. Int. Ed.,* 51:8529-8533; and Maier et al. (2013) *Molecular Therapy* 21, 1570-1578 (the contents of each of which are incorporated herein by reference in their entirety).

In some embodiments, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-1 O-amine, (15Z)—N,N-dimethyl eptacos-15-en-1 O-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-1 O-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcyclopropyl methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecyIcyclopropyl]tetradecan-5-amine, N,N-dimethyl-3-{7-[(1S,2R)-2-octylcyclopropyl] heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy) propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy) methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan- 2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy) propan-2-amine, (2S)-1-[(11Z,14Z)-icosa-11,14-dien-1-yloxy]-N,N-dimethyl-3-(pentyloxy) propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy) propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy) propan-2-amine, 1-[(9Z)-hexadec-9-en-1-yloxy]-N,N-dimethyl-3-(octyloxy) propan-2-amine, (2R)—N,N-dimethyl-H (1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy) propan-2-amine, N,N-dimethyl-1-{[8-(2-oclylcyclopropyl) octyl] oxy}-3-(octyloxy) propan-2-amine and (11E,20Z,23Z)—N,N-dimethylnonacosa-11,20,2-trien-10-amine or a pharmaceutically acceptable salt or stereoisomer thereof.

In some embodiments, the LNP formulations of the RNA (e.g., mRNA) vaccines may contain PEG-c-DOMG at 3% lipid molar ratio. In some embodiments, the LNP formulations of the RNA (e.g., mRNA) vaccines may contain PEG-c-DOMG at 1.5% lipid molar ratio.

In some embodiments, the pharmaceutical compositions of the RNA (e.g., mRNA) vaccines may include at least one of the PEGylated lipids described in International Publication No. WO2012099755, the contents of which are herein incorporated by reference in their entirety.

In some embodiments, the LNP formulation may contain PEG-DMG 2000 (1,2-dimyristoyl-sn-glycero-3-phophoethanolamine-N-[methoxy (polyethylene glycol)-2000). In some embodiments, the LNP formulation may contain PEG-DMG 2000, a cationic lipid known in the art and at least one other component. In some embodiments, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA (e.g., mRNA) vaccines, PNAS 2012; PMID: 22908294, the contents of each of which are herein incorporated by reference in their entirety).

The lipid nanoparticles described herein may be made in a sterile environment.

In some embodiments, the LNP formulation may be formulated in a nanoparticle such as a nucleic acid-lipid particle. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle.

The nanoparticle formulations may comprise a phosphate conjugate. The phosphate conjugate may increase in vivo circulation times and/or increase the targeted delivery of the nanoparticle. As a non-limiting example, the phosphate conjugates may include a compound of any one of the formulas described in International Application No. WO2013033438, the contents of which are herein incorporated by reference in its entirety.

The nanoparticle formulation may comprise a polymer conjugate. The polymer conjugate may be a water soluble conjugate. The polymer conjugate may have a structure as described in U.S. patent application No. 20130059360, the contents of which are herein incorporated by reference in its entirety. In some embodiments, polymer conjugates with the polynucleotides of the present disclosure may be made using the methods and/or segmented polymeric reagents described in U.S. patent application No. 20130072709, the contents of which are herein incorporated by reference in its entirety. In some embodiments, the polymer conjugate may have pendant side groups comprising ring moieties such as, but not limited to, the polymer conjugates described in U.S. Patent Publication No. US20130196948, the contents which are herein incorporated by reference in its entirety.

The nanoparticle formulations may comprise a conjugate to enhance the delivery of nanoparticles of the present disclosure in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al. (*Science* 2013 339, 971-975), herein incorporated by reference in its entirety). As shown by Rodriguez et al., the self peptides delayed macrophage-mediated clearance of nanoparticles which enhanced delivery of the nanoparticles. In another aspect, the conjugate may be the membrane protein CD47 (e.g., see Rodriguez et al. *Science* 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA (e.g., mRNA) vaccines of the present disclosure are formulated in nanoparticles which comprise a conjugate to enhance the delivery of the nanoparticles of the present disclosure in a subject. The conjugate may be the CD47 membrane or the conjugate may be derived from the CD47 membrane protein, such as the "self" peptide described previously. In some embodiments, the nanoparticle may comprise PEG and a conjugate of CD47 or a derivative thereof. In some embodiments, the nanoparticle may comprise both the "self" peptide described above and the membrane protein CD47.

In some embodiments, a "self" peptide and/or CD47 protein may be conjugated to a virus-like particle or pseudovirion, as described herein for delivery of the RNA (e.g., mRNA) vaccines of the present disclosure.

In some embodiments, RNA (e.g., mRNA) vaccine pharmaceutical compositions comprising the polynucleotides of the present disclosure and a conjugate that may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Patent Publication No. US20130184443, the contents of which are herein incorporated by reference in their entirety.

The nanoparticle formulations may be a carbohydrate nanoparticle comprising a carbohydrate carrier and a RNA (e.g., mRNA) vaccine. As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in their entirety).

Nanoparticle formulations of the present disclosure may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA (e.g., mRNA) vaccines within the central nervous system. As a non-limiting example nanoparticles comprising a hydrophilic coating and methods of making such nanoparticles are described in U.S. Patent Publication No. US20130183244, the contents of which are herein incorporated by reference in their entirety.

In some embodiments, the lipid nanoparticles of the present disclosure may be hydrophilic polymer particles. Non-limiting examples of hydrophilic polymer particles and methods of making hydrophilic polymer particles are described in U.S. Patent Publication No. US20130210991, the contents of which are herein incorporated by reference in their entirety.

In some embodiments, the lipid nanoparticles of the present disclosure may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbon.

In some embodiments, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosa tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104 (5): 1482-487; Lai et al. *Adv Drug Deliv Rev.* 2009 61 (2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Patent Publication No. WO2013110028, the contents of each of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in their entirety. The polymeric material may additionally be irradiated. As a non-limiting example, the polymeric material may be gamma irradiated (see e.g., International App. No.

WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho) esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer (such as a branched polyether-polyamide block copolymer described in International Publication No. WO2013012476, herein incorporated by reference in its entirety), and (poly(ethylene glycol))-(poly(propylene oxide))-(poly(ethylene glycol)) triblock copolymer (see e.g., U.S. Publication 20120121718 and U.S. Publication 20100003337 and U.S. Pat. No. 8,263,665, the contents of each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; the contents of which are herein incorporated by reference in their entirety). A non-limiting scalable method to produce nanoparticles which can penetrate human mucus is described by Xu et al. (see, e.g., J Control Release 2013, 170 (2): 279-86; the contents of which are herein incorporated by reference in their entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin B4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see e.g., U.S. Publication 20100215580 and U.S. Publication 20080166414 and US20130164343; the contents of each of which are herein incorporated by reference in their entirety).

In some embodiments, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion, which may increase the delivery of the mucus penetrating lipid nanoparticles to the mucosal tissue.

In some embodiments, the mucus penetrating lipid nanoparticles may be a hypotonic formulation comprising a mucosal penetration enhancing coating. The formulation may be hypotonice for the epithelium to which it is being delivered. Non-limiting examples of hypotonic formulations may be found in International Patent Publication No. WO2013110028, the contents of which are herein incorporated by reference in their entirety.

In some embodiments, in order to enhance the delivery through the mucosal barrier the RNA (e.g., mRNA) vaccine formulation may comprise or be a hypotonic solution. Hypotonic solutions were found to increase the rate at which mucoinert particles such as, but not limited to, mucus-penetrating particles, were able to reach the vaginal epithelial surface (see e.g., Ensign et al. Biomaterials 2013 34 (28): 6922-9, the contents of which are herein incorporated by reference in their entirety).

In some embodiments, the RNA (e.g., mRNA) vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132, the contents of each of which are incorporated herein by reference in their entirety).

In some embodiments, such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319:627-630; Peer and Lieberman, Gene Ther. 2011 18:1127-1133, the contents of each of which are incorporated herein by reference in their entirety). One example of passive targeting of formulations to liver cells includes the DLin-DMA, DLin-KC2-DMA and DLin-MC3-

DMA-based lipid nanoparticle formulations, which have been shown to bind to apolipoprotein E and promote binding and uptake of these formulations into hepatocytes in vivo (Akinc et al. Mol Ther. 2010 18:1357-1364, the contents of which are incorporated herein by reference in their entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133, the contents of each of which are incorporated herein by reference in their entirety).

In some embodiments, the RNA (e.g., mRNA) vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In some embodiments, the lipid nanoparticle may be a self-assembly lipid-polymer nanoparticle (see Zhang et al., ACS Nano, 2008, 2 (8), pp 1696-1702; the contents of which are herein incorporated by reference in their entirety). As a non-limiting example, the SLN may be the SLN described in International Patent Publication No. WO2013105101, the contents of which are herein incorporated by reference in their entirety. As another non-limiting example, the SLN may be made by the methods or processes described in International Patent Publication No. WO2013105101, the contents of which are herein incorporated by reference in their entirety.

Liposomes, lipoplexes, or lipid nanoparticles may be used to improve the efficacy of polynucleotides directed protein production as these formulations may be able to increase cell transfection by the RNA (e.g., mRNA) vaccine; and/or increase the translation of encoded protein. One such example involves the use of lipid encapsulation to enable the effective systemic delivery of polyplex plasmid DNA (Heyes et al., Mol Ther. 2007 15:713-720; the contents of which are incorporated herein by reference in their entirety). The liposomes, lipoplexes, or lipid nanoparticles may also be used to increase the stability of the polynucleotide.

In some embodiments, the RNA (e.g., mRNA) vaccines of the present disclosure can be formulated for controlled release and/or targeted delivery. As used herein, "controlled release" refers to a pharmaceutical composition or compound release profile that conforms to a particular pattern of release to effect a therapeutic outcome. In some embodiments, the RNA (e.g., mRNA) vaccines may be encapsulated into a delivery agent described herein and/or known in the art for controlled release and/or targeted delivery. As used herein, the term "encapsulate" means to enclose, surround or encase. As it relates to the formulation of the compounds of the disclosure, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the disclosure may be enclosed, surrounded or encased within the delivery agent. "Partially encapsulation" means that less than 10, 10, 20, 30, 40 50 or less of the pharmaceutical composition or compound of the disclosure may be enclosed, surrounded or encased within the delivery agent. Advantageously, encapsulation may be determined by measuring the escape or the activity of the pharmaceutical composition or compound of the disclosure using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the disclosure are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012131104 and WO2012131106, the contents of each of which are incorporated herein by reference in their entirety).

In some embodiments, the RNA (e.g., mRNA) vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc Deerfield, IL), PEG-based sealants, and COSEAL® (Baxter International, Inc Deerfield, IL).

In some embodiments, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the RNA (e.g., mRNA) vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA (e.g., mRNA) vaccine controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In some embodiments, the degradable polyesters may include a PEG conjugation to form a PEGylated polymer.

In some embodiments, the RNA (e.g., mRNA) vaccine controlled release and/or targeted delivery formulation comprising at least one polynucleotide may comprise at least one PEG and/or PEG related polymer derivatives as described in U.S. Pat. No. 8,404,222, the contents of which are incorporated herein by reference in their entirety.

In some embodiments, the RNA (e.g., mRNA) vaccine controlled release delivery formulation comprising at least one polynucleotide may be the controlled release polymer system described in US20130130348, the contents of which are incorporated herein by reference in their entirety.

In some embodiments, the RNA (e.g., mRNA) vaccines of the present disclosure may be encapsulated in a therapeutic nanoparticle, referred to herein as "therapeutic nanoparticle RNA (e.g., mRNA) vaccines." Therapeutic nanoparticles may be formulated by methods described herein and known in the art such as, but not limited to, International Pub Nos. WO2010005740, WO2010030763, WO2010005721, WO2010005723, WO2012054923, U.S. Publication Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211; the contents of each of which are herein incorporated by reference in their entirety. In some embodiments, therapeutic polymer nanoparticles may be identified by the methods described in US Pub No. US20120140790, the contents of which are herein incorporated by reference in their entirety.

In some embodiments, the therapeutic nanoparticle RNA (e.g., mRNA) vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present disclosure (see International Pub No. 2010075072 and US Pub No. US20100216804, US20110217377 and US20120201859, the contents of each of which are incorporated herein by reference in their entirety). In another non-limiting example, the sustained release formulation may comprise agents which permit persistent bioavailability such as, but not limited to, crystals, macromolecular gels and/or particulate suspensions (see U.S. Patent Publication No US20130150295, the contents of each of which are incorporated herein by reference in their entirety).

In some embodiments, the therapeutic nanoparticle RNA (e.g., mRNA) vaccines may be formulated to be target specific. As a non-limiting example, the therapeutic nanoparticles may include a corticosteroid (see International Pub. No. WO2011084518, the contents of which are incorporated herein by reference in their entirety). As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, the contents of each of which are incorporated herein by reference in their entirety.

In some embodiments, the nanoparticles of the present disclosure may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly (4-hydroxy-L-proline ester) or combinations thereof. In yet another embodiment, the diblock copolymer may be a high-X diblock copolymer such as those described in International Patent Publication No. WO2013120052, the contents of which are incorporated herein by reference in their entirety.

As a non-limiting example the therapeutic nanoparticle comprises a PLGA-PEG block copolymer (see U.S. Publication No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in their entirety). In yet another non-limiting example, the therapeutic nanoparticle is a stealth nanoparticle or a target-specific stealth nanoparticle as described in U.S. Patent Publication No. US20130172406, the contents of which are herein incorporated by reference in their entirety.

In some embodiments, the therapeutic nanoparticle may comprise a multiblock copolymer (see e.g., U.S. Pat. Nos. 8,263,665 and 8,287,910 and U.S. Patent Pub. No. US20130195987, the contents of each of which are herein incorporated by reference in their entirety).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20 (12): 1995-2000; as a controlled gene delivery system in Li et al. Controlled Gene Delivery System Based on Thermosensitive Biodegradable Hydrogel. Pharmaceutical Research 2003 20 (6): 884-888; and Chang et al., Non-ionic amphiphilic biodegradable PEG-PLGA-PEG copolymer enhances gene delivery efficiency in rat skeletal muscle. J Controlled Release. 2007 118:245-253, the contents of each of which are herein incorporated by reference in their entirety). The RNA (e.g., mRNA) vaccines of the present disclosure may be formulated in lipid nanoparticles comprising the PEG-PLGA-PEG block copolymer.

In some embodiments, the therapeutic nanoparticle may comprise a multiblock copolymer (see e.g., U.S. Pat. Nos. 8,263,665 and 8,287,910 and U.S. Patent Pub. No. US20130195987, the contents of each of which are herein incorporated by reference in their entirety).

In some embodiments, the block copolymers described herein may be included in a polyion complex comprising a non-polymeric micelle and the block copolymer. (see e.g., U.S. Publication No. 20120076836, the contents of which are herein incorporated by reference in their entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In some embodiments, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or U.S. Patent Publication No US20130121954, the contents of each of which are herein incorporated by reference in their entirety. In some embodiments, the poly(vinyl ester) polymers may be conjugated to the polynucleotides described herein.

In some embodiments, the therapeutic nanoparticle may comprise at least one diblock copolymer. The diblock copolymer may be, but it not limited to, a poly(lactic) acid-poly (ethylene) glycol copolymer (see, e.g., International Patent Publication No. WO2013044219, the contents of which are herein incorporated by reference in their entirety). As a non-limiting example, the therapeutic nanoparticle may be used to treat cancer (see International publication No. WO2013044219, the contents of which are herein incorporated by reference in their entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethylene imine, poly(amidoamine) dendrimers, poly(beta-amino esters) (see, e.g., U.S. Pat. No. 8,287,849, the contents of which are herein incorporated by reference in their entirety) and combinations thereof.

In some embodiments, the nanoparticles described herein may comprise an amine cationic lipid such as those described in International Patent Application No. WO2013059496, the contents of which are herein incorporated by reference in their entirety. In some embodiments, the cationic lipids may have an amino-amine or an amino-amide moiety.

In some embodiments, the therapeutic nanoparticles may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In some embodiments, the degradable polyesters may include a PEG conjugation to form a PEGylated polymer.

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent, which may enhance a Th1-based response of the immune system (see International Pub No. WO2010123569 and U.S. Publication No. US20110223201, the contents of each of which are herein incorporated by reference in their entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA (e.g., mRNA) vaccines after 24 hours and/or at a pH of 4.5 (see International Publication Nos. WO2010138193 and WO2010138194 and US Pub Nos. US20110020388 and US20110027217, each of which is herein incorporated by reference in their entireties).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In some embodiments, the RNA (e.g., mRNA) vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encode at least one antigen. As a non-limiting example, the synthetic nanocarrier may include at least one antigen and an excipient for a vaccine dosage form (see International Publication No. WO2011150264 and U.S. Publication No. US20110293723, the contents of each of which are herein incorporated by reference in their entirety). As another non-limiting example, a vaccine dosage form may include at least two synthetic nanocarriers with the same or different antigens and an excipient (see International Publication No. WO2011150249 and U.S. Publication No. US20110293701, the contents of each of which are herein incorporated by reference in their entirety). The vaccine dosage form may be selected by methods described herein, known in the art and/or described in International Publication No. WO2011150258 and U.S. Publication No. US20120027806, the contents of each of which are herein incorporated by reference in their entirety).

In some embodiments, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a mycobacterium (see, e.g., U.S. Pat. No. 8,241,610, the content of which is herein incorporated by reference in its entirety). In some embodiments, the synthetic nanocarrier may comprise at least one polynucleotide and an adjuvant. As a non-limiting example, the synthetic nanocarrier comprising and adjuvant may be formulated by the methods described in International Publication No. WO2011150240 and U.S. Publication No. US20110293700, the contents of each of which are herein incorporated by reference in their entirety.

In some embodiments, the synthetic nanocarrier may encapsulate at least one polynucleotide that encodes a peptide, fragment or region from a virus. As a non-limiting example, the synthetic nanocarrier may include, but is not limited to, any of the nanocarriers described in International Publication No. WO2012024621, WO201202629, WO2012024632 and U.S. Publication No. US20120064110, US20120058153 and US20120058154, the contents of each of which are herein incorporated by reference in their entirety.

In some embodiments, the synthetic nanocarrier may be coupled to a polynucleotide which may be able to trigger a humoral and/or cytotoxic T lymphocyte (CTL) response (see, e.g., International Publication No. WO2013019669, the contents of which are herein incorporated by reference in their entirety).

In some embodiments, the RNA (e.g., mRNA) vaccine may be encapsulated in, linked to and/or associated with zwitterionic lipids. Non-limiting examples of zwitterionic lipids and methods of using zwitterionic lipids are described in U.S. Patent Publication No. US20130216607, the contents of which are herein incorporated by reference in their entirety. In some aspects, the zwitterionic lipids may be used in the liposomes and lipid nanoparticles described herein.

In some embodiments, the RNA (e.g., mRNA) vaccine may be formulated in colloid nanocarriers as described in U.S. Patent Publication No. US20130197100, the contents of which are herein incorporated by reference in their entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Publication No. 20120282343, the contents of which are herein incorporated by reference in their entirety.

In some embodiments, LNPs comprise the lipid KL52 (an amino-lipid disclosed in U.S. Application Publication No. 2012/0295832, the contents of which are herein incorporated by reference in their entirety. Activity and/or safety (as measured by examining one or more of ALT/AST, white blood cell count and cytokine induction, for example) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA (e.g., mRNA) vaccine may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um, or less than 1000 um.

In some embodiments, RNA (e.g., mRNA) vaccines may be delivered using smaller LNPs, which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nm, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Examples of microfluidic mixers may include, but are not limited to, a slit interdigital micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1: e37; Chen, D. et al., Rapid discovery of potent siRNA-containing lipid nanoparticles enabled by controlled microfluidic formulation. J Am Chem Soc. 2012. 134 (16): 6948-51, the contents of each of which are herein incorporated by reference in their entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, the contents of each of which are herein incorporated by reference in their entirety.

In some embodiments, the RNA (e.g., mRNA) vaccine of the present disclosure may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In some embodiments, the RNA (e.g., mRNA) vaccines of the present disclosure may be formulated in lipid nanoparticles created using microfluidic technology (see, e.g., Whitesides, George M. The Origins and the Future of Microfluidics. Nature, 2006 442:368-373; and Abraham et al. Chaotic Mixer for Microchannels. Science, 2002 295:647-651; each of which is herein incorporated by reference in its entirety). As a non-limiting example, controlled microfluidic formulation includes a passive method for mixing streams of steady pressure-driven flows in micro channels at a low Reynolds number (see, e.g., Abraham et al. Chaotic Mixer for Microchannels. Science, 2002 295:647-651, the contents of which are herein incorporated by reference in their entirety).

In some embodiments, the RNA (e.g., mRNA) vaccines of the present disclosure may be formulated in lipid nanoparticles created using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the RNA (e.g., mRNA) vaccines of the disclosure may be formulated for delivery using the drug encapsulating microspheres described in International Patent Publication No. WO2013063468 or U.S. Pat. No. 8,440,614, the contents of each of which are herein incorporated by reference in their entirety. The microspheres may comprise a compound of the formula (I), (II), (III), (IV), (V) or (VI) as described in International Patent Publication No. WO2013063468, the contents of which are herein incorporated by reference in their entirety. In some embodiments, the amino acid, peptide, polypeptide, lipids (APPL) are useful in delivering the RNA (e.g., mRNA) vaccines of the disclosure to cells (see International Patent Publication No. WO2013063468, the contents of which are herein incorporated by reference in their entirety).

In some embodiments, the RNA (e.g., mRNA) vaccines of the disclosure may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm.

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the lipid nanoparticle may be a limit size lipid nanoparticle described in International Patent Publication No. WO2013059922, the contents of which are herein incorporated by reference in their entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In some embodiments, the limit size lipid nanoparticle may comprise a polyethylene glycol-lipid such as, but not limited to, DLPE-PEG, DMPE-PEG, DPPC-PEG and DSPE-PEG.

In some embodiments, the RNA (e.g., mRNA) vaccines may be delivered, localized and/or concentrated in a specific location using the delivery methods described in International Patent Publication No. WO2013063530, the contents of which are herein incorporated by reference in their entirety. As a non-limiting example, a subject may be administered an empty polymeric particle prior to, simultaneously with or after delivering the RNA (e.g., mRNA) vaccines to the subject. The empty polymeric particle undergoes a change in volume once in contact with the subject and becomes lodged, embedded, immobilized or entrapped at a specific location in the subject.

In some embodiments, the RNA (e.g., mRNA) vaccines may be formulated in an active substance release system (see, e.g., U.S. Patent Publication No. US20130102545, the contents of which are herein incorporated by reference in their entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA (e.g., mRNA) vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, the contents of which are herein incorporated by reference in their entirety. As another non-limiting example, the nanoparticle described in International Patent Publication No. WO2013052167, the contents of which are herein incorporated by reference in their entirety, may be used to deliver the RNA (e.g., mRNA) vaccines described herein.

In some embodiments, the RNA (e.g., mRNA) vaccines may be formulated in porous nanoparticle-supported lipid bilayers (protocells). Protocells are described in International Patent Publication No. WO2013056132, the contents of which are herein incorporated by reference in their entirety.

In some embodiments, the RNA (e.g., mRNA) vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the contents of which are herein incorporated by reference in their entirety. As another non-limiting example, the polymer nanoparticle for oral and parenteral formulations may be made by the methods described in European Patent No. EP2073848B1, the contents of which are herein incorporated by reference in their entirety.

In some embodiments, the RNA (e.g., mRNA) vaccines described herein may be formulated in nanoparticles used in imaging. The nanoparticles may be liposome nanoparticles such as those described in U.S. Patent Publication No US20130129636, herein incorporated by reference in its entirety. As a non-limiting example, the liposome may comprise gadolinium (III) 2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see, e.g., U.S. Patent Publication No US20130129636, the contents of which are herein incorporated by reference in their entirety).

In some embodiments, the nanoparticles which may be used in the present disclosure are formed by the methods described in U.S. Patent Application No. US20130130348, the contents of which are herein incorporated by reference in their entirety.

The nanoparticles of the present disclosure may further include nutrients such as, but not limited to, those which deficiencies can lead to health hazards from anemia to neural tube defects (see, e.g., the nanoparticles described in International Patent Publication No WO2013072929, the contents of which are herein incorporated by reference in their entirety). As a non-limiting example, the nutrient may be iron in the form of ferrous, ferric salts or elemental iron, iodine, folic acid, vitamins or micronutrients.

In some embodiments, the RNA (e.g., mRNA) vaccines of the present disclosure may be formulated in a swellable nanoparticle. The swellable nanoparticle may be, but is not limited to, those described in U.S. Pat. No. 8,440,231, the contents of which are herein incorporated by reference in their entirety. As a non-limiting embodiment, the swellable nanoparticle may be used for delivery of the RNA (e.g., mRNA) vaccines of the present disclosure to the pulmonary system (see, e.g., U.S. Pat. No. 8,440,231, the contents of which are herein incorporated by reference in their entirety).

The RNA (e.g., mRNA) vaccines of the present disclosure may be formulated in polyanhydride nanoparticles such as, but not limited to, those described in U.S. Pat. No. 8,449,916, the contents of which are herein incorporated by reference in their entirety.

The nanoparticles and microparticles of the present disclosure may be geometrically engineered to modulate macrophage and/or the immune response. In some embodiments, the geometrically engineered particles may have varied shapes, sizes and/or surface charges in order to incorporated the polynucleotides of the present disclosure for targeted delivery such as, but not limited to, pulmonary delivery (see, e.g., International Publication No WO2013082111, the contents of which are herein incorporated by reference in their entirety). Other physical features the geometrically engineering particles may have include, but are not limited to, fenestrations, angled arms, asymmetry and surface roughness, charge which can alter the interactions with cells and tissues. As a non-limiting example, nanoparticles of the present disclosure may be made by the methods described in International Publication No WO2013082111, the contents of which are herein incorporated by reference in their entirety.

In some embodiments, the nanoparticles of the present disclosure may be water soluble nanoparticles such as, but not limited to, those described in International Publication No. WO2013090601, the contents of which are herein incorporated by reference in their entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments the nanoparticles of the present disclosure may be developed by the methods described in U.S. Patent Publication No. US20130172406, the contents of which are herein incorporated by reference in their entirety.

In some embodiments, the nanoparticles of the present disclosure are stealth nanoparticles or target-specific stealth nanoparticles such as, but not limited to, those described in U.S. Patent Publication No. US20130172406, the contents of which are herein incorporated by reference in their entirety. The nanoparticles of the present disclosure may be made by the methods described in U.S. Patent Publication No. US20130172406, the contents of which are herein incorporated by reference in their entirety.

In some embodiments, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in U.S. Patent Publication No. US20130171646, the contents of which are herein incorporated by reference in their entirety. The nanoparticle may comprise a nucleic acid such as, but not limited to, polynucleotides described herein and/or known in the art.

At least one of the nanoparticles of the present disclosure may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in their entirety.

In some embodiments the RNA (e.g., mRNA) vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, $VP^{22}$ derived or analog peptides, Pestivirus Erns, HSV, $VP^{22}$ (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from Drosophila antennapedia), pAntp, pIsl, FGF, Lactoferrin, Transportan, Buforin-2, Bac715-24, SynB, SynB (1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy) propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanolamine, DOSPA, DODAB, DOIC, DMEPC, DOGS: Dioctadecylamidoglicylspermin, DIMRI: Dimyristooxypropyl dimethyl hydroxyethyl ammonium bromide, DOTAP: dioleoyloxy-3-(trimethylammonio) propane, DC-6-14: O,O-ditetradecanoyl-N-.alpha.-trimethylammonioacetyl) diethanolamine chloride, CLIP1: rac-[(2,3-dioctadecyloxypropyl) (2-hydroxyethyl)]-dimethylammonium chloride, CLIP6: rac-[2 (2,3-dihexadecyloxypropyloxymethyloxy)ethyl]-trimethylammonium, CLIP9: rac-[2 (2,3-dihexadecyloxypropyloxysuccinyloxy)ethyl]-trimethylammonium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly (ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole), etc.

In other embodiments the RNA (e.g., mRNA) vaccine is not associated with a cationic or polycationic compounds.

In some embodiments, a nanoparticle comprises compounds of Formula (I):

(I)

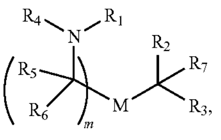

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ(R)$_2$, and unsubstituted $C_{1-6}$ alkyl, where Q is selected from a carbocycle, heterocycle, —OR, —O$(CH_2)_n$N(R)$_2$, —C(O)OR, —OC(O)R, —$CX_3$, —$CX_2$H, —$CXH_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)$R_8$, —O$(CH_2)_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)O R, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N(R)$_2$, —C(O)OR, —OC(O)R, —$CX_3$, —$CX_2$H, —$CXH_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)$R_8$, —O$(CH_2)_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)O R, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHOR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is $—(CH_2)_nQ$ or $—(CH_2)_nCHQR$, where Q is $—N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of $—(CH_2)_nQ$, $—(CH_2)_nCHQR$, —CHQR, and $—CQ(R)_2$, where Q is $—N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

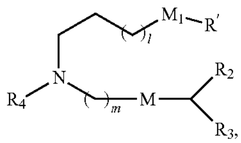

or a salt or isomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or $—(CH_2)_nQ$, in which Q is OH, $—NHC(S)N(R)_2$, $—NHC(O)N(R)_2$, —N(R)C(O)R, $—N(R)S(O)_2R$, $—N(R)R_8$, $—NHC(═NR_9)N(R)_2$, $—NHC(═CHR_9)N(R)_2$, $—OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

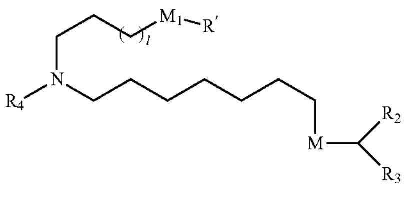

or a salt or isomer thereof, wherein 1 is selected from 1, 2, 3, 4, and 5; $M_1$ is a bond or M'; $R_4$ is unsubstituted $C_{1-3}$ alkyl, or $—(CH_2)_nQ$, in which n is 2, 3, or 4, and Q is OH, $—NHC(S)N(R)_2$, $—NHC(O)N(R)_2$, —N(R)C(O)R, $—N(R)S(O)_2R$, $—N(R)R_8$, $—NHC(═NR_9)N(R)_2$, $—NHC(═CHR_9)N(R)_2$, $—OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

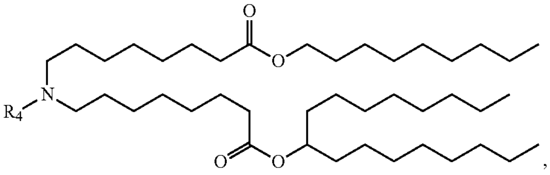

, (IIb)

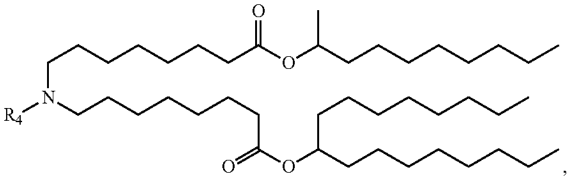

, (IIc)

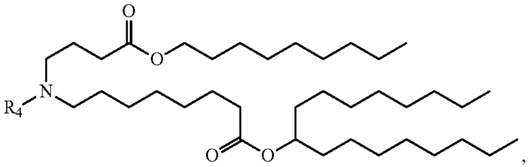

, or (IIe)

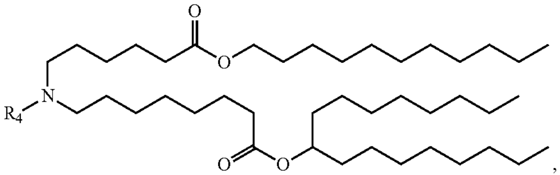

, or a salt or isomer thereof, wherein $R_4$ is as described herein.

In some embodiments, a subset of compounds of Formula (I) includes those of Formula (IId):

(IId)

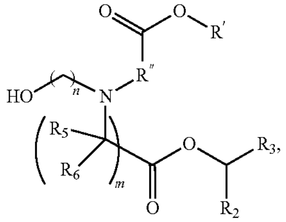

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, a subset of compounds of Formula (I) includes those of Formula (IIa), (IIb), (IIc), or (IIe):

(IIa)

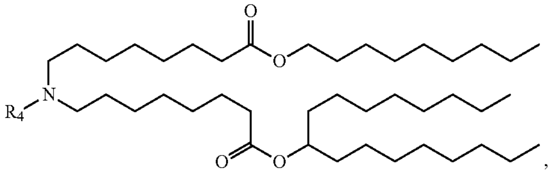

, (IIb)

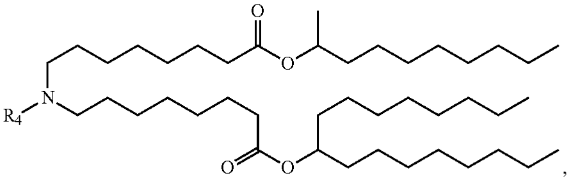

, (IIc)

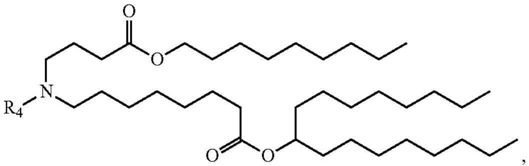

, or (IIe)

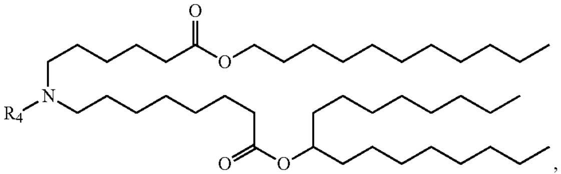

, or a salt or isomer thereof, wherein $R_4$ is as described herein.

In some embodiments, a subset of compounds of Formula (I) includes those of Formula (IId):

(IId)

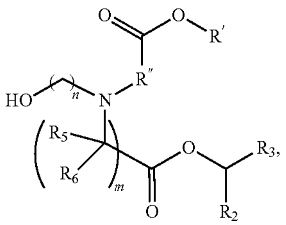

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)
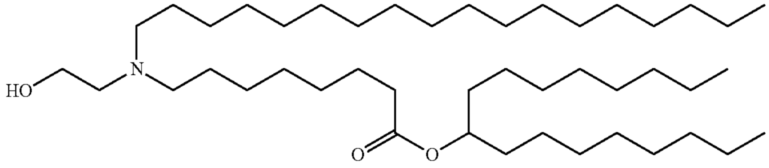,
(Compound 2)
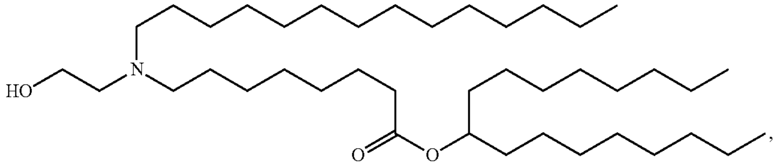,
(Compound 3)
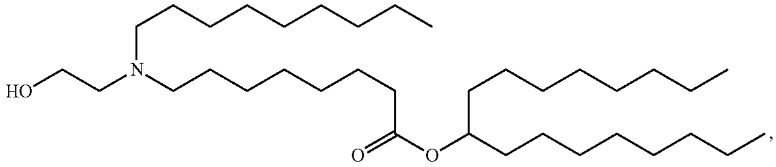,
(Compound 4)
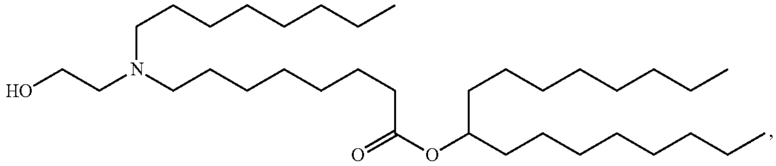,
(Compound 5)
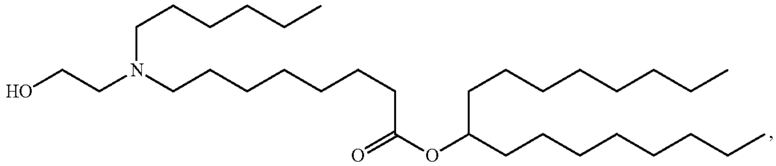,
(Compound 6)
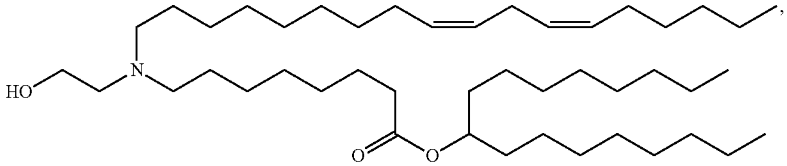,
(Compound 7)
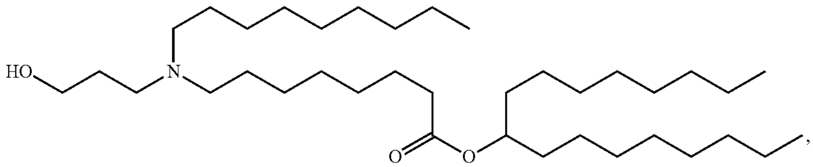,
(Compound 8)
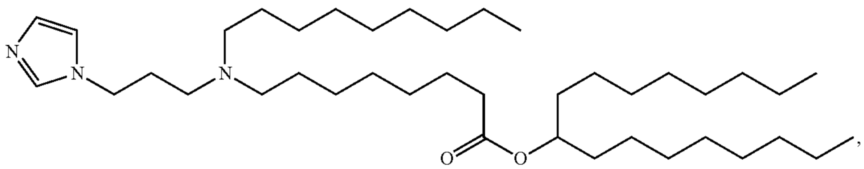, -continued
(Compound 9)
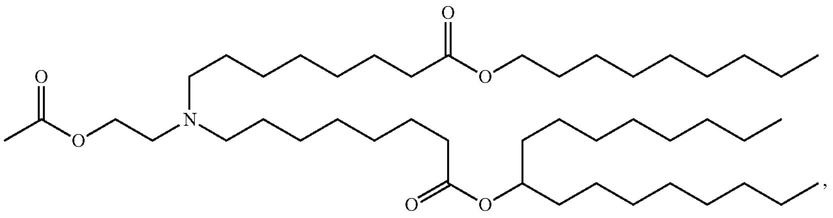
(Compound 10)
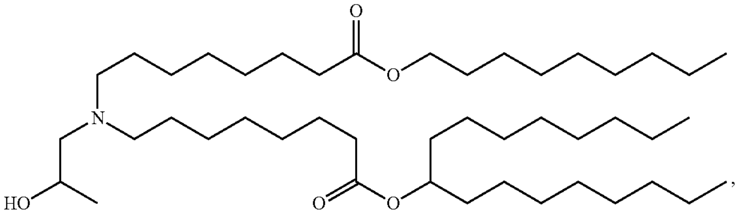
(Compound 11)
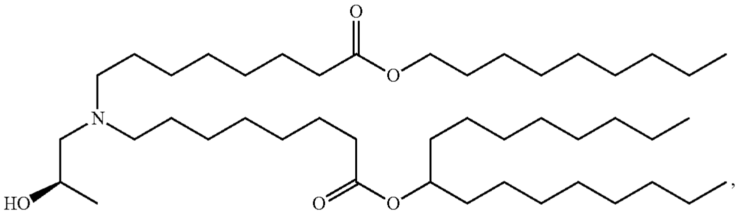
(Compound 12)
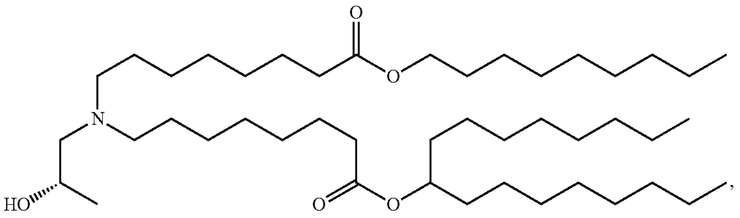
(Compound 13)
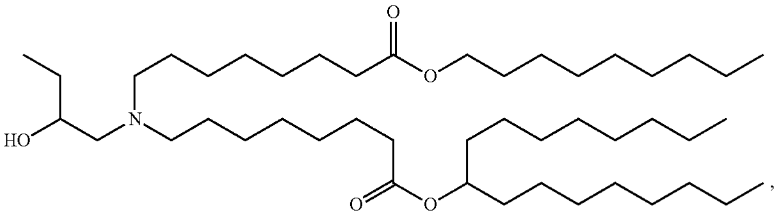
(Compound 14)
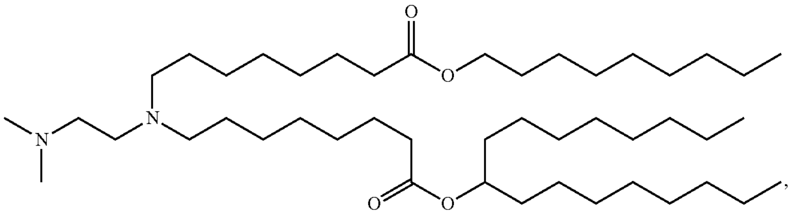
(Compound 15)
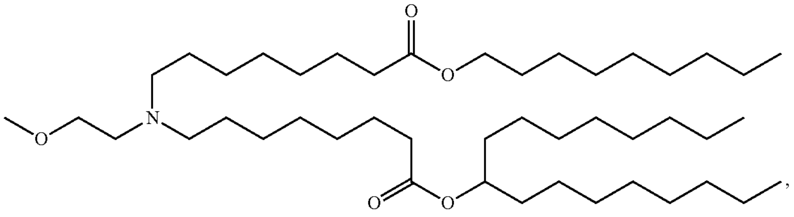

-continued
(Compound 16)
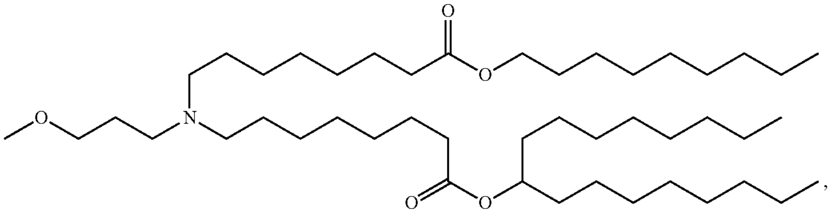
(Compound 17)
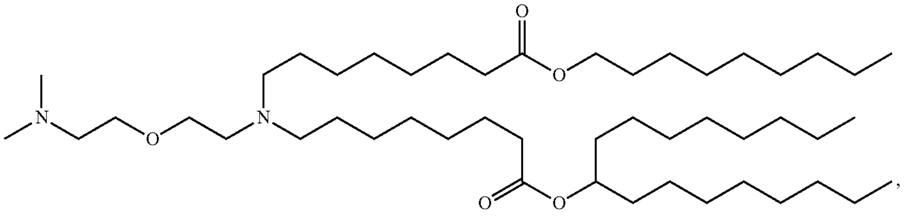
(Compound 18)
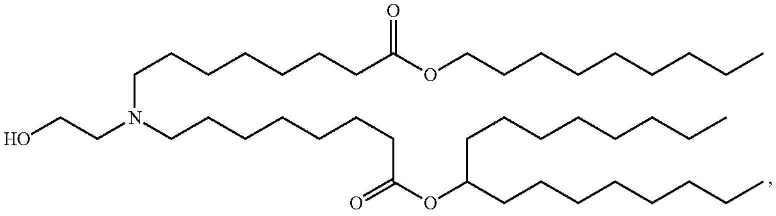
(Compound 19)
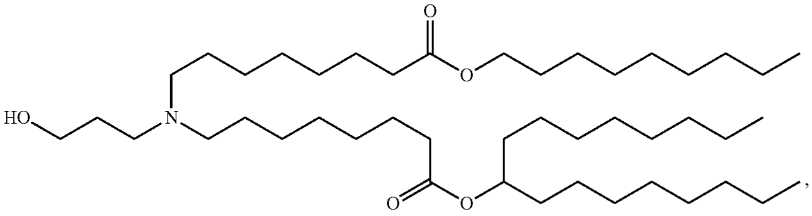
(Compound 20)
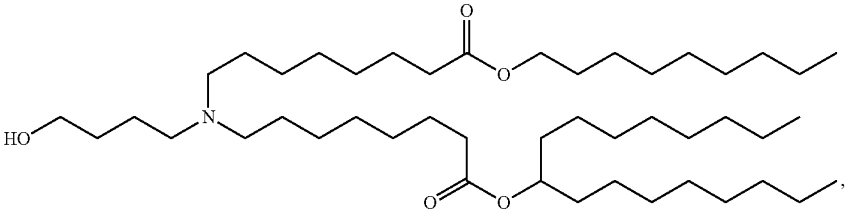
(Compound 21)
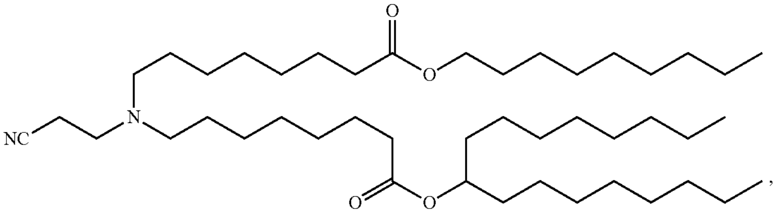
(Compound 22)
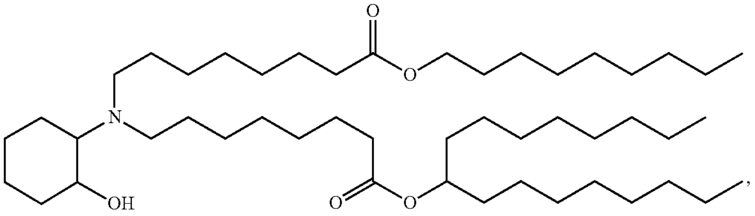

-continued
(Compound 23)
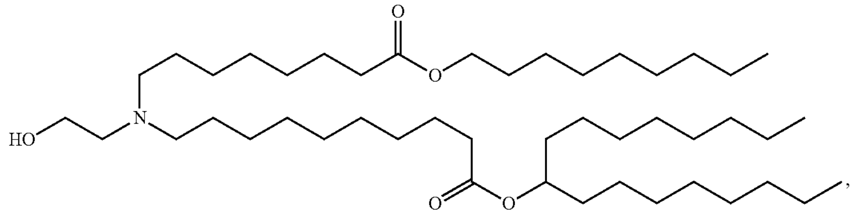
(Compound 24)
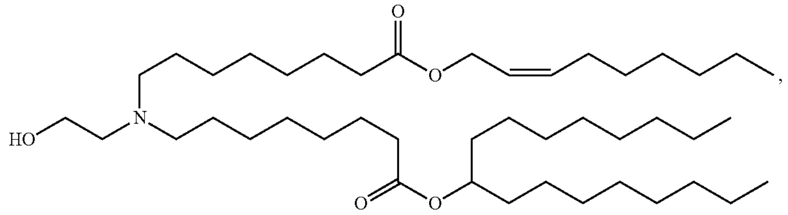
(Compound 25)
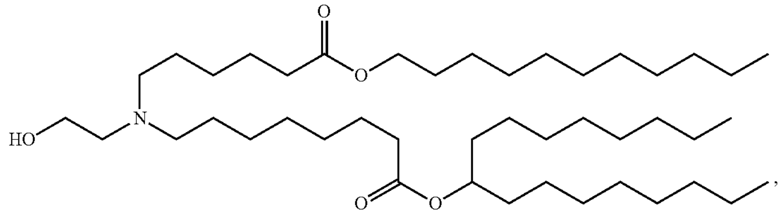
(Compound 26)
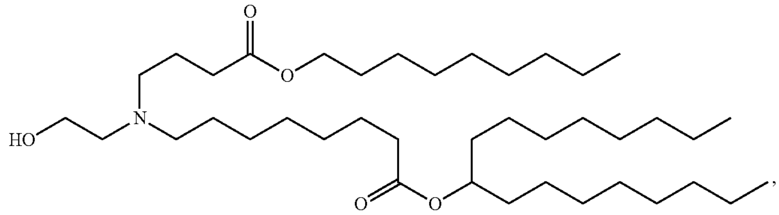
(Compound 27)
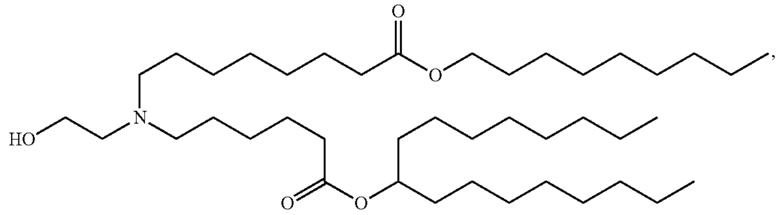
(Compound 28)
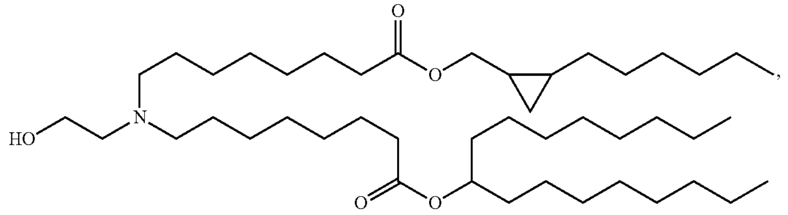
(Compound 29)
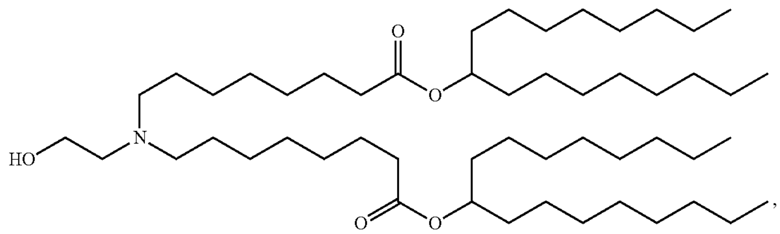

-continued
(Compound 30)
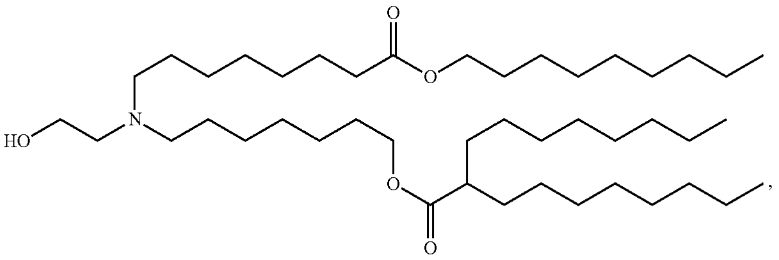
(Compound 31)
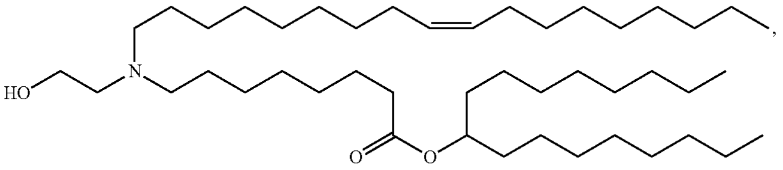
(Compound 32)
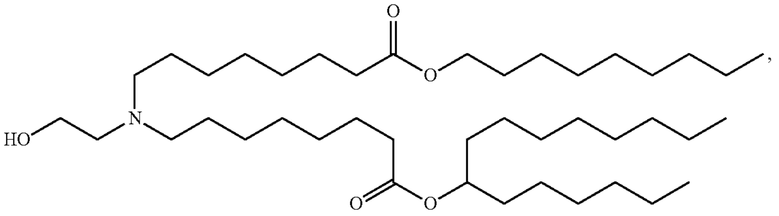
(Compound 33)
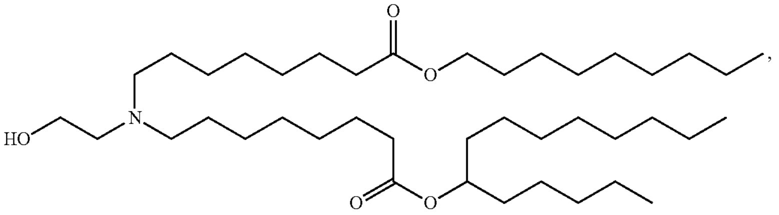
(Compound 34)
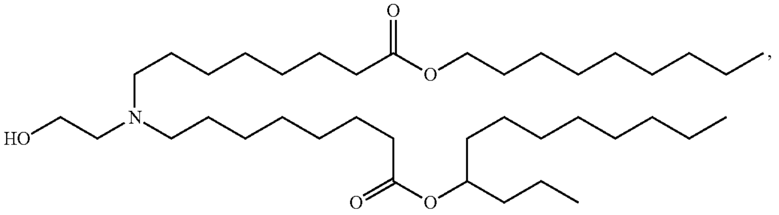
(Compound 35)
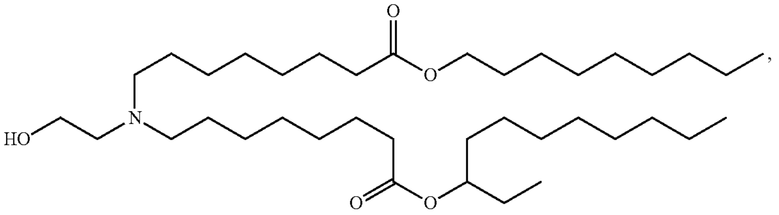
(Compound 36)
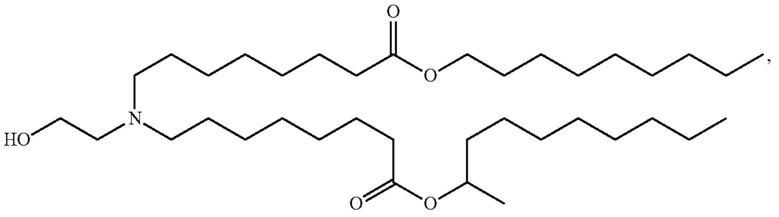

-continued
(Compound 37)
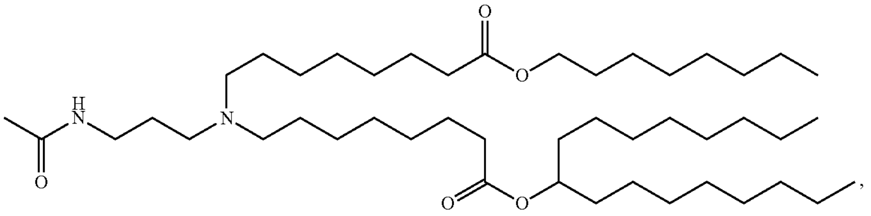
(Compound 38)
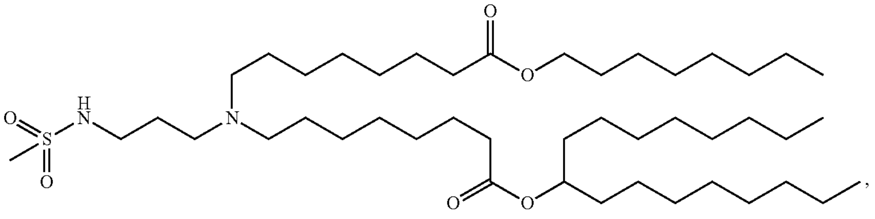
(Compound 39)
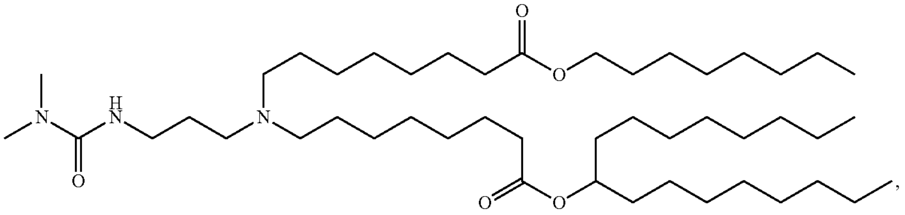
(Compound 40)
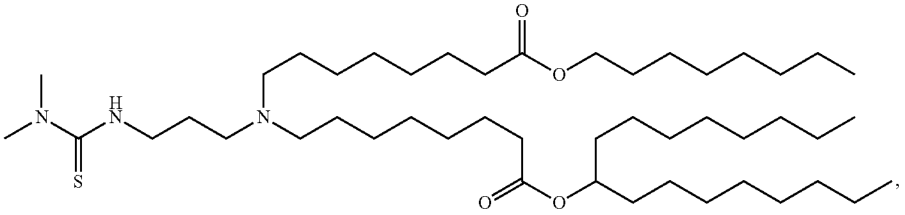
(Compound 41)
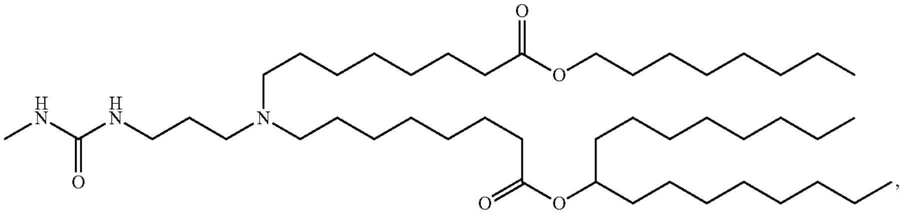
(Compound 42)
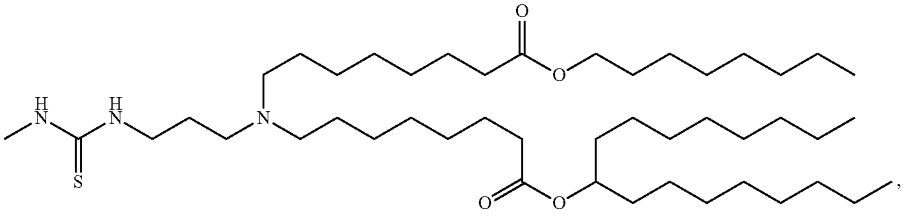
(Compound 43)
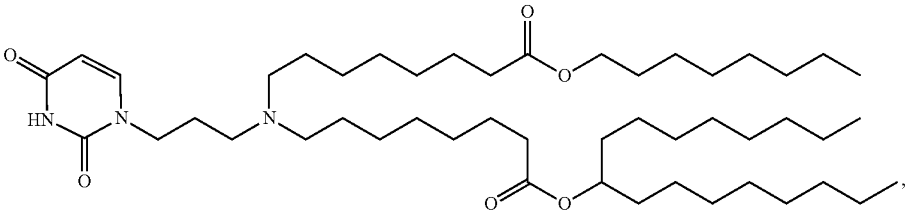

-continued
(Compound 44)
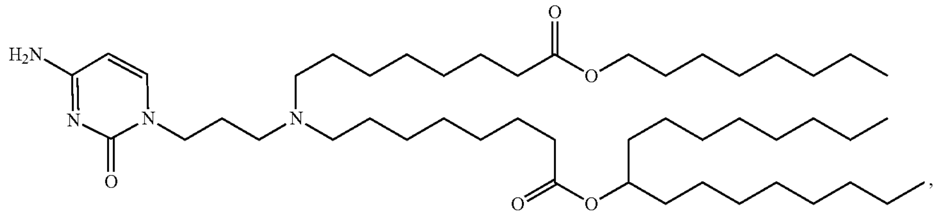
(Compound 45)
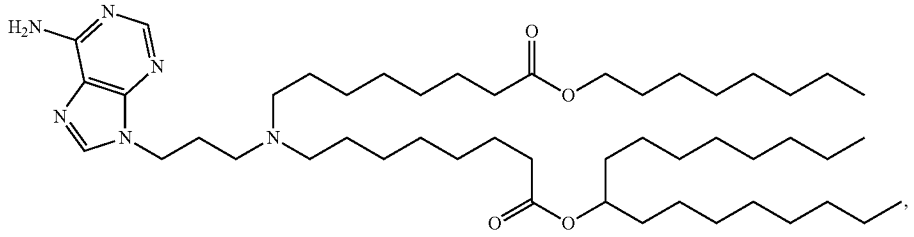
(Compound 46)
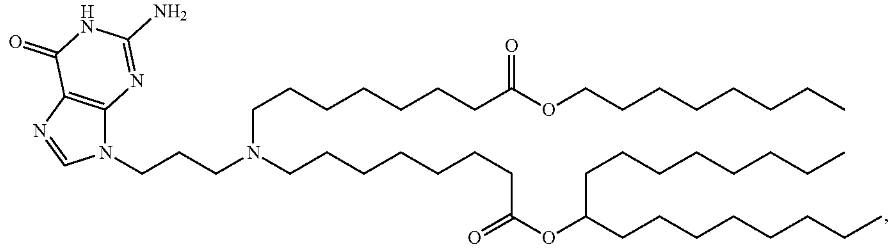
(Compound 47)
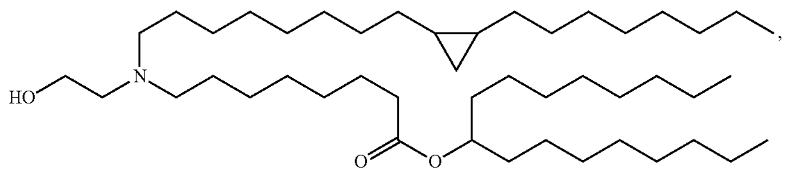
(Compound 48)
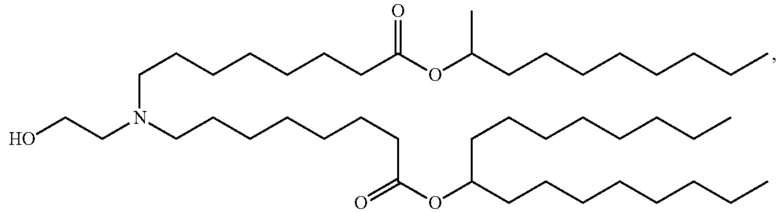
(Compound 49)
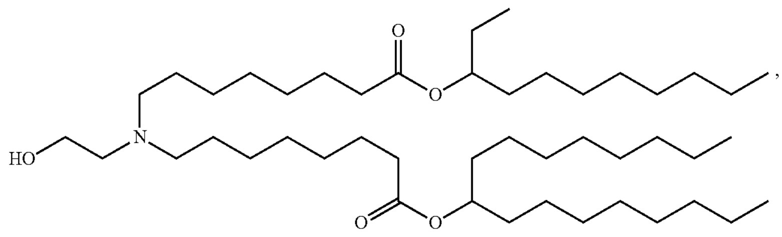

-continued
(Compound 50)
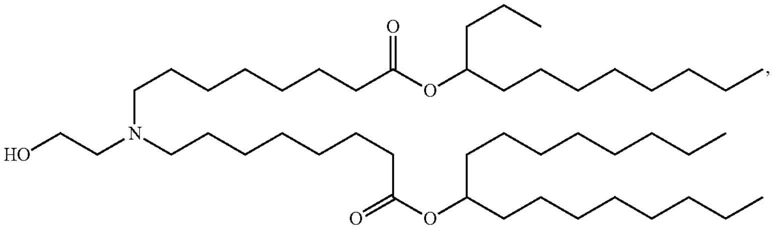,
(Compound 51)
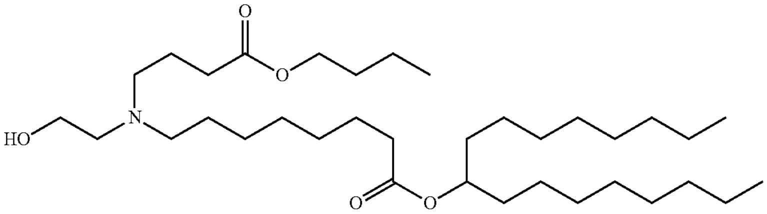,
(Compound 52)
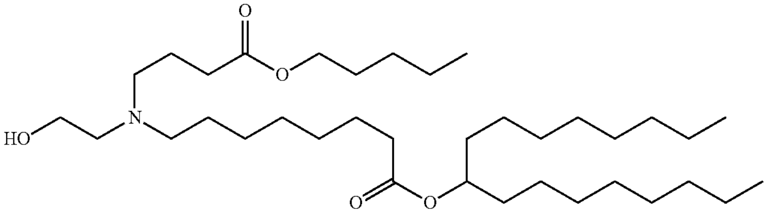,
(Compound 53)
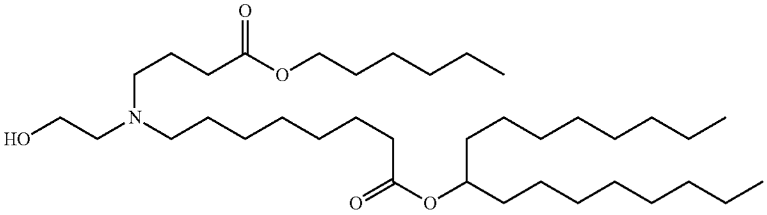,
(Compound 54)
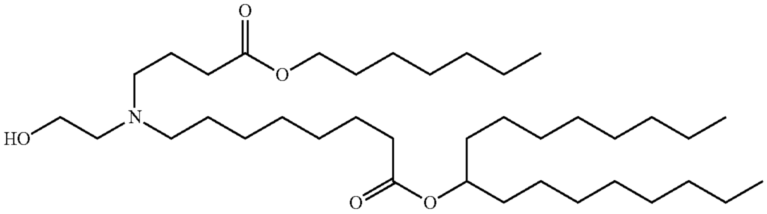,
(Compound 55)
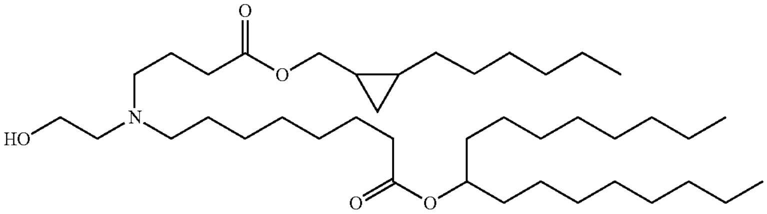, -continued
(Compound 56)
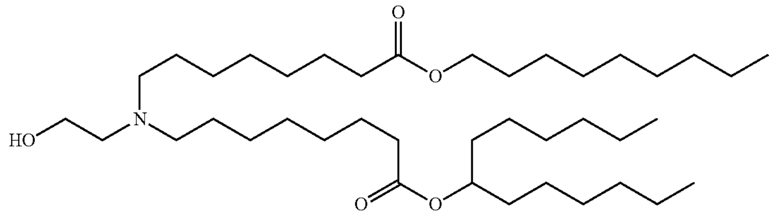
,
(Compound 57)
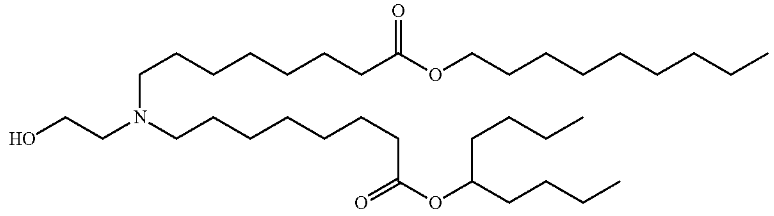
,
(Compound 58)
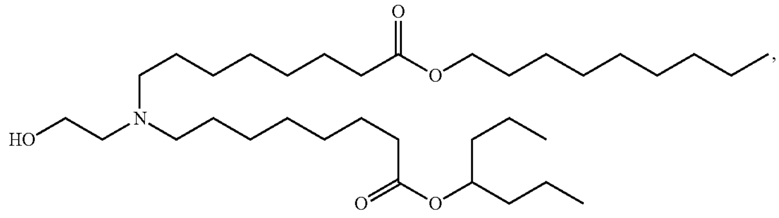
,
(Compound 59)
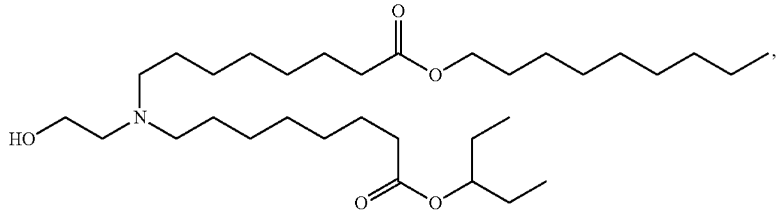
,
(Compound 60)
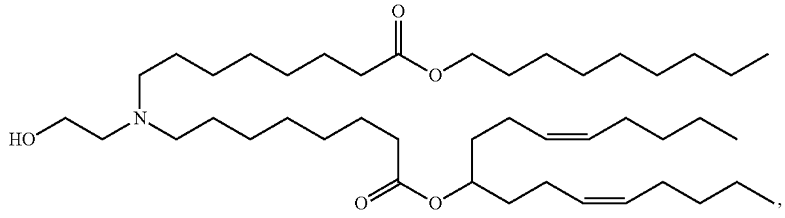
, and
(Compound 61)
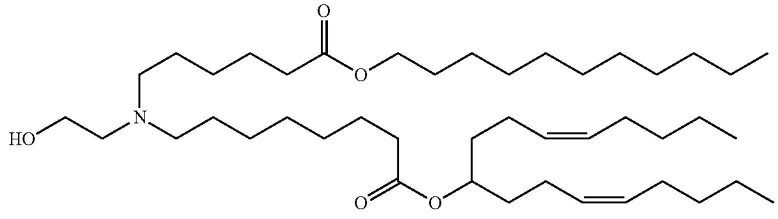
.

In further embodiments, the compound of Formula (I) is selected from the group consisting of:
(Compound 62)
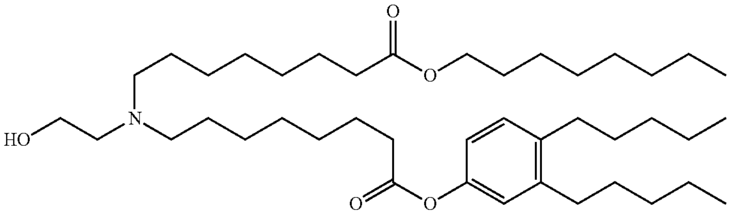
,
(Compound 63)
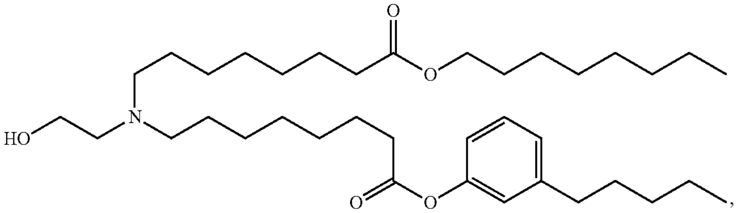
, and
(Compound 64)
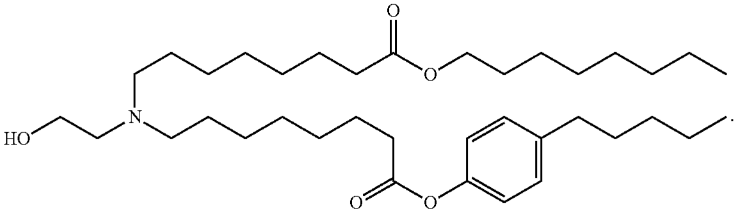
.
In some embodiments, the compound of Formula (I) is selected from the group consisting of:
(Compound 65)
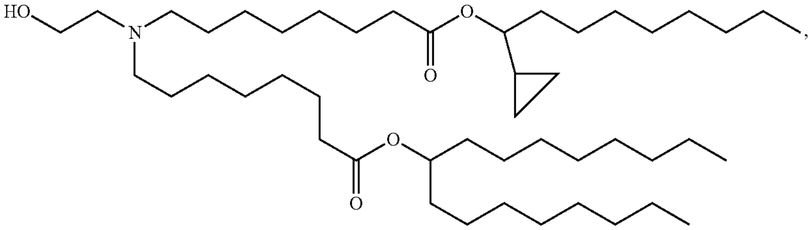
,
(Compound 66)
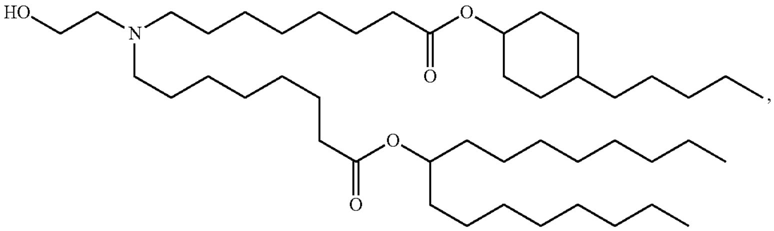
,
(Compound 67)
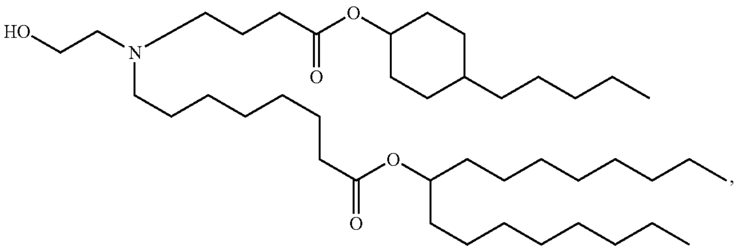
, -continued
(Compound 68)
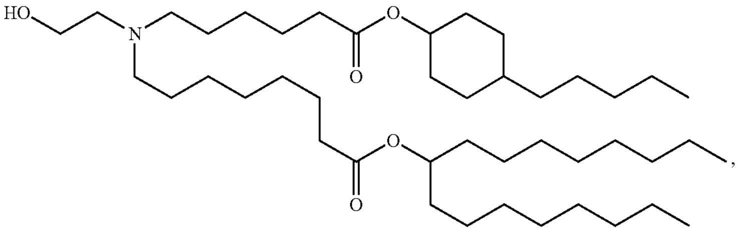
(Compound 69)
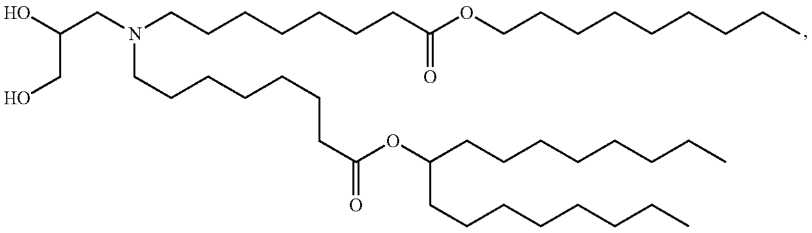
(Compound 70)
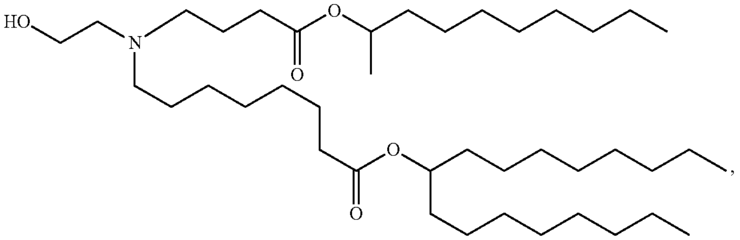
(Compound 71)
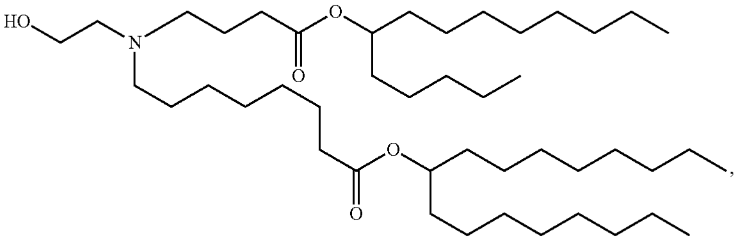
(Compound 72)
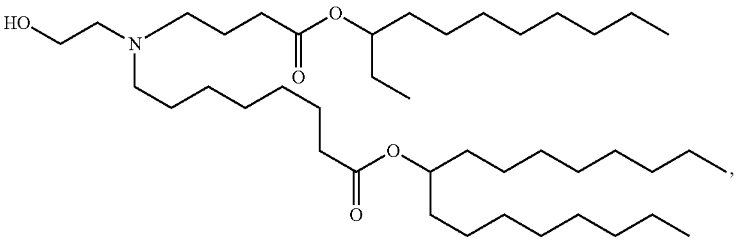
(Compound 73)
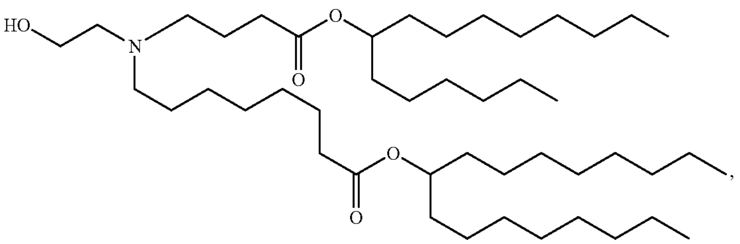

-continued
(Compound 74)
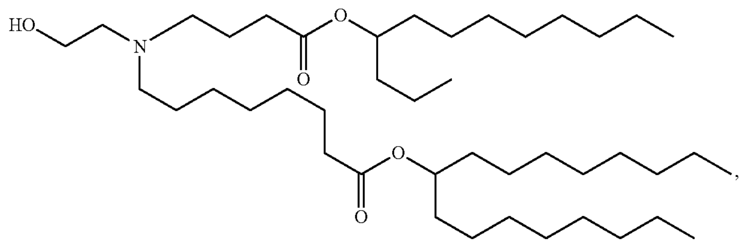
(Compound 75)
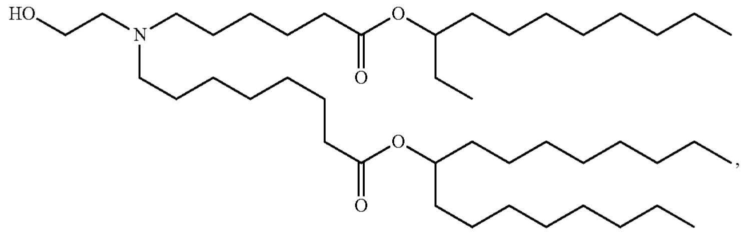
(Compound 76)
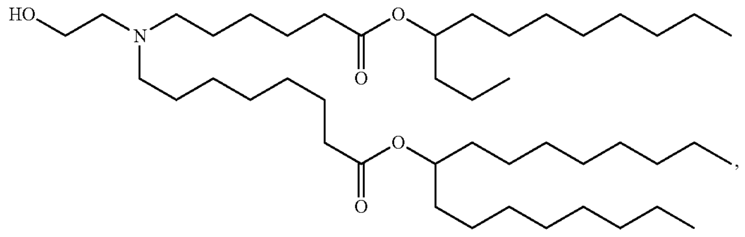
(Compound 77)
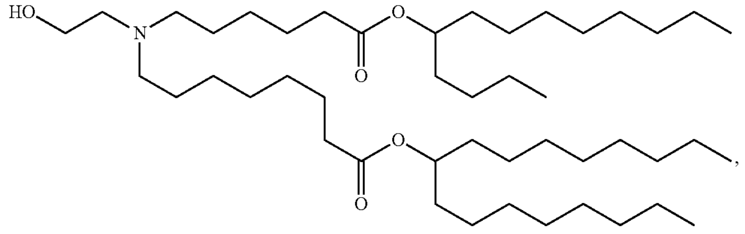
(Compound 78)
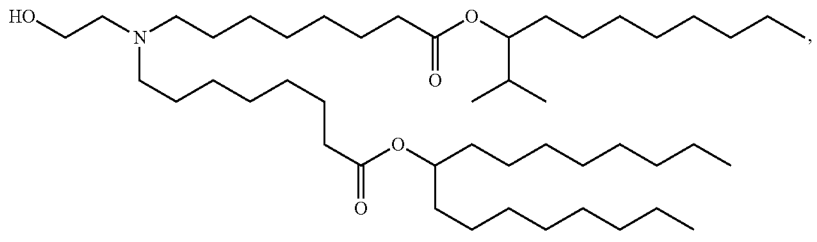
(Compound 79)
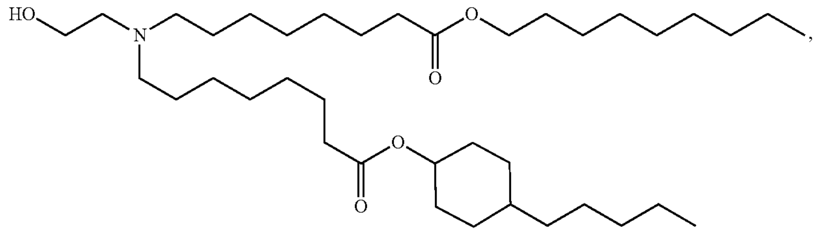

-continued
(Compound 80)
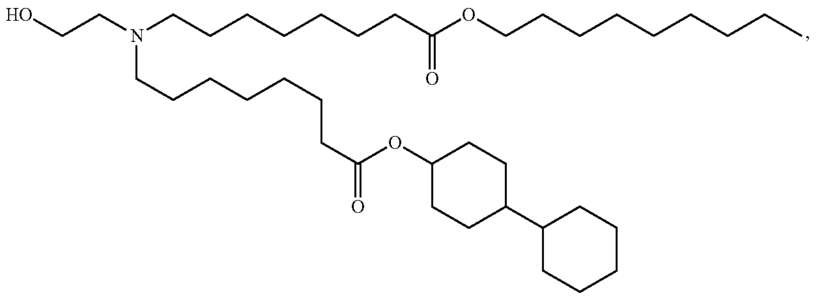
(Compound 81)
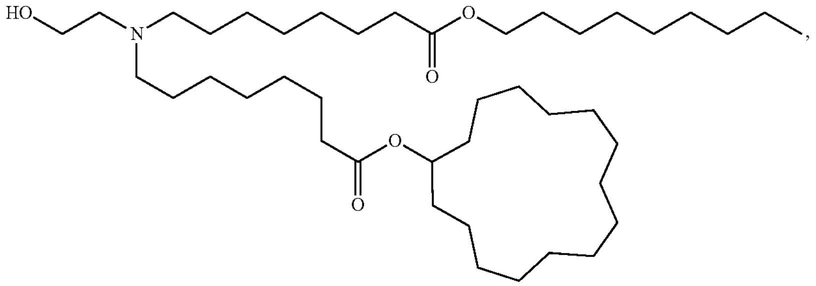
(Compound 82)
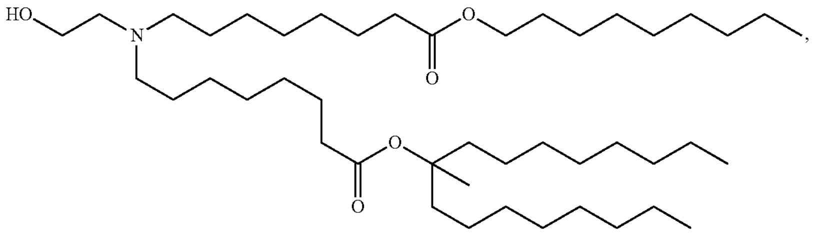
(Compound 83)
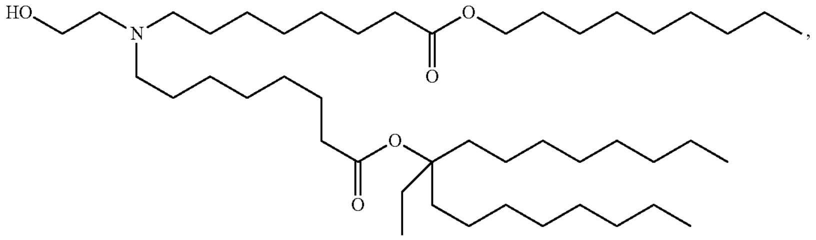
(Compound 84)
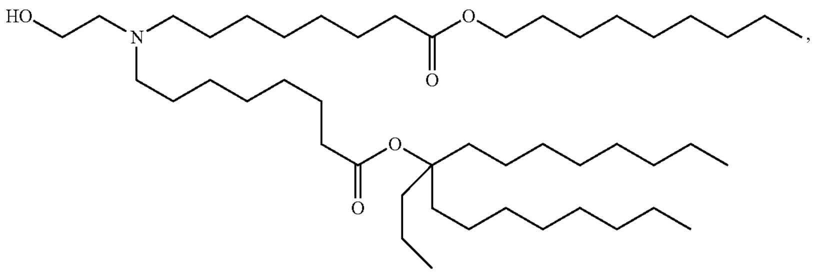
(Compound 85)
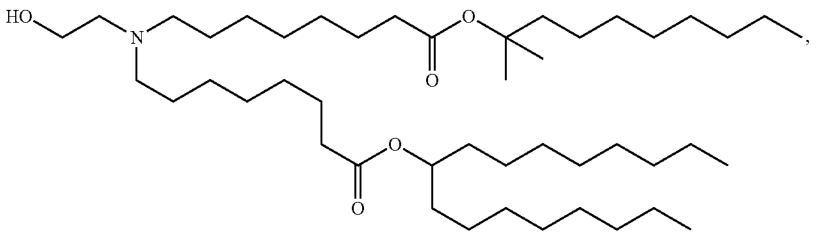

-continued
(Compound 86)
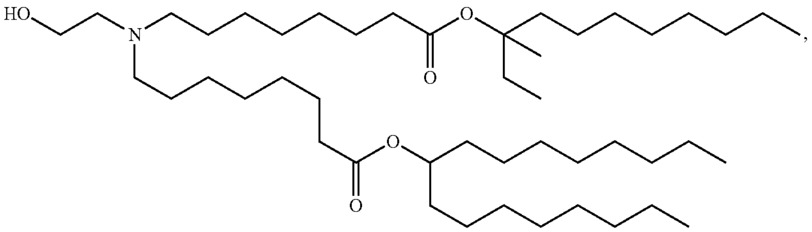
(Compound 87)
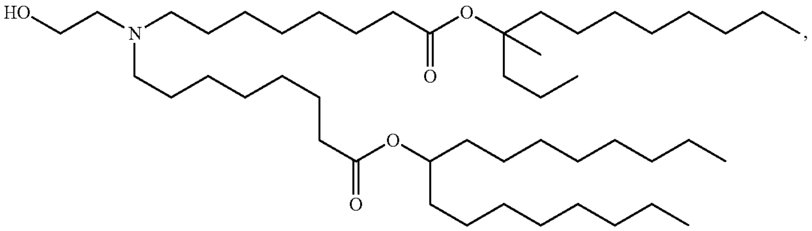
(Compound 88)
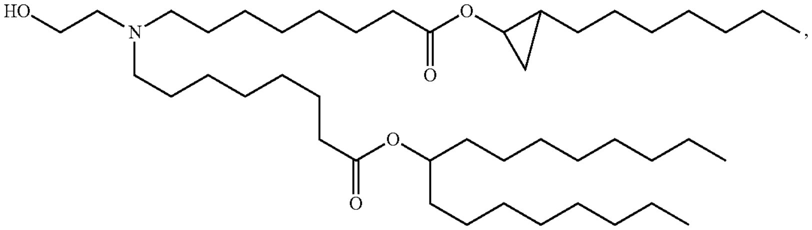
(Compound 89)
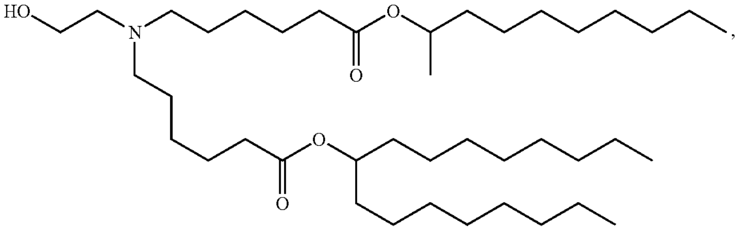
(Compound 90)
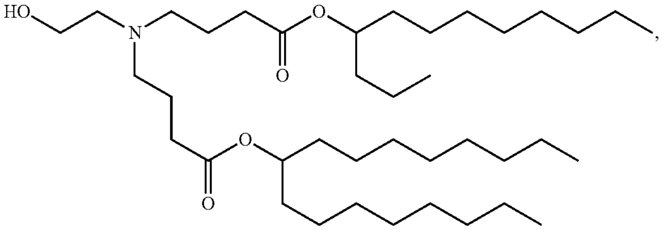
(Compound 91)
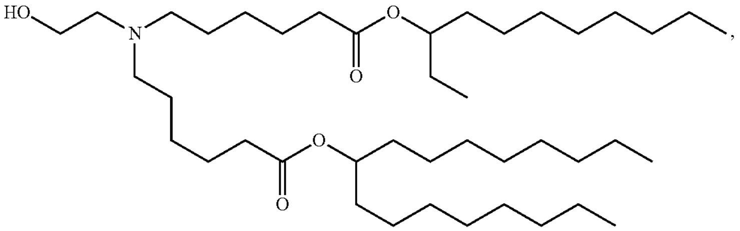

-continued
(Compound 92)
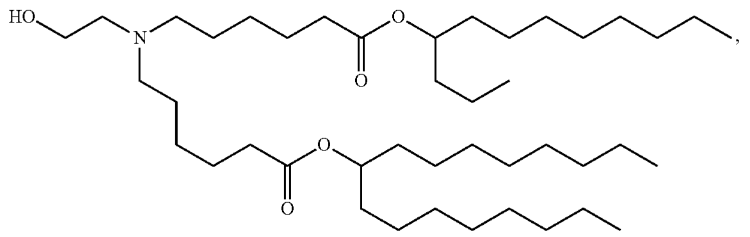
(Compound 93)
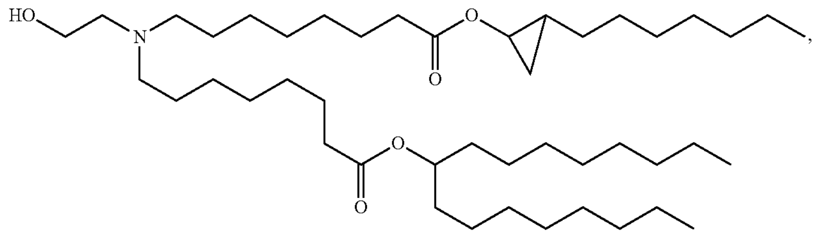
(Compound 94)
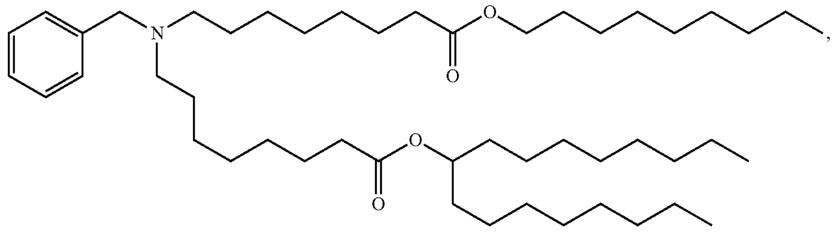
(Compound 95)
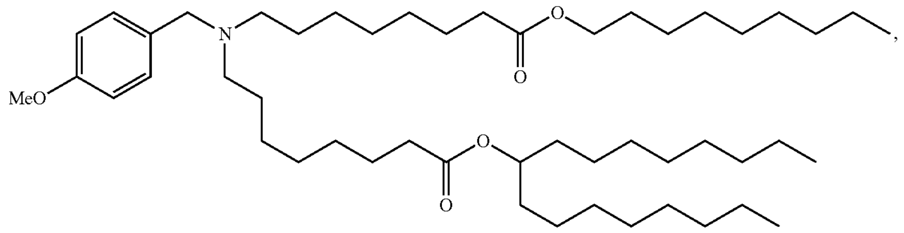
(Compound 96)
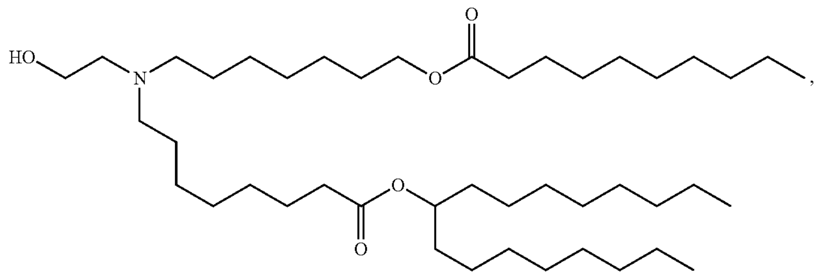
(Compound 97)
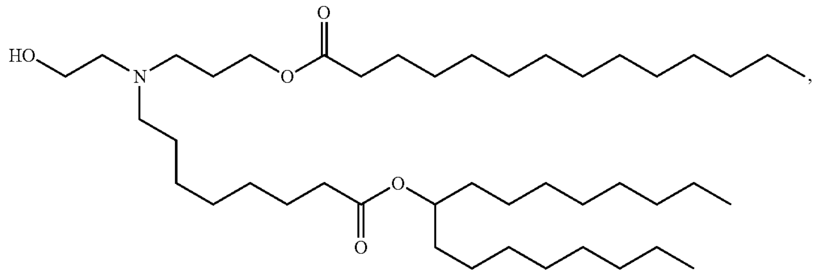

-continued
(Compound 98)
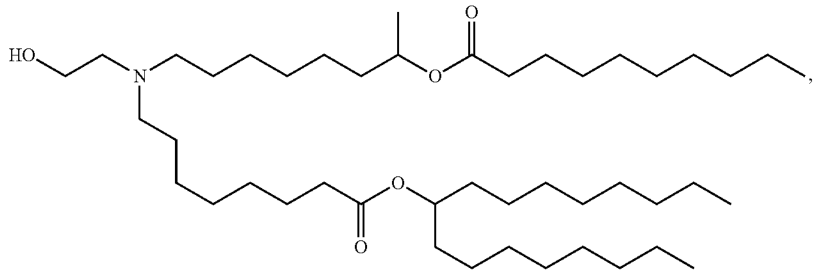
(Compound 99)
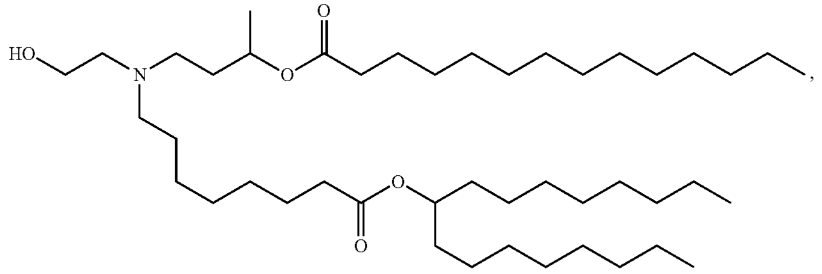
(Compound 100)
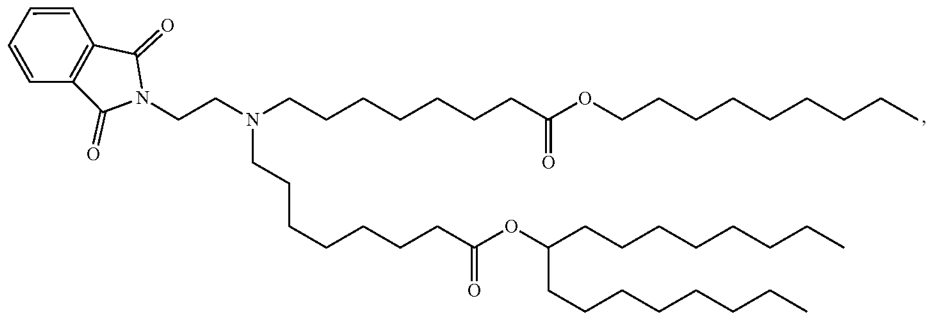
(Compound 101)
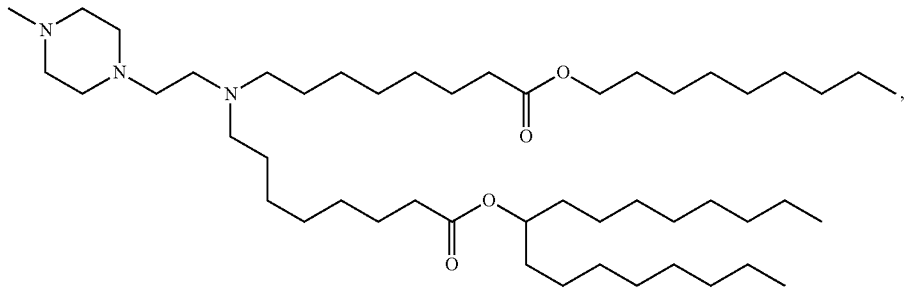
(Compound 102)
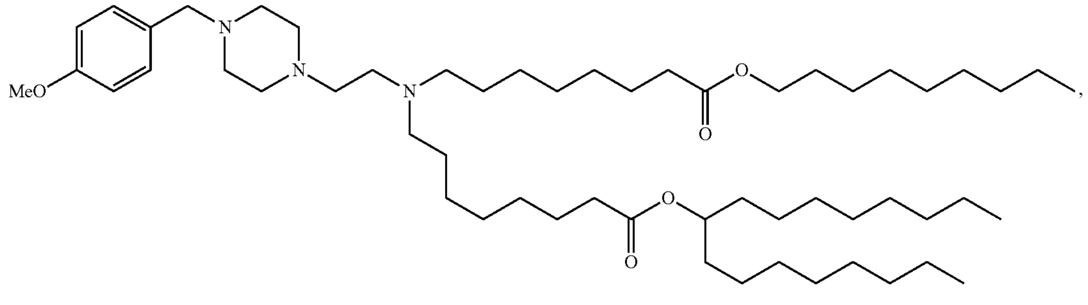

-continued
(Compound 103)
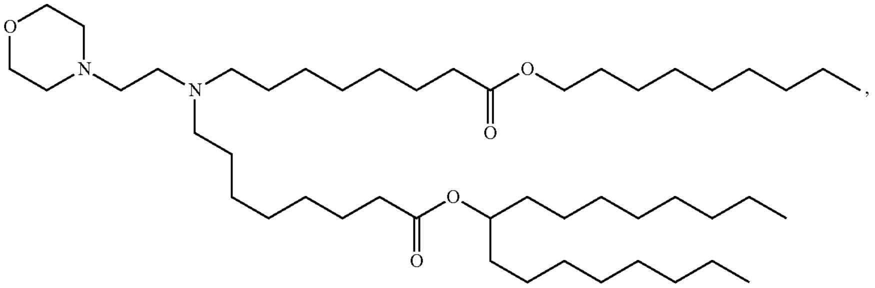
(Compound 104)
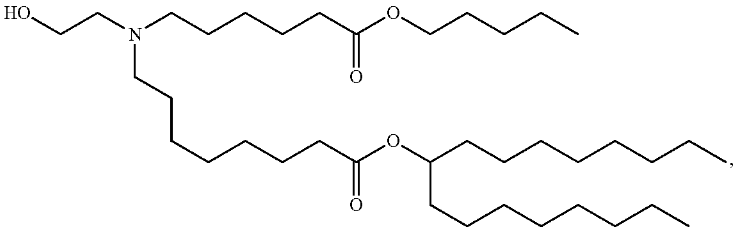
(Compound 105)
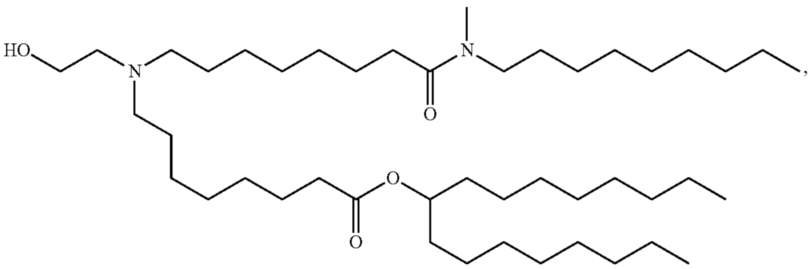
(Compound 106)
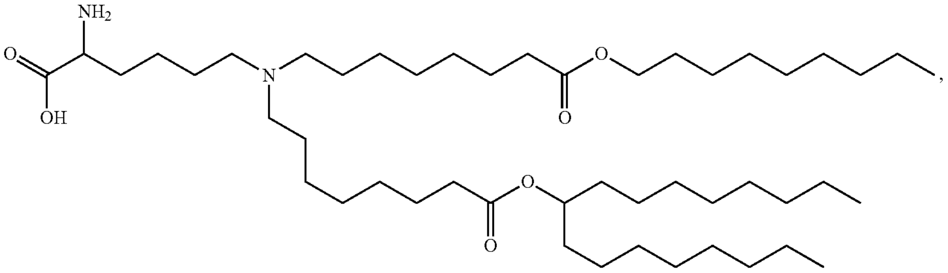
(Compound 107)
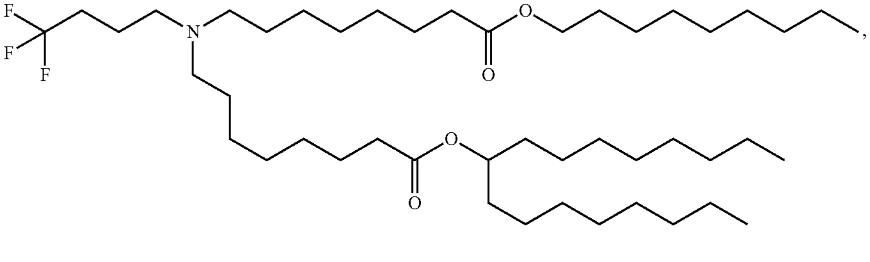

-continued
(Compound 108)
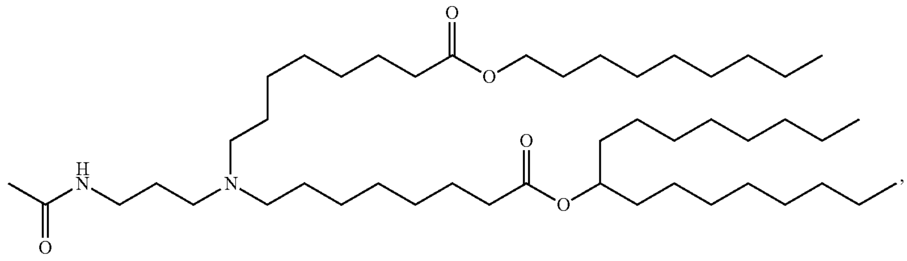,
(Compound 109)
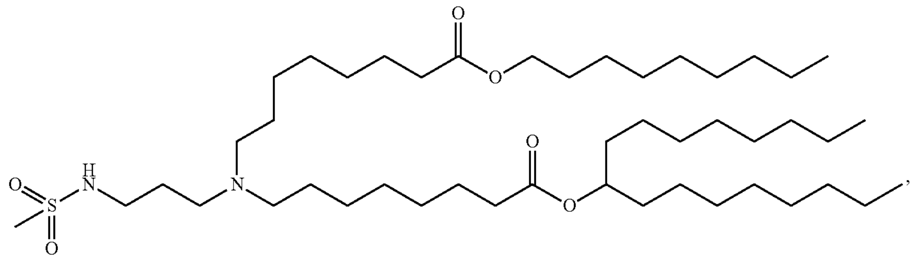,
(Compound 110)
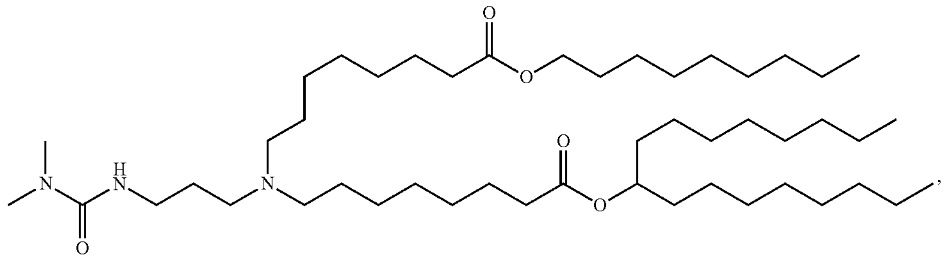,
(Compound 111)
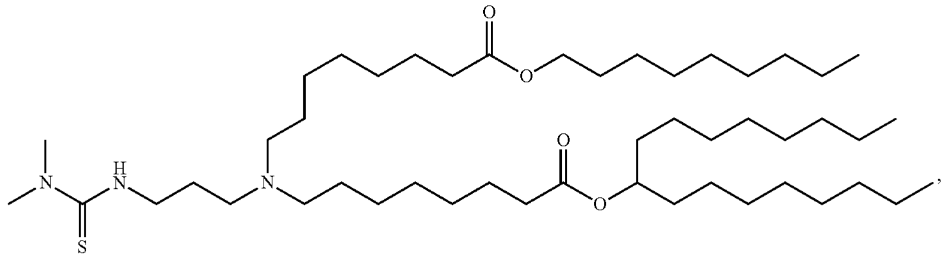,
(Compound 112)
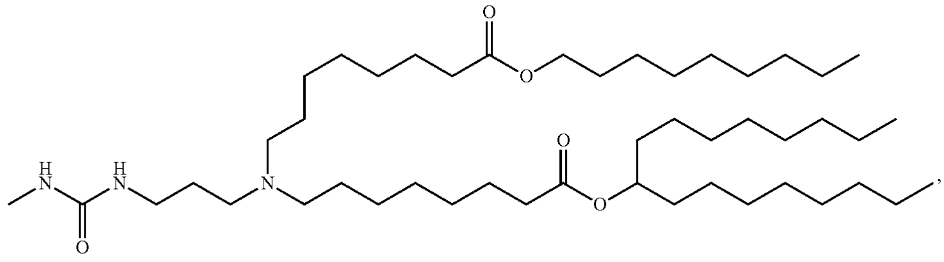,
(Compound 113)
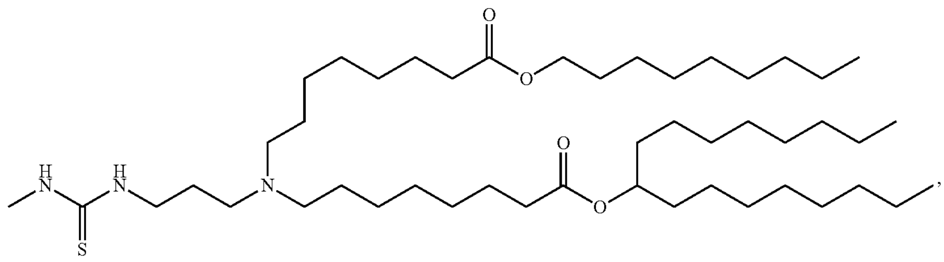, -continued
(Compound 114)
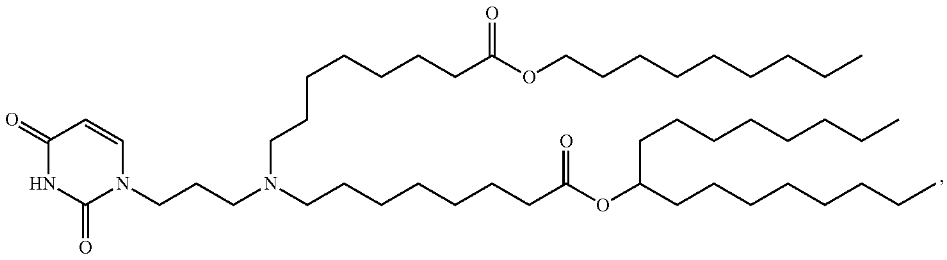,
(Compound 115)
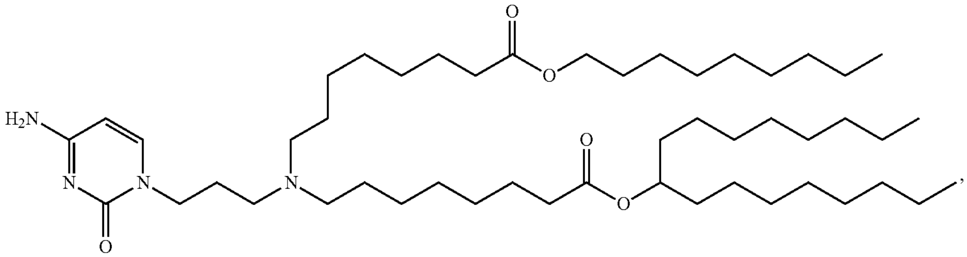,
(Compound 116)
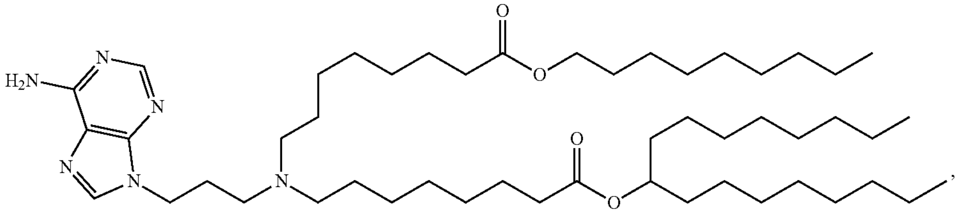,
(Compound 117)
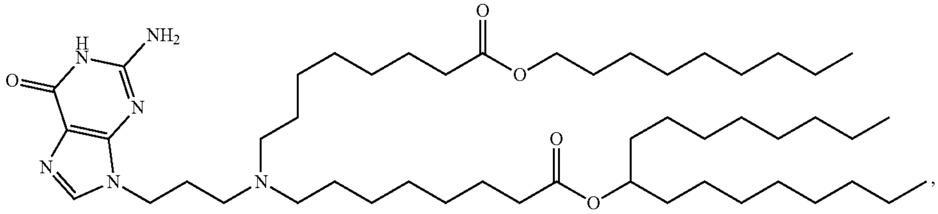,
(Compound 118)
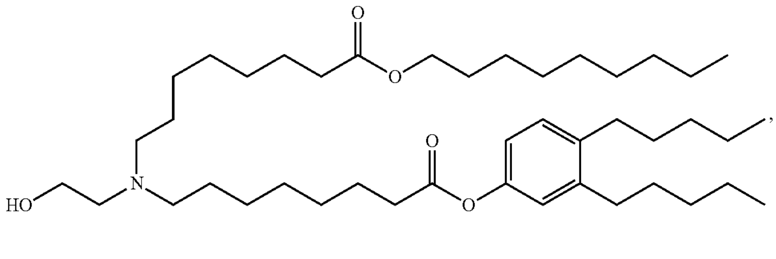,
(Compound 119)
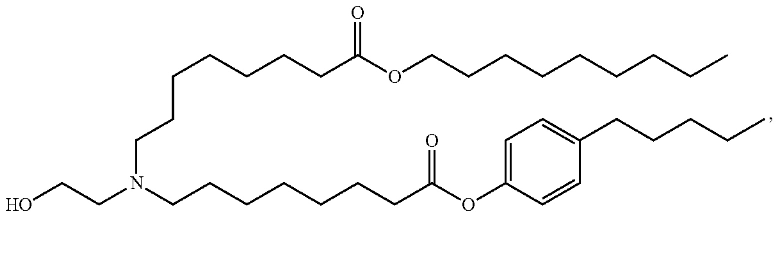, -continued
(Compound 120)
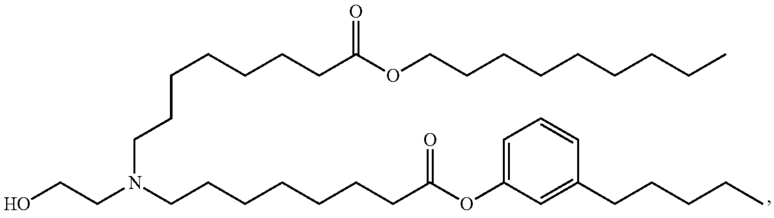
,
(Compound 121)
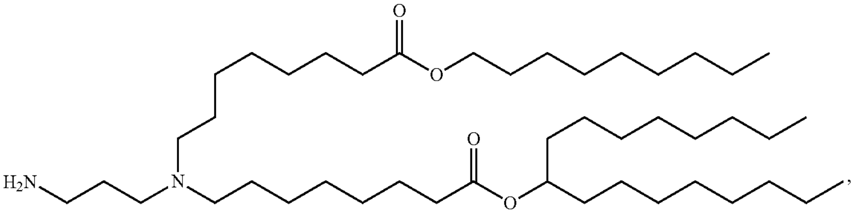
,
(Compound 122)
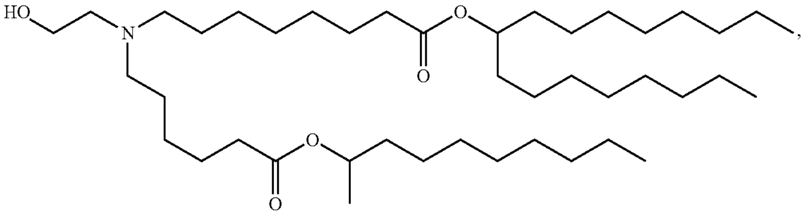
,
(Compound 123)
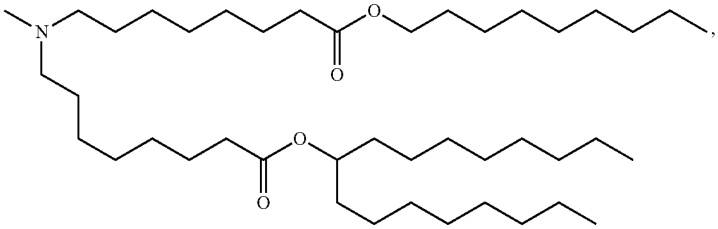
,
(Compound 124)
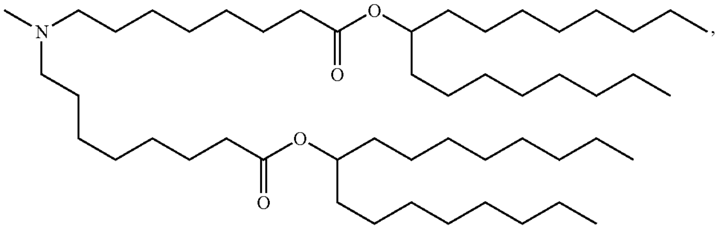
,
(Compound 125)
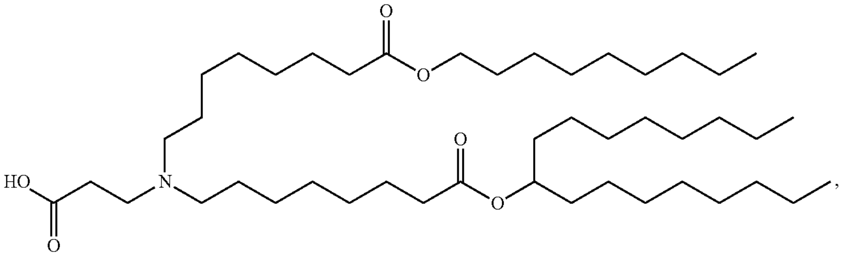
, -continued
(Compound 126)
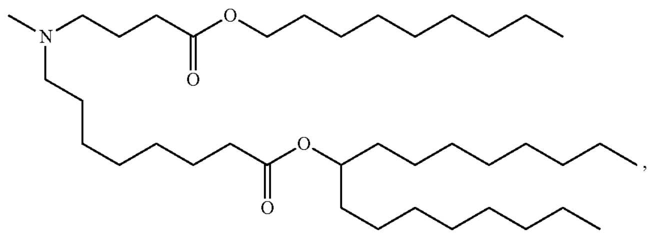
(Compound 127)
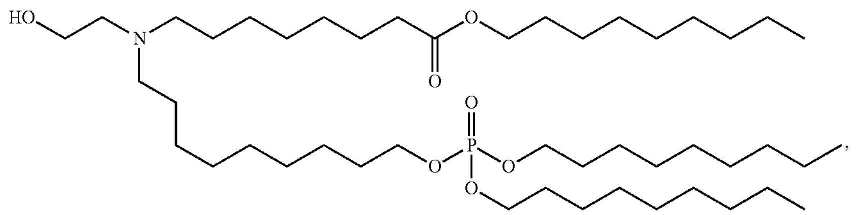
(Compound 128)
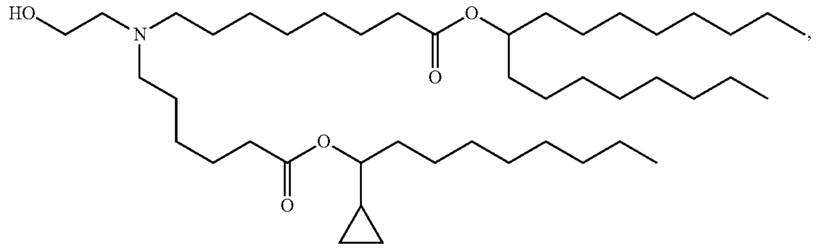
(Compound 129)
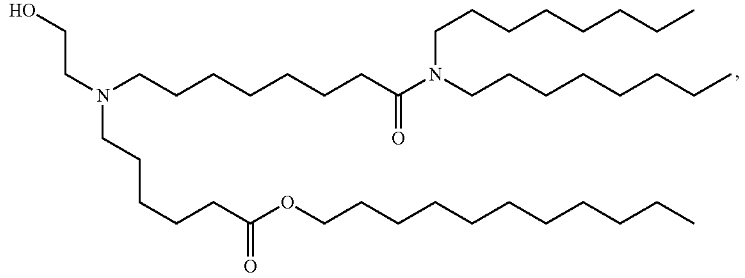
(Compound 130)
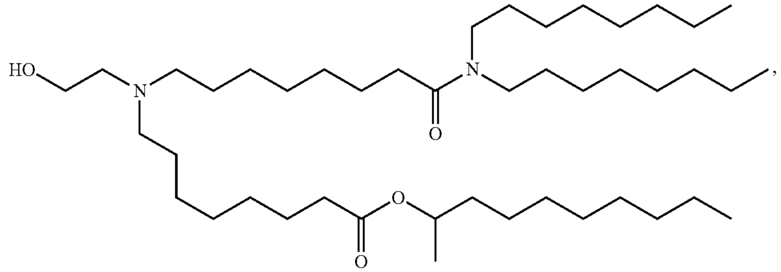
(Compound 131)
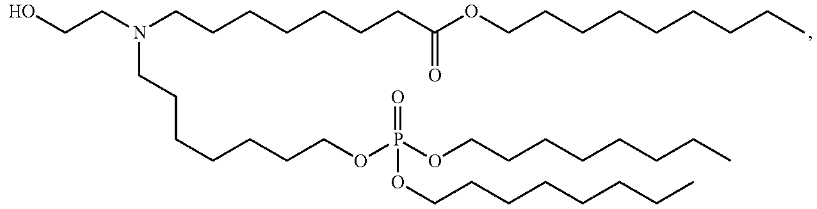

-continued
(Compound 132)
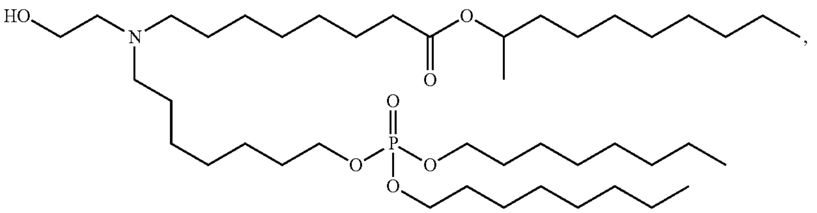
(Compound 133)
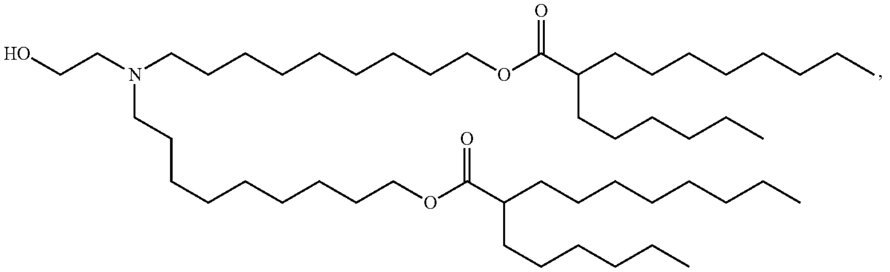
(Compound 134)
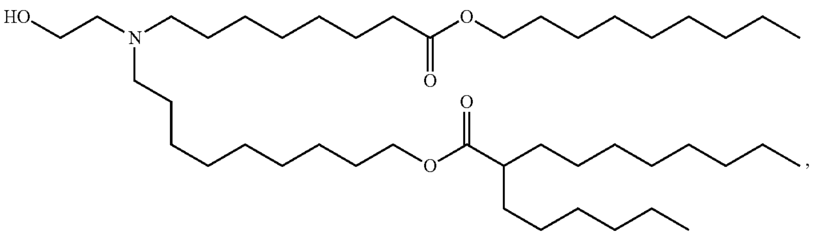
(Compound 135)
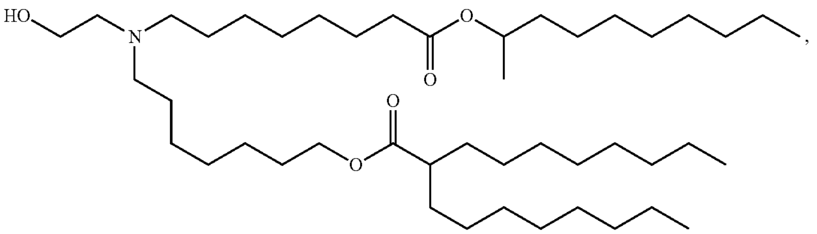
(Compound 136)
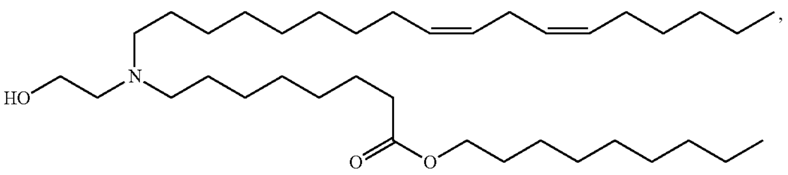
(Compound 137)
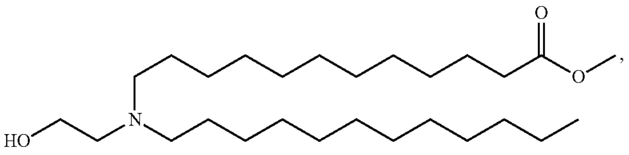
(Compound 138)
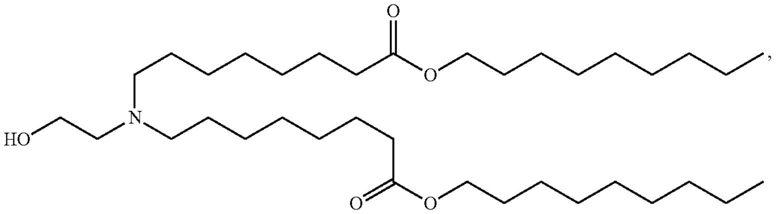

-continued
(Compound 139)
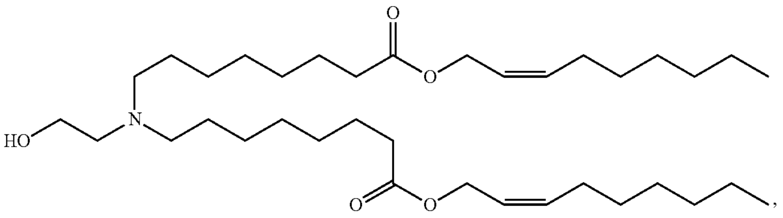
(Compound 140)
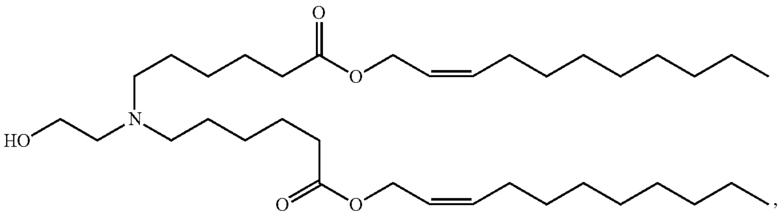
(Compound 141)
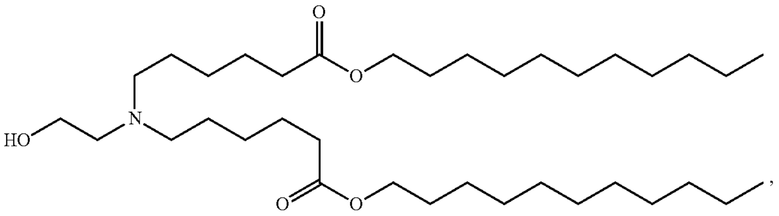
(Compound 142)
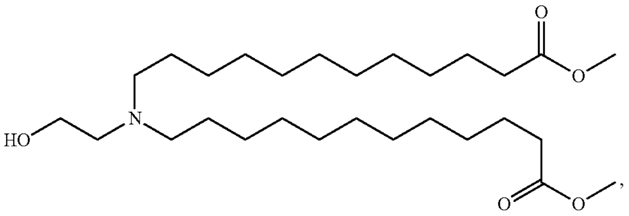
(Compound 143)
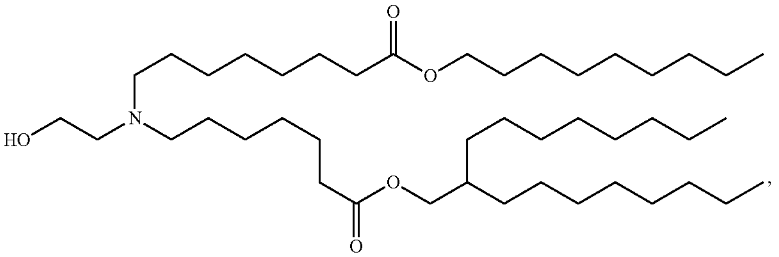
(Compound 144)
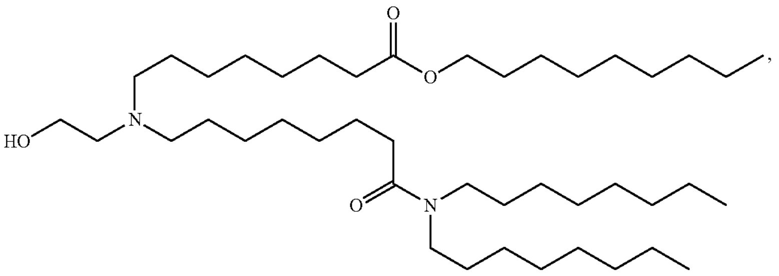

-continued
(Compound 145)
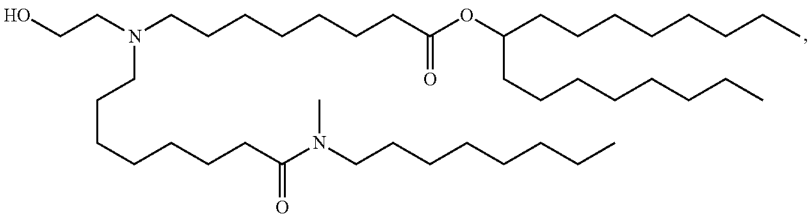
(Compound 146)
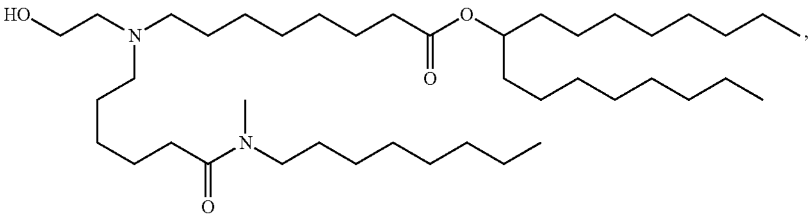
(Compound 147)
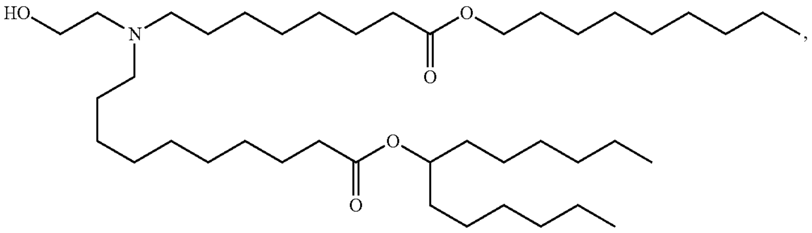
(Compound 148)
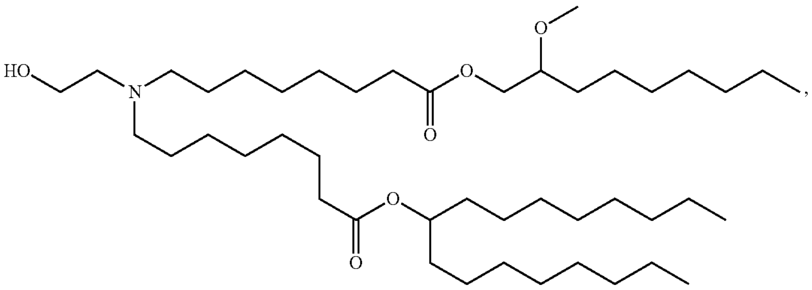
(Compound 149)
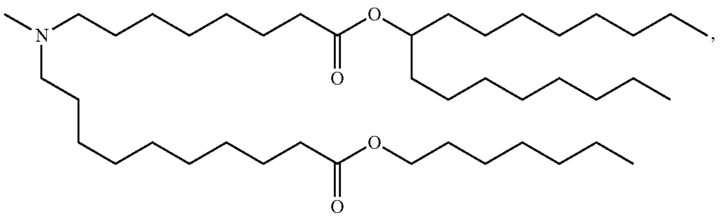
(Compound 150)
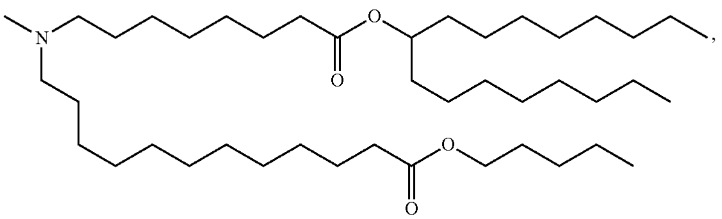

-continued
(Compound 151)
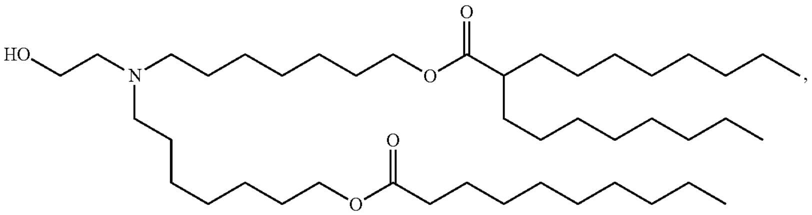
(Compound 152)
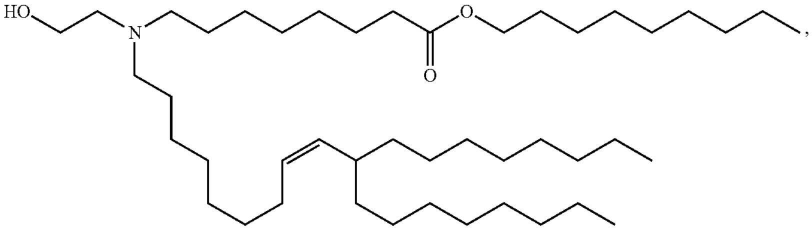
(Compound 153)
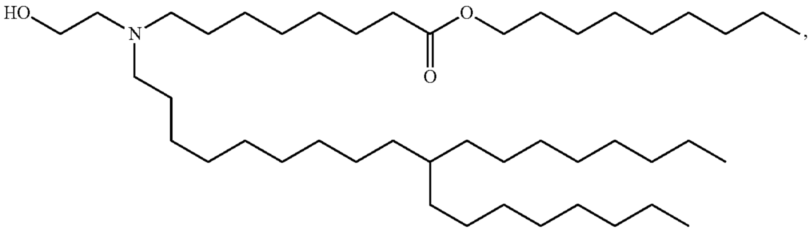
(Compund 154)
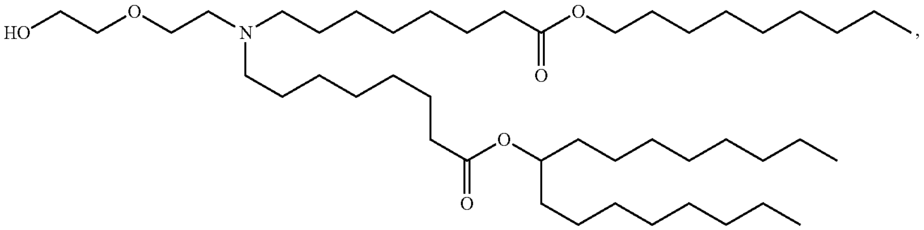
(Compund 155)
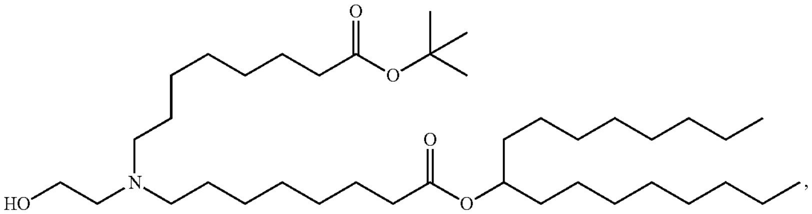
(Compund 156)
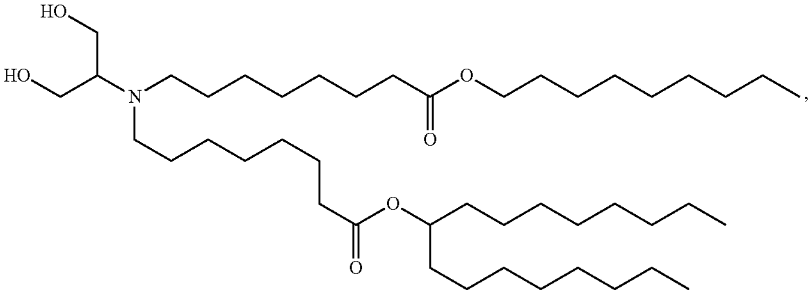

-continued
(Compound 157)
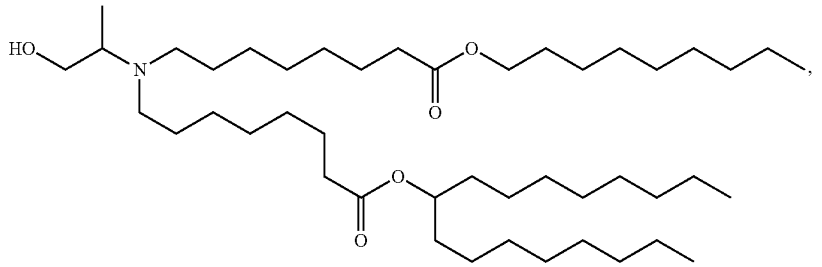
(Compound 158)
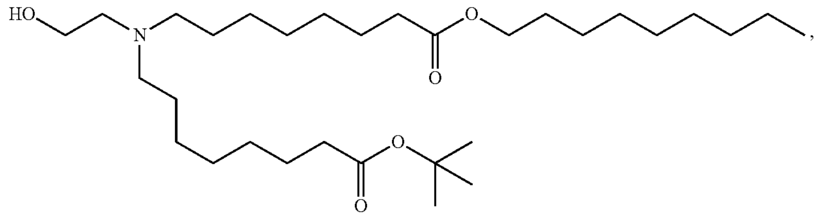
(Compound 159)
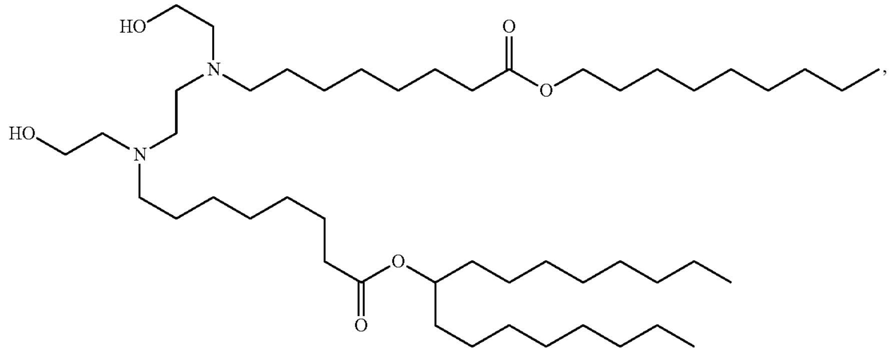
(Compound 160)
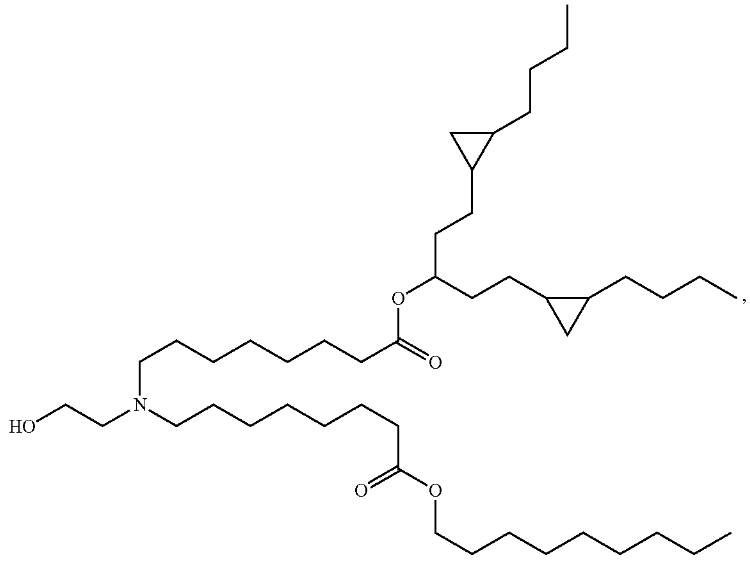

-continued
(Compound 161)
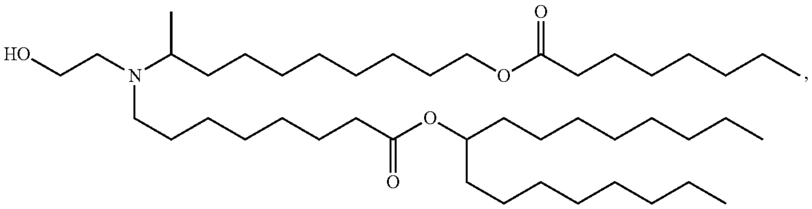
(Compound 162)
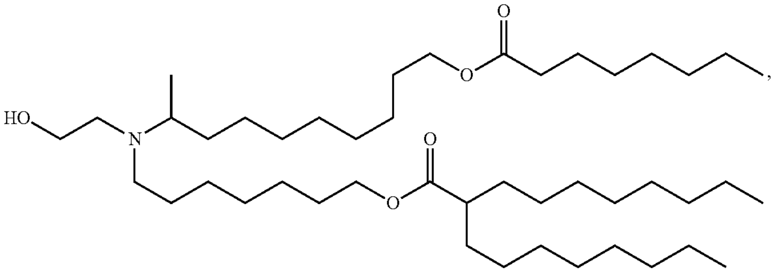
(Compound 163)
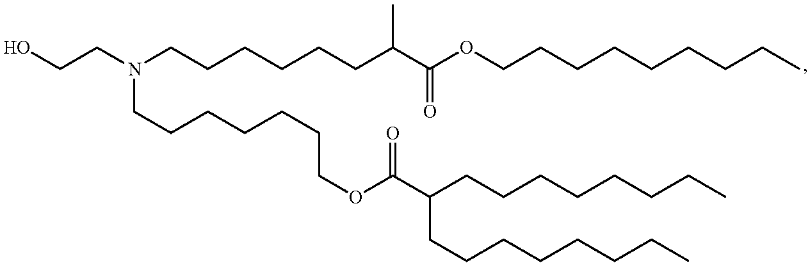
(Compound 164)
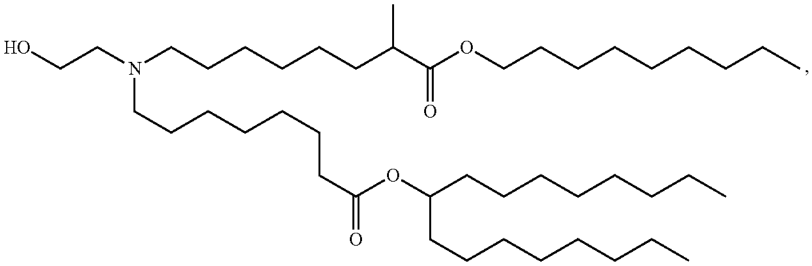
(Compound 164)
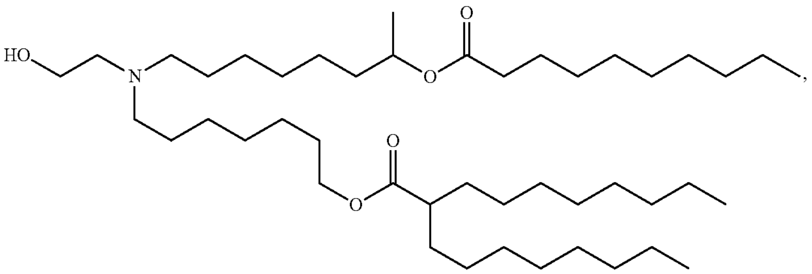
(Compound 166)
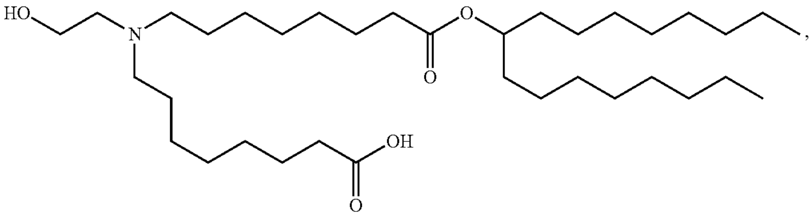

-continued
(Compound 167)
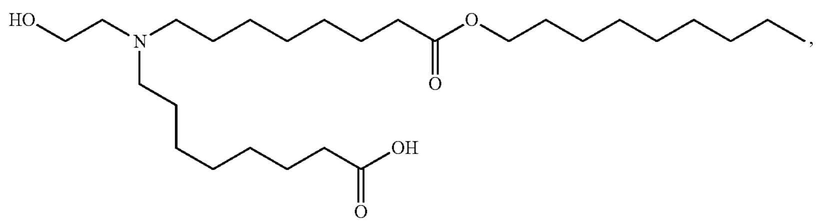
(Compound 168)
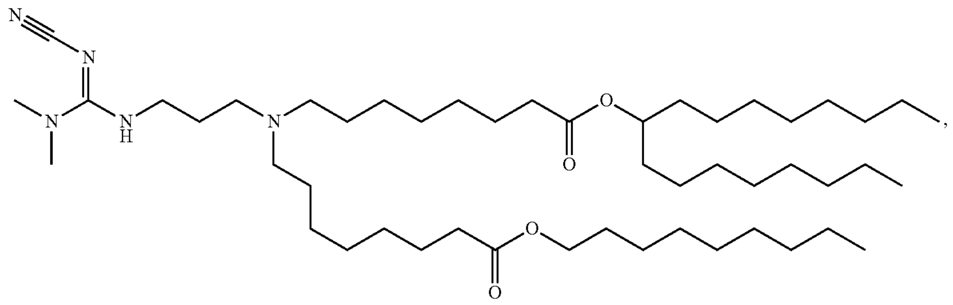
(Compound 169)
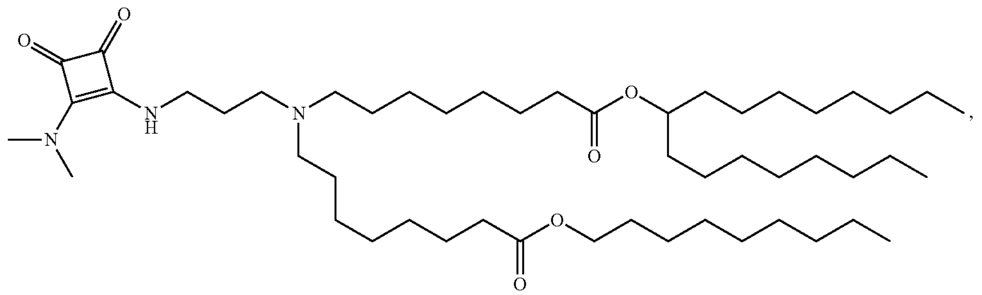
(Compound 170)
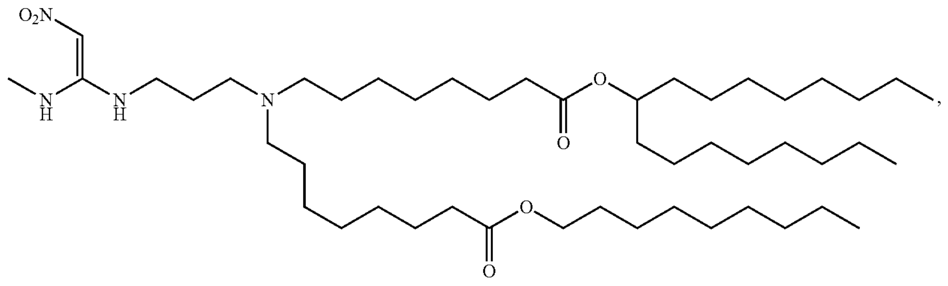
(Compound 171)
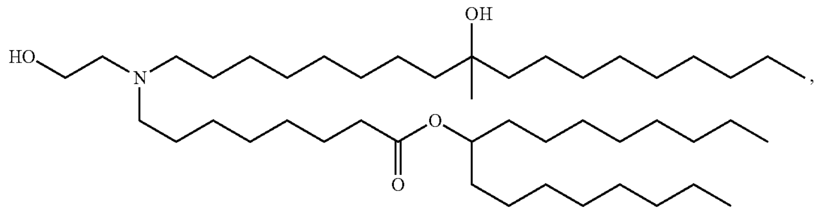
(Compound 172)
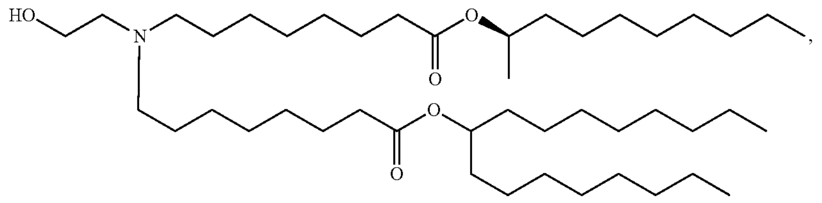

-continued
(Compound 173)
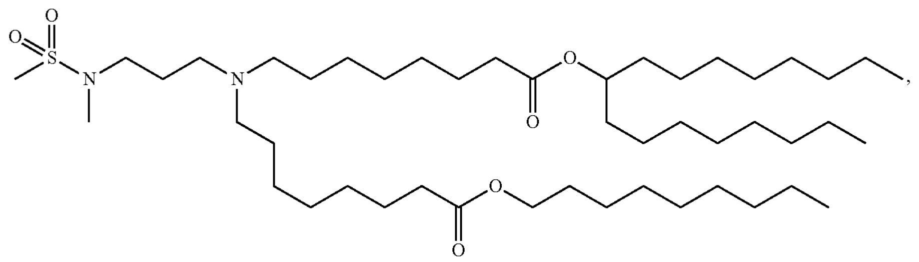
(Compound 174)
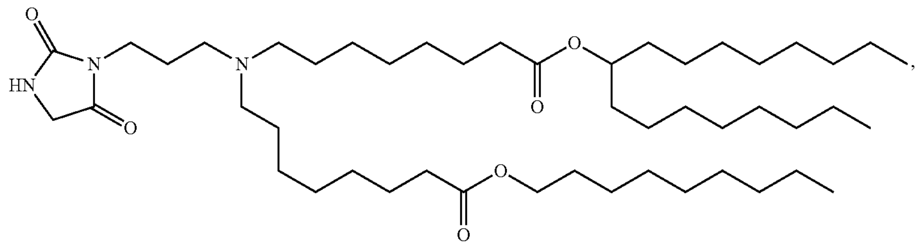
(Compound 175)
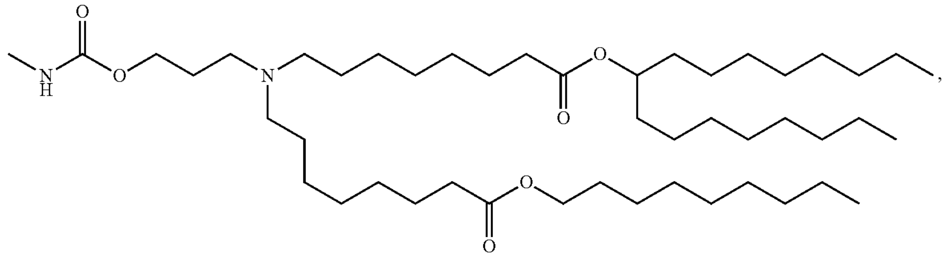
(Compound 176)
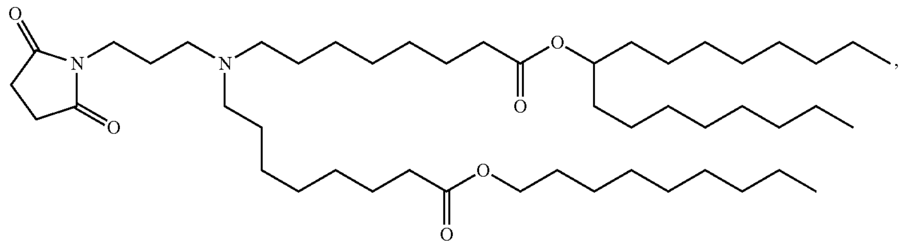
(Compound 177)
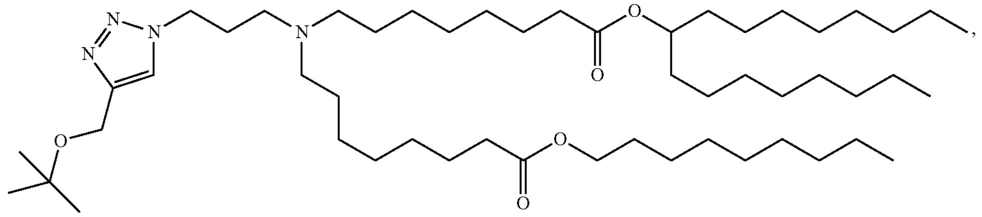
(Compound 178)
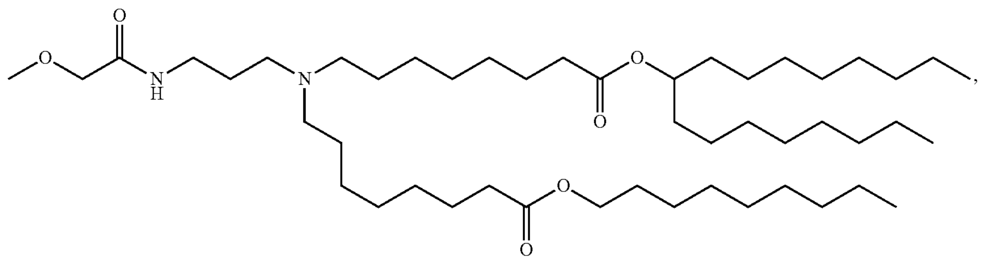

-continued
(Compound 179)
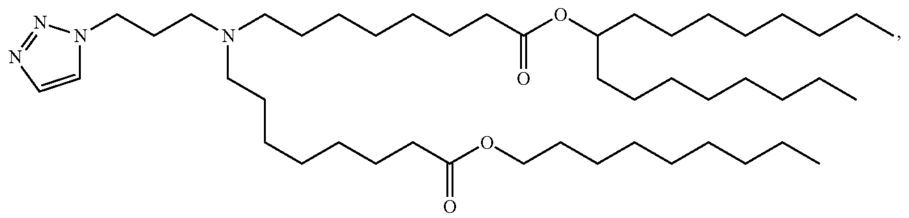
(Compound 180)
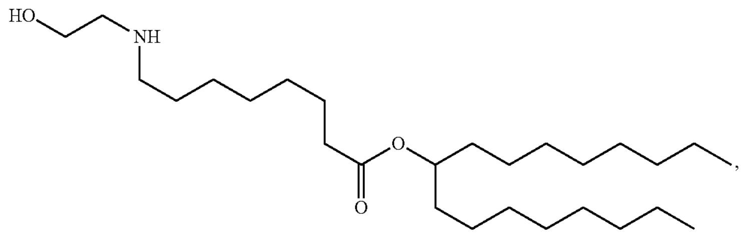
(Compound 181)
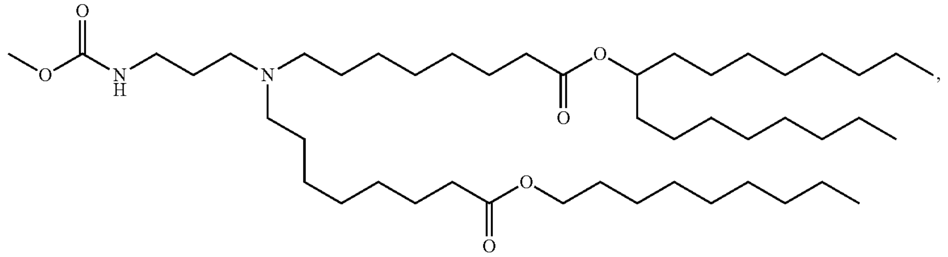
(Compound 182)
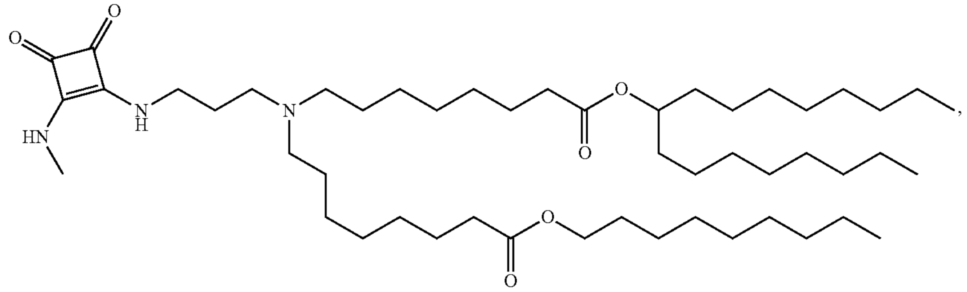
(Compound 183)
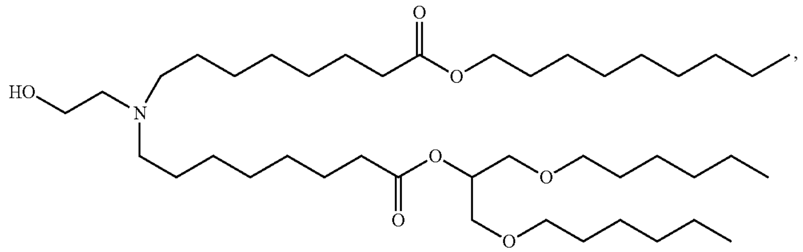
(Compound 184)
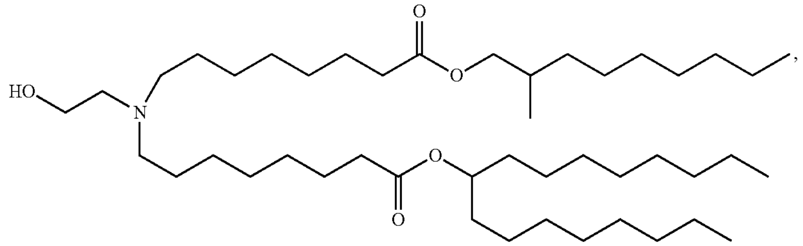

-continued
(Compound 185)
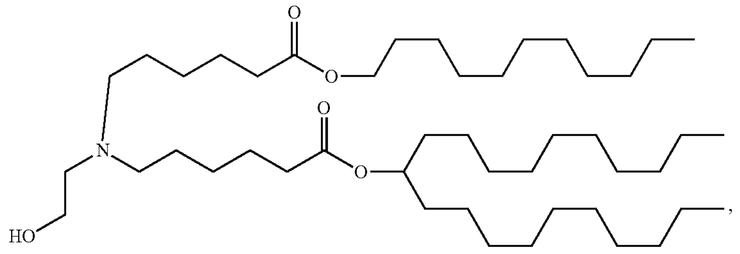
(Compound 186)
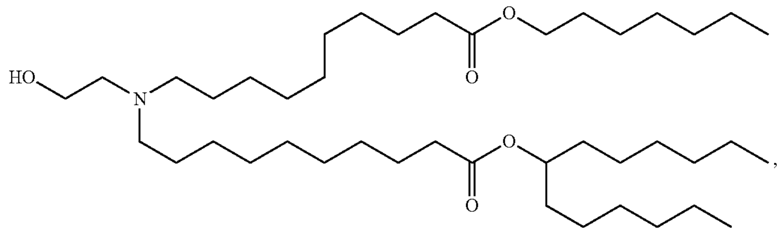
(Compound 187)
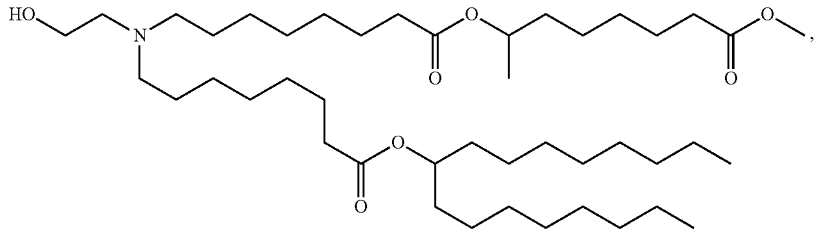
(Compound 188)
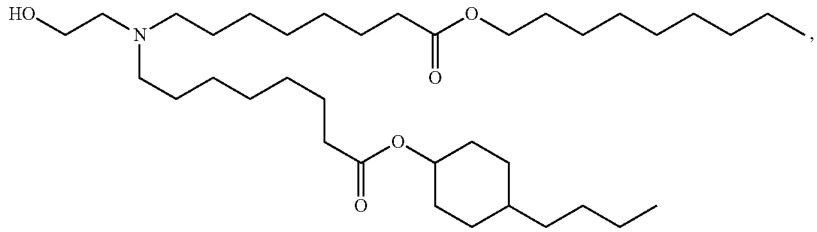
(Compound 189)
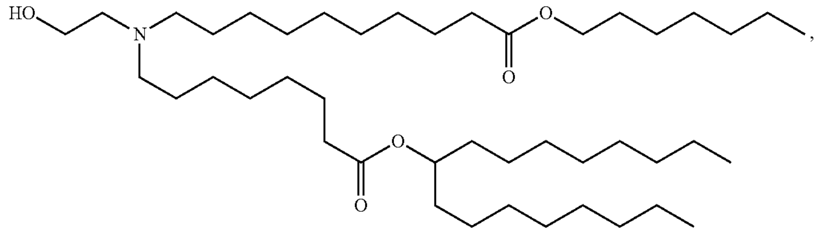
(Compound 190)
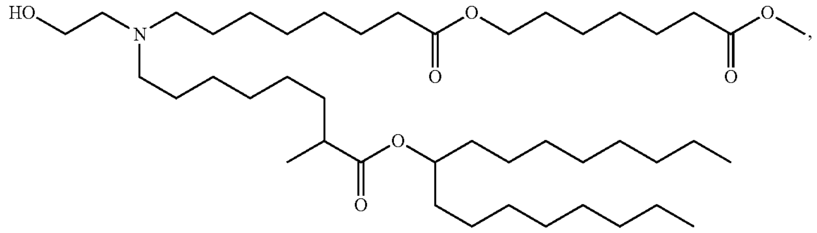

-continued
(Compound 191)
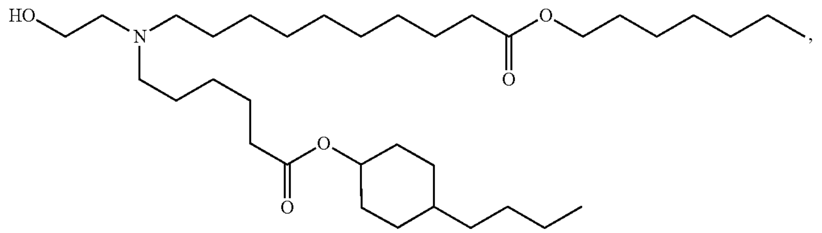
(Compound 192)
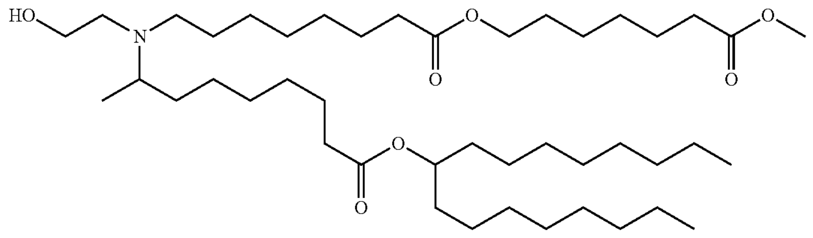
(Compound 193)
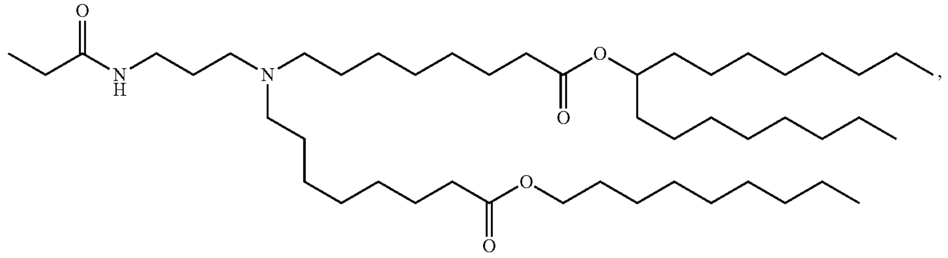
(Compound 194)
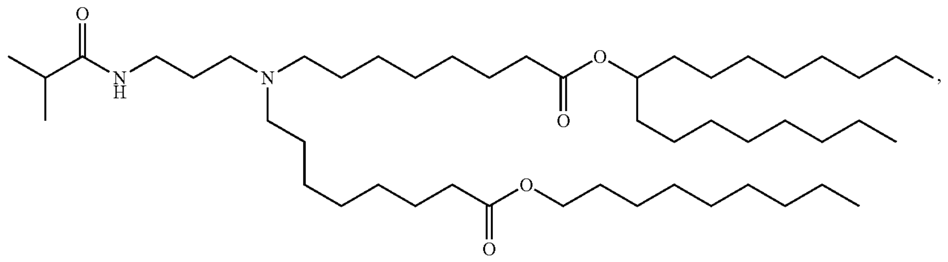
(Compound 195)
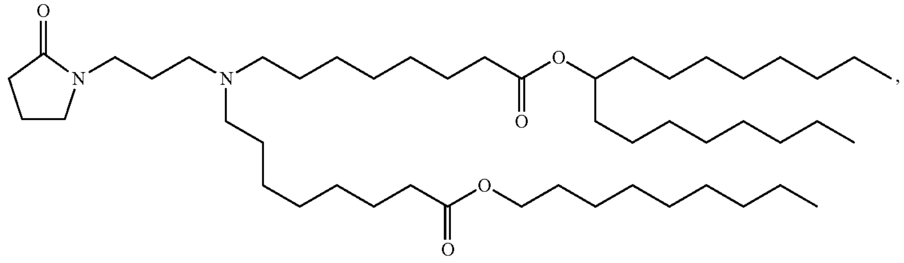

-continued
(Compound 196)
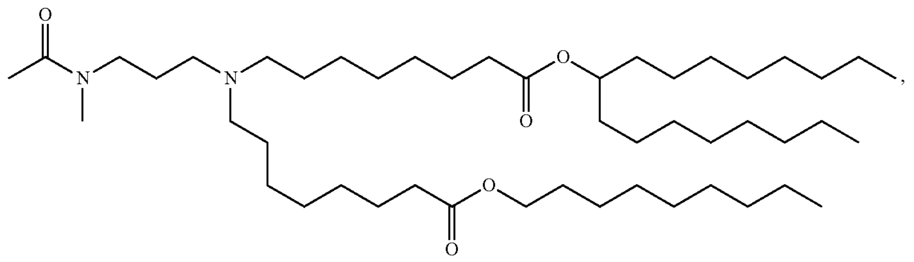
(Compound 197)
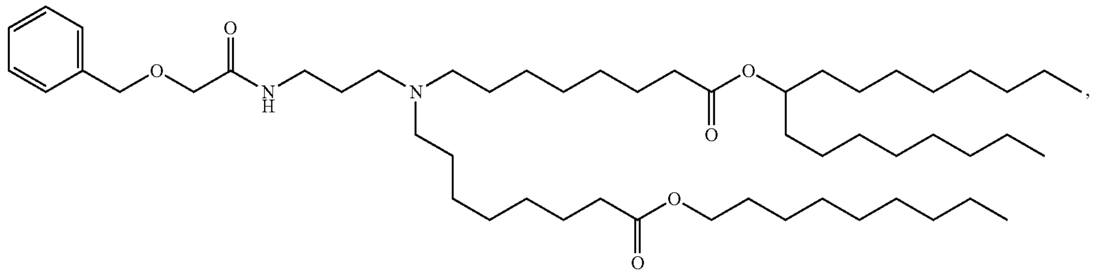
(Compound 198)
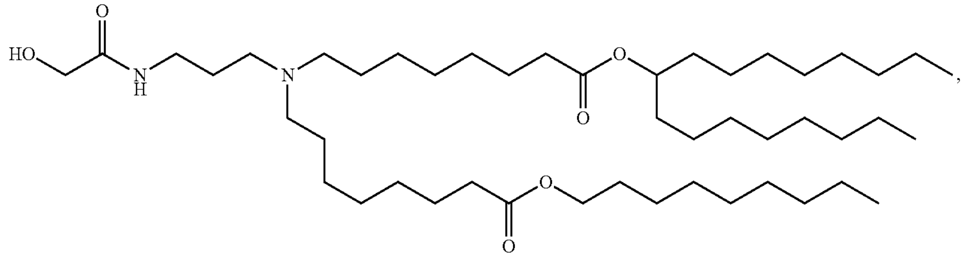
(Compound 199)
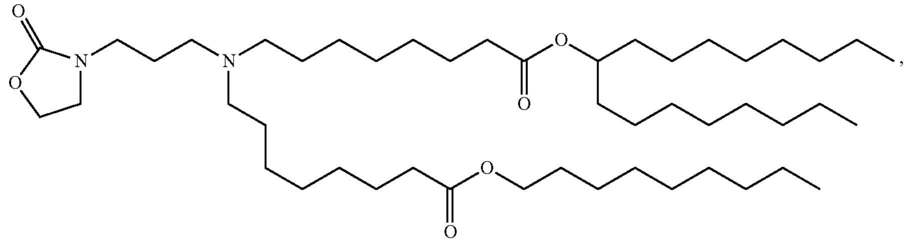
(Compound 200)
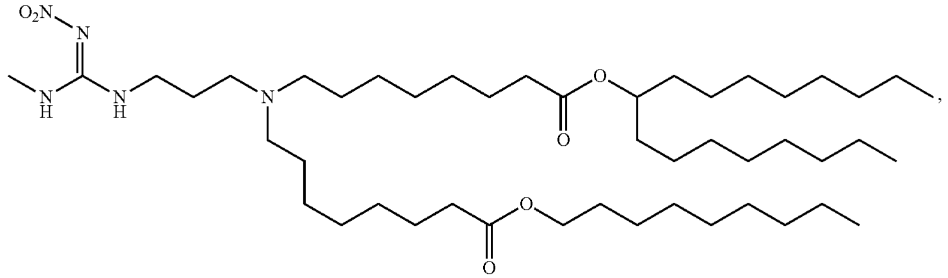
(Compound 201)
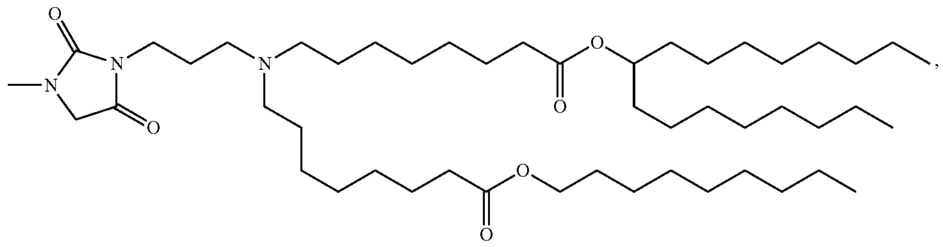

-continued
(Compound 202)
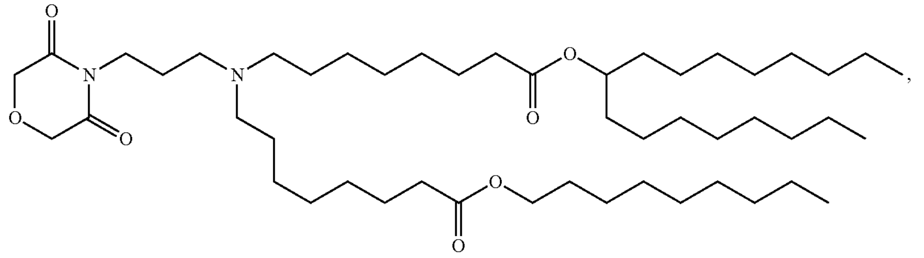
(Compound 203)
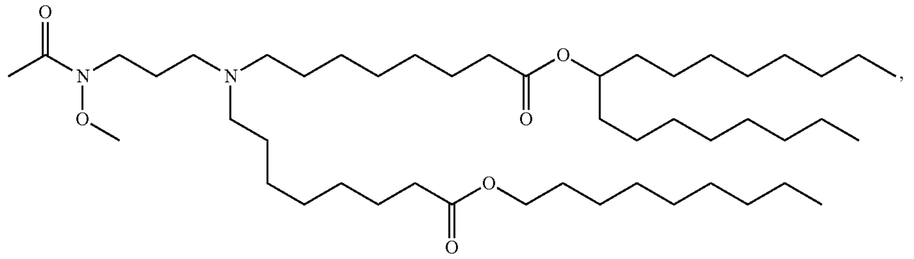
(Compound 204)
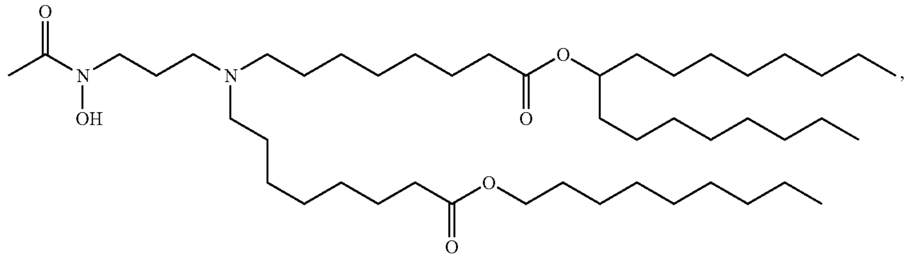
(Compound 205)
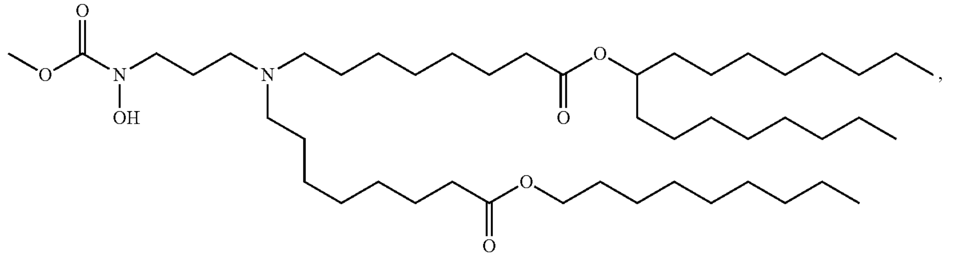
(Compound 206)
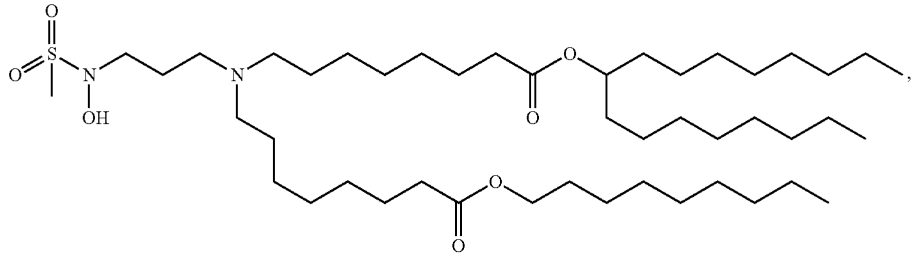
(Compound 207)
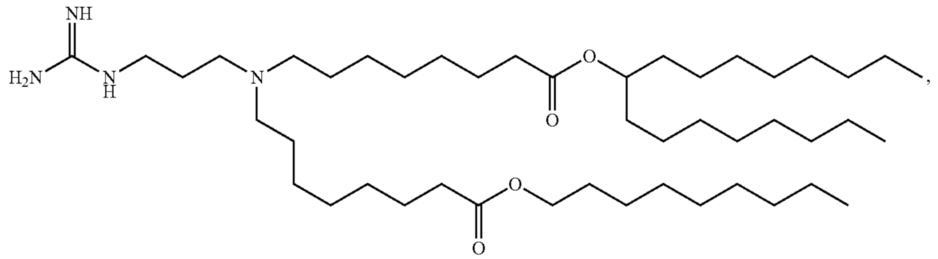

-continued
(Compound 208)
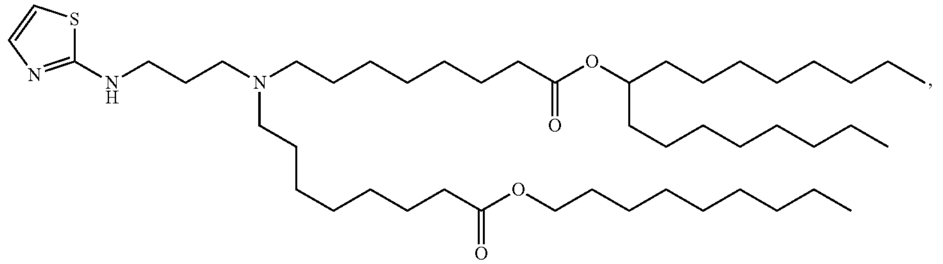
(Compound 209)
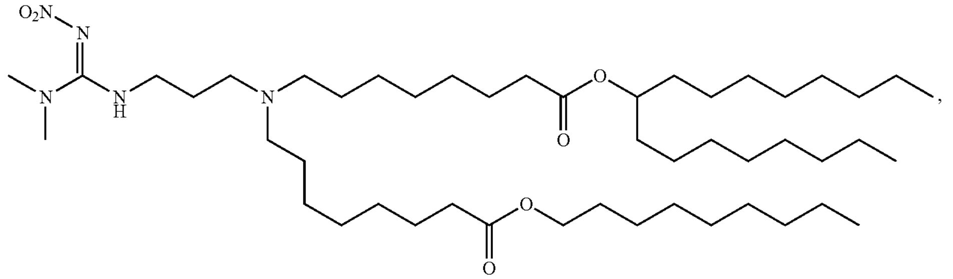
(Compound 210)
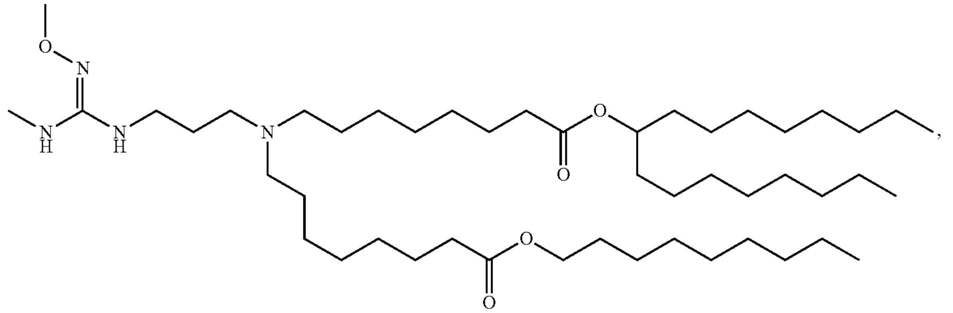
(Compound 211)
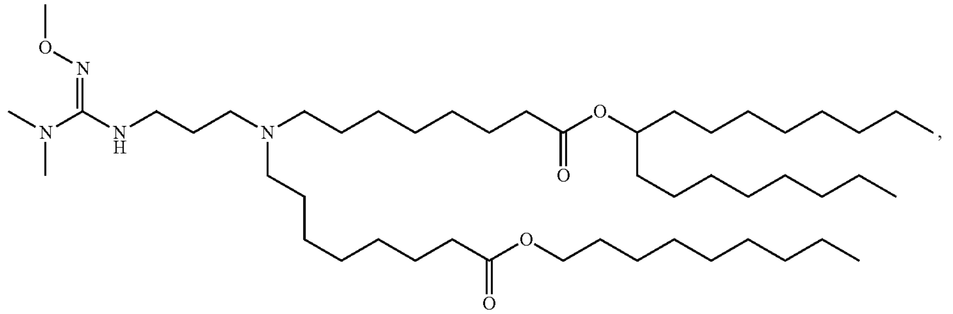
(Compound 212)
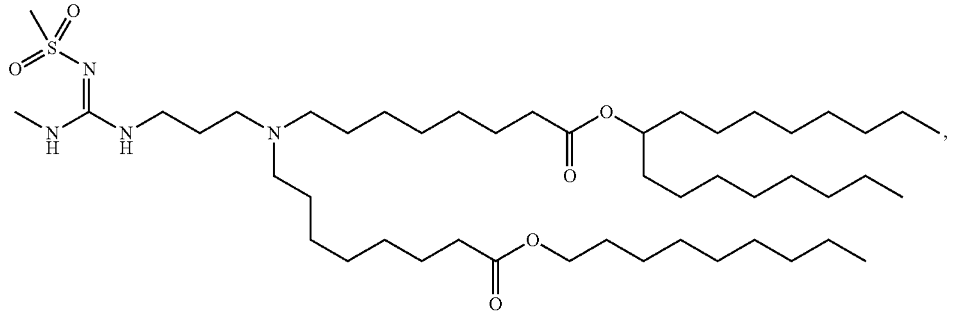

-continued
(Compound 213)
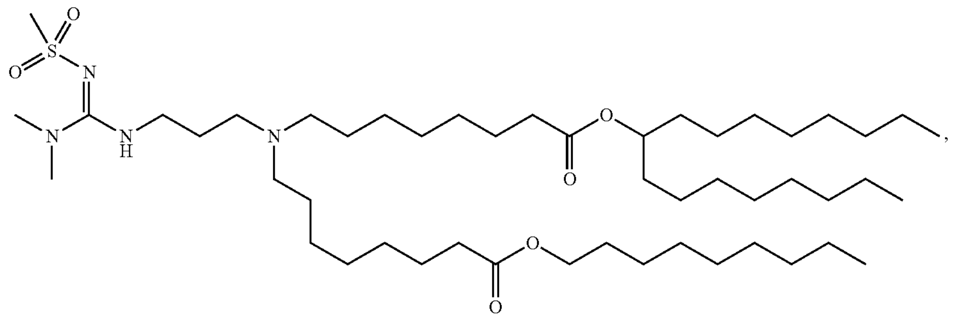
(Compound 214)
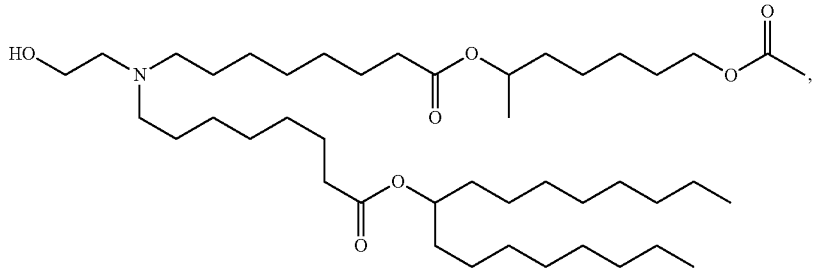
(Compound 215)
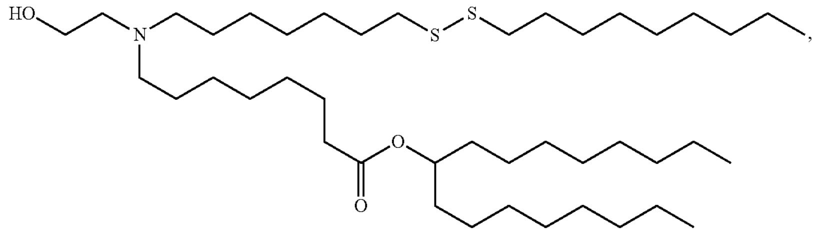
(Compound 216)
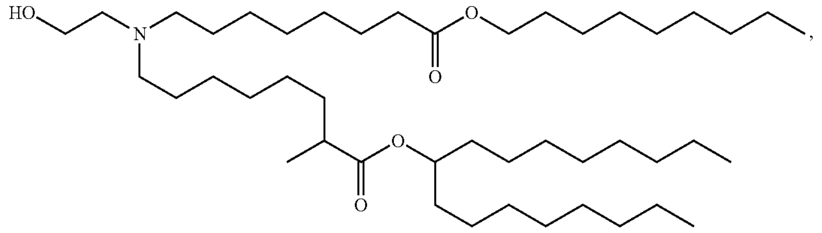
(Compound 217)
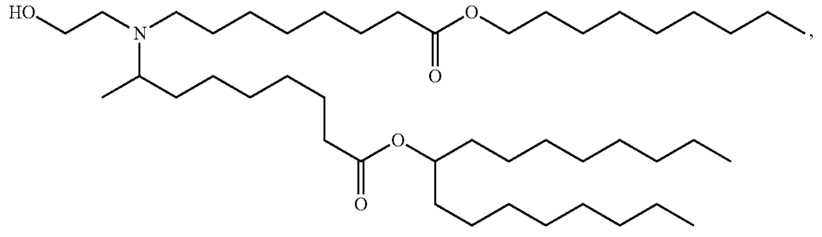
(Compound 218)
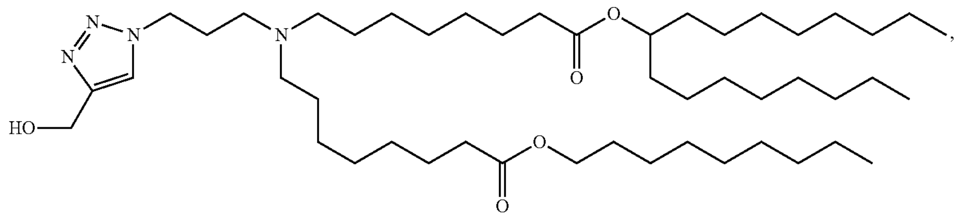

-continued
(Compound 219)
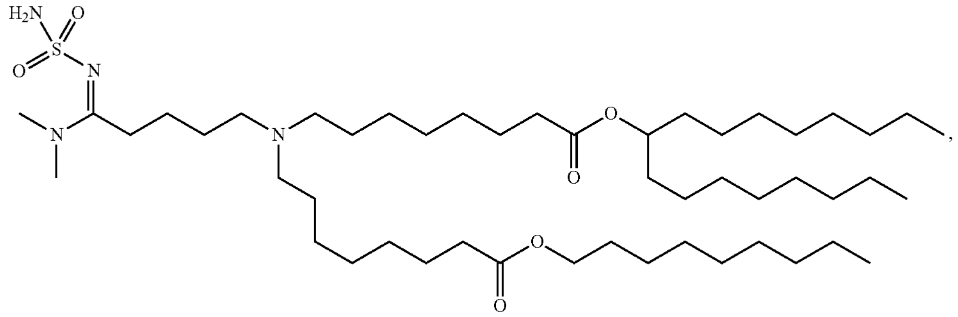
(Compound 220)
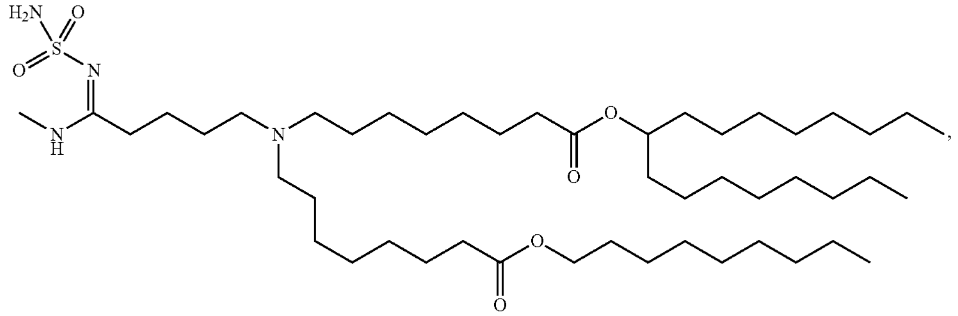
(Compound 221)
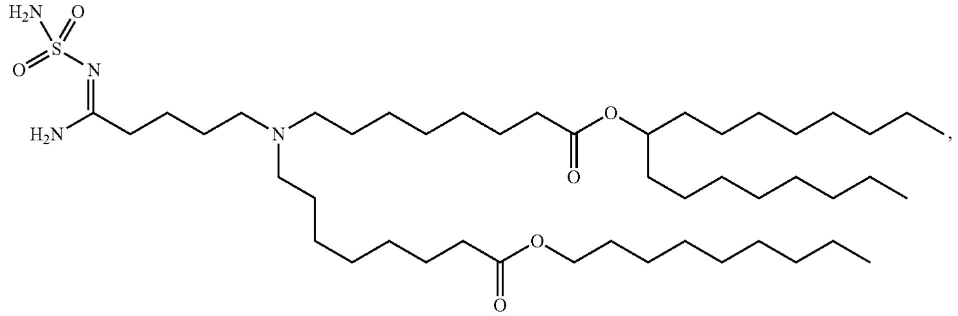
(Compound 222)
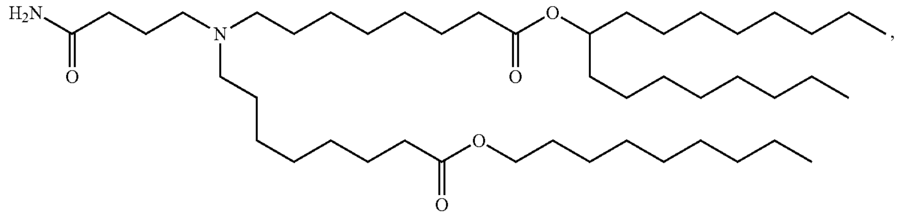
(Compound 223)
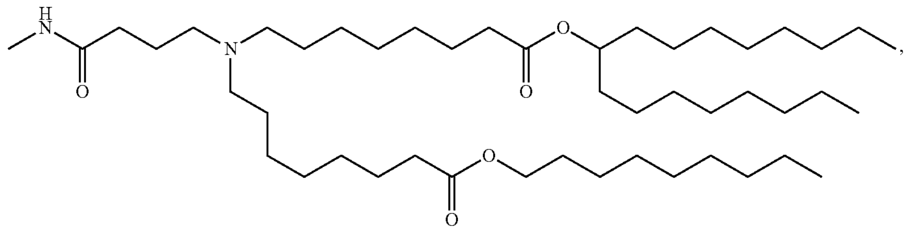

-continued
(Compound 224)
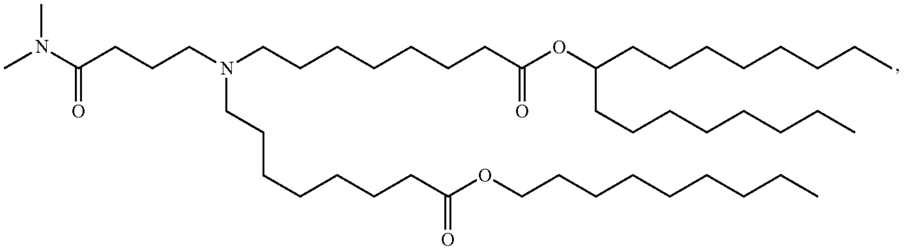
(Compound 225)
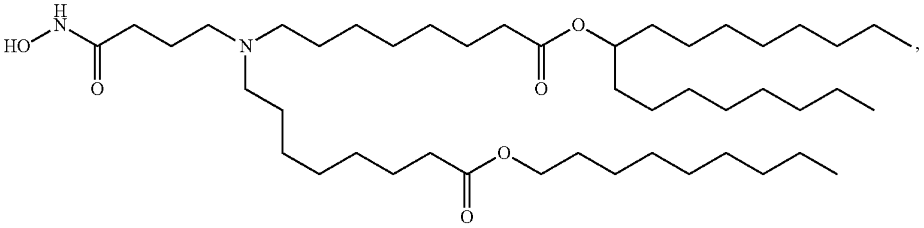
(Compound 226)
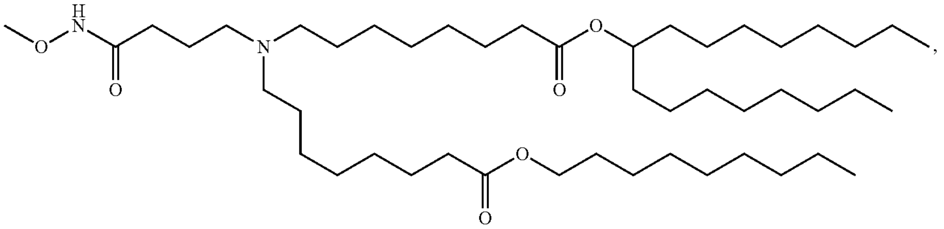
(Compound 227)
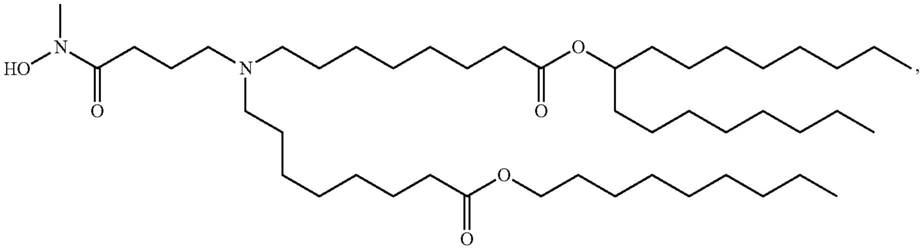
(Compound 228)
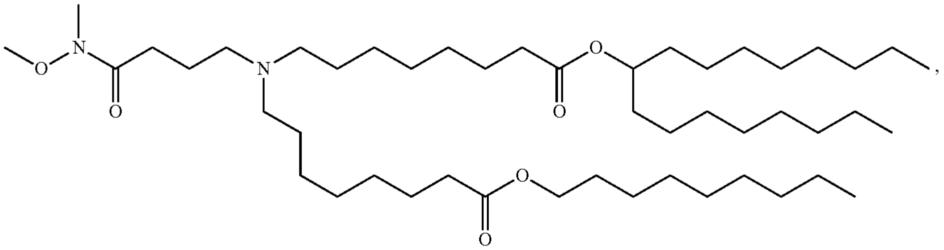
(Compound 229)
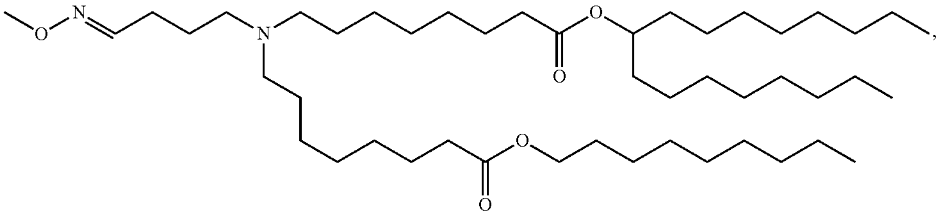

-continued (Compound 230)

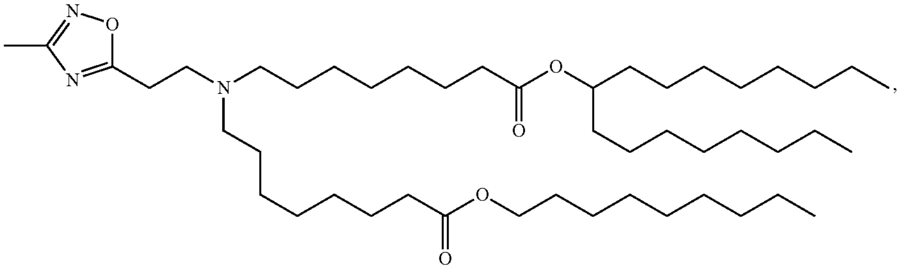

(Compound 231)

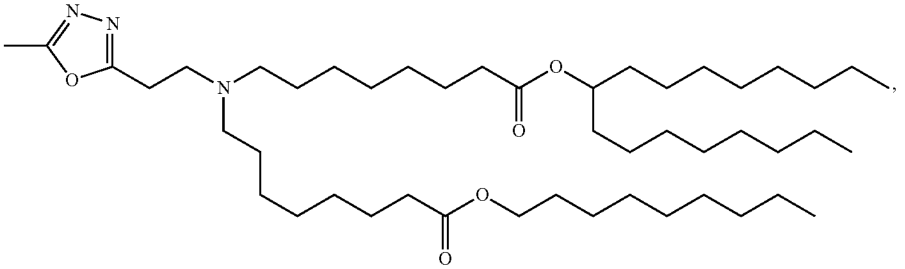

(Compound 232)

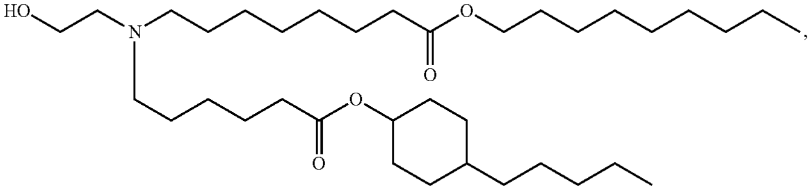

and salts and isomers thereof.

In some embodiments, a nanoparticle comprises the following compound:

(Compound 233)

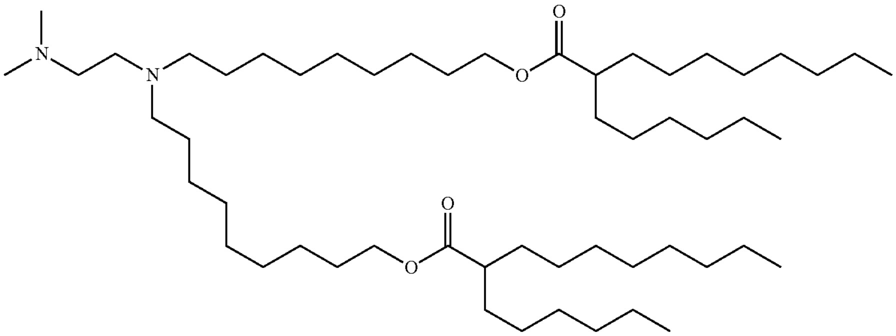

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

In some embodiments, the disclosure features a pharmaceutical composition comprising a nanoparticle composition according to the preceding embodiments and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In some embodiments, the disclosure provides a method of delivering a therapeutic and/or prophylactic (e.g., RNA, such as mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In some embodiments, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) an mRNA encoding the polypeptide of interest, whereby the mRNA is capable of being translated in the cell to produce the polypeptide.

In some embodiments, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In some embodiments, the disclosure features a method for the enhanced delivery of a therapeutic and/or prophylactic (e.g., an mRNA) to a target tissue (e.g., a liver, spleen, lung, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue.

In some embodiments, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of Formula (I), (IA), (II), (IIa), (IIb), (IIc), (IId) or (IIe). For example, the cellular immune response is an innate immune response, an adaptive immune response, or both.

The disclosure also includes methods of synthesizing a compound of Formula (I), (IA), (II), (IIa), (IIb), (IIc), (IId) or (IIe) and methods of making a nanoparticle composition including a lipid component comprising the compound of Formula (I), (IA), (II), (IIa), (IIb), (IIc), (IId) or (IIe).

Modes of Vaccine Administration

Respiratory virus RNA (e.g. mRNA) vaccines may be administered by any route which results in a therapeutically effective outcome. These include, but are not limited, to intradermal, intramuscular, and/or subcutaneous administration. The present disclosure provides methods comprising administering RNA (e.g., mRNA) vaccines to a subject in need thereof. The exact amount required will vary from subject to subject, depending on the species, age, and general condition of the subject, the severity of the disease, the particular composition, its mode of administration, its mode of activity, and the like. Respiratory virus RNA (e.g., mRNA) vaccines compositions are typically formulated in dosage unit form for ease of administration and uniformity of dosage. It will be understood, however, that the total daily usage of RNA (e.g., mRNA) vaccine compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, respiratory virus RNA (e.g. mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see, e.g., the range of unit doses described in International Publication No WO2013078199, the contents of which are herein incorporated by reference in their entirety). The desired dosage may be delivered three times a day, two times a day, once a day, every other day, every third day, every week, every two weeks, every three weeks, every four weeks, every 2 months, every three months, every 6 months, etc. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, respiratory virus RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, respiratory virus RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, respiratory virus RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a respiratory virus RNA (e.g., mRNA) vaccine composition may be administered three or four times.

In some embodiments, respiratory virus RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg. In some embodiments, the respiratory virus RNA (e.g., mRNA) vaccine for use in a method of vaccinating a subject is administered to the subject as a single dosage of between 10 μg/kg and 400 μg/kg of the nucleic acid vaccine (in an effective amount to vaccinate the subject). In some embodiments the RNA (e.g., mRNA) vaccine for use in a method of vaccinating a subject is administered to the subject as a single dosage of between 10 μg and 400 μg of the nucleic acid vaccine (in an effective amount to vaccinate the subject). In some embodiments, a respiratory virus RNA (e.g., mRNA) vaccine for use in a method of vaccinating a subject is administered to the subject as a single dosage of 25-1000 μg (e.g., a single dosage of mRNA encoding hMPV, PIV3, RSV, MeV and/or BetaCoV antigen). In some embodiments, a respiratory virus RNA (e.g., mRNA) vaccine is administered to the subject as a single dosage of 25, 50, 100, 150, 200, 250, 300, 350, 400, 450, 500, 550, 600, 650, 700, 750, 800, 850, 900, 950 or 1000 μg. For example, a respiratory virus RNA (e.g., mRNA) vaccine may be administered to a subject as a single dose of 25-100, 25-500, 50-100, 50-500, 50-1000, 100-500, 100-1000, 250-500, 250-1000, or 500-1000 μg. In some embodiments, a respiratory virus RNA (e.g., mRNA) vaccine for use in a method of vaccinating a subject is administered to the subject as two dosages, the combination of which equals 25-1000 μg of the respiratory virus RNA (e.g., mRNA) vaccine.

A respiratory virus RNA (e.g. mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Respiratory Virus RNA (e.g., mRNA) Vaccine Formulations and Methods of Use

Some aspects of the present disclosure provide formulations of the respiratory virus RNA (e.g., mRNA) vaccine, wherein the RNA (e.g., mRNA) vaccine is formulated in an effective amount to produce an antigen specific immune response in a subject (e.g., production of antibodies specific to an hMPV, PIV3, RSV, MeV and/or BetaCoV antigenic polypeptide). "An effective amount" is a dose of an RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-hMPV, anti-PIV3, anti-RSV, anti-MeV and/or anti-BetaCoV antigenic polypeptide antibody titer produced in a subject administered a respiratory virus RNA (e.g., mRNA) vaccine as provided herein. An antibody titer is a measurement of the amount of antibodies within a subject, for example, antibodies that are specific to a particular antigen (e.g., an anti-hMPV, anti-PIV3, anti-RSV, anti-MeV and/or anti-BetaCoV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the respiratory virus RNA (e.g., mRNA) vaccine.

In some embodiments, an anti-antigenic polypeptide (e.g., an anti-hMPV, anti-PIV3, anti-RSV, anti-MeV and/or anti-BetaCoV antigenic polypeptide) antibody titer produced in a subject is increased by at least 1 log relative to a control. For example, anti-antigenic polypeptide antibody titer produced in a subject may be increased by at least 1.5, at least 2, at least 2.5, or at least 3 log relative to a control. In some embodiments, the anti-antigenic polypeptide antibody titer produced in the subject is increased by 1, 1.5, 2, 2.5 or 3 log relative to a control. In some embodiments, the anti-antigenic polypeptide antibody titer produced in the subject is increased by 1-3 log relative to a control. For example, the anti-antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-antigenic polypeptide (e.g., an anti-hMPV, anti-PIV3, anti-RSV, anti-MeV and/or anti-BetaCoV antigenic polypeptide) antibody titer produced in a subject is increased at least 2 times relative to a control. For example, the anti-antigenic polypeptide antibody titer produced in a subject may be increased at least 3 times, at least 4 times, at least 5 times, at least 6 times, at least 7 times, at least 8 times, at least 9 times, or at least 10 times relative to a control. In some embodiments, the anti-antigenic polypeptide antibody titer produced in the subject is increased 2, 3, 4, 5, 6, 7, 8, 9, or 10 times relative to a control. In some embodiments, the anti-antigenic polypeptide antibody titer produced in a subject is increased 2-10 times relative to a control. For example, the anti-antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-antigenic polypeptide (e.g., an anti-hMPV, anti-PIV3, anti-RSV, anti-MeV and/or anti-BetaCoV antigenic polypeptide) antibody titer produced in a subject who has not been administered a respiratory virus RNA (e.g., mRNA) vaccine of the present disclosure. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject who has been administered a live attenuated hMPV, PIV3, RSV, MeV and/or BetaCoV vaccine. An attenuated vaccine is a vaccine produced by reducing the virulence of a viable (live). An attenuated virus is altered in a manner that renders it harmless or less virulent relative to live, unmodified virus. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject administered inactivated hMPV, PIV3, RSV, MeV and/or BetaCoV vaccine. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject administered a recombinant or purified hMPV, PIV3, RSV, MeV and/or BetaCoV protein vaccine. Recombinant protein vaccines typically include protein antigens that either have been produced in a heterologous expression system (e.g., bacteria or yeast) or purified from large amounts of the pathogenic organism. In some embodiments, a control is an anti-antigenic polypeptide (e.g., an anti-hMPV, anti-PIV3, anti-RSV, anti-MeV and/or anti-BetaCoV antigenic polypeptide) antibody titer produced in a subject who has been administered an hMPV, PIV3, RSV, MeV and/or BetaCoV virus-like particle (VLP) vaccine. For example, an hMPV VLP vaccine used as a control may be a hMPV VLPs, comprising (or consisting of) viral matrix (M) and fusion (F) proteins, generated by expressing viral proteins in suspension-adapted human embryonic kidney epithelial (293-F) cells (see, e.g., Cox R G et al., *J Virol.* 2014 June; 88 (11): 6368-6379, the contents of which are herein incorporated by reference).

In some embodiments, an effective amount of a respiratory virus RNA (e.g., mRNA) vaccine is a dose that is reduced compared to the standard of care dose of a recombinant hMPV, PIV3, RSV, MeV and/or BetaCoV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified hMPV, PIV3, RSV, MeV and/or BetaCoV protein vaccine, or a live attenuated or inactivated hMPV, PIV3, RSV, MeV and/or BetaCoV vaccine, that a physician/clinician or other medical professional would administer to a subject to treat or prevent hMPV, PIV3, RSV, MeV and/or BetaCoV, or a hMPV-, PIV3-, RSV-, MeV- and/or BetaCoV-related condition, while following the standard of care guideline for treating or preventing hMPV, PIV3, RSV, MeV and/or BetaCoV, or a hMPV-, PIV3-, RSV-, MeV- and/or BetaCoV-related condition.

In some embodiments, the anti-antigenic polypeptide (e.g., an anti-hMPV, anti-PIV3, anti-RSV, anti-MeV and/or anti-BetaCoV antigenic polypeptide) antibody titer produced in a subject administered an effective amount of a respiratory virus RNA (e.g., mRNA) vaccine is equivalent to an anti-antigenic polypeptide (e.g., an anti-hMPV, anti-PIV3, anti-RSV, anti-MeV and/or anti-BetaCoV antigenic polypeptide) antibody titer produced in a control subject administered a standard of care dose of a recombinant or purified hMPV, PIV3, RSV, MeV and/or BetaCoV protein vaccine or a live attenuated or inactivated hMPV, PIV3, RSV, MeV and/or BetaCoV vaccine.

In some embodiments, an effective amount of a respiratory virus RNA (e.g., mRNA) vaccine is a dose equivalent to an at least 2-fold reduction in a standard of care dose of a recombinant or purified hMPV, PIV3, RSV, MeV and/or BetaCoV protein vaccine. For example, an effective amount of a respiratory virus RNA (e.g., mRNA) vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified hMPV, PIV3, RSV, MeV and/or BetaCoV protein vaccine. In some embodiments, an effective amount of a respiratory virus RNA (e.g., mRNA) vaccine is a dose equivalent to an at least at least 100-fold, at least 500-fold, or at least 1000-fold reduction in a standard of care dose of a recombinant or purified hMPV, PIV3, RSV, MeV and/or BetaCoV protein vaccine. In some embodiments, an effective amount of a respiratory virus RNA (e.g., mRNA) vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified hMPV, PIV3, RSV, MeV and/or BetaCoV protein vaccine. In some embodiments, the anti-antigenic polypeptide antibody titer produced in a subject administered an effective amount of a respiratory virus RNA (e.g., mRNA) vaccine is equivalent to an anti-antigenic polypeptide antibody titer produced in a control subject administered the standard of care dose of a recombinant or protein hMPV, PIV3, RSV, MeV and/or BetaCoV protein vaccine or a live attenuated or inactivated hMPV, PIV3, RSV, MeV and/or BetaCoV vaccine. In some embodiments, an effective amount of a respiratory virus RNA (e.g., mRNA) vaccine is a dose equivalent to a 2-fold to 1000-fold (e.g., 2-fold to 100-fold, 10-fold to 1000-fold) reduction in the standard of care dose of a recombinant or purified hMPV, PIV3, RSV, MeV and/or BetaCoV protein vaccine, wherein the anti-antigenic polypeptide antibody titer produced in the subject is equivalent to an anti-antigenic polypeptide antibody titer produced in a control subject administered the standard of care dose of a recombinant or purified hMPV, PIV3, RSV, MeV and/or BetaCoV protein vaccine or a live attenuated or inactivated hMPV, PIV3, RSV, MeV and/or BetaCoV vaccine.

In some embodiments, the effective amount of a respiratory virus RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant hMPV, PIV3, RSV, MeV and/or BetaCoV protein vaccine. In some embodiments, the anti-antigenic polypeptide antibody titer produced in the subject is equivalent to an anti-antigenic polypeptide antibody titer produced in a control subject administered the standard of care dose of a recombinant or purified hMPV, PIV3, RSV, MeV and/or BetaCoV protein vaccine or a live attenuated or inactivated hMPV, PIV3, RSV, MeV and/or BetaCoV vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant hMPV, PIV3, RSV, MeV and/or BetaCoV protein vaccine. In some embodiments, an anti-antigenic polypeptide antibody titer produced in the subject is equivalent to an anti-antigenic polypeptide antibody titer produced in a control subject administered the standard of care dose of a recombinant or purified hMPV, PIV3, RSV, MeV and/or BetaCoV protein vaccine or a live attenuated or inactivated hMPV, PIV3, RSV, MeV and/or BetaCoV vaccine.

In some embodiments, the effective amount of a respiratory virus RNA (e.g., mRNA) vaccine is a total dose of 50-1000 μg. In some embodiments, the effective amount of a respiratory virus RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of a respiratory virus RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 μg administered to the subject a total of two times. In some embodiments, the effective amount of a respiratory virus RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of a respiratory virus RNA (e.g., mRNA) vaccine is a total dose of 25, 50, 100, 150, 200, 250, 300, 350, 400, 450, or 500 μg administered to the subject a total of two times.

Examples of Additional Embodiments of the Disclosure

Additional embodiments of the present disclosure are encompassed by the following numbered paragraphs:

1. A respiratory virus vaccine, comprising: at least one ribonucleic acid (RNA) polynucleotide having an open reading frame encoding at least one, at least two, at least three, at least four or at least five antigenic polypeptides selected from human metapneumovirus (hMPV) antigenic polypeptides or immunogenic fragments thereof, human parainfluenza virus type 3 (PIV3) antigenic polypeptides or immunogenic fragments thereof, respiratory syncytial virus (RSV) antigenic polypeptides or immunogenic fragments thereof, measles virus (MeV) antigenic polypeptides or immunogenic fragments thereof, and betacoronavirus (BetaCoV) antigenic polypeptides or immunogenic fragments thereof.

2. The respiratory virus vaccine of paragraph 1, comprising:

at least one RNA polynucleotide having an open reading frame encoding a hMPV antigenic polypeptide or an immunogenic fragment thereof and a PIV3 antigenic polypeptide or an immunogenic fragment thereof; or at least two RNA polynucleotides, one having an open reading frame encoding a hMPV antigenic polypeptide or an immunogenic fragment thereof and one having an open reading frame encoding a PIV3 antigenic polypeptide or an immunogenic fragment thereof.

3. The respiratory virus vaccine of paragraph 2, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13.

4. The respiratory virus vaccine of paragraph 1, comprising:

at least one RNA polynucleotide having an open reading frame encoding a hMPV antigenic polypeptide or an immunogenic fragment thereof and a RSV antigenic polypeptide or an immunogenic fragment thereof; or at least two RNA polynucleotides, one having an open reading frame encoding a hMPV antigenic polypeptide or an immunogenic fragment thereof and one having an open reading frame encoding a RSV antigenic polypeptide or an immunogenic fragment thereof.

5. The respiratory virus vaccine of paragraph 4, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8.

6. The respiratory virus vaccine of paragraph 1, comprising:

at least one RNA polynucleotide having an open reading frame encoding a hMPV antigenic polypeptide or an immunogenic fragment thereof and MeV antigenic polypeptide or an immunogenic fragment thereof; or at least two RNA polynucleotides, one having an open reading frame encoding a hMPV antigenic polypeptide or an immunogenic fragment thereof and one having an open reading frame encoding a MeV antigenic polypeptide or an immunogenic fragment thereof.

7. The respiratory virus vaccine of paragraph 6, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

8. The respiratory virus vaccine of paragraph 1, comprising:

at least one RNA polynucleotide having an open reading frame encoding a hMPV antigenic polypeptide or an immunogenic fragment thereof and a BetaCoV antigenic polypeptide or an immunogenic fragment thereof; or at least two RNA polynucleotides, one having an open reading frame encoding a hMPV antigenic polypeptide or an immunogenic fragment thereof and one having an open reading frame encoding a BetaCoV antigenic polypeptide or an immunogenic fragment thereof.

9. The respiratory virus vaccine of paragraph 8, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

10. The respiratory virus vaccine of paragraph 1, comprising:

at least one RNA polynucleotide having an open reading frame encoding a PIV3 antigenic polypeptide or an immunogenic fragment thereof and a RSV antigenic polypeptide or an immunogenic fragment thereof; or at least two RNA polynucleotides, one having an open reading frame encoding a PIV3 antigenic polypeptide or an immunogenic fragment thereof and one having an open reading frame encoding a RSV antigenic polypeptide or an immunogenic fragment thereof.

11. The respiratory virus vaccine of paragraph 10, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13.

12. The respiratory virus vaccine of paragraph 1, comprising:

at least one RNA polynucleotide having an open reading frame encoding a PIV3 antigenic polypeptide or an immunogenic fragment thereof and a MeV antigenic polypeptide or an immunogenic fragment thereof; or at least two RNA polynucleotides, one having an open reading frame encoding a PIV3 antigenic polypeptide or an immunogenic fragment thereof and one having an open reading frame encoding a MeV antigenic polypeptide or an immunogenic fragment thereof.

13. The respiratory virus vaccine of paragraph 12, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

14. The respiratory virus vaccine of paragraph 1, comprising:

at least one RNA polynucleotide having an open reading frame encoding a PIV3 antigenic polypeptide or an immunogenic fragment thereof and a BetaCoV antigenic polypeptide or an immunogenic fragment thereof; or at least two RNA polynucleotides, one having an open reading frame encoding a PIV3 antigenic polypeptide or an immunogenic fragment thereof and one having an open reading frame encoding a BetaCoV antigenic polypeptide or an immunogenic fragment thereof.

15. The respiratory virus vaccine of paragraph 14, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

16. The respiratory virus vaccine of paragraph 1, comprising:

at least one RNA polynucleotide having an open reading frame encoding a RSV antigenic polypeptide or an immunogenic fragment thereof and a MeV antigenic polypeptide or an immunogenic fragment thereof; or at least two RNA polynucleotides, one having an open reading frame encoding a RSV antigenic polypeptide or an immunogenic fragment thereof and one having an open reading frame encoding a MeV antigenic polypeptide or an immunogenic fragment thereof.

17. The respiratory virus vaccine of paragraph 16, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

18. The respiratory virus vaccine of paragraph 1, comprising:

at least one RNA polynucleotide having an open reading frame encoding a RSV antigenic polypeptide or an immunogenic fragment thereof and a BetaCoV antigenic polypeptide or an immunogenic fragment thereof; or at least two RNA polynucleotides, one having an open reading frame encoding a RSV antigenic polypeptide or an immunogenic fragment thereof and one having an open reading frame encoding a BetaCoV antigenic polypeptide or an immunogenic fragment thereof.

19. The respiratory virus vaccine of paragraph 18, wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

20. The respiratory virus vaccine of paragraph 1, comprising:

at least one RNA polynucleotide having an open reading frame encoding a MeV antigenic polypeptide or an immunogenic fragment thereof and a BetaCoV antigenic polypeptide or an immunogenic fragment thereof; or at least two RNA polynucleotides, one having an open reading frame encoding a MeV antigenic polypeptide or an immunogenic fragment thereof and one having an open reading frame encoding a BetaCoV antigenic polypeptide or an immunogenic fragment thereof.

21. The respiratory virus vaccine of paragraph 20, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

22. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, and a RSV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a PIV3 antigenic polypeptide or an immunogenic fragment thereof, and one having an open reading frame encoding a RSV antigenic polypeptide or an immunogenic fragment thereof.

23. The respiratory virus vaccine of paragraph 22, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13.

24. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, and a MeV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a PIV3 antigenic polypeptide or an immunogenic fragment thereof, and one having an open reading frame encoding a MeV antigenic polypeptide or an immunogenic fragment thereof.

25. The respiratory virus vaccine of paragraph 24, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

26. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, and a BetaCoV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a PIV3 antigenic polypeptide or an immunogenic fragment thereof, and one having an open reading frame encoding a BetaCoV antigenic polypeptide or an immunogenic fragment thereof.

27. The respiratory virus vaccine of paragraph 26, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13 and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

28. The respiratory virus vaccine of paragraph 1, comprising:

at least one RNA polynucleotide having an open reading frame encoding a hMPV antigenic polypeptide or an immunogenic fragment thereof, a RSV antigenic polypeptide or an immunogenic fragment thereof, and a MeV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a RSV antigenic polypeptide or an immunogenic fragment thereof, and one having an open reading frame encoding a MeV antigenic polypeptide or an immunogenic fragment thereof.

29. The respiratory virus vaccine of paragraph 28, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

30. The respiratory virus vaccine of paragraph 1, comprising:

at least one RNA polynucleotide having an open reading frame encoding a hMPV antigenic polypeptide or an immunogenic fragment thereof, a RSV antigenic polypeptide or an immunogenic fragment thereof, and a BetaCoV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a RSV antigenic polypeptide or an immunogenic fragment thereof, and one having an open reading frame encoding a BetaCoV antigenic polypeptide or an immunogenic fragment thereof.

31. The respiratory virus vaccine of paragraph 30, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

32. The respiratory virus vaccine of paragraph 1, comprising:

at least one RNA polynucleotide having an open reading frame encoding a hMPV antigenic polypeptide or an immunogenic fragment thereof, a MeV antigenic polypeptide or an immunogenic fragment thereof, and a BetaCoV antigenic polypeptide or an immunogenic fragment thereof; or at least two or three RNA polynucleotides, one having an open reading frame encoding a hMPV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

33. The respiratory virus vaccine of paragraph 32, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

34. The respiratory virus vaccine of paragraph 1, comprising:

at least one RNA polynucleotide having an open reading frame encoding a PIV3 antigenic polypeptide or an immunogenic fragment thereof, a RSV antigenic polypeptide or an immunogenic fragment thereof, and a MeV antigenic polypeptide or an immunogenic fragment thereof; or at least two or three RNA polynucleotides, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a MeV antigenic polypeptide or an immunogenic fragment thereof.

35. The respiratory virus vaccine of paragraph 34, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

36. The respiratory virus vaccine of paragraph 1, comprising:

at least one RNA polynucleotide having an open reading frame encoding a PIV3 antigenic polypeptide or an immunogenic fragment thereof, a RSV antigenic polypeptide or an immunogenic fragment thereof, and a BetaCoV antigenic polypeptide or an immunogenic fragment thereof; or at least two or three RNA polynucleotides, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a BetaCoV antigenic polypeptide or an immunogenic fragment thereof.

37. The respiratory virus vaccine of paragraph 36, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

38. The respiratory virus vaccine of paragraph 1, comprising:

at least one RNA polynucleotide having an open reading frame encoding a RSV antigenic polypeptide or an immunogenic fragment thereof, a MeV antigenic polypeptide or an immunogenic fragment thereof, and a BetaCoV antigenic polypeptide or an immunogenic fragment thereof; or at least two or three RNA polynucleotides, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

39. The respiratory virus vaccine of paragraph 38, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

40. The respiratory virus vaccine of paragraph 1, comprising:

at least one RNA polynucleotide having an open reading frame encoding a PIV3 antigenic polypeptide or an immunogenic fragment thereof, a MeV antigenic polypeptide or an immunogenic fragment thereof, and a BetaCoV antigenic polypeptide or an immunogenic fragment thereof; or at least two or three RNA polynucleotides, one having an open reading frame encoding a PIV3 antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

41. The respiratory virus vaccine of paragraph 40, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 23-34 or an amino acid sequence having at least 90% or 95% identity to an amino acid sequence identified by any one of SEQ ID NO: 23-34.

42. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a RSV antigenic polypeptide or an immunogenic fragment thereof, and a MeV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a MeV antigenic polypeptide or an immunogenic fragment thereof.

43. The respiratory virus vaccine of paragraph 42, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50.

44. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a RSV antigenic polypeptide or an immunogenic fragment thereof, and a BetaCoV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a RSV antigenic polypeptide or an immunogenic fragment thereof, and one having an open reading frame encoding a BetaCoV antigenic polypeptide or an immunogenic fragment thereof.

45. The respiratory virus vaccine of paragraph 44, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

46. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a MeV antigenic polypeptide or an immunogenic fragment thereof, and a BetaCoV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

47. The respiratory virus vaccine of paragraph 46, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

48. The respiratory virus vaccine of paragraph 1, comprising:

at least one RNA polynucleotide having an open reading frame encoding a hMPV antigenic polypeptide or an immunogenic fragment thereof, a RSV antigenic polypeptide or an immunogenic fragment thereof, a MeV antigenic polypeptide or an immunogenic fragment thereof, and a BetaCoV antigenic polypeptide or an immunogenic fragment thereof; or at least two, three or four RNA polynucleotides, one having an open reading frame encoding a hMPV antigenic polypeptide or an immunogenic fragment thereof, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

49. The respiratory virus vaccine of paragraph 48, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

50. The respiratory virus vaccine of paragraph 1, comprising:

at least one RNA polynucleotide having an open reading frame encoding a PIV3 antigenic polypeptide or an immunogenic fragment thereof, a RSV antigenic polypeptide or an immunogenic fragment thereof, a MeV antigenic polypeptide or an immunogenic fragment thereof, and a BetaCoV antigenic polypeptide or an immunogenic fragment thereof; or at least two, three or four RNA polynucleotides, one having an open reading frame encoding a PIV3 antigenic polypeptide or an immunogenic fragment thereof, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

51. The respiratory virus vaccine of paragraph 50, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

52. The respiratory virus vaccine of paragraph 1, comprising:

at least one RNA polynucleotide having an open reading frame encoding a hMPV antigenic polypeptide or an immunogenic fragment thereof, a PIV3 antigenic polypeptide or an immunogenic fragment thereof, a RSV antigenic polypeptide or an immunogenic fragment thereof, a MeV antigenic polypeptide or an immunogenic fragment thereof, and a BetaCoV antigenic polypeptide or an immunogenic fragment thereof; or at least two, three, four or five RNA polynucleotides, one having an open reading frame encoding a hMPV antigenic polypeptide or an immunogenic fragment thereof, one having an open reading frame encoding a PIV3 antigenic polypeptide or an immunogenic fragment thereof, one having an open reading frame encoding a RSV antigenic polypeptide or an immunogenic fragment thereof, one having an open reading frame encoding a MeV antigenic polypeptide or an immunogenic fragment thereof, and one having an open reading frame encoding a BetaCoV antigenic polypeptide or an immunogenic fragment thereof.

53. The respiratory virus vaccine of paragraph 52, wherein the hMPV antigenic polypeptide comprises an amino acid sequence identified by any one of SEQ ID NO: 5-8 or an amino acid sequence having at least 90% or 95% identity to an amino acid sequence identified by any one of SEQ ID NO: 5-8, wherein the PIV3 antigenic polypeptide comprises an amino acid sequence identified by any one of SEQ ID NO: 12-13 or an amino acid sequence having at least 90% or 95% identity to an amino acid sequence identified by any one of SEQ ID NO: 12-13, wherein the MeV antigenic polypeptide comprises an amino acid sequence identified by any one of SEQ ID NO: 47-50 or an amino acid sequence having at least 90% or 95% identity to an amino acid sequence identified by any one of SEQ ID NO: 47-50, and/or wherein the BetaCoV antigenic polypeptide comprises an amino acid sequence identified by any one of SEQ ID NO: 24-34 or an amino acid sequence having at least 90% or 95% identity to an amino acid sequence identified by any one of SEQ ID NO: 24-34.

54. The vaccine of any one of paragraphs 1-53, wherein at least one RNA polynucleotide has less than 80% identity to wild-type mRNA sequence.

55. The vaccine of any one of paragraphs 1-53, wherein at least one RNA polynucleotide has at least 80% identity to wild-type mRNA sequence, but does not include wild-type mRNA sequence.

56. The vaccine of any one of paragraphs 1-55, wherein at least one antigenic polypeptide has membrane fusion activity, attaches to cell receptors, causes fusion of viral and cellular membranes, and/or is responsible for binding of the virus to a cell being infected.

57. The vaccine of any one of paragraphs 1-56, wherein at least one RNA polynucleotide comprises at least one chemical modification.

58. The vaccine of paragraph 57, wherein the chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

59. The vaccine of paragraph 57 or 58, wherein the chemical modification is in the 5-position of the uracil.

60. The vaccine of any one of paragraphs 57-59, wherein the chemical modification is a N1-methylpseudouridine or N1-ethylpseudouridine.

61. The vaccine of any one of paragraphs 57-60, wherein at least 80%, at least 90% or 100% of the uracil in the open reading frame have a chemical modification.

62. The vaccine of any one of paragraphs 1-61, wherein at least one RNA polynucleotide further encodes at least one 5' terminal cap, optionally wherein the 5' terminal cap is 7mG(5')ppp(5')NlmpNp.

63. The vaccine of any one of paragraphs 1-62, wherein at least one antigenic polypeptide or immunogenic fragment thereof is fused to a signal peptide selected from: a HuIgGk signal peptide (METPAQLLFLLLLWLPDTTG; SEQ ID NO: 15); IgE heavy chain epsilon-1 signal peptide (MDWTWILFLVAAATRVHS; SEQ ID NO: 16); Japanese encephalitis PRM signal sequence (MLG-SNSGQRVVFTILLLLVAPAYS; SEQ ID NO: 17), VSVg protein signal sequence (MKCLLYLAFLFIGVNCA; SEQ ID NO: 18) and Japanese encephalitis JEV signal sequence (MWLVSLAIVTACAGA; SEQ ID NO:19).

64. The vaccine of paragraph 63, wherein the signal peptide is fused to the N-terminus or the C-terminus of at least one antigenic polypeptide.

65. The vaccine of any one of paragraphs 1-64, wherein the antigenic polypeptide or immunogenic fragment thereof comprises a mutated N-linked glycosylation site.

66. The vaccine of any one of paragraphs 1-65 formulated in a nanoparticle, optionally a a lipid nanoparticle.

67. The vaccine of paragraph 66, wherein the lipid nanoparticle comprises a cationic lipid, a PEG-modified lipid, a sterol and a non-cationic lipid; optionally wherein the lipid nanoparticle carrier comprises a molar ratio of about 20-60% cationic lipid, 0.5-15% PEG-modified lipid, 25-55% sterol, and 25% non-cationic lipid; optionally wherein the cationic lipid is an ionizable cationic lipid and the non-cationic lipid is a neutral lipid, and the sterol is a cholesterol; and optionally wherein the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319). Formula (II) 68. The vaccine of paragraph 66 or 67, wherein the nanoparticle (e.g., lipid nanoparticle) comprises a compound of Formula (I) and/or Formula (II), optionally Compound 3, 18, 20, 25, 26, 29, 30, 60, 108-112, or 122.

69. The vaccine of any one of paragraphs 1-68 further comprising an adjuvant, optionally a flagellin protein or peptide that optionally comprises an amino acid sequence identified by any one of SEQ ID NO: 54-56.

70. The vaccine of any one of paragraphs 1-69, wherein the open reading frame is codon-optimized.

71. The vaccine of any one of paragraphs 1-70 formulated in an effective amount to produce an antigen-specific immune response.

72. A method of inducing an immune response in a subject, the method comprising administering to the subject the vaccine of any one of paragraphs 1-71 in an amount effective to produce an antigen-specific immune response in the subject.

73. The method of paragraph 72, wherein the subject is administered a single dose of the vaccine, or wherein the subject is administered a first dose and then a booster dose of the vaccine.

74. The method of paragraph 72 or 73, wherein the vaccine is administered to the subject by intradermal injection or intramuscular injection.

75. The method of any one of paragraphs 72-74, wherein an anti-antigenic polypeptide antibody titer produced in the subject is increased by at least 1 log relative to a control, and/or wherein the anti-antigenic polypeptide antibody titer produced in the subject is increased at least 2 times relative to a control.

76. The method of any one of paragraphs 72-75, wherein the control is an anti-antigenic polypeptide antibody titer produced in a subject who has not been administered a vaccine against the virus, and/or wherein the control is an anti-antigenic polypeptide antibody titer produced in a subject who has been administered a live attenuated vaccine or an inactivated vaccine against the virus, and/or, wherein the control is an anti-antigenic polypeptide antibody titer produced in a subject who has been administered a recombinant protein vaccine or purified protein vaccine against the virus, and/or wherein the control is an anti-antigenic polypeptide antibody titer produced in a subject who has been administered a VLP vaccine against the virus.

77. The method of any one of paragraphs 72-76, wherein the effective amount is a dose equivalent to an at least 2-fold reduction in the standard of care dose of a recombinant protein vaccine or a purified protein vaccine against the virus, and wherein an anti-antigenic polypeptide antibody titer produced in the subject is equivalent to an anti-antigenic polypeptide antibody titer produced in a control subject administered the standard of care dose of a recombinant protein vaccine or a purified protein vaccine against the virus, respectively; and/or wherein the effective amount is a dose equivalent to an at least 2-fold reduction in the standard of care dose of a live attenuated vaccine or an inactivated vaccine against the virus, and wherein an anti-antigenic polypeptide antibody titer produced in the subject is equivalent to an anti-antigenic polypeptide antibody titer produced in a control subject administered the standard of care dose of a live attenuated vaccine or an inactivated vaccine against the virus, respectively; and/or wherein the effective amount is a dose equivalent to an at least 2-fold reduction in the standard of care dose of a VLP vaccine against the virus, and wherein an anti-antigenic polypeptide antibody titer produced in the subject is equivalent to an anti-antigenic polypeptide antibody titer produced in a control subject administered the standard of care dose of a VLP vaccine against the virus.

78. The method of any one of paragraphs 72-77, wherein the effective amount is a total dose of 50 μg-1000 μg, optionally wherein the effective amount is a dose of 25 μg, 100 μg, 400 μg, or 500 μg administered to the subject a total of two times.

79. The method of any one of paragraphs 72-78, wherein the efficacy of the vaccine against the virus is greater than 65%; and/or wherein the vaccine immunizes the subject against the virus for up to 2 years or wherein the vaccine immunizes the subject against the virus for more than 2 years.

80. The method of any one of paragraphs 72-79, wherein the subject has an age of about 5 years old or younger or wherein the subject has an age of about 60 years old or older; and/or wherein the subject has a chronic pulmonary disease; and/or the subject has been exposed to the virus, wherein the subject is infected with the virus, or wherein the subject is at risk of infection by the virus; and/or wherein the subject is immunocompromised.

81. The respiratory virus vaccine of any one of paragraphs 1-71, comprising at least one (e.g., at least two, at least three, at least four, or at least five) RNA polynucleotide having an open reading frame encoding at least one (e.g., at least two, at least three, at least four, or at least five) antigenic polypeptide selected from hMPV antigenic polypeptides (SEQ ID NO: 5-8), PIV3 antigenic polypeptides (SEQ ID NO: 12-13), RSV antigenic polypeptides, MeV antigenic polypeptides (SEQ ID NO: 47-50) and BetaCoV antigenic polypeptides (e.g., MERS-CoV, SARS-CoV, HCoV-OC43, HCoV-229E, HCoV-NL63, HCoV-NL, HCoV-NH or HCoV-HKU1; (SEQ ID NO: 24-34)), formulated in a cationic lipid nanoparticle (a) having a molar ratio of about 20-60% cationic lipid, about 5-25% non-cationic lipid, about 25-55% sterol, and about 0.5-15% PEG-modified lipid, and/or (b) comprising a compound of Formula (I) and/or Formula (II), wherein the at least one (e.g., at least two, at least three, at least four, or at least five) RNA polynucleotide comprises at least one chemical modification.

82. The respiratory virus vaccine of any one of paragraphs 1-71, comprising at least one (e.g., at least two, at least three, at least four, or at least five) RNA polynucleotide having an open reading frame encoding at least one (e.g., at least two, at least three, at least four, or at least five) antigenic polypeptide selected from hMPV antigenic polypeptides (SEQ ID NO: 5-8), PIV3 antigenic polypeptides (SEQ ID NO: 12-13), RSV antigenic polypeptides, MeV antigenic polypeptides (SEQ ID NO: 47-50) and BetaCoV antigenic polypeptides (e.g., MERS-CoV, SARS-CoV, HCoV-OC43, HCoV-229E, HCoV-NL63, HCoV-NL, HCoV-NH or HCoV-HKU1; (SEQ ID NO: 24-34)), formulated in a cationic lipid nanoparticle (a) having a molar ratio of about 20-60% cationic lipid, about 5-25% non-cationic lipid, about 25-55% sterol, and about 0.5-15% PEG-modified lipid, and/or (b) comprising at least one (e.g., at least 1, 2, 3, 4, 5, 6, 7, 8, 9, 10, 11, 12, 13, or 14) Compound selected from Compounds 3, 18, 20, 25, 26, 29, 30, 60, 108-112 and 122.

83. The respiratory virus vaccine of paragraphs 81 or 82, wherein the at least one antigenic polypeptide is selected from hMPV antigenic polypeptides (e.g., SEQ ID NO: 5-8).

84. The respiratory virus vaccine of any one of paragraphs 81-83, wherein the at least one antigenic polypeptide is selected from PIV3 antigenic polypeptides (e.g., SEQ ID NO: 12-13).

85. The respiratory virus vaccine of any one of paragraphs 81-84, wherein the at least one antigenic polypeptide is selected from RSV antigenic polypeptides.

86. The respiratory virus vaccine of any one of paragraphs 81-85, wherein the at least one antigenic polypeptide is selected from MeV antigenic polypeptides (e.g., SEQ ID NO: 47-50).

87. The respiratory virus vaccine of any one of paragraphs 81-86, wherein the at least one antigenic polypeptide is selected from BetaCoV antigenic polypeptides (e.g., SEQ ID NO: 24-34).

88. The respiratory virus vaccine of paragraph 87, wherein the BetaCoV antigenic polypeptides are MERS antigenic polypeptides.

89. The respiratory virus vaccine of paragraph 87, wherein the BetaCoV antigenic polypeptides are SARS antigenic polypeptides.

90. The respiratory virus vaccine of any one of paragraphs 81-89, wherein the at least one (e.g., at least two, at least three, at least four, or at least five) RNA polynucleotide comprises at least one chemical modification (e.g., selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine).

91. A respiratory virus vaccine, comprising:

at least one messenger ribonucleic acid (mRNA) polynucleotide having a 5' terminal cap, an open reading frame encoding at least one respiratory virus antigenic polypeptide, and a 3' polyA tail.

92. The vaccine of paragraph 91, wherein the at least one mRNA polynucleotide comprises a sequence identified by any one of SEQ ID NO: 57-80.

93. The vaccine of paragraph 91 or 92, wherein the 5' terminal cap is or comprises 7mG(5')ppp(5')NlmpNp.

94. The vaccine of any one of paragraphs 91-93, wherein 100% of the uracil in the open reading frame is modified to include N1-methyl pseudouridine at the 5-position of the uracil.

95. The vaccine of any one of paragraphs 91-94, wherein the vaccine is formulated in a lipid nanoparticle comprising: DLin-MC3-DMA; cholesterol; 1,2-Distearoyl-sn-glycero-3-phosphocholine (DSPC); and polyethylene glycol (PEG) 2000-DMG.

96. The vaccine of paragraph 95, wherein the lipid nanoparticle further comprises trisodium citrate buffer, sucrose and water.

97. A respiratory syncytial virus (RSV) vaccine, comprising:

at least one messenger ribonucleic acid (mRNA) polynucleotide having a 5' terminal cap 7mG(5')ppp(5')NlmpNp, a sequence identified by any one of SEQ ID NO: 57-80 and a 3' polyA tail, formulated in a lipid nanoparticle comprising DLin-MC3-DMA, cholesterol, 1,2-Distearoyl-sn-glycero-3-phosphocholine (DSPC), and polyethylene glycol (PEG) 2000-DMG, wherein the uracil nucleotides of the sequence identified by any one of SEQ ID NO: 57-80 are modified to include N1-methyl pseudouridine at the 5-position of the uracil nucleotide.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Manufacture of Polynucleotides

According to the present disclosure, the manufacture of polynucleotides and/or parts or regions thereof may be accomplished utilizing the methods taught in International Publication WO2014/152027, entitled "Manufacturing Methods for Production of RNA Transcripts," the contents of which is incorporated herein by reference in its entirety.

Purification methods may include those taught in International Publication WO2014/152030 and International Publication WO2014/152031, each of which is incorporated herein by reference in its entirety.

Detection and characterization methods of the polynucleotides may be performed as taught in International Publication WO2014/144039, which is incorporated herein by reference in its entirety.

Characterization of the polynucleotides of the disclosure may be accomplished using polynucleotide mapping, reverse transcriptase sequencing, charge distribution analysis, detection of RNA impurities, or any combination of two or more of the foregoing. "Characterizing" comprises determining the RNA transcript sequence, determining the purity of the RNA transcript, or determining the charge heterogeneity of the RNA transcript, for example. Such methods are taught in, for example, International Publication WO2014/144711 and International Publication WO2014/144767, the content of each of which is incorporated herein by reference in its entirety.

Example 2: Chimeric Polynucleotide Synthesis

According to the present disclosure, two regions or parts of a chimeric polynucleotide may be joined or ligated using triphosphate chemistry. A first region or part of 100 nucleotides or less is chemically synthesized with a 5' monophosphate and terminal 3'desOH or blocked OH, for example. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

For ligation methods, ligation with DNA T4 ligase, followed by treatment with DNase should readily avoid concatenation.

The entire chimeric polynucleotide need not be manufactured with a phosphate-sugar backbone. If one of the regions or parts encodes a polypeptide, then such region or part may comprise a phosphate-sugar backbone.

Ligation is then performed using any known click chemistry, orthoclick chemistry, solulink, or other bioconjugate chemistries known to those in the art.

Synthetic Route

The chimeric polynucleotide may be made using a series of starting segments. Such segments include:

(a) a capped and protected 5' segment comprising a normal 3'OH (SEG. 1)

(b) a 5' triphosphate segment, which may include the coding region of a polypeptide and a normal 3'OH (SEG. 2)

(c) a 5' monophosphate segment for the 3' end of the chimeric polynucleotide (e.g., the tail) comprising cordycepin or no 3'OH (SEG. 3)

After synthesis (chemical or IVT), segment 3 (SEG. 3) may be treated with cordycepin and then with pyrophosphatase to create the 5' monophosphate.

Segment 2 (SEG. 2) may then be ligated to SEG. 3 using RNA ligase. The ligated polynucleotide is then purified and treated with pyrophosphatase to cleave the diphosphate. The treated SEG.2-SEG. 3 construct may then be purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA may be performed using 2× KAPA HIFI™ HotStart ReadyMix by Kapa Biosystems (Woburn, MA). This system includes 2× KAPA ReadyMix 12.5 μl; Forward Primer (10 μM) 0.75 μl; Reverse Primer (10 μM) 0.75 μl; Template cDNA 100 ng; and $dH_20$ diluted to 25.0 μl. The reaction conditions may be at 95° C. for 5 min. The reaction may be performed for 25 cycles of 98° C. for 20 sec, then 58° C. for 15 sec, then 72° C. for 45 sec, then 72° C. for 5 min, then 4° C. to termination.

The reaction may be cleaned up using Invitrogen's PURELINK™ PCR Micro Kit (Carlsbad, CA) per manufacturer's instructions (up to 5 μg). Larger reactions may require a cleanup using a product with a larger capacity. Following the cleanup, the cDNA may be quantified using the NANODROP™ and analyzed by agarose gel electrophoresis to confirm that the cDNA is the expected size. The cDNA may then be submitted for sequencing analysis before proceeding to the in vitro transcription reaction.

Example 4: In Vitro Transcription (IVT)

The in vitro transcription reaction generates RNA polynucleotides. Such polynucleotides may comprise a region or part of the polynucleotides of the disclosure, including chemically modified RNA (e.g., mRNA) polynucleotides. The chemically modified RNA polynucleotides can be uniformly modified polynucleotides. The in vitro transcription reaction utilizes a custom mix of nucleotide triphosphates (NTPs). The NTPs may comprise chemically modified NTPs, or a mix of natural and chemically modified NTPs, or natural NTPs.

A typical in vitro transcription reaction includes the following:

| | | |
|---|---|---|
| 1) | Template cDNA | 1.0 μg |
| 2) | 10× transcription buffer (400 mM Tris-HCl pH 8.0, 190 mM $MgCl_2$, 50 mM DTT, 10 mM Spermidine) | 2.0 μl |
| 3) | Custom NTPs (25 mM each) | 0.2 μl |
| 4) | RNase Inhibitor | 20 U |
| 5) | T7 RNA polymerase | 3000 U |
| 6) | $dH_20$ | up to 20.0 μl. and |
| 7) | Incubation at 37° C. for 3 hr-5 hrs. | |

The crude IVT mix may be stored at 4° C. overnight for cleanup the next day. 1 U of RNase-free DNase may then be used to digest the original template. After 15 minutes of incubation at 37° C., the mRNA may be purified using Ambion's MEGACLEAR™ Kit (Austin, TX) following the manufacturer's instructions. This kit can purify up to 500 μg of RNA. Following the cleanup, the RNA polynucleotide may be quantified using the NanoDrop and analyzed by agarose gel electrophoresis to confirm the RNA polynucleotide is the proper size and that no degradation of the RNA has occurred.

Example 5: Enzymatic Capping

Capping of a RNA polynucleotide is performed as follows where the mixture includes: IVT RNA 60 μg-180 μg and $dH_20$ up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_20$ (Up to 28 μl); and incubation at 37° C. for 30 minutes for 60 μg RNA or up to 2 hours for 180 μg of RNA.

The RNA polynucleotide may then be purified using Ambion's MEGACLEAR™ Kit (Austin, TX) following the manufacturer's instructions. Following the cleanup, the RNA may be quantified using the NANODROP™ (ThermoFisher, Waltham, MA) and analyzed by agarose gel electrophoresis to confirm the RNA polynucleotide is the proper size and that no degradation of the RNA has occurred. The RNA polynucleotide product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing capped IVT RNA (100 μl); RNase Inhibitor (20 U); 10× Tailing Buffer (0.5 M Tris-HCl (pH 8.0), 2.5 M NaCl, 100 mM $MgCl_2$) (12.0 μl); 20 mM ATP (6.0 μl); Poly-A Polymerase (20 U); $dH_20$ up to 123.5 μl and incubation at 37° C. for 30 min. If the poly-A tail is already in the transcript, then the tailing reaction may be skipped and proceed directly to cleanup with Ambion's MEGACLEAR™ kit (Austin, TX) (up to 500 μg). Poly-A Polymerase may be a recombinant enzyme expressed in yeast.

It should be understood that the processivity or integrity of the poly A tailing reaction may not always result in an exact size polyA tail. Hence, polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 7: Natural 5' Caps and 5' Cap Analogues

5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5')G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 8: Capping Assays

Protein Expression Assay

Polynucleotides (e.g., mRNA) encoding a polypeptide, containing any of the caps taught herein, can be transfected into cells at equal concentrations. The amount of protein secreted into the culture medium can be assayed by ELISA at 6, 12, 24 and/or 36 hours post-transfection. Synthetic polynucleotides that secrete higher levels of protein into the medium correspond to a synthetic polynucleotide with a higher translationally-competent cap structure.

Purity Analysis Synthesis

RNA (e.g., mRNA) polynucleotides encoding a polypeptide, containing any of the caps taught herein can be compared for purity using denaturing Agarose-Urea gel electrophoresis or HPLC analysis. RNA polynucleotides with a single, consolidated band by electrophoresis correspond to the higher purity product compared to polynucleotides with multiple bands or streaking bands. Chemically modified RNA polynucleotides with a single HPLC peak also correspond to a higher purity product. The capping reaction with a higher efficiency provides a more pure polynucleotide population.

Cytokine Analysis

RNA (e.g., mRNA) polynucleotides encoding a polypeptide, containing any of the caps taught herein can be transfected into cells at multiple concentrations. The amount of pro-inflammatory cytokines, such as TNF-alpha and IFN-beta, secreted into the culture medium can be assayed by ELISA at 6, 12, 24 and/or 36 hours post-transfection. RNA polynucleotides resulting in the secretion of higher levels of pro-inflammatory cytokines into the medium correspond to a polynucleotides containing an immune-activating cap structure.

Capping Reaction Efficiency

RNA (e.g., mRNA) polynucleotides encoding a polypeptide, containing any of the caps taught herein can be analyzed for capping reaction efficiency by LC-MS after nuclease treatment. Nuclease treatment of capped polynucleotides yield a mixture of free nucleotides and the capped 5'-5-triphosphate cap structure detectable by LC-MS. The amount of capped product on the LC-MS spectra can be expressed as a percent of total polynucleotide from the reaction and correspond to capping reaction efficiency. The cap structure with a higher capping reaction efficiency has a higher amount of capped product by LC-MS.

Example 9: Agarose Gel Electrophoresis of Modified RNA or RT PCR Products

Individual RNA polynucleotides (200-400 ng in a 20 μl volume) or reverse transcribed PCR products (200-400 ng) may be loaded into a well on a non-denaturing 1.2% Agarose E-Gel (Invitrogen, Carlsbad, CA) and run for 12-15 minutes, according to the manufacturer protocol.

Example 10: Nanodrop Modified RNA Quantification and UV Spectral Data

Chemically modified RNA polynucleotides in TE buffer (1 μl) are used for Nanodrop UV absorbance readings to quantitate the yield of each polynucleotide from an chemical synthesis or in vitro transcription reaction.

Example 11: Formulation of Modified mRNA Using Lipidoids

RNA (e.g., mRNA) polynucleotides may be formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may be used as a starting point. After formation of the particle, polynucleotide is added and allowed to integrate with the complex. The encapsulation efficiency is determined using a standard dye exclusion assays.

Example 12: Immunogenicity Study

The instant study is designed to test the immunogenicity in mice of candidate hMPV vaccines comprising a mRNA polynucleotide encoding Fusion (F) glycoprotein, major surface glycoprotein G, or a combination thereof, obtained from hMPV.

Mice are immunized intravenously (IV), intramuscularly (IM), or intradermally (ID) with candidate vaccines. Candidate vaccines are chemically modified or unmodified. A total of four immunizations are given at 3-week intervals (i.e., at weeks 0, 3, 6, and 9), and sera are collected after each immunization until weeks 33-51. Serum antibody titers against Fusion (F) glycoprotein or major surface glycoprotein (G) protein are determined by ELISA. Sera collected from each mouse during weeks 10-16 are pooled, and total IgG purified. Purified antibodies are used for immunoelectron microscopy, antibody-affinity testing, and in vitro protection assays.

Example 13: hMPV Rodent Challenge

The instant study is designed to test the efficacy in cotton rats of candidate hMPV vaccines against a lethal challenge using an hMPV vaccine comprising mRNA encoding Fusion (F) glycoprotein, major surface glycoprotein G, or a combination of both antigens obtained from hMPV. Cotton rats are challenged with a lethal dose of the hMPV.

Animals are immunized intravenously (IV), intramuscularly (IM), or intradermally (ID) at week 0 and week 3 with candidate hMPV vaccines with and without adjuvant. Candidate vaccines are chemically modified or unmodified. The animals are then challenged with a lethal dose of hMPV on week 7 via IV, IM or ID. Endpoint is day 13 post infection, death or euthanasia. Animals displaying severe illness as determined by >30% weight loss, extreme lethargy or paralysis are euthanized. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %) or DLin-MC3-DMA (50 mol %), the non-cationic lipid is DSPC (10 mol %), the PEG lipid is PEG-DOMG (1.5 mol %) and the structural lipid is cholesterol (38.5 mol %), for example.

Example 14: Immunogenicity of hMPV mRNA Vaccine in BALB/c Mice

Figures 2A, 2B, 2C:
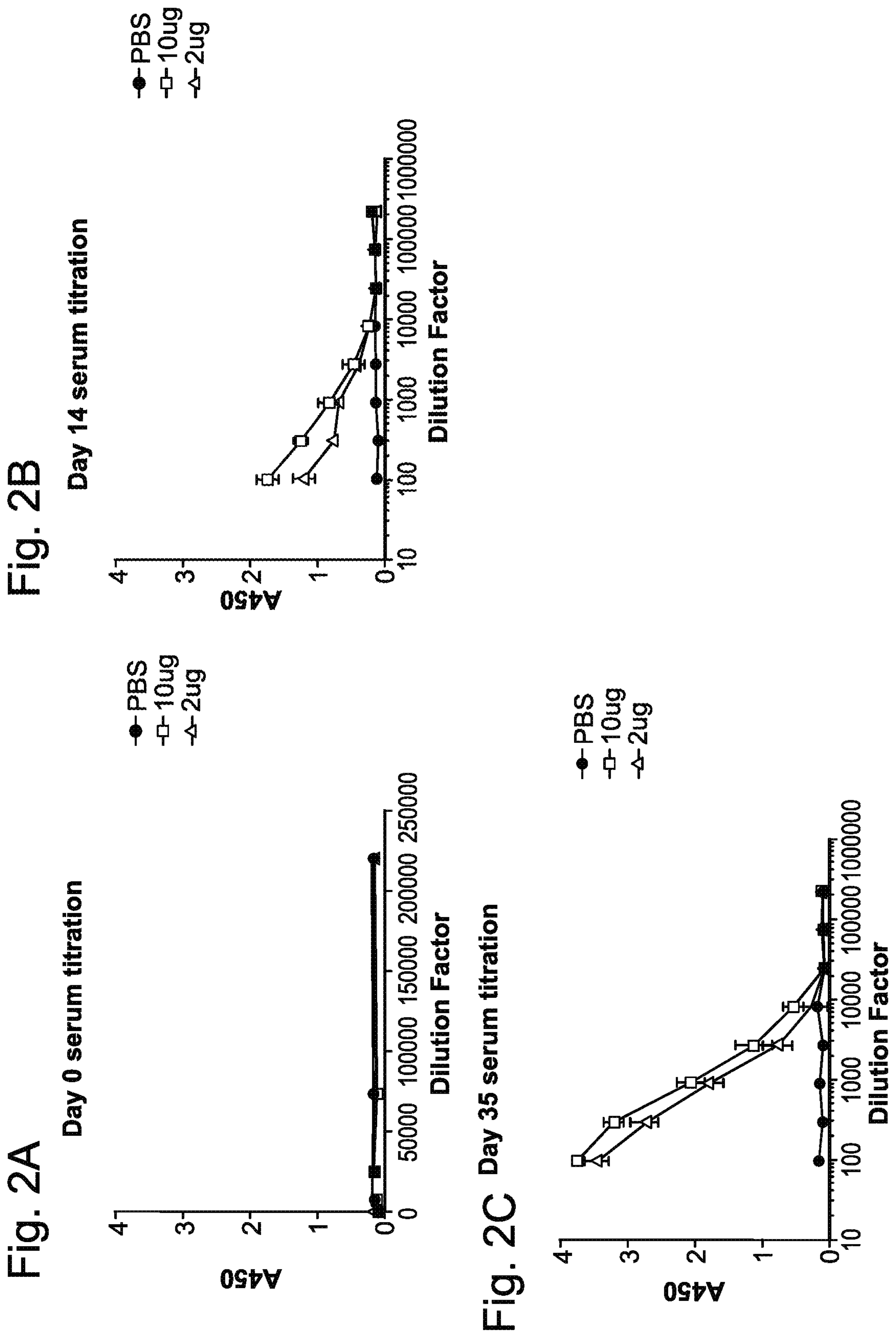
FIGS. 2A-2C are graphs showing the levels of anti-hMPV fusion protein-specific antibodies in the serum of mice immunized with hMPV mRNA vaccines on day 0 (FIG. 2A), day 14 (FIG. 2B) and day 35 (FIG. 2C) post immunization. The mice were immunized with a single dose (2 μg or 10 μg) on day 0 and were given a boost dose (2 μg or 10 μg) on day 21. hMPV fusion protein-specific antibodies were detected at up to 1:10000 dilution of serum on day 35 for both doses.

The instant study was designed to test the immunogenicity in BALB/c mice of hMPV vaccines comprising an mRNA polynucleotide encoding the hMPV Fusion (F) glycoprotein. The mRNA polynucleotide encodes the full-length fusion protein and comprises the wild-type nucleotide sequence obtained from the hMPV A2a strain. Mice were divided into 3 groups (n=8 for each group) and immunized intramuscularly (IM) with PBS, a 10 μg dose of mRNA vaccines encoding hMPV fusion protein, or a 2 μg dose of mRNA vaccines encoding hMPV fusion protein. A total of two immunizations were given at 3-week intervals (i.e., at weeks 0, and 3 weeks), and sera were collected after each immunization according to the schedule described in Table 1. Serum antibody titers against hMPV fusion glycoprotein were determined by ELISA and antibodies were detected in the sera collected on day 14 onward. Both vaccine doses tested induced comparable levels of immune response in mice (FIGS. 2A-2C).

Figures 3A, 3B, 3C:
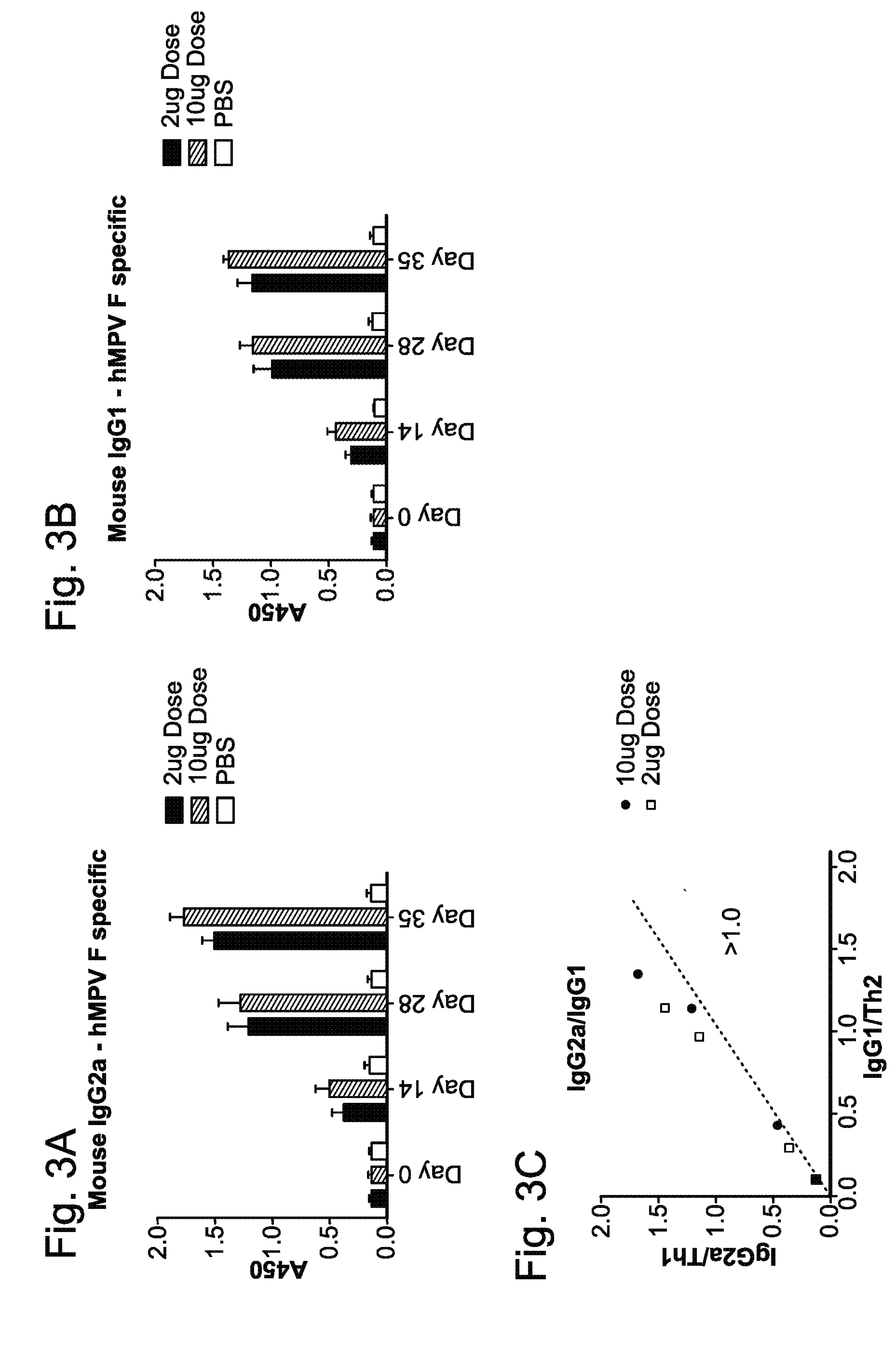
FIGS. 3A-3C are graphs showing the result of IgG isotyping in the serum of mice immunized with hMPV mRNA vaccines. The levels of hMPV fusion protein-specific IgG2a (FIG. 3A) and IgG1 (FIG. 3B) antibodies in the serum are measured by ELISA.

Additionally, mice sera were used for IgG isotyping (FIGS. 3A-3C). Both hMPV fusion protein-specific IgG1 and IgG2a were detected in mice sera. hMPV fusion protein mRNA vaccine also induced Th1 and Th2 cytokine responses, with a Th1 bias.

Figure 4:
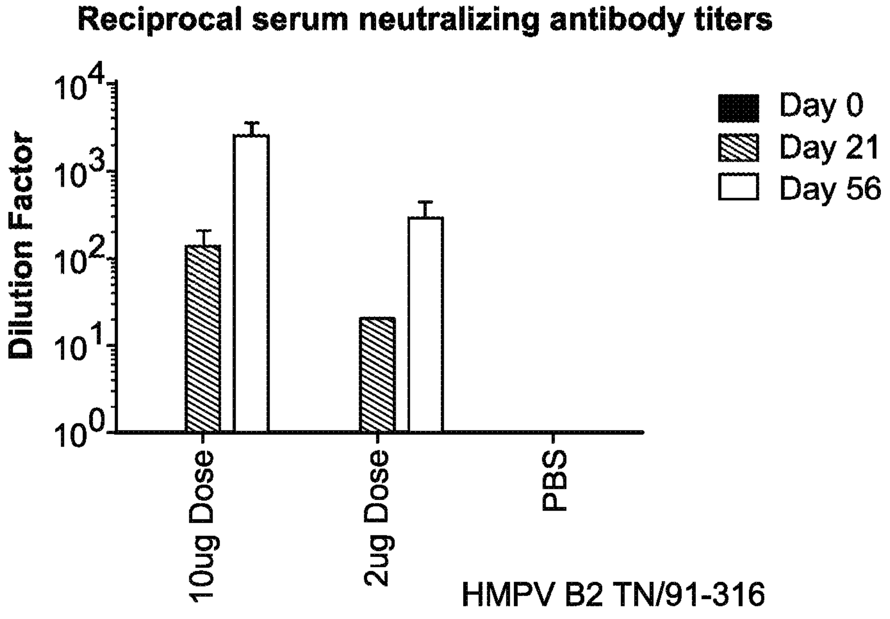
FIG. 4 is a graph showing in vitro neutralization of a hMPV B2 strain (TN/91-316) using the sera of mice immunized with a mRNA vaccine encoding hMPV fusion protein. Mouse serum obtained from mice receiving a 10 μg or a 2 μg dose contained hMPV-neutralizing antibodies.

Sera from mice immunized with either 10 μg or 2 μg doses of the hMPV fusion protein mRNA vaccine contain neutralizing antibodies. The ability of these antibodies to neutralize hMPV B2 strain was also tested. The antibody-containing sera successfully neutralized the hMPV B2 virus (FIG. 4).

Example 15: T-Cell Stimulation

The instant study was designed to test T-cell stimulation in the splenocytes of mice immunized with mRNA vaccines encoding hMPV fusion protein, as described herein. Immunization of BALB/c mice was performed as described in Example 14. The splenocytes for each group were pooled and split into two parts. One part of splenocytes from each group of mice was stimulated with hMPV-free media, Concanavalin A or a hMPV fusion protein peptide pool comprising 15-mers (15 amino acids long); while the other part of splenocytes from each group of mice was stimulated with hMPV-free media, Concanavalin A or inactivated hMPV virus. Secreted mouse cytokines were measured using the Meso Scale Discovery (MSD) assay.

Figures 5A, 5B, 5C:
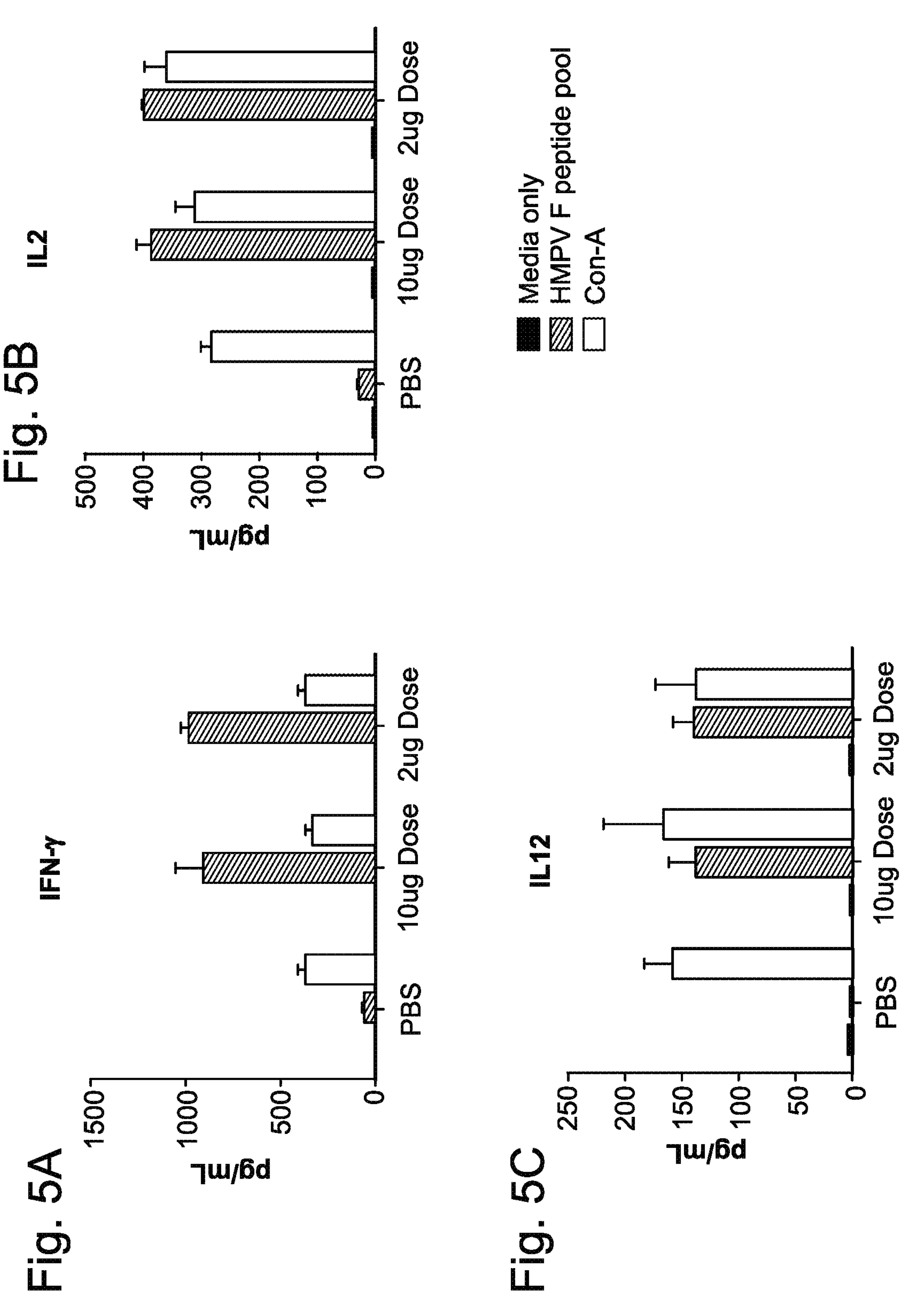
FIGS. 5A-5C are graphs showing a Th1 cytokine response induced by a hMPV fusion peptide pool (15-mers-5O (overlap)) in splenocytes isolated from mice immunized with the hMPV mRNA vaccines. Virus-free media was used as a negative control and Concanavalin A (ConA, a positive control for splenocyte stimulation) was included. The cytokines tested included IFN-γ (FIG. 5A), IL-2 (FIG. 5B) and IL12 (FIG. 5C).
Figures 6A, 6B, 6C, 6D, 6E:
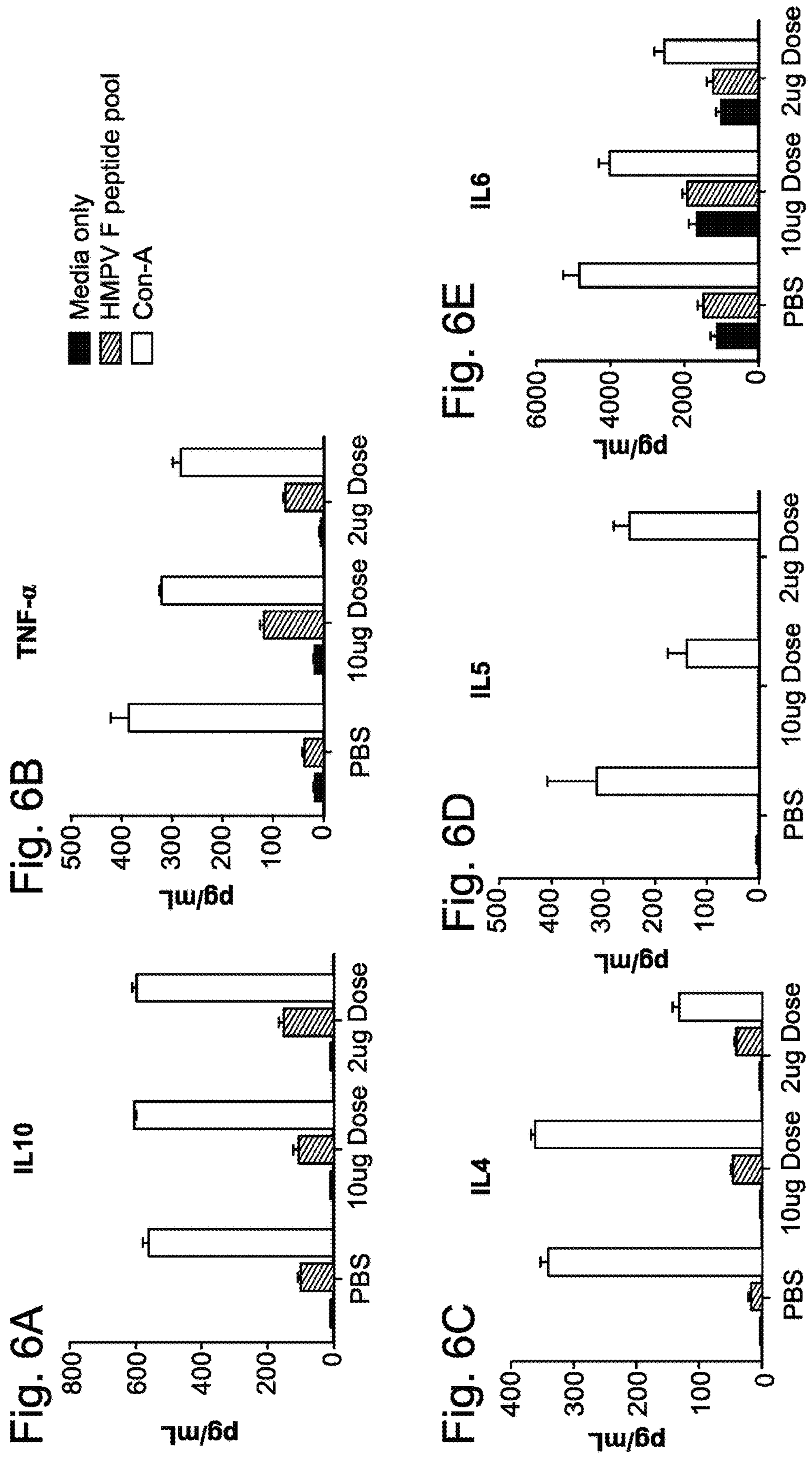
FIGS. 6A-6E are graphs showing the Th2 cytokine response induced by a hMPV fusion peptide pool (15-mers-5O) in splenocytes isolated from mice immunized with the hMPV mRNA vaccines. Virus-free media was used as a negative control and Concanavalin A was also included. The cytokines tested included IL-10 (FIG. 6A), TNF-α (FIG. 6B), IL4 (FIG. 6C), IL-5 (FIG. 6D) and IL-6 (FIG. 6E).

Cytokines specific to Th1 or Th2 responses were measured. For Th1 response, IFN—Y, IL2 and IL12 were detected from splenocytes stimulated with the hMPV fusion protein peptide pool at a level comparable to that of Concanavalin A (FIGS. 5A-5C). For a Th2 response, the hMPV fusion protein peptide pool induced the secretion of detectable IL10, TNF-α, IL4 and IL, but not IL5, while Concanavalin A stimulated the secretion of all the above-mentioned Th2 cytokines (FIGS. 6A-6E) at a much higher level.

Figures 7A, 7B, 7C:
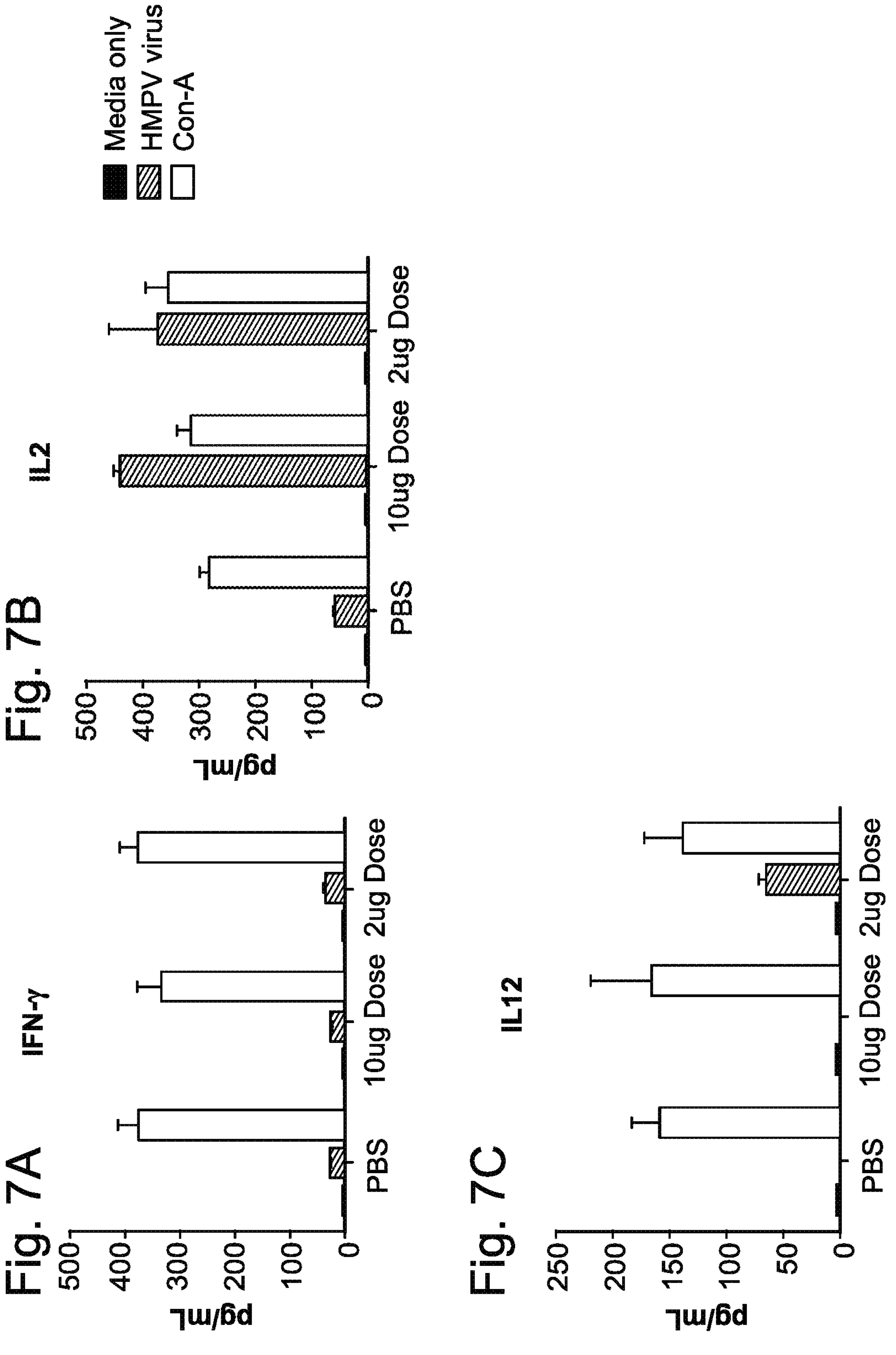
FIGS. 7A-7C are graphs showing the Th1 response induced by inactivated hMPV virus in splenocytes isolated from mice immunized with hMPV mRNA vaccines. Virus-free media was used as a negative control and Concanavalin A was included. The cytokines tested included IFN-γ (FIG. 7A), IL-2 (FIG. 7B) and IL12 (FIG. 7C).
Figures 8A, 8B, 8C, 8D, 8E:
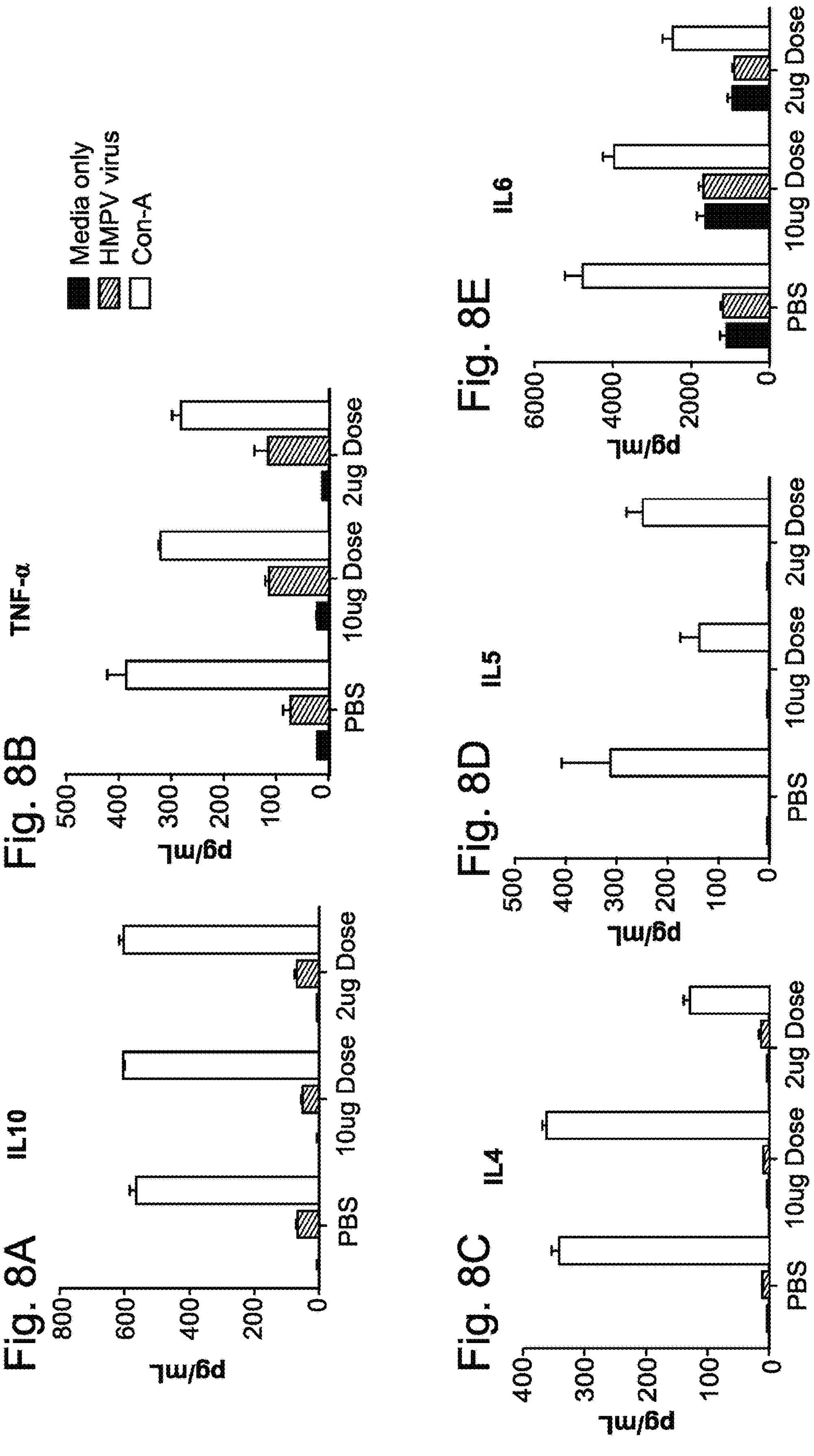
FIGS. 8A-8E are graphs showing the Th2 response induced by inactivated hMPV virus in splenocytes isolated from mice immunized with the hMPV mRNA vaccines. Virus-free media was used as a negative control and Concanavalin A was included. The cytokines tested include IL-10 (FIG. 8A), TNF-α (FIG. 8B), IL4 (FIG. 8C), IL-5 (FIG. 8D) and IL-6 (FIG. 8E).

In contrast, inactivated hMPV virus only induced the secretion of IL2 in the Th1 response comparable to that of Concanavalin A (FIGS. 7A-7C). For the Th2 response, the inactivated hMPV virus induced the secretion of detectable IL10, TNF-α, IL4 and IL6, but not IL5, while Concanavalin A stimulated the secretion of all the above-mentioned Th2 cytokines (FIGS. 8A-8E) at a much higher level.

Example 16: hMPV Rodent Challenge in Cotton Rats Immunized with mRNA Vaccine Encoding hMPV Fusion Protein The instant study was designed to test the efficacy in cotton rats of hMPV vaccines against a lethal challenge. mRNA vaccines encoding hMPV fusion protein were used. The mRNA polynucleotide encodes a full-length fusion protein and comprises the wild-type nucleotide sequence obtained from the hMPV A2a strain.

Figure 9A:
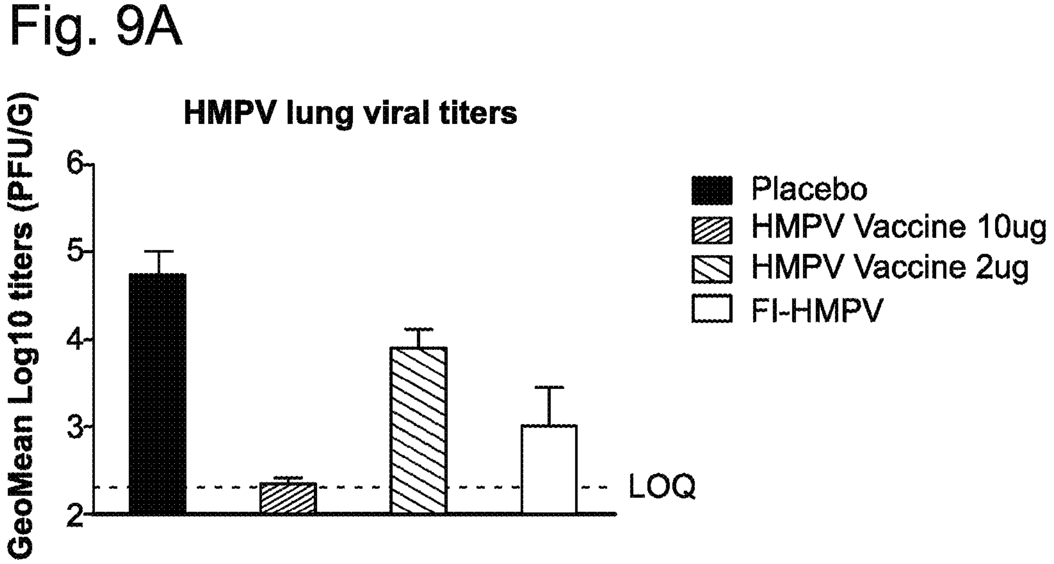
FIGS. 9A-9B are graphs showing the results of cotton rat challenge experiments. Two different doses of the hMPV mRNA vaccines were used (2 μg or 10 μg doses) to immunize the cotton rats before challenge. The hMPV mRNA vaccines reduced the viral titer in the lung and nose of the cotton rat, with the 10 μg dose being more effective in reducing viral titer. Use of a 10 μg dose resulted in 100% protection in the lung and a ~2 log reduction in nose viral titer. Use of a 2 μg dose resulted in a 1 log reduction in lung vital titer and no reduction in nose viral titer. The vaccine was administered on Day 0, and a boost was administered on Day 21.
Figure 9B:
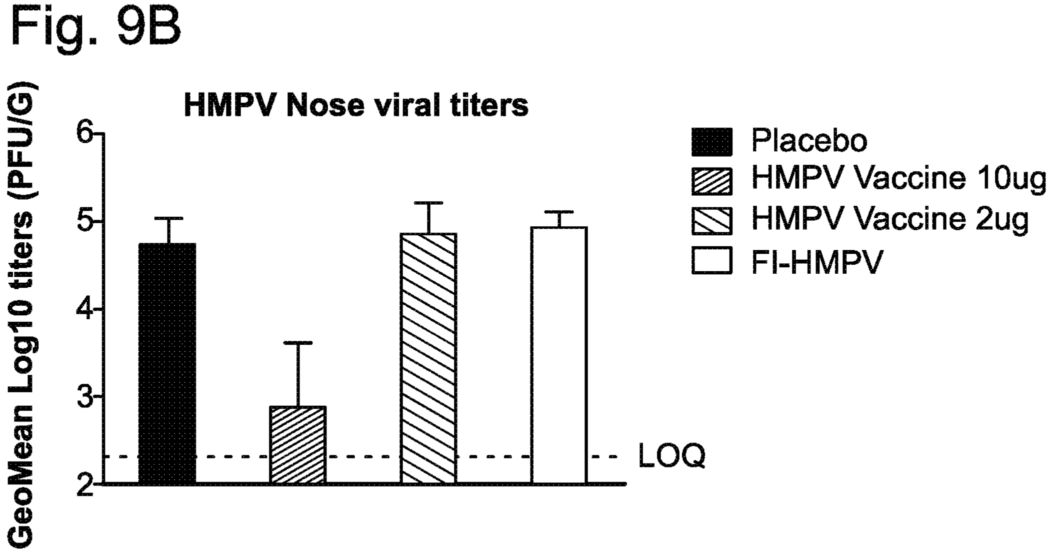

Cotton rats were immunized intramuscularly (IM) at week 0 and week 3 with the mRNA vaccines encoding hMPV fusion protein with either 2 μg or 10 μg doses for each immunization. The animals were then challenged with a lethal dose of hMPV in week 7 post initial immunization via IV, IM or ID. The endpoint was day 13 post infection, death or euthanasia. Viral titers in the noses and lungs of the cotton rats were measured. The results (FIGS. 9A and 9B) show that a 10 μg dose of mRNA vaccine protected the cotton mice 100% in the lung and drastically reduced the viral titer in the nose after challenge (~2 log reduction). Moreover, a 2 μg dose of mRNA vaccine showed a 1 log reduction in lung viral titer in the cotton mice challenged.

Figure 10:
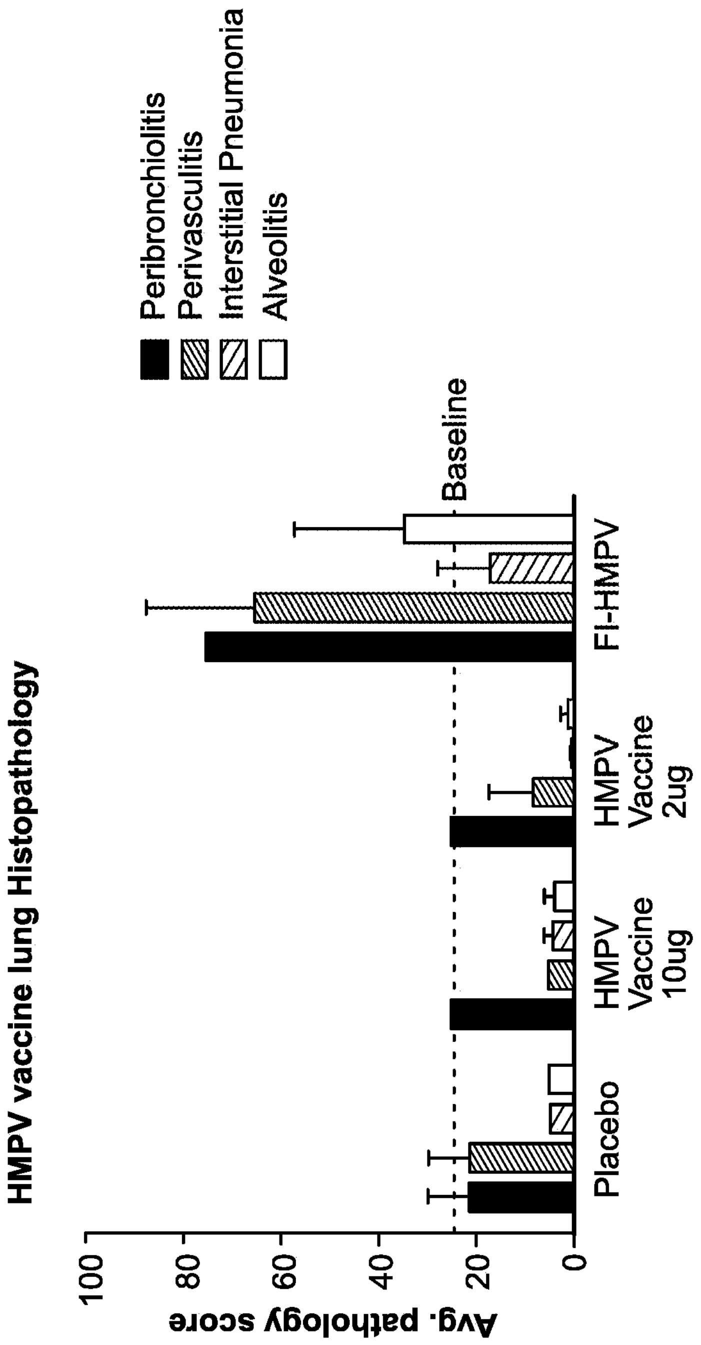
FIG. 10 is a graph showing the lung histopathology of cotton rats that received hMPV mRNA vaccines. Pathology associated with vaccine-enhanced disease was not observed in immunized groups.

Further, the histopathology of the lungs of the cotton mice immunized and challenged showed no pathology associated with vaccine-enhanced disease (FIG. 10).

Example 17: Immunogenicity Study

The instant study is designed to test the immunogenicity in mice of candidate PIV3 vaccines comprising a mRNA polynucleotide encoding hemagglutinin-neuraminidase or fusion protein (F or F0) obtained from PIV3.

Mice are immunized intravenously (IV), intramuscularly (IM), or intradermally (ID) with candidate vaccines. Candidate vaccines are chemically modified or unmodified. A total of four immunizations are given at 3-week intervals (i.e., at weeks 0, 3, 6, and 9), and sera are collected after each immunization until weeks 33-51. Serum antibody titers against hemagglutinin-neuraminidase or fusion protein (F or F0) are determined by ELISA. Sera collected from each mouse during weeks 10-16 are, optionally, pooled, and total IgGs are purified. Purified antibodies are used for immunoelectron microscopy, antibody-affinity testing, and in vitro protection assays.

Example 18: PIV3 Rodent Challenge

The instant study is designed to test the efficacy in cotton rats of candidate PIV3 vaccines against a lethal challenge using a PIV3 vaccine comprising mRNA encoding hemagglutinin-neuraminidase or fusion protein (F or F0) obtained from PIV3. Cotton rats are challenged with a lethal dose of the PIV3.

Animals are immunized intravenously (IV), intramuscularly (IM), or intradermally (ID) at week 0 and week 3 with candidate PIV3 vaccines with and without adjuvant. Candidate vaccines are chemically modified or unmodified. The animals are then challenged with a lethal dose of PIV3 on week 7 via IV, IM or ID. Endpoint is day 13 post infection, death or euthanasia. Animals displaying severe illness as determined by >30% weight loss, extreme lethargy or paralysis are euthanized. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %) or DLin-MC3-DMA (50 mol %), the non-cationic lipid is DSPC (10 mol %), the PEG lipid is PEG-DOMG (1.5 mol %) and the structural lipid is cholesterol (38.5 mol %), for example.

Example 19: hMPV/PIV Cotton Rat Challenge

The instant study was designed to test the efficacy in cotton rats of candidate hMPV mRNA vaccines, PIV3 mRNA vaccines, or hMPV/PIV combination mRNA vaccines against a lethal challenge using PIV3 strain or hMPV/A2 strain. The study design is shown in Table 9.

Cotton rats of 10-12 weeks old were divided into 12 groups (n=5), and each group was vaccinated with mRNA vaccines indicated in Table 9. The PIV3 vaccine comprises mRNA encoding hemagglutinin-neuraminidase or fusion protein (F or F0) obtained from PIV3. The hMPV mRNA vaccine encodes the full-length hMPV fusion protein. The hMPV/PIV combination mRNA vaccine is a mixture of the PIV3 vaccine and hMPV vaccine at a 1:1 ratio.

Cotton rats were immunized intramuscularly (IM) at week 0 and week 3 with candidate vaccines with the doses indicated in Table 9. Cotton rats immunized with hMPV mRNA vaccines or hMPV/PIV combination mRNA vaccines were challenged with a lethal dose of hMPV/A2 strain on week 7 via IM. Cotton rats immunized with PIV mRNA vaccines or hMPV/PIV combination mRNA vaccines were challenged with a lethal dose of PIV3 strain on week 7 via IM.

The endpoint was day 13 post infection, death or euthanasia. Animals displaying severe illness as determined by >30% weight loss, extreme lethargy or paralysis were euthanized. Body temperature and weight were assessed and recorded daily.

Figure 11:
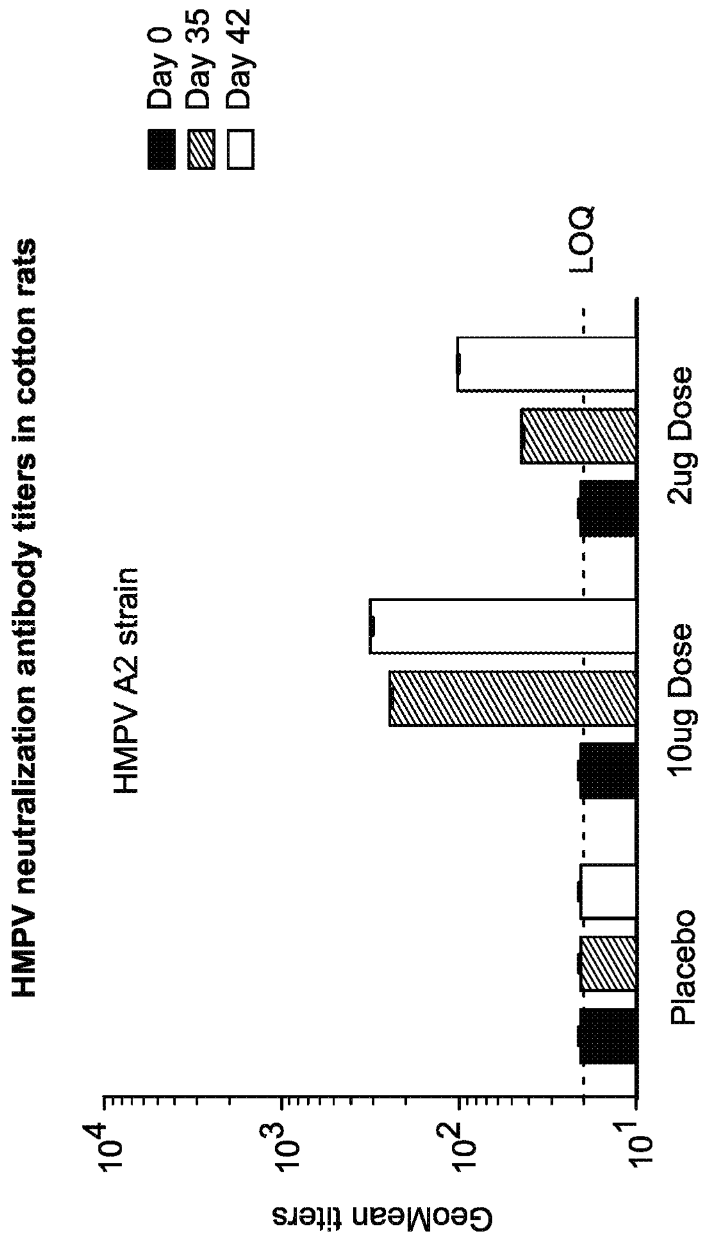
FIG. 11 is a graph showing hMPV neutralization antibody titers in cotton rats that received hMPV mRNA vaccines (2 μg or 10 μg doses) on days 35 and 42 post immunization.
Figure 12:
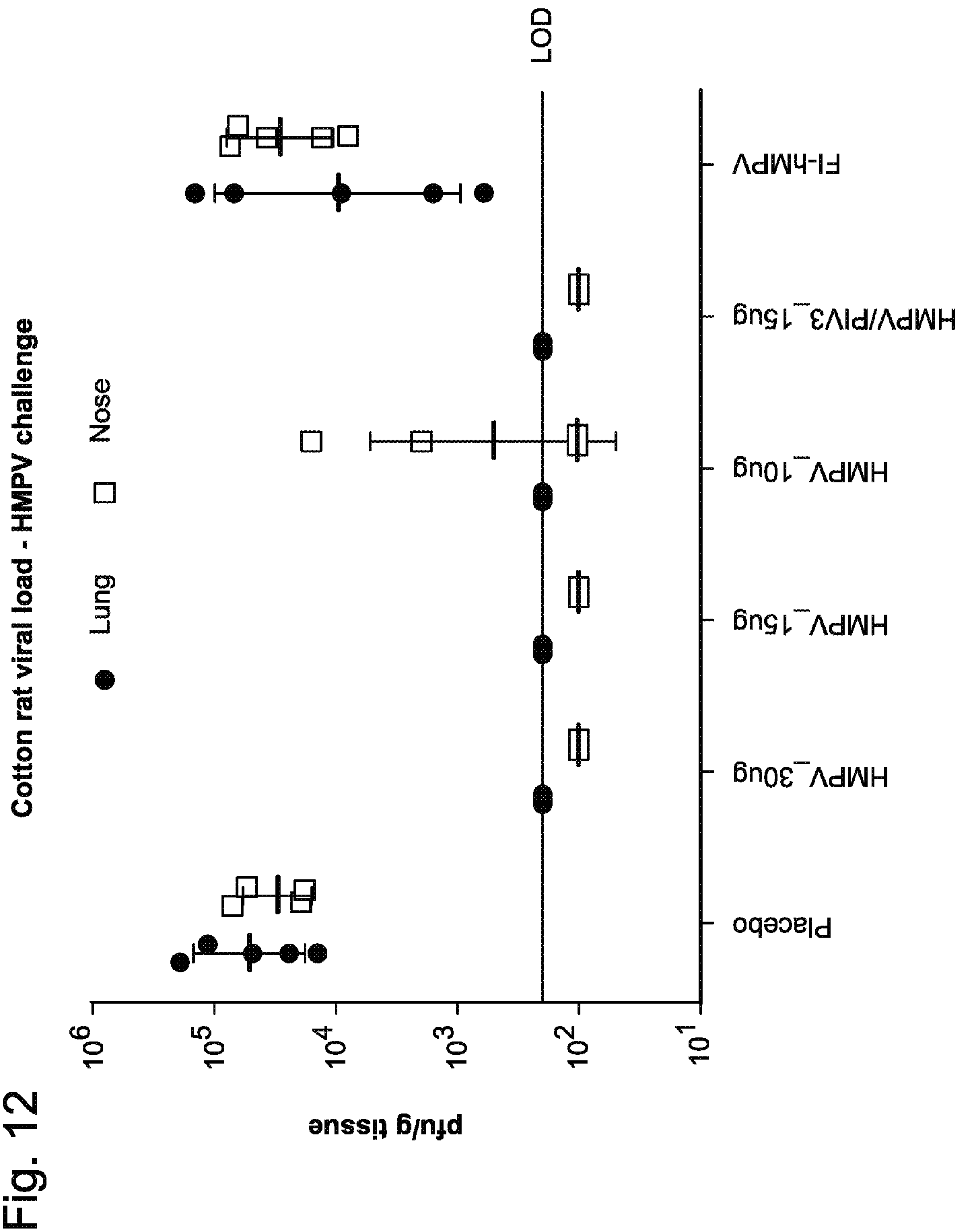
FIG. 12 is a graph showing the lung and nose viral load in cotton rats challenged with a hMPV/A2 strain after immunization with the indicated mRNA vaccines (hMPV mRNA vaccine or hMPV/PIV mRNA combination vaccine). Vaccinated cotton rats showed reduced lung and nose viral loads after challenge, compared to control.
Figure 13:
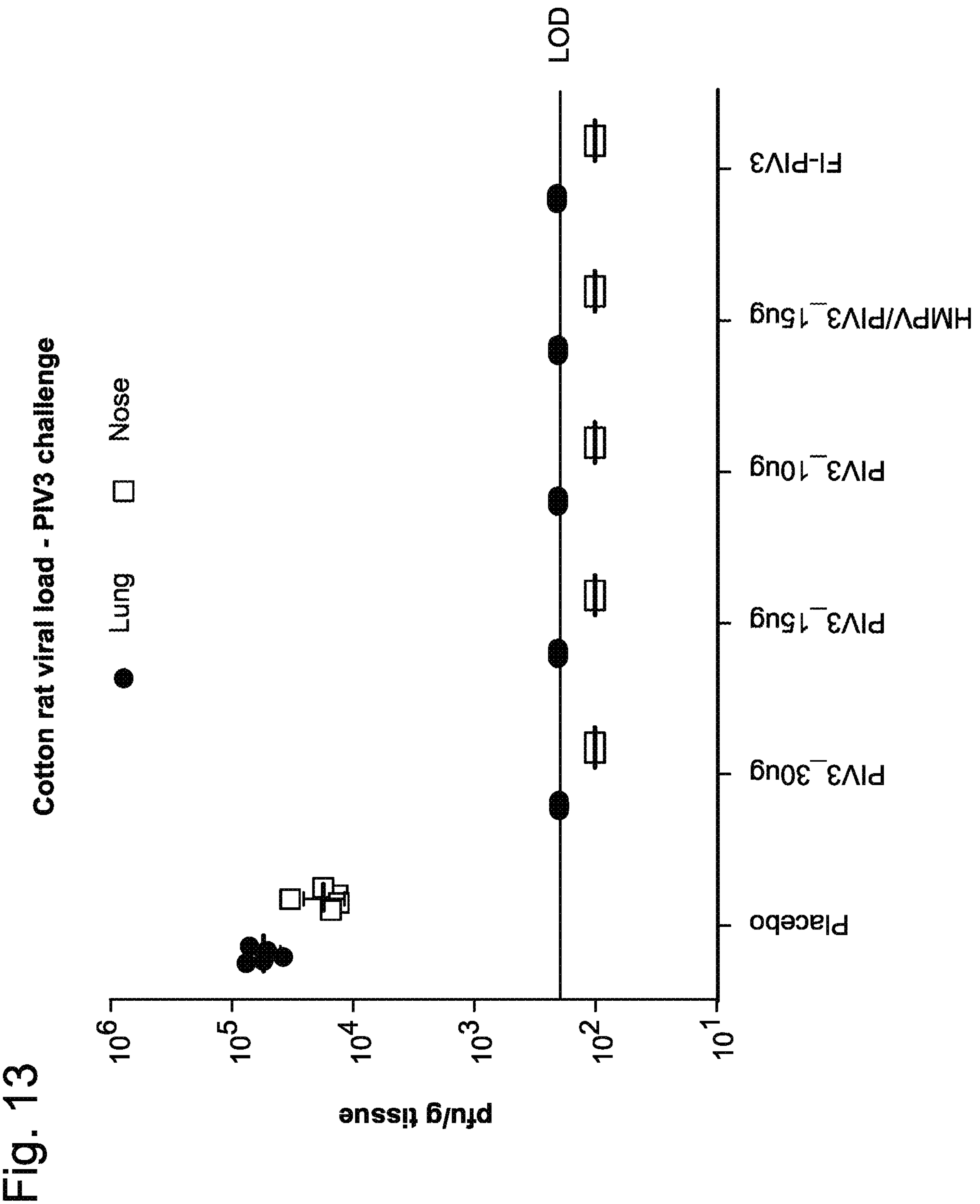
FIG. 13 is a graph showing the lung and nose viral load in cotton rats challenged with PIV3 strain after immunization with indicated mRNA vaccines (PIV mRNA vaccine or hMPV/PIV combination vaccine). Vaccinated cotton rats showed reduced lung and nose viral loads after challenge, compared to control.
Figure 14:
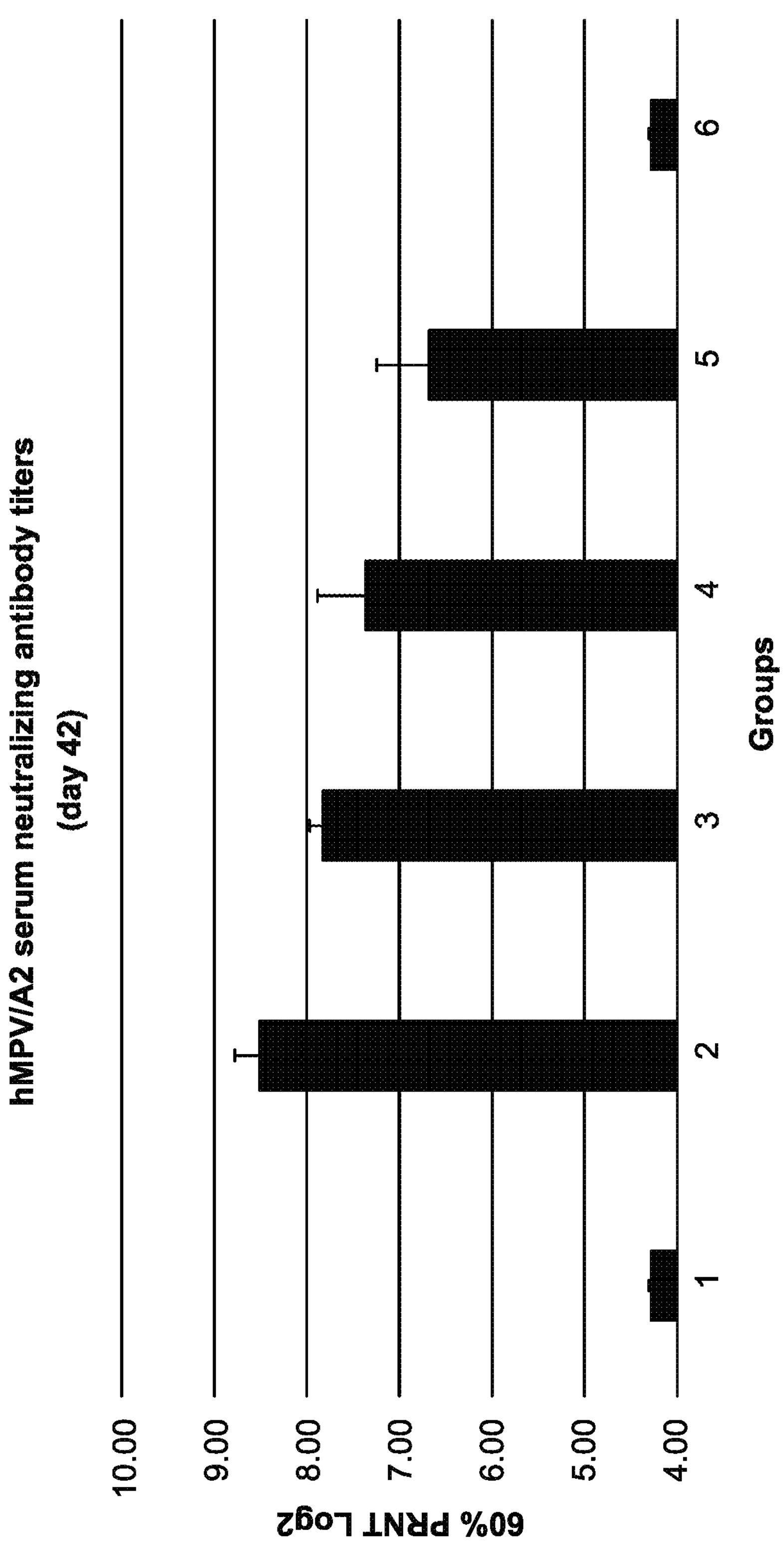
FIG. 14 is a graph showing hMPV neutralizing antibody titers in cotton rats that received different dosages of hMPV mRNA vaccines or hMPV/PIV combination mRNA vaccines on day 42 post immunization. The dosages of the vaccine are indicated in Table 9.
Figure 15:
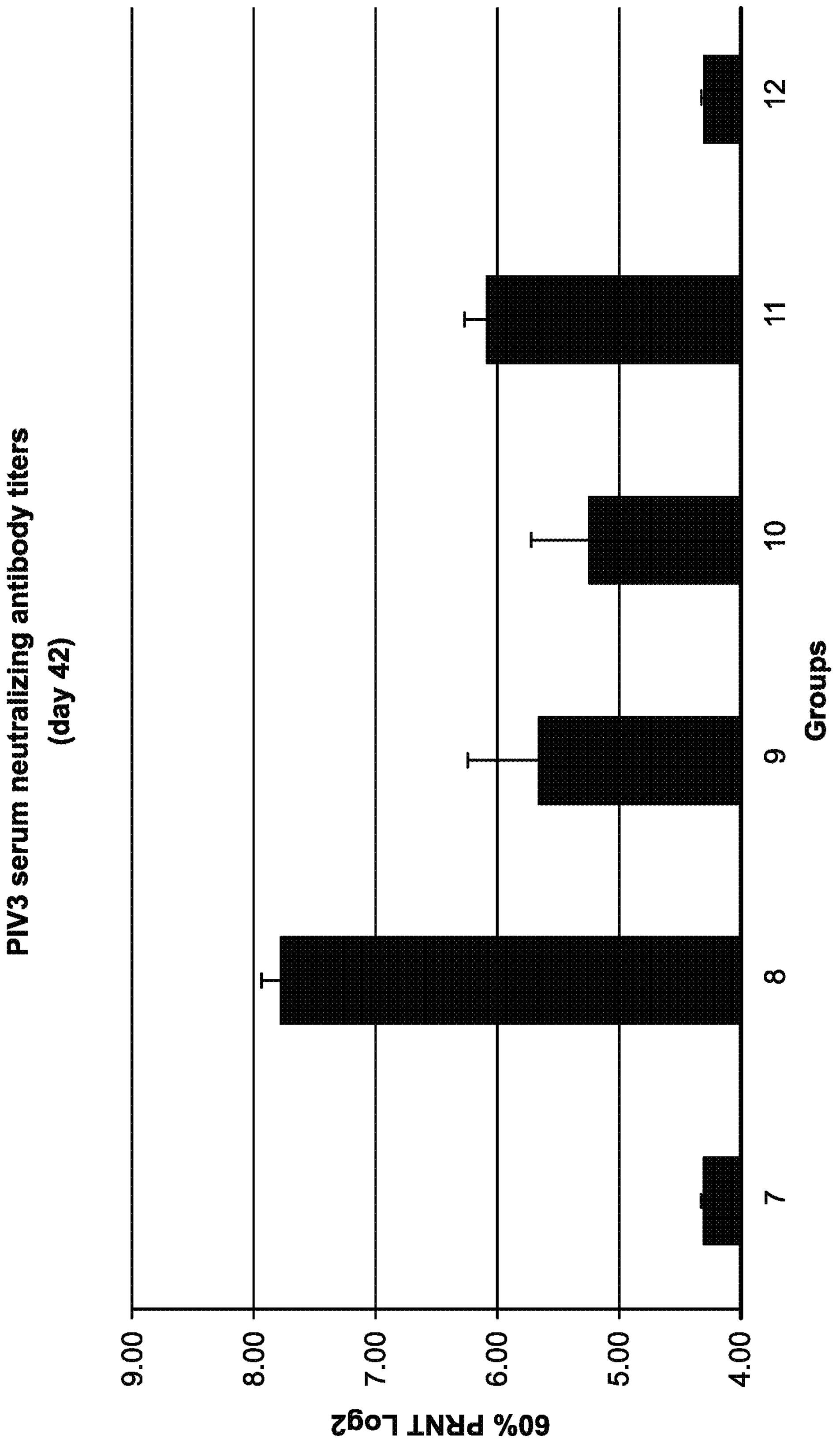
FIG. 15 is a graph showing PIV3 neutralizing antibody titers in cotton rats that received different dosages of PIV mRNA vaccines or hMPV/PIV combination mRNA vaccines on day 42 post immunization. The dosages of the vaccine are indicated in Table 9.
Figure 16:
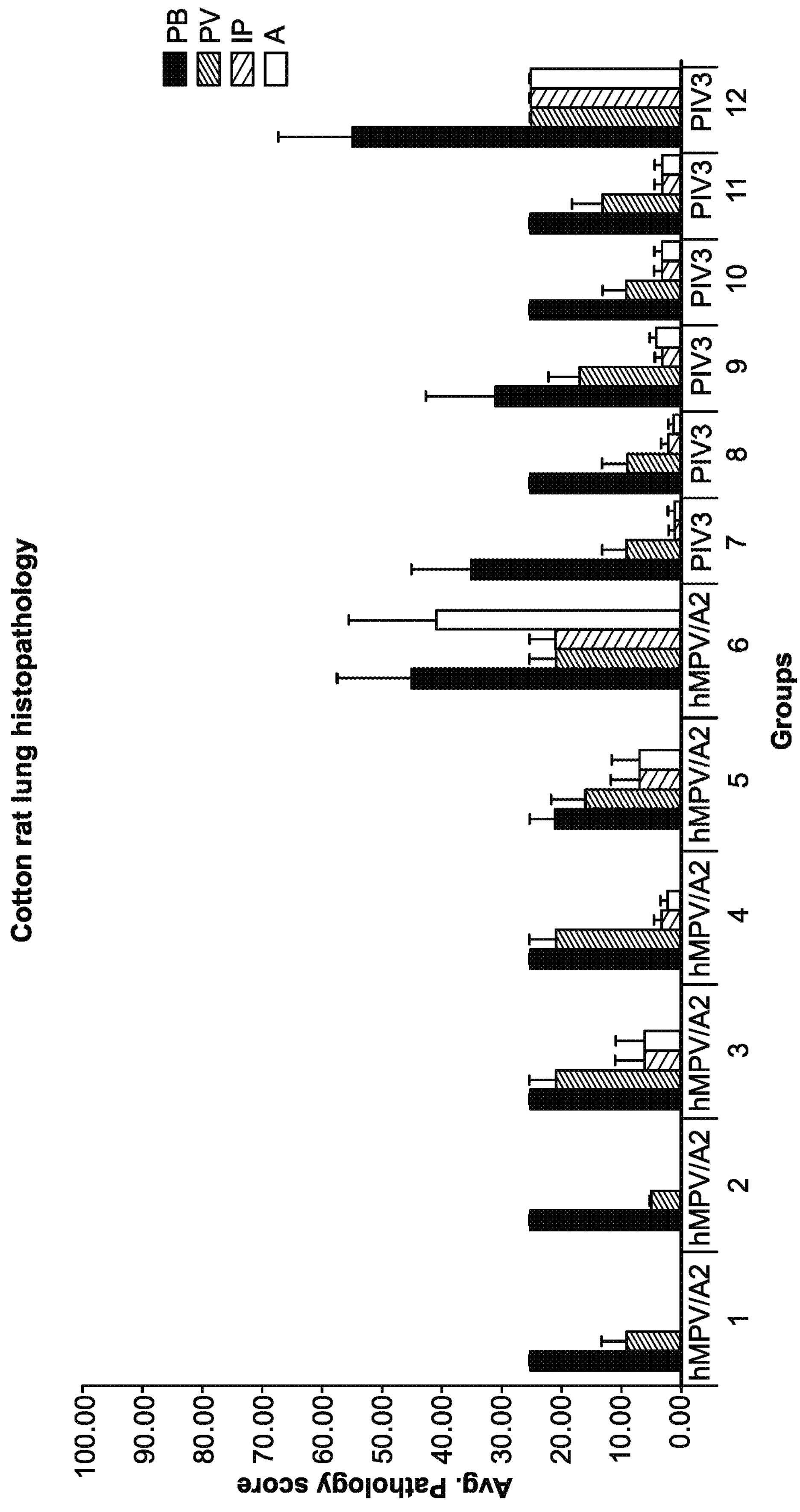
FIG. 16 is a graph showing the lung histopathology score of cotton rats immunized with hMPV mRNA vaccines, PIV mRNA vaccines or hMPV/PIV combination mRNA vaccines as indicated in Table 9. Low occurrence of alevolitis and interstitial pneumonia was observed, indicating no antibody-dependent enhancement (ADE) of hMPV associated diseases.

Lung and nose hMPV/A2 (FIG. 12) or PIV3 (FIG. 13) viral titers were assessed. Lung histopathology of the immunized and challenged cotton rat immunized and challenged were assessed to determine pathology associated with vaccine enhance disease. Neutralization antibody titers in the serum of immunized cotton rats on day 0 and 42 post immunization were assessed (FIG. 11).

hMPV/A2 (FIG. 14) or PIV3 (FIG. 15) neutralizing antibody titers in the serum samples of the immunized cotton rat 42 days post immunization were measured. All mRNA vaccines tested induced strong neutralizing antibodies cotton rats. Lung histopathology of the immunized cotton rats were also evaluated (FIG. 16). Low occurrence of alevolitis and interstitial pneumonia was observed, indicating no antibody-dependent enhancement (ADE) of hMPV or PIV associated diseases.

Example 20: Betacoronavirus Immunogenicity Study

The instant study is designed to test the immunogenicity in rabbits of candidate betacoronavirus (e.g., MERS-CoV, SARS-CoV, HCoV-OC43, HCoV-229E, HCoV-NL63, HCoV-NL, HCoV-NH or HCoV-HKU1 or a combination thereof) vaccines comprising a mRNA polynucleotide encoding the spike(S) protein, the S1 subunit (S1) of the spike protein, or the S2 subunit (S2) of the spike protein obtained from a betacoronavirus (e.g., MERS-CoV, SARS-CoV, HCoV-OC43, HCoV-229E, HCoV-NL63, HCoV-NL, HCoV-NH or HCoV-HKU1).

Rabbits are vaccinated on week 0 and 3 via intravenous (IV), intramuscular (IM), or intradermal (ID) routes. One group remains unvaccinated and one is administered inactivated betacoronavirus. Serum is collected from each rabbit on weeks 1, 3 (pre-dose) and 5. Individual bleeds are tested for anti-S, anti-S1 or anti-S2 activity via a virus neutralization assay from all three time points, and pooled samples from week 5 only are tested by Western blot using inactivated betacoronavirus (e.g., inactivated MERS-CoV, SARS-CoV, HCoV-OC43, HCoV-229E, HCoV-NL63, HCoV-NL, HCoV-NH or HCoV-HKU1).

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %) or DLin-MC3-DMA (50 mol %), the non-cationic lipid is DSPC (10 mol %), the PEG lipid is PEG-DOMG (1.5 mol %) and the structural lipid is cholesterol (38.5 mol %), for example.

Example 21: Betacoronavirus Challenge

The instant study is designed to test the efficacy in rabbits of candidate betacoronavirus (e.g., MERS-CoV, SARS-CoV, HCoV-OC43, HCoV-HKU1 or a combination thereof) vaccines against a lethal challenge using a betacoronavirus (e.g., MERS-CoV, SARS-CoV, HCoV-OC43, HCoV-HKU1 or a combination thereof) vaccine comprising mRNA encoding the spike(S) protein, the S1 subunit (S1) of the spike protein, or the S2 subunit (S2) of the spike protein obtained from betacoronavirus (e.g., MERS-CoV, SARS-CoV, HCoV-OC43, HCoV-229E, HCoV-NL63, HCoV-NL, HCoV-NH or HCoV-HKU1). Rabbits are challenged with a lethal dose (10×LD90; ~ 100 plaque-forming units; PFU) of betacoronavirus (e.g., MERS-CoV, SARS-CoV, HCoV-OC43, HCoV-229E, HCoV-NL63, HCoV-NL, HCoV-NH or HCoV-HKU1).

The animals used are 6-8 week old female rabbits in groups of 10. Rabbits are vaccinated on weeks 0 and 3 via an IM, ID or IV route of administration. Candidate vaccines are chemically modified or unmodified. Rabbit serum is tested for microneutralization (see Example 14). Rabbits are then challenged with ~1 LD90 of betacoronavirus (e.g., MERS-CoV, SARS-CoV, HCoV-OC43, HCoV-229E, HCoV-NL63, HCoV-NL, HCoV-NH or HCoV-HKU1) on week 7 via an IN, IM, ID or IV route of administration. Endpoint is day 13 post infection, death or euthanasia. Animals displaying severe illness as determined by >30% weight loss, extreme lethargy or paralysis are euthanized. Body temperature and weight are assessed and recorded daily.

Example 22: Microneutralization Assay

Nine serial 2-fold dilutions (1:50-1:12,800) of rabbit serum are made in 50 μl virus growth medium (VGM) with trypsin in 96 well microtiter plates. Fifty microliters of virus containing ~50 pfu of betacoronavirus (e.g., MERS-CoV, SARS-CoV, HCoV-OC43, HCoV-229E, HCoV-NL63, HCoV-NL, HCoV-NH or HCoV-HKU1) is added to the serum dilutions and allowed to incubate for 60 minutes at room temperature (RT). Positive control wells of virus without sera and negative control wells without virus or sera are included in triplicate on each plate. While the serum-virus mixtures incubate, a single cell suspension of Madin-Darby Canine-Kidney cells are prepared by trypsinizing (Gibco 0.5% bovine pancrease trypsin in EDTA) a confluent monolayer and suspended cells are transferred to a 50 ml centrifuge tube, topped with sterile PBS and gently mixed. The cells are then pelleted at 200 g for 5 minutes, supernatant aspirated and cells resuspended in PBS. This procedure is repeated once and the cells are resuspended at a concentration of $3\times10^5$/ml in VGM with porcine trypsin. Then, 100 μl of cells are added to the serum-virus mixtures and the plates incubated at 35° C. in $CO_2$ for 5 days. The plates are fixed with 80% acetone in phosphate buffered saline (PBS) for 15 minutes at RT, air dried and then blocked for 30 minutes containing PBS with 0.5% gelatin and 2% FCS. An antibody to the S proteins, S1 protein or S2 protein is diluted in PBS with 0.5% gelatin/2% FCS/0.5% Tween 20 and incubated at RT for 2 hours. Wells are washed and horseradish peroxidase-conjugated goat anti-mouse IgG added, followed by another 2 hour incubation. After washing, O-phenylenediamine dihydrochloride is added and the neutralization titer is defined as the titer of serum that reduced color development by 50% compared to the positive control wells.

Example 23: MERS CoV Vaccine Immunogenicity Study in Mice

The instant study was designed to test the immunogenicity in mice of candidate MERS-CoV vaccines comprising a mRNA polynucleotide encoding the full-length Spike(S) protein, or the S2 subunit (S2) of the Spike protein obtained from MERS-CoV.

Mice were vaccinated with a 10 μg dose of MERS-CoV mRNA vaccine encoding either the full-length MERS-CoV Spike(S) protein, or the S2 subunit (S2) of the Spike protein on days 0 and 21. Sera were collected from each mice on days 0, 21, 42, and 56. Individual bleeds were tested for anti-S, anti-S2 activity via a virus neutralization assay from all four time points.

Figure 17:
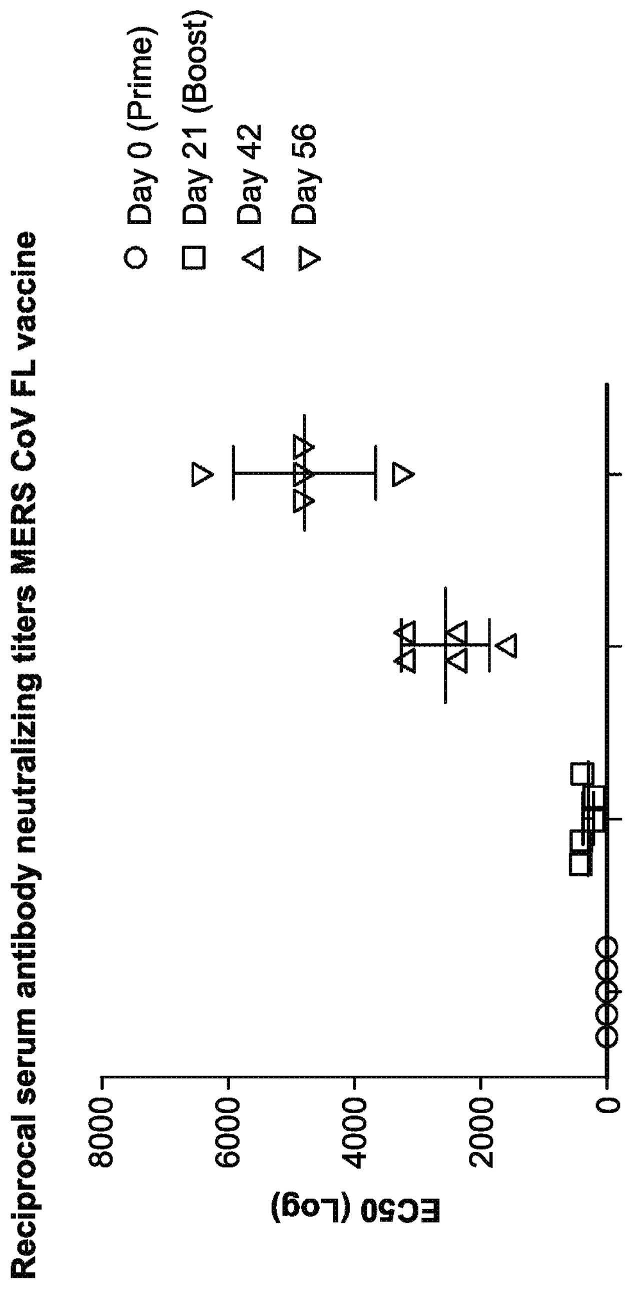
FIG. 17 is a graph showing the reciprocal MERS-CoV neutralizing antibody titers in mice immunized with beta-coronavirus mRNA vaccine encoding the MERS-CoV full-length Spike protein, on days 0, 21, 42, and 56 post immunization.
Figure 18:
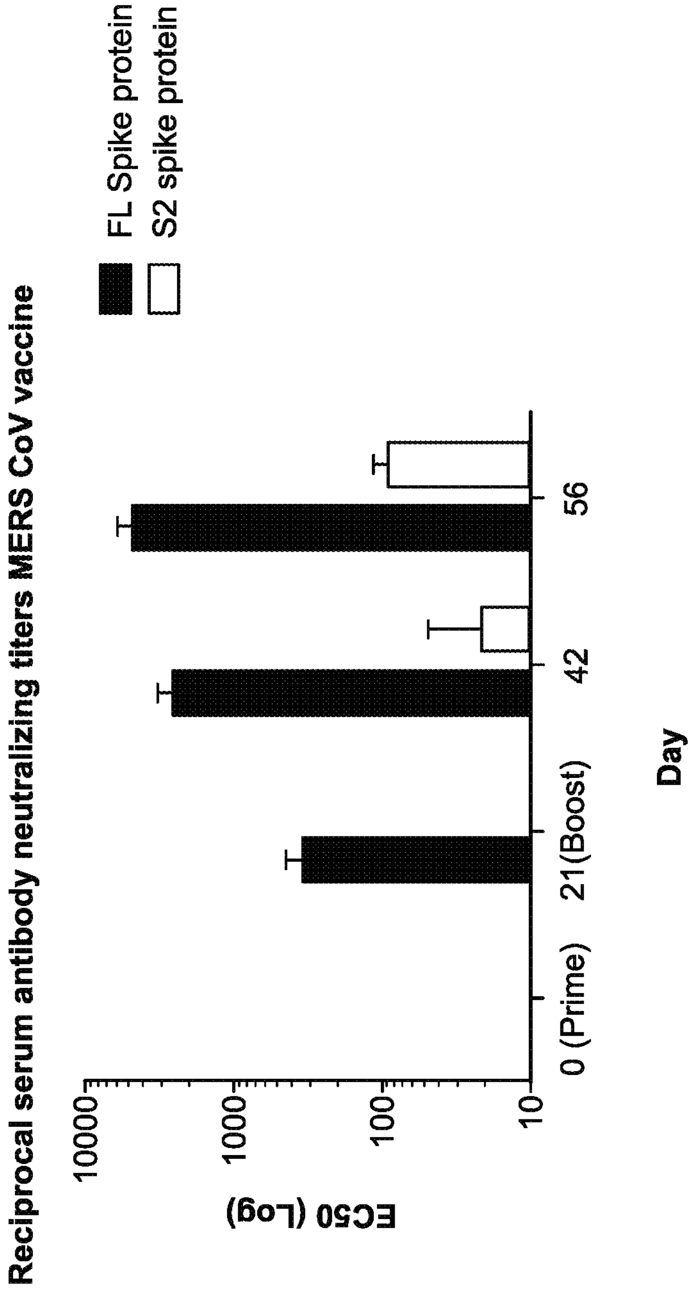
FIG. 18 is a graph showing the reciprocal MERS-CoV neutralizing antibody titers in mice immunized with beta-coronavirus mRNA vaccine encoding either the MERS-CoV full-length Spike protein, or the S2 subunit of the Spike protein. The full length spike protein induced a stronger immune response compared to the S2 subunit alone.

As shown in FIG. 17, the MERS-CoV vaccine encoding the full-length S protein induced strong immune response after the boost dose on day 21. Further, full-length S protein vaccine generated much higher neutralizing antibody titers as compared to S2 alone (FIG. 18).

Example 24: MERS CoV Vaccine Immunogenicity Study in New Zealand White Rabbits

The instant study was designed to test the immunogenicity of candidate MERS-CoV mRNA vaccines encoding the full-length Spike(S) protein. The New Zealand white rabbits used in this study weighed about 4-5 kg. The rabbits were divided into three groups (Group 1a, Group 1b, and Group 2, n=8). Rabbits in Group 1a were immunized intramuscularly (IM) with one 20 μg dose of the MERS-CoV mRNA vaccine encoding the full-length Spike protein on day 0. Rabbits in Group 1b were immunized intramuscularly (IM) with one 20 μg dose of the MERS-CoV mRNA vaccine encoding the full-length Spike protein on day 0, and again on day 21 (booster dose). Group 2 received placebo (PBS). The immunized rabbits were then challenged and samples were collected 4 days after challenge. The viral loads in the lungs, bronchoalveolar lavage (Bal), nose, and throat of the rabbits were determined, e.g., via quantitative PCR. Replicating virus in the lung tissues of the rabbits were also detected. Lung histopathology were evaluated and the neutralizing antibody titers in serum samples of the rabbits were determined.

Figure 19A:
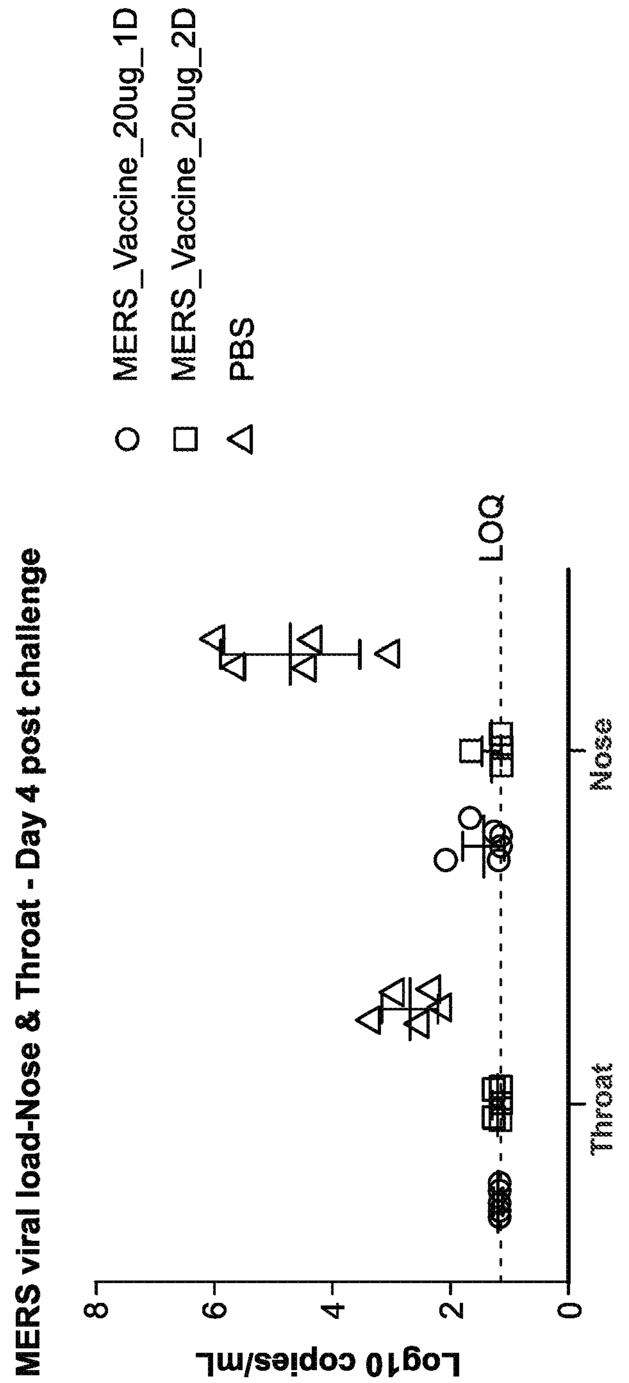
FIGS. 19A-19C are graphs showing the viral load in the nose and throat, the bronchoalveolar lavage (BAL), or the lungs of New Zealand white rabbits 4 days post challenge with MERS-CoV. The New Zealand white rabbits were immunized with one 20 μg-dose (on day 0) or two 20 μg-doses (on day 0 and 21) of MERS-CoV mRNA vaccine encoding the full-length Spike protein before challenge.
Figure 19B:
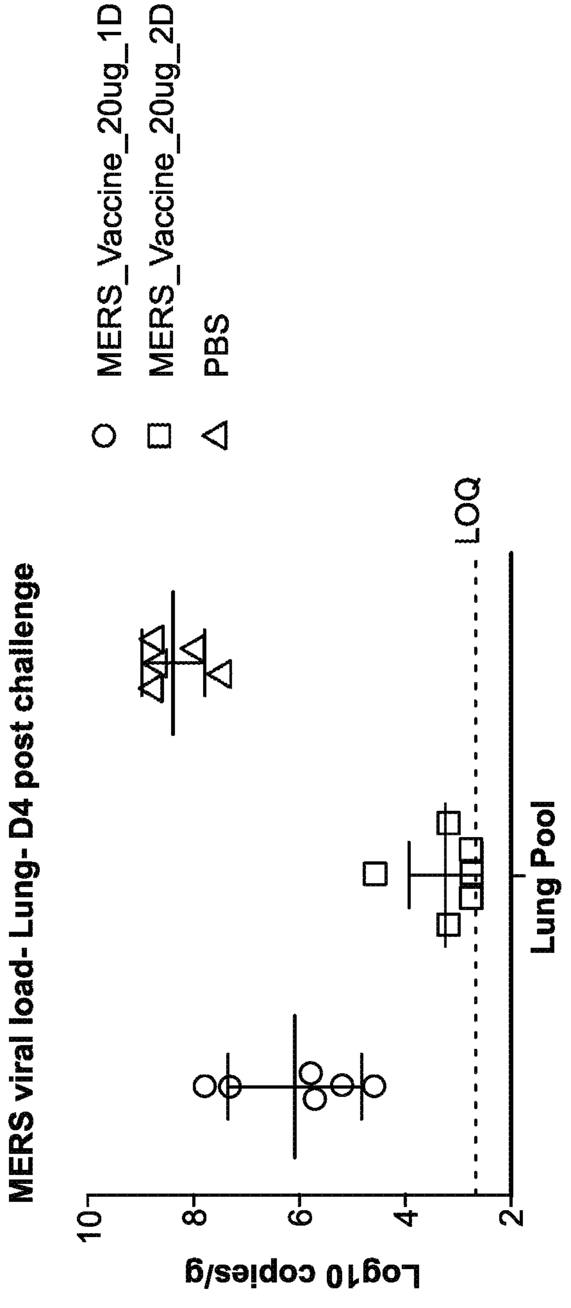
Figure 19C:
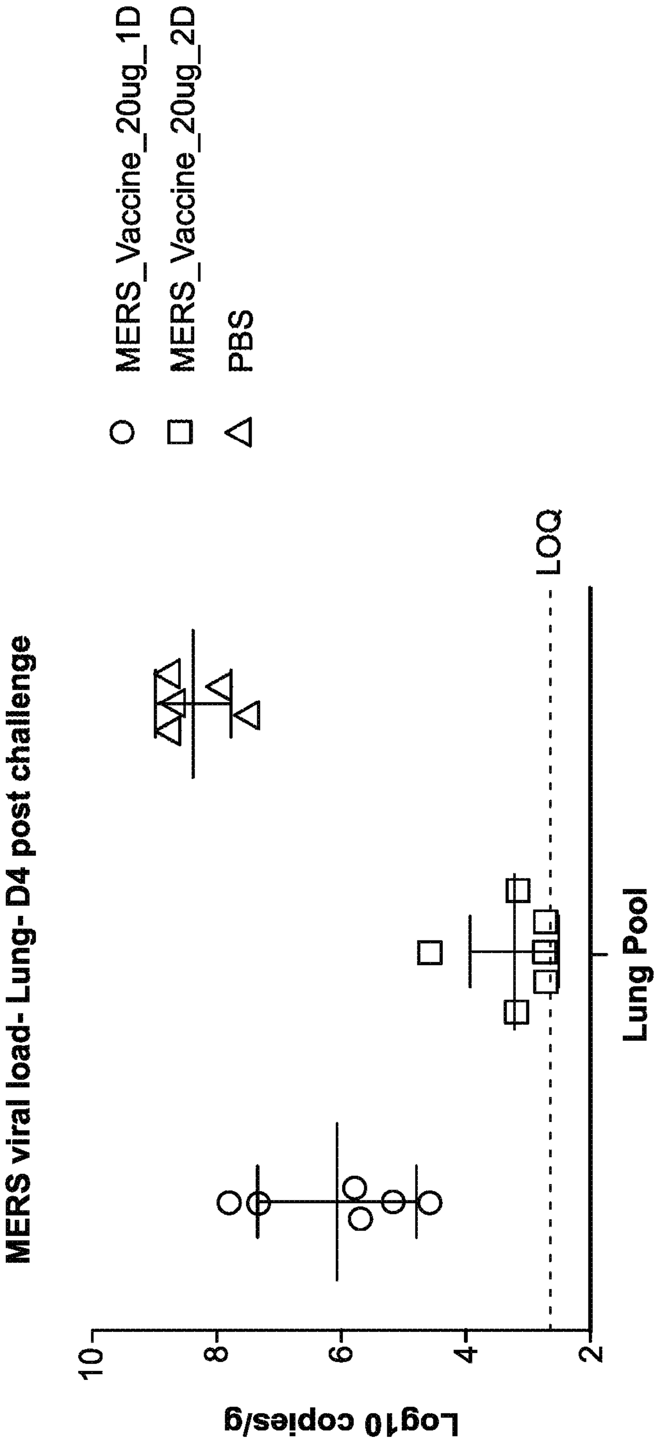

Two 20 μg doses of MERS-CoV mRNA vaccine resulted in a 3 log reduction of viral load in the nose and led to complete protection in the throat of the New Zealand white rabbits (FIG. 19A). Two 20 μg doses of MERS-CoV mRNA vaccine also resulted in a 4 log reduction of viral load in the BAL of the New Zealand white rabbits (FIG. 19B). One 20 μg dose of MERS-CoV mRNA vaccine resulted in a 2 log reduction of viral load, while two 20 μg doses of MERS-CoV mRNA vaccine resulted in an over 4 log reduction of viral load in the lungs of the New Zealand white rabbits (FIG. 19C).

Figure 20A:
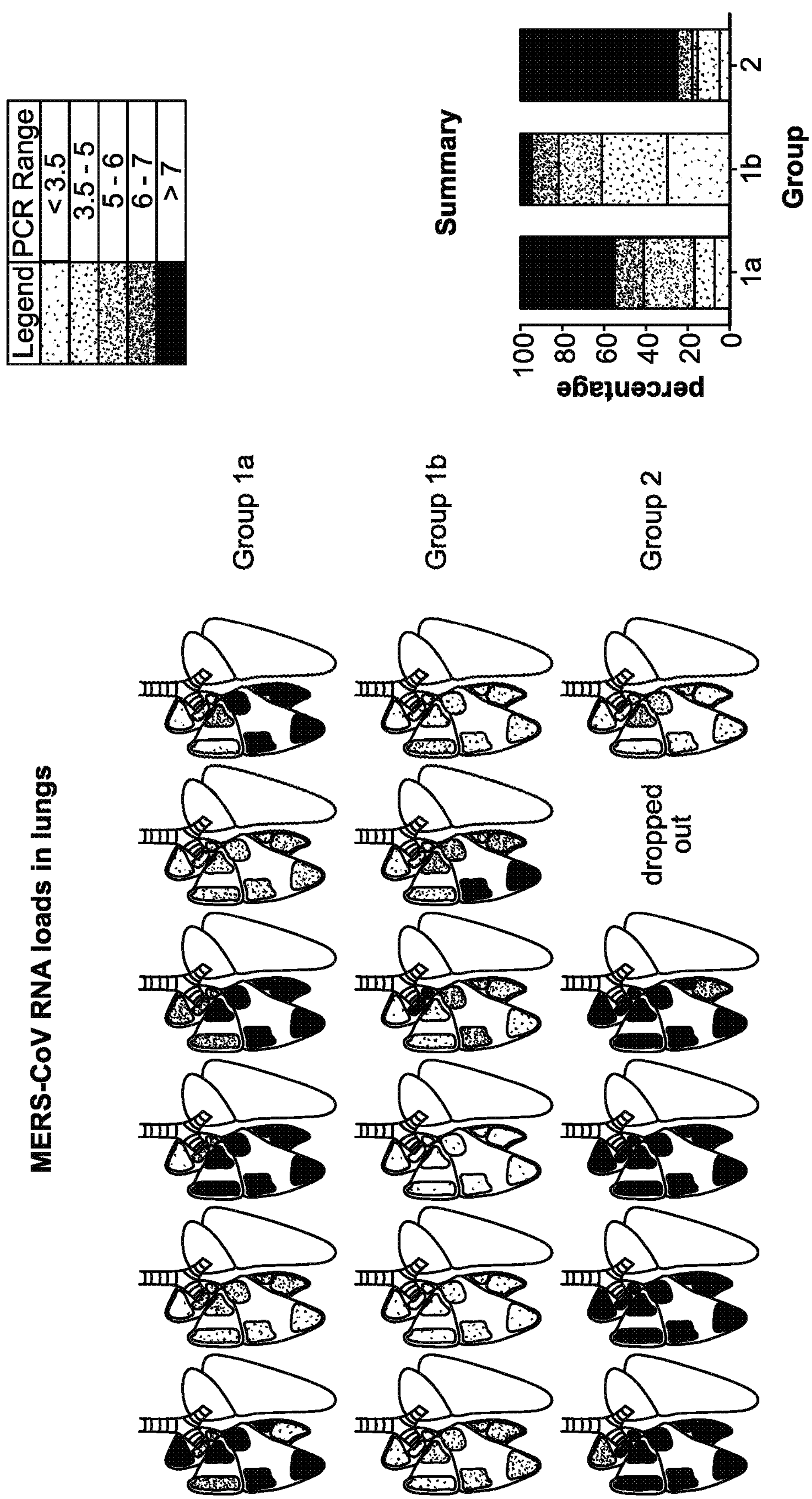
FIGS. 20A-20B are images and graphs showing viral load or replicating virus detected by PCR in the lungs of New Zealand white rabbits 4 days post challenge with MERS-CoV. The New Zealand white rabbits were immunized with a single 20 μg dose (on day 0, Group 1a) of MERS-CoV mRNA vaccine encoding the full-length Spike protein, two 20 μg doses (on day 0 and 21, Group 1b) of MERS-CoV mRNA vaccine encoding the full-length Spike protein, or placebo (Group 2) before challenge.
Figure 20B:
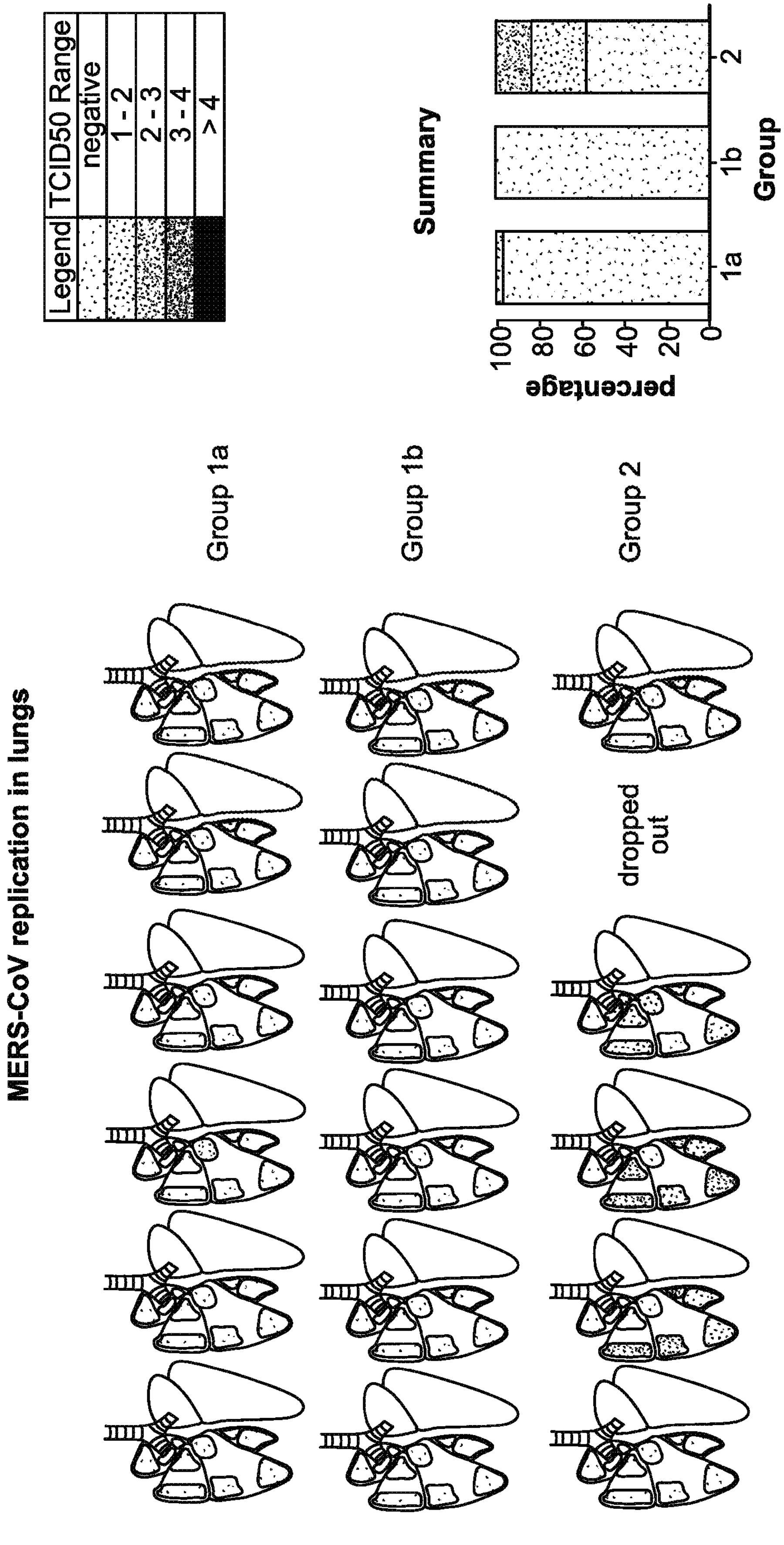

Quantitative PCR results show that two 20 μg doses of MERS-CoV mRNA vaccine reduced over 99% (2 log) of viruses in the lungs of New Zealand white rabbits (FIG. 20A). No replicating virus were detected in the lungs (FIG. 20B).

Figure 21:
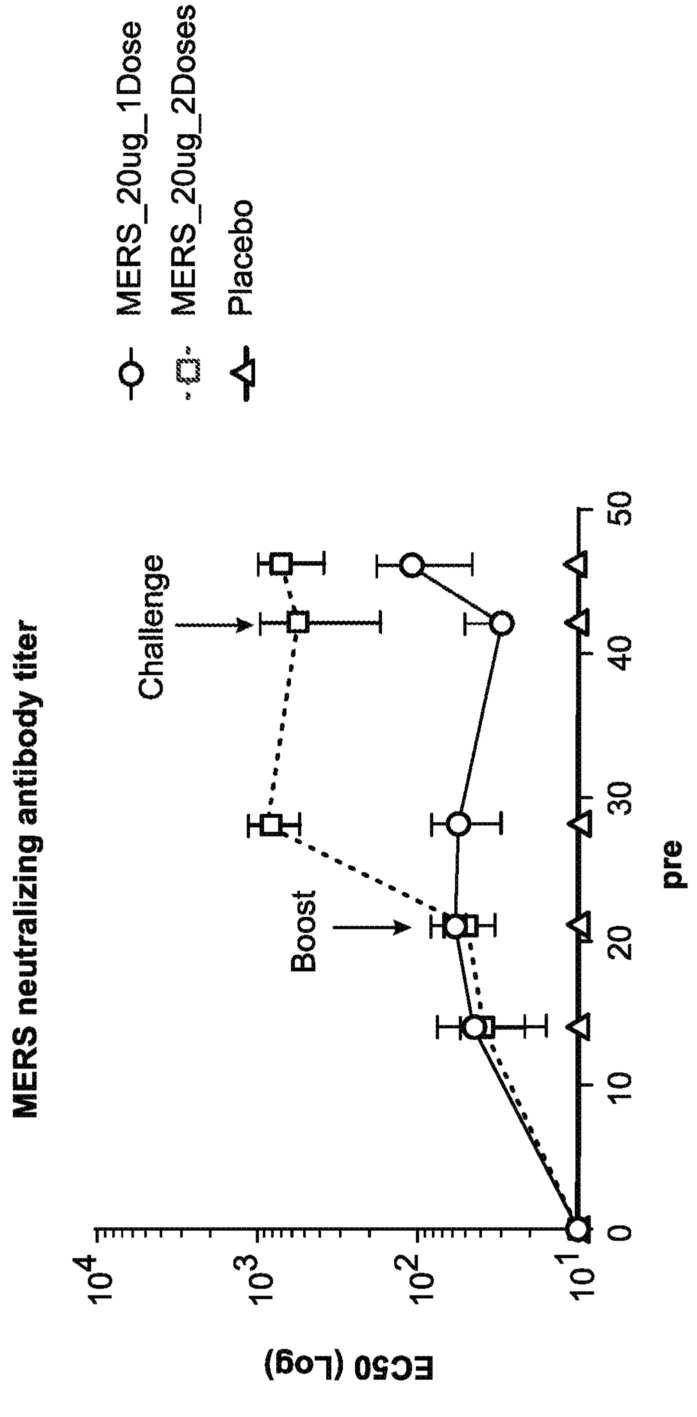
FIG. 21 is a graph showing the MERS-CoV neutralizing antibody titers in New Zealand white rabbits immunized with MERS-CoV mRNA vaccine encoding the full-length Spike protein. The results show that two doses of 20 μg MERS-CoV mRNA vaccine induced a significant amount of neutralizing antibodies against MERS-CoV ($EC_{50}$ between 500-1000). The MERS-CoV mRNA vaccine induced antibody titer is 3-5 fold better than any other vaccines tested in the same model.

Further, as shown in FIG. 21, two 20 μg doses of MERS-CoV mRNA vaccine induced significant amount of neutralizing antibodies against MERS-CoV ($EC_{50}$ between 500-1000). The MERS-CoV mRNA vaccine induced antibody titer is 3-5 fold better than any other vaccines tested in the same model.

Example 25: Immunogenicity Study

The instant study is designed to test the immunogenicity in mice of candidate MeV vaccines comprising a mRNA polynucleotide encoding MeV hemagglutinin (HA) protein, MeV Fusion (F) protein or a combination of both.

Mice are immunized intravenously (IV), intramuscularly (IM), or intradermally (ID) with candidate vaccines. Up to three immunizations are given at 3-week intervals (i.e., at weeks 0, 3, 6, and 9), and sera are collected after each immunization until weeks 33-51. Serum antibody titers against MeV HA protein or MeV F protein are determined by ELISA.

Example 26: MeV Rodent Challenge

The instant study is designed to test the efficacy in transgenic mice of candidate MeV vaccines against a lethal challenge using a MeV vaccine comprising mRNA encoding MeV HA protein or MeV F protein. The transgenic mice express human receptor CD46 or signaling lymphocyte activation molecule (SLAM) (also referred to as CD150). Humans are the only natural host for MeV infection, thus transgenic lines are required for this study. CD46 is a complement regulatory protein that protects host tissue from complement deposition by binding to complement components C3b and C4b. Its expression on murine fibroblast and lymphoid cell lines renders these otherwise refractory cells permissive for MeV infection, and the expression of CD46 on primate cells parallels the clinical tropism of MeV infection in humans and nonhuman primates (Rall G F et al. *PNAS USA* 1997; 94 (9): 4659-63). SLAM is a type 1 membrane glycoprotein belonging to the immunoglobulin superfamily. It is expressed on the surface of activated lymphocytes, macrophages, and dendritic cells and is thought to play an important role in lymphocyte signaling. SLAM is a receptor for both wild-type and vaccine MeV strains (Sellin C I et al. *J Virol.* 2006; 80 (13): 6420-29).

CD46 or SLAM/CD150 transgenic mice are challenged with a lethal dose of the MeV. Animals are immunized intravenously (IV), intramuscularly (IM), or intradermally (ID) at week 0 and week 3 with candidate MeV vaccines with and without adjuvant. The animals are then challenged with a lethal dose of MeV on week 7 via IV, IM or ID. Endpoint is day 13 post infection, death or euthanasia. Animals displaying severe illness as determined by >30% weight loss, extreme lethargy or paralysis are euthanized. Body temperature and weight are assessed and recorded daily.

In experiments where a lipid nanoparticle (LNP) formulation is used, the formulation may include a cationic lipid, non-cationic lipid, PEG lipid and structural lipid in the ratios 50:10:1.5:38.5. The cationic lipid is DLin-KC2-DMA (50 mol %), the non-cationic lipid is DSPC (10 mol %), the PEG lipid is PEG-DOMG (1.5 mol %) and the structural lipid is cholesterol (38.5 mol %), for example.

TABLE 1

| hMPV Immunogenicity studies bleeding schedule | | | | | | | | | | |
|---|---|---|---|---|---|---|---|---|---|---|
| | Animal groups | | Day | | | | | | | |
| | (n = 8) | vaccine | −2 | 0 | 7 | 14 | 21 | 28 | 35 | 56 |
| Placebo | Group 1 (n = 8) | PBS (IM) | Pre-Bleed | Prime | Bleeds | Bleeds | Bleeds/ Boost | Bleeds | Bleeds | Harvest Spleens/ Terminal Bleeds |
| 10 μg Dose | Group 2 (n = 8) | 10 μg (IM) | | | | | | | | |
| 2 μg Dose | Group 3 (n = 8) | 2 μg (IM) | | | | | | | | |

Total n = 24

Each of the sequences described herein encompasses a chemically modified sequence or an unmodified sequence which includes no nucleotide modifications.

TABLE 2

| Description | Sequence | SEQ ID NO: |
|---|---|---|
| | hMPV Nucleic Acid Sequences | |
| gi\|122891979\|gb\|EF051124.1\| Human metapneumovirus isolate TN/92-4 fusion protein gene, complete genome | ATGAGCTGGAAGGTGGTGATTATCTTCAGCCTGCTGATTA<br>CACCTCAACACGGCCTGAAGGAGAGCTACCTGGAAGAGA<br>GCTGCTCCACCATCACCGAGGGCTACCTGAGCGTGCTGC<br>GGACCGGCTGGTACACCAACGTGTTCACCCTGGAGGTGG<br>GCGACGTGGAGAACCTGACCTGCAGCGACGGCCCTAGCC<br>TGATCAAGACCGAGCTGGACCTGACCAAGAGCGCTCTGA<br>GAGAGCTGAAGACCGTGTCCGCCGACCAGCTGGCCAGAG<br>AGGAACAGATCGAGAACCCTCGGCAGAGCAGATTCGTGC<br>TGGGCGCCATCGCTCTGGGAGTCGCCGCTGCCGCTGCAG<br>TGACAGCTGGAGTGGCCATTGCTAAGACCATCAGACTGG<br>AAAGCGAGGTGACAGCCATCAACAATGCCCTGAAGAAG<br>ACCAACGAGGCCGTGAGCACCCTGGGCAATGGAGTGAGA<br>GTGCTGGCCACAGCCGTGCGGGAGCTGAAGGACTTCGTG<br>AGCAAGAACCTGACCAGAGCCATCAACAAGAACAAGTG<br>CGACATCGATGACCTGAAGATGGCCGTGAGCTTCTCCCA<br>GTTCAACAGACGGTTCCTGAACGTGGTGAGACAGTTCTC<br>CGACAACGCTGGAATCACACCTGCCATTAGCCTGGACCT<br>GATGACCGACGCCGAGCTGGCTAGAGCCGTGCCCAACAT<br>GCCCACCAGCGCTGGCCAGATCAAGCTGATGCTGGAGAA<br>CAGAGCCATGGTGCGGAGAAAGGGCTTCGGCATCCTGAT<br>TGGGGTGTATGGAAGCTCCGTGATCTACATGGTGCAGCT<br>GCCCATCTTCGGCGTGATCGACACACCCTGCTGGATCGTG<br>AAGGCCGCTCCTAGCTGCTCCGAGAAGAAAGGAAACTAT<br>GCCTGTCTGCTGAGAGAGGACCAGGGCTGGTACTGCCAG<br>AACGCCGGAAGCACAGTGTACTATCCCAACGAGAAGGAC<br>TGCGAGACCAGAGGCGACCACGTGTTCTGCGACACCGCT<br>GCCGGAATCAACGTGGCCGAGCAGAGCAAGGAGTGCAA<br>CATCAACATCAGCACAACCAACTACCCCTGCAAGGTGAG<br>CACCGGACGGCACCCCATCAGCATGGTGGCTCTGAGCCC<br>TCTGGGCGCTCTGGTGGCCTGCTATAAGGGCGTGTCCTGT<br>AGCATCGGCAGCAATCGGGTGGGCATCATCAAGCAGCTG<br>AACAAGGGATGCTCCTACATCACCAACCAGGACGCCGAC<br>ACCGTGACCATCGACAACACCGTGTACCAGCTGAGCAAG<br>GTGGAGGGCGAGCAGCACGTGATCAAGGGCAGACCCGT<br>GAGCTCCAGCTTCGACCCCATCAAGTTCCCTGAGGACCA<br>GTTCAACGTGGCCCTGGACCAGGTGTTTGAGAACATCGA<br>GAACAGCCAGGCCCTGGTGGACCAGAGCAACAGAATCCT<br>GTCCAGCGCTGAGAAGGGCAACACCGGCTTCATCATTGT<br>GATCATTCTGATCGCCGTGCTGGGCAGCTCCATGATCCTG<br>GTGAGCATCTTCATCATTATCAAGAAGACCAAGAAACCC<br>ACCGGAGCCCCTCCTGAGCTGAGCGGCGTGACCAACAAT<br>GGCTTCATTCCCCACAACTGA | 1 |
| gb\|AY525843.1\|: 3065-4684 Human metapneumovirus isolate NL/1/99, complete genome | ATGTCTTGGAAAGTGATGATCATCATTTCGTTACTCATAA<br>CACCCCAGCACGGGCTAAAGGAGAGTTATTTGGAAGAAT<br>CATGTAGTACTATAACTGAGGGATACCTCAGTGTTTTAAG<br>AACAGGCTGGTACACTAATGTCTTCACATTAGAAGTTGGT<br>GATGTTGAAAATCTTACATGTACTGATGGACCTAGCTTAA<br>TCAAAACAGAACTTGATCTAACAAAAAGTGCTTTAAGGG<br>AACTCAAAACAGTCTCTGCTGATCAGTTGGCGAGAGAGG | 2 |

TABLE 2-continued

| Description | Sequence | SEQ ID NO: |
|---|---|---|
| | AGCAAATTGAAAATCCCAGACAATCAAGATTTGTCTTAG<br>GTGCGATAGCTCTCGGAGTTGCTACAGCAGCAGCAGTCA<br>CAGCAGGCATTGCAATAGCCAAAACCATAAGGCTTGAGA<br>GTGAGGTGAATGCAATTAAAGGTGCTCTCAAACAAACTA<br>ATGAAGCAGTATCCACATTAGGGAATGGTGTGCGGGTCC<br>TAGCCACTGCAGTGAGAGAGCTAAAAGAATTTGTGAGCA<br>AAAACCTGACTAGTGCAATCAACAGGAACAAATGTGACA<br>TTGCTGATCTGAAGATGGCTGTCAGCTTCAGTCAATTCAA<br>CAGAAGATTTCTAAATGTTGTGCGGCAGTTTTCAGACAAT<br>GCAGGGATAACACCAGCAATATCATTGGACCTGATGACT<br>GATGCTGAGTTGGCCAGAGCTGTATCATACATGCCAACA<br>TCTGCAGGGCAGATAAAACTGATGTTGGAGAACCGCGCA<br>ATGGTAAGGAGAAAAGGATTTGGAATCCTGATAGGGGTC<br>TACGGAAGCTCTGTGATTTACATGGTTCAATTGCCGATCT<br>TTGGTGTCATAGATACACCTTGTTGGATCATCAAGGCAGC<br>TCCCTCTTGCTCAGAAAAAAACGGGAATTATGCTTGCCTC<br>CTAAGAGAGGATCAAGGGTGGTATTGTAAAAATGCAGGA<br>TCTACTGTTTACTACCCAAATGAAAAAGACTGCGAAACA<br>AGAGGTGATCATGTTTTTTGTGACACAGCAGCAGGGATC<br>AATGTTGCTGAGCAATCAAGAGAATGCAACATCAACATA<br>TCTACTACCAACTACCCATGCAAAGTCAGCACAGGAAGA<br>CACCCTATAAGCATGGTTGCACTATCACCTCTCGGTGCTT<br>TGGTGGCTTGCTATAAAGGGGTAAGCTGCTCGATTGGCA<br>GCAATTGGGT<br>TGGAATCATCAAACAATTACCCAAAGGCTGCTCATACAT<br>AACCAACCAGGATGCAGACACTGTAACAATTGACAATAC<br>CGTGTATCAACTAAGCAAAGTTGAAGGTGAACAGCATGT<br>AATAAAAGGGAGACCAGTTTCAAGCAGTTTTGATCCAAT<br>CAAGTTTCCTGAGGATCAGTTCAATGTTGCGCTTGATCAA<br>GTCTTCGAAAGCATTGAGAACAGTCAGGCACTAGTGGAC<br>CAGTCAAACAAAATTCTAAACAGTGCAGAAAAAGGAAA<br>CACTGGTTTCATTATCGTAGTAATTTTGGTTGCTGTTCTTG<br>GTCTAACCATGATTTCAGTGAGCATCATCATCATAATCAA<br>GAAAACAAGGAAGCCCACAGGAGCACCTCCAGAGCTGA<br>ATGGTGTCACCAACGGCGGTTTCATACCACATAGTTA | |
| gb\|KJ627414.1\|: 3015-4634 Human metapneumovirus strain hMPV/*Homo sapiens*/PER/ CFI0497/2010/B, complete genome | ATGTCTTGGAAAGTGATGATTATCATTTCGTTACTCATAA<br>CACCTCAGCATGGACTAAAAGAAAGTTATTTAGAAGAAT<br>CATGTAGTACTATAACTGAAGGATATCTCAGTGTTTTAAG<br>AACAGGTTGGTACACCAATGTCTTTACATTAGAAGTTGGT<br>GATGTTGAAAATCTTACATGTACTGATGGACCTAGCTTAA<br>TCAAAACAGAACTTGACCTAACCAAAAGTGCTTTAAGAG<br>AACTCAAAACAGTTTCTGCTGATCAGTTAGCGAGAGAAG<br>AACAAATTGAAAATCCCAGACAATCAAGGTTTGTCCTAG<br>GTGCAATAGCTCTTGGAGTTGCCACAGCAGCAGCAGTCA<br>CAGCAGGCATTGCAATAGCCAAAACTATAAGGCTTGAGA<br>GTGAAGTGAATGCAATCAAAGGTGCTCTCAAAACAACCA<br>ATGAGGCAGTATCAACACTAGGAAATGGAGTGCGGGTCC<br>TAGCCACTGCAGTAAGAGAGCTGAAAGAATTTGTGAGCA<br>AAAACCTGACTAGTGCGATCAACAAGAACAAGTGTGACA<br>TTGCTGATTTGAAGATGGCTGTCAGCTTCAGTCAGTTCAA<br>CAGAAGATTCCTAAATGTTGTGCGGCAGTTTTCAGACAAT<br>GCAGGGATAACACCAGCAATATCATTGGACCTGATGAAT<br>GATGCTGAGCTGGCCAGAGCTGTATCATACATGCCAACA<br>TCTGCAGGACAGATAAAACTAATGTTAGAGAACCGTGCA<br>ATGGTGAGGAGAAAAGGATTTGGAATCTTGATAGGGGTC<br>TACGGAAGCTCTGTGATTTACATGGTCCAGCTGCCGATCT<br>TTGGTGTCATAAATACACCTTGTTGGATAATCAAGGCAGC<br>TCCCTCTTGTTCAGAAAAAGATGGAAATTATGCTTGCCTC<br>CTAAGAGAGGATCAAGGGTGGTATTGTAAAAATGCAGGA<br>TCCACTGTTTACTACCCAAATGAAAAAGACTGCGAAACA<br>AGAGGTGATCATGTTTTTTGTGACACAGCAGCAGGGATC<br>AATGTTGCTGAGCAATCAAGAGAATGCAACATCAACATA<br>TCTACCACCAACTACCCATGCAAAGTCAGCACAGGAAGA<br>CACCCTATCAGCATGGTTGCACTATCACCTCTCGGTGCTT<br>TGGTAGCTTGCTACAAAGGGGTTAGCTGCTCGACTGGCA<br>GTAATCAGGTTGGAATAATCAAACAACTACCTAAAGGCT<br>GCTCATACATAACTAACCAGGACGCAGACACTGTAACAA<br>TTGACAACACTGTGTATCAACTAAGCAAAGTTGAGGGTG<br>AACAGCATGTAATAAAAGGGAGACCAGTTTCAAGCAGTT<br>TTGATCCAATCAGGTTTCCTGAGGATCAGTTCAATGTTGC<br>GCTTGATCAAGTCTTTGAAAGCATTGAAAACAGTCAAGC<br>ACTAGTGGACCAGTCAAACAAAATTCTGAACAGTGCAGA<br>AAAAGGAAACACTGGT<br>TTCATTATTGTAATAATTTTGATTGCTGTTCTTGGGTTAAC<br>CATGATTTCAGTGAGCATCATCATCATAATCAAAAAAAC | 3 |

TABLE 2-continued

| Description | Sequence | SEQ ID NO: |
|---|---|---|
| | AAGGAAGCCCACAGGGGCACCTCCGGAGCTGAATGGTGT TACCAACGGCGGTTTCATACCGCATAGTTAG | |
| gb\|KJ723483.1\|: 5586-7310 Human respiratory syncytial virus strain RSVA/*Homo sapiens*/USA/84I-215A-01/1984, complete genome | ATGGAGTTGCCAATCCTCAAAACAAATGCAATTACCACA ATCCTTGCTGCAGTCACACTCTGTTTCGCTTCCAGTCAAA ACATCACTGAAGAATTTTATCAATCAACATGCAGTGCAG TTAGCAAAGGCTATCTTAGTGCTCTAAGAACTGGTTGGTA TACTAGTGTTATAACTATAGAATTAAGTAATATCAAGGA AAATAAGTGTAATGGAACAGATGCTAAGGTAAAATTGAT AAAACAAGAATTAGATAAATATAAAAATGCTGTAACAGA ATTGCAGTTGCTCATGCAAAGCACACCAGCAGCCAACAA TCGAGCCAGAAGAGAACTACCAAGGTTTATGAATTATAC ACTCAATAATACCAAAAATACCAATGTAACATTAAGCAA GAAAAGGAAAAGAAGATTTCTTGGCTTTTTGTTAGGTGTT GGATCTGCAATCGCCAGTGGCATTGCTGTATCTAAGGTCC TGCACCTAGAAGGGGAAGTGAACAAAATCAAAAGTGCTC TACTATCCACAAACAAGGCTGTAGTCAGCTTATCAAATG GAGTTAGTGTCTTAACCAGCAAAGTGTTAGACCTCAAAA ACTATATAGATAAACAGTTGTTACCTATTGTGAACAAGC AAAGCTGCAGCATATCAAACATTGAAACTGTGATAGAGT TCCAACAAAAGAACAACAGACTACTAGAGATTACCAGGG AATTTAGTGTTAATGCAGGTGTAACTACACCTGTAAGCAC TTATATGTTAACTAATAGTGAATTATTATCATTAATCAAT GATATGCCTATAACAAATGATCAGAAAAAGTTAATGTCC AACAATGTTCAAATAGTTAGACAGCAAAGTTACTCTATC ATGTCCATAATAAAGGAGGAAGTCTTAGCATATGTAGTA CAATTACCACTATATGGTGTAATAGATACACCCTGTTGGA AACTGCACACATCCCCTCTATGTACAACCAACACAAAGG AAGGGTCCAACATCTGCTTAACAAGAACCGACAGAGGAT GGTATTGTGACAATGCAGGATCAGTATCTTTCTTCCCACA AGCTGAAACATGTAAAGTTCAATCGAATCGGGTATTTTGT GACACAATGAACAGTTTAACATTACCAAGTGAAGTAAAT CTCTGCAACATTGACATATTCAACCCCAAATATGATTGCA AAATTATGACTTCAAAAACAGATGTAAGCAGCTCCGTTA TCACATCTCTAGGAGCCATTGTGTCATGCTATGGCAAAAC TAAATGTACAGCATCCAATAAAAATCGTGGGATCATAAA GACATTTTCTAACGGGTGTGATTATGTATCAAATAAGGG GGTGGATACTGTGTCTGTAGGTAATACATTATATTATGTA AATAAGCAAGAAGGCAAAAGTCTCTATGTAAAAGGTGAA CCAATAATAAATTTCTATGACCCATTAGTGTTCCCCTCTG ATGAATTTGATGCATCAATATCTCAAGTCAATGAGAAGA TTAACCAGAGCCTAGCATTTATTCGTAAATCCGATGAATT ATTACATAATGTAAATGCTGGTAAATCCACCACAAATAT CATGATAACTACTATAATTATAGTGATTATAGTAATATTG TTATCATTAATTGCAGTTGGACTGCTCCTATACTGCAAGG CCAGAAGCACACCAGTCACACTAAGTAAGGATCAACTGA GTGGTATAAATAATATTGCATTTAGTAACTGA | 4 |
| | hMPV mRNA Sequences | |
| gi\|122891979\|gb\|EF051124.1\| Human metapneumovirus isolate TN/92-4 fusion protein gene, complete genome | AUGAGCUGGAAGGUGGUGAUUAUCUUCAGCCUGCUGAU UACACCUCAACACGGCCUGAAGGAGAGCUACCUGGAAG AGAGCUGCUCCACCAUCACCGAGGGCUACCUGAGCGUG CUGCGGACCGGCUGGUACACCAACGUGUUCACCCUGGA GGUGGGCGACGUGGAGAACCUGACCUGCAGCGACGGCC CUAGCCUGAUCAAGACCGAGCUGGACCUGACCAAGAGC GCUCUGAGAGAGCUGAAGACCGUGUCCGCCGACCAGCU GGCCAGAGAGGAACAGAUCGAGAACCCUCGGCAGAGCA GAUUCGUGCUGGGCGCCAUCGCUCUGGGAGUCGCCGCU GCCGCUGCAGUGACAGCUGGAGUGGCCAUUGCUAAGAC CAUCAGACUGGAAAGCGAGGUGACAGCCAUCAACAAUG CCCUGAAGAAGACCAACGAGGCCGUGAGCACCCUGGGC AAUGGAGUGAGAGUGCUGGCCACAGCCGUGCGGGAGCU GAAGGACUUCGUGAGCAAGAACCUGACCAGAGCCAUCA ACAAGAACAAGUGCGACAUCGAUGACCUGAAGAUGGCC GUGAGCUUCUCCCAGUUCAACAGACGGUUCCUGAACGU GGUGAGACAGUUCUCCGACAACGCUGGAAUCACACCUG CCAUUAGCCUGGACCUGAUGACCGACGCCGAGCUGGCU AGAGCCGUGCCCAACAUGCCCACCAGCGCUGGCCAGAU CAAGCUGAUGCUGGAGAACAGAGCCAUGGUGCGGAGAA AGGGCUUCGGCAUCCUGAUUGGGGUGUAUGGAAGCUCC GUGAUCUACAUGGUGCAGCUGCCCAUCUUCGGCGUGAU CGACACACCCUGCUGGAUCGUGAAGGCCGCUCCUAGCU GCUCCGAGAAGAAAGGAAACUAUGCCUGUCUGCUGAGA GAGGACCAGGGCUGGUACUGCCAGAACGCCGGAAGCAC AGUGUACUAUCCCAACGAGAAGGACUGCGAGACCAGAG | 57 |

TABLE 2-continued

<table>
<tr><th>Description</th><th>Sequence</th><th>SEQ ID NO:</th></tr>
<tr><td></td><td>GCGACCACGUGUUCUGCGACACCGCUGCCGGAAUCAAC<br>GUGGCCGAGCAGAGCAAGGAGUGCAACAUCAACAUCAG<br>CACAACCAACUACCCCUGCAAGGUGAGCACCGGACGGC<br>ACCCCAUCAGCAUGGUGGCUCUGAGCCCUCUGGGCGCU<br>CUGGUGGCCUGCUAUAAGGGCGUGUCCUGUAGCAUCGG<br>CAGCAAUCGGGUGGGCAUCAUCAAGCAGCUGAACAAGG<br>GAUGCUCCUACAUCACCAACCAGGACGCCGACACCGUG<br>ACCAUCGACAACACCGUGUACCAGCUGAGCAAGGUGGA<br>GGGCGAGCAGCACGUGAUCAAGGGCAGACCCGUGAGCU<br>CCAGCUUCGACCCCAUCAAGUUCCCUGAGGACCAGUUC<br>AACGUGGCCCUGGACCAGGUGUUUGAGAACAUCGAGAA<br>CAGCCAGGCCCUGGUGGACCAGAGCAACAGAAUCCUGU<br>CCAGCGCUGAGAAGGGCAACACCGGCUUCAUCAUUGUG<br>AUCAUUCUGAUCGCCGUGCUGGGCAGCUCCAUGAUCCU<br>GGUGAGCAUCUUCAUCAUUAUCAAGAAGACCAAGAAAC<br>CCACCGGAGCCCCUCCUGAGCUGAGCGGCGUGACCAAC<br>AAUGGCUUCAUUCCCCACAACUGA</td><td></td></tr>
<tr><td>gb|AY525843.1|:<br>3065-4684 Human<br>metapneumovirus<br>isolate NL/1/99,<br>complete genome</td><td>AUGUCUUGGAAAGUGAUGAUCAUCAUUUCGUUACUCAU<br>AACACCCCAGCACGGGCUAAAGGAGAGUUAUUUGGAAG<br>AAUCAUGUAGUACUAUAACUGAGGGAUACCUCAGUGUU<br>UUAAGAACAGGCUGGUACACUAAUGUCUUCACAUUAGA<br>AGUUGGUGAUGUUGAAAAUCUUACAUGUACUGAUGGA<br>CCUAGCUUAAUCAAAACAGAACUUGAUCUAACAAAAAG<br>UGCUUUAAGGGAACUCAAAACAGUCUCUGCUGAUCAGU<br>UGGCGAGAGAGGAGCAAAUUGAAAAUCCCAGACAAUCA<br>AGAUUUGUCUUAGGUGCGAUAGCUCUCGGAGUUGCUAC<br>AGCAGCAGCAGUCACAGCAGGCAUUGCAAUAGCCAAAA<br>CCAUAAGGCUUGAGAGUGAGGUGAAUGCAAUUAAAGG<br>UGCUCUCAAACAAACUAAUGAAGCAGUAUCCACAUUAG<br>GGAAUGGUGUGCGGGUCCUAGCCACUGCAGUGAGAGAG<br>CUAAAAGAAUUUGUGAGCAAAAACCUGACUAGUGCAAU<br>CAACAGGAACAAAUGUGACAUUGCUGAUCUGAAGAUGG<br>CUGUCAGCUUCAGUCAAUUCAACAGAAGAUUUCUAAAU<br>GUUGUGCGGCAGUUUUCAGACAAUGCAGGGAUAACACC<br>AGCAAUAUCAUUGGACCUGAUGACUGAUGCUGAGUUGG<br>CCAGAGCUGUAUCAUACAUGCCAACAUCUGCAGGGCAG<br>AUAAAACUGAUGUUGGAGAACCGCGCAAUGGUAAGGAG<br>AAAAGGAUUUGGAAUCCUGAUAGGGGUCUACGGAAGCU<br>CUGUGAUUUACAUGGUUCAAUUGCCGAUCUUUGGUGUC<br>AUAGAUACACCUUGUUGGAUCAUCAAGGCAGCUCCCUC<br>UUGCUCAGAAAAAAACGGGAAUUAUGCUUGCCUCCUAA<br>GAGAGGAUCAAGGGUGGUAUUGUAAAAAUGCAGGAUC<br>UACUGUUUACUACCCAAAUGAAAAAGACUGCGAAACAA<br>GAGGUGAUCAUGUUUUUUGUGACACAGCAGCAGGGAUC<br>AAUGUUGCUGAGCAAUCAAGAGAAUGCAACAUCAACAU<br>AUCUACUACCAACUACCCAUGCAAAGUCAGCACAGGAA<br>GACACCCUAUAAGCAUGGUUGCACUAUCACCUCUCGGU<br>GCUUUGGUGGCUUGCUAUAAAGGGGUAAGCUGCUCGAU<br>UGGCAGCAAUUGGGU<br>UGGAAUCAUCAAACAAUUACCCAAAGGCUGCUCAUACA<br>UAACCAACCAGGAUGCAGACACUGUAACAAUUGACAAU<br>ACCGUGUAUCAACUAAGCAAAGUUGAAGGUGAACAGCA<br>UGUAAUAAAAGGGAGACCAGUUUCAAGCAGUUUUGAUC<br>CAAUCAAGUUUCCUGAGGAUCAGUUCAAUGUUGCGCUU<br>GAUCAAGUCUUCGAAAGCAUUGAGAACAGUCAGGCACU<br>AGUGGACCAGUCAAACAAAAUUCUAAACAGUGCAGAAA<br>AAGGAAACACUGGUUUCAUUAUCGUAGUAAUUUUGGU<br>UGCUGUUCUUGGUCUAACCAUGAUUUCAGUGAGCAUCA<br>UCAUCAUAAUCAAGAAAACAAGGAAGCCCACAGGAGCA<br>CCUCCAGAGCUGAAUGGUGUCACCAACGGCGGUUUCAU<br>ACCACAUAGUUAG</td><td>58</td></tr>
<tr><td>gb|KJ627414.1|:<br>3015-4634 Human<br>metapneumovirus<br>strain hMPV/Homo<br>sapiens/PER/<br>CFI0497/2010/B,<br>complete genome</td><td>AUGUCUUGGAAAGUGAUGAUUAUCAUUUCGUUACUCAU<br>AACACCUCAGCAUGGACUAAAAGAAAGUUAUUUAGAAG<br>AAUCAUGUAGUACUAUAACUGAAGGAUAUCUCAGUGUU<br>UUAAGAACAGGUUGGUACACCAAUGUCUUUACAUUAGA<br>AGUUGGUGAUGUUGAAAAUCUUACAUGUACUGAUGGA<br>CCUAGCUUAAUCAAAACAGAACUUGACCUAACCAAAAG<br>UGCUUUAAGAGAACUCAAAACAGUUUCUGCUGAUCAGU<br>UAGCGAGAGAAGAACAAAUUGAAAAUCCCAGACAAUCA<br>AGGUUUGUCCUAGGUGCAAUAGCUCUUGGAGUUGCCAC<br>AGCAGCAGCAGUCACAGCAGGCAUUGCAAUAGCCAAAA<br>CUAUAAGGCUUGAGAGUGAAGUGAAUGCAAUCAAAGG<br>UGCUCUCAAAACAACCAAUGAGGCAGUAUCAACACUAG<br>GAAAUGGAGUGCGGGUCCUAGCCACUGCAGUAAGAGAG</td><td>59</td></tr>
</table>

TABLE 2-continued

| Description | Sequence | SEQ ID NO: |
|---|---|---|
| | CUGAAAGAAUUUGUGAGCAAAAACCUGACUAGUGCGAU<br>CAACAAGAACAAGUGUGACAUUGCUGAUUUGAAGAUGG<br>CUGUCAGCUUCAGUCAGUUCAACAGAAGAUUCCUAAAU<br>GUUGUGCGGCAGUUUUCAGACAAUGCAGGGAUAACACC<br>AGCAAUAUCAUUGGACCUGAUGAAUGAUGCUGAGCUGG<br>CCAGAGCUGUAUCAUACAUGCCAACAUCUGCAGGACAG<br>AUAAAACUAAUGUUAGAGAACCGUGCAAUGGUGAGGA<br>GAAAAGGAUUUGGAAUCUUGAUAGGGGUCUACGGAAG<br>CUCUGUGAUUUACAUGGUCCAGCUGCCGAUCUUUGGUG<br>UCAUAAAUACACCUUGUUGGAUAAUCAAGGCAGCUCCC<br>UCUUGUUCAGAAAAAGAUGGAAAUUAUGCUUGCCUCCU<br>AAGAGAGGAUCAAGGGUGGUAUUGUAAAAAUGCAGGA<br>UCCACUGUUUACUACCCAAAUGAAAAAGACUGCGAAAC<br>AAGAGGUGAUCAUGUUUUUUGUGACACAGCAGCAGGGA<br>UCAAUGUUGCUGAGCAAUCAAGAGAAUGCAACAUCAAC<br>AUAUCUACCACCAACUACCCAUGCAAAGUCAGCACAGG<br>AAGACACCCUAUCAGCAUGGUUGCACUAUCACCUCUCG<br>GUGCUUUGGUAGCUUGCUACAAAGGGGUUAGCUGCUCG<br>ACUGGCAGUAAUCAGGUUGGAAUAAUCAAACAACUACC<br>UAAAGGCUGCUCAUACAUAACUAACCAGGACGCAGACA<br>CUGUAACAAUUGACAACACUGUGUAUCAACUAAGCAAA<br>GUUGAGGGUGAACAGCAUGUAAUAAAAGGGAGACCAG<br>UUUCAAGCAGUUUUGAUCCAAUCAGGUUUCCUGAGGAU<br>CAGUUCAAUGUUGCGCUUGAUCAAGUCUUUGAAAGCAU<br>UGAAAACAGUCAAGCACUAGUGGACCAGUCAAACAAAA<br>UUCUGAACAGUGCAGAAAAAGGAAACACUGGU<br>UUCAUUAUUGUAAUAAUUUUGAUUGCUGUUCUUGGGU<br>UAACCAUGAUUUCAGUGAGCAUCAUCAUCAUAAUCAAA<br>AAAACAAGGAAGCCCACAGGGGCACCUCCGGAGCUGAA<br>UGGUGUUACCAACGGCGGUUUCAUACCGCAUAGUUAG | |
| gb\|KJ723483.1\|: 5586-7310 Human respiratory syncytial virus strain RSVA/*Homo sapiens*/USA/84I-215A-01/1984, complete genome | AUGGAGUUGCCAAUCCUCAAAACAAAUGCAAUUACCAC<br>AAUCCUUGCUGCAGUCACACUCUGUUUCGCUUCCAGUC<br>AAAACAUCACUGAAGAAUUUUAUCAAUCAACAUGCAGU<br>GCAGUUAGCAAAGGCUAUCUUAGUGCUCUAAGAACUGG<br>UUGGUAUACUAGUGUUAUAACUAUAGAAUUAAGUAAU<br>AUCAAGGAAAAUAAGUGUAAUGGAACAGAUGCUAAGG<br>UAAAAUUGAUAAAACAAGAAUUAGAUAAAUAUAAAAA<br>UGCUGUAACAGAAUUGCAGUUGCUCAUGCAAAGCACAC<br>CAGCAGCCAACAAUCGAGCCAGAAGAGAACUACCAAGG<br>UUUAUGAAUUAUACACUCAAUAAUACCAAAAAUACCAA<br>UGUAACAUUAAGCAAGAAAAGGAAAAGAAGAUUUCUU<br>GGCUUUUUGUUAGGUGUUGGAUCUGCAAUCGCCAGUGG<br>CAUUGCUGUAUCUAAGGUCCUGCACCUAGAAGGGGAAG<br>UGAACAAAAUCAAAAGUGCUCUACUAUCCACAAACAAG<br>GCUGUAGUCAGCUUAUCAAAUGGAGUUAGUGUCUUAAC<br>CAGCAAAGUGUUAGACCUCAAAAACUAUAUAGAUAAAC<br>AGUUGUUACCUAUUGUGAACAAGCAAAGCUGCAGCAUA<br>UCAAACAUUGAAACUGUGAUAGAGUUCCAACAAAAGAA<br>CAACAGACUACUAGAGAUUACCAGGGAAUUUAGUGUUA<br>AUGCAGGUGUAACUACACCUGUAAGCACUUAUAUGUUA<br>ACUAAUAGUGAAUUAUUAUCAUUAAUCAAUGAUAUGCC<br>UAUAACAAAUGAUCAGAAAAAGUUAAUGUCCAACAAUG<br>UUCAAAUAGUUAGACAGCAAAGUUACUCUAUCAUGUCC<br>AUAAUAAAGGAGGAAGUCUUAGCAUAUGUAGUACAAU<br>UACCACUAUAUGGUGUAAUAGAUACACCCUGUUGGAAA<br>CUGCACACAUCCCCUCUAUGUACAACCAACACAAAGGA<br>AGGGUCCAACAUCUGCUUAACAAGAACCGACAGAGGAU<br>GGUAUUGUGACAAUGCAGGAUCAGUAUCUUUCUUCCCA<br>CAAGCUGAAACAUGUAAAGUUCAAUCGAAUCGGGUAUU<br>UUGUGACACAAUGAACAGUUUAACAUUACCAAGUGAAG<br>UAAAUCUCUGCAACAUUGACAUAUUCAACCCCAAAUAU<br>GAUUGCAAAAUUAUGACUUCAAAAACAGAUGUAAGCAG<br>CUCCGUUAUCACAUCUCUAGGAGCCAUUGUGUCAUGCU<br>AUGGCAAAACUAAAUGUACAGCAUCCAAUAAAAAUCGU<br>GGGAUCAUAAAGACAUUUUCUAACGGGUGUGAUUAUG<br>UAUCAAAUAAGGGGGUGGAUACUGUGUCUGUAGGUAA<br>UACAUUAUAUUAUGUAAAUAAGCAAGAAGGCAAAAGU<br>CUCUAUGUAAAAGGUGAACCAAUAAUAAAUUUCUAUGA<br>CCCAUUAGUGUUCCCCUCUGAUGAAUUUGAUGCAUCAA<br>UAUCUCAAGUCAAUGAGAAGAUUAACCAGAGCCUAGCA<br>UUUAUUCGUAAAUCCGAUGAAUUAUUACAUAAUGUAA<br>AUGCUGGUAAAUCCACCACAAAUAUCAUGAUAACUACU<br>AUAAUUAUAGUGAUUAUAGUAAUAUUGUUAUCAUUAA | 60 |

TABLE 2-continued

| Description | Sequence | SEQ ID NO: |
|---|---|---|
| | UUGCAGUUGGACUGCUCCUAUACUGCAAGGCCAGAAGC<br>ACACCAGUCACACUAAGUAAGGAUCAACUGAGUGGUAU<br>AAAUAAUAUUGCAUUUAGUAACUGA | |

TABLE 3 hMPV Amino Acid Sequences

| Description | Sequence | SEQ ID NO: |
|---|---|---|
| gi\|122891979\|gb\|<br>EF051124.1\|<br>Human<br>metapneumovirus<br>isolate TN/92-4<br>fusion protein<br>gene,<br>complete cds | MSWKVVIIFSLLITPQHGLKESY<br>LEESCSTITEGYLSVLRTGWYTN<br>VFTLEVGDVENLTCSDGPSLIKT<br>ELDLTKSALRELKTVSADQLARE<br>EQIENPRQSRFVLGAIALGVAAA<br>AAVTAGVAIAKTIRLESEVTAIN<br>NALKKTNEAVSTLGNGVRVLATA<br>VRELKDFVSKNLTRAINKNKCDI<br>DDLKMAVSFSQFNRRFLNVVRQF<br>SDNAGITPAISLDLMTDAELARA<br>VPNMPTSAGQIKLMLENRAMVRR<br>KGFGILIGVYGSSVIYMVQLPIF<br>GVIDTPCWIVKAAPSCSEKKGNY<br>ACLLREDQGWYCQNAGSTVYYPN<br>EKDCETRGDHVFCDTAAGINVAE<br>QSKECNINISTTNYPCKVSTGRH<br>PISMVALSPLGALVACYKGVSCS<br>IGSNRVGIIKQLNKGCSYITNQD<br>ADTVTIDNTVYQLSKVEGEQHVI<br>KGRPVSSSFDPIKFPEDQFNVAL<br>DQVFENIENSQALVDQSNRILSS<br>AEKGNTGFIIVIILIAVLGSSMI<br>LVSIFIIIKKTKKPTGAPPELSG<br>VTNNGFIPHN | 5 |
| gb\|AY525843.1\|:<br>3065-4684 Human<br>metapneumovirus<br>isolate NL/1/99,<br>complete cds | MSWKVMIIISLLITPQHGLKESY<br>LEESCSTITEGYLSVLRTGWYTN<br>VFTLEVGDVENLTCTDGPSLIKT<br>ELDLTKSALRELKTVSADQLARE<br>EQIENPRQSRFVLGAIALGVATA<br>AAVTAGIAIAKTIRLESEVNAIK<br>GALKQTNEAVSTLGNGVRVLATA<br>VRELKEFVSKNLTSAINRNKCDI<br>ADLKMAVSFSQFNRRFLNVVRQF<br>SDNAGITPAISLDLMTDAELARA<br>VSYMPTSAGQIKLMLENRAMVRR<br>KGFGILIGVYGSSVIYMVQLPIF<br>GVIDTPCWIIKAAPSCSEKNGNY<br>ACLLREDQGWYCKNAGSTVYYPN<br>EKDCETRGDHVFCDTAAGINVAE<br>QSRECNINISTTNYPCKVSTGRH<br>PISMVALSPLGALVACYKGVSCS<br>IGSNWVGIIKQLPKGCSYITNQD<br>ADTVTIDNTVYQLSKVEGEQHVI<br>KGRPVSSSFDPIKFPEDQFNVAL<br>DQVFESIENSQALVDQSNKILNS<br>AEKGNTGFIIVVILVAVLGLTMI<br>SVSIIIIIKKTRKPTGAPPELNG<br>VTNGGFIPHS | 6 |
| gb\|KJ627414.1\|:<br>3015-4634 Human<br>metapneumovirus<br>strain hMPV/*Homo*<br>*sapiens*/PER/<br>CFI0497/2010/B,<br>complete cds | MSWKVMIIISLLITPQHGLKESY<br>LEESCSTITEGYLSVLRTGWYTN<br>VFTLEVGDVENLTCTDGPSLIKT<br>ELDLTKSALRELKTVSADQLARE<br>EQIENPRQSRFVLGAIALGVATA<br>AAVTAGIAIAKTIRLESEVNAIK<br>GALKTTNEAVSTLGNGVRVLATA<br>VRELKEFVSKNLTSAINKNKCDI<br>ADLKMAVSFSQFNRRFLNVVRQF<br>SDNAGITPAISLDLMNDAELARA<br>VSYMPTSAGQIKLMLENRAMVRR<br>KGFGILIGVYGSSVIYMVQLPIF<br>GVINTPCWIIKAAPSCSEKDGNY<br>ACLLREDQGWYCKNAGSTVYYPN<br>EKDCETRGDHVFCDTAAGINVAE<br>QSRECNINISTTNYPCKVSTGRH<br>PISMVALSPLGALVACYKGVSCS<br>TGSNQVGIIKQLPKGCSYITNQD<br>ADTVTIDNTVYQLSKVEGEQHVI<br>KGRPVSSSFDPIRFPEDQFNVAL<br>DQVFESIENSQALVDQSNKILNS<br>AEKGNTGFIIVIILIAVLGLTMI<br>SVSIIIIIKKTRKPTGAPPELNG<br>VTNGGFIPHS | 7 |
| gb\|KJ723483.1\|:<br>5586-7310 Human<br>respiratory<br>syncytial virus<br>strain RSVA/*Homo*<br>*sapiens*/USA/84I-<br>215A-01/1984,<br>complete cds | MELPILKTNAITTILAAVTLCFA<br>SSQNITEEFYQSTCSAVSKGYLS<br>ALRTGWYTSVITIELSNIKENKC<br>NGTDAKVKLIKQELDKYKNAVTE<br>LQLLMQSTPAANNRARRELPRFM<br>NYTLNNTKNTNVTLSKKRKRRFL<br>GFLLGVGSAIASGIAVSKVLHLE<br>GEVNKIKSALLSTNKAVVSLSNG<br>VSVLTSKVLDLKNYIDKQLLPIV<br>NKQSCSISNIETVIEFQQKNNRL<br>LEITREFSVNAGVTTPVSTYMLT<br>NSELLSLINDMPITNDQKKLMSN<br>NVQIVRQQSYSIMSIIKEEVLAY<br>VVQLPLYGVIDTPCWKLHTSPLC<br>TTNTKEGSNICLTRTDRGWYCDN<br>AGSVSFFPQAETCKVQSNRVFCD<br>TMNSLTLPSEVNLCNIDIFNPKY<br>DCKIMTSKTDVSSSVITSLGAIV<br>SCYGKTKCTASNKNRGIIKTFSN<br>GCDYVSNKGVDTVSVGNTLYYVN<br>KQEGKSLYVKGEPIINFYDPLVF<br>PSDEFDASISQVNEKINQSLAFI<br>RKSDELLHNVNAGKSTTNIMITT<br>IIIVIIVILLSLIAVGLLLYCKA<br>RSTPVTLSKDQLSGINNIAFSN | 8 |

TABLE 4 hMPV NCBI Accession Numbers (Amino Acid Sequences)

| Virus | GenBank Accession |
|---|---|
| F [Human metapneumovirus] [Human metapneumovirus] | AEK26895.1 |
| fusion glycoprotein [Human metapneumovirus] | ACJ53565.1 |
| fusion glycoprotein [Human metapneumovirus] | ACJ53566.1 |
| fusion glycoprotein [Human metapneumovirus] | ACJ53569.1 |
| fusion protein [Human metapneumovirus] | AEZ52347.1 |
| fusion glycoprotein [Human metapneumovirus] | ACJ53574.1 |
| fusion glycoprotein [Human metapneumovirus] | AHV79473.1 |
| fusion glycoprotein [Human metapneumovirus] | ACJ53570.1 |
| fusion glycoprotein [Human metapneumovirus] | ACJ53567.1 |
| fusion protein [Human metapneumovirus] | AAS22125.1 |
| fusion glycoprotein [Human metapneumovirus] | AHV79795.1 |
| fusion glycoprotein [Human metapneumovirus] | AHV79455.1 |
| fusion glycoprotein [Human metapneumovirus] | ACJ53568.1 |
| fusion protein [Human metapneumovirus] | AAS22109.1 |
| fusion glycoprotein [Human metapneumovirus] | AGU68417.1 |
| fusion glycoprotein [Human metapneumovirus] | AGJ74228.1 |
| fusion glycoprotein [Human metapneumovirus] | ACJ53575.1 |
| fusion protein [Human metapneumovirus] | AAU25820.1 |
| fusion glycoprotein [Human metapneumovirus] | AGU68377.1 |
| fusion glycoprotein [Human metapneumovirus] | AGU68371.1 |
| fusion glycoprotein [Human metapneumovirus] | AGJ74087.1 |
| fusion glycoprotein [Human metapneumovirus] | ACJ53560.1 |
| fusion glycoprotein [Human metapneumovirus] | AHV79858.1 |
| fusion glycoprotein [Human metapneumovirus] | ACJ53577.1 |
| fusion protein [Human metapneumovirus] | AAS22085.1 |
| fusion protein [Human metapneumovirus] | AEZ52348.1 |
| fusion glycoprotein [Human metapneumovirus] | AGJ74044.1 |
| fusion glycoprotein [Human metapneumovirus] | ACJ53563.1 |
| fusion glycoprotein precursor [Human metapneumovirus] | YP_012608.1 |
| fusion glycoprotein [Human metapneumovirus] | AGJ74053.1 |
| fusion protein [Human metapneumovirus] | BAM37562.1 |
| fusion glycoprotein [Human metapneumovirus] | ACJ53561.1 |
| fusion glycoprotein [Human metapneumovirus] | AGU68387.1 |
| fusion [Human metapneumovirus] | AGL74060.1 |
| fusion glycoprotein precursor [Human metapneumovirus] | AAV88364.1 |
| fusion protein [Human metapneumovirus] | AAN52910.1 |
| fusion protein [Human metapneumovirus] | AAN52915.1 |
| fusion protein [Human metapneumovirus] | BAM37564.1 |
| fusion glycoprotein precursor [Human metapneumovirus] | BAH59618.1 |
| fusion protein [Human metapneumovirus] | AAQ90144.1 |
| fusion glycoprotein [Human metapneumovirus] | AHV79446.1 |
| fusion protein [Human metapneumovirus] | AEL87260.1 |
| fusion glycoprotein [Human metapneumovirus] | AHV79867.1 |
| fusion protein [Human metapneumovirus] | ABQ66027.2 |
| fusion glycoprotein [Human metapneumovirus] | ACJ53621.1 |
| fusion protein [Human metapneumovirus] | AAN52911.1 |
| fusion glycoprotein [Human metapneumovirus] | AHV79536.1 |
| fusion glycoprotein [Human metapneumovirus] | AGU68411.1 |
| fusion protein [Human metapneumovirus] | AEZ52346.1 |
| fusion protein [Human metapneumovirus] | AAN52913.1 |
| fusion protein [Human metapneumovirus] | AAN52908.1 |
| fusion glycoprotein [Human metapneumovirus] | ACJ53553.1 |
| fusion glycoprotein [Human metapneumovirus] | AIY25727.1 |
| fusion protein [Human metapneumovirus] | ABM67072.1 |
| fusion protein [Human metapneumovirus] | AEZ52361.1 |
| fusion protein [Human metapneumovirus] | AAS22093.1 |
| fusion glycoprotein [Human metapneumovirus] | AGH27049.1 |
| fusion protein [Human metapneumovirus] | AAK62968.2 |
| fusion glycoprotein [Human metapneumovirus] | ACJ53556.1 |
| fusion glycoprotein [Human metapneumovirus] | ACJ53620.1 |
| fusion protein [Human metapneumovirus] | ABQ58820.1 |
| F [Human metapneumovirus] [Human metapneumovirus] | AEK26886.1 |
| fusion glycoprotein [Human metapneumovirus] | ACJ53619.1 |
| fusion glycoprotein [Human metapneumovirus] | ACJ53555.1 |
| fusion [Human metapneumovirus] | AGL74057.1 |
| fusion protein [Human metapneumovirus] | ABD27850.1 |
| fusion protein [Human metapneumovirus] | AEZ52349.1 |
| fusion protein [Human metapneumovirus] | ABD27848.1 |
| fusion protein [Human metapneumovirus] | ABD27846.1 |
| fusion protein [Human metapneumovirus] | ABQ66021.1 |
| fusion protein [Human metapneumovirus] | AFM57710.1 |
| fusion protein [Human metapneumovirus] | AFM57709.1 |
| fusion protein [Human metapneumovirus] | ABH05968.1 |
| fusion protein [Human metapneumovirus] | AEZ52350.1 |
| fusion protein [Human metapneumovirus] | AFM57712.1 |

TABLE 4-continued hMPV NCBI Accession Numbers (Amino Acid Sequences)

| Virus | GenBank Accession |
|---|---|
| fusion protein [Human metapneumovirus] | AEZ52364.1 |
| fusion protein [Human metapneumovirus] | AAN52912.1 |
| fusion protein [Human metapneumovirus] | AEZ52363.1 |
| fusion [Human metapneumovirus] | AGL74059.1 |
| fusion glycoprotein [Human metapneumovirus] | ACJ53583.1 |
| fusion protein [Human metapneumovirus] | AEZ52356.1 |
| fusion protein [Human metapneumovirus] | AEZ52353.1 |
| fusion glycoprotein [Human metapneumovirus] | ACJ53581.1 |
| fusion glycoprotein [Human metapneumovirus] | ACJ53578.1 |
| fusion protein [Human metapneumovirus] | AAS22117.1 |
| fusion protein [Human metapneumovirus] | BAN75965.1 |
| fusion protein [Human metapneumovirus] | AGF92105.1 |
| fusion protein [Human metapneumovirus] | AAS22077.1 |
| fusion protein [Human metapneumovirus] | AAN52909.1 |
| fusion glycoprotein [Human metapneumovirus] | ACJ53586.1 |
| fusion protein [Human metapneumovirus] | AAQ90145.1 |
| fusion glycoprotein [Human metapneumovirus] | AGT75042.1 |
| fusion [Human metapneumovirus] | AGL74058.1 |
| fusion protein [Human metapneumovirus] | AEL87263.1 |
| fusion glycoprotein [Human metapneumovirus] | AGH27057.1 |
| fusion glycoprotein [Human metapneumovirus] | AHV79491.1 |
| F [Human metapneumovirus] [Human metapneumovirus] | AEK26906.1 |
| fusion glycoprotein [Human metapneumovirus] | ACJ53580.1 |
| fusion protein [Human metapneumovirus] | AEZ52354.1 |
| fusion protein [Human metapneumovirus] | AAN52914.1 |
| G [Human metapneumovirus] [Human metapneumovirus] | AEK26901.1 |
| glycoprotein [Human metapneumovirus] | AFI56738.1 |
| glycoprotein [Human metapneumovirus] | AFI56739.1 |
| glycoprotein [Human metapneumovirus] | AFI56745.1 |
| G protein [Human metapneumovirus] | AAQ62718.1 |
| G protein [Human metapneumovirus] | AAQ62719.1 |
| attachment glycoprotein G [Human metapneumovirus] | AGH27104.1 |
| G protein [Human metapneumovirus] | AAQ62729.1 |
| G protein [Human metapneumovirus] | AAQ62728.1 |
| glycoprotein [Human metapneumovirus] | AFI56753.1 |
| glycoprotein [Human metapneumovirus] | AFI56746.1 |
| glycoprotein [Human metapneumovirus] | AFI56750.1 |
| glycoprotein [Human metapneumovirus] | AFI56747.1 |
| G protein [Human metapneumovirus] | AAQ62721.1 |
| glycoprotein [Human metapneumovirus] | AAT46573.1 |
| glycoprotein [Human metapneumovirus] | AFI56748.1 |
| glycoprotein [Human metapneumovirus] | AFI56736.1 |
| glycoprotein [Human metapneumovirus] | AFI56749.1 |
| attachment glycoprotein G [Human metapneumovirus] | AGH27131.1 |
| attachment glycoprotein G [Human metapneumovirus] | AHV79558.1 |
| glycoprotein [Human metapneumovirus] | AFI56740.1 |
| glycoprotein [Human metapneumovirus] | AFI56741.1 |
| glycoprotein [Human metapneumovirus] | AFI56744.1 |
| attachment glycoprotein G [Human metapneumovirus] | AHV79790.1 |
| attachment glycoprotein G [Human metapneumovirus] | AGH27122.1 |
| attachment glycoprotein G [Human metapneumovirus] | AHV79763.1 |
| attachment glycoprotein G [Human metapneumovirus] | AGZ48849.1 |
| glycoprotein [Human metapneumovirus] | AFI56743.1 |
| attachment glycoprotein G [Human metapneumovirus] | AHV79450.1 |
| glycoprotein [Human metapneumovirus] | AFI56751.1 |
| attachment glycoprotein [Human metapneumovirus] | AAS48482.1 |
| attachment glycoprotein G [Human metapneumovirus] | AHV79889.1 |
| attachment surface glycoprotein [Human metapneumovirus] | AGW43050.1 |
| glycoprotein [Human metapneumovirus] | AFI56754.1 |
| attachment glycoprotein G [Human metapneumovirus] | AHV79601.1 |
| glycoprotein [Human metapneumovirus] | AFI56752.1 |
| attachment glycoprotein G [Human metapneumovirus] | AHV79871.1 |
| G protein [Human metapneumovirus] | AEZ68099.1 |
| attachment glycoprotein G [Human metapneumovirus] | AHV79817.1 |
| attachment glycoprotein G [Human metapneumovirus] | AHV79943.1 |
| attachment glycoprotein G [Human metapneumovirus] | BAN75968.1 |
| attachment surface glycoprotein [Human metapneumovirus] | AGW43045.1 |
| attachment glycoprotein G [Human metapneumovirus] | AHV79628.1 |
| attachment glycoprotein [Human metapneumovirus] | AFK49783.1 |
| G protein [Human metapneumovirus] | AAQ62723.1 |
| attachment glycoprotein [Human metapneumovirus] | ABD27839.1 |
| attachment surface glycoprotein [Human metapneumovirus] | AGW43046.1 |

TABLE 4-continued

| hMPV NCBI Accession Numbers (Amino Acid Sequences) | |
|---|---|
| Virus | GenBank Accession |
| G protein [Human metapneumovirus] | AAQ62717.1 |
| glycoprotein [Human metapneumovirus] | AFI56742.1 |
| attachment protein [Human metapneumovirus] | ABQ44522.1 |
| glycoprotein [Human metapneumovirus] | AFI56735.1 |
| attachment surface glycoprotein [Human metapneumovirus] | AGW43065.1 |
| G protein [Human metapneumovirus] | AAQ62724.1 |
| attachment surface glycoprotein [Human metapneumovirus] | AGW43075.1 |
| attachment surface glycoprotein [Human metapneumovirus] | AGW43062.1 |
| glycoprotein [Human metapneumovirus] | AAT46579.1 |
| attachment surface glycoprotein [Human metapneumovirus] | AGW43064.1 |
| attachment surface glycoprotein [Human metapneumovirus] | AGW43054.1 |
| attachment surface glycoprotein [Human metapneumovirus] | AGW43042.1 |
| attachment surface glycoprotein [Human metapneumovirus] | AGW43078.1 |
| attachment surface glycoprotein [Human metapneumovirus] | AGW43067.1 |
| G protein [Human metapneumovirus] | AAQ62722.1 |
| attachment surface glycoprotein metapneumovirus] | AGW43063.1 |
| glycoprotein [Human metapneumovirus] | AAT46571.1 |
| glycoprotein [Human metapneumovirus] | AAT46578.1 |
| attachment glycoprotein G [Human metapneumovirus] | AGJ74232.1 |
| glycoprotein [Human metapneumovirus] | AAT46580.1 |
| glycoprotein [Human metapneumovirus] | AAT46574.1 |
| attachment surface glycoprotein [Human metapneumovirus] | AGW43061.1 |
| attachment glycoprotein [Human metapneumovirus] | AFK49791.1 |
| attachment surface glycoprotein [Human metapneumovirus] | AGW43047.1 |
| glycoprotein [Human metapneumovirus] | ABC26386.1 |
| attachment glycoprotein [Human metapneumovirus] | AAS48466.1 |
| attachment surface glycoprotein [Human metapneumovirus] | AGW43048.1 |
| attachment glycoprotein G [Human metapneumovirus] | AGH27140.1 |
| attachment surface glycoprotein [Human metapneumovirus] | AGW43049.1 |
| attachment glycoprotein G [Human metapneumovirus] | AGJ74082.1 |
| attachment glycoprotein G [Human metapneumovirus] | AHV79442.1 |
| attachment glycoprotein G [Human metapneumovirus] | AGJ74091.1 |
| attachment glycoprotein G [Human metapneumovirus] | AHV79477.1 |
| attachment surface glycoprotein [Human metapneumovirus] | AGW43056.1 |
| attachment protein [Human metapneumovirus] | ABQ44523.1 |
| attachment glycoprotein G [Human metapneumovirus] | BAH59622.1 |
| attachment surface glycoprotein [Human metapneumovirus] | AGW43070.1 |
| glycoprotein [Human metapneumovirus] | AAT46585.1 |
| attachment glycoprotein G [Human metapneumovirus] | AGU68409.1 |
| attachment glycoprotein G [Human metapneumovirus] | AGJ74223.1 |
| attachment glycoprotein [Human metapneumovirus] | AAS22129.1 |
| attachment glycoprotein G [Human metapneumovirus] | AGJ74048.1 |
| G protein [Human metapneumovirus] | AAQ62725.1 |
| glycoprotein [Human metapneumovirus] | ABC26384.1 |
| attachment protein [Human metapneumovirus] | ABQ44525.1 |
| attachment glycoprotein G [Human metapneumovirus] | YP_012612.1 |
| attachment surface glycoprotein [Human metapneumovirus] | AGW43071.1 |
| attachment glycoprotein G [Human metapneumovirus] | AGJ74162.1 |
| attachment glycoprotein G [Human metapneumovirus] | AGH27095.1 |
| attachment glycoprotein G [Human metapneumovirus] | AHV79531.1 |
| G protein [Human metapneumovirus] | AAQ62726.1 |
| attachment glycoprotein [Human metapneumovirus] | AAS48465.1 |
| attachment surface glycoprotein [Human metapneumovirus] | AGW43058.1 |
| P [Human metapneumovirus] [Human metapneumovirus] | AEK26894.1 |
| phosphoprotein [Human metapneumovirus] | AHV79631.1 |
| phosphoprotein [Human metapneumovirus] | AHV79901.1 |
| phosphoprotein [Human metapneumovirus] | AHV79570.1 |
| phosphoprotein [Human metapneumovirus] | AGJ74076.1 |
| phosphoprotein [Human metapneumovirus] | AAS22123.1 |

TABLE 4-continued

| hMPV NCBI Accession Numbers (Amino Acid Sequences) | |
|---|---|
| Virus | GenBank Accession |
| phosphoprotein [Human metapneumovirus] | ABB16895.1 |
| phosphoprotein [Human metapneumovirus] | AHV79579.1 |
| phosphoprotein [Human metapneumovirus] | AGJ74244.1 |
| phosphoprotein [Human metapneumovirus] | AHV79856.1 |
| phosphoprotein [Human metapneumovirus] | ACJ70113.1 |
| phosphoprotein [Human metapneumovirus] | AGZ48843.1 |
| phosphoprotein [Human metapneumovirus] | AHV79498.1 |
| phosphoprotein [Human metapneumovirus] | AHV79480.1 |
| phosphoprotein [Human metapneumovirus] | ABQ43382.1 |
| phosphoprotein [Human metapneumovirus] | AAS22107.1 |
| phosphoprotein [Human metapneumovirus] | ABB16898.1 |
| phosphoprotein [Human metapneumovirus] | AGH27134.1 |
| phosphoprotein [Human metapneumovirus] | ABB16899.1 |
| phosphoprotein [Human metapneumovirus] | AGH27098.1 |
| phosphoprotein [Human metapneumovirus] | AAN52866.1 |
| phosphoprotein [Human metapneumovirus] | AAS22083.1 |
| phosphoprotein [Human metapneumovirus] | YP_012606.1 |
| phosphoprotein [Human metapneumovirus] | AHV79973.1 |
| phosphoprotein [Human metapneumovirus] | AHV79462.1 |
| phosphoprotein [Human metapneumovirus] | AGJ74042.1 |
| phosphoprotein [Human metapneumovirus] | AAV88362.1 |
| P [Human metapneumovirus] [Human metapneumovirus] | AIL23591.1 |
| phosphoprotein [Human metapneumovirus] | AHV79453.1 |
| phosphoprotein [Human metapneumovirus] | AGJ74261.1 |
| phosphoprotein [Human metapneumovirus] | AGH27116.1 |
| phosphoprotein [Human metapneumovirus] | ABB16444.1 |
| phosphoprotein [Human metapneumovirus] | ABB16445.1 |
| phosphoprotein [Human metapneumovirus] | AHV79507.1 |
| phosphoprotein [Human metapneumovirus] | BAH59616.1 |
| phosphoprotein [Human metapneumovirus] | ABB16443.1 |
| phosphoprotein [Human metapneumovirus] | ABQ43388.1 |
| phosphoprotein [Human metapneumovirus] | ABQ43389.1 |
| phosphoprotein [Human metapneumovirus] | ABQ43395.1 |
| phosphoprotein [Human metapneumovirus] | ABQ43385.1 |
| phosphoprotein [Human metapneumovirus] | AAP84042.1 |
| phosphoprotein [Human metapneumovirus] | AAN52868.1 |
| phosphoprotein [Human metapneumovirus] | AAP84041.1 |
| phosphoprotein [Human metapneumovirus] | AGH27080.1 |
| phosphoprotein [Human metapneumovirus] | ABQ43387.1 |
| phosphoprotein [Human metapneumovirus] | AAS22099.1 |
| phosphoprotein [Human metapneumovirus] | ABB16896.1 |
| phosphoprotein [Human metapneumovirus] | AGJ74094.1 |
| phosphoprotein [Human metapneumovirus] | AEZ68089.1 |
| phosphoprotein [Human metapneumovirus] | ABK97002.1 |
| phosphoprotein [Human metapneumovirus] | AAP13486.1 |
| phosphoprotein [Human metapneumovirus] | AHV79444.1 |
| phosphoprotein [Human metapneumovirus] | AHV79865.1 |
| phosphoprotein [Human metapneumovirus] | AGJ74226.1 |
| phosphoprotein [Human metapneumovirus] | ABQ43383.1 |
| phosphoprotein [Human metapneumovirus] | AAN52863.1 |
| phosphoprotein [Human metapneumovirus] | AHV79775.1 |
| phosphoprotein [Human metapneumovirus] | AEZ68094.1 |
| phosphoprotein [Human metapneumovirus] | AHV79883.1 |
| phosphoprotein [Human metapneumovirus] | AEZ68092.1 |
| phosphoprotein [Human metapneumovirus] | ABQ43390.1 |
| phosphoprotein [Human metapneumovirus] | ABQ43386.1 |
| phosphoprotein [Human metapneumovirus] | ABQ43391.1 |
| phosphoprotein [Human metapneumovirus] | ACS16062.1 |
| phosphoprotein [Human metapneumovirus] | AEZ68090.1 |
| phosphoprotein [Human metapneumovirus] | AAK62967.1 |
| phosphoprotein [Human metapneumovirus] | AEZ68093.1 |
| phosphoprotein [Human metapneumovirus] | AEZ68088.1 |
| phosphoprotein [Human metapneumovirus] | ABQ43392.1 |
| phosphoprotein [Human metapneumovirus] | ABQ43393.1 |
| phosphoprotein [Human metapneumovirus] | ABQ43384.1 |
| phosphoprotein [Human metapneumovirus] | ABQ43394.1 |
| phosphoprotein [Human metapneumovirus] | ABK96999.1 |
| phosphoprotein [Human metapneumovirus] | AHV79489.1 |
| phosphoprotein [Human metapneumovirus] | AGJ74235.1 |
| phosphoprotein [Human metapneumovirus] | AAS22075.1 |
| phosphoprotein [Human metapneumovirus] | AAS22115.1 |
| phosphoprotein [Human metapneumovirus] | AII17601.1 |
| phosphoprotein [Human metapneumovirus] | ABK97000.1 |
| phosphoprotein [Human metapneumovirus] | AHV79561.1 |
| phosphoprotein [Human metapneumovirus] | AGT75040.1 |

TABLE 4-continued

| hMPV NCBI Accession Numbers (Amino Acid Sequences) | |
|---|---|
| Virus | GenBank Accession |
| phosphoprotein [Human metapneumovirus] | AAN52864.1 |
| phosphoprotein [Human metapneumovirus] | ABK97001.1 |
| phosphoprotein [Human metapneumovirus] | AGT74979.1 |
| phosphoprotein [Human metapneumovirus] | AHV79955.1 |
| phosphoprotein [Human metapneumovirus] | AGH27055.1 |
| phosphoprotein [Human metapneumovirus] | AAV88361.1 |
| phosphoprotein [Human metapneumovirus] | ABQ43397.1 |
| phosphoprotein [Human metapneumovirus] | AGJ74173.1 |
| P [Human metapneumovirus] [Human metapneumovirus] | AEK26904.1 |
| phosphoprotein [Human metapneumovirus] | ACJ70104.1 |
| phosphoprotein [Human metapneumovirus] | ABK97003.1 |
| phosphoprotein [Human metapneumovirus] | AGT74955.1 |
| phosphoprotein [Human metapneumovirus] | AAN52856.1 |
| phosphoprotein [Human metapneumovirus] | AAN52862.1 |
| phosphoprotein [Human metapneumovirus] | AGJ74138.1 |
| phosphoprotein [Human metapneumovirus] | AHV79613.1 |
| phosphoprotein [Human metapneumovirus] | AGJ74060.1 |
| phosphoprotein [Human metapneumovirus] | AAQ67684.1 |
| phosphoprotein [Human metapneumovirus] | AEA02278.1 |
| N [Human metapneumovirus] [Human metapneumovirus] | AEK26899.1 |
| nucleoprotein [Human metapneumovirus] | ACS16061.1 |
| nucleoprotein [Human metapneumovirus] | AAS88425.1 |
| nucleoprotein [Human metapneumovirus] | YP_012605.1 |
| nucleoprotein [Human metapneumovirus] | AHV79882.1 |
| nucleoprotein [Human metapneumovirus] | AHV79774.1 |
| nucleocapsid protein [Human metapneumovirus] | AAN52886.1 |
| nucleoprotein [Human metapneumovirus] | AAS22082.1 |
| nucleoprotein [Human metapneumovirus] | AHV79864.1 |
| nucleoprotein [Human metapneumovirus] | AHV79828.1 |
| nucleoprotein [Human metapneumovirus] | AGJ74084.1 |
| nucleocapsid protein [Human metapneumovirus] | AAN52888.1 |
| N [Human metapneumovirus] [Human metapneumovirus] | AIL23590.1 |
| nucleoprotein [Human metapneumovirus] | AAK62966.1 |
| nucleoprotein [Human metapneumovirus] | AHV79972.1 |
| nucleoprotein [Human metapneumovirus] | AHV79470.1 |
| nucleoprotein [Human metapneumovirus] | AHV79452.1 |
| nucleoprotein [Human metapneumovirus] | AGJ74243.1 |
| nucleoprotein [Human metapneumovirus] | AHV79533.1 |
| nucleoprotein [Human metapneumovirus] | AGJ74181.1 |
| nucleoprotein [Human metapneumovirus] | AHV79497.1 |
| nucleoprotein [Human metapneumovirus] | AHV79702.1 |
| nucleoprotein [Human metapneumovirus] | AHV79648.1 |
| nucleoprotein [Human metapneumovirus] | AHV79435.1 |
| putative nucleoprotein [Human metapneumovirus] | AGJ74260.1 |
| nucleocapsid protein [Human metapneumovirus] | AAN52887.1 |
| nucleoprotein [Human metapneumovirus] | AGU68386.1 |
| nucleocapsid protein [Human metapneumovirus] | AAN52899.1 |
| nucleoprotein [Human metapneumovirus] | AAR17673.1 |
| nucleocapsid protein [Human metapneumovirus] | AAN52898.1 |
| nucleoprotein [Human metapneumovirus] | AEA02277.1 |
| nucleoprotein [Human metapneumovirus] | AHV79612.1 |
| nucleoprotein [Human metapneumovirus] | AGU68416.1 |
| nucleoprotein [Human metapneumovirus] | AGU68408.1 |
| nucleoprotein [Human metapneumovirus] | AGU68370.1 |
| nucleoprotein [Human metapneumovirus] | AAQ67683.1 |
| nucleoprotein [Human metapneumovirus] | AGJ74137.1 |
| nucleoprotein [Human metapneumovirus] | AGU68344.1 |
| nucleocapsid protein [Human metapneumovirus] | ABK96997.1 |
| nucleoprotein [Human metapneumovirus] | AGU68413.1 |
| nucleocapsid protein [Human metapneumovirus] | AAN52891.1 |
| nucleoprotein [Human metapneumovirus] | AGU68360.1 |
| nucleoprotein [Human metapneumovirus] | AGU68353.1 |
| nucleocapsid protein [Human metapneumovirus] | ABK96996.1 |
| nucleoprotein [Human metapneumovirus] | AAR17666.1 |
| N [Human metapneumovirus] [Human metapneumovirus] | AEK26903.1 |
| nucleoprotein [Human metapneumovirus] | AGT75039.1 |
| nucleoprotein [Human metapneumovirus] | AGU68410.1 |
| nucleoprotein [Human metapneumovirus] | AAS22074.1 |
| nucleoprotein [Human metapneumovirus] | AHV79560.1 |
| nucleoprotein [Human metapneumovirus] | AGT74978.1 |
| nucleoprotein [Human metapneumovirus] | AGJ74128.1 |
| nucleoprotein [Human metapneumovirus] | AAR17663.1 |
| nucleoprotein [Human metapneumovirus] | AAR17662.1 |
| nucleoprotein [Human metapneumovirus] | AAR17664.1 |
| nucleoprotein [Human metapneumovirus] | AAR17657.1 |

TABLE 4-continued

| hMPV NCBI Accession Numbers (Amino Acid Sequences) | |
|---|---|
| Virus | GenBank Accession |
| nucleoprotein [Human metapneumovirus] | AAR17659.1 |
| nucleoprotein [Human metapneumovirus] | AAR17661.1 |
| nucleoprotein [Human metapneumovirus] | AGU68352.1 |
| nucleoprotein [Human metapneumovirus] | AGU68373.1 |
| nucleoprotein [Human metapneumovirus] | AGU68376.1 |
| nucleoprotein [Human metapneumovirus] | AGU68342.1 |
| nucleoprotein [Human metapneumovirus] | AGU68365.1 |
| nucleoprotein [Human metapneumovirus] | AGU68363.1 |
| nucleoprotein [Human metapneumovirus] | AGU68398.1 |
| nucleoprotein [Human metapneumovirus] | AGU68348.1 |
| nucleoprotein [Human metapneumovirus] | AGU68354.1 |
| nucleoprotein [Human metapneumovirus] | AGU68391.1 |
| nucleoprotein [Human metapneumovirus] | AGU68389.1 |
| nucleoprotein [Human metapneumovirus] | AGU68399.1 |
| nucleoprotein [Human metapneumovirus] | AGU68337.1 |
| nucleoprotein [Human metapneumovirus] | AAR17660.1 |
| nucleoprotein [Human metapneumovirus] | AAR17667.1 |
| nucleoprotein [Human metapneumovirus] | AGU68402.1 |
| nucleoprotein [Avian metapneumovirus type C] | CDN30025.1 |
| nucleoprotein [Avian metapneumovirus] | AGZ87947.1 |
| Nucleoprotein [Avian metapneumovirus type C] | CAL25113.1 |
| nucleocapsid protein [Avian metapneumovirus] | ABO42286.1 |
| nucleocapsid protein [Avian metapneumovirus] | AAK38430.1 |
| nucleocapsid protein [Avian metapneumovirus] | AAK54155.1 |
| nucleocapsid protein [Avian metapneumovirus] | AAK38426.1 |
| nucleocapsid protein [Avian metapneumovirus] | AAK38425.1 |
| nucleocapsid protein [Avian metapneumovirus] | AAK38424.1 |
| nucleocapsid protein [Avian metapneumovirus] | AAF05909.1 |
| nucleocapsid protein [Avian metapneumovirus] | AAK38435.1 |
| nucleocapsid protein [Avian metapneumovirus] | AAK38428.1 |
| nucleoprotein [Human metapneumovirus] | AAR17669.1 |
| nucleocapsid protein [Avian metapneumovirus] | AAK38429.1 |
| nucleocapsid protein [Avian metapneumovirus] | AAK38427.1 |
| nucleocapsid protein [Avian metapneumovirus] | AAK38423.1 |
| nucleocapsid protein [Avian metapneumovirus] | AAK38434.1 |
| nucleoprotein [Human metapneumovirus] | AGU68338.1 |
| nucleoprotein [Avian metapneumovirus] | YP_443837.1 |
| nucleoprotein [Human metapneumovirus] | AGU68384.1 |
| nucleocapsid protein [Avian metapneumovirus] | AAK38431.1 |
| nucleoprotein [Human metapneumovirus] | AGU68405.1 |
| nucleoprotein [Human metapneumovirus] | AGU68382.1 |
| nucleoprotein [Human metapneumovirus] | AGU68395.1 |
| nucleocapsid [Human metapneumovirus] | AAL35389.3 |
| nucleoprotein [Human metapneumovirus] | AEZ68064.1 |

TABLE 5

| Description | Sequence | SEQ ID NO: |
|---|---|---|
| | PIV3 Nucleic Acid Sequences | |
| >gb\|KJ672601.1\|: 4990-6609 Human parainfluenza virus 3 strain HPIV3/Homo sapiens/PER/FLA4815/2008 [fusion glycoprotein F0] | ATGCCAATTTCAATACTGTTAATTATTACAACCATGATC ATGGCATCACACTGCCAAATAGACATCACAAAACTACA GCATGTAGGTGTATTGGTCAACAGTCCCAAAGGGATGA AGATATCACAAAACTTCGAAACAAGATATCTAATCCTGA GTCTCATACCAAAAATAGAAGATTCTAACTCTTGTGGTG ACCAACAGATCAAGCAATACAAGAGGTTATTGGATAGA CTGATCATTCCTTTATATGATGGACTAAGATTACAGAAG GATGTGATAGTGACTAATCAAGAATCCAATGAAAACAC TGATCCCAGAACAGAACGATTCTTTGGAGGGGTAATTGG AACTATTGCTCTAGGAGTAGCAACCTCAGCACAAATTAC AGCAGCAGTTGCTCTGGTTGAAGCCAAGCAGGCAAGAT CAGACATTGAAAAACTCAAGGAAGCAATCAGGGACACA AATAAAGCAGTGCAGTCAGTTCAGAGCTCTGTAGGAAA TTTGATAGTAGCAATTAAATCAGTCCAGGATTATGTCAA CAAAGAAATCGTGCCATCGATTGCGAGACTAGGTTGTG AAGCAGCAGGACTTCAGTTAGGGATTGCATTAACACAG CATTACTCAGAATTAACAAATATATTTGGTGATAACATA GGATCGTTACAAGAAAAAGGAATAAAATTACAAGGTAT AGCATCATTATACCGTACAAATATCACAGAAATATTCAC AACATCAACAGTTGACAAATATGATATTTATGATCTATT | 9 |

TABLE 5-continued

| Description | Sequence | SEQ ID NO: |
|---|---|---|
| | ATTTACAGAATCAATAAAGGTGAGAGTTATAGATGTTGA TTTGAATGATTACTCAATAACCCTCCAAGTCAGACTCCC TTTATTGACCAGACTGCTGAACACTCAAATCTACAAAGT AGATTCCATATCATACAATATCCAAAATAGAGAATGGTA TATCCCTCTTCCCAGCCATATCATGACGAAAGGGGCATT TCTAGGTGGAGCAGATGTCAAAGAATGCATAGAAGCAT TCAGCAGTTATATATGCCCTTCTGATCCAGGATTTGTACT AAACCATGAAATGGAGAGCTGTCTATCAGGAAACATAT CCCAATGTCCAAGAACCACAGTCACATCAGACATAGTTC CTAGGTATGCATTTGTCAATGGAGGAGTGGTTGCGAATT GTATAACAACTACATGTACATGCAATGGTATCGGTAATA GAATCAACCAACCACCTGATCAAGGAGTCAAAATTATA ACACATAAAGAATGTAATACAATAGGTATCAACGGAAT GCTATTCAACACAAACAAAGAAGGAACTCTTGCATTCTA CACACCAGACGACATAACATTAAACAATTCTGTTGCACT TGATCCGATTGACATATCAATCGAGCTCAACAAGGCCAA ATCAGATCTTGAGGAATCAAAAGAATGGATAAGAAGGT CAAATCAAAAGCTAGATTCTATTGGAAGTTGGCATCAAT CTAGCACTACAATCATAGTTATTTTGATAATGATGATTA TATTGTTTATAATTAATATAACAATAATTACAATTGCAA TTAAGTATTACAGAATTCAAAAGAGAAATCGAGTGGAT CAAAATGATAAGCCGTATGTATTAACAAACAAG | |
| gi\|612507167\|gb\| AHX22430.1\| hemagglutinin-neuraminidase [Human parainfluenza virus 3] | ATGGAATACTGGAAGCACACCAACCACGGAAAGGATGC TGGTAATGAGCTGGAGACATCCACAGCCACTCATGGCA ACAAGCTCACCAACAAGATAACATATATATTGTGGACG ATAACCCTGGTGTTATTATCAATAGTCTTCATCATAGTG CTAACTAATTCCATCAAAAGTGAAAAGGCCCGCGAATC ATTGCTACAAGACATAAATAATGAGTTTATGGAAGTTAC AGAAAAGATCCAAGTGGCATCGGATAATACTAATGATC TAATACAGTCAGGAGTGAATACAAGGCTTCTTACAATTC AGAGTCATGTCCAGAATTATATACCAATATCATTGACAC AACAAATATCGGATCTTAGGAAATTCATTAGTGAAATTA CAATTAGAAATGATAATCAAGAAGTGCCACCACAAAGA ATAACACATGATGTGGGTATAAAACCTTTAAATCCAGAT GATTTCTGGAGATGCACGTCTGGTCTTCCATCTTTGATG AAAACTCCAAAAATAAGATTAATGCCGGGACCAGGATT ATTAGCTATGCCAACGACTGTTGATGGCTGTGTCAGAAC CCCGTCCTTAGTGATAAATGATCTGATTTATGCTTACAC CTCAAATCTAATTACTCGAGGTTGCCAGGATATAGGGAA ATCATATCAAGTATTACAGATAGGGATAATAACTGTAAA CTCAGACTTGGTACCTGACTTAAATCCTAGGATCTCTCA TACCTTCAACATAAATGACAATAGAAAGTCATGTTCTCT AGCACTCCTAAATACAGATGTATATCAACTGTGTTCAAC CCCAAAAGTTGATGAAAGATCAGATTATGCATCATCAG GCATAGAAGATATTGTACTTGATATTGTCAATTATGATG GCTCAATCTCGACAACAAGATTTAAGAATAATAATATAA GTTTTGATCAACCATATGCGGCATTATACCCATCTGTTG GACCAGGGATATACTACAAAGGCAAAATAATATTTCTC GGGTATGGAGGTCTTGAACATCCAATAAATGAGAATGC AATCTGCAACACAACTGGGTGTCCTGGGAAAACACAGA GAGACTGTAATCAAGCATCTCATAGTCCATGGTTTTCAG ATAGAAGGATGGTCAACTCTATAATTGTTGTTGACAAGG GCTTGAACTCAGTTCCAAAATTGAAGGTATGGACGATAT CTATGAGACAAAATTACTGGGGGTCAGAAGGAAGATTA CTTCTACTAGGTAACAAGATCTACATATACACAAGATCT ACAAGTTGGCACAGCAAGTTACAATTAGGAATAATTGA CATTACTGACTACAGTGATATAAGGATAAAATGGACAT GGCATAATGTGCTATCAAGACCAGGAAACAATGAATGT CCATGGGGACATTCATGTCCGGATGGATGTATAACGGG AGTATATACCGATGCATATCCACTCAATCCCACAGGAAG CATTGTATCATCTGTCATATTGGACTCACAAAAATCGAG AGTCAACCCAGTCATAACTTACTCAACAGCAACCGAAA GGGTAAACGAGCTGGCTATCCGAAACAAAACACTCTCA GCTGGGTACACAACAACAAGCTGCATTACACACTATAA CAAAGGGTATTGTTTTCATATAGTAGAAATAAATCATAA AAGCTTAAACACATTTCAACCCATGTTGTTCAAAACAGA GATTCCAAAAAGCTGCAGT | 10 |
| HPIV3_HN_Codon Optimized | ATGGAATACTGGAAGCACACCAACCACGGCAAGGACGC CGGCAACGAGCTGGAAACCAGCACAGCCACACACGGCA ACAAGCTGACCAACAAGATCACCTACATCCTGTGGACC ATCACCCTGGTGCTGCTGAGCATCGTGTTCATCATCGTG CTGACCAATAGCATCAAGAGCGAGAAGGCCAGAGAGAG CCTGCTGCAGGACATCAACAACGAGTTCATGGAAGTGA CCGAGAAGATCCAGGTGGCCAGCGACAACACCAACGAC CTGATCCAGAGCGGCGTGAACACCCGGCTGCTGACCATC | 11 |

TABLE 5-continued

| Description | Sequence | SEQ ID NO: |
|---|---|---|
| | CAGAGCCACGTGCAGAACTACATCCCCATCAGCCTGACC<br>CAGCAGATCAGCGACCTGCGGAAGTTCATCAGCGAGAT<br>CACCATCCGGAACGACAACCAGGAAGTGCCCCCCCAGA<br>GAATCACCCACGACGTGGGCATCAAGCCCCTGAACCCC<br>GACGATTTCTGGCGGTGTACAAGCGGCCTGCCCAGCCTG<br>ATGAAGACCCCCAAGATCCGGCTGATGCCTGGCCCTGG<br>ACTGCTGGCCATGCCTACCACAGTGGATGGCTGTGTGCG<br>GACCCCCAGCCTCGTGATCAACGATCTGATCTACGCCTA<br>CACCAGCAACCTGATCACCCGGGGCTGCCAGGATATCG<br>GCAAGAGCTACCAGGTGCTGCAGATCGGCATCATCACC<br>GTGAACTCCGACCTGGTGCCCGACCTGAACCCTCGGATC<br>AGCCACACCTTCAACATCAACGACAACAGAAAGAGCTG<br>CAGCCTGGCTCTGCTGAACACCGACGTGTACCAGCTGTG<br>CAGCACCCCCAAGGTGGACGAGAGAAGCGACTACGCCA<br>GCAGCGGCATCGAGGATATCGTGCTGGACATCGTGAAC<br>TACGACGGCAGCATCAGCACCACCCGGTTCAAGAACAA<br>CAACATCAGCTTCGACCAGCCCTACGCCGCCCTGTACCC<br>TTCTGTGGGCCCTGGCATCTACTACAAGGGCAAGATCAT<br>CTTCCTGGGCTACGGCGGCCTGGAACACCCCATCAACGA<br>GAACGCCATCTGCAACACCACCGGCTGCCCTGGCAAGA<br>CCCAGAGAGACTGCAATCAGGCCAGCCACAGCCCCTGG<br>TTCAGCGACCGCAGAATGGTCAACTCTATCATCGTGGTG<br>GACAAGGGCCTGAACAGCGTGCCCAAGCTGAAAGTGTG<br>GACAATCAGCATGCGCCAGAACTACTGGGGCAGCGAGG<br>GCAGACTTCTGCTGCTGGGAAACAAGATCTACATCTACA<br>CCCGGTCCACCAGCTGGCACAGCAAACTGCAGCTGGGA<br>ATCATCGACATCACCGACTACAGCGACATCCGGATCAA<br>GTGGACCTGGCACAACGTGCTGAGCAGACCCGGCAACA<br>ATGAGTGCCCTTGGGGCCACAGCTGCCCCGATGGATGTA<br>TCACCGGCGTGTACACCGACGCCTACCCCCTGAATCCTA<br>CCGGCTCCATCGTGTCCAGCGTGATCCTGGACAGCCAGA<br>AAAGCAGAGTGAACCCCGTGATCACATACAGCACCGCC<br>ACCGAGAGAGTGAACGAACTGGCCATCAGAAACAAGAC<br>CCTGAGCGCCGGCTACACCACCACAAGCTGCATCACAC<br>ACTACAACAAGGGCTACTGCTTCCACATCGTGGAAATCA<br>ACCACAAGTCCCTGAACACCTTCCAGCCCATGCTGTTCA<br>AGACCGAGATCCCCAAGAGCTGCTCC | |
| HPIV3_F_Codon Optimized | ATGCCCATCAGCATCCTGCTGATCATCACCACAATGATC<br>ATGGCCAGCCACTGCCAGATCGACATCACCAAGCTGCA<br>GCACGTGGGCGTGCTCGTGAACAGCCCCAAGGGCATGA<br>AGATCAGCCAGAACTTCGAGACACGCTACCTGATCCTGA<br>GCCTGATCCCCAAGATCGAGGACAGCAACAGCTGCGGC<br>GACCAGCAGATCAAGCAGTACAAGCGGCTGCTGGACAG<br>ACTGATCATCCCCCTGTACGACGGCCTGCGGCTGCAGAA<br>AGACGTGATCGTGACCAACCAGGAAAGCAACGAGAACA<br>CCGACCCCCGGACCGAGAGATTCTTCGGCGGCGTGATCG<br>GCACAATCGCCCTGGGAGTGGCCACAAGCGCCCAGATT<br>ACAGCCGCTGTGGCCCTGGTGGAAGCCAAGCAGGCCAG<br>AAGCGACATCGAGAAGCTGAAAGAGGCCATCCGGGACA<br>CCAACAAGGCCGTGCAGAGCGTGCAGTCCAGCGTGGGC<br>AATCTGATCGTGGCCATCAAGTCCGTGCAGGACTACGTG<br>AACAAAGAAATCGTGCCCTCTATCGCCCGGCTGGGCTGT<br>GAAGCTGCCGGACTGCAGCTGGGCATTGCCCTGACACA<br>GCACTACAGCGAGCTGACCAACATCTTCGGCGACAACA<br>TCGGCAGCCTGCAGGAAAAGGGCATTAAGCTGCAGGGA<br>ATCGCCAGCCTGTACCGCACCAACATCACCGAGATCTTC<br>ACCACCAGCACCGTGGATAAGTACGACATCTACGACCT<br>GCTGTTCACCGAGAGCATCAAAGTGCGCGTGATCGACGT<br>GGACCTGAACGACTACAGCATCACCCTGCAAGTGCGGC<br>TGCCCCTGCTGACCAGACTGCTGAACACCCAGATCTACA<br>AGGTGGACAGCATCTCCTACAACATCCAGAACCGCGAG<br>TGGTACATCCCTCTGCCCAGCCACATTATGACCAAGGGC<br>GCCTTTCTGGGCGGAGCCGACGTGAAAGAGTGCATCGA<br>GGCCTTCAGCAGCTACATCTGCCCCAGCGACCCTGGCTT<br>CGTGCTGAACCACGAGATGGAAAGCTGCCTGAGCGGCA<br>ACATCAGCCAGTGCCCCAGAACCACCGTGACCTCCGAC<br>ATCGTGCCCAGATACGCCTTCGTGAATGGCGGCGTGGTG<br>GCCAACTGCATCACCACCACCTGTACCTGCAACGGCATC<br>GGCAACCGGATCAACCAGCCTCCCGATCAGGGCGTGAA<br>GATTATCACCCACAAAGAGTGTAACACCATCGGCATCA<br>ACGGCATGCTGTTCAATACCAACAAAGAGGGCACCCTG<br>GCCTTCTACACCCCCGACGATATCACCCTGAACAACTCC<br>GTGGCTCTGGACCCCATCGACATCTCCATCGAGCTGAAC<br>AAGGCCAAGAGCGACCTGGAAGAGTCCAAAGAGTGGAT<br>CCGGCGGAGCAACCAGAAGCTGGACTCTATCGGCAGCT<br>GGCACCAGAGCAGCACCACCATCATCGTGATCCTGATTA | 12 |

TABLE 5-continued

| Description | Sequence | SEQ ID NO: |
|---|---|---|
| | TGATGATTATCCTGTTCATCATCAACATTACCATCATCAC TATCGCCATTAAGTACTACCGGATCCAGAAACGGAACC GGGTGGACCAGAATGACAAGCCCTACGTGCTGACAAAC AAG | |
| | PIV3 mRNA Sequences | |
| >gb\|KJ672601.1\|: 4990-6609 Human parainfluenza virus 3 strain HPIV3/*Homo sapiens*/PER/FLA4 815/2008 [fusion glycoprotein F0] | AUGCCAAUUUCAAUACUGUUAAUUAUUACAACCAUGA UCAUGGCAUCACACUGCCAAAUAGACAUCACAAAACU ACAGCAUGUAGGUGUAUUGGUCAACAGUCCCAAAGGG AUGAAGAUAUCACAAAACUUCGAAACAAGAUAUCUAA UCCUGAGUCUCAUACCAAAAAUAGAAGAUUCUAACUC UUGUGGUGACCAACAGAUCAAGCAAUACAAGAGGUUA UUGGAUAGACUGAUCAUUCCUUUAUAUGAUGGACUAA GAUUACAGAAGGAUGUGAUAGUGACUAAUCAAGAAUC CAAUGAAAACACUGAUCCCAGAACAGAACGAUUCUUU GGAGGGGUAAUUGGAACUAUUGCUCUAGGAGUAGCAA CCUCAGCACAAAUUACAGCAGCAGUUGCUCUGGUUGA AGCCAAGCAGGCAAGAUCAGACAUUGAAAAACUCAAG GAAGCAAUCAGGGACACAAAUAAAGCAGUGCAGUCAG UUCAGAGCUCUGUAGGAAAUUUGAUAGUAGCAAUUAA AUCAGUCCAGGAUUAUGUCAACAAAGAAAUCGUGCCA UCGAUUGCGAGACUAGGUUGUGAAGCAGCAGGACUUC AGUUAGGGAUUGCAUUAACACAGCAUUACUCAGAAUU AACAAAUAUAUUUGGUGAUAACAUAGGAUCGUUACAA GAAAAAGGAAUAAAAUUACAAGGUAUAGCAUCAUUAU ACCGUACAAAUAUCACAGAAAUAUUCACAACAUCAAC AGUUGACAAAUAUGAUAUUUAUGAUCUAUUAUUUACA GAAUCAAUAAAGGUGAGAGUUAUAGAUGUUGAUUUGA AUGAUUACUCAAUAACCCUCCAAGUCAGACUCCCUUU AUUGACCAGACUGCUGAACACUCAAAUCUACAAAGUA GAUUCCAUAUCAUACAAUAUCCAAAAUAGAGAAUGGU AUAUCCCUCUUCCCAGCCAUAUCAUGACGAAAGGGGC AUUUCUAGGUGGAGCAGAUGUCAAAGAAUGCAUAGAA GCAUUCAGCAGUUAUAUAUGCCCUUCUGAUCCAGGAU UUGUACUAAACCAUGAAAUGGAGAGCUGUCUAUCAGG AAACAUAUCCCAAUGUCCAAGAACCACAGUCACAUCA GACAUAGUUCCUAGGUAUGCAUUUGUCAAUGGAGGAG UGGUUGCGAAUUGUAUAACAACUACAUGUACAUGCAA UGGUAUCGGUAAUAGAAUCAACCAACCACCUGAUCAA GGAGUCAAAAUUAUAACACAUAAAGAAUGUAAUACAA UAGGUAUCAACGGAAUGCUAUUCAACACAAACAAAGA AGGAACUCUUGCAUUCUACACACCAGACGACAUAACA UUAAACAAUUCUGUUGCACUUGAUCCGAUUGACAUAU CAAUCGAGCUCAACAAGGCCAAAUCAGAUCUUGAGGA AUCAAAAGAAUGGAUAAGAAGGUCAAAUCAAAAGCUA GAUUCUAUUGGAAGUUGGCAUCAAUCUAGCACUACAA UCAUAGUUAUUUUGAUAAUGAUGAUUAUAUUGUUUAU AAUUAAUAUAACAAUAAUUACAAUUGCAAUUAAGUAU UACAGAAUUCAAAAGAGAAAUCGAGUGGAUCAAAAUG AUAAGCCGUAUGUAUUAACAAACAAG | 61 |
| gi\|612507167\|gb\|AHX22430.1\| hemagglutinin-neuraminidase [Human parainfluenza virus 3] | AUGGAAUACUGGAAGCACACCAACCACGGAAAGGAUG CUGGUAAUGAGCUGGAGACAUCCACAGCCACUCAUGG CAACAAGCUCACCAACAAGAUAACAUAUAUAUUGUGG ACGAUAACCCUGGUGUUAUUAUCAAUAGUCUUCAUCA UAGUGCUAACUAAUUCCAUCAAAAGUGAAAAGGCCCG CGAAUCAUUGCUACAAGACAUAAAUAAUGAGUUUAUG GAAGUUACAGAAAAGAUCCAAGUGGCAUCGGAUAAUA CUAAUGAUCUAAUACAGUCAGGAGUGAAUACAAGGCU UCUUACAAUUCAGAGUCAUGUCCAGAAUUAUAUACCA AUAUCAUUGACACAACAAAUAUCGGAUCUUAGGAAAU UCAUUAGUGAAAUUACAAUUAGAAAUGAUAAUCAAGA AGUGCCACCACAAAGAAUAACACAUGAUGUGGGUAUA AAACCUUUAAAUCCAGAUGAUUUCUGGAGAUGCACGU CUGGUCUUCCAUCUUUGAUGAAAACUCCAAAAAUAAG AUUAAUGCCGGGACCAGGAUUAUUAGCUAUGCCAACG ACUGUUGAUGGCUGUGUCAGAACCCCGUCCUUAGUGA UAAAUGAUCUGAUUUAUGCUUACACCUCAAAUCUAAU UACUCGAGGUUGCCAGGAUAUAGGGAAAUCAUAUCAA GUAUUACAGAUAGGGAUAAUAACUGUAAACUCAGACU UGGUACCUGACUUAAAUCCUAGGAUCUCUCAUACCUU CAACAUAAAUGACAAUAGAAAGUCAUGUUCUCUAGCA CUCCUAAAUACAGAUGUAUAUCAACUGUGUUCAACCC CAAAAGUUGAUGAAAGAUCAGAUUAUGCAUCAUCAGG CAUAGAAGAUAUUGUACUUGAUAUUGUCAAUUAUGAU GGCUCAAUCUCGACAACAAGAUUUAAGAAUAAUAAUA | 62 |

TABLE 5-continued

| Description | Sequence | SEQ ID NO: |
|---|---|---|
| | UAAGUUUUGAUCAACCAUAUGCGGCAUUAUACCCAUC<br>UGUUGGACCAGGGAUAUACUACAAAGGCAAAAUAAUA<br>UUUCUCGGGUAUGGAGGUCUUGAACAUCCAAUAAAUG<br>AGAAUGCAAUCUGCAACACAACUGGGUGUCCUGGGAA<br>AACACAGAGAGACUGUAAUCAAGCAUCUCAUAGUCCA<br>UGGUUUUCAGAUAGAAGGAUGGUCAACUCUAUAAUUG<br>UUGUUGACAAGGGCUUGAACUCAGUUCCAAAAUUGAA<br>GGUAUGGACGAUAUCUAUGAGACAAAAUUACUGGGGG<br>UCAGAAGGAAGAUUACUUCUACUAGGUAACAAGAUCU<br>ACAUAUACACAAGAUCUACAAGUUGGCACAGCAAGUU<br>ACAAUUAGGAAUAAUUGACAUUACUGACUACAGUGAU<br>AUAAGGAUAAAAUGGACAUGGCAUAAUGUGCUAUCAA<br>GACCAGGAAACAAUGAAUGUCCAUGGGGACAUUCAUG<br>UCCGGAUGGAUGUAUAACGGGAGUAUAUACCGAUGCA<br>UAUCCACUCAAUCCCACAGGAAGCAUUGUAUCAUCUG<br>UCAUAUUGGACUCACAAAAAUCGAGAGUCAACCCAGU<br>CAUAACUUACUCAACAGCAACCGAAAGGGUAAACGAG<br>CUGGCUAUCCGAAACAAAACACUCUCAGCUGGGUACA<br>CAACAACAAGCUGCAUUACACACUAUAACAAAGGGUA<br>UUGUUUUCAUAUAGUAGAAAUAAAUCAUAAAAGCUUA<br>AACACAUUUCAACCCAUGUUGUUCAAAACAGAGAUUC<br>CAAAAAGCUGCAGU | |
| HPIV3_HN_Codon Optimized | AUGGAAUACUGGAAGCACACCAACCACGGCAAGGACG<br>CCGGCAACGAGCUGGAAACCAGCACAGCCACACACGGC<br>AACAAGCUGACCAACAAGAUCACCUACAUCCUGUGGA<br>CCAUCACCCUGGUGCUGCUGAGCAUCGUGUUCAUCAUC<br>GUGCUGACCAAUAGCAUCAAGAGCGAGAAGGCCAGAG<br>AGAGCCUGCUGCAGGACAUCAACAACGAGUUCAUGGA<br>AGUGACCGAGAAGAUCCAGGUGGCCAGCGACAACACC<br>AACGACCUGAUCCAGAGCGGCGUGAACACCCGGCUGCU<br>GACCAUCCAGAGCCACGUGCAGAACUACAUCCCCAUCA<br>GCCUGACCCAGCAGAUCAGCGACCUGCGGAAGUUCAUC<br>AGCGAGAUCACCAUCCGGAACGACAACCAGGAAGUGC<br>CCCCCCAGAGAAUCACCCACGACGUGGGCAUCAAGCCC<br>CUGAACCCCGACGAUUUCUGGCGGUGUACAAGCGGCC<br>UGCCCAGCCUGAUGAAGACCCCCAAGAUCCGGCUGAUG<br>CCUGGCCCUGGACUGCUGGCCAUGCCUACCACAGUGGA<br>UGGCUGUGUGCGGACCCCCAGCCUCGUGAUCAACGAUC<br>UGAUCUACGCCUACACCAGCAACCUGAUCACCCGGGGC<br>UGCCAGGAUAUCGGCAAGAGCUACCAGGUGCUGCAGA<br>UCGGCAUCAUCACCGUGAACUCCGACCUGGUGCCCGAC<br>CUGAACCCUCGGAUCAGCCACACCUUCAACAUCAACGA<br>CAACAGAAAGAGCUGCAGCCUGGCUCUGCUGAACACC<br>GACGUGUACCAGCUGUGCAGCACCCCCAAGGUGGACG<br>AGAGAAGCGACUACGCCAGCAGCGGCAUCGAGGAUAU<br>CGUGCUGGACAUCGUGAACUACGACGGCAGCAUCAGC<br>ACCACCCGGUUCAAGAACAACAACAUCAGCUUCGACCA<br>GCCCUACGCCGCCCUGUACCCUUCUGUGGGCCCUGGCA<br>UCUACUACAAGGGCAAGAUCAUCUUCCUGGGCUACGG<br>CGGCCUGGAACACCCCAUCAACGAGAACGCCAUCUGCA<br>ACACCACCGGCUGCCCUGGCAAGACCCAGAGAGACUGC<br>AAUCAGGCCAGCCACAGCCCCUGGUUCAGCGACCGCAG<br>AAUGGUCAACUCUAUCAUCGUGGUGGACAAGGGCCUG<br>AACAGCGUGCCCAAGCUGAAAGUGUGGACAAUCAGCA<br>UGCGCCAGAACUACUGGGGCAGCGAGGGCAGACUUCU<br>GCUGCUGGGAAACAAGAUCUACAUCUACACCCGGUCC<br>ACCAGCUGGCACAGCAAACUGCAGCUGGGAAUCAUCG<br>ACAUCACCGACUACAGCGACAUCCGGAUCAAGUGGACC<br>UGGCACAACGUGCUGAGCAGACCCGGCAACAAUGAGU<br>GCCCUUGGGGCCACAGCUGCCCCGAUGGAUGUAUCACC<br>GGCGUGUACACCGACGCCUACCCCCUGAAUCCUACCGG<br>CUCCAUCGUGUCCAGCGUGAUCCUGGACAGCCAGAAA<br>AGCAGAGUGAACCCCGUGAUCACAUACAGCACCGCCAC<br>CGAGAGAGUGAACGAACUGGCCAUCAGAAACAAGACC<br>CUGAGCGCCGGCUACACCACCACAAGCUGCAUCACACA<br>CUACAACAAGGGCUACUGCUUCCACAUCGUGGAAAUC<br>AACCACAAGUCCCUGAACACCUUCCAGCCCAUGCUGUU<br>CAAGACCGAGAUCCCCAAGAGCUGCUCC | 63 |
| HPIV3_F_Codon Optimized mRNA sequence | AUGCCCAUCAGCAUCCUGCUGAUCAUCACCACAAUGAU<br>CAUGGCCAGCCACUGCCAGAUCGACAUCACCAAGCUGC<br>AGCACGUGGGCGUGCUCGUGAACAGCCCCAAGGGCAU<br>GAAGAUCAGCCAGAACUUCGAGACACGCUACCUGAUC<br>CUGAGCCUGAUCCCCAAGAUCGAGGACAGCAACAGCU<br>GCGGCGACCAGCAGAUCAAGCAGUACAAGCGGCUGCU<br>GGACAGACUGAUCAUCCCCCUGUACGACGGCCUGCGGC | 64 |

TABLE 5-continued

| Description | Sequence | SEQ ID NO: |
|---|---|---|
| | UGCAGAAAGACGUGAUCGUGACCAACCAGGAAAGCAA CGAGAACACCGACCCCCGGACCGAGAGAUUCUUCGGCG GCGUGAUCGGCACAAUCGCCCUGGGAGUGGCCACAAG CGCCCAGAUUACAGCCGCUGUGGCCCUGGUGGAAGCCA AGCAGGCCAGAAGCGACAUCGAGAAGCUGAAAGAGGC CAUCCGGGACACCAACAAGGCCGUGCAGAGCGUGCAG UCCAGCGUGGGCAAUCUGAUCGUGGCCAUCAAGUCCG UGCAGGACUACGUGAACAAAGAAAUCGUGCCCUCUAU CGCCCGGCUGGGCUGUGAAGCUGCCGGACUGCAGCUG GGCAUUGCCCUGACACAGCACUACAGCGAGCUGACCAA CAUCUUCGGCGACAACAUCGGCAGCCUGCAGGAAAAG GGCAUUAAGCUGCAGGGAAUCGCCAGCCUGUACCGCA CCAACAUCACCGAGAUCUUCACCACCAGCACCGUGGAU AAGUACGACAUCUACGACCUGCUGUUCACCGAGAGCA UCAAAGUGCGCGUGAUCGACGUGGACCUGAACGACUA CAGCAUCACCCUGCAAGUGCGGCUGCCCCUGCUGACCA GACUGCUGAACACCCAGAUCUACAAGGUGGACAGCAU CUCCUACAACAUCCAGAACCGCGAGUGGUACAUCCCUC UGCCCAGCCACAUUAUGACCAAGGGCGCCUUUCUGGGC GGAGCCGACGUGAAAGAGUGCAUCGAGGCCUUCAGCA GCUACAUCUGCCCCAGCGACCCUGGCUUCGUGCUGAAC CACGAGAUGGAAAGCUGCCUGAGCGGCAACAUCAGCC AGUGCCCCAGAACCACCGUGACCUCCGACAUCGUGCCC AGAUACGCCUUCGUGAAUGGCGGCGUGGUGGCCAACU GCAUCACCACCACCUGUACCUGCAACGGCAUCGGCAAC CGGAUCAACCAGCCUCCCGAUCAGGGCGUGAAGAUUA UCACCCACAAAGAGUGUAACACCAUCGGCAUCAACGGC AUGCUGUUCAAUACCAACAAAGAGGGCACCCUGGCCU UCUACACCCCCGACGAUAUCACCCUGAACAACUCCGUG GCUCUGGACCCCAUCGACAUCUCCAUCGAGCUGAACAA GGCCAAGAGCGACCUGGAAGAGUCCAAAGAGUGGAUC CGGCGGAGCAACCAGAAGCUGGACUCUAUCGGCAGCU GGCACCAGAGCAGCACCACCAUCAUCGUGAUCCUGAUU AUGAUGAUUAUCCUGUUCAUCAUCAACAUUACCAUCA UCACUAUCGCCAUUAAGUACUACCGGAUCCAGAAACG GAACCGGGUGGACCAGAAUGACAAGCCCUACGUGCUG ACAAACAAG | |

TABLE 6

| PIV3 Amino Acid Sequences | | |
|---|---|---|
| Description | Sequence | SEQ ID NO: |
| >gi\|612507166\|gb\|AHX22429.1\| fusion glycoprotein F0 [Human parainfluenza virus 3] | MPISILLIITTMIMASHCQIDIT KLQHVGVLVNSPKGMKISQNFET RYLILSLIPKIEDSNSCGDQQIK QYKRLLDRLIIPLYDGLRLQKDV IVTNQESNENTDPRTERFFGGVI GTIALGVATSAQITAAVALVEAK QARSDIEKLKEAIRDTNKAVQSV QSSVGNLIVAIKSVQDYVNKEIV PSIARLGCEAAGLQLGIALTQHY SELTNIFGDNIGSLQEKGIKLQG IASLYRTNITEIFTTSTVDKYDI YDLLFTESIKVRVIDVDLNDYSI TLQVRLPLLTRLLNTQIYKVDSI SYNIQNREWYIPLPSHIMTKGAF LGGADVKECIEAFSSYICPSDPG FVLNHEMESCLSGNISQCPRTTV TSDIVPRYAFVNGGVVANCITTT CTCNGIGNRINQPPDQGVKIITH KECNTIGINGMLFNTNKEGTLAF YTPDDITLNNSVALDPIDISIEL NKAKSDLEESKEWIRRSNQKLDS IGSWHQSSTTIIVILIMMIILFI INITIIITIAIKYYRIQKRNRVDQ NDKPYVLTNK | 13 |
| gi\|612507167\|gb\|AHX22430.1\| hemagglutinin- | MEYWKHTNHGKDAGNELETSTAT HGNKLTNKITYILWTITLVLLSI VFIIVLTNSIKSEKARESLLQDI | 14 |

TABLE 6-continued

| PIV3 Amino Acid Sequences | | |
|---|---|---|
| Description | Sequence | SEQ ID NO: |
| neuraminidase [Human parainfluenza virus 3] | NNEFMEVTEKIQVASDNTNDLIQ SGVNTRLLTIQSHVQNYIPISLT QQISDLRKFISEITIRNDNQEVP PQRITHDVGIKPLNPDDFWRCTS GLPSLMKTPKIRLMPGPGLLAMP TTVDGCVRTPSLVINDLIYAYTS NLITRGCQDIGKSYQVLQIGIIT VNSDLVPDLNPRISHTFNINDNR KSCSLALLNTDVYQLCSTPKVDE RSDYASSGIEDIVLDIVNYDGSI STTRFKNNNISFDQPYAALYPSV GPGIYYKGKIIFLGYGGLEHPIN ENAICNTTGCPGKTQRDCNQASH SPWFSDRRMVNSIIVVDKGLNSV PKLKVWTISMRQNYWGSEGRLLL LGNKIYIYTRSTSWHSKLQLGII DITDYSDIRIKWTWHNVLSRPGN NECPWGHSCPDGCITGVYTDAYP LNPTGSIVSSVILDSQKSRVNPV ITYSTATERVNELAIRNKTLSAG YTTTSCITHYNKGYCFHIVEINH KSLNTFQPMLFKTEIPKSCS | |

TABLE 7

PIV3 NCBI Accession Numbers (Nucleic Acid and Amino Acid Sequences)

| Description | GenBank Accession |
|---|---|
| Fusion glycoprotein F0 [Human parainfluenza virus 3] HPIV3/*Homo sapiens*/PER/FLA4815/2008 | KJ672601.1\|:4990-6609 AHX22429 (Fusion protein) |
| hemagglutinin-neuraminidase [Human parainfluenza virus 3] HPIV3/*Homo sapiens*/PER/FLA4815/2008 | KJ672601.1\|:6724-8442 AHX22430 (HN protein) |
| Recombinant PIV3/PIV1 virus fusion glycoprotein (F) and hemagglutinin (HN) genes, complete cds; and RNA dependent RNA polymerase (L) gene, partial cds. | AF016281 AAC23947 (hemagglutinin) |
| Recombinant PIV3/PIV1 virus fusion glycoprotein (F) and hemagglutinin (HN) genes, complete cds; and RNA dependent RNA polymerase (L) gene, partial cds. | AF016281 AAC23947 (fusion protein) |
| hemagglutinin-neuraminidase [Human parainfluenza virus 3] | BAO32044.1 |
| hemagglutinin-neuraminidase [Human parainfluenza virus 3] | BAO32051.1 |
| C protein [Human parainfluenza virus 3] | NP_599251.1 |
| C protein [Human parainfluenza virus 3] | ABZ85670.1 |
| C protein [Human parainfluenza virus 3] | AGT75164.1 |
| C protein [Human parainfluenza virus 3] | AAB48686.1 |
| C protein [Human parainfluenza virus 3] | AHX22115.1 |
| C protein [Human parainfluenza virus 3] | AGW51066.1 |
| C protein [Human parainfluenza virus 3] | AGW51162.1 |
| C protein [Human parainfluenza virus 3] | AGT75252.1 |
| C protein [Human parainfluenza virus 3] | AGT75188.1 |
| C protein [Human parainfluenza virus 3] | AGW51218.1 |
| C protein [Human parainfluenza virus 3] | AGW51074.1 |
| C protein [Human parainfluenza virus 3] | AGT75323.1 |
| C protein [Human parainfluenza virus 3] | AGT75307.1 |
| C protein [Human parainfluenza virus 3] | AHX22131.1 |
| C protein [Human parainfluenza virus 3] | AGW51243.1 |
| C protein [Human parainfluenza virus 3] | AGT75180.1 |
| C protein [Human parainfluenza virus 3] | AGT75212.1 |
| C protein [Human parainfluenza virus 3] | AGW51186.1 |
| C protein [Human parainfluenza virus 3] | AHX22075.1 |
| C protein [Human parainfluenza virus 3] | AHX22163.1 |
| C protein [Human parainfluenza virus 3] | AGT75196.1 |
| C protein [Human parainfluenza virus 3] | AHX22491.1 |
| C protein [Human parainfluenza virus 3] | AHX22139.1 |
| C protein [Human parainfluenza virus 3] | AGW51138.1 |
| C protein [Human parainfluenza virus 3] | AGW51114.1 |
| C protein [Human parainfluenza virus 3] | AGT75220.1 |
| C protein [Human parainfluenza virus 3] | AHX22251.1 |
| RecName: Full = Protein C; AltName: Full = VP18 protein | P06165.1 |
| C protein [Human parainfluenza virus 3] | AHX22187.1 |
| C protein [Human parainfluenza virus 3] | AGT75228.1 |
| C protein [Human parainfluenza virus 3] | AHX22179.1 |
| C protein [Human parainfluenza virus 3] | AHX22427.1 |
| C protein [Human parainfluenza virus 3] | AGW51210.1 |
| nonstructural protein C [Human parainfluenza virus 3] | BAA00922.1 |
| C protein [Human parainfluenza virus 3] | AHX22315.1 |
| C protein [Human parainfluenza virus 3] | AGW51259.1 |
| C protein [Human parainfluenza virus 3] | AHX22435.1 |
| C protein [Human parainfluenza virus 3] | AHX22123.1 |
| C protein [Human parainfluenza virus 3] | AHX22299.1 |
| C protein [Human parainfluenza virus 3] | AGW51267.1 |
| unnamed protein product [Human parainfluenza virus 3] | CAA28430.1 |
| C protein [Human parainfluenza virus 3] | AGW51178.1 |
| C protein [Human parainfluenza virus 3] | AHX22411.1 |
| RecName: Full = Protein C | P06164.1 |
| phosphoprotein [Human parainfluenza virus 3] | NP_067149.1 |
| phosphoprotein [Human parainfluenza virus 3] | AAB48685.1 |
| phosphoprotein [Human parainfluenza virus 3] | AHX22498.1 |
| phosphoprotein [Human parainfluenza virus 3] | AHX22490.1 |
| phosphoprotein [Human parainfluenza virus 3] | AGT75259.1 |
| phosphoprotein [Human parainfluenza virus 3] | AGW51137.1 |
| phosphoprotein [Human parainfluenza virus 3] | AGW51145.1 |
| phosphoprotein [Human parainfluenza virus 3] | AGT75298.1 |
| phosphoprotein [Human parainfluenza virus 3] | AGW51113.1 |
| phosphoprotein [Human parainfluenza virus 3] | AGT75203.1 |
| phosphoprotein [Human parainfluenza virus 3] | AGT75163.1 |
| phosphoprotein [Human parainfluenza virus 3] | AHX22506.1 |
| phosphoprotein [Human parainfluenza virus 3] | AGW51129.1 |
| phosphoprotein [Human parainfluenza virus 3] | AHX22194.1 |

TABLE 7-continued

PIV3 NCBI Accession Numbers (Nucleic Acid and Amino Acid Sequences)

| Description | GenBank Accession |
|---|---|
| phosphoprotein [Human parainfluenza virus 3] | AGT75211.1 |
| phosphoprotein [Human parainfluenza virus 3] | AHX22258.1 |
| phosphoprotein [Human parainfluenza virus 3] | AGW51121.1 |
| phosphoprotein [Human parainfluenza virus 3] | AGT75282.1 |
| phosphoprotein [Human parainfluenza virus 3] | AHX22146.1 |
| phosphoprotein [Human parainfluenza virus 3] | AHX22138.1 |
| phosphoprotein [Human parainfluenza virus 3] | AHX22322.1 |
| phosphoprotein [Human parainfluenza virus 3] | AHX22370.1 |
| phosphoprotein [Human parainfluenza virus 3] | AHX22098.1 |
| phosphoprotein [Human parainfluenza virus 3] | AHX22130.1 |
| phosphoprotein [Human parainfluenza virus 3] | AHX22418.1 |
| phosphoprotein [Human parainfluenza virus 3] | AHX22114.1 |
| phosphoprotein [Human parainfluenza virus 3] | AHX22410.1 |
| phosphoprotein [Human parainfluenza virus 3] | AGT75306.1 |
| phosphoprotein [Human parainfluenza virus 3] | AHX22170.1 |
| phosphoprotein [Human parainfluenza virus 3] | AHX22266.1 |
| phosphoprotein [Human parainfluenza virus 3] | AHX22090.1 |
| phosphoprotein [Human parainfluenza virus 3] | AGT75195.1 |
| phosphoprotein [Human parainfluenza virus 3] | AHX22226.1 |
| phosphoprotein [Human parainfluenza virus 3] | AHX22178.1 |
| phosphoprotein [Human parainfluenza virus 3] | AHX22122.1 |
| phosphoprotein [Human parainfluenza virus 3] | AHX22186.1 |
| phosphoprotein [Human parainfluenza virus 3] | AHX22066.1 |
| phosphoprotein [Human parainfluenza virus 3] | AHX22522.1 |
| phosphoprotein [Human parainfluenza virus 3] | AGW51225.1 |
| phosphoprotein [Human parainfluenza virus 3] | BAN29032.1 |
| phosphoprotein [Human parainfluenza virus 3] | ABZ85669.1 |
| phosphoprotein [Human parainfluenza virus 3] | AHX22426.1 |
| phosphoprotein [Human parainfluenza virus 3] | AHX22058.1 |
| phosphoprotein [Simian Agent 10] | ADR00400.1 |
| phosphoprotein [Human parainfluenza virus 3] | AHX22250.1 |
| phosphoprotein [Human parainfluenza virus 3] | AHX22434.1 |
| phosphoprotein [Human parainfluenza virus 3] | AHX22298.1 |
| phosphoprotein [Human parainfluenza virus 3] | AHX22442.1 |
| phosphoprotein [Human parainfluenza virus 3] | AHX22074.1 |
| phosphoprotein [Human parainfluenza virus 3] | AGW51153.1 |
| phosphoprotein [Human parainfluenza virus 3] | AGW51241.1 |
| phosphoprotein [Human parainfluenza virus 3] | AHX22210.1 |
| phosphoprotein [Human parainfluenza virus 3] | AGW51105.1 |
| phosphoprotein [Human parainfluenza virus 3] | AGT75251.1 |
| phosphoprotein [Human parainfluenza virus 3] | AHX22362.1 |
| phosphoprotein [Human parainfluenza virus 3] | AHX22474.1 |
| phosphoprotein [Human parainfluenza virus 3] | AGW51217.1 |
| phosphoprotein [Human parainfluenza virus 3] | AIG60038.1 |
| phosphoprotein [Human parainfluenza virus 3] | AHX22378.1 |
| phosphoprotein [Human parainfluenza virus 3] | AGW51057.1 |
| phosphoprotein [Human parainfluenza virus 3] | AGT75187.1 |
| phosphoprotein [Human parainfluenza virus 3] | AGW51233.1 |
| phosphoprotein [Human parainfluenza virus 3] | AHX22482.1 |
| phosphoprotein [Human parainfluenza virus 3] | AGW51161.1 |
| phosphoprotein [Human parainfluenza virus 3] | AHX22306.1 |
| phosphoprotein [Human parainfluenza virus 3] | AHX22162.1 |
| phosphoprotein [Human parainfluenza virus 3] | ACJ70087.1 |
| phosphoprotein [Human parainfluenza virus 3] | AHX22466.1 |
| phosphoprotein [Human parainfluenza virus 3] | AHX22346.1 |
| phosphoprotein [Human parainfluenza virus 3] | AGW51089.1 |
| phosphoprotein [Human parainfluenza virus 3] | AGW51073.1 |
| phosphoprotein [Human parainfluenza virus 3] | AGW51185.1 |
| phosphoprotein [Human parainfluenza virus 3] | AGW51065.1 |
| phosphoprotein [Human parainfluenza virus 3] | ABY47603.1 |
| phosphoprotein [Human parainfluenza virus 3] | AGW51049.1 |
| phosphoprotein [Human parainfluenza virus 3] | AHX22330.1 |
| phosphoprotein [Human parainfluenza virus 3] | AGW51250.1 |
| phosphoprotein [Human parainfluenza virus 3] | AGT75227.1 |
| phosphoprotein [Human parainfluenza virus 3] | AGW51282.1 |
| phosphoprotein [Human parainfluenza virus 3] | AGW51209.1 |
| phosphoprotein [Human parainfluenza virus 3] | AGW51193.1 |
| phosphoprotein [Human parainfluenza virus 3] | AGT75322.1 |
| phosphoprotein [Human parainfluenza virus 3] | AGT75219.1 |
| phosphoprotein [Human parainfluenza virus 3] | AGW51258.1 |
| phosphoprotein [Human parainfluenza virus 3] | AGW51041.1 |
| phosphoprotein [Human parainfluenza virus 3] | ACD99698.1 |
| phosphoprotein [Human parainfluenza virus 3] | AGW51266.1 |
| phosphoprotein [Human parainfluenza virus 3] | AGT75179.1 |

TABLE 7-continued

PIV3 NCBI Accession Numbers (Nucleic Acid and Amino Acid Sequences)

| Description | GenBank Accession |
|---|---|
| phosphoprotein [Human parainfluenza virus 3] | AHX22282.1 |
| phosphoprotein [Human parainfluenza virus 3] | AGW51169.1 |
| phosphoprotein [Human parainfluenza virus 3] | AGW51274.1 |
| phosphoprotein [Human parainfluenza virus 3] | AGW51201.1 |
| phosphoprotein [Human parainfluenza virus 3] | AGW51177.1 |
| RecName: Full = Phosphoprotein; Short = Protein P | P06162.1 |
| P protein [Human parainfluenza virus 3] | AAA66818.1 |
| phosphoprotein [Human parainfluenza virus 3] | AAA46866.1 |
| phosphoprotein [Human parainfluenza virus 3] | BAA00031.1 |
| polymerase-associated nucleocapsid phosphoprotein (version 2) - parainfluenza virus type 3 [Human parainfluenza virus 3] | RRNZP5 |
| phosphoprotein [Human parainfluenza virus 3] | AGT75171.1 |
| phosphoprotein [Human parainfluenza virus 3] | BAA00921.1 |
| D protein [Human parainfluenza virus 3] | NP_599250.1 |
| D protein [Human parainfluenza virus 3] | AHX22377.1 |
| D protein [Human parainfluenza virus 3] | AHX22121.1 |
| D protein [Human parainfluenza virus 3] | AGT75297.1 |
| D protein [Human parainfluenza virus 3] | AGW51136.1 |
| D protein [Human parainfluenza virus 3] | AGW51242.1 |
| D protein [Human parainfluenza virus 3] | AGW51112.1 |
| D protein [Human parainfluenza virus 3] | AHX22497.1 |
| D protein [Human parainfluenza virus 3] | AHX22145.1 |
| D protein [Human parainfluenza virus 3] | AGT75202.1 |
| D protein [Human parainfluenza virus 3] | AHX22385.1 |
| D protein [Human parainfluenza virus 3] | AGW51216.1 |
| D protein [Human parainfluenza virus 3] | AGT75281.1 |
| D protein [Human parainfluenza virus 3] | AGT75194.1 |
| D protein [Human parainfluenza virus 3] | AHX22521.1 |
| D protein [Human parainfluenza virus 3] | AGW51120.1 |
| D protein [Human parainfluenza virus 3] | AGT75313.1 |
| D protein [Human parainfluenza virus 3] | AHX22249.1 |
| D protein [Human parainfluenza virus 3] | AHX22097.1 |
| D protein [Human parainfluenza virus 3] | AGW51144.1 |
| D protein [Human parainfluenza virus 3] | AHX22089.1 |
| D protein [Human parainfluenza virus 3] | AHX22225.1 |
| D protein [Human parainfluenza virus 3] | AHX22137.1 |
| D protein [Human parainfluenza virus 3] | AHX22065.1 |
| D protein [Human parainfluenza virus 3] | AGW51224.1 |
| D protein [Human parainfluenza virus 3] | AGT75210.1 |
| D protein [Human parainfluenza virus 3] | AHX22393.1 |
| D protein [Human parainfluenza virus 3] | AGT75258.1 |
| D protein [Human parainfluenza virus 3] | AHX22345.1 |
| D protein [Human parainfluenza virus 3] | AGT75250.1 |
| D protein [Human parainfluenza virus 3] | AHX22113.1 |
| D protein [Human parainfluenza virus 3] | AGW51232.1 |
| D protein [Human parainfluenza virus 3] | AHX22057.1 |
| D protein [Human parainfluenza virus 3] | AHX22209.1 |
| D protein [Human parainfluenza virus 3] | AGW51056.1 |
| D protein [Human parainfluenza virus 3] | AHX22161.1 |
| D protein [Simian Agent 10] | ADR00402.1 |
| D protein [Human parainfluenza virus 3] | AHX22361.1 |
| D protein [Human parainfluenza virus 3] | AGW51281.1 |
| D protein [Human parainfluenza virus 3] | AGW51184.1 |
| D protein [Human parainfluenza virus 3] | AGW51160.1 |
| D protein [Human parainfluenza virus 3] | AHX22465.1 |
| D protein [Human parainfluenza virus 3] | AHX22329.1 |
| D protein [Human parainfluenza virus 3] | AGW51064.1 |
| D protein [Human parainfluenza virus 3] | AGW51040.1 |
| D protein [Human parainfluenza virus 3] | AGT75226.1 |
| D protein [Human parainfluenza virus 3] | AHX22425.1 |
| D protein [Human parainfluenza virus 3] | AHX22305.1 |
| D protein [Human parainfluenza virus 3] | AGW51249.1 |
| D protein [Human parainfluenza virus 3] | AHX22481.1 |
| D protein [Human parainfluenza virus 3] | AHX22281.1 |
| D protein [Human parainfluenza virus 3] | AGW51048.1 |
| D protein [Human parainfluenza virus 3] | AHX22297.1 |
| D protein [Human parainfluenza virus 3] | AGW51088.1 |
| D protein [Human parainfluenza virus 3] | AGT75305.1 |
| D protein [Human parainfluenza virus 3] | AHX22185.1 |
| D protein [Human parainfluenza virus 3] | AGW51104.1 |
| D protein [Human parainfluenza virus 3] | AHX22081.1 |
| D protein [Human parainfluenza virus 3] | AGW51192.1 |
| D protein [Human parainfluenza virus 3] | AHX22489.1 |
| D protein [Human parainfluenza virus 3] | AHX22441.1 |

TABLE 7-continued

PIV3 NCBI Accession Numbers (Nucleic Acid and Amino Acid Sequences)

| Description | GenBank Accession |
|---|---|
| D protein [Human parainfluenza virus 3] | AHX22409.1 |
| D protein [Human parainfluenza virus 3] | AHX22369.1 |
| D protein [Human parainfluenza virus 3] | AHX22321.1 |
| D protein [Human parainfluenza virus 3] | AHX22073.1 |
| D protein [Human parainfluenza virus 3] | AGW51152.1 |
| D protein [Human parainfluenza virus 3] | AGW51072.1 |
| D protein [Human parainfluenza virus 3] | AGT75321.1 |
| D protein [Human parainfluenza virus 3] | AHX22257.1 |
| D protein [Human parainfluenza virus 3] | AHX22129.1 |
| D protein [Human parainfluenza virus 3] | AHX22417.1 |
| D protein [Human parainfluenza virus 3] | AGT75218.1 |
| D protein [Human parainfluenza virus 3] | AHX22265.1 |
| D protein [Human parainfluenza virus 3] | AGT75178.1 |
| D protein [Human parainfluenza virus 3] | AHX22433.1 |
| D protein [Human parainfluenza virus 3] | AGW51273.1 |
| D protein [Human parainfluenza virus 3] | AGW51208.1 |
| D protein [Human parainfluenza virus 3] | AGT75170.1 |
| D protein [Human parainfluenza virus 3] | AGT75162.1 |
| D protein [Human parainfluenza virus 3] | AGW51257.1 |
| D protein [Human parainfluenza virus 3] | AGW51200.1 |
| D protein [Human parainfluenza virus 3] | AGW51176.1 |
| D protein [Human parainfluenza virus 3] | AGT75186.1 |
| D protein [Human parainfluenza virus 3] | AGW51265.1 |
| D protein [Human parainfluenza virus 3] | AGW51168.1 |

TABLE 8

Signal Peptides

| Description | Sequence | SEQ ID NO: |
|---|---|---|
| HuIgG$_k$ signal peptide | METPAQLLFLLLLWLPDTTG | 15 |
| IgE heavy chain epsilon -1 signal peptide | MDWTWILFLVAAATRVHS | 16 |
| Japanese encephalitis PRM signal sequence | MLGSNSGQRVVFTILLLLVAPAYS | 17 |
| VSVg protein signal sequence | MKCLLYLAFLFIGVNCA | 18 |
| Japanese encephalitis JEV signal sequence | MWLVSLAIVTACAGA | 19 |

TABLE 9 hMPV/PIV Cotton Rat Challenge Study Design

| Group | n | Test Article | [conc]/μg | Route | Challenge |
|---|---|---|---|---|---|
| 1 | 5 | Placebo | n/a | IM | hMPV/A2 |
| 2 | 5 | hMPV vaccine mRNA | 30 | IM | hMPV/A2 |
| 3 | 5 | hMPV vaccine mRNA | 15 | IM | hMPV/A2 |
| 4 | 5 | hMPV vaccine mRNA | 10 | IM | hMPV/A2 |
| 5 | 5 | hMPV/PIV3 vaccine mRNA (15/15) | 30 | IM | hMPV/A2 |
| 6 | 5 | FI-hMPV | n/a | IM | hMPV/A2 |
| 7 | 5 | Placebo | n/a | IM | PIV3 |
| 8 | 5 | PIV3 vaccine mRNA | 30 | IM | PIV3 |
| 9 | 5 | PIV3 vaccine mRNA | 15 | IM | PIV3 |
| 10 | 5 | PIV3 vaccine mRNA | 10 | IM | PIV3 |
| 11 | 5 | hMPV/PIV3 vaccine mRNA (15/15) | 30 | IM | PIV3 |
| 12 | 5 | FI-PIV3 | n/a | IM | PIV3 |
| | 60 | | | | |

TABLE 10

| Strain | Nucleic Acid Sequence | SEQ ID NO: |
|---|---|---|
| Betacoronavirus Nucleic Acid Sequence | | |
| gb\|KJ156934.1\|: 21405-25466 Middle East respiratory syndrome coronavirus isolate Riyadh_14_2013, spike protein (nucleotide) | ATGATACACTCAGTGTTTCTACTGATGTTCTTGTTAACACC TACAGAAAGTTACGTTGATGTAGGGCCAGATTCTGTTAAG TCTGCTTGTATTGAGGTTGATATACAACAGACCTTCTTTGA TAAAACTTGGCCTAGGCCAATTGATGTTTCTAAGGCTGAC GGTATTATATACCCTCAAGGCCGTACATATTCTAACATAA CTATCACTTATCAAGGTCTTTTTCCCTATCAGGGAGACCAT GGTGATATGTATGTTTACTCTGCAGGACATGCTACAGGCA CAACTCCACAAAAGTTGTTTGTAGCTAACTATTCTCAGGA CGTCAAACAGTTTGCTAATGGGTTTGTCGTCCGTATAGGA GCAGCTGCCAATTCCACTGGCACTGTTATTATTAGCCCATC TACCAGCGCTACTATACGAAAAATTTACCCTGCTTTTATGC | 20 |

TABLE 10-continued

| Strain | Nucleic Acid Sequence | SEQ ID NO: |
|---|---|---|
| | TGGGTTCTTCAGTTGGTAATTTCTCAGATGGTAAAATGGG<br>CCGCTTCTTCAATCATACTCTAGTTCTTTTGCCCGATGGAT<br>GTGGCACTTTACTTAGAGCTTTTATTGTATTCTAGAGCCT<br>CGCTCTGGAAATCATTGTCCTGCTGGCAATTCCTATACTTC<br>TTTTGCCACTTATCACACTCCTGCAACAGATTGTTCTGATG<br>GCAATTACAATCGTAATGCCAGTCTGAACTCTTTTAAGGA<br>GTATTTTAATTTACGTAACTGCACCTTTATGTACACTTATA<br>ACATTACCGAAGATGAGATTTTAGAGTGGTTTGGCATTAC<br>ACAAACTGCTCAAGGTGTTCACCTCTTCTCATCTCGGTATG<br>TTGATTTGTACGGCGGCAATATGTTTCAATTTGCCACCTTG<br>CCTGTTTATGATACTATTAAGTATTATTCTATCATTCCTCA<br>CAGTATTCGTTCTATCCAAAGTGATAGAAAAGCTTGGGCT<br>GCCTTCTACGTATATAAACTTCAACCGTTAACTTTCCTGTT<br>GGATTTTTCTGTTGATGGTTATATACGCAGAGCTATAGACT<br>GTGGTTTTAATGATTTGTCACAACTCCACTGCTCATATGAA<br>TCCTTCGATGTTGAATCTGGAGTTTATTCAGTTTCGTCTTT<br>CGAAGCAAAACCTTCTGGCTCAGTTGTGGAACAGGCTGAA<br>GGTGTTGAATGTGATTTTTCACCTCTTCTGTCTGGCACACC<br>TCCTCAGGTTTATAATTTCAAGCGTTTGGTTTTTACCAATT<br>GCAATTATAATCTTACCAAATTGCTTTCACTTTTTTCTGTG<br>AATGATTTTACTTGTAGTCAAATATCTCCAGCAGCAATTGC<br>TAGCAACTGTTATTCTTCACTGATTTTGGATTATTTTTCAT<br>ACCCACTTAGTATGAAATCCGATCTCAGTGTTAGTTCTGCT<br>GGTCCAATATCCCAGTTTAATTATAAACAGTCCTTTTCTAA<br>TCCCACATGTTTGATCTTAGCGACTGTTCCTCATAACCTTA<br>CTACTATTACTAAGCCTCTTAAGTACAGCTATATTAACAA<br>GTGCTCTCGTCTTCTTTCTGATGATCGTACTGAAGTACCTC<br>AGTTAGTGAACGCTAATCAATACTCACCCTGTGTATCCATT<br>GTCCCATCCACTGTGTGGGAAGACGGTGATTATTATAGGA<br>AACAACTATCTCCACTTGAAGGTGGTGGCTGGCTTGTTGC<br>TAGTGGCTCAACTGTTGCCATGACTGAGCAATTACAGATG<br>GGCTTTGGTATTACAGTTCAATATGGTACAGACACCAATA<br>GTGTTTGCCCCAAGCTTGAATTTGCTAATGACACAAAAAT<br>TGCCTCTCAATTAGGCAATTGCGTGGAATATTCCCTCTATG<br>GTGTTTCGGGCCGTGGTGTTTTTCAGAATTGCACAGCTGTA<br>GGTGTTCGACAGCAGCGCTTTGTTTATGATGCGTACCAGA<br>ATTTAGTTGGCTATTATTCTGATGATGGCAACTACTACTGT<br>CTGCGTGCTTGTGTTAGTGTTCCTGTTTCTGTCATCTATGA<br>TAAAGAAACTAAAACCCACGCTACTCTATTTGGTAGTGTT<br>GCATGTGAACACATTTCTTCTACCATGTCTCAATACTCCCG<br>TTCTACGCGATCAATGCTTAAACGGCGAGATTCTACATAT<br>GGCCCCCTTCAGACACCTGTTGGTTGTGTCCTAGGACTTGT<br>TAATTCCTCTTTGTTCGTAGAGGACTGCAAGTTGCCTCTCG<br>GTCAATCTCTCTGTGCTCTTCCTGACACACCTAGTACTCTC<br>ACACCTCGCAGTGTGCGCTCTGTGCCAGGTGAAATGCGCT<br>TGGCATCCATTGCTTTTAATCATCCCATTCAGGTTGATCAA<br>CTTAATAGTAGTTATTTTAAATTAAGTATACCCACTAATTT<br>TTCCTTTGGTGTGACTCAGGAGTACATTCAGACAACCATTC<br>AGAAAGTTACTGTTGATTGTAAACAGTACGTTTGCAATGG<br>TTTCCAGAAGTGTGAGCAATTACTGCGCGAGTATGGCCAG<br>TTTTGTTCCAAAATAAACCAGGCTCTCCATGGTGCCAATTT<br>ACGCCAGGATGATTCTGTACGTAATTTGTTTGCGAGCGTG<br>AAAAGCTCTCAATCATCTCCTATCATACCAGGTTTTGGAG<br>GTGACTTTAATTTGACACTTCTAGAACCTGTTTCTATATCT<br>ACTGGCAGTCGTAGTGCACGTAGTGCTATTGAGGATTTGC<br>TATTTGACAAAGTCACTATAGCTGATCCTGGTTATATGCA<br>AGGTTACGATGATTGTATGCAGCAAGGTCCAGCATCAGCT<br>CGTGATCTTATTTGTGCTCAATATGTGGCTGGTTATAAAGT<br>ATTACCTCCTCTTATGGATGTTAATATGGAAGCCGCGTATA<br>CTTCATCTTTGCTTGGCAGCATAGCAGGTGTTGGCTGGACT<br>GCTGGCTTATCCTCCTTTGCTGCTATTCCATTTGCACAGAG<br>TATYTTTTATAGGTTAAACGGTGTTGGCATTACTCAACAG<br>GTTCTTTCAGAGAACCAAAAGCTTATTGCCAATAAGTTTA<br>ATCAGGCTCTGGGAGCTATGCAAACAGGCTTCACTACAAC<br>TAATGAAGCTTTTCGGAAGGTTCAGGATGCTGTGAACAAC<br>AATGCACAGGCTCTATCCAAATTAGCTAGCGAGCTATCTA<br>ATACTTTTGGTGCTATTTCCGCCTCTATTGGAGACATCATA<br>CAACGTCTTGATGTTCTCGAACAGGACGCCCAAATAGACA<br>GACTTATTAATGGCCGTTTGACAACACTAAATGCTTTTGTT<br>GCACAGCAGCTTGTTCGTTCCGAATCAGCTGCTCTTTCCGC<br>TCAATTGGCTAAAGATAAAGTCAATGAGTGTGTCAAGGCA<br>CAATCCAAGCGTTCTGGATTTTGCGGTCAAGGCACACATA<br>TAGTGTCCTTTGTTGTAAATGCCCCTAATGGCCTTTACTTT<br>ATGCATGTTGGTTATTACCCTAGCAACCACATTGAGGTTGT<br>TTCTGCTTATGGTCTTTGCGATGCAGCTAACCCTACTAATT<br>GTATAGCCCCTGTTAATGGCTACTTTATTAAAACTAATAAC<br>ACTAGGATTGTTGATGAGTGGTCATATACTGGCTCGTCCTT | |

TABLE 10-continued

| Strain | Nucleic Acid Sequence | SEQ ID NO: |
|---|---|---|
| | CTATGCACCTGAGCCCATCACCTCTCTTAATACTAAGTATG TTGCACCACAGGTGACATACCAAAACATTTCTACTAACCT CCCTCCTCCTCTTCTCGGCAATTCCACCGGGATTGACTTCC AAGATGAGTTGGATGAGTTTTTCAAAAATGTTAGCACCAG TATACCTAATTTTGGTTCTCTAACACAGATTAATACTACAT TACTCGATCTTACCTACGAGATGTTGTCTCTTCAACAAGTT GTTAAAGCCCTTAATGAGTCTTACATAGACCTTAAAGAGC TTGGCAATTATACTTATTACAACAAATGGCCGTGGTACAT TTGGCTTGGTTTCATTGCTGGGCTTGTTGCCTTAGCTCTAT GCGTCTTCTTCATACTGTGCTGCACTGGTTGTGGCACAAAC TGTATGGGAAAACTTAAGTGTAATCGTTGTTGTGATAGAT ACGAGGAATACGACCTCGAGCCGCATAAGGTTCATGTTCA CTAA | |
| MERS S FL SPIKE 2cEMC/2012 (XBaI change(T to G)) (nucleotide) | ATGATACACTCAGTGTTTCTACTGATGTTCTTGTTAACACC TACAGAAAGTTACGTTGATGTAGGGCCAGATTCTGTTAAG TCTGCTTGTATTGAGGTTGATATACAACAGACTTTCTTTGA TAAAACTTGGCCTAGGCCAATTGATGTTTCTAAGGCTGAC GGTATTATATACCCTCAAGGCCGTACATATTCTAACATAA CTATCACTTATCAAGGTCTTTTTCCCTATCAGGGAGACCAT GGTGATATGTATGTTTACTCTGCAGGACATGCTACAGGCA CAACTCCACAAAAGTTGTTTGTAGCTAACTATTCTCAGGA CGTCAAACAGTTTGCTAATGGGTTTGTCGTCCGTATAGGA GCAGCTGCCAATTCCACTGGCACTGTTATTATTAGCCCATC TACCAGCGCTACTATACGAAAAATTTACCCTGCTTTTATGC TGGGTTCTTCAGTTGGTAATTTCTCAGATGGTAAAATGGG CCGCTTCTTCAATCATACTCTAGTTCTTTTGCCCGATGGAT GTGGCACTTTACTTAGAGCTTTTTATTGTATTCTGGAGCCT CGCTCTGGAAATCATTGTCCTGCTGGCAATTCCTATACTTC TTTTGCCACTTATCACACTCCTGCAACAGATTGTTCTGATG GCAATTACAATCGTAATGCCAGTCTGAACTCTTTTAAGGA GTATTTTAATTTACGTAACTGCACCTTTATGTACACTTATA ACATTACCGAAGATGAGATTTTAGAGTGGTTTGGCATTAC ACAAACTGCTCAAGGTGTTCACCTCTTCTCATCTCGGTATG TTGATTTGTACGGCGGCAATATGTTTCAATTTGCCACCTTG CCTGTTTATGATACTATTAAGTATTATTCTATCATTCCTCA CAGTATTCGTTCTATCCAAAGTGATAGAAAAGCTTGGGCT GCCTTCTACGTATATAAACTTCAACCGTTAACTTTCCTGTT GGATTTTTCTGTTGATGGTTATATACGCAGAGCTATAGACT GTGGTTTTAATGATTTGTCACAACTCCACTGCTCATATGAA TCCTTCGATGTTGAATCTGGAGTTTATTCAGTTTCGTCTTT CGAAGCAAAACCTTCTGGCTCAGTTGTGGAACAGGCTGAA GGTGTTGAATGTGATTTTTCACCTCTTCTGTCTGGCACACC TCCTCAGGTTTATAATTTCAAGCGTTTGGTTTTTACCAATT GCAATTATAATCTTACCAAATTGCTTTCACTTTTTTCTGTG AATGATTTTACTTGTAGTCAAATATCTCCAGCAGCAATTGC TAGCAACTGTTATTCTTCACTGATTTTGGATTACTTTTCAT ACCCACTTAGTATGAAATCCGATCTCAGTGTTAGTTCTGCT GGTCCAATATCCCAGTTTAATTATAAACAGTCCTTTTCTAA TCCCACATGTTTGATTTTAGCGACTGTTCCTCATAACCTTA CTACTATTACTAAGCCTCTTAAGTACAGCTATATTAACAA GTGCTCTCGTCTTCTTTCTGATGATCGTACTGAAGTACCTC AGTTAGTGAACGCTAATCAATACTCACCCTGTGTATCCATT GTCCCATCCACTGTGTGGGAAGACGGTGATTATTATAGGA AACAACTATCTCCACTTGAAGGTGGTGGCTGGCTTGTTGC TAGTGGCTCAACTGTTGCCATGACTGAGCAATTACAGATG GGCTTTGGTATTACAGTTCAATATGGTACAGACACCAATA GTGTTTGCCCCAAGCTTGAATTTGCTAATGACACAAAAAT TGCCTCTCAATTAGGCAATTGCGTGGAATATTCCCTCTATG GTGTTTCGGGCCGTGGTGTTTTTCAGAATTGCACAGCTGTA GGTGTTCGACAGCAGCGCTTTGTTTATGATGCGTACCAGA ATTTAGTTGGCTATTATTCTGATGATGGCAACTACTACTGT TTGCGTGCTTGTGTTAGTGTTCCTGTTTCTGTCATCTATGAT AAAGAAACTAAAACCCACGCTACTCTATTTGGTAGTGTTG CATGTGAACACATTTCTTCTACCATGTCTCAATACTCCCGT TCTACGCGATCAATGCTTAAACGGCGAGATTCTACATATG GCCCCCTTCAGACACCTGTTGGTTGTGTCCTAGGACTTGTT AATTCCTCTTTGTTCGTAGAGGACTGCAAGTTGCCTCTTGG TCAATCTCTCTGTGCTCTTCCTGACACACCTAGTACTCTCA CACCTCGCAGTGTGCGCTCTGTTCCAGGTGAAATGCGCTT GGCATCCATTGCTTTTAATCATCCTATTCAGGTTGATCAAC TTAATAGTAGTTATTTTAAATTAAGTATACCCACTAATTTT TCCTTTGGTGTGACTCAGGAGTACATTCAGACAACCATTC AGAAAGTTACTGTTGATTGTAAACAGTACGTTTGCAATGG TTTCCAGAAGTGTGAGCAATTACTGCGCGAGTATGGCCAG TTTTGTTCCAAAATAAACCAGGCTCTCCATGGTGCCAATTT ACGCCAGGATGATTCTGTACGTAATTTGTTTGCGAGCGTG | 21 |

TABLE 10-continued

| Strain | Nucleic Acid Sequence | SEQ ID NO: |
|---|---|---|
| | AAAAGCTCTCAATCATCTCCTATCATACCAGGTTTTGGAG<br>GTGACTTTAATTTGACACTTCTGGAACCTGTTTCTATATCT<br>ACTGGCAGTCGTAGTGCACGTAGTGCTATTGAGGATTTGC<br>TATTTGACAAAGTCACTATAGCTGATCCTGGTTATATGCA<br>AGGTTACGATGATTGCATGCAGCAAGGTCCAGCATCAGCT<br>CGTGATCTTATTTGTGCTCAATATGTGGCTGGTTACAAAGT<br>ATTACCTCCTCTTATGGATGTTAATATGGAAGCCGCGTATA<br>CTTCATCTTTGCTTGGCAGCATAGCAGGTGTTGGCTGGACT<br>GCTGGCTTATCCTCCTTTGCTGCTATTCCATTTGCACAGAG<br>TATCTTTTATAGGTTAAACGGTGTTGGCATTACTCAACAGG<br>TTCTTTCAGAGAACCAAAAGCTTATTGCCAATAAGTTTAA<br>TCAGGCTCTGGGAGCTATGCAAACAGGCTTCACTACAACT<br>AATGAAGCTTTTCAGAAGGTTCAGGATGCTGTGAACAACA<br>ATGCACAGGCTCTATCCAAATTAGCTAGCGAGCTATCTAA<br>TACTTTTGGTGCTATTTCCGCCTCTATTGGAGACATCATAC<br>AACGTCTTGATGTTCTCGAACAGGACGCCCAAATAGACAG<br>ACTTATTAATGGCCGTTTGACAACACTAAATGCTTTTGTTG<br>CACAGCAGCTTGTTCGTTCCGAATCAGCTGCTCTTTCCGCT<br>CAATTGGCTAAAGATAAAGTCAATGAGTGTGTCAAGGCAC<br>AATCCAAGCGTTCTGGATTTTGCGGTCAAGGCACACATAT<br>AGTGTCCTTTGTTGTAAATGCCCCTAATGGCCTTTACTTCA<br>TGCATGTTGGTTATTACCCTAGCAACCACATTGAGGTTGTT<br>TCTGCTTATGGTCTTTGCGATGCAGCTAACCCTACTAATTG<br>TATAGCCCCTGTTAATGGCTACTTTATTAAAACTAATAACA<br>CTAGGATTGTTGATGAGTGGTCATATACTGGCTCGTCCTTC<br>TATGCACCTGAGCCCATTACCTCCCTTAATACTAAGTATGT<br>TGCACCACAGGTGACATACCAAAACATTTCTACTAACCTC<br>CCTCCTCCTCTTCTCGGCAATTCCACCGGGATTGACTTCCA<br>AGATGAGTTGGATGAGTTTTTCAAAAATGTTAGCACCAGT<br>ATACCTAATTTTGGTTCCCTAACACAGATTAATACTACATT<br>ACTCGATCTTACCTACGAGATGTTGTCTCTTCAACAAGTTG<br>TTAAAGCCCTTAATGAGTCTTACATAGACCTTAAAGAGCT<br>TGGCAATTATACTTATTACAACAAATGGCCGTGGTACATT<br>TGGCTTGGTTTCATTGCTGGGCTTGTTGCCTTAGCTCTATG<br>CGTCTTCTTCATACTGTGCTGCACTGGTTGTGGCACAAACT<br>GTATGGGAAAACTTAAGTGTAATCGTTGTTGTGATAGATA<br>CGAGGAATACGACCTCGAGCCGCATAAGGTTCATGTTCAC<br>TAA | |
| Novel_MERS_S2_<br>subunit_trimeric<br>vaccine<br>(nucleotide) | ATGATCCACTCCGTGTTCCTCCTCATGTTCCTGTTGACCCC<br>CACTGAGTCAGACTGCAAGCTCCCGCTGGGACAGTCCCTG<br>TGTGCGCTGCCTGACACTCCTAGCACTCTGACCCCACGCTC<br>CGTGCGGTCGGTGCCTGGCGAAATGCGGCTGGCCTCCATC<br>GCCTTCAATCACCCAATCCAAGTGGATCAGCTGAATAGCT<br>CGTATTTCAAGCTGTCCATCCCCACGAACTTCTCGTTCGGG<br>GTCACCCAGGAGTACATCCAGACCACAATTCAGAAGGTCA<br>CCGTCGATTGCAAGCAATACGTGTGCAACGGCTTCCAGAA<br>GTGCGAGCAGCTGCTGAGAGAATACGGGCAGTTTTGCAGC<br>AAGATCAACCAGGCGCTGCATGGAGCTAACTTGCGCCAGG<br>ACGACTCCGTGCGCAACCTCTTTGCCTCTGTGAAGTCATCC<br>CAGTCCTCCCCAATCATCCCGGGATTCGGAGGGGACTTCA<br>ACCTGACCCTCCTGGAGCCCGTGTCGATCAGCACCGGTAG<br>CAGATCGGCGCGCTCAGCCATTGAAGATCTTCTGTTCGAC<br>AAGGTCACCATCGCCGATCCGGGCTACATGCAGGGATACG<br>ACGACTGTATGCAGCAGGGACCAGCCTCCGCGAGGGACCT<br>CATCTGCGCGCAATACGTGGCCGGGTACAAAGTGCTGCCT<br>CCTCTGATGGATGTGAACATGGAGGCCGCTTATACTTCGT<br>CCCTGCTCGGCTCTATCGCCGGCGTGGGGTGGACCGCCGG<br>CCTGTCCTCCTTCGCCGCTATCCCCTTTGCACAATCCATTT<br>TCTACCGGCTCAACGGCGTGGGCATTACTCAACAAGTCCT<br>GTCGGAGAACCAGAAGTTGATCGCAAACAAGTTCAATCA<br>GGCCCTGGGGGCCATGCAGACTGGATTCACTACGACTAAC<br>GAAGCGTTCCAGAAGGTCCAGGACGCTGTGAACAACAAC<br>GCCCAGGCGCTCTCAAAGCTGGCCTCCGAACTCAGCAACA<br>CCTTCGGAGCCATCAGCGCATCGATCGGTGACATAATTCA<br>GCGGCTGGACGTGCTGGAGCAGGACGCCCAGATCGACCG<br>CCTCATCAACGGACGGCTGACCACCTTGAATGCCTTCGTG<br>GCACAACAGCTGGTCCGGAGCGAATCAGCGGCACTTTCCG<br>CCCAACTCGCCAAGGACAAAGTCAACGAATGCGTGAAGG<br>CCCAGTCCAAGAGGTCCGGTTTCTGCGGTCAAGGAACCCA<br>TATTGTGTCCTTCGTCGTGAACGCGCCCAACGGTCTGTACT<br>TTATGCACGTCGGCTACTACCCGAGCAATCATATCGAAGT<br>GGTGTCCGCCTACGGCCTGTGCGATGCCGCTAACCCCACT<br>AACTGTATTGCCCCTGTGAACGGATATTTTATTAAGACCA<br>ACAACACCCGCATTGTGGACGAATGGTCATACACCGGTTC<br>GTCCTTCTACGCGCCCGAGCCCATCACTTCACTGAACACC<br>AAATACGTGGCTCCGCAAGTGACCTACCAGAACATCTCCA | 22 |

TABLE 10-continued

| Strain | Nucleic Acid Sequence | SEQ ID NO: |
|---|---|---|
| | CCAATTTGCCGCCGCCGCTGCTCGGAAACAGCACCGGAAT<br>TGATTTCCAAGATGAACTGGACGAATTCTTCAAGAACGTG<br>TCCACTTCCATTCCCAACTTCGGAAGCCTGACACAGATCA<br>ACACCACCCTTCTCGACCTGACCTACGAGATGCTGAGCCT<br>TCAACAAGTGGTCAAGGCCCTGAACGAGAGCTACATCGAC<br>CTGAAGGAGCTGGGCAACTATACCTACTACAACAAGTGGC<br>CGGACAAGATTGAGGAGATTCTGTCGAAAATCTACCACAT<br>TGAAAACGAGATCGCCAGAATCAAGAAGCTTATCGGCGA<br>AGCC | |
| MERS_S0_Full-length Spike protein (nucleotide, codon optimized) | ATGGAAACCCCTGCCCAGCTGCTGTTCCTGCTGCTGCTGTG<br>GCTGCCTGATACCACCGGCAGCTATGTGGACGTGGGCCCC<br>GATAGCGTGAAGTCCGCCTGTATCGAAGTGGACATCCAGC<br>AGACCTTTTTCGACAAGACCTGGCCCAGACCCATCGACGT<br>GTCCAAGGCCGACGGCATCATCTATCCACAAGGCCGGACC<br>TACAGCAACATCACCATTACCTACCAGGGCCTGTTCCCAT<br>ATCAAGGCGACCACGGCGATATGTACGTGTACTCTGCCGG<br>CCACGCCACCGGCACCACACCCCAGAAACTGTTCGTGGCC<br>AACTACAGCCAGGACGTGAAGCAGTTCGCCAACGGCTTCG<br>TCGTGCGGATTGGCGCCGCTGCCAATAGCACCGGCACAGT<br>GATCATCAGCCCCAGCACCAGCGCCACCATCCGGAAGATC<br>TACCCCGCCTTCATGCTGGGCAGCTCCGTGGGCAATTTCA<br>GCGACGGCAAGATGGGCCGGTTCTTCAACCACACCCTGGT<br>GCTGCTGCCCGATGGCTGTGGCACACTGCTGAGAGCCTTC<br>TACTGCATCCTGGAACCCAGAAGCGGCAACCACTGCCCTG<br>CCGGCAATAGCTACACCAGCTTCGCCACCTACCACACACC<br>CGCCACCGATTGCTCCGACGGCAACTACAACCGGAACGCC<br>AGCCTGAACAGCTTCAAAGAGTACTTCAACCTGCGGAACT<br>GCACCTTCATGTACACCTACAATATCACCGAGGACGAGAT<br>CCTGGAATGGTTCGGCATCACCCAGACCGCCCAGGGCGTG<br>CACCTGTTCAGCAGCAGATACGTGGACCTGTACGGCGGCA<br>ACATGTTCCAGTTTGCCACCCTGCCCGTGTACGACACCATC<br>AAGTACTACAGCATCATCCCCCACAGCATCCGGTCCATCC<br>AGAGCGACAGAAAAGCCTGGGCCGCCTTCTACGTGTACAA<br>GCTGCAGCCCCTGACCTTCCTGCTGGACTTCAGCGTGGAC<br>GGCTACATCAGACGGGCCATCGACTGCGGCTTCAACGACC<br>TGAGCCAGCTGCACTGCTCCTACGAGAGCTTCGACGTGGA<br>AAGCGGCGTGTACAGCGTGTCCAGCTTCGAGGCCAAGCCT<br>AGCGGCAGCGTGGTGGAACAGGCTGAGGGCGTGGAATGC<br>GACTTCAGCCCTCTGCTGAGCGGCACCCCTCCCCAGGTGT<br>ACAACTTCAAGCGGCTGGTGTTCACCAACTGCAATTACAA<br>CCTGACCAAGCTGCTGAGCCTGTTCTCCGTGAACGACTTC<br>ACCTGTAGCCAGATCAGCCCTGCCGCCATTGCCAGCAACT<br>GCTACAGCAGCCTGATCCTGGACTACTTCAGCTACCCCCT<br>GAGCATGAAGTCCGATCTGAGCGTGTCCTCCGCCGGACCC<br>ATCAGCCAGTTCAACTACAAGCAGAGCTTCAGCAACCCTA<br>CCTGCCTGATTCTGGCCACCGTGCCCCACAATCTGACCAC<br>CATCACCAAGCCCCTGAAGTACAGCTACATCAACAAGTGC<br>AGCAGACTGCTGTCCGACGACCGGACCGAAGTGCCCCAGC<br>TCGTGAACGCCAACCAGTACAGCCCCTGCGTGTCCATCGT<br>GCCCAGCACCGTGTGGGAGGACGGCGACTACTACAGAAA<br>GCAGCTGAGCCCCCTGGAAGGCGGCGGATGGCTGGTGGCT<br>TCTGGAAGCACAGTGGCCATGACCGAGCAGCTGCAGATG<br>GGCTTTGGCATCACCGTGCAGTACGGCACCGACACCAACA<br>GCGTGTGCCCCAAGCTGGAATTCGCCAATGACACCAAGAT<br>CGCCAGCCAGCTGGGAAACTGCGTGGAATACTCCCTGTAT<br>GGCGTGTCCGGACGGGGCGTGTTCCAGAATTGCACAGCAG<br>TGGGAGTGCGGCAGCAGAGATTCGTGTACGATGCCTACCA<br>GAACCTCGTGGGCTACTACAGCGACGACGGCAATTACTAC<br>TGCCTGCGGGCCTGTGTGTCCGTGCCCGTGTCCGTGATCTA<br>CGACAAAGAGACAAAGACCCACGCCACACTGTTCGGCTCC<br>GTGGCCTGCGAGCACATCAGCTCCACCATGAGCCAGTACT<br>CCCGCTCCACCCGGTCCATGCTGAAGCGGAGAGATAGCAC<br>CTACGGCCCCCTGCAGACACCTGTGGGATGTGTGCTGGGC<br>CTCGTGAACAGCTCCCTGTTTGTGGAAGATTGCAAGCTGC<br>CCCTGGGCCAGAGCCTGTGTGCCCTGCCAGATACCCCTAG<br>CACCCTGACCCCTAGAAGCGTGCGCTCTGTGCCCGGCGAA<br>ATGCGGCTGGCCTCTATCGCCTTCAATCACCCCATCCAGGT<br>GGACCAGCTGAACTCCAGCTACTTCAAGCTGAGCATCCCC<br>ACCAACTTCAGCTTCGGCGTGACCCAGGAGTACATCCAGA<br>CCACAATCCAGAAAGTGACCGTGGACTGCAAGCAGTACGT<br>GTGCAACGGCTTTCAGAAGTGCGAACAGCTGCTGCGCGAG<br>TACGGCCAGTTCTGCAGCAAGATCAACCAGGCCCTGCACG<br>GCGCCAACCTGAGACAGGATGACAGCGTGCGGAACCTGTT<br>CGCCAGCGTGAAAAGCAGCCAGTCCAGCCCCATCATCCCT<br>GGCTTCGGCGGCGACTTTAACCTGACCCTGCTGGAACCTG<br>TGTCCATCAGCACCGGCTCCAGAAGCGCCAGATCCGCCAT | 23 |

TABLE 10-continued

| Strain | Nucleic Acid Sequence | SEQ ID NO: |
|---|---|---|
| | CGAGGACCTGCTGTTCGACAAAGTGACCATTGCCGACCCC<br>GGCTACATGCAGGGCTACGACGATTGCATGCAGCAGGGCC<br>CAGCCAGCGCCAGGGATCTGATCTGTGCCCAGTATGTGGC<br>CGGCTACAAGGTGCTGCCCCCCCTGATGGACGTGAACATG<br>GAAGCCGCCTACACCTCCAGCCTGCTGGGCTCTATTGCTG<br>GCGTGGGATGGACAGCCGGCCTGTCTAGCTTTGCCGCCAT<br>CCCTTTCGCCCAGAGCATCTTCTACCGGCTGAACGGCGTG<br>GGCATCACACAACAGGTGCTGAGCGAGAACCAGAAGCTG<br>ATCGCCAACAAGTTTAACCAGGCACTGGGCGCCATGCAGA<br>CCGGCTTCACCACCACCAACGAGGCCTTCAGAAAGGTGCA<br>GGACGCCGTGAACAACAACGCCCAGGCTCTGAGCAAGCT<br>GGCCTCCGAGCTGAGCAATACCTTCGGCGCCATCAGCGCC<br>TCCATCGGCGACATCATCCAGCGGCTGGACGTGCTGGAAC<br>AGGACGCCCAGATCGACCGGCTGATCAACGGCAGACTGA<br>CCACCCTGAACGCCTTCGTGGCACAGCAGCTCGTGCGGAG<br>CGAATCTGCCGCTCTGTCTGCTCAGCTGGCCAAGGACAAA<br>GTGAACGAGTGCGTGAAGGCCCAGTCCAAGCGGAGCGGC<br>TTTTGTGGCCAGGGCACCCACATCGTGTCCTTCGTCGTGAA<br>TGCCCCCAACGGCCTGTACTTTATGCACGTGGGCTATTACC<br>CCAGCAACCACATCGAGGTGGTGTCCGCCTATGGCCTGTG<br>CGACGCCGCCAATCCTACCAACTGTATCGCCCCCGTGAAC<br>GGCTACTTCATCAAGACCAACAACACCCGGATCGTGGACG<br>AGTGGTCCTACACAGGCAGCAGCTTCTACGCCCCCGAGCC<br>CATCACCTCCCTGAACACCAAATACGTGGCCCCCCAAGTG<br>ACATACCAGAACATCTCCACCAACCTGCCCCCTCCACTGC<br>TGGGAAATTCCACCGGCATCGACTTCCAGGACGAGCTGGA<br>CGAGTTCTTCAAGAACGTGTCCACCTCCATCCCCAACTTCG<br>GCAGCCTGACCCAGATCAACACCACTCTGCTGGACCTGAC<br>CTACGAGATGCTGTCCCTGCAACAGGTCGTGAAAGCCCTG<br>AACGAGAGCTACATCGACCTGAAAGAGCTGGGGAACTAC<br>ACCTACTACAACAAGTGGCCTTGGTACATTTGGCTGGGCT<br>TTATCGCCGGCCTGGTGGCCCTGGCCCTGTGCGTGTTCTTC<br>ATCCTGTGCTGCACCGGCTGCGGCACCAATTGCATGGGCA<br>AGCTGAAATGCAACCGGTGCTGCGACAGATACGAGGAAT<br>ACGACCTGGAACCTCACAAAGTGCATGTGCAC | |
| | Betacoronavirus mRNA Sequences | |
| gb\|KJ156934.1\|: 21405-25466 Middle East respiratory syndrome coronavirus isolate Riyadh_14_2013, spike protein (nucleotide) | AUGAUACACUCAGUGUUUCUACUGAUGUUCUUGUUAAC<br>ACCUACAGAAAGUUACGUUGAUGUAGGGCCAGAUUCUG<br>UUAAGUCUGCUUGUAUUGAGGUUGAUAUACAACAGACC<br>UUCUUUGAUAAAACUUGGCCUAGGCCAAUUGAUGUUUC<br>UAAGGCUGACGGUAUUAUAUACCCUCAAGGCCGUACAU<br>AUUCUAACAUAACUAUCACUUAUCAAGGUCUUUUUCCCU<br>AUCAGGGAGACCAUGGUGAUAUGUAUGUUUACUCUGCA<br>GGACAUGCUACAGGCACAACUCCACAAAAGUUGUUUGU<br>AGCUAACUAUUCUCAGGACGUCAAACAGUUUGCUAAUG<br>GGUUUGUCGUCCGUAUAGGAGCAGCUGCCAAUUCCACUG<br>GCACUGUUAUUAUUAGCCCAUCUACCAGCGCUACUAUAC<br>GAAAAAUUUACCCUGCUUUUAUGCUGGGUUCUUCAGUU<br>GGUAAUUUCUCAGAUGGUAAAAUGGGCCGCUUCUUCAA<br>UCAUACUCUAGUUCUUUUGCCCGAUGGAUGUGGCACUU<br>UACUUAGAGCUUUUUAUUGUAUUCUAGAGCCUCGCUCU<br>GGAAAUCAUUGUCCUGCUGGCAAUUCCUAUACUUCUUU<br>UGCCACUUAUCACACUCCUGCAACAGAUUGUUCUGAUGG<br>CAAUUACAAUCGUAAUGCCAGUCUGAACUCUUUUAAGG<br>AGUAUUUUAAUUUACGUAACUGCACCUUUAUGUACACU<br>UAUAACAUUACCGAAGAUGAGAUUUUAGAGUGGUUUGG<br>CAUUACACAAACUGCUCAAGGUGUUCACCUCUUCUCAUC<br>UCGGUAUGUUGAUUUGUACGGCGGCAAUAUGUUUCAAU<br>UUGCCACCUUGCCUGUUUAUGAUACUAUUAAGUAUUAU<br>UCUAUCAUUCCUCACAGUAUUCGUUCUAUCCAAAGUGAU<br>AGAAAAGCUUGGGCUGCCUUCUACGUAUAUAAACUUCA<br>ACCGUUAACUUUCCUGUUGGAUUUUUCUGUUGAUGGUU<br>AUAUACGCAGAGCUAUAGACUGUGGUUUUAAUGAUUUG<br>UCACAACUCCACUGCUCAUAUGAAUCCUUCGAUGUUGAA<br>UCUGGAGUUUAUUCAGUUUCGUCUUUCGAAGCAAAACC<br>UUCUGGCUCAGUUGUGGAACAGGCUGAAGGUGUUGAAU<br>GUGAUUUUUCACCUCUUCUGUCUGGCACACCUCCUCAGG<br>UUUAUAAUUUCAAGCGUUUGGUUUUUACCAAUUGCAAU<br>UAUAAUCUUACCAAAUUGCUUUCACUUUUUUCUGUGAA<br>UGAUUUUACUUGUAGUCAAAUAUCUCCAGCAGCAAUUG<br>CUAGCAACUGUUAUUCUUCACUGAUUUUGGAUUAUUUU<br>UCAUACCCACUUAGUAUGAAAUCCGAUCUCAGUGUUAG<br>UUCUGCUGGUCCAAUAUCCCAGUUUAAUUAUAAACAGU<br>CCUUUUCUAAUCCCACAUGUUUGAUCUUAGCGACUGUUC<br>CUCAUAACCUUACUACUAUUACUAAGCCUCUUAAGUACA | 65 |

TABLE 10-continued

| Strain | Nucleic Acid Sequence | SEQ ID NO: |
|---|---|---|
| | GCUAUAUUAACAAGUGCUCUCGUCUUCUUUCUGAUGAU<br>CGUACUGAAGUACCUCAGUUAGUGAACGCUAAUCAAUA<br>CUCACCCUGUGUAUCCAUUGUCCCAUCCACUGUGUGGGA<br>AGACGGUGAUUAUUAUAGGAAACAACUAUCUCCACUUG<br>AAGGUGGUGGCUGGCUUGUUGCUAGUGGCUCAACUGUU<br>GCCAUGACUGAGCAAUUACAGAUGGGCUUUGGUAUUAC<br>AGUUCAAUAUGGUACAGACACCAAUAGUGUUUGCCCCA<br>AGCUUGAAUUUGCUAAUGACACAAAAAUUGCCUCUCAA<br>UUAGGCAAUUGCGUGGAAUAUUCCCUCUAUGGUGUUUC<br>GGGCCGUGGUGUUUUUCAGAAUUGCACAGCUGUAGGUG<br>UUCGACAGCAGCGCUUUGUUUAUGAUGCGUACCAGAAU<br>UUAGUUGGCUAUUAUUCUGAUGAUGGCAACUACUACUG<br>UCUGCGUGCUUGUGUUAGUGUUCCUGUUUCUGUCAUCU<br>AUGAUAAAGAAACUAAAACCCACGCUACUCUAUUUGGU<br>AGUGUUGCAUGUGAACACAUUUCUUCUACCAUGUCUCA<br>AUACUCCCGUUCUACGCGAUCAAUGCUUAAACGGCGAGA<br>UUCUACAUAUGGCCCCCUUCAGACACCUGUUGGUUGUGU<br>CCUAGGACUUGUUAAUUCCUCUUUGUUCGUAGAGGACU<br>GCAAGUUGCCUCUCGGUCAAUCUCUCUGUGCUCUUCCUG<br>ACACACCUAGUACUCUCACACCUCGCAGUGUGCGCUCUG<br>UGCCAGGUGAAAUGCGCUUGGCAUCCAUUGCUUUUAAU<br>CAUCCCAUUCAGGUUGAUCAACUUAAUAGUAGUUAUUU<br>UAAAUUAAGUAUACCCACUAAUUUUUCCUUUGGUGUGA<br>CUCAGGAGUACAUUCAGACAACCAUUCAGAAAGUUACU<br>GUUGAUUGUAAACAGUACGUUUGCAAUGGUUUCCAGAA<br>GUGUGAGCAAUUACUGCGCGAGUAUGGCCAGUUUUGUU<br>CCAAAAUAAACCAGGCUCUCCAUGGUGCCAAUUUACGCC<br>AGGAUGAUUCUGUACGUAAUUUGUUUGCGAGCGUGAAA<br>AGCUCUCAAUCAUCUCCUAUCAUACCAGGUUUUGGAGGU<br>GACUUUAAUUUGACACUUCUAGAACCUGUUUCUAUAUC<br>UACUGGCAGUCGUAGUGCACGUAGUGCUAUUGAGGAUU<br>UGCUAUUUGACAAAGUCACUAUAGCUGAUCCUGGUUAU<br>AUGCAAGGUUACGAUGAUUGUAUGCAGCAAGGUCCAGC<br>AUCAGCUCGUGAUCUUAUUUGUGCUCAAUAUGUGGCUG<br>GUUAUAAAGUAUUACCUCCUCUUAUGGAUGUUAAUAUG<br>GAAGCCGCGUAUACUUCAUCUUUGCUUGGCAGCAUAGCA<br>GGUGUUGGCUGGACUGCUGGCUUAUCCUCCUUUGCUGCU<br>AUUCCAUUUGCACAGAGUAUYUUUUAUAGGUUAAACGG<br>UGUUGGCAUUACUCAACAGGUUCUUUCAGAGAACCAAA<br>AGCUUAUUGCCAAUAAGUUUAAUCAGGCUCUGGGAGCU<br>AUGCAAACAGGCUUCACUACAACUAAUGAAGCUUUUCG<br>GAAGGUUCAGGAUGCUGUGAACAACAAUGCACAGGCUC<br>UAUCCAAAUUAGCUAGCGAGCUAUCUAAUACUUUUGGU<br>GCUAUUUCCGCCUCUAUUGGAGACAUCAUACAACGUCUU<br>GAUGUUCUCGAACAGGACGCCCAAAUAGACAGACUUAU<br>UAAUGGCCGUUUGACAACACUAAAUGCUUUUGUUGCAC<br>AGCAGCUUGUUCGUUCCGAAUCAGCUGCUCUUUCCGCUC<br>AAUUGGCUAAAGAUAAAGUCAAUGAGUGUGUCAAGGCA<br>CAAUCCAAGCGUUCUGGAUUUUGCGGUCAAGGCACACAU<br>AUAGUGUCCUUUGUUGUAAAUGCCCCUAAUGGCCUUUA<br>CUUUAUGCAUGUUGGUUAUUACCCUAGCAACCACAUUG<br>AGGUUGUUUCUGCUUAUGGUCUUUGCGAUGCAGCUAAC<br>CCUACUAAUUGUAUAGCCCCUGUUAAUGGCUACUUUAU<br>UAAAACUAAUAACACUAGGAUUGUUGAUGAGUGGUCAU<br>AUACUGGCUCGUCCUUCUAUGCACCUGAGCCCAUCACCU<br>CUCUUAAUACUAAGUAUGUUGCACCACAGGUGACAUACC<br>AAAACAUUUCUACUAACCUCCCUCCUCCUCUUCUCGGCA<br>AUUCCACCGGGAUUGACUUCCAAGAUGAGUUGGAUGAG<br>UUUUUCAAAAAUGUUAGCACCAGUAUACCUAAUUUUGG<br>UUCUCUAACACAGAUUAAUACUACAUUACUCGAUCUUAC<br>CUACGAGAUGUUGUCUCUUCAACAAGUUGUUAAAGCCC<br>UUAAUGAGUCUUACAUAGACCUUAAAGAGCUUGGCAAU<br>UAUACUUAUUACAACAAAUGGCCGUGGUACAUUUGGCU<br>UGGUUUCAUUGCUGGGCUUGUUGCCUUAGCUCUAUGCG<br>UCUUCUUCAUACUGUGCUGCACUGGUUGUGGCACAAACU<br>GUAUGGGAAAACUUAAGUGUAAUCGUUGUUGUGAUAGA<br>UACGAGGAAUACGACCUCGAGCCGCAUAAGGUUCAUGU<br>UCACUAA | |
| MERS S FL<br>SPIKE<br>2cEMC/2012<br>(XBaI change(U<br>to G)) (nucleotide) | AUGAUACACUCAGUGUUUCUACUGAUGUUCUUGUUAAC<br>ACCUACAGAAAGUUACGUUGAUGUAGGGCCAGAUUCUG<br>UUAAGUCUGCUUGUAUUGAGGUUGAUAUACAACAGACU<br>UUCUUUGAUAAAACUUGGCCUAGGCCAAUUGAUGUUUC<br>UAAGGCUGACGGUAUUAUAUACCCUCAAGGCCGUACAU<br>AUUCUAACAUAACUAUCACUUAUCAAGGUCUUUUUCCCU<br>AUCAGGGAGACCAUGGUGAUAUGUAUGUUUACUCUGCA<br>GGACAUGCUACAGGCACAACUCCACAAAAGUUGUUUGU | 66 |

TABLE 10-continued

| Strain | Nucleic Acid Sequence | SEQ ID NO: |
|---|---|---|
| | AGCUAACUAUUCUCAGGACGUCAAACAGUUUGCUAAUG | |
| | GGUUUGUCGUCCGUAUAGGAGCAGCUGCCAAUUCCACUG | |
| | GCACUGUUAUUAUUAGCCCAUCUACCAGCGCUACUAUAC | |
| | GAAAAAUUUACCCUGCUUUUAUGCUGGGUUCUUCAGUU | |
| | GGUAAUUUCUCAGAUGGUAAAAUGGGCCGCUUCUUCAA | |
| | UCAUACUCUAGUUCUUUUGCCCGAUGGAUGUGGCACUU | |
| | UACUUAGAGCUUUUUAUUGUAUUCUGGAGCCUCGCUCU | |
| | GGAAAUCAUUGUCCUGCUGGCAAUUCCUAUACUUCUUU | |
| | UGCCACUUAUCACACUCCUGCAACAGAUUGUUCUGAUGG | |
| | CAAUUACAAUCGUAAUGCCAGUCUGAACUCUUUUAAGG | |
| | AGUAUUUUAAUUUACGUAACUGCACCUUUAUGUACACU | |
| | UAUAACAUUACCGAAGAUGAGAUUUUAGAGUGGUUUGG | |
| | CAUUACACAAACUGCUCAAGGUGUUCACCUCUUCUCAUC | |
| | UCGGUAUGUUGAUUUGUACGGCGGCAAUAUGUUUCAAU | |
| | UUGCCACCUUGCCUGUUUAUGAUACUAUUAAGUAUUAU | |
| | UCUAUCAUUCCUCACAGUAUUCGUUCUAUCCAAAGUGAU | |
| | AGAAAAGCUUGGGCUGCCUUCUACGUAUAUAAACUUCA | |
| | ACCGUUAACUUUCCUGUUGGAUUUUUCUGUUGAUGGUU | |
| | AUAUACGCAGAGCUAUAGACUGUGGUUUUAAUGAUUUG | |
| | UCACAACUCCACUGCUCAUAUGAAUCCUUCGAUGUUGAA | |
| | UCUGGAGUUUAUUCAGUUUCGUCUUUCGAAGCAAAACC | |
| | UUCUGGCUCAGUUGUGGAACAGGCUGAAGGUGUUGAAU | |
| | GUGAUUUUUCACCUCUUCUGUCUGGCACACCUCCUCAGG | |
| | UUUAUAAUUUCAAGCGUUUGGUUUUUACCAAUUGCAAU | |
| | UAUAAUCUUACCAAAUUGCUUUCACUUUUUUCUGUGAA | |
| | UGAUUUUACUUGUAGUCAAAUAUCUCCAGCAGCAAUUG | |
| | CUAGCAACUGUUAUUCUUCACUGAUUUUGGAUUACUUU | |
| | UCAUACCCACUUAGUAUGAAAUCCGAUCUCAGUGUUAG | |
| | UUCUGCUGGUCCAAUAUCCCAGUUUAAUUAUAAACAGU | |
| | CCUUUUCUAAUCCCACAUGUUUGAUUUUAGCGACUGUUC | |
| | CUCAUAACCUUACUACUAUUACUAAGCCUCUUAAGUACA | |
| | GCUAUAUUAACAAGUGCUCUCGUCUUCUUUCUGAUGAU | |
| | CGUACUGAAGUACCUCAGUUAGUGAACGCUAAUCAAUA | |
| | CUCACCCUGUGUAUCCAUUGUCCCAUCCACUGUGUGGGA | |
| | AGACGGUGAUUAUUAUAGGAAACAACUAUCUCCACUUG | |
| | AAGGUGGUGGCUGGCUUGUUGCUAGUGGCUCAACUGUU | |
| | GCCAUGACUGAGCAAUUACAGAUGGGCUUUGGUAUUAC | |
| | AGUUCAAUAUGGUACAGACACCAAUAGUGUUUGCCCCA | |
| | AGCUUGAAUUUGCUAAUGACACAAAAAUUGCCUCUCAA | |
| | UUAGGCAAUUGCGUGGAAUAUUCCCUCUAUGGUGUUUC | |
| | GGGCCGUGGUGUUUUUCAGAAUUGCACAGCUGUAGGUG | |
| | UUCGACAGCAGCGCUUUGUUUAUGAUGCGUACCAGAAU | |
| | UUAGUUGGCUAUUAUUCUGAUGAUGGCAACUACUACUG | |
| | UUUGCGUGCUUGUGUUAGUGUUCCUGUUUCUGUCAUCU | |
| | AUGAUAAAGAAACUAAAACCCACGCUACUCUAUUUGGU | |
| | AGUGUUGCAUGUGAACACAUUUCUUCUACCAUGUCUCA | |
| | AUACUCCCGUUCUACGCGAUCAAUGCUUAAACGGCGAGA | |
| | UUCUACAUAUGGCCCCCUUCAGACACCUGUUGGUUGUGU | |
| | CCUAGGACUUGUUAAUUCCUCUUUGUUCGUAGAGGACU | |
| | GCAAGUUGCCUCUUGGUCAAUCUCUCUGUGCUCUUCCUG | |
| | ACACACCUAGUACUCUCACACCUCGCAGUGUGCGCUCUG | |
| | UUCCAGGUGAAAUGCGCUUGGCAUCCAUUGCUUUUAAU | |
| | CAUCCUAUUCAGGUUGAUCAACUUAAUAGUAGUUAUUU | |
| | UAAAUUAAGUAUACCCACUAAUUUUUCCUUUGGUGUGA | |
| | CUCAGGAGUACAUUCAGACAACCAUUCAGAAAGUUACU | |
| | GUUGAUUGUAAACAGUACGUUUGCAAUGGUUUCCAGAA | |
| | GUGUGAGCAAUUACUGCGCGAGUAUGGCCAGUUUUGUU | |
| | CCAAAAUAAACCAGGCUCUCCAUGGUGCCAAUUUACGCC | |
| | AGGAUGAUUCUGUACGUAAUUUGUUUGCGAGCGUGAAA | |
| | AGCUCUCAAUCAUCUCCUAUCAUACCAGGUUUUGGAGGU | |
| | GACUUUAAUUUGACACUUCUGGAACCUGUUUCUAUAUC | |
| | UACUGGCAGUCGUAGUGCACGUAGUGCUAUUGAGGAUU | |
| | UGCUAUUUGACAAAGUCACUAUAGCUGAUCCUGGUUAU | |
| | AUGCAAGGUUACGAUGAUUGCAUGCAGCAAGGUCCAGC | |
| | AUCAGCUCGUGAUCUUAUUUGUGCUCAAUAUGUGGCUG | |
| | GUUACAAAGUAUUACCUCCUCUUAUGGAUGUUAAUAUG | |
| | GAAGCCGCGUAUACUUCAUCUUUGCUUGGCAGCAUAGCA | |
| | GGUGUUGGCUGGACUGCUGGCUUAUCCUCCUUUGCUGCU | |
| | AUUCCAUUUGCACAGAGUAUCUUUUAUAGGUUAAACGG | |
| | UGUUGGCAUUACUCAACAGGUUCUUUCAGAGAACCAAA | |
| | AGCUUAUUGCCAAUAAGUUUAAUCAGGCUCUGGGAGCU | |
| | AUGCAAACAGGCUUCACUACAACUAAUGAAGCUUUUCA | |
| | GAAGGUUCAGGAUGCUGUGAACAACAAUGCACAGGCUC | |
| | UAUCCAAAUUAGCUAGCGAGCUAUCUAAUACUUUUGGU | |
| | GCUAUUUCCGCCUCUAUUGGAGACAUCAUACAACGUCUU | |
| | GAUGUUCUCGAACAGGACGCCCAAAUAGACAGACUUAU | |
| | UAAUGGCCGUUUGACAACACUAAAUGCUUUUGUUGCAC | |

TABLE 10-continued

| Strain | Nucleic Acid Sequence | SEQ ID NO: |
|---|---|---|
| | AGCAGCUUGUUCGUUCCGAAUCAGCUGCUCUUUCCGCUC<br>AAUUGGCUAAAGAUAAAGUCAAUGAGUGUGUCAAGGCA<br>CAAUCCAAGCGUUCUGGAUUUUGCGGUCAAGGCACACAU<br>AUAGUGUCCUUUGUUGUAAAUGCCCCUAAUGGCCUUUA<br>CUUCAUGCAUGUUGGUUAUUACCCUAGCAACCACAUUGA<br>GGUUGUUUCUGCUUAUGGUCUUUGCGAUGCAGCUAACC<br>CUACUAAUUGUAUAGCCCCUGUUAAUGGCUACUUUAUU<br>AAAACUAAUAACACUAGGAUUGUUGAUGAGUGGUCAUA<br>UACUGGCUCGUCCUUCUAUGCACCUGAGCCCAUUACCUC<br>CCUUAAUACUAAGUAUGUUGCACCACAGGUGACAUACCA<br>AAACAUUUCUACUAACCUCCCUCCUCCUCUUCUCGGCAA<br>UUCCACCGGGAUUGACUUCCAAGAUGAGUUGGAUGAGU<br>UUUUCAAAAAUGUUAGCACCAGUAUACCUAAUUUUGGU<br>UCCCUAACACAGAUUAAUACUACAUUACUCGAUCUUACC<br>UACGAGAUGUUGUCUCUUCAACAAGUUGUUAAAGCCCU<br>UAAUGAGUCUUACAUAGACCUUAAAGAGCUUGGCAAUU<br>AUACUUAUUACAACAAAUGGCCGUGGUACAUUUGGCUU<br>GGUUUCAUUGCUGGGCUUGUUGCCUUAGCUCUAUGCGU<br>CUUCUUCAUACUGUGCUGCACUGGUUGUGGCACAAACUG<br>UAUGGGAAAACUUAAGUGUAAUCGUUGUUGUGAUAGAU<br>ACGAGGAAUACGACCUCGAGCCGCAUAAGGUUCAUGUUC<br>ACUAA | |
| Novel_MERS_S2_<br>subunit_trimeric<br>vaccine<br>(nucleotide) | AUGAUCCACUCCGUGUUCCUCCUCAUGUUCCUGUUGACC<br>CCCACUGAGUCAGACUGCAAGCUCCCGCUGGGACAGUCC<br>CUGUGUGCGCUGCCUGACACUCCUAGCACUCUGACCCCA<br>CGCUCCGUGCGGUCGGUGCCUGGCGAAAUGCGGCUGGCC<br>UCCAUCGCCUUCAAUCACCCAAUCCAAGUGGAUCAGCUG<br>AAUAGCUCGUAUUUCAAGCUGUCCAUCCCCACGAACUUC<br>UCGUUCGGGGUCACCCAGGAGUACAUCCAGACCACAAUU<br>CAGAAGGUCACCGUCGAUUGCAAGCAAUACGUGUGCAAC<br>GGCUUCCAGAAGUGCGAGCAGCUGCUGAGAGAAUACGG<br>GCAGUUUUGCAGCAAGAUCAACCAGGCGCUGCAUGGAGC<br>UAACUUGCGCCAGGACGACUCCGUGCGCAACCUCUUUGC<br>CUCUGUGAAGUCAUCCCAGUCCUCCCCAAUCAUCCCGGG<br>AUUCGGAGGGGACUUCAACCUGACCCUCCUGGAGCCCGU<br>GUCGAUCAGCACCGGUAGCAGAUCGGCGCGCUCAGCCAU<br>UGAAGAUCUUCUGUUCGACAAGGUCACCAUCGCCGAUCC<br>GGGCUACAUGCAGGGAUACGACGACUGUAUGCAGCAGG<br>GACCAGCCUCCGCGAGGGACCUCAUCUGCGCGCAAUACG<br>UGGCCGGGUACAAAGUGCUGCCUCCUCUGAUGGAUGUG<br>AACAUGGAGGCCGCUUAUACUUCGUCCCUGCUCGGCUCU<br>AUCGCCGGCGUGGGGUGGACCGCCGGCCUGUCCUCCUUC<br>GCCGCUAUCCCCUUUGCACAAUCCAUUUUCUACCGGCUC<br>AACGGCGUGGGCAUUACUCAACAAGUCCUGUCGGAGAAC<br>CAGAAGUUGAUCGCAAACAAGUUCAAUCAGGCCCUGGG<br>GGCCAUGCAGACUGGAUUCACUACGACUAACGAAGCGUU<br>CCAGAAGGUCCAGGACGCUGUGAACAACAACGCCCAGGC<br>GCUCUCAAAGCUGGCCUCCGAACUCAGCAACACCUUCGG<br>AGCCAUCAGCGCAUCGAUCGGUGACAUAAUUCAGCGGCU<br>GGACGUGCUGGAGCAGGACGCCCAGAUCGACCGCCUCAU<br>CAACGGACGGCUGACCACCUUGAAUGCCUUCGUGGCACA<br>ACAGCUGGUCCGGAGCGAAUCAGCGGCACUUUCCGCCCA<br>ACUCGCCAAGGACAAAGUCAACGAAUGCGUGAAGGCCCA<br>GUCCAAGAGGUCCGGUUUCUGCGGUCAAGGAACCCAUAU<br>UGUGUCCUUCGUCGUGAACGCGCCCAACGGUCUGUACUU<br>UAUGCACGUCGGCUACUACCCGAGCAAUCAUAUCGAAGU<br>GGUGUCCGCCUACGGCCUGUGCGAUGCCGCUAACCCCAC<br>UAACUGUAUUGCCCCUGUGAACGGAUAUUUUAUUAAGA<br>CCAACAACACCCGCAUUGUGGACGAAUGGUCAUACACCG<br>GUUCGUCCUUCUACGCGCCCGAGCCCAUCACUUCACUGA<br>ACACCAAAUACGUGGCUCCGCAAGUGACCUACCAGAACA<br>UCUCCACCAAUUUGCCGCCGCCGCUGCUCGGAAACAGCA<br>CCGGAAUUGAUUUCCAAGAUGAACUGGACGAAUUCUUC<br>AAGAACGUGUCCACUUCCAUUCCCAACUUCGGAAGCCUG<br>ACACAGAUCAACACCACCCUUCUCGACCUGACCUACGAG<br>AUGCUGAGCCUUCAACAAGUGGUCAAGGCCCUGAACGAG<br>AGCUACAUCGACCUGAAGGAGCUGGGCAACUAUACCUAC<br>UACAACAAGUGGCCGGACAAGAUUGAGGAGAUUCUGUC<br>GAAAAUCUACCACAUUGAAAACGAGAUCGCCAGAAUCA<br>AGAAGCUUAUCGGCGAAGCC | 67 |

TABLE 10-continued

| Strain | Nucleic Acid Sequence | SEQ ID NO: |
|---|---|---|
| MERS_S0_Full-length Spike protein (nucleotide, codon optimized) | AUGGAAACCCCUGCCCAGCUGCUGUUCCUGCUGCUGCUG UGGCUGCCUGAUACCACCGGCAGCUAUGUGGACGUGGGC CCCGAUAGCGUGAAGUCCGCCUGUAUCGAAGUGGACAUC CAGCAGACCUUUUUCGACAAGACCUGGCCCAGACCCAUC GACGUGUCCAAGGCCGACGGCAUCAUCUAUCCACAAGGC CGGACCUACAGCAACAUCACCAUUACCUACCAGGGCCUG UUCCCAUAUCAAGGCGACCACGGCGAUAUGUACGUGUAC UCUGCCGGCCACGCCACCGGCACCACACCCCAGAAACUG UUCGUGGCCAACUACAGCCAGGACGUGAAGCAGUUCGCC AACGGCUUCGUCGUGCGGAUUGGCGCCGCUGCCAAUAGC ACCGGCACAGUGAUCAUCAGCCCCAGCACCAGCGCCACC AUCCGGAAGAUCUACCCCGCCUUCAUGCUGGGCAGCUCC GUGGGCAAUUUCAGCGACGGCAAGAUGGGCCGGUUCUU CAACCACACCCUGGUGCUGCUGCCCGAUGGCUGUGGCAC ACUGCUGAGAGCCUUCUACUGCAUCCUGGAACCCAGAAG CGGCAACCACUGCCCUGCCGGCAAUAGCUACACCAGCUU CGCCACCUACCACACACCCGCCACCGAUUGCUCCGACGG CAACUACAACCGGAACGCCAGCCUGAACAGCUUCAAAGA GUACUUCAACCUGCGGAACUGCACCUUCAUGUACACCUA CAAUAUCACCGAGGACGAGAUCCUGGAAUGGUUCGGCA UCACCCAGACCGCCCAGGGCGUGCACCUGUUCAGCAGCA GAUACGUGGACCUGUACGGCGGCAACAUGUUCCAGUUU GCCACCCUGCCCGUGUACGACACCAUCAAGUACUACAGC AUCAUCCCCCACAGCAUCCGGUCCAUCCAGAGCGACAGA AAAGCCUGGGCCGCCUUCUACGUGUACAAGCUGCAGCCC CUGACCUUCCUGCUGGACUUCAGCGUGGACGGCUACAUC AGACGGGCCAUCGACUGCGGCUUCAACGACCUGAGCCAG CUGCACUGCUCCUACGAGAGCUUCGACGUGGAAAGCGGC GUGUACAGCGUGUCCAGCUUCGAGGCCAAGCCUAGCGGC AGCGUGGUGGAACAGGCUGAGGGCGUGGAAUGCGACUU CAGCCCUCUGCUGAGCGGCACCCCUCCCCAGGUGUACAA CUUCAAGCGGCUGGUGUUCACCAACUGCAAUUACAACCU GACCAAGCUGCUGAGCCUGUUCUCCGUGAACGACUUCAC CUGUAGCCAGAUCAGCCCUGCCGCCAUUGCCAGCAACUG CUACAGCAGCCUGAUCCUGGACUACUUCAGCUACCCCCU GAGCAUGAAGUCCGAUCUGAGCGUGUCCUCCGCCGGACC CAUCAGCCAGUUCAACUACAAGCAGAGCUUCAGCAACCC UACCUGCCUGAUUCUGGCCACCGUGCCCCACAAUCUGAC CACCAUCACCAAGCCCCUGAAGUACAGCUACAUCAACAA GUGCAGCAGACUGCUGUCCGACGACCGGACCGAAGUGCC CCAGCUCGUGAACGCCAACCAGUACAGCCCCUGCGUGUC CAUCGUGCCCAGCACCGUGUGGGAGGACGGCGACUACUA CAGAAAGCAGCUGAGCCCCCUGGAAGGCGGCGGAUGGCU GGUGGCUUCUGGAAGCACAGUGGCCAUGACCGAGCAGCU GCAGAUGGGCUUUGGCAUCACCGUGCAGUACGGCACCGA CACCAACAGCGUGUGCCCCAAGCUGGAAUUCGCCAAUGA CACCAAGAUCGCCAGCCAGCUGGGAAACUGCGUGGAAUA CUCCCUGUAUGGCGUGUCCGGACGGGGCGUGUUCCAGAA UUGCACAGCAGUGGGAGUGCGGCAGCAGAGAUUCGUGU ACGAUGCCUACCAGAACCUCGUGGGCUACUACAGCGACG ACGGCAAUUACUACUGCCUGCGGGCCUGUGUGUCCGUGC CCGUGUCCGUGAUCUACGACAAAGAGACAAAGACCCACG CCACACUGUUCGGCUCCGUGGCCUGCGAGCACAUCAGCU CCACCAUGAGCCAGUACUCCCGCUCCACCCGGUCCAUGC UGAAGCGGAGAGAUAGCACCUACGGCCCCCUGCAGACAC CUGUGGGAUGUGUGCUGGGCCUCGUGAACAGCUCCCUGU UUGUGGAAGAUUGCAAGCUGCCCCUGGGCCAGAGCCUGU GUGCCCUGCCAGAUACCCCUAGCACCCUGACCCCUAGAA GCGUGCGCUCUGUGCCCGGCGAAAUGCGGCUGGCCUCUA UCGCCUUCAAUCACCCCAUCCAGGUGGACCAGCUGAACU CCAGCUACUUCAAGCUGAGCAUCCCCACCAACUUCAGCU UCGGCGUGACCCAGGAGUACAUCCAGACCACAAUCCAGA AAGUGACCGUGGACUGCAAGCAGUACGUGUGCAACGGC UUUCAGAAGUGCGAACAGCUGCUGCGCGAGUACGGCCAG UUCUGCAGCAAGAUCAACCAGGCCCUGCACGGCGCCAAC CUGAGACAGGAUGACAGCGUGCGGAACCUGUUCGCCAGC GUGAAAAGCAGCCAGUCCAGCCCCAUCAUCCCUGGCUUC GGCGGCGACUUUAACCUGACCCUGCUGGAACCUGUGUCC AUCAGCACCGGCUCCAGAAGCGCCAGAUCCGCCAUCGAG GACCUGCUGUUCGACAAAGUGACCAUUGCCGACCCCGGC UACAUGCAGGGCUACGACGAUUGCAUGCAGCAGGGCCCA GCCAGCGCCAGGGAUCUGAUCUGUGCCCAGUAUGUGGCC GGCUACAAGGUGCUGCCCCCCCUGAUGGACGUGAACAUG GAAGCCGCCUACACCUCCAGCCUGCUGGGCUCUAUUGCU GGCGUGGGAUGGACAGCCGGCCUGUCUAGCUUUGCCGCC AUCCCUUUCGCCCAGAGCAUCUUCUACCGGCUGAACGGC | 68 |

TABLE 10-continued

| Strain | Nucleic Acid Sequence | SEQ ID NO: |
|---|---|---|
| | GUGGGCAUCACACAACAGGUGCUGAGCGAGAACCAGAA GCUGAUCGCCAACAAGUUUAACCAGGCACUGGGCGCCAU GCAGACCGGCUUCACCACCACCAACGAGGCCUUCAGAAA GGUGCAGGACGCCGUGAACAACAACGCCCAGGCUCUGAG CAAGCUGGCCUCCGAGCUGAGCAAUACCUUCGGCGCCAU CAGCGCCUCCAUCGGCGACAUCAUCCAGCGGCUGGACGU GCUGGAACAGGACGCCCAGAUCGACCGGCUGAUCAACGG CAGACUGACCACCCUGAACGCCUUCGUGGCACAGCAGCU CGUGCGGAGCGAAUCUGCCGCUCUGUCUGCUCAGCUGGC CAAGGACAAAGUGAACGAGUGCGUGAAGGCCCAGUCCA AGCGGAGCGGCUUUUGUGGCCAGGGCACCCACAUCGUGU CCUUCGUCGUGAAUGCCCCCAACGGCCUGUACUUUAUGC ACGUGGGCUAUUACCCCAGCAACCACAUCGAGGUGGUGU CCGCCUAUGGCCUGUGCGACGCCGCCAAUCCUACCAACU GUAUCGCCCCCGUGAACGGCUACUUCAUCAAGACCAACA ACACCCGGAUCGUGGACGAGUGGUCCUACACAGGCAGCA GCUUCUACGCCCCCGAGCCCAUCACCUCCCUGAACACCA AAUACGUGGCCCCCCAAGUGACAUACCAGAACAUCUCCA CCAACCUGCCCCCUCCACUGCUGGGAAAUUCCACCGGCA UCGACUUCCAGGACGAGCUGGACGAGUUCUUCAAGAACG UGUCCACCUCCAUCCCCAACUUCGGCAGCCUGACCCAGA UCAACACCACUCUGCUGGACCUGACCUACGAGAUGCUGU CCCUGCAACAGGUCGUGAAAGCCCUGAACGAGAGCUACA UCGACCUGAAAGAGCUGGGGAACUACACCUACUACAACA AGUGGCCUUGGUACAUUUGGCUGGGCUUUAUCGCCGGCC UGGUGGCCCUGGCCCUGUGCGUGUUCUUCAUCCUGUGCU GCACCGGCUGCGGCACCAAUUGCAUGGGCAAGCUGAAAU GCAACCGGUGCUGCGACAGAUACGAGGAAUACGACCUGG AACCUCACAAAGUGCAUGUGCAC | |

TABLE 11

Betacoronavirus Amino Acid Sequences

| Strain | Amino Acid Sequence | SEQ ID NO: |
|---|---|---|
| gb\|KJ156934.1\|: 21405-25466 Middle East respiratory syndrome coronavirus isolate Riyadh_14_2013, spike protein (amino acid) | MIHSVFLLMFLLTPTESYVDVGPDSVKSACIEVDIQQTFFDKT WPRPIDVSKADGIIYPQGRTYSNITITYQGLFPYQGDHGDMY VYSAGHATGTTpQKLFVANYSQDVKQFANGFVVRIGAAANS TGTVIISPSTSATIRKIYPAFMLGSSVGNFSDGKMGRFFNHTL VLLPDGCGTLLRAFYCILEPRSGNHCPAGNSYTSFATYHTPA TDCSDGNYNRNASLNSFKEYFNLRNCTFMYTYNITEDEILEW FGITQTAQGVHLFSSRYVDLYGGNMFQFATLPVYDTIKYYSII PHSIRSIQSDRKAWAAFYVYKLQPLTFLLDFSVDGYIRRAIDC GFNDLSQLHCSYESFDVESGVYSVSSFEAKPSGSVVEQAEGV ECDFSPLLSGTPPQVYNFKRLVFTNCNYNLTKLLSLFSVNDFt CSQISPAAIASNCYSSLILDYFSYPLSMKSDLSVSSAGPISQFN YKQSFSNPTCLILATVPHNLTTITKPLKYSYINKCSRLLSDDRT EVPQLVNANQYSPCVSIVPSTVWEDGDYYRKQLSPLEGGGW LVASGSTVAMTEQLQMGFGITVQYGTDTNSVCPKLEFANDT KIASQLGNCVEYSLYGVSGRGVFQNCTAVGVRQQRFVYDA YQNLVGYYSDDGNYYCLRACVSVPVSVIYDKETKTHATLFG SVACEHISSTMSQYSRSTRSMLKRRDSTYGPLQTPVGCVLGL VNSSLFVEDCKLPLGQSLCALPDTPSTLTPRSVRSVPGEMRLA SIAFNHPIQVDQLNSSYFKLSIPTNFSFGVTQEYIQTTIQKVTV DCKQYVCNGFQKCEQLLREYGQFCSKINqALHGANLRQDDS VRNLFASVKSSQSSPIIPGFGGDFNLTLLEPVSISTGSRSARSAI EDLLFDKVTIADPGYMQGYDDCMQQGPASARDLICAQYVA GYKVLPPLMDVNMEAAYTSSLLGSIAGVGWTAGLSSFAAIPF AQSIFYRLNGVGITQQVLSENQKLIANKFNQALGAMQTGFTT TNEAFrKVQDAVNNNAQALSKLASELSNTFGAISASIGDIIQR LDVLEQDAQIDRLINGRLTTLNAFVAQQLVRSESAALSAQLA KDKVNECVKAQSKRSGFCGQGTHIVSFVVNAPNGLYFMHV GYYPSNHIEVVSAYGLCDAANPTNCIAPVNGYFIKTNNTRIV DEWSYTGSSFYAPEPITSLNTKYVAPQVTYQNISTNLPPPLLG NSTGIDFQDELDEFFKNVSTSIPNFGSLTQINTTLLDLTYEMLS LQQVVKALNESYIDLKELGNYTYYNKWPWYIWLGFIAGLVA LALCVFFILCCTGCGTNCMGKLKCNRCCDRYEEYDLEPHKV HVH | 24 |

TABLE 11-continued

| Betacoronavirus Amino Acid Sequences | | |
|---|---|---|
| Strain | Amino Acid Sequence | SEQ ID NO: |
| MERS S FL SPIKE 2cEMC/2012 (XBaI change(T to G)) (amino acid) | MIHSVFLLMFLLTPTESYVDVGPDSVKSACIEVDIQQTFFDKT<br>WPRPIDVSKADGIIYPQGRTYSNITITYQGLFPYQGDHGDMY<br>VYSAGHATGTTPQKLFVANYSQDVKQFANGFVVRIGAAANS<br>TGTVIISPSTSATIRKIYPAFMLGSSVGNFSDGKMGRFFNHTL<br>VLLPDGCGTLLRAFYCILEPRSGNHCPAGNSYTSFATYHTPA<br>TDCSDGNYNRNASLNSFKEYFNLRNCTFMYTYNITEDEILEW<br>FGITQTAQGVHLFSSRYVDLYGGNMFQFATLPVYDTIKYYSII<br>PHSIRSIQSDRKAWAAFYVYKLQPLTFLLDFSVDGYIRRAIDC<br>GFNDLSQLHCSYESFDVESGVYSVSSFEAKPSGSVVEQAEGV<br>ECDFSPLLSGTPPQVYNFKRLVFTNCNYNLTKLLSLFSVNDFT<br>CSQISPAAIASNCYSSLILDYFSYPLSMKSDLSVSSAGPISQFN<br>YKQSFSNPTCLILATVPHNLTTITKPLKYSYINKCSRLLSDDRT<br>EVPQLVNANQYSPCVSIVPSTVWEDGDYYRKQLSPLEGGGW<br>LVASGSTVAMTEQLQMGFGITVQYGTDTNSVCPKLEFANDT<br>KIASQLGNCVEYSLYGVSGRGVFQNCTAVGVRQQRFVYDA<br>YQNLVGYYSDDGNYYCLRACVSVPVSVIYDKETKTHATLFG<br>SVACEHISSTMSQYSRSTRSMLKRRDSTYGPLQTPVGCVLGL<br>VNSSLFVEDCKLPLGQSLCALPDTPSTLTPRSVRSVPGEMRLA<br>SIAFNHPIQVDQLNSSYFKLSIPTNFSFGVTQEYIQTTIQKVTV<br>DCKQYVCNGFQKCEQLLREYGQFCSKINQALHGANLRQDDS<br>VRNLFASVKSSQSSPIIPGFGGDFNLTLLEPVSISTGSRSARSAI<br>EDLLFDKVTIADPGYMQGYDDCMQQGPASARDLICAQYVA<br>GYKVLPPLMDVNMEAAYTSSLLGSIAGVGWTAGLSSFAAIPF<br>AQSIFYRLNGVGITQQVLSENQKLIANKFNQALGAMQTGFTT<br>TNEAFQKVQDAVNNNAQALSKLASELSNTFGAISASIGDIIQR<br>LDVLEQDAQIDRLINGRLTTLNAFVAQQLVRSESAALSAQLA<br>KDKVNECVKAQSKRSGFCGQGTHIVSFVVNAPNGLYFMHV<br>GYYPSNHIEVVSAYGLCDAANPTNCIAPVNGYFIKTNNTRIV<br>DEWSYTGSSFYAPEPITSLNTKYVAPQVTYQNISTNLPPPLLG<br>NSTGIDFQDELDEFFKNVSTSIPNFGSLTQINTTLLDLTYEMLS<br>LQQVVKALNESYIDLKELGNYTYYNKWPWYIWLGFIAGLVA<br>LALCVFFILCCTGCGTNCMGKLKCNRCCDRYEEYDLEPHKV<br>HVH | 25 |
| Novel_MERS_S2_ subunit_trimeric vaccine (amino acid) | MIHSVFLLMFLLTPTESDCKLPLGQSLCALPDTPSTLTPRSVR<br>SVPGEMRLASIAFNHPIQVDQLNSSYFKLSIPTNFSFGVTQEYI<br>QTTIQKVTVDCKQYVCNGFQKCEQLLREYGQFCSKINQALH<br>GANLRQDDSVRNLFASVKSSQSSPIIPGFGGDFNLTLLEPVSIS<br>TGSRSARSAIEDLLFDKVTIADPGYMQGYDDCMQQGPASAR<br>DLICAQYVAGYKVLPPLMDVNMEAAYTSSLLGSIAGVGWTA<br>GLSSFAAIPFAQSIFYRLNGVGITQQVLSENQKLIANKFNQAL<br>GAMQTGFTTTNEAFQKVQDAVNNNAQALSKLASELSNTFG<br>AISASIGDIIQRLDVLEQDAQIDRLINGRLTTLNAFVAQQLVRS<br>ESAALSAQLAKDKVNECVKAQSKRSGFCGQGTHIVSFVVNA<br>PNGLYFMHVGYYPSNHIEVVSAYGLCDAANPTNCIAPVNGY<br>FIKTNNTRIVDEWSYTGSSFYAPEPITSLNTKYVAPQVTYQNI<br>STNLPPPLLGNSTGIDFQDELDEFFKNVSTSIPNFGSLTQINTTL<br>LDLTYEMLSLQQVVKALNESYIDLKELGNYTYYNKWPDKIE<br>EILSKIYHIENEIARIKKLIGEA | 26 |
| Isolate A1-Hasa_1_2013 (NCBI accession #AGN70962) | MIHSVFLLMFLLTPTESYVDVGPDSVKSACIEVDIQQTFFDKT<br>WPRPIDVSKADGIIYPQGRTYSNITITYQGLFPYQGDHGDMY<br>VYSAGHATGTTPQKLFVANYSQDVKQFANGFVVRIGAAANS<br>TGTVIISPSTSATIRKIYPAFMLGSSVGNFSDGKMGRFFNHTL<br>VLLPDGCGTLLRAFYCILEPRSGNHCPAGNSYTSFATYHTPA<br>TDCSDGNYNRNASLNSFKEYFNLRNCTFMYTYNITEDEILEW<br>FGITQTAQGVHLFSSRYVDLYGGNMFQFATLPVYDTIKYYSII<br>PHSIRSIQSDRKAWAAFYVYKLQPLTFLLDFSVDGYIRRAIDC<br>GFNDLSQLHCSYESFDVESGVYSVSSFEAKPSGSVVEQAEGV<br>ECDFSPLLSGTPPQVYNFKRLVFTNCNYNLTKLLSLFSVNDFT<br>CSQISPAAIASNCYSSLILDYFSYPLSMKSDLSVSSAGPISQFN<br>YKQSFSNPTCLILATVPHNLTTITKPLKYSYINKCSRLLSDDRT<br>EVPQLVNANQYSPCVSIVPSTVWEDGDYYRKQLSPLEGGGW<br>LVASGSTVAMTEQLQMGFGITVQYGTDTNSVCPKLEFANDT<br>KIASQLGNCVEYSLYGVSGRGVFQNCTAVGVRQQRFVYDA<br>YQNLVGYYSDDGNYYCLRACVSVPVSVIYDKETKTHATLFG<br>SVACEHISSTMSQYSRSTRSMLKRRDSTYGPLQTPVGCVLGL<br>VNSSLFVEDCKLPLGQSLCALPDTPSTLTPRSVRSVPGEMRLA<br>SIAFNHPIQVDQLNSSYFKLSIPTNFSFGVTQEYIQTTIQKVTV<br>DCKQYVCNGFQKCEQLLREYGQFCSKINQALHGANLRQDDS<br>VRNLFASVKSSQSSPIIPGFGGDFNLTLLEPVSISTGSRSARSAI<br>EDLLFDKVTIADPGYMQGYDDCMQQGPASARDLICAQYVA<br>GYKVLPPLMDVNMEAAYTSSLLGSIAGVGWTAGLSSFAAIPF<br>AQSIFYRLNGVGITQQVLSENQKLIANKFNQALGAMQTGFTT | 27 |

TABLE 11-continued

| Betacoronavirus Amino Acid Sequences | | |
|---|---|---|
| Strain | Amino Acid Sequence | SEQ ID NO: |
| | TNEAFRKVQDAVNNNAQALSKLASELSNTFGAISASIGDIIQR<br>LDVLEQDAQIDRLINGRLTTLNAFVAQQLVRSESAALSAQLA<br>KDKVNECVKAQSKRSGFCGQGTHIVSFVVNAPNGLYFMHV<br>GYYPSNHIEVVSAYGLCDAANPTNCIAPVNGYFIKTNNTRIV<br>DEWSYTGSSFYAPEPITSLNTKYVAPHVTYQNISTNLPPPLLG<br>NSTGIDFQDELDEFFKNVSTSIPNFGSLTQINTTLLDLTYEMLS<br>LQQVVKALNESYIDLKELGNYTYYNKWPWYIWLGFIAGLVA<br>LALCVFFILCCTGCGTNCMGKLKCNRCCDRYEEYDLEPHKV<br>HVH | |
| Middle East respiratory syndrome coronavirus S protein UniProtKB - R9UQ53 | MIHSVFLLMFLLTPTESYVDVGPDSVKSACIEVDIQQTFFDKT<br>WPRPIDVSKADGIIYPQGRTYSNITITYQGLFPYQGDHGDMY<br>VYSAGHATGTTPQKLFVANYSQDVKQFANGFVVRIGAAANS<br>TGTVIISPSTSATIRKIYPAFMLGSSVGNFSDGKMGRFFNHTL<br>VLLPDGCGTLLRAFYCILEPRSGNHCPAGNSYTSFATYHTPA<br>TDCSDGNYNRNASLNSFKEYFNLRNCTFMYTYNITEDEILEW<br>FGITQTAQGVHLFSSRYVDLYGGNMFQFATLPVYDTIKYYSII<br>PHSIRSIQSDRKAWAAFYVYKLQPLTFLLDFSVDGYIRRAIDC<br>GFNDLSQLHCSYESFDVESGVYSVSSFEAKPSGSVVEQAEGV<br>ECDFSPLLSGTPPQVYNFKRLVFTNCNYNLTKLLSLFSVNDFT<br>CSQISPAAIASNCYSSLILDYFSYPLSMKSDLSVSSAGPISQFN<br>YKQSFSNPTCLILATVPHNLTTITKPLKYSYINKCSRLLSDDRT<br>EVPQLVNANQYSPCVSIVPSTVWEDGDYYRKQLSPLEGGGW<br>LVASGSTVAMTEQLQMGFGITVQYGTDTNSVCPKLEFANDT<br>KIASQLGNCVEYSLYGVSGRGVFQNCTAVGVRQQRFVYDA<br>YQNLVGYYSDDGNYYCLRACVSVPVSVIYDKETKTHATLFG<br>SVACEHISSTMSQYSRSTRSMLKRRDSTYGPLQTPVGCVLGL<br>VNSSLFVEDCKLPLGQSLCALPDTPSTLTPRSVRSVPGEMRLA<br>SIAFNHPIQVDQLNSSYFKLSIPTNFSFGVTQEYIQTTIQKVTV<br>DCKQYVCNGFQKCEQLLREYGQFCSKINQALHGANLRQDDS<br>VRNLFASVKSSQSSPIIPGFGGDFNLTLLEPVSISTGSRSARSAI<br>EDLLFDKVTIADPGYMQGYDDCMQQGPASARDLICAQYVA<br>GYKVLPPLMDVNMEAAYTSSLLGSIAGVGWTAGLSSFAAIPF<br>AQSIFYRLNGVGITQQVLSENQKLIANKFNQALGAMQTGFTT<br>TNEAFRKVQDAVNNNAQALSKLASELSNTFGAISASIGDIIQR<br>LDVLEQDAQIDRLINGRLTTLNAFVAQQLVRSESAALSAQLA<br>KDKVNECVKAQSKRSGFCGQGTHIVSFVVNAPNGLYFMHV<br>GYYPSNHIEVVSAYGLCDAANPTNCIAPVNGYFIKTNNTRIV<br>DEWSYTGSSFYAPEPITSLNTKYVAPHVTYQNISTNLPPPLLG<br>NSTGIDFQDELDEFFKNVSTSIPNFGSLTQINTTLLDLTYEMLS<br>LQQVVKALNESYIDLKELGNYTYYNKWPWYIWLGFIAGLVA<br>LALCVFFILCCTGCGTNCMGKLKCNRCCDRYEEYDLEPHKV<br>HVH | 28 |
| Human SARS coronavirus (SARS-CoV) (Severe acute respiratory syndrome coronavirus) Spike glycoprotein UniProtKB-P59594 | MFIFLLFLTLTSGSDLDRCTTFDDVQAPNYTQHTSSMRGVYY<br>PDEIFRSDTLYLTQDLFLPFYSNVTGFHTINHTFGNPVIPFKDG<br>IYFAATEKSNVVRGWVFGSTMNNKSQSVIIINNSTNVVIRAC<br>NFELCDNPFFAVSKPMGTQTHTMIFDNAFNCTFEYISDAFSLD<br>VSEKSGNFKHLREFVFKNKDGFLYVYKGYQPIDVVRDLPSGF<br>NTLKPIFKLPLGINITNFRAILTAFSPAQDIWGTSAAAYFVGYL<br>KPTTFMLKYDENGTITDAVDCSQNPLAELKCSVKSFEIDKGI<br>YQTSNFRVVPSGDVVRFPNITNLCPFGEVFNATKFPSVYAWE<br>RKKISNCVADYSVLYNSTFFSTFKCYGVSATKLNDLCFSNVY<br>ADSFVVKGDDVRQIAPGQTGVIADYNYKLPDDFMGCVLAW<br>NTRNIDATSTGNYNYKYRYLRHGKLRPFERDISNVPFSPDGK<br>PCTPPALNCYWPLNDYGFYTTTGIGYQPYRVVVLSFELLNAP<br>ATVCGPKLSTDLIKNQCVNFNFNGLTGTGVLTPSSKRFQPFQ<br>QFGRDVSDFTDSVRDPKTSEILDISPCSFGGVSVITPGTNASSE<br>VAVLYQDVNCTDVSTAIHADQLTPAWRIYSTGNNVFQTQAG<br>CLIGAEHVDTSYECDIPIGAGICASYHTVSLLRSTSQKSIVAYT<br>MSLGADSSIAYSNNTIAIPTNFSISITTEVMPVSMAKTSVDCN<br>MYICGDSTECANLLLQYGSFCTQLNRALSGIAAEQDRNTREV<br>FAQVKQMYKTPTLKYFGGFNFSQILPDPLKPTKRSFIEDLLFN<br>KVTLADAGFMKQYGECLGDINARDLICAQKFNGLTVLPPLL<br>TDDMIAAYTAALVSGTATAGWTFGAGAALQIPFAMQMAYR<br>FNGIGVTQNVLYENQKQIANQFNKAISQIQESLTTTSTALGKL<br>QDVVNQNAQALNTLVKQLSSNFGAISSVLNDILSRLDKVEAE<br>VQIDRLITGRLQSLQTYVTQQLIRAAEIRASANLAATKMSEC<br>VLGQSKRVDFCGKGYHLMSFPQAAPHGVVFLHVTYVPSQER<br>NFTTAPAICHEGKAYFPREGVFVFNGTSWFITQRNFFSPQIITT<br>DNTFVSGNCDVVIGIINNTVYDPLQPELDSFKEELDKYFKNH<br>TSPDVDLGDISGINASVVNIQKEIDRLNEVAKNLNESLIDLQE<br>LGKYEQYIKWPWYVWLGFIAGLIAIVMVTILLCCMTSCCSCL<br>KGACSCGSCCKFDEDDSEPVLKGVKLHYT | 29 |

TABLE 11-continued

Betacoronavirus Amino Acid Sequences

| Strain | Amino Acid Sequence | SEQ ID NO: |
|---|---|---|
| Human coronavirus OC43 (HCoV-OC43) Spike glycoprotein UniProtKB-P36334 | MFLILLISLPTAFAVIGDLKCTSDNINDKDTGPPPISTDTVDVT<br>NGLGTYYVLDRVYLNTTLFLNGYYPTSGSTYRNMALKGSVL<br>LSRLWFKPPFLSDFINGIFAKVKNTKVIKDRVMYSEFPAITIGS<br>TFVNTSYSVVVQPRTINSTQDGDNKLQGLLEVSVCQYNMCE<br>YPQTICHPNLGNHRKELWHLDTGVVSCLYKRNFTYDVNAD<br>YLYFHFYQEGGTFYAYFTDTGVVTKFLFNVYLGMALSHYYV<br>MPLTCNSKLTLEYWVTPLTSRQYLLAFNQDGIIFNAEDCMSD<br>FMSEIKCKTQSIAPPTGVYELNGYTVQPIADVYRRKPNLPNC<br>NIEAWLNDKSVPSPLNWERKTFSNCNFNMSSLMSFIQADSFT<br>CNNIDAAKIYGMCFSSITIDKFAIPNGRKVDLQLGNLGYLQSF<br>NYRIDTTATSCQLYYNLPAANVSVSRFNPSTWNKRFGFIEDS<br>VFKPRPAGVLTNHDVVYAQHCFKAPKNFCPCKLNGSCVGSG<br>PGKNNGIGTCPAGTNYLTCDNLCTPDPITFTGTYKCPQTKSL<br>VGIGEHCSGLAVKSDYCGGNSCTCRPQAFLGWSADSCLQGD<br>KCNIFANFILHDVNSGLTCSTDLQKANTDIILGVCVNYDLYGI<br>LGQGIFVEVNATYYNSWQNLLYDSNGNLYGFRDYIINRTFMI<br>RSCYSGRVSAAFHANSSEPALLFRNIKCNYVFNNSLTRQLQPI<br>NYFDSYLGCVVNAYNSTAISVQTCDLTVGSGYCVDYSKNRR<br>SRGAITTGYRFTNFEPFTVNSVNDSLEPVGGLYEIQIPSEFTIG<br>NMVEFIQTSSPKVTIDCAAFVCGDYAACKSQLVEYGSFCDNI<br>NAILTEVNELLDTTQLQVANSLMNGVTLSTKLKDGVNFNVD<br>DINFSPVLGCLGSECSKASSRSAIEDLLFDKVKLSDVGFVEAY<br>NNCTGGAEIRDLICVQSYKGIKVLPPLLSENQISGYTLAATSA<br>SLFPPWTAAAGVPFYLNVQYRINGLGVTMDVLSQNQKLIAN<br>AFNNALYAIQEGFDATNSALVKIQAVVNANAEALNNLLQQL<br>SNRFGAISASLQEILSRLDALEAEAQIDRLINGRLTALNAYVS<br>QQLSDSTLVKFSAAQAMEKVNECVKSQSSRINFCGNGNHIIS<br>LVQNAPYGLYFIHFSYVPTKYVTARVSPGLCIAGDRGIAPKS<br>GYFVNVNNTWMYTGSGYYYPEPITENNVVVMSTCAVNYTK<br>APYVMLNTSIPNLPDFKEELDQWFKNQTSVAPDLSLDYINVT<br>FLDLQVEMNRLQEAIKVLNQSYINLKDIGTYEYYVKWPWYV<br>WLLICLAGVAMLVLLFFICCCTGCGTSCFKKCGGCCDDYTG<br>YQELVIKTSHDD | 30 |
| Human coronavirus HKU1 (isolate N5) (HCoV-HKU1) Spike glycoprotein UniProtKB-Q0ZME7 | MFLIIFILPTTLAVIGDFNCTNSFINDYNKTIPRISEDVVDVSL<br>GLGTYYVLNRVYLNTTLLFTGYFPKSGANFRDLALKGSIYLST<br>LWYKPPFLSDFNNGIFSKVKNTKLYVNNTLYSEFSTIVIGSVF<br>VNTSYTIVVQPHNGILEITACQYTMCEYPHTVCKSKGSIRNES<br>WHIDSSEPLCLFKKNFTYNVSADWLYFHFYQERGVFYAYYA<br>DVGMPTTFLFSLYLGTILSHYYVMPLTCNAISSNTDNETLEY<br>WVTPLSRRQYLLNFDEHGVITNAVDCSSSFLSEIQCKTQSFAP<br>NTGVYDLSGFTVKPVATVYRRIPNLPDCDIDNWLNNVSVPSP<br>LNWERRIFSNCNFNLSTLLRLVHVDSFSCNNLDKSKIFGSCFN<br>SITVDKFAIPNRRRDDLQLGSSGFLQSSNYKIDISSSSCQLYYS<br>LPLVNVTINNFNPSSWNRRYGFGSFNLSSYDVVYSDHCFSVN<br>SDFCPCADPSVVNSCAKSKPPSAICPAGTKYRHCDLDTTLYV<br>KNWCRCSCLPDPISTYSPNTCPQKKVVVGIGEHCPGLGINEE<br>KCGTQLNHSSCFCSPDAFLGWSFDSCISNNRCNIFSNFIFNGIN<br>SGTTCSNDLLYSNTEISTGVCVNYDLYGITGQGIFKEVSAAY<br>YNNWQNLLYDSNGNIIGFKDFLTNKTYTILPCYSGRVSAAFY<br>QNSSSPALLYRNLKCSYVLNNISFISQPFYFDSYLGCVLNAVN<br>LTSYSVSSCDLRMGSGFCIDYALPSSRRKRRGISSPYRFVTFEP<br>FNVSFVNDSVETVGGLFEIQIPTNFTIAGHEEFIQTSSPKVTIDC<br>SAFVCSNYAACHDLLSEYGTFCDNINSILNEVNDLLDITQLQV<br>ANALMQGVTLSSNLNTNLHSDVDNIDFKSLLGCLGSQCGSSS<br>RSLLEDLLFNKVKLSDVGFVEAYNNCTGGSEIRDLLCVQSFN<br>GIKVLPPILSETQISGYTTAATVAAMFPPWSAAAGVPFSLNVQ<br>YRINGLGVTMDVLNKNQKLIANAFNKALLSIQNGFTATNSAL<br>AKIQSVVNANAQALNSLLQQLFNKFGAISSSLQEILSRLDNLE<br>AQVQIDRLINGRLTALNAYVSQQLSDITLIKAGASRAIEKVNE<br>CVKSQSPRINFCGNGNHILSLVQNAPYGLLFIHFSYKPTSFKT<br>VLVSPGLCLSGDRGIAPKQGYFIKQNDSWMFTGSSYYYPEPIS<br>DKNVVFMNSCSVNFTKAPFIYLNNSIPNLSDFEAELSLWFKN<br>HTSIAPNLTFNSHINATFLDLYYEMNVIQESIKSLNSSFINLKEI<br>GTYEMYVKWPWYIWLLIVILFIIFLMILFFICCCTGCGSACFSK<br>CHNCCDEYGGHNDFVIKASHDD | 31 |
| Novel_SARS_S2 | MFIFLLFLTLTSGSDLDRALSGIAAEQDRNTREVFAQVKQMY<br>KTPTLKYFGGFNFSQILPDPLKPTKRSFIEDLLFNKVTLADAG<br>FMKQYGECLGDINARDLICAQKFNGLTVLPPLLTDDMIAAYT<br>AALVSGTATAGWTFGAGAALQIPFAMQMAYRFNGIGVTQN<br>VLYENQKQIANQFNKAISQIQESLTTTSTALGKLQDVVNQNA<br>QALNTLVKQLSSNFGAISSVLNDILSRLDKVEAEVQIDRLITG<br>RLQSLQTYVTQQLIRAAEIRASANLAATKMSECVLGQSKRV<br>DFCGKGYHLMSFPQAAPHGVVFLHVTYVPSQERNFTTAPAIC | 32 |

TABLE 11-continued

| Betacoronavirus Amino Acid Sequences | | |
|---|---|---|
| Strain | Amino Acid Sequence | SEQ ID NO: |
| | HEGKAYFPREGVFVFNGTSWFITQRNFFSPQIITTDNTFVSGN CDVVIGIINNTVYDPLQPELDSFKEELDKYFKNHTSPDVDLG DISGINASVVNIQKEIDRLNEVAKNLNESLIDLQELGKYEQYI KWPWYVWLGFIAGLIAIVMVTILLCCMTSCCSCLKGACSCGS CCKFDEDDSEPVLKGVKLHYT | |
| Novel_MERS_S2 | MIHSVFLLMFLLTPTESDCKLPLGQSLCALPDTPSTLTPRSVR SVPGEMRLASIAFNHPIQVDQLNSSYFKLSIPTNFSFGVTQEYI QTTIQKVTVDCKQYVCNGFQKCEQLLREYGQFCSKINQALH GANLRQDDSVRNLFASVKSSQSSPIIPGFGGDFNLTLLEPVSIS TGSRSARSAIEDLLFDKVTIADPGYMQGYDDCMQQGPASAR DLICAQYVAGYKVLPPLMDVNMEAAYTSSLLGSIAGVGWTA GLSSFAAIPFAQSIFYRLNGVGITQQVLSENQKLIANKFNQAL GAMQTGFTTTNEAFQKVQDAVNNNAQALSKLASELSNTFG AISASIGDIIQRLDVLEQDAQIDRLINGRLTTLNAFVAQQLVRS ESAALSAQLAKDKVNECVKAQSKRSGFCGQGTHIVSFVVNA PNGLYFMHVGYYPSNHIEVVSAYGLCDAANPTNCIAPVNGY FIKTNNTRIVDEWSYTGSSFYAPEPITSLNTKYVAPQVTYQNI STNLPPPLLGNSTGIDFQDELDEFFKNVSTSIPNFGSLTQINTTL LDLTYEMLSLQQVVKALNESYIDLKELGNYTYYNKWP | 33 |
| Novel_Trimeric_ SARS_S2 | MFIFLLFLTLTSGSDLDRALSGIAAEQDRNTREVFAQVKQMY KTPTLKYFGGFNFSQILPDPLKPTKRSFIEDLLFNKVTLADAG FMKQYGECLGDINARDLICAQKFNGLTVLPPLLTDDMIAAYT AALVSGTATAGWTFGAGAALQIPFAMQMAYRFNGIGVTQN VLYENQKQIANQFNKAISQIQESLTTTSTALGKLQDVVNQNA QALNTLVKQLSSNFGAISSVLNDILSRLDKVEAEVQIDRLITG RLQSLQTYVTQQLIRAAEIRASANLAATKMSECVLGQSKRV DFCGKGYHLMSFPQAAPHGVVFLHVTYVPSQERNFTTAPAIC HEGKAYFPREGVFVFNGTSWFITQRNFFSPQIITTDNTFVSGN CDVVIGIINNTVYDPLQPELDSFKEELDKYFKNHTSPDVDLG DISGINASVVNIQKEIDRLNEVAKNLNESLIDLQELGKYEQYI KWPWYVWLGFIAGLIAIVMVTILLCCMTSCCSCLKGACSCGS CCKFDEDDSEPVLKGVKLHYT | 34 |

TABLE 12

| Full-length Spike Glycoprotein Amino Acid Sequences (*Homo sapiens* strains) | | | | |
|---|---|---|---|---|
| GenBank Accession | Country | Collection Date | Release Date | Virus Name |
| AFY13307 | United Kingdom | Sep. 11, 2012 | Dec. 5, 2012 | Betacoronavirus England 1, complete genome |
| AFS88936 | | Jun. 13, 2012 | Sep. 27, 2012 | Human betacoronavirus 2c EMC/2012, complete genome |
| AGG22542 | United Kingdom | Sep. 19, 2012 | Feb. 27, 2013 | Human betacoronavirus 2c England-Qatar/2012, complete genome |
| AHY21469 | Jordan | 2012 | May 4, 2014 | Human betacoronavirus 2c Jordan-N3/2012 isolate MG167, complete genome |
| AGH58717 | Jordan | April 2012 | Mar. 25, 2013 | Human betacoronavirus 2c Jordan-N3/2012, complete genome |
| AGV08444 | Saudi Arabia | May 7, 2013 | Sep. 17, 2013 | Middle East respiratory syndrome coronavirus isolate Al-Hasa_12_2013, complete genome |
| AGV08546 | Saudi Arabia | May 11, 2013 | Sep. 17, 2013 | Middle East respiratory syndrome coronavirus isolate Al-Hasa_15_2013, complete genome |
| AGV08535 | Saudi Arabia | May 12, 2013 | Sep. 17, 2013 | Middle East respiratory syndrome coronavirus isolate Al-Hasa_16_2013, complete genome |
| AGV08558 | Saudi Arabia | May 15, 2013 | Sep. 17, 2013 | Middle East respiratory syndrome coronavirus isolate Al-Hasa_17_2013, complete genome |
| AGV08573 | Saudi Arabia | May 23, 2013 | Sep. 17, 2013 | Middle East respiratory syndrome coronavirus isolate Al-Hasa_18_2013, complete genome |
| AGV08480 | Saudi Arabia | May 23, 2013 | Sep. 17, 2013 | Middle East respiratory syndrome coronavirus isolate Al-Hasa_19_2013, complete genome |

TABLE 12-continued

Full-length Spike Glycoprotein Amino Acid Sequences (*Homo sapiens* strains)

| GenBank Accession | Country | Collection Date | Release Date | Virus Name |
|---|---|---|---|---|
| AGN70962 | Saudi Arabia | May 9, 2013 | Jun. 10, 2013 | Middle East respiratory syndrome coronavirus isolate Al-Hasa_1_2013, complete genome |
| AGV08492 | Saudi Arabia | May 30, 2013 | Sep. 17, 2013 | Middle East respiratory syndrome coronavirus isolate Al-Hasa_21_2013, complete genome |
| AHI48517 | Saudi Arabia | May 2, 2013 | Feb. 6, 2014 | Middle East respiratory syndrome coronavirus isolate Al-Hasa_25_2013, complete genome |
| AGN70951 | Saudi Arabia | Apr. 21, 2013 | Jun. 10, 2013 | Middle East respiratory syndrome coronavirus isolate Al-Hasa_2_2013, complete genome |
| AGN70973 | Saudi Arabia | Apr. 22, 2013 | Jun. 10, 2013 | Middle East respiratory syndrome coronavirus isolate Al-Hasa_3_2013, complete genome |
| AGN70929 | Saudi Arabia | May 1, 2013 | Jun. 10, 2013 | Middle East respiratory syndrome coronavirus isolate Al-Hasa_4_2013, complete genome |
| AGV08408 | Saudi Arabia | Jun. 19, 2012 | Sep. 17, 2013 | Middle East respiratory syndrome coronavirus isolate Bisha_1_2012, complete genome |
| AGV08467 | Saudi Arabia | May 13, 2013 | Sep. 17, 2013 | Middle East respiratory syndrome coronavirus isolate Buraidah_1_2013, complete genome |
| AID50418 | United Kingdom | Feb. 10, 2013 | Jun. 18, 2014 | Middle East respiratory syndrome coronavirus isolate England/2/2013, complete genome |
| AJD81451 | United Kingdom | Feb. 10, 2013 | Jan. 18, 2015 | Middle East respiratory syndrome coronavirus isolate England/3/2013, complete genome |
| AJD81440 | United Kingdom | Feb. 13, 2013 | Jan. 18, 2015 | Middle East respiratory syndrome coronavirus isolate England/4/2013, complete genome |
| AHB33326 | France | May 7, 2013 | Dec. 7, 2013 | Middle East respiratory syndrome coronavirus isolate FRA/UAE, complete genome |
| AIZ48760 | USA | June 2014 | Dec. 14, 2014 | Middle East respiratory syndrome coronavirus isolate Florida/USA-2_Saudi Arabia_2014, complete genome |
| AGV08455 | Saudi Arabia | Jun. 4, 2013 | Sep. 17, 2013 | Middle East respiratory syndrome coronavirus isolate Hafr-Al-Batin_1_2013, complete genome |
| AHI48561 | Saudi Arabia | Aug. 5, 2013 | Feb. 6, 2014 | Middle East respiratory syndrome coronavirus isolate Hafr-Al-Batin_2_2013, complete genome |
| AHI48539 | Saudi Arabia | Aug. 28, 2013 | Feb. 6, 2014 | Middle East respiratory syndrome coronavirus isolate Hafr-Al-Batin_6_2013, complete genome |
| AIZ74417 | France | Apr. 26, 2013 | Mar. 10, 2015 | Middle East respiratory syndrome coronavirus isolate Hu-France (UAE) - FRA1_1627-2013_BAL_Sanger, complete genome |
| AIZ74433 | France | May 7, 2013 | Mar. 10, 2015 | Middle East respiratory syndrome coronavirus isolate Hu-France - FRA2_130569-2013_IS_HTS, complete genome |
| AIZ74439 | France | May 7, 2013 | Mar. 10, 2015 | Middle East respiratory syndrome coronavirus isolate Hu-France - FRA2_130569-2013_InSpu_Sanger, complete genome |
| AIZ74450 | France | May 7, 2013 | Mar. 10, 2015 | Middle East respiratory syndrome coronavirus isolate Hu-France - FRA2_130569-2013_Isolate_Sanger, complete genome |
| AKK52602 | Saudi Arabia | Feb. 10, 2015 | Jun. 8, 2015 | Middle East respiratory syndrome coronavirus isolate Hu/Riyadh_KSA_2959_2015, complete genome |
| AKK52612 | Saudi Arabia | Mar. 1, 2015 | Jun. 8, 2015 | Middle East respiratory syndrome coronavirus isolate Hu/Riyadh_KSA_4050_2015, complete genome |

TABLE 12-continued

Full-length Spike Glycoprotein Amino Acid Sequences (*Homo sapiens* strains)

| GenBank Accession | Country | Collection Date | Release Date | Virus Name |
|---|---|---|---|---|
| AHN10812 | Saudi Arabia | Nov. 6, 2013 | Mar. 24, 2014 | Middle East respiratory syndrome coronavirus isolate Jeddah_1_2013, complete genome |
| AID55071 | Saudi Arabia | Apr. 21, 2014 | Nov. 12, 2014 | Middle East respiratory syndrome coronavirus isolate Jeddah_C10306/KSA/2014-04-20, complete genome |
| AID55066 | Saudi Arabia | 2014 | Nov. 12, 2014 | Middle East respiratory syndrome coronavirus isolate Jeddah_C7149/KSA/2014-04-05, complete genome |
| AID55067 | Saudi Arabia | 2014 | Nov. 12, 2014 | Middle East respiratory syndrome coronavirus isolate Jeddah_C7569/KSA/2014-04-03, complete genome |
| AID55068 | Saudi Arabia | Apr. 7, 2014 | Nov. 12, 2014 | Middle East respiratory syndrome coronavirus isolate Jeddah_C7770/KSA/2014-04-07, complete genome |
| AID55069 | Saudi Arabia | Apr. 12, 2014 | Nov. 12, 2014 | Middle East respiratory syndrome coronavirus isolate Jeddah_C8826/KSA/2014-04-12, complete genome |
| AID55070 | Saudi Arabia | Apr. 14, 2014 | Nov. 12, 2014 | Middle East respiratory syndrome coronavirus isolate Jeddah_C9055/KSA/2014-04-14, complete genome |
| AHE78108 | Saudi Arabia | Nov. 5, 2013 | May 1, 2014 | Middle East respiratory syndrome coronavirus isolate MERS-CoV-Jeddah-human-1, complete genome |
| AKL59401 | South Korea | May 20, 2015 | Jun. 9, 2015 | Middle East respiratory syndrome coronavirus isolate MERS-CoV/KOR/KNIH/002_05_2015, complete genome |
| ALD51904 | Thailand | Jun. 17, 2015 | Jul. 7, 2015 | Middle East respiratory syndrome coronavirus isolate MERS-CoV/THA/CU/17_06_2015, complete genome |
| AID55072 | Saudi Arabia | Apr. 15, 2014 | Nov. 12, 2014 | Middle East respiratory syndrome coronavirus isolate Makkah_C9355/KSA/Makkah/2014-04-15, complete genome |
| AHC74088 | Qatar | Oct. 13, 2013 | Dec. 23, 2013 | Middle East respiratory syndrome coronavirus isolate Qatar3, complete genome |
| AHC74098 | Qatar | Oct. 17, 2013 | Dec. 23, 2013 | Middle East respiratory syndrome coronavirus isolate Qatar4, complete genome |
| AHI48572 | Saudi Arabia | Aug. 15, 2013 | Feb. 6, 2014 | Middle East respiratory syndrome coronavirus isolate Riyadh_14_2013, complete genome |
| AGV08379 | Saudi Arabia | Oct. 23, 2012 | Sep. 17, 2013 | Middle East respiratory syndrome coronavirus isolate Riyadh_1_2012, complete genome |
| AID55073 | Saudi Arabia | Apr. 22, 2014 | Nov. 12, 2014 | Middle East respiratory syndrome coronavirus isolate Riyadh_2014KSA_683/KSA/2014, complete genome |
| AGV08584 | Saudi Arabia | Oct. 30, 2012 | Sep. 17, 2013 | Middle East respiratory syndrome coronavirus isolate Riyadh_2_2012, complete genome |
| AGV08390 | Saudi Arabia | Feb. 5, 2013 | Sep. 17, 2013 | Middle East respiratory syndrome coronavirus isolate Riyadh_3_2013, complete genome |
| AHI48605 | Saudi Arabia | Mar. 1, 2013 | Feb. 6, 2014 | Middle East respiratory syndrome coronavirus isolate Riyadh_4_2013, complete genome |
| AHI48583 | Saudi Arabia | Jul. 2, 2013 | Feb. 6, 2014 | Middle East respiratory syndrome coronavirus isolate Riyadh_5_2013, complete genome |
| AHI48528 | Saudi Arabia | Jul. 17, 2013 | Feb. 6, 2014 | Middle East respiratory syndrome coronavirus isolate Riyadh_9_2013, complete genome |

TABLE 12-continued

Full-length Spike Glycoprotein Amino Acid Sequences (*Homo sapiens* strains)

| GenBank Accession | Country | Collection Date | Release Date | Virus Name |
|---|---|---|---|---|
| AHI48594 | Saudi Arabia | Jun. 12, 2013 | Feb. 6, 2014 | Middle East respiratory syndrome coronavirus isolate Taif_1_2013, complete genome |
| AHI48550 | Saudi Arabia | Jun. 12, 2013 | Feb. 6, 2014 | Middle East respiratory syndrome coronavirus isolate Wadi-Ad-Dawasir_1_2013, complete genome |
| AIY60558 | United Arab Emirates | Mar. 7, 2014 | Dec. 6, 2014 | Middle East respiratory syndrome coronavirus strain Abu Dhabi/Gayathi_UAE_2_2014, complete genome |
| AIY60538 | United Arab Emirates | Apr. 10, 2014 | Dec. 6, 2014 | Middle East respiratory syndrome coronavirus strain Abu Dhabi_UAE_16_2014, complete genome |
| AIY60528 | United Arab Emirates | Apr. 10, 2014 | Dec. 6, 2014 | Middle East respiratory syndrome coronavirus strain Abu Dhabi_UAE_18_2014, complete genome |
| AIY60588 | United Arab Emirates | Apr. 13, 2014 | Dec. 6, 2014 | Middle East respiratory syndrome coronavirus strain Abu Dhabi_UAE_26_2014, complete genome |
| AIY60548 | United Arab Emirates | Apr. 19, 2014 | Dec. 6, 2014 | Middle East respiratory syndrome coronavirus strain Abu Dhabi_UAE_30_2014, complete genome |
| AIY60568 | United Arab Emirates | Apr. 17, 2014 | Dec. 6, 2014 | Middle East respiratory syndrome coronavirus strain Abu Dhabi_UAE_33_2014, complete genome |
| AIY60518 | United Arab Emirates | Apr. 7, 2014 | Dec. 6, 2014 | Middle East respiratory syndrome coronavirus strain Abu Dhabi_UAE_8_2014, complete genome |
| AIY60578 | United Arab Emirates | Nov. 15, 2013 | Dec. 6, 2014 | Middle East respiratory syndrome coronavirus strain Abu Dhabi_UAE_9_2013, complete genome |
| AKJ80137 | China | May 27, 2015 | Jun. 5, 2015 | Middle East respiratory syndrome coronavirus strain ChinaGD01, complete genome |
| AHZ64057 | USA | May 10, 2014 | May 14, 2014 | Middle East respiratory syndrome coronavirus strain Florida/USA-2_Saudi Arabia_2014, complete genome |
| AKM76229 | Oman | Oct. 28, 2013 | Jun. 23, 2015 | Middle East respiratory syndrome coronavirus strain Hu/Oman_2285_2013, complete genome |
| AKM76239 | Oman | Dec. 28, 2013 | Jun. 23, 2015 | Middle East respiratory syndrome coronavirus strain Hu/Oman_2874_2013, complete genome |
| AKI29284 | Saudi Arabia | Jan. 6, 2015 | May 27, 2015 | Middle East respiratory syndrome coronavirus strain Hu/Riyadh-KSA-2049/2015, complete genome |
| AKI29265 | Saudi Arabia | Jan. 21, 2015 | May 27, 2015 | Middle East respiratory syndrome coronavirus strain Hu/Riyadh-KSA-2343/2015, complete genome |
| AKI29255 | Saudi Arabia | Jan. 21, 2015 | May 27, 2015 | Middle East respiratory syndrome coronavirus strain Hu/Riyadh-KSA-2345/2015, complete genome |
| AKI29275 | Saudi Arabia | Jan. 26, 2015 | May 27, 2015 | Middle East respiratory syndrome coronavirus strain Hu/Riyadh-KSA-2466/2015, complete genome |
| AKK52582 | Saudi Arabia | Feb. 10, 2015 | Jun. 8, 2015 | Middle East respiratory syndrome coronavirus strain Hu/Riyadh_KSA_2959_2015, complete genome |
| AKK52592 | Saudi Arabia | Mar. 1, 2015 | Jun. 8, 2015 | Middle East respiratory syndrome coronavirus strain Hu/Riyadh_KSA_4050_2015, complete genome |

TABLE 12-continued

| Full-length Spike Glycoprotein Amino Acid Sequences (*Homo sapiens* strains) | | | | |
|---|---|---|---|---|
| GenBank Accession | Country | Collection Date | Release Date | Virus Name |
| AHZ58501 | USA | Apr. 30, 2014 | May 13, 2014 | Middle East respiratory syndrome coronavirus strain Indiana/USA-1_Saudi Arabia_2014, complete genome |
| AGN52936 | United Arab Emirates | 2013 | Jun. 10, 2013 | Middle East respiratory syndrome coronavirus, complete genome |

TABLE 13

| Description | Sequence | SEQ ID NO: |
|---|---|---|
| | MeV Nucleic Acid Sequences | |
| GC_F_MEASLES_ B3.1 Sequence, NT (5' UTR, ORF, 3' UTR) Sequence Length: 1864 | TCAAGCTTTTGGACCCTCGTACAGAAGCTAATACGACT<br>CACTATAGGGAAATAAGAGAGAAAAGAAGAGTAAGAA<br>GAAATATAAGAGCCACCATGGGTCTCAAGGTGAACGTC<br>TCTGCCGTATTCATGGCAGTACTGTTAACTCTCCAAACA<br>CCCGCCGGTCAAATTCATTGGGGCAATCTCTCTAAGAT<br>AGGGGTAGTAGGAATAGGAAGTGCAAGCTACAAAGTT<br>ATGACTCGTTCCAGCCATCAATCATTAGTCATAAAATT<br>AATGCCCAATATAACTCTCCTCAATAACTGCACGAGGG<br>TAGAGATTGCAGAATACAGGAGACTACTAAGAACAGTT<br>TTGGAACCAATTAGGGATGCACTTAATGCAATGACCCA<br>GAACATAAGGCCGGTTCAGAGCGTAGCTTCAAGTAGGA<br>GACACAAGAGATTTGCGGGAGTAGTCCTGGCAGGTGCG<br>GCCCTAGGTGTTGCCACAGCTGCTCAGATAACAGCCGG<br>CATTGCACTTCACCGGTCCATGCTGAACTCTCAGGCCAT<br>CGACAATCTGAGAGCGAGCCTGGAAACTACTAATCAGG<br>CAATTGAGGCAATCAGACAAGCAGGGCAGGAGATGAT<br>ATTGGCTGTTCAGGGTGTCCAAGACTACATCAATAATG<br>AGCTGATACCGTCTATGAACCAGCTATCTTGTGATCTA<br>ATCGGTCAGAAGCTCGGGCTCAAATTGCTTAGATACTA<br>TACAGAAATCCTGTCATTATTTGGCCCCAGCCTACGGG<br>ACCCCATATCTGCGGAGATATCTATCCAGGCTTTGAGTT<br>ATGCACTTGGAGGAGATATCAATAAGGTGTTAGAAAAG<br>CTCGGATACAGTGGAGGCGATTTACTAGGCATCTTAGA<br>GAGCAGAGGAATAAAGGCTCGGATAACTCACGTCGAC<br>ACAGAGTCCTACTTCATAGTCCTCAGTATAGCCTATCCG<br>ACGCTGTCCGAGATTAAGGGGGTGATTGTCCACCGGCT<br>AGAGGGGGTCTCGTACAACATAGGCTCTCAAGAGTGGT<br>ATACCACTGTGCCCAAGTATGTTGCAACCCAAGGGTAC<br>CTTATCTCGAATTTTGATGAGTCATCATGTACTTTCATG<br>CCAGAGGGGACTGTGTGCAGCCAAAATGCCTTGTACCC<br>GATGAGTCCTCTGCTCCAAGAATGCCTCCGGGGGTCCA<br>CCAAGTCCTGTGCTCGTACACTCGTATCCGGGTCTTTTG<br>GGAACCGGTTCATTTTATCACAAGGGAACCTAATAGCC<br>AATTGTGCATCAATTCTTTGTAAGTGTTACACAACAGGT<br>ACGATTATTAATCAAGACCCTGACAAGATCCTAACATA<br>CATTGCTGCCGATCGCTGCCCGGTAGTCGAGGTGAACG<br>GCGTGACCATCCAAGTCGGGAGCAGGAGGTATCCAGA<br>CGCTGTGTACTTGCACAGAATTGACCTCGGTCCTCCCAT<br>ATCATTGGAGAGGTTGGACGTAGGGACAAATCTGGGG<br>AATGCAATTGCCAAATTGGAGGATGCCAAGGAATTGTT<br>GGAATCATCGGACCAGATATTGAGAAGTATGAAAGGTT<br>TATCGAGCACTAGCATAGTCTACATCCTGATTGCAGTG<br>TGTCTTGGAGGGTTGATAGGGATCCCCACTTTAATATGT<br>TGCTGCAGGGGGCGTTGTAACAAAAAGGGAGAACAAG<br>TTGGTATGTCAAGACCAGGCCTAAAGCCTGACCTTACA<br>GGAACATCAAAATCCTATGTAAGATCGCTTTGATGATA<br>ATAGGCTGGAGCCTCGGTGGCCAAGCTTCTTGCCCCTT<br>GGGCCTCCCCCCAGCCCCTCCTCCCCTTCCTGCACCCGT<br>ACCCCCGTGGTCTTTGAATAAAGTCTGAGTGGGCGGC | 35 |
| GC_F_MEASLES_ B3.1 ORF Sequence, NT | ATGGGTCTCAAGGTGAACGTCTCTGCCGTATTCATGGC<br>AGTACTGTTAACTCTCCAAACACCCGCCGGTCAAATTC<br>ATTGGGGCAATCTCTCTAAGATAGGGGTAGTAGGAATA<br>GGAAGTGCAAGCTACAAAGTTATGACTCGTTCCAGCCA<br>TCAATCATTAGTCATAAAATTAATGCCCAATATAACTCT<br>CCTCAATAACTGCACGAGGGTAGAGATTGCAGAATACA<br>GGAGACTACTAAGAACAGTTTTGGAACCAATTAGGGAT | 36 |

TABLE 13-continued

| Description | Sequence | SEQ ID NO: |
|---|---|---|
| | GCACTTAATGCAATGACCCAGAACATAAGGCCGGTTCA GAGCGTAGCTTCAAGTAGGAGACACAAGAGATTTGCG GGAGTAGTCCTGGCAGGTGCGGCCCTAGGTGTTGCCAC AGCTGCTCAGATAACAGCCGGCATTGCACTTCACCGGT CCATGCTGAACTCTCAGGCCATCGACAATCTGAGAGCG AGCCTGGAAACTACTAATCAGGCAATTGAGGCAATCAG ACAAGCAGGGCAGGAGATGATATTGGCTGTTCAGGGTG TCCAAGACTACATCAATAATGAGCTGATACCGTCTATG AACCAGCTATCTTGTGATCTAATCGGTCAGAAGCTCGG GCTCAAATTGCTTAGATACTATACAGAAATCCTGTCATT ATTTGGCCCCAGCCTACGGGACCCCATATCTGCGGAGA TATCTATCCAGGCTTTGAGTTATGCACTTGGAGGAGAT ATCAATAAGGTGTTAGAAAAGCTCGGATACAGTGGAG GCGATTTACTAGGCATCTTAGAGAGCAGAGGAATAAAG GCTCGGATAACTCACGTCGACACAGAGTCCTACTTCAT AGTCCTCAGTATAGCCTATCCGACGCTGTCCGAGATTA AGGGGGTGATTGTCCACCGGCTAGAGGGGGTCTCGTAC AACATAGGCTCTCAAGAGTGGTATACCACTGTGCCCAA GTATGTTGCAACCCAAGGGTACCTTATCTCGAATTTTGA TGAGTCATCATGTACTTTCATGCCAGAGGGGACTGTGT GCAGCCAAAATGCCTTGTACCCGATGAGTCCTCTGCTC CAAGAATGCCTCCGGGGGTCCACCAAGTCCTGTGCTCG TACACTCGTATCCGGGTCTTTTGGGAACCGGTTCATTTT ATCACAAGGGAACCTAATAGCCAATTGTGCATCAATTC TTTGTAAGTGTTACACAACAGGTACGATTATTAATCAA GACCCTGACAAGATCCTAACATACATTGCTGCCGATCG CTGCCCGGTAGTCGAGGTGAACGGCGTGACCATCCAAG TCGGGAGCAGGAGGTATCCAGACGCTGTGTACTTGCAC AGAATTGACCTCGGTCCTCCCATATCATTGGAGAGGTT GGACGTAGGGACAAATCTGGGGAATGCAATTGCCAAA TTGGAGGATGCCAAGGAATTGTTGGAATCATCGGACCA GATATTGAGAAGTATGAAAGGTTTATCGAGCACTAGCA TAGTCTACATCCTGATTGCAGTGTGTCTTGGAGGGTTGA TAGGGATCCCCACTTTAATATGTTGCTGCAGGGGGCGT TGTAACAAAAAGGGAGAACAAGTTGGTATGTCAAGAC CAGGCCTAAAGCCTGACCTTACAGGAACATCAAAATCC TATGTAAGATCGCTTTGA | |
| GC_F_MEASLES_ B3.1 mRNA Sequence (assumes T100 tail) mRNA Sequence Length: 1925 | G*GGGAAATAAGAGAGAAAAGAAGAGTAAGAAGAAAT ATAAGAGCCACCATGGGTCTCAAGGTGAACGTCTCTGC CGTATTCATGGCAGTACTGTTAACTCTCCAAACACCCG CCGGTCAAATTCATTGGGGCAATCTCTCTAAGATAGGG GTAGTAGGAATAGGAAGTGCAAGCTACAAAGTTATGA CTCGTTCCAGCCATCAATCATTAGTCATAAAATTAATGC CCAATATAACTCTCCTCAATAACTGCACGAGGGTAGAG ATTGCAGAATACAGGAGACTACTAAGAACAGTTTTGGA ACCAATTAGGGATGCACTTAATGCAATGACCCAGAACA TAAGGCCGGTTCAGAGCGTAGCTTCAAGTAGGAGACAC AAGAGATTTGCGGGAGTAGTCCTGGCAGGTGCGGCCCT AGGTGTTGCCACAGCTGCTCAGATAACAGCCGGCATTG CACTTCACCGGTCCATGCTGAACTCTCAGGCCATCGAC AATCTGAGAGCGAGCCTGGAAACTACTAATCAGGCAAT TGAGGCAATCAGACAAGCAGGGCAGGAGATGATATTG GCTGTTCAGGGTGTCCAAGACTACATCAATAATGAGCT GATACCGTCTATGAACCAGCTATCTTGTGATCTAATCG GTCAGAAGCTCGGGCTCAAATTGCTTAGATACTATACA GAAATCCTGTCATTATTTGGCCCCAGCCTACGGGACCC CATATCTGCGGAGATATCTATCCAGGCTTTGAGTTATGC ACTTGGAGGAGATATCAATAAGGTGTTAGAAAAGCTCG GATACAGTGGAGGCGATTTACTAGGCATCTTAGAGAGC AGAGGAATAAAGGCTCGGATAACTCACGTCGACACAG AGTCCTACTTCATAGTCCTCAGTATAGCCTATCCGACGC TGTCCGAGATTAAGGGGGTGATTGTCCACCGGCTAGAG GGGGTCTCGTACAACATAGGCTCTCAAGAGTGGTATAC CACTGTGCCCAAGTATGTTGCAACCCAAGGGTACCTTA TCTCGAATTTTGATGAGTCATCATGTACTTTCATGCCAG AGGGGACTGTGTGCAGCCAAAATGCCTTGTACCCGATG AGTCCTCTGCTCCAAGAATGCCTCCGGGGGTCCACCAA GTCCTGTGCTCGTACACTCGTATCCGGGTCTTTTGGGAA CCGGTTCATTTTATCACAAGGGAACCTAATAGCCAATT GTGCATCAATTCTTTGTAAGTGTTACACAACAGGTACG ATTATTAATCAAGACCCTGACAAGATCCTAACATACAT TGCTGCCGATCGCTGCCCGGTAGTCGAGGTGAACGGCG TGACCATCCAAGTCGGGAGCAGGAGGTATCCAGACGCT GTGTACTTGCACAGAATTGACCTCGGTCCTCCCATATCA TTGGAGAGGTTGGACGTAGGGACAAATCTGGGGAATG CAATTGCCAAATTGGAGGATGCCAAGGAATTGTTGGAA | 37 |

TABLE 13-continued

| Description | Sequence | SEQ ID NO: |
|---|---|---|
| | TCATCGGACCAGATATTGAGAAGTATGAAAGGTTTATC GAGCACTAGCATAGTCTACATCCTGATTGCAGTGTGTC TTGGAGGGTTGATAGGGATCCCCACTTTAATATGTTGCT GCAGGGGGCGTTGTAACAAAAAGGGAGAACAAGTTGG TATGTCAAGACCAGGCCTAAAGCCTGACCTTACAGGAA CATCAAAATCCTATGTAAGATCGCTTTGATGATAATAG GCTGGAGCCTCGGTGGCCAAGCTTCTTGCCCCTTGGGC CTCCCCCCAGCCCCTCCTCCCCTTCCTGCACCCGTACCC CCGTGGTCTTTGAATAAAGTCTGAGTGGGCGGCAAAAA AAAAAAAAAAAAAAAAAAAAAAAAAAAAAAAAAAAA AAAAAAAAAAAAAAAAAAAAAAAAAAAAAAAAAAAA AAAAAAAAAAAAAAAAAAAAAAATCTAG | |
| GC_F_MEASLES_ D8 Sequence, NT (5' UTR, ORF, 3' UTR) Sequence Length: 1864 | TCAAGCTTTTGGACCCTCGTACAGAAGCTAATACGACT CACTATAGGGAAATAAGAGAGAAAAGAAGAGTAAGAA GAAATATAAGAGCCACCATGGGTCTCAAGGTGAACGTC TCTGTCATATTCATGGCAGTACTGTTAACTCTTCAAACA CCCACCGGTCAAATCCATTGGGGCAATCTCTCTAAGAT AGGGGTGGTAGGGGTAGGAAGTGCAAGCTACAAAGTT ATGACTCGTTCCAGCCATCAATCATTAGTCATAAAGTT AATGCCCAATATAACTCTCCTCAACAATTGCACGAGGG TAGGGATTGCAGAATACAGGAGACTACTGAGAACAGTT CTGGAACCAATTAGAGATGCACTTAATGCAATGACCCA GAATATAAGACCGGTTCAGAGTGTAGCTTCAAGTAGGA GACACAAGAGATTTGCGGGAGTTGTCCTGGCAGGTGCG GCCCTAGGCGTTGCCACAGCTGCTCAAATAACAGCCGG TATTGCACTTCACCAGTCCATGCTGAACTCTCAAGCCAT CGACAATCTGAGAGCGAGCCTAGAAACTACTAATCAGG CAATTGAGGCAATCAGACAAGCAGGGCAGGAGATGAT ATTGGCTGTTCAGGGTGTCCAAGACTACATCAATAATG AGCTGATACCGTCTATGAATCAACTATCTTGTGATTTAA TCGGCCAGAAGCTAGGGCTCAAATTGCTCAGATACTAT ACAGAAATCCTGTCATTATTTGGCCCCAGCTTACGGGA CCCCATATCTGCGGAGATATCTATCCAGGCTTTGAGCT ATGCGCTTGGAGGAGATATCAATAAGGTGTTGGAAAAG CTCGGATACAGTGGAGGTGATCTACTGGGCATCTTAGA GAGCAGAGGAATAAAGGCCCGGATAACTCACGTCGAC ACAGAGTCCTACTTCATTGTACTCAGTATAGCCTATCCG ACGCTATCCGAGATTAAGGGGGTGATTGTCCACCGGCT AGAGGGGGTCTCGTACAACATAGGCTCTCAAGAGTGGT ATACCACTGTGCCCAAGTATGTTGCAACCCAAGGGTAC CTTATCTCGAATTTTGATGAGTCATCATGCACTTTCATG CCAGAGGGGACTGTGTGCAGCCAGAATGCCTTGTACCC GATGAGTCCTCTGCTCCAAGAATGCCTCCGGGGGTCCA CTAAGTCCTGTGCTCGTACACTCGTATCCGGGTCTTTCG GGAACCGGTTCATTTTATCACAGGGGAACCTAATAGCC AATTGTGCATCAATCCTTTGCAAGTGTTACACAACAGG AACAATCATTAATCAAGACCCTGACAAGATCCTAACAT ACATTGCTGCCGATCACTGCCCGGTGGTCGAGGTGAAT GGCGTGACCATCCAAGTCGGGAGCAGGAGGTATCCGG ACGCTGTGTACTTGCACAGGATTGACCTCGGTCCTCCC ATATCTTTGGAGAGGTTGGACGTAGGGACAAATCTGGG GAATGCAATTGCTAAGTTGGAGGATGCCAAGGAATTGT TGGAGTCATCGGACCAGATATTGAGGAGTATGAAAGGT TTATCGAGCACTAGTATAGTTTACATCCTGATTGCAGTG TGTCTTGGAGGATTGATAGGGATCCCCGCTTTAATATGT TGCTGCAGGGGGCGTTGTAACAAGAAGGGAGAACAAG TTGGTATGTCAAGACCAGGCCTAAAGCCTGATCTTACA GGAACATCAAAATCCTATGTAAGGTCACTCTGATGATA ATAGGCTGGAGCCTCGGTGGCCAAGCTTCTTGCCCCTT GGGCCTCCCCCCAGCCCCTCCTCCCCTTCCTGCACCCGT ACCCCCGTGGTCTTTGAATAAAGTCTGAGTGGGCGGC | 38 |
| GC_F_MEASLES_ D8 ORF Sequence, NT | ATGGGTCTCAAGGTGAACGTCTCTGTCATATTCATGGC AGTACTGTTAACTCTTCAAACACCCACCGGTCAAATCC ATTGGGGCAATCTCTCTAAGATAGGGGTGGTAGGGGTA GGAAGTGCAAGCTACAAAGTTATGACTCGTTCCAGCCA TCAATCATTAGTCATAAAGTTAATGCCCAATATAACTCT CCTCAACAATTGCACGAGGGTAGGGATTGCAGAATACA GGAGACTACTGAGAACAGTTCTGGAACCAATTAGAGAT GCACTTAATGCAATGACCCAGAATATAAGACCGGTTCA GAGTGTAGCTTCAAGTAGGAGACACAAGAGATTTGCGG GAGTTGTCCTGGCAGGTGCGGCCCTAGGCGTTGCCACA GCTGCTCAAATAACAGCCGGTATTGCACTTCACCAGTC CATGCTGAACTCTCAAGCCATCGACAATCTGAGAGCGA GCCTAGAAACTACTAATCAGGCAATTGAGGCAATCAGA CAAGCAGGGCAGGAGATGATATTGGCTGTTCAGGGTGT | 39 |

TABLE 13-continued

| Description | Sequence | SEQ ID NO: |
|---|---|---|
| | CCAAGACTACATCAATAATGAGCTGATACCGTCTATGA | |
| | ATCAACTATCTTGTGATTTAATCGGCCAGAAGCTAGGG | |
| | CTCAAATTGCTCAGATACTATACAGAAATCCTGTCATT | |
| | ATTTGGCCCCAGCTTACGGGACCCCATATCTGCGGAGA | |
| | TATCTATCCAGGCTTTGAGCTATGCGCTTGGAGGAGAT | |
| | ATCAATAAGGTGTTGGAAAAGCTCGGATACAGTGGAG | |
| | GTGATCTACTGGGCATCTTAGAGAGCAGAGGAATAAAG | |
| | GCCCGGATAACTCACGTCGACACAGAGTCCTACTTCAT | |
| | TGTACTCAGTATAGCCTATCCGACGCTATCCGAGATTA | |
| | AGGGGGTGATTGTCCACCGGCTAGAGGGGGTCTCGTAC | |
| | AACATAGGCTCTCAAGAGTGGTATACCACTGTGCCCAA | |
| | GTATGTTGCAACCCAAGGGTACCTTATCTCGAATTTTGA | |
| | TGAGTCATCATGCACTTTCATGCCAGAGGGGACTGTGT | |
| | GCAGCCAGAATGCCTTGTACCCGATGAGTCCTCTGCTC | |
| | CAAGAATGCCTCCGGGGGTCCACTAAGTCCTGTGCTCG | |
| | TACACTCGTATCCGGGTCTTTCGGGAACCGGTTCATTTT | |
| | ATCACAGGGGAACCTAATAGCCAATTGTGCATCAATCC | |
| | TTTGCAAGTGTTACACAACAGGAACAATCATTAATCAA | |
| | GACCCTGACAAGATCCTAACATACATTGCTGCCGATCA | |
| | CTGCCCGGTGGTCGAGGTGAATGGCGTGACCATCCAAG | |
| | TCGGGAGCAGGAGGTATCCGGACGCTGTGTACTTGCAC | |
| | AGGATTGACCTCGGTCCTCCCATATCTTTGGAGAGGTT | |
| | GGACGTAGGGACAAATCTGGGGAATGCAATTGCTAAGT | |
| | TGGAGGATGCCAAGGAATTGTTGGAGTCATCGGACCAG | |
| | ATATTGAGGAGTATGAAAGGTTTATCGAGCACTAGTAT | |
| | AGTTTACATCCTGATTGCAGTGTGTCTTGGAGGATTGAT | |
| | AGGGATCCCCGCTTTAATATGTTGCTGCAGGGGGCGTT | |
| | GTAACAAGAAGGGAGAACAAGTTGGTATGTCAAGACC | |
| | AGGCCTAAAGCCTGATCTTACAGGAACATCAAAATCCT | |
| | ATGTAAGGTCACTCTGA | |
| GC_F_MEASLES_ | G*GGGAAATAAGAGAGAAAAGAAGAGTAAGAAGAAAT | 40 |
| D8 | ATAAGAGCCACCATGGGTCTCAAGGTGAACGTCTCTGT | |
| mRNA Sequence | CATATTCATGGCAGTACTGTTAACTCTTCAAACACCCAC | |
| (assumes T100 tail) | CGGTCAAATCCATTGGGGCAATCTCTCTAAGATAGGGG | |
| Sequence Length: | TGGTAGGGGTAGGAAGTGCAAGCTACAAAGTTATGACT | |
| 1925 | CGTTCCAGCCATCAATCATTAGTCATAAAGTTAATGCC | |
| | CAATATAACTCTCCTCAACAATTGCACGAGGGTAGGGA | |
| | TTGCAGAATACAGGAGACTACTGAGAACAGTTCTGGAA | |
| | CCAATTAGAGATGCACTTAATGCAATGACCCAGAATAT | |
| | AAGACCGGTTCAGAGTGTAGCTTCAAGTAGGAGACACA | |
| | AGAGATTTGCGGGAGTTGTCCTGGCAGGTGCGGCCCTA | |
| | GGCGTTGCCACAGCTGCTCAAATAACAGCCGGTATTGC | |
| | ACTTCACCAGTCCATGCTGAACTCTCAAGCCATCGACA | |
| | ATCTGAGAGCGAGCCTAGAAACTACTAATCAGGCAATT | |
| | GAGGCAATCAGACAAGCAGGGCAGGAGATGATATTGG | |
| | CTGTTCAGGGTGTCCAAGACTACATCAATAATGAGCTG | |
| | ATACCGTCTATGAATCAACTATCTTGTGATTTAATCGGC | |
| | CAGAAGCTAGGGCTCAAATTGCTCAGATACTATACAGA | |
| | AATCCTGTCATTATTTGGCCCCAGCTTACGGGACCCCAT | |
| | ATCTGCGGAGATATCTATCCAGGCTTTGAGCTATGCGC | |
| | TTGGAGGAGATATCAATAAGGTGTTGGAAAAGCTCGGA | |
| | TACAGTGGAGGTGATCTACTGGGCATCTTAGAGAGCAG | |
| | AGGAATAAAGGCCCGGATAACTCACGTCGACACAGAG | |
| | TCCTACTTCATTGTACTCAGTATAGCCTATCCGACGCTA | |
| | TCCGAGATTAAGGGGGTGATTGTCCACCGGCTAGAGGG | |
| | GGTCTCGTACAACATAGGCTCTCAAGAGTGGTATACCA | |
| | CTGTGCCCAAGTATGTTGCAACCCAAGGGTACCTTATC | |
| | TCGAATTTTGATGAGTCATCATGCACTTTCATGCCAGAG | |
| | GGGACTGTGTGCAGCCAGAATGCCTTGTACCCGATGAG | |
| | TCCTCTGCTCCAAGAATGCCTCCGGGGGTCCACTAAGT | |
| | CCTGTGCTCGTACACTCGTATCCGGGTCTTTCGGGAACC | |
| | GGTTCATTTTATCACAGGGGAACCTAATAGCCAATTGT | |
| | GCATCAATCCTTTGCAAGTGTTACACAACAGGAACAAT | |
| | CATTAATCAAGACCCTGACAAGATCCTAACATACATTG | |
| | CTGCCGATCACTGCCCGGTGGTCGAGGTGAATGGCGTG | |
| | ACCATCCAAGTCGGGAGCAGGAGGTATCCGGACGCTGT | |
| | GTACTTGCACAGGATTGACCTCGGTCCTCCCATATCTTT | |
| | GGAGAGGTTGGACGTAGGGACAAATCTGGGGAATGCA | |
| | ATTGCTAAGTTGGAGGATGCCAAGGAATTGTTGGAGTC | |
| | ATCGGACCAGATATTGAGGAGTATGAAAGGTTTATCGA | |
| | GCACTAGTATAGTTTACATCCTGATTGCAGTGTGTCTTG | |
| | GAGGATTGATAGGGATCCCCGCTTTAATATGTTGCTGC | |
| | AGGGGGCGTTGTAACAAGAAGGGAGAACAAGTTGGTA | |
| | TGTCAAGACCAGGCCTAAAGCCTGATCTTACAGGAACA | |
| | TCAAAATCCTATGTAAGGTCACTCTGATGATAATAGGC | |
| | TGGAGCCTCGGTGGCCAAGCTTCTTGCCCCTTGGGCCTC | |

TABLE 13-continued

| Description | Sequence | SEQ ID NO: |
|---|---|---|
| | CCCCCAGCCCCTCCTCCCCTTCCTGCACCCGTACCCCCG TGGTCTTTGAATAAAGTCTGAGTGGGCGGCAAAAAAAA AAAAAAAAAAAAAAAAAAAAAAAAAAAAAAAAAAAAA AAAAAAAAAAAAAAAAAAAAAAAAAAAAAAAAAAAAA AAAAAAAAAAAAAAAAAAAAATCTAG | |
| GC_H_MEASLES_ B3 Sequence, NT (5' UTR, ORF, 3' UTR) Sequence Length: 2065 | TCAAGCTTTTGGACCCTCGTACAGAAGCTAATACGACT CACTATAGGGAAATAAGAGAGAAAAGAAGAGTAAGAA GAAATATAAGAGCCACCATGTCACCGCAACGAGACCG GATAAATGCCTTCTACAAAGATAACCCTTATCCCAAGG GAAGTAGGATAGTTATTAACAGAGAACATCTTATGATT GACAGACCCTATGTTCTGCTGGCTGTTCTGTTCGTCATG TTTCTGAGCTTGATCGGATTGCTGGCAATTGCAGGCATT AGACTTCATCGGGCAGCCATCTACACCGCGGAGATCCA TAAAAGCCTCAGTACCAATCTGGATGTGACTAACTCCA TCGAGCATCAGGTCAAGGACGTGCTGACACCACTCTTT AAAATCATCGGGGATGAAGTGGGCCTGAGAACACCTC AGAGATTCACTGACCTAGTGAAATTCATCTCGGACAAG ATTAAATTCCTTAATCCGGATAGGGAGTACGACTTCAG AGATCTCACTTGGTGCATCAACCCGCCAGAGAGGATCA AACTAGATTATGATCAATACTGTGCAGATGTGGCTGCT GAAGAGCTCATGAATGCATTGGTGAACTCAACTCTACT GGAGACCAGAACAACCACTCAGTTCCTAGCTGTCTCAA AGGGAAACTGCTCAGGGCCCACTACAATCAGAGGTCA ATTCTCAAACATGTCGCTGTCCTTGTTGGACTTGTACTT AGGTCGAGGTTACAATGTGTCATCTATAGTCACTATGA CATCCCAGGGAATGTATGGGGGAACCTACCTAGTTGAA AAGCCTAATCTGAACAGCAAAGGGTCAGAGTTGTCACA ACTGAGCATGTACCGAGTGTTTGAAGTAGGTGTGATCA GAAACCCGGGTTTGGGGGCTCCGGTGTTCCATATGACA AACTATTTTGAGCAACCAGTCAGTAATGGTCTCGGCAA CTGTATGGTGGCTTTGGGGGAGCTCAAACTCGCAGCCC TTTGTCACGGGGACGATTCTATCATAATTCCCTATCAGG GATCAGGGAAAGGTGTCAGCTTCCAGCTCGTCAAGCTG GGTGTCTGGAAATCCCCAACCGACATGCAATCCTGGGT CCCCTTATCAACGGATGATCCAGTGGTAGACAGGCTTT ACCTCTCATCTCACAGAGGTGTCATCGCTGACAATCAA GCAAAATGGGCTGTCCCGACAACACGAACAGATGACA AGTTGCGAATGGAGACATGCTTCCAGCAGGCGTGTAAA GGTAAAATCCAAGCACTCTGCGAGAATCCCGAGTGGGT ACCATTGAAGGATAACAGGATTCCTTCATACGGGGTCC TGTCTGTTGATCTGAGTCTGACGGTTGAGCTTAAAATCA AAATTGCTTCGGGATTCGGGCCATTGATCACACACGGC TCAGGGATGGACCTATACAAATCCAACTGCAACAATGT GTATTGGCTGACTATTCCGCCAATGAGAAATCTAGCCT TAGGCGTAATCAACACATTGGAGTGGATACCGAGATTC AAGGTTAGTCCCAACCTCTTCACTGTCCCAATTAAGGA AGCAGGCGAAGACTGCCATGCCCCAACATACCTACCTG CGGAGGTGGACGGTGATGTCAAACTCAGTTCCAACCTG GTGATTCTACCTGGTCAAGATCTCCAATATGTTTTGGCA ACCTACGATACCTCCAGGGTTGAGCATGCTGTGGTTTA TTACGTTTACAGCCCAAGCCGCTCATTTTCTTACTTTTA TCCTTTTAGGTTGCCTATAAAGGGGGTCCCAATCGAAC TACAAGTGGAATGCTTCACATGGGATCAAAAACTCTGG TGCCGTCACTTCTGTGTGCTTGCGGACTCAGAATCCGGT GGACTTATCACTCACTCTGGGATGGTGGGCATGGGAGT CAGCTGCACAGCTACCCGGGAAGATGGAACCAATCGC AGATAATGATAATAGGCTGGAGCCTCGGTGGCCAAGCT TCTTGCCCCTTGGGCCTCCCCCCAGCCCCTCCTCCCCTT CCTGCACCCGTACCCCCGTGGTCTTTGAATAAAGTCTG AGTGGGCGGC | 41 |
| GC_H_MEASLES_ B3 ORF Sequence, NT | ATGTCACCGCAACGAGACCGGATAAATGCCTTCTACAA AGATAACCCTTATCCCAAGGGAAGTAGGATAGTTATTA ACAGAGAACATCTTATGATTGACAGACCCTATGTTCTG CTGGCTGTTCTGTTCGTCATGTTTCTGAGCTTGATCGGA TTGCTGGCAATTGCAGGCATTAGACTTCATCGGGCAGC CATCTACACCGCGGAGATCCATAAAAGCCTCAGTACCA ATCTGGATGTGACTAACTCCATCGAGCATCAGGTCAAG GACGTGCTGACACCACTCTTTAAAATCATCGGGGATGA AGTGGGCCTGAGAACACCTCAGAGATTCACTGACCTAG TGAAATTCATCTCGGACAAGATTAAATTCCTTAATCCG GATAGGGAGTACGACTTCAGAGATCTCACTTGGTGCAT CAACCCGCCAGAGAGGATCAAACTAGATTATGATCAAT ACTGTGCAGATGTGGCTGCTGAAGAGCTCATGAATGCA TTGGTGAACTCAACTCTACTGGAGACCAGAACAACCAC TCAGTTCCTAGCTGTCTCAAAGGGAAACTGCTCAGGGC | 42 |

TABLE 13-continued

| Description | Sequence | SEQ ID NO: |
|---|---|---|
| | CCACTACAATCAGAGGTCAATTCTCAAACATGTCGCTG<br>TCCTTGTTGGACTTGTACTTAGGTCGAGGTTACAATGTG<br>TCATCTATAGTCACTATGACATCCCAGGGAATGTATGG<br>GGGAACCTACCTAGTTGAAAAGCCTAATCTGAACAGCA<br>AAGGGTCAGAGTTGTCACAACTGAGCATGTACCGAGTG<br>TTTGAAGTAGGTGTGATCAGAAACCCGGGTTTGGGGGC<br>TCCGGTGTTCCATATGACAAACTATTTTGAGCAACCAG<br>TCAGTAATGGTCTCGGCAACTGTATGGTGGCTTTGGGG<br>GAGCTCAAACTCGCAGCCCTTTGTCACGGGGACGATTC<br>TATCATAATTCCCTATCAGGGATCAGGGAAAGGTGTCA<br>GCTTCCAGCTCGTCAAGCTGGGTGTCTGGAAATCCCCA<br>ACCGACATGCAATCCTGGGTCCCCTTATCAACGGATGA<br>TCCAGTGGTAGACAGGCTTTACCTCTCATCTCACAGAG<br>GTGTCATCGCTGACAATCAAGCAAAATGGGCTGTCCCG<br>ACAACACGAACAGATGACAAGTTGCGAATGGAGACAT<br>GCTTCCAGCAGGCGTGTAAAGGTAAAATCCAAGCACTC<br>TGCGAGAATCCCGAGTGGGTACCATTGAAGGATAACAG<br>GATTCCTTCATACGGGGTCCTGTCTGTTGATCTGAGTCT<br>GACGGTTGAGCTTAAAATCAAAATTGCTTCGGGATTCG<br>GGCCATTGATCACACACGGCTCAGGGATGGACCTATAC<br>AAATCCAACTGCAACAATGTGTATTGGCTGACTATTCC<br>GCCAATGAGAAATCTAGCCTTAGGCGTAATCAACACAT<br>TGGAGTGGATACCGAGATTCAAGGTTAGTCCCAACCTC<br>TTCACTGTCCCAATTAAGGAAGCAGGCGAAGACTGCCA<br>TGCCCCAACATACCTACCTGCGGAGGTGGACGGTGATG<br>TCAAACTCAGTTCCAACCTGGTGATTCTACCTGGTCAA<br>GATCTCCAATATGTTTTGGCAACCTACGATACCTCCAG<br>GGTTGAGCATGCTGTGGTTTATTACGTTTACAGCCCAA<br>GCCGCTCATTTTCTTACTTTTATCCTTTTAGGTTGCCTAT<br>AAAGGGGGTCCCAATCGAACTACAAGTGGAATGCTTCA<br>CATGGGATCAAAAACTCTGGTGCCGTCACTTCTGTGTG<br>CTTGCGGACTCAGAATCCGGTGGACTTATCACTCACTCT<br>GGGATGGTGGGCATGGGAGTCAGCTGCACAGCTACCCG<br>GGAAGATGGAACCAATCGCAGATAA | |
| GC_H_MEASLES_<br>B3<br>mRNA Sequence<br>(assumes T100 tail)<br>Sequence Length:<br>2126 | G*GGGAAATAAGAGAGAAAAGAAGAGTAAGAAGAAAT<br>ATAAGAGCCACCATGTCACCGCAACGAGACCGGATAA<br>ATGCCTTCTACAAAGATAACCCTTATCCCAAGGGAAGT<br>AGGATAGTTATTAACAGAGAACATCTTATGATTGACAG<br>ACCCTATGTTCTGCTGGCTGTTCTGTTCGTCATGTTTCT<br>GAGCTTGATCGGATTGCTGGCAATTGCAGGCATTAGAC<br>TTCATCGGGCAGCCATCTACACCGCGGAGATCCATAAA<br>AGCCTCAGTACCAATCTGGATGTGACTAACTCCATCGA<br>GCATCAGGTCAAGGACGTGCTGACACCACTCTTTAAAA<br>TCATCGGGGATGAAGTGGGCCTGAGAACACCTCAGAG<br>ATTCACTGACCTAGTGAAATTCATCTCGGACAAGATTA<br>AATTCCTTAATCCGGATAGGGAGTACGACTTCAGAGAT<br>CTCACTTGGTGCATCAACCCGCCAGAGAGGATCAAACT<br>AGATTATGATCAATACTGTGCAGATGTGGCTGCTGAAG<br>AGCTCATGAATGCATTGGTGAACTCAACTCTACTGGAG<br>ACCAGAACAACCACTCAGTTCCTAGCTGTCTCAAAGGG<br>AAACTGCTCAGGGCCCACTACAATCAGAGGTCAATTCT<br>CAAACATGTCGCTGTCCTTGTTGGACTTGTACTTAGGTC<br>GAGGTTACAATGTGTCATCTATAGTCACTATGACATCC<br>CAGGGAATGTATGGGGGAACCTACCTAGTTGAAAAGCC<br>TAATCTGAACAGCAAAGGGTCAGAGTTGTCACAACTGA<br>GCATGTACCGAGTGTTTGAAGTAGGTGTGATCAGAAAC<br>CCGGGTTTGGGGGCTCCGGTGTTCCATATGACAAACTA<br>TTTTGAGCAACCAGTCAGTAATGGTCTCGGCAACTGTA<br>TGGTGGCTTTGGGGGAGCTCAAACTCGCAGCCCTTTGT<br>CACGGGGACGATTCTATCATAATTCCCTATCAGGGATC<br>AGGGAAAGGTGTCAGCTTCCAGCTCGTCAAGCTGGGTG<br>TCTGGAAATCCCCAACCGACATGCAATCCTGGGTCCCC<br>TTATCAACGGATGATCCAGTGGTAGACAGGCTTTACCT<br>CTCATCTCACAGAGGTGTCATCGCTGACAATCAAGCAA<br>AATGGGCTGTCCCGACAACACGAACAGATGACAAGTTG<br>CGAATGGAGACATGCTTCCAGCAGGCGTGTAAAGGTAA<br>AATCCAAGCACTCTGCGAGAATCCCGAGTGGGTACCAT<br>TGAAGGATAACAGGATTCCTTCATACGGGGTCCTGTCT<br>GTTGATCTGAGTCTGACGGTTGAGCTTAAAATCAAAAT<br>TGCTTCGGGATTCGGGCCATTGATCACACACGGCTCAG<br>GGATGGACCTATACAAATCCAACTGCAACAATGTGTAT<br>TGGCTGACTATTCCGCCAATGAGAAATCTAGCCTTAGG<br>CGTAATCAACACATTGGAGTGGATACCGAGATTCAAGG<br>TTAGTCCCAACCTCTTCACTGTCCCAATTAAGGAAGCA<br>GGCGAAGACTGCCATGCCCCAACATACCTACCTGCGGA<br>GGTGGACGGTGATGTCAAACTCAGTTCCAACCTGGTGA | 43 |

TABLE 13-continued

| Description | Sequence | SEQ ID NO: |
|---|---|---|
| | TTCTACCTGGTCAAGATCTCCAATATGTTTTGGCAACCT<br>ACGATACCTCCAGGGTTGAGCATGCTGTGGTTTATTAC<br>GTTTACAGCCCAAGCCGCTCATTTTCTTACTTTTATCCT<br>TTTAGGTTGCCTATAAAGGGGGGTCCCAATCGAACTACA<br>AGTGGAATGCTTCACATGGGATCAAAAACTCTGGTGCC<br>GTCACTTCTGTGTGCTTGCGGACTCAGAATCCGGTGGA<br>CTTATCACTCACTCTGGGATGGTGGGCATGGGAGTCAG<br>CTGCACAGCTACCCGGGAAGATGGAACCAATCGCAGAT<br>AATGATAATAGGCTGGAGCCTCGGTGGCCAAGCTTCTT<br>GCCCCTTGGGCCTCCCCCCAGCCCCTCCTCCCCTTCCTG<br>CACCCGTACCCCCGTGGTCTTTGAATAAAGTCTGAGTG<br>GGCGGCAAAAAAAAAAAAAAAAAAAAAAAAAAAAAA<br>AAAAAAAAAAAAAAAAAAAAAAAAAAAAAAAAAAAA<br>AAAAAAAAAAAAAAAAAAAAAAAAAAAAAAAAAATC<br>TAG | |
| GC_H_MEASLES_<br>D8<br>Sequence, NT (5'<br>UTR, ORF, 3'<br>UTR)<br>Sequence Length:<br>2065 | TCAAGCTTTTGGACCCTCGTACAGAAGCTAATACGACT<br>CACTATAGGGAAATAAGAGAGAAAAGAAGAGTAAGAA<br>GAAATATAAGAGCCACCATGTCACCACAACGAGACCG<br>GATAAATGCCTTCTACAAAGACAACCCCCATCCTAAGG<br>GAAGTAGGATAGTTATTAACAGAGAACATCTTATGATT<br>GATAGACCTTATGTTTTGCTGGCTGTTCTATTCGTCATG<br>TTTCTGAGCTTGATCGGGTTGCTAGCCATTGCAGGCATT<br>AGACTTCATCGGGCAGCCATCTACACCGCAGAGATCCA<br>TAAAAGCCTCAGCACCAATCTGGATGTAACTAACTCAA<br>TCGAGCATCAGGTTAAGGACGTGCTGACACCACTCTTC<br>AAGATCATCGGTGATGAAGTGGGCTTGAGGACACCTCA<br>GAGATTCACTGACCTAGTGAAGTTCATCTCTGACAAGA<br>TTAAATTCCTTAATCCGGACAGGGAATACGACTTCAGA<br>GATCTCACTTGGTGTATCAACCCGCCAGAGAGAATCAA<br>ATTGGATTATGATCAATACTGTGCAGATGTGGCTGCTG<br>AAGAACTCATGAATGCATTGGTGAACTCAACTCTACTG<br>GAGACCAGGGCAACCAATCAGTTCCTAGCTGTCTCAAA<br>GGGAAACTGCTCAGGGCCCACTACAATCAGAGGCCAAT<br>TCTCAAACATGTCGCTGTCCCTGTTGGACTTGTATTTAA<br>GTCGAGGTTACAATGTGTCATCTATAGTCACTATGACA<br>TCCCAGGGAATGTACGGGGGAACTTACCTAGTGGAAAA<br>GCCTAATCTGAGCAGCAAAGGGTCAGAGTTGTCACAAC<br>TGAGCATGCACCGAGTGTTTGAAGTAGGTGTTATCAGA<br>AATCCGGGTTTGGGGGCTCCGGTATTCCATATGACAAA<br>CTATCTTGAGCAACCAGTCAGTAATGATTTCAGCAACT<br>GCATGGTGGCTTTGGGGGAGCTCAAGTTCGCAGCCCTC<br>TGTCACAGGGAAGATTCTATCACAATTCCCTATCAGGG<br>ATCAGGGAAAGGTGTCAGCTTCCAGCTTGTCAAGCTAG<br>GTGTCTGGAAATCCCCAACCGACATGCAATCCTGGGTC<br>CCCCTATCAACGGATGATCCAGTGATAGACAGGCTTTA<br>CCTCTCATCTCACAGAGGCGTTATCGCTGACAATCAAG<br>CAAAATGGGCTGTCCCGACAACACGGACAGATGACAA<br>GTTGCGAATGGAGACATGCTTCCAGCAGGCGTGTAAGG<br>GTAAAATCCAAGCACTTTGCGAGAATCCCGAGTGGACA<br>CCATTGAAGGATAACAGGATTCCTTCATACGGGGTCTT<br>GTCTGTTGATCTGAGTCTGACAGTTGAGCTTAAAATCA<br>AAATTGTTTCAGGATTCGGGCCATTGATCACACACGGT<br>TCAGGGATGGACCTATACAAATCCAACCACAACAATAT<br>GTATTGGCTGACTATCCCGCCAATGAAGAACCTGGCCT<br>TAGGTGTAATCAACACATTGGAGTGGATACCGAGATTC<br>AAGGTTAGTCCCAACCTCTTCACTGTTCCAATTAAGGA<br>AGCAGGCGAGGACTGCCATGCCCCAACATACCTACCTG<br>CGGAGGTGGATGGTGATGTCAAACTCAGTTCCAATCTG<br>GTGATTCTACCTGGTCAAGATCTCCAATATGTTCTGGCA<br>ACCTACGATACTTCCAGAGTTGAACATGCTGTAGTTTAT<br>TACGTTTACAGCCCAAGCCGCTCATTTTCTTACTTTTAT<br>CCTTTTAGGTTGCCTGTAAGGGGGGTCCCCATTGAATTA<br>CAAGTGGAATGCTTCACATGGGACCAAAAACTCTGGTG<br>CCGTCACTTCTGTGTGCTTGCGGACTCAGAATCTGGTGG<br>ACATATCACTCACTCTGGGATGGTGGGCATGGGAGTCA<br>GCTGCACAGCCACTCGGGAAGATGGAACCAGCCGCAG<br>ATAGTGATAATAGGCTGGAGCCTCGGTGGCCAAGCTTC<br>TTGCCCCTTGGGCCTCCCCCCAGCCCCTCCTCCCCTTCC<br>TGCACCCGTACCCCCGTGGTCTTTGAATAAAGTCTGAG<br>TGGGCGGC | 44 |
| GC_H_MEASLES_<br>D8<br>ORF Sequence, NT | ATGTCACCACAACGAGACCGGATAAATGCCTTCTACAA<br>AGACAACCCCCATCCTAAGGGAAGTAGGATAGTTATTA<br>ACAGAGAACATCTTATGATTGATAGACCTTATGTTTTGC<br>TGGCTGTTCTATTCGTCATGTTTCTGAGCTTGATCGGGT<br>TGCTAGCCATTGCAGGCATTAGACTTCATCGGGCAGCC | 45 |

TABLE 13-continued

| Description | Sequence | SEQ ID NO: |
|---|---|---|
| | ATCTACACCGCAGAGATCCATAAAAGCCTCAGCACCAA<br>TCTGGATGTAACTAACTCAATCGAGCATCAGGTTAAGG<br>ACGTGCTGACACCACTCTTCAAGATCATCGGTGATGAA<br>GTGGGCTTGAGGACACCTCAGAGATTCACTGACCTAGT<br>GAAGTTCATCTCTGACAAGATTAAATTCCTTAATCCGG<br>ACAGGGAATACGACTTCAGAGATCTCACTTGGTGTATC<br>AACCCGCCAGAGAGAATCAAATTGGATTATGATCAATA<br>CTGTGCAGATGTGGCTGCTGAAGAACTCATGAATGCAT<br>TGGTGAACTCAACTCTACTGGAGACCAGGGCAACCAAT<br>CAGTTCCTAGCTGTCTCAAAGGGAAACTGCTCAGGGCC<br>CACTACAATCAGAGGCCAATTCTCAAACATGTCGCTGT<br>CCCTGTTGGACTTGTATTTAAGTCGAGGTTACAATGTGT<br>CATCTATAGTCACTATGACATCCCAGGGAATGTACGGG<br>GGAACTTACCTAGTGGAAAAGCCTAATCTGAGCAGCAA<br>AGGGTCAGAGTTGTCACAACTGAGCATGCACCGAGTGT<br>TTGAAGTAGGTGTTATCAGAAATCCGGGTTTGGGGGCT<br>CCGGTATTCCATATGACAAACTATCTTGAGCAACCAGT<br>CAGTAATGATTTCAGCAACTGCATGGTGGCTTTGGGGG<br>AGCTCAAGTTCGCAGCCCTCTGTCACAGGGAAGATTCT<br>ATCACAATTCCCTATCAGGGATCAGGGAAAGGTGTCAG<br>CTTCCAGCTTGTCAAGCTAGGTGTCTGGAAATCCCCAA<br>CCGACATGCAATCCTGGGTCCCCCTATCAACGGATGAT<br>CCAGTGATAGACAGGCTTTACCTCTCATCTCACAGAGG<br>CGTTATCGCTGACAATCAAGCAAAATGGGCTGTCCCGA<br>CAACACGGACAGATGACAAGTTGCGAATGGAGACATG<br>CTTCCAGCAGGCGTGTAAGGGTAAAATCCAAGCACTTT<br>GCGAGAATCCCGAGTGGACACCATTGAAGGATAACAG<br>GATTCCTTCATACGGGGTCTTGTCTGTTGATCTGAGTCT<br>GACAGTTGAGCTTAAAATCAAAATTGTTTCAGGATTCG<br>GGCCATTGATCACACACGGTTCAGGGATGGACCTATAC<br>AAATCCAACCACAACAATATGTATTGGCTGACTATCCC<br>GCCAATGAAGAACCTGGCCTTAGGTGTAATCAACACAT<br>TGGAGTGGATACCGAGATTCAAGGTTAGTCCCAACCTC<br>TTCACTGTTCCAATTAAGGAAGCAGGCGAGGACTGCCA<br>TGCCCCAACATACCTACCTGCGGAGGTGGATGGTGATG<br>TCAAACTCAGTTCCAATCTGGTGATTCTACCTGGTCAAG<br>ATCTCCAATATGTTCTGGCAACCTACGATACTTCCAGA<br>GTTGAACATGCTGTAGTTTATTACGTTTACAGCCCAAGC<br>CGCTCATTTTCTTACTTTTATCCTTTTAGGTTGCCTGTAA<br>GGGGGGTCCCCATTGAATTACAAGTGGAATGCTTCACA<br>TGGGACCAAAAACTCTGGTGCCGTCACTTCTGTGTGCTT<br>GCGGACTCAGAATCTGGTGGACATATCACTCACTCTGG<br>GATGGTGGGCATGGGAGTCAGCTGCACAGCCACTCGGG<br>AAGATGGAACCAGCCGCAGATAG | |
| GC_H_MEASLES_<br>D8<br>mRNA Sequence<br>(assumes T100 tail)<br>Sequence Length:<br>2126 | G*GGGAAATAAGAGAGAAAAGAAGAGTAAGAAGAAAT<br>ATAAGAGCCACCATGTCACCACAACGAGACCGGATAA<br>ATGCCTTCTACAAAGACAACCCCCATCCTAAGGGAAGT<br>AGGATAGTTATTAACAGAGAACATCTTATGATTGATAG<br>ACCTTATGTTTTGCTGGCTGTTCTATTCGTCATGTTTCTG<br>AGCTTGATCGGGTTGCTAGCCATTGCAGGCATTAGACT<br>TCATCGGGCAGCCATCTACACCGCAGAGATCCATAAAA<br>GCCTCAGCACCAATCTGGATGTAACTAACTCAATCGAG<br>CATCAGGTTAAGGACGTGCTGACACCACTCTTCAAGAT<br>CATCGGTGATGAAGTGGGCTTGAGGACACCTCAGAGAT<br>TCACTGACCTAGTGAAGTTCATCTCTGACAAGATTAAA<br>TTCCTTAATCCGGACAGGGAATACGACTTCAGAGATCT<br>CACTTGGTGTATCAACCCGCCAGAGAGAATCAAATTGG<br>ATTATGATCAATACTGTGCAGATGTGGCTGCTGAAGAA<br>CTCATGAATGCATTGGTGAACTCAACTCTACTGGAGAC<br>CAGGGCAACCAATCAGTTCCTAGCTGTCTCAAAGGGAA<br>ACTGCTCAGGGCCCACTACAATCAGAGGCCAATTCTCA<br>AACATGTCGCTGTCCCTGTTGGACTTGTATTTAAGTCGA<br>GGTTACAATGTGTCATCTATAGTCACTATGACATCCCA<br>GGGAATGTACGGGGGAACTTACCTAGTGGAAAAGCCT<br>AATCTGAGCAGCAAAGGGTCAGAGTTGTCACAACTGAG<br>CATGCACCGAGTGTTTGAAGTAGGTGTTATCAGAAATC<br>CGGGTTTGGGGGCTCCGGTATTCCATATGACAAACTAT<br>CTTGAGCAACCAGTCAGTAATGATTTCAGCAACTGCAT<br>GGTGGCTTTGGGGGAGCTCAAGTTCGCAGCCCTCTGTC<br>ACAGGGAAGATTCTATCACAATTCCCTATCAGGGATCA<br>GGGAAAGGTGTCAGCTTCCAGCTTGTCAAGCTAGGTGT<br>CTGGAAATCCCCAACCGACATGCAATCCTGGGTCCCCC<br>TATCAACGGATGATCCAGTGATAGACAGGCTTTACCTC<br>TCATCTCACAGAGGCGTTATCGCTGACAATCAAGCAAA<br>ATGGGCTGTCCCGACAACACGGACAGATGACAAGTTGC<br>GAATGGAGACATGCTTCCAGCAGGCGTGTAAGGGTAA | 46 |

TABLE 13-continued

| Description | Sequence | SEQ ID NO: |
| --- | --- | --- |
| | AATCCAAGCACTTTGCGAGAATCCCGAGTGGACACCAT<br>TGAAGGATAACAGGATTCCTTCATACGGGGTCTTGTCT<br>GTTGATCTGAGTCTGACAGTTGAGCTTAAAATCAAAAT<br>TGTTTCAGGATTCGGGCCATTGATCACACACGGTTCAG<br>GGATGGACCTATACAAATCCAACCACAACAATATGTAT<br>TGGCTGACTATCCCGCCAATGAAGAACCTGGCCTTAGG<br>TGTAATCAACACATTGGAGTGGATACCGAGATTCAAGG<br>TTAGTCCCAACCTCTTCACTGTTCCAATTAAGGAAGCA<br>GGCGAGGACTGCCATGCCCCAACATACCTACCTGCGGA<br>GGTGGATGGTGATGTCAAACTCAGTTCCAATCTGGTGA<br>TTCTACCTGGTCAAGATCTCCAATATGTTCTGGCAACCT<br>ACGATACTTCCAGAGTTGAACATGCTGTAGTTTATTAC<br>GTTTACAGCCCAAGCCGCTCATTTTCTTACTTTTATCCT<br>TTTAGGTTGCCTGTAAGGGGGGTCCCCATTGAATTACA<br>AGTGGAATGCTTCACATGGGACCAAAAACTCTGGTGCC<br>GTCACTTCTGTGTGCTTGCGGACTCAGAATCTGGTGGA<br>CATATCACTCACTCTGGGATGGTGGGCATGGGAGTCAG<br>CTGCACAGCCACTCGGGAAGATGGAACCAGCCGCAGA<br>TAGTGATAATAGGCTGGAGCCTCGGTGGCCAAGCTTCT<br>TGCCCCTTGGGCCTCCCCCCAGCCCCTCCTCCCCTTCCT<br>GCACCCGTACCCCCGTGGTCTTTGAATAAAGTCTGAGT<br>GGGCGGCAAAAAAAAAAAAAAAAAAAAAAAAAAAAA<br>AAAAAAAAAAAAAAAAAAAAAAAAAAAAAAAAAAAA<br>AAAAAAAAAAAAAAAAAAAAAAAAAAAAAAAAAAAT<br>CTAG | |
| | MeV mRNA Sequences | |
| GC_F_MEASLES_<br>B3.1<br>Sequence, NT (5'<br>UTR, ORF, 3'<br>UTR)<br>Sequence Length:<br>1864 | UCAAGCUUUUGGACCCUCGUACAGAAGCUAAUACGAC<br>UCACUAUAGGGAAAUAAGAGAGAAAAGAAGAGUAAG<br>AAGAAAUAUAAGAGCCACCAUGGGUCUCAAGGUGAA<br>CGUCUCUGCCGUAUUCAUGGCAGUACUGUUAACUCUC<br>CAAACACCCGCCGGUCAAAUUCAUUGGGGCAAUCUCU<br>CUAAGAUAGGGGUAGUAGGAAUAGGAAGUGCAAGCU<br>ACAAAGUUAUGACUCGUUCCAGCCAUCAAUCAUUAGU<br>CAUAAAAUUAAUGCCCAAUAUAACUCUCCUCAAUAAC<br>UGCACGAGGGUAGAGAUUGCAGAAUACAGGAGACUA<br>CUAAGAACAGUUUUGGAACCAAUUAGGGAUGCACUU<br>AAUGCAAUGACCCAGAACAUAAGGCCGGUUCAGAGCG<br>UAGCUUCAAGUAGGAGACACAAGAGAUUUGCGGGAG<br>UAGUCCUGGCAGGUGCGGCCCUAGGUGUUGCCACAGC<br>UGCUCAGAUAACAGCCGGCAUUGCACUUCACCGGUCC<br>AUGCUGAACUCUCAGGCCAUCGACAAUCUGAGAGCGA<br>GCCUGGAAACUACUAAUCAGGCAAUUGAGGCAAUCAG<br>ACAAGCAGGGCAGGAGAUGAUAUUGGCUGUUCAGGG<br>UGUCCAAGACUACAUCAAUAAUGAGCUGAUACCGUCU<br>AUGAACCAGCUAUCUUGUGAUCUAAUCGGUCAGAAGC<br>UCGGGCUCAAAUUGCUUAGAUACUAUACAGAAAUCCU<br>GUCAUUAUUUGGCCCCAGCCUACGGGACCCCAUAUCU<br>GCGGAGAUAUCUAUCCAGGCUUUGAGUUAUGCACUU<br>GGAGGAGAUAUCAAUAAGGUGUUAGAAAAGCUCGGA<br>UACAGUGGAGGCGAUUUACUAGGCAUCUUAGAGAGC<br>AGAGGAAUAAAGGCUCGGAUAACUCACGUCGACACAG<br>AGUCCUACUUCAUAGUCCUCAGUAUAGCCUAUCCGAC<br>GCUGUCCGAGAUUAAGGGGGUGAUUGUCCACCGGCUA<br>GAGGGGGUCUCGUACAACAUAGGCUCUCAAGAGUGG<br>UAUACCACUGUGCCCAAGUAUGUUGCAACCCAAGGGU<br>ACCUUAUCUCGAAUUUUGAUGAGUCAUCAUGUACUU<br>UCAUGCCAGAGGGGACUGUGUGCAGCCAAAAUGCCUU<br>GUACCCGAUGAGUCCUCUGCUCCAAGAAUGCCUCCGG<br>GGGUCCACCAAGUCCUGUGCUCGUACACUCGUAUCCG<br>GGUCUUUUGGGAACCGGUUCAUUUUAUCACAAGGGA<br>ACCUAAUAGCCAAUUGUGCAUCAAUUCUUUGUAAGU<br>GUUACACAACAGGUACGAUUAUUAAUCAAGACCCUGA<br>CAAGAUCCUAACAUACAUUGCUGCCGAUCGCUGCCCG<br>GUAGUCGAGGUGAACGGCGUGACCAUCCAAGUCGGGA<br>GCAGGAGGUAUCCAGACGCUGUGUACUUGCACAGAAU<br>UGACCUCGGUCCUCCCAUAUCAUUGGAGAGGUUGGAC<br>GUAGGGACAAAUCUGGGGAAUGCAAUUGCCAAAUUG<br>GAGGAUGCCAAGGAAUUGUUGGAAUCAUCGGACCAG<br>AUAUUGAGAAGUAUGAAAGGUUUAUCGAGCACUAGC<br>AUAGUCUACAUCCUGAUUGCAGUGUGUCUUGGAGGG<br>UUGAUAGGGAUCCCCACUUUAAUAUGUUGCUGCAGG<br>GGGCGUUGUAACAAAAAGGGAGAACAAGUUGGUAUG<br>UCAAGACCAGGCCUAAAGCCUGACCUUACAGGAACAU<br>CAAAAUCCUAUGUAAGAUCGCUUUGAUGAUAAUAGG<br>CUGGAGCCUCGGUGGCCAAGCUUCUUGCCCCUUGGGC | 69 |

TABLE 13-continued

| Description | Sequence | SEQ ID NO: |
|---|---|---|
| | CUCCCCCCAGCCCCUCCUCCCCUUCCUGCACCCGUACC CCCGUGGUCUUUGAAUAAAGUCUGAGUGGGCGGC | |
| GC_F_MEASLES_ B3.1 ORF Sequence, NT | AUGGGUCUCAAGGUGAACGUCUCUGCCGUAUUCAUGG CAGUACUGUUAACUCUCCAAACACCCGCCGGUCAAAU UCAUUGGGGCAAUCUCUCUAAGAUAGGGGUAGUAGG AAUAGGAAGUGCAAGCUACAAAGUUAUGACUCGUUC CAGCCAUCAAUCAUUAGUCAUAAAAUUAAUGCCCAAU AUAACUCUCCUCAAUAACUGCACGAGGGUAGAGAUUG CAGAAUACAGGAGACUACUAAGAACAGUUUUGGAAC CAAUUAGGGAUGCACUUAAUGCAAUGACCCAGAACAU AAGGCCGGUUCAGAGCGUAGCUUCAAGUAGGAGACAC AAGAGAUUUGCGGGAGUAGUCCUGGCAGGUGCGGCCC UAGGUGUUGCCACAGCUGCUCAGAUAACAGCCGGCAU UGCACUUCACCGGUCCAUGCUGAACUCUCAGGCCAUC GACAAUCUGAGAGCGAGCCUGGAAACUACUAAUCAGG CAAUUGAGGCAAUCAGACAAGCAGGGCAGGAGAUGA UAUUGGCUGUUCAGGGUGUCCAAGACUACAUCAAUA AUGAGCUGAUACCGUCUAUGAACCAGCUAUCUUGUGA UCUAAUCGGUCAGAAGCUCGGGCUCAAAUUGCUUAGA UACUAUACAGAAAUCCUGUCAUUAUUUGGCCCCAGCC UACGGGACCCCAUAUCUGCGGAGAUAUCUAUCCAGGC UUUGAGUUAUGCACUUGGAGGAGAUAUCAAUAAGGU GUUAGAAAAGCUCGGAUACAGUGGAGGCGAUUUACU AGGCAUCUUAGAGAGCAGAGGAAUAAAGGCUCGGAU AACUCACGUCGACACAGAGUCCUACUUCAUAGUCCUC AGUAUAGCCUAUCCGACGCUGUCCGAGAUUAAGGGGG UGAUUGUCCACCGGCUAGAGGGGGUCUCGUACAACAU AGGCUCUCAAGAGUGGUAUACCACUGUGCCCAAGUAU GUUGCAACCCAAGGGUACCUUAUCUCGAAUUUUGAUG AGUCAUCAUGUACUUUCAUGCCAGAGGGGACUGUGU GCAGCCAAAAUGCCUUGUACCCGAUGAGUCCUCUGCU CCAAGAAUGCCUCCGGGGGUCCACCAAGUCCUGUGCU CGUACACUCGUAUCCGGGUCUUUUGGGAACCGGUUCA UUUUAUCACAAGGGAACCUAAUAGCCAAUUGUGCAUC AAUUCUUUGUAAGUGUUACACAACAGGUACGAUUAU UAAUCAAGACCCUGACAAGAUCCUAACAUACAUUGCU GCCGAUCGCUGCCCGGUAGUCGAGGUGAACGGCGUGA CCAUCCAAGUCGGGAGCAGGAGGUAUCCAGACGCUGU GUACUUGCACAGAAUUGACCUCGGUCCUCCCAUAUCA UUGGAGAGGUUGGACGUAGGGACAAAUCUGGGGAAU GCAAUUGCCAAAUUGGAGGAUGCCAAGGAAUUGUUG GAAUCAUCGGACCAGAUAUUGAGAAGUAUGAAAGGU UUAUCGAGCACUAGCAUAGUCUACAUCCUGAUUGCAG UGUGUCUUGGAGGGUUGAUAGGGAUCCCCACUUUAA UAUGUUGCUGCAGGGGGCGUUGUAACAAAAAGGGAG AACAAGUUGGUAUGUCAAGACCAGGCCUAAAGCCUGA CCUUACAGGAACAUCAAAAUCCUAUGUAAGAUCGCUU UGA | 70 |
| GC_F_MEASLES_ B3.1 mRNA Sequence (assumes T100 tail) mRNA Sequence Length: 1925 | G*GGGAAAUAAGAGAGAAAAGAAGAGUAAGAAGAAA UAUAAGAGCCACCAUGGGUCUCAAGGUGAACGUCUCU GCCGUAUUCAUGGCAGUACUGUUAACUCUCCAAACAC CCGCCGGUCAAAUUCAUUGGGGCAAUCUCUCUAAGAU AGGGGUAGUAGGAAUAGGAAGUGCAAGCUACAAAGU UAUGACUCGUUCCAGCCAUCAAUCAUUAGUCAUAAAA UUAAUGCCCAAUAUAACUCUCCUCAAUAACUGCACGA GGGUAGAGAUUGCAGAAUACAGGAGACUACUAAGAA CAGUUUUGGAACCAAUUAGGGAUGCACUUAAUGCAA UGACCCAGAACAUAAGGCCGGUUCAGAGCGUAGCUUC AAGUAGGAGACACAAGAGAUUUGCGGGAGUAGUCCU GGCAGGUGCGGCCCUAGGUGUUGCCACAGCUGCUCAG AUAACAGCCGGCAUUGCACUUCACCGGUCCAUGCUGA ACUCUCAGGCCAUCGACAAUCUGAGAGCGAGCCUGGA AACUACUAAUCAGGCAAUUGAGGCAAUCAGACAAGCA GGGCAGGAGAUGAUAUUGGCUGUUCAGGGUGUCCAA GACUACAUCAAUAAUGAGCUGAUACCGUCUAUGAACC AGCUAUCUUGUGAUCUAAUCGGUCAGAAGCUCGGGCU CAAAUUGCUUAGAUACUAUACAGAAAUCCUGUCAUU AUUUGGCCCCAGCCUACGGGACCCCAUAUCUGCGGAG AUAUCUAUCCAGGCUUUGAGUUAUGCACUUGGAGGA GAUAUCAAUAAGGUGUUAGAAAAGCUCGGAUACAGU GGAGGCGAUUUACUAGGCAUCUUAGAGAGCAGAGGA AUAAAGGCUCGGAUAACUCACGUCGACACAGAGUCCU ACUUCAUAGUCCUCAGUAUAGCCUAUCCGACGCUGUC CGAGAUUAAGGGGGUGAUUGUCCACCGGCUAGAGGG GGUCUCGUACAACAUAGGCUCUCAAGAGUGGUAUACC | 71 |

TABLE 13-continued

| Description | Sequence | SEQ ID NO: |
|---|---|---|
| | ACUGUGCCCAAGUAUGUUGCAACCCAAGGGUACCUUA UCUCGAAUUUUGAUGAGUCAUCAUGUACUUUCAUGCC AGAGGGGACUGUGUGCAGCCAAAAUGCCUUGUACCCG AUGAGUCCUCUGCUCCAAGAAUGCCUCCGGGGGUCCA CCAAGUCCUGUGCUCGUACACUCGUAUCCGGGUCUUU UGGGAACCGGUUCAUUUUAUCACAAGGGAACCUAAU AGCCAAUUGUGCAUCAAUUCUUUGUAAGUGUUACAC AACAGGUACGAUUAUUAAUCAAGACCCUGACAAGAUC CUAACAUACAUUGCUGCCGAUCGCUGCCCGGUAGUCG AGGUGAACGGCGUGACCAUCCAAGUCGGGAGCAGGAG GUAUCCAGACGCUGUGUACUUGCACAGAAUUGACCUC GGUCCUCCCAUAUCAUUGGAGAGGUUGGACGUAGGG ACAAAUCUGGGGAAUGCAAUUGCCAAAUUGGAGGAU GCCAAGGAAUUGUUGGAAUCAUCGGACCAGAUAUUG AGAAGUAUGAAAGGUUUAUCGAGCACUAGCAUAGUC UACAUCCUGAUUGCAGUGUGUCUUGGAGGGUUGAUA GGGAUCCCCACUUUAAUAUGUUGCUGCAGGGGGCGUU GUAACAAAAAGGGAGAACAAGUUGGUAUGUCAAGAC CAGGCCUAAAGCCUGACCUUACAGGAACAUCAAAAUC CUAUGUAAGAUCGCUUUGAUGAUAAUAGGCUGGAGC CUCGGUGGCCAAGCUUCUUGCCCCUUGGGCCUCCCCC CAGCCCCUCCUCCCCUUCCUGCACCCGUACCCCCGUGG UCUUUGAAUAAAGUCUGAGUGGGCGGCAAAAAAAAA AAAAAAAAAAAAAAAAAAAAAAAAAAAAAAAAAAAAA AAAAAAAAAAAAAAAAAAAAAAAAAAAAAAAAAAAAA AAAAAAAAAAAAAAAAAAAAUCUAG | |
| GC_F_MEASLES_ D8 Sequence, NT (5' UTR, ORF, 3' UTR) Sequence Length: 1864 | UCAAGCUUUUGGACCCUCGUACAGAAGCUAAUACGAC UCACUAUAGGGAAAUAAGAGAGAAAAGAAGAGUAAG AAGAAAUAUAAGAGCCACCAUGGGUCUCAAGGUGAA CGUCUCUGUCAUAUUCAUGGCAGUACUGUUAACUCUU CAAACACCCACCGGUCAAAUCCAUUGGGGCAAUCUCU CUAAGAUAGGGGUGGUAGGGGUAGGAAGUGCAAGCU ACAAAGUUAUGACUCGUUCCAGCCAUCAAUCAUUAGU CAUAAAGUUAAUGCCCAAUAUAACUCUCCUCAACAAU UGCACGAGGGUAGGGAUUGCAGAAUACAGGAGACUA CUGAGAACAGUUCUGGAACCAAUUAGAGAUGCACUU AAUGCAAUGACCCAGAAUAUAAGACCGGUUCAGAGU GUAGCUUCAAGUAGGAGACACAAGAGAUUUGCGGGA GUUGUCCUGGCAGGUGCGGCCCUAGGCGUUGCCACAG CUGCUCAAAUAACAGCCGGUAUUGCACUUCACCAGUC CAUGCUGAACUCUCAAGCCAUCGACAAUCUGAGAGCG AGCCUAGAAACUACUAAUCAGGCAAUUGAGGCAAUCA GACAAGCAGGGCAGGAGAUGAUAUUGGCUGUUCAGG GUGUCCAAGACUACAUCAAUAAUGAGCUGAUACCGUC UAUGAAUCAACUAUCUUGUGAUUUAAUCGGCCAGAA GCUAGGGCUCAAAUUGCUCAGAUACUAUACAGAAAUC CUGUCAUUAUUUGGCCCCAGCUUACGGGACCCCAUAU CUGCGGAGAUAUCUAUCCAGGCUUUGAGCUAUGCGCU UGGAGGAGAUAUCAAUAAGGUGUUGGAAAAGCUCGG AUACAGUGGAGGUGAUCUACUGGGCAUCUUAGAGAG CAGAGGAAUAAAGGCCCGGAUAACUCACGUCGACACA GAGUCCUACUUCAUUGUACUCAGUAUAGCCUAUCCGA CGCUAUCCGAGAUUAAGGGGGUGAUUGUCCACCGGCU AGAGGGGGUCUCGUACAACAUAGGCUCUCAAGAGUG GUAUACCACUGUGCCCAAGUAUGUUGCAACCCAAGGG UACCUUAUCUCGAAUUUUGAUGAGUCAUCAUGCACUU UCAUGCCAGAGGGGACUGUGUGCAGCCAGAAUGCCUU GUACCCGAUGAGUCCUCUGCUCCAAGAAUGCCUCCGG GGGUCCACUAAGUCCUGUGCUCGUACACUCGUAUCCG GGUCUUUCGGGAACCGGUUCAUUUUAUCACAGGGGA ACCUAAUAGCCAAUUGUGCAUCAAUCCUUUGCAAGUG UUACACAACAGGAACAAUCAUUAAUCAAGACCCUGAC AAGAUCCUAACAUACAUUGCUGCCGAUCACUGCCCGG UGGUCGAGGUGAAUGGCGUGACCAUCCAAGUCGGGA GCAGGAGGUAUCCGGACGCUGUGUACUUGCACAGGAU UGACCUCGGUCCUCCCAUAUCUUUGGAGAGGUUGGAC GUAGGGACAAAUCUGGGGAAUGCAAUUGCUAAGUUG GAGGAUGCCAAGGAAUUGUUGGAGUCAUCGGACCAG AUAUUGAGGAGUAUGAAAGGUUUAUCGAGCACUAGU AUAGUUUACAUCCUGAUUGCAGUGUGUCUUGGAGGA UUGAUAGGGAUCCCCGCUUUAAUAUGUUGCUGCAGG GGGCGUUGUAACAAGAAGGGAGAACAAGUUGGUAUG UCAAGACCAGGCCUAAAGCCUGAUCUUACAGGAACAU CAAAAUCCUAUGUAAGGUCACUCUGAUGAUAAUAGG | 72 |

TABLE 13-continued

| Description | Sequence | SEQ ID NO: |
|---|---|---|
| | CUGGAGCCUCGGUGGCCAAGCUUCUUGCCCCUUGGGC CUCCCCCCAGCCCCUCCUCCCCUUCCUGCACCCGUACC CCCGUGGUCUUUGAAUAAAGUCUGAGUGGGCGGC | |
| GC_F_MEASLES_ D8 ORF Sequence, NT | AUGGGUCUCAAGGUGAACGUCUCUGUCAUAUUCAUG GCAGUACUGUUAACUCUUCAAACACCCACCGGUCAAA UCCAUUGGGGCAAUCUCUCUAAGAUAGGGGUGGUAG GGGUAGGAAGUGCAAGCUACAAAGUUAUGACUCGUU CCAGCCAUCAAUCAUUAGUCAUAAAGUUAAUGCCCAA UAUAACUCUCCUCAACAAUUGCACGAGGGUAGGGAUU GCAGAAUACAGGAGACUACUGAGAACAGUUCUGGAA CCAAUUAGAGAUGCACUUAAUGCAAUGACCCAGAAUA UAAGACCGGUUCAGAGUGUAGCUUCAAGUAGGAGAC ACAAGAGAUUUGCGGGAGUUGUCCUGGCAGGUGCGG CCCUAGGCGUUGCCACAGCUGCUCAAAUAACAGCCGG UAUUGCACUUCACCAGUCCAUGCUGAACUCUCAAGCC AUCGACAAUCUGAGAGCGAGCCUAGAAACUACUAAUC AGGCAAUUGAGGCAAUCAGACAAGCAGGGCAGGAGA UGAUAUUGGCUGUUCAGGGUGUCCAAGACUACAUCA AUAAUGAGCUGAUACCGUCUAUGAAUCAACUAUCUU GUGAUUUAAUCGGCCAGAAGCUAGGGCUCAAAUUGC UCAGAUACUAUACAGAAAUCCUGUCAUUAUUUGGCCC CAGCUUACGGGACCCCAUAUCUGCGGAGAUAUCUAUC CAGGCUUUGAGCUAUGCGCUUGGAGGAGAUAUCAAU AAGGUGUUGGAAAAGCUCGGAUACAGUGGAGGUGAU CUACUGGGCAUCUUAGAGAGCAGAGGAAUAAAGGCCC GGAUAACUCACGUCGACACAGAGUCCUACUUCAUUGU ACUCAGUAUAGCCUAUCCGACGCUAUCCGAGAUUAAG GGGGUGAUUGUCCACCGGCUAGAGGGGGUCUCGUACA ACAUAGGCUCUCAAGAGUGGUAUACCACUGUGCCCAA GUAUGUUGCAACCCAAGGGUACCUUAUCUCGAAUUUU GAUGAGUCAUCAUGCACUUUCAUGCCAGAGGGGACUG UGUGCAGCCAGAAUGCCUUGUACCCGAUGAGUCCUCU GCUCCAAGAAUGCCUCCGGGGGUCCACUAAGUCCUGU GCUCGUACACUCGUAUCCGGGUCUUUCGGGAACCGGU UCAUUUUAUCACAGGGGAACCUAAUAGCCAAUUGUGC AUCAAUCCUUUGCAAGUGUUACACAACAGGAACAAUC AUUAAUCAAGACCCUGACAAGAUCCUAACAUACAUUG CUGCCGAUCACUGCCCGGUGGUCGAGGUGAAUGGCGU GACCAUCCAAGUCGGGAGCAGGAGGUAUCCGGACGCU GUGUACUUGCACAGGAUUGACCUCGGUCCUCCCAUAU CUUUGGAGAGGUUGGACGUAGGGACAAAUCUGGGGA AUGCAAUUGCUAAGUUGGAGGAUGCCAAGGAAUUGU UGGAGUCAUCGGACCAGAUAUUGAGGAGUAUGAAAG GUUUAUCGAGCACUAGUAUAGUUUACAUCCUGAUUG CAGUGUGUCUUGGAGGAUUGAUAGGGAUCCCCGCUU UAAUAUGUUGCUGCAGGGGGCGUUGUAACAAGAAGG GAGAACAAGUUGGUAUGUCAAGACCAGGCCUAAAGCC UGAUCUUACAGGAACAUCAAAAUCCUAUGUAAGGUC ACUCUGA | 73 |
| GC_F_MEASLES_ D8 mRNA Sequence (assumes T100 tail) Sequence Length: 1925 | G*GGGAAAUAAGAGAGAAAAGAAGAGUAAGAAGAAA UAUAAGAGCCACCAUGGGUCUCAAGGUGAACGUCUCU GUCAUAUUCAUGGCAGUACUGUUAACUCUUCAAACAC CCACCGGUCAAAUCCAUUGGGGCAAUCUCUCUAAGAU AGGGGUGGUAGGGGUAGGAAGUGCAAGCUACAAAGU UAUGACUCGUUCCAGCCAUCAAUCAUUAGUCAUAAAG UUAAUGCCCAAUAUAACUCUCCUCAACAAUUGCACGA GGGUAGGGAUUGCAGAAUACAGGAGACUACUGAGAA CAGUUCUGGAACCAAUUAGAGAUGCACUUAAUGCAA UGACCCAGAAUAUAAGACCGGUUCAGAGUGUAGCUUC AAGUAGGAGACACAAGAGAUUUGCGGGAGUUGUCCU GGCAGGUGCGGCCCUAGGCGUUGCCACAGCUGCUCAA AUAACAGCCGGUAUUGCACUUCACCAGUCCAUGCUGA ACUCUCAAGCCAUCGACAAUCUGAGAGCGAGCCUAGA AACUACUAAUCAGGCAAUUGAGGCAAUCAGACAAGCA GGGCAGGAGAUGAUAUUGGCUGUUCAGGGUGUCCAA GACUACAUCAAUAAUGAGCUGAUACCGUCUAUGAAUC AACUAUCUUGUGAUUUAAUCGGCCAGAAGCUAGGGC UCAAAUUGCUCAGAUACUAUACAGAAAUCCUGUCAUU AUUUGGCCCCAGCUUACGGGACCCCAUAUCUGCGGAG AUAUCUAUCCAGGCUUUGAGCUAUGCGCUUGGAGGA GAUAUCAAUAAGGUGUUGGAAAAGCUCGGAUACAGU GGAGGUGAUCUACUGGGCAUCUUAGAGAGCAGAGGA AUAAAGGCCCGGAUAACUCACGUCGACACAGAGUCCU ACUUCAUUGUACUCAGUAUAGCCUAUCCGACGCUAUC CGAGAUUAAGGGGGUGAUUGUCCACCGGCUAGAGGG | 74 |

TABLE 13-continued

| Description | Sequence | SEQ ID NO: |
|---|---|---|
| | GGUCUCGUACAACAUAGGCUCUCAAGAGUGGUAUACC<br>ACUGUGCCCAAGUAUGUUGCAACCCAAGGGUACCUUA<br>UCUCGAAUUUUGAUGAGUCAUCAUGCACUUUCAUGCC<br>AGAGGGGACUGUGUGCAGCCAGAAUGCCUUGUACCCG<br>AUGAGUCCUCUGCUCCAAGAAUGCCUCCGGGGGUCCA<br>CUAAGUCCUGUGCUCGUACACUCGUAUCCGGGUCUUU<br>CGGGAACCGGUUCAUUUUAUCACAGGGGAACCUAAUA<br>GCCAAUUGUGCAUCAAUCCUUUGCAAGUGUUACACAA<br>CAGGAACAAUCAUUAAUCAAGACCCUGACAAGAUCCU<br>AACAUACAUUGCUGCCGAUCACUGCCCGGUGGUCGAG<br>GUGAAUGGCGUGACCAUCCAAGUCGGGAGCAGGAGG<br>UAUCCGGACGCUGUGUACUUGCACAGGAUUGACCUCG<br>GUCCUCCCAUAUCUUUGGAGAGGUUGGACGUAGGGAC<br>AAAUCUGGGGAAUGCAAUUGCUAAGUUGGAGGAUGC<br>CAAGGAAUUGUUGGAGUCAUCGGACCAGAUAUUGAG<br>GAGUAUGAAAGGUUUAUCGAGCACUAGUAUAGUUUA<br>CAUCCUGAUUGCAGUGUGUCUUGGAGGAUUGAUAGG<br>GAUCCCCGCUUUAAUAUGUUGCUGCAGGGGGCGUUGU<br>AACAAGAAGGGAGAACAAGUUGGUAUGUCAAGACCA<br>GGCCUAAAGCCUGAUCUUACAGGAACAUCAAAAUCCU<br>AUGUAAGGUCACUCUGAUGAUAAUAGGCUGGAGCCU<br>CGGUGGCCAAGCUUCUUGCCCCUUGGGCCUCCCCCCA<br>GCCCCUCCUCCCCUUCCUGCACCCGUACCCCCGUGGUC<br>UUUGAAUAAAGUCUGAGUGGGCGGCAAAAAAAAAAA<br>AAAAAAAAAAAAAAAAAAAAAAAAAAAAAAAAAAAA<br>AAAAAAAAAAAAAAAAAAAAAAAAAAAAAAAAAAAA<br>AAAAAAAAAAAAAAAAAUCUAG | |
| GC_H_MEASLES_<br>B3<br>Sequence, NT (5'<br>UTR, ORF, 3'<br>UTR)<br>Sequence Length:<br>2065 | UCAAGCUUUUGGACCCUCGUACAGAAGCUAAUACGAC<br>UCACUAUAGGGAAAUAAGAGAGAAAAGAAGAGUAAG<br>AAGAAAUAUAAGAGCCACCAUGUCACCGCAACGAGAC<br>CGGAUAAAUGCCUUCUACAAAGAUAACCCUUAUCCCA<br>AGGGAAGUAGGAUAGUUAUUAACAGAGAACAUCUUA<br>UGAUUGACAGACCCUAUGUUCUGCUGGCUGUUCUGUU<br>CGUCAUGUUUCUGAGCUUGAUCGGAUUGCUGGCAAU<br>UGCAGGCAUUAGACUUCAUCGGGCAGCCAUCUACACC<br>GCGGAGAUCCAUAAAAGCCUCAGUACCAAUCUGGAUG<br>UGACUAACUCCAUCGAGCAUCAGGUCAAGGACGUGCU<br>GACACCACUCUUUAAAAUCAUCGGGGAUGAAGUGGGC<br>CUGAGAACACCUCAGAGAUUCACUGACCUAGUGAAAU<br>UCAUCUCGGACAAGAUUAAAUUCCUUAAUCCGGAUAG<br>GGAGUACGACUUCAGAGAUCUCACUUGGUGCAUCAAC<br>CCGCCAGAGAGGAUCAAACUAGAUUAUGAUCAAUACU<br>GUGCAGAUGUGGCUGCUGAAGAGCUCAUGAAUGCAU<br>UGGUGAACUCAACUCUACUGGAGACCAGAACAACCAC<br>UCAGUUCCUAGCUGUCUCAAAGGGAAACUGCUCAGGG<br>CCCACUACAAUCAGAGGUCAAUUCUCAAACAUGUCGC<br>UGUCCUUGUUGGACUUGUACUUAGGUCGAGGUUACA<br>AUGUGUCAUCUAUAGUCACUAUGACAUCCCAGGGAAU<br>GUAUGGGGGAACCUACCUAGUUGAAAAGCCUAAUCU<br>GAACAGCAAAGGGUCAGAGUUGUCACAACUGAGCAU<br>GUACCGAGUGUUUGAAGUAGGUGUGAUCAGAAACCC<br>GGGUUUGGGGGCUCCGGUGUUCCAUAUGACAAACUA<br>UUUUGAGCAACCAGUCAGUAAUGGUCUCGGCAACUGU<br>AUGGUGGCUUUGGGGGAGCUCAAACUCGCAGCCCUUU<br>GUCACGGGGACGAUUCUAUCAUAAUUCCCUAUCAGGG<br>AUCAGGGAAAGGUGUCAGCUUCCAGCUCGUCAAGCUG<br>GGUGUCUGGAAAUCCCCAACCGACAUGCAAUCCUGGG<br>UCCCCUUAUCAACGGAUGAUCCAGUGGUAGACAGGCU<br>UUACCUCUCAUCUCACAGAGGUGUCAUCGCUGACAAU<br>CAAGCAAAAUGGGCUGUCCCGACAACACGAACAGAUG<br>ACAAGUUGCGAAUGGAGACAUGCUUCCAGCAGGCGUG<br>UAAAGGUAAAAUCCAAGCACUCUGCGAGAAUCCCGAG<br>UGGGUACCAUUGAAGGAUAACAGGAUUCCUUCAUAC<br>GGGGUCCUGUCUGUUGAUCUGAGUCUGACGGUUGAG<br>CUUAAAAUCAAAAUUGCUUCGGGAUUCGGGCCAUUG<br>AUCACACACGGCUCAGGGAUGGACCUAUACAAAUCCA<br>ACUGCAACAAUGUGUAUUGGCUGACUAUUCCGCCAAU<br>GAGAAAUCUAGCCUUAGGCGUAAUCAACACAUUGGA<br>GUGGAUACCGAGAUUCAAGGUUAGUCCCAACCUCUUC<br>ACUGUCCCAAUUAAGGAAGCAGGCGAAGACUGCCAUG<br>CCCCAACAUACCUACCUGCGGAGGUGGACGGUGAUGU<br>CAAACUCAGUUCCAACCUGGUGAUUCUACCUGGUCAA<br>GAUCUCCAAUAUGUUUUGGCAACCUACGAUACCUCCA<br>GGGUUGAGCAUGCUGUGGUUUAUUACGUUUACAGCC<br>CAAGCCGCUCAUUUUCUUACUUUUAUCCUUUUAGGUU<br>GCCUAUAAAGGGGGUCCCAAUCGAACUACAAGUGGAA | 75 |

TABLE 13-continued

| Description | Sequence | SEQ ID NO: |
|---|---|---|
| | UGCUUCACAUGGGAUCAAAAACUCUGGUGCCGUCACU UCUGUGUGCUUGCGGACUCAGAAUCCGGUGGACUUAU CACUCACUCUGGGAUGGUGGGCAUGGGAGUCAGCUGC ACAGCUACCCGGGAAGAUGGAACCAAUCGCAGAUAAU GAUAAUAGGCUGGAGCCUCGGUGGCCAAGCUUCUUGC CCCUUGGGCCUCCCCCCAGCCCCUCCUCCCCUUCCUGC ACCCGUACCCCCGUGGUCUUUGAAUAAAGUCUGAGUG GGCGGC | |
| GC_H_MEASLES_ B3 ORF Sequence, NT | AUGUCACCGCAACGAGACCGGAUAAAUGCCUUCUACA AAGAUAACCCUUAUCCCAAGGGAAGUAGGAUAGUUA UUAACAGAGAACAUCUUAUGAUUGACAGACCCUAUG UUCUGCUGGCUGUUCUGUUCGUCAUGUUUCUGAGCUU GAUCGGAUUGCUGGCAAUUGCAGGCAUUAGACUUCA UCGGGCAGCCAUCUACACCGCGGAGAUCCAUAAAAGC CUCAGUACCAAUCUGGAUGUGACUAACUCCAUCGAGC AUCAGGUCAAGGACGUGCUGACACCACUCUUUAAAAU CAUCGGGGAUGAAGUGGGCCUGAGAACACCUCAGAGA UUCACUGACCUAGUGAAAUUCAUCUCGGACAAGAUUA AAUUCCUUAAUCCGGAUAGGGAGUACGACUUCAGAG AUCUCACUUGGUGCAUCAACCCGCCAGAGAGGAUCAA ACUAGAUUAUGAUCAAUACUGUGCAGAUGUGGCUGC UGAAGAGCUCAUGAAUGCAUUGGUGAACUCAACUCU ACUGGAGACCAGAACAACCACUCAGUUCCUAGCUGUC UCAAAGGGAAACUGCUCAGGGCCCACUACAAUCAGAG GUCAAUUCUCAAACAUGUCGCUGUCCUUGUUGGACUU GUACUUAGGUCGAGGUUACAAUGUGUCAUCUAUAGU CACUAUGACAUCCCAGGGAAUGUAUGGGGGAACCUAC CUAGUUGAAAAGCCUAAUCUGAACAGCAAAGGGUCA GAGUUGUCACAACUGAGCAUGUACCGAGUGUUUGAA GUAGGUGUGAUCAGAAACCCGGGUUUGGGGGCUCCG GUGUUCCAUAUGACAAACUAUUUUGAGCAACCAGUCA GUAAUGGUCUCGGCAACUGUAUGGUGGCUUUGGGGG AGCUCAAACUCGCAGCCCUUUGUCACGGGGACGAUUC UAUCAUAAUUCCCUAUCAGGGAUCAGGGAAAGGUGU CAGCUUCCAGCUCGUCAAGCUGGGUGUCUGGAAAUCC CCAACCGACAUGCAAUCCUGGGUCCCCUUAUCAACGG AUGAUCCAGUGGUAGACAGGCUUUACCUCUCAUCUCA CAGAGGUGUCAUCGCUGACAAUCAAGCAAAAUGGGCU GUCCCGACAACACGAACAGAUGACAAGUUGCGAAUGG AGACAUGCUUCCAGCAGGCGUGUAAAGGUAAAAUCCA AGCACUCUGCGAGAAUCCCGAGUGGGUACCAUUGAAG GAUAACAGGAUUCCUUCAUACGGGGUCCUGUCUGUUG AUCUGAGUCUGACGGUUGAGCUUAAAAUCAAAAUUG CUUCGGGAUUCGGGCCAUUGAUCACACACGGCUCAGG GAUGGACCUAUACAAAUCCAACUGCAACAAUGUGUAU UGGCUGACUAUUCCGCCAAUGAGAAAUCUAGCCUUAG GCGUAAUCAACACAUUGGAGUGGAUACCGAGAUUCA AGGUUAGUCCCAACCUCUUCACUGUCCCAAUUAAGGA AGCAGGCGAAGACUGCCAUGCCCCAACAUACCUACCU GCGGAGGUGGACGGUGAUGUCAAACUCAGUUCCAACC UGGUGAUUCUACCUGGUCAAGAUCUCCAAUAUGUUU UGGCAACCUACGAUACCUCCAGGGUUGAGCAUGCUGU GGUUUAUUACGUUUACAGCCCAAGCCGCUCAUUUUCU UACUUUUAUCCUUUUAGGUUGCCUAUAAAGGGGGUC CCAAUCGAACUACAAGUGGAAUGCUUCACAUGGGAUC AAAAACUCUGGUGCCGUCACUUCUGUGUGCUUGCGGA CUCAGAAUCCGGUGGACUUAUCACUCACUCUGGGAUG GUGGGCAUGGGAGUCAGCUGCACAGCUACCCGGGAAG AUGGAACCAAUCGCAGAUAA | 76 |
| GC_H_MEASLES_ B3 mRNA Sequence (assumes T100 Tail) Sequence Length: 2126 | G*GGGAAAUAAGAGAGAAAAGAAGAGUAAGAAGAAA UAUAAGAGCCACCAUGUCACCGCAACGAGACCGGAUA AAUGCCUUCUACAAAGAUAACCCUUAUCCCAAGGGAA GUAGGAUAGUUAUUAACAGAGAACAUCUUAUGAUUG ACAGACCCUAUGUUCUGCUGGCUGUUCUGUUCGUCAU GUUUCUGAGCUUGAUCGGAUUGCUGGCAAUUGCAGG CAUUAGACUUCAUCGGGCAGCCAUCUACACCGCGGAG AUCCAUAAAAGCCUCAGUACCAAUCUGGAUGUGACUA ACUCCAUCGAGCAUCAGGUCAAGGACGUGCUGACACC ACUCUUUAAAAUCAUCGGGGAUGAAGUGGGCCUGAG AACACCUCAGAGAUUCACUGACCUAGUGAAAUUCAUC UCGGACAAGAUUAAAUUCCUUAAUCCGGAUAGGGAG UACGACUUCAGAGAUCUCACUUGGUGCAUCAACCCGC CAGAGAGGAUCAAACUAGAUUAUGAUCAAUACUGUG CAGAUGUGGCUGCUGAAGAGCUCAUGAAUGCAUUGG UGAACUCAACUCUACUGGAGACCAGAACAACCACUCA | 77 |

TABLE 13-continued

| Description | Sequence | SEQ ID NO: |
|---|---|---|
| | GUUCCUAGCUGUCUCAAAGGGAAACUGCUCAGGGCCC<br>ACUACAAUCAGAGGUCAAUUCUCAAACAUGUCGCUGU<br>CCUUGUUGGACUUGUACUUAGGUCGAGGUUACAAUG<br>UGUCAUCUAUAGUCACUAUGACAUCCCAGGGAAUGUA<br>UGGGGGAACCUACCUAGUUGAAAAGCCUAAUCUGAAC<br>AGCAAAGGGUCAGAGUUGUCACAACUGAGCAUGUACC<br>GAGUGUUUGAAGUAGGUGUGAUCAGAAACCCGGGUU<br>UGGGGGCUCCGGUGUUCCAUAUGACAAACUAUUUUG<br>AGCAACCAGUCAGUAAUGGUCUCGGCAACUGUAUGGU<br>GGCUUUGGGGGAGCUCAAACUCGCAGCCCUUUGUCAC<br>GGGGACGAUUCUAUCAUAAUUCCCUAUCAGGGAUCAG<br>GGAAAGGUGUCAGCUUCCAGCUCGUCAAGCUGGGUGU<br>CUGGAAAUCCCCAACCGACAUGCAAUCCUGGGUCCCC<br>UUAUCAACGGAUGAUCCAGUGGUAGACAGGCUUUACC<br>UCUCAUCUCACAGAGGUGUCAUCGCUGACAAUCAAGC<br>AAAAUGGGCUGUCCCGACAACACGAACAGAUGACAAG<br>UUGCGAAUGGAGACAUGCUUCCAGCAGGCGUGUAAA<br>GGUAAAAUCCAAGCACUCUGCGAGAAUCCCGAGUGGG<br>UACCAUUGAAGGAUAACAGGAUUCCUUCAUACGGGG<br>UCCUGUCUGUUGAUCUGAGUCUGACGGUUGAGCUUA<br>AAAUCAAAAUUGCUUCGGGAUUCGGGCCAUUGAUCAC<br>ACACGGCUCAGGGAUGGACCUAUACAAAUCCAACUGC<br>AACAAUGUGUAUUGGCUGACUAUUCCGCCAAUGAGA<br>AAUCUAGCCUUAGGCGUAAUCAACACAUUGGAGUGG<br>AUACCGAGAUUCAAGGUUAGUCCCAACCUCUUCACUG<br>UCCCAAUUAAGGAAGCAGGCGAAGACUGCCAUGCCCC<br>AACAUACCUACCUGCGGAGGUGGACGGUGAUGUCAAA<br>CUCAGUUCCAACCUGGUGAUUCUACCUGGUCAAGAUC<br>UCCAAUAUGUUUUGGCAACCUACGAUACCUCCAGGGU<br>UGAGCAUGCUGUGGUUUAUUACGUUUACAGCCCAAGC<br>CGCUCAUUUUCUUACUUUUAUCCUUUUAGGUUGCCUA<br>UAAAGGGGGUCCCAAUCGAACUACAAGUGGAAUGCU<br>UCACAUGGGAUCAAAAACUCUGGUGCCGUCACUUCUG<br>UGUGCUUGCGGACUCAGAAUCCGGUGGACUUAUCACU<br>CACUCUGGGAUGGUGGGCAUGGGAGUCAGCUGCACAG<br>CUACCCGGGAAGAUGGAACCAAUCGCAGAUAAUGAUA<br>AUAGGCUGGAGCCUCGGUGGCCAAGCUUCUUGCCCCU<br>UGGGCCUCCCCCCAGCCCCUCCUCCCCUUCCUGCACCC<br>GUACCCCCGUGGUCUUUGAAUAAAGUCUGAGUGGGCG<br>GCAAAAAAAAAAAAAAAAAAAAAAAAAAAAAAAAAA<br>AAAAAAAAAAAAAAAAAAAAAAAAAAAAAAAAAAAA<br>AAAAAAAAAAAAAAAAAAAAAAAAAAAAAAAUCUAG | |
| GC_H_MEASLES_<br>D8<br>Sequence, NT (5'<br>UTR, ORF, 3'<br>UTR)<br>Sequence Length:<br>2065 | UCAAGCUUUUGGACCCUCGUACAGAAGCUAAUACGAC<br>UCACUAUAGGGAAAUAAGAGAGAAAAGAAGAGUAAG<br>AAGAAAUAUAAGAGCCACCAUGUCACCACAACGAGAC<br>CGGAUAAAUGCCUUCUACAAAGACAACCCCCAUCCUA<br>AGGGAAGUAGGAUAGUUAUUAACAGAGAACAUCUUA<br>UGAUUGAUAGACCUUAUGUUUUGCUGGCUGUUCUAU<br>UCGUCAUGUUUCUGAGCUUGAUCGGUUGCUAGCCAU<br>UGCAGGCAUUAGACUUCAUCGGGCAGCCAUCUACACC<br>GCAGAGAUCCAUAAAAGCCUCAGCACCAAUCUGGAUG<br>UAACUAACUCAAUCGAGCAUCAGGUUAAGGACGUGCU<br>GACACCACUCUUCAAGAUCAUCGGUGAUGAAGUGGGC<br>UUGAGGACACCUCAGAGAUUCACUGACCUAGUGAAGU<br>UCAUCUCUGACAAGAUUAAAUUCCUUAAUCCGGACAG<br>GGAAUACGACUUCAGAGAUCUCACUUGGUGUAUCAAC<br>CCGCCAGAGAGAAUCAAAUUGGAUUAUGAUCAAUAC<br>UGUGCAGAUGUGGCUGCUGAAGAACUCAUGAAUGCA<br>UUGGUGAACUCAACUCUACUGGAGACCAGGGCAACCA<br>AUCAGUUCCUAGCUGUCUCAAAGGGAAACUGCUCAGG<br>GCCCACUACAAUCAGAGGCCAAUUCUCAAACAUGUCG<br>CUGUCCCUGUUGGACUUGUAUUUAAGUCGAGGUUAC<br>AAUGUGUCAUCUAUAGUCACUAUGACAUCCCAGGGAA<br>UGUACGGGGGAACUUACCUAGUGGAAAAGCCUAAUC<br>UGAGCAGCAAAGGGUCAGAGUUGUCACAACUGAGCA<br>UGCACCGAGUGUUUGAAGUAGGUGUUAUCAGAAAUC<br>CGGGUUUGGGGGCUCCGGUAUUCCAUAUGACAAACUA<br>UCUUGAGCAACCAGUCAGUAAUGAUUUCAGCAACUGC<br>AUGGUGGCUUUGGGGGAGCUCAAGUUCGCAGCCCUCU<br>GUCACAGGGAAGAUUCUAUCACAAUUCCCUAUCAGGG<br>AUCAGGGAAAGGUGUCAGCUUCCAGCUUGUCAAGCUA<br>GGUGUCUGGAAAUCCCCAACCGACAUGCAAUCCUGGG<br>UCCCCCUAUCAACGGAUGAUCCAGUGAUAGACAGGCU<br>UUACCUCUCAUCUCACAGAGGCGUUAUCGCUGACAAU<br>CAAGCAAAAUGGGCUGUCCCGACAACACGGACAGAUG<br>ACAAGUUGCGAAUGGAGACAUGCUUCCAGCAGGCGUG | 78 |

TABLE 13-continued

| Description | Sequence | SEQ ID NO: |
|---|---|---|
| | UAAGGGUAAAAUCCAAGCACUUUGCGAGAAUCCCGAG<br>UGGACACCAUUGAAGGAUAACAGGAUUCCUUCAUACG<br>GGGUCUUGUCUGUUGAUCUGAGUCUGACAGUUGAGC<br>UUAAAAUCAAAAUUGUUUCAGGAUUCGGGCCAUUGA<br>UCACACACGGUUCAGGGAUGGACCUAUACAAAUCCAA<br>CCACAACAAUAUGUAUUGGCUGACUAUCCCGCCAAUG<br>AAGAACCUGGCCUUAGGUGUAAUCAACACAUUGGAG<br>UGGAUACCGAGAUUCAAGGUUAGUCCCAACCUCUUCA<br>CUGUUCCAAUUAAGGAAGCAGGCGAGGACUGCCAUGC<br>CCCAACAUACCUACCUGCGGAGGUGGAUGGUGAUGUC<br>AAACUCAGUUCCAAUCUGGUGAUUCUACCUGGUCAAG<br>AUCUCCAAUAUGUUCUGGCAACCUACGAUACUUCCAG<br>AGUUGAACAUGCUGUAGUUUAUUACGUUUACAGCCC<br>AAGCCGCUCAUUUUCUUACUUUUAUCCUUUUAGGUUG<br>CCUGUAAGGGGGGUCCCCAUUGAAUUACAAGUGGAA<br>UGCUUCACAUGGGACCAAAAACUCUGGUGCCGUCACU<br>UCUGUGUGCUUGCGGACUCAGAAUCUGGUGGACAUA<br>UCACUCACUCUGGGAUGGUGGGCAUGGGAGUCAGCUG<br>CACAGCCACUCGGGAAGAUGGAACCAGCCGCAGAUAG<br>UGAUAAUAGGCUGGAGCCUCGGUGGCCAAGCUUCUUG<br>CCCCUUGGGCCUCCCCCCAGCCCCUCCUCCCCUUCCUG<br>CACCCGUACCCCCGUGGUCUUUGAAUAAAGUCUGAGU<br>GGGCGGC | |
| GC_H_MEASLES_<br>D8<br>ORF Sequence, NT | AUGUCACCACAACGAGACCGGAUAAAUGCCUUCUACA<br>AAGACAACCCCCAUCCUAAGGGAAGUAGGAUAGUUAU<br>UAACAGAGAACAUCUUAUGAUUGAUAGACCUUAUGU<br>UUUGCUGGCUGUUCUAUUCGUCAUGUUUCUGAGCUU<br>GAUCGGGUUGCUAGCCAUUGCAGGCAUUAGACUUCAU<br>CGGGCAGCCAUCUACACCGCAGAGAUCCAUAAAAGCC<br>UCAGCACCAAUCUGGAUGUAACUAACUCAAUCGAGCA<br>UCAGGUUAAGGACGUGCUGACACCACUCUUCAAGAUC<br>AUCGGUGAUGAAGUGGGCUUGAGGACACCUCAGAGA<br>UUCACUGACCUAGUGAAGUUCAUCUCUGACAAGAUUA<br>AAUUCCUUAAUCCGGACAGGGAAUACGACUUCAGAGA<br>UCUCACUUGGUGUAUCAACCCGCCAGAGAGAAUCAAA<br>UUGGAUUAUGAUCAAUACUGUGCAGAUGUGGCUGCU<br>GAAGAACUCAUGAAUGCAUUGGUGAACUCAACUCUAC<br>UGGAGACCAGGGCAACCAAUCAGUUCCUAGCUGUCUC<br>AAAGGGAAACUGCUCAGGGCCCACUACAAUCAGAGGC<br>CAAUUCUCAAACAUGUCGCUGUCCCUGUUGGACUUGU<br>AUUUAAGUCGAGGUUACAAUGUGUCAUCUAUAGUCA<br>CUAUGACAUCCCAGGGAAUGUACGGGGGAACUUACCU<br>AGUGGAAAAGCCUAAUCUGAGCAGCAAAGGGUCAGA<br>GUUGUCACAACUGAGCAUGCACCGAGUGUUUGAAGU<br>AGGUGUUAUCAGAAAUCCGGGUUUGGGGGCUCCGGU<br>AUUCCAUAUGACAAACUAUCUUGAGCAACCAGUCAGU<br>AAUGAUUUCAGCAACUGCAUGGUGGCUUUGGGGGAG<br>CUCAAGUUCGCAGCCCUCUGUCACAGGGAAGAUUCUA<br>UCACAAUUCCCUAUCAGGGAUCAGGGAAAGGUGUCAG<br>CUUCCAGCUUGUCAAGCUAGGUGUCUGGAAAUCCCCA<br>ACCGACAUGCAAUCCUGGGUCCCCCUAUCAACGGAUG<br>AUCCAGUGAUAGACAGGCUUUACCUCUCAUCUCACAG<br>AGGCGUUAUCGCUGACAAUCAAGCAAAAUGGGCUGUC<br>CCGACAACACGGACAGAUGACAAGUUGCGAAUGGAGA<br>CAUGCUUCCAGCAGGCGUGUAAGGGUAAAAUCCAAGC<br>ACUUUGCGAGAAUCCCGAGUGGACACCAUUGAAGGAU<br>AACAGGAUUCCUUCAUACGGGGUCUUGUCUGUUGAUC<br>UGAGUCUGACAGUUGAGCUUAAAAUCAAAAUUGUUU<br>CAGGAUUCGGGCCAUUGAUCACACACGGUUCAGGGAU<br>GGACCUAUACAAAUCCAACCACAACAAUAUGUAUUGG<br>CUGACUAUCCCGCCAAUGAAGAACCUGGCCUUAGGUG<br>UAAUCAACACAUUGGAGUGGAUACCGAGAUUCAAGG<br>UUAGUCCCAACCUCUUCACUGUUCCAAUUAAGGAAGC<br>AGGCGAGGACUGCCAUGCCCCAACAUACCUACCUGCG<br>GAGGUGGAUGGUGAUGUCAAACUCAGUUCCAAUCUG<br>GUGAUUCUACCUGGUCAAGAUCUCCAAUAUGUUCUGG<br>CAACCUACGAUACUUCCAGAGUUGAACAUGCUGUAGU<br>UUAUUACGUUUACAGCCCAAGCCGCUCAUUUUCUUAC<br>UUUUAUCCUUUUAGGUUGCCUGUAAGGGGGGUCCCCA<br>UUGAAUUACAAGUGGAAUGCUUCACAUGGGACCAAA<br>AACUCUGGUGCCGUCACUUCUGUGUGCUUGCGGACUC<br>AGAAUCUGGUGGACAUAUCACUCACUCUGGGAUGGU<br>GGGCAUGGGAGUCAGCUGCACAGCCACUCGGGAAGAU<br>GGAACCAGCCGCAGAUAG | 79 |

TABLE 13-continued

| Description | Sequence | SEQ ID NO: |
|---|---|---|
| GC_H_MEASLES_ D8 mRNA Sequence (assumes T100 tail) Sequence Length: 2126 | G*GGGAAAUAAGAGAGAAAAGAAGAGUAAGAAGAAA UAUAAGAGCCACCAUGUCACCACAACGAGACCGGAUA AAUGCCUUCUACAAAGACAACCCCCAUCCUAAGGGAA GUAGGAUAGUUAUUAACAGAGAACAUCUUAUGAUUG AUAGACCUUAUGUUUUGCUGGCUGUUCUAUUCGUCA UGUUUCUGAGCUUGAUCGGGUUGCUAGCCAUUGCAG GCAUUAGACUUCAUCGGGCAGCCAUCUACACCGCAGA GAUCCAUAAAAGCCUCAGCACCAAUCUGGAUGUAACU AACUCAAUCGAGCAUCAGGUUAAGGACGUGCUGACAC CACUCUUCAAGAUCAUCGGUGAUGAAGUGGGCUUGA GGACACCUCAGAGAUUCACUGACCUAGUGAAGUUCAU CUCUGACAAGAUUAAAUUCCUUAAUCCGGACAGGGAA UACGACUUCAGAGAUCUCACUUGGUGUAUCAACCCGC CAGAGAGAAUCAAAUUGGAUUAUGAUCAAUACUGUG CAGAUGUGGCUGCUGAAGAACUCAUGAAUGCAUUGG UGAACUCAACUCUACUGGAGACCAGGGCAACCAAUCA GUUCCUAGCUGUCUCAAAGGGAAACUGCUCAGGGCCC ACUACAAUCAGAGGCCAAUUCUCAAACAUGUCGCUGU CCCUGUUGGACUUGUAUUUAAGUCGAGGUUACAAUG UGUCAUCUAUAGUCACUAUGACAUCCCAGGGAAUGUA CGGGGGAACUUACCUAGUGGAAAAGCCUAAUCUGAGC AGCAAAGGGUCAGAGUUGUCACAACUGAGCAUGCACC GAGUGUUUGAAGUAGGUGUUAUCAGAAAUCCGGGUU UGGGGGCUCCGGUAUUCCAUAUGACAAACUAUCUUGA GCAACCAGUCAGUAAUGAUUUCAGCAACUGCAUGGUG GCUUUGGGGGAGCUCAAGUUCGCAGCCCUCUGUCACA GGGAAGAUUCUAUCACAAUUCCCUAUCAGGGAUCAGG GAAAGGUGUCAGCUUCCAGCUUGUCAAGCUAGGUGUC UGGAAAUCCCCAACCGACAUGCAAUCCUGGGUCCCCC UAUCAACGGAUGAUCCAGUGAUAGACAGGCUUUACCU CUCAUCUCACAGAGGCGUUAUCGCUGACAAUCAAGCA AAAUGGGCUGUCCCGACAACACGGACAGAUGACAAGU UGCGAAUGGAGACAUGCUUCCAGCAGGCGUGUAAGG GUAAAAUCCAAGCACUUUGCGAGAAUCCCGAGUGGAC ACCAUUGAAGGAUAACAGGAUUCCUUCAUACGGGGUC UUGUCUGUUGAUCUGAGUCUGACAGUUGAGCUUAAA AUCAAAAUUGUUUCAGGAUUCGGGCCAUUGAUCACAC ACGGUUCAGGGAUGGACCUAUACAAAUCCAACCACAA CAAUAUGUAUUGGCUGACUAUCCCGCCAAUGAAGAAC CUGGCCUUAGGUGUAAUCAACACAUUGGAGUGGAUA CCGAGAUUCAAGGUUAGUCCCAACCUCUUCACUGUUC CAAUUAAGGAAGCAGGCGAGGACUGCCAUGCCCCAAC AUACCUACCUGCGGAGGUGGAUGGUGAUGUCAAACUC AGUUCCAAUCUGGUGAUUCUACCUGGUCAAGAUCUCC AAUAUGUUCUGGCAACCUACGAUACUUCCAGAGUUGA ACAUGCUGUAGUUUAUUACGUUUACAGCCCAAGCCGC UCAUUUUCUUACUUUUAUCCUUUUAGGUUGCCUGUA AGGGGGGUCCCCAUUGAAUUACAAGUGGAAUGCUUC ACAUGGGACCAAAAACUCUGGUGCCGUCACUUCUGUG UGCUUGCGGACUCAGAAUCUGGUGGACAUAUCACUCA CUCUGGGAUGGUGGGCAUGGGAGUCAGCUGCACAGCC ACUCGGGAAGAUGGAACCAGCCGCAGAUAGUGAUAA UAGGCUGGAGCCUCGGUGGCCAAGCUUCUUGCCCCUU GGGCCUCCCCCCAGCCCCUCCUCCCCUUCCUGCACCCG UACCCCCGUGGUCUUUGAAUAAAGUCUGAGUGGGCGG CAAAAAAAAAAAAAAAAAAAAAAAAAAAAAAAAAAA AAAAAAAAAAAAAAAAAAAAAAAAAAAAAAAAAAAA AAAAAAAAAAAAAAAAAAAAAAAAAAAAAAUCUAG | 80 |

TABLE 14

MeV Amino Acid Sequences

| Description | Sequence | SEQ ID NO: |
|---|---|---|
| GC_F_MEASLES_B3.1 ORF Sequence, AA | MGLKVNVSAVFMAVLLTLQTPAGQIHWGNLSKIGVV GIGSASYKVMTRSSHQSLVIKLMPNITLLNNCTRVEIA EYRRLLRTVLEPIRDALNAMTQNIRPVQSVASSRRHK RFAGVVLAGAALGVATAAQITAGIALHRSMLNSQAID NLRASLETTNQAIEAIRQAGQEMILAVQGVQDYINNE LIPSMNQLSCDLIGQKLGLKLLRYYTEILSLFGPSLRDP ISAEISIQALSYALGGDINKVLEKLGYSGGDLLGILESR | 47 |

TABLE 14-continued

| MeV Amino Acid Sequences | | |
|---|---|---|
| Description | Sequence | SEQ ID NO: |
| | GIKARITHVDTESYFIVLSIAYPTLSEIKGVIVHRLEGVS YNIGSQEWYTTVPKYVATQGYLISNFDESSCTFMPEG TVCSQNALYPMSPLLQECLRGSTKSCARTLVSGSFGN RFILSQGNLIANCASILCKCYTTGTIINQDPDKILTYIAA DRCPVVEVNGVTIQVGSRRYPDAVYLHRIDLGPPISLE RLDVGTNLGNAIAKLEDAKELLESSDQILRSMKGLSST SIVYILIAVCLGGLIGIPTLICCCRGRCNKKGEQVGMSR PGLKPDLTGTSKSYVRSL* | |
| GC_F_MEASLES_D8 ORF Sequence, AA | MGLKVNVSVIFMAVLLTLQTPTGQIHWGNLSKIGVVG VGSASYKVMTRSSHQSLVIKLMPNITLLNNCTRVGIAE YRRLLRTVLEPIRDALNAMTQNIRPVQSVASSRRHKR FAGVVLAGAALGVATAAQITAGIALHQSMLNSQAIDN LRASLETTNQAIEAIRQAGQEMILAVQGVQDYINNELI PSMNQLSCDLIGQKLGLKLLRYYTEILSLFGPSLRDPIS AEISIQALSYALGGDINKVLEKLGYSGGDLLGILESRGI KARITHVDTESYFIVLSIAYPTLSEIKGVIVHRLEGVSY NIGSQEWYTTVPKYVATQGYLISNFDESSCTFMPEGT VCSQNALYPMSPLLQECLRGSTKSCARTLVSGSFGNR FILSQGNLIANCASILCKCYTTGTIINQDPDKILTYIAAD HCPVVEVNGVTIQVGSRRYPDAVYLHRIDLGPPISLER LDVGTNLGNAIAKLEDAKELLESSDQILRSMKGLSSTS IVYILIAVCLGGLIGIPALICCCRGRCNKKGEQVGMSRP GLKPDLTGTSKSYVRSL* | 48 |
| GC_H_MEASLES_B3 ORF Sequence, AA | MSPQRDRINAFYKDNPYPKGSRIVINREHLMIDRPYVL LAVLFVMFLSLIGLLAIAGIRLHRAAIYTAEIHKSLSTN LDVTNSIEHQVKDVLTPLFKIIGDEVGLRTPQRFTDLV KFISDKIKFLNPDREYDFRDLTWCINPPERIKLDYDQY CADVAAEELMNALVNSTLLETRTTTQFLAVSKGNCS GPTTIRGQFSNMSLSLLDLYLGRGYNVSSIVTMTSQG MYGGTYLVEKPNLNSKGSELSQLSMYRVFEVGVIRNP GLGAPVFHMTNYFEQPVSNGLGNCMVALGELKLAAL CHGDDSIIIPYQGSGKGVSFQLVKLGVWKSPTDMQSW VPLSTDDPVVDRLYLSSHRGVIADNQAKWAVPTTRT DDKLRMETCFQQACKGKIQALCENPEWVPLKDNRIPS YGVLSVDLSLTVELKIKIASGFGPLITHGSGMDLYKSN CNNVYWLTIPPMRNLALGVINTLEWIPRFKVSPNLFTV PIKEAGEDCHAPTYLPAEVDGDVKLSSNLVILPGQDL QYVLATYDTSRVEHAVVYYVYSPSRSFSYFYPFRLPIK GVPIELQVECFTWDQKLWCRHFCVLADSESGGLITHS GMVGMGVSCTATREDGTNRR* | 49 |
| GC_H_MEASLES_D8 ORF Sequence, AA | MSPQRDRINAFYKDNPHPKGSRIVINREHLMIDRPYVL LAVLFVMFLSLIGLLAIAGIRLHRAAIYTAEIHKSLSTN LDVTNSIEHQVKDVLTPLFKIIGDEVGLRTPQRFTDLV KFISDKIKFLNPDREYDFRDLTWCINPPERIKLDYDQY CADVAAEELMNALVNSTLLETRATNQFLAVSKGNCS GPTTIRGQFSNMSLSLLDLYLSRGYNVSSIVTMTSQGM YGGTYLVEKPNLSSKGSELSQLSMHRVFEVGVIRNPG LGAPVFHMTNYLEQPVSNDFSNCMVALGELKFAALC HREDSITIPYQGSGKGVSFQLVKLGVWKSPTDMQSW VPLSTDDPVIDRLYLSSHRGVIADNQAKWAVPTTRTD DKLRMETCFQQACKGKIQALCENPEWTPLKDNRIPSY GVLSVDLSLTVELKIKIVSGFGPLITHGSGMDLYKSNH NNMYWLTIPPMKNLALGVINTLEWIPRFKVSPNLFTV PIKEAGEDCHAPTYLPAEVDGDVKLSSNLVILPGQDL QYVLATYDTSRVEHAVVYYVYSPSRSFSYFYPFRLPV RGVPIELQVECFTWDQKLWCRHFCVLADSESGGHITH SGMVGMGVSCTATREDGTSRR* | 50 |

TABLE 15

| MeV NCBI Accession Numbers (Amino Acid Sequences) | | |
|---|---|---|
| Type | Virus Name | GenBank Accession |
| hemagglutinin | hemagglutinin [Measles virus strain Moraten] | AAF85673.1 |
| hemagglutinin | hemagglutinin [Measles virus strain Rubeovax] | AAF85689.1 |
| hemagglutinin | hemagglutinin [Measles virus] | AAF89824.1 |
| hemagglutinin | hemagglutinin protein [Measles virus] | CAA91369.1 |
| hemagglutinin | hemagglutinin [Measles virus] | BAJ23068.1 |

TABLE 15-continued

MeV NCBI Accession Numbers (Amino Acid Sequences)

| Type | Virus Name | GenBank Accession |
|---|---|---|
| hemagglutinin | hemagglutinin protein [Measles virus] | BAB39848.1 |
| hemagglutinin | hemagglutinin [Measles virus] | AAA50551.1 |
| hemagglutinin | RecName: Full = Hemagglutinin glycoprotein | P08362.1 |
| hemagglutinin | hemagglutinin [Measles virus] | AAB63802.1 |
| hemagglutinin | hemagglutinin [Measles virus] | AAA56650.1 |
| hemagglutinin | hemagglutinin [Measles virus] | AAA56642.1 |
| hemagglutinin | hemagglutinin [Measles virus] | AAA74936.1 |
| hemagglutinin | hemagglutinin protein [Measles virus] | BAH56665.1 |
| hemagglutinin | hemagglutinin [Measles virus] | ACC86105.1 |
| hemagglutinin | hemagglutinin [Measles virus strain Edmonston-Zagreb] | AAF85697.1 |
| hemagglutinin | hemagglutinin [Measles virus] | AAR89413.1 |
| hemagglutinin | hemagglutinin [Measles virus] | AAA56653.1 |
| hemagglutinin | RecName: Full = Hemagglutinin glycoprotein | P35971.1 |
| hemagglutinin | Hemagglutinin [Measles virus] | CAB94916.1 |
| hemagglutinin | hemagglutinin [Measles virus] | AAC03036.1 |
| hemagglutinin | hemagglutinin [Measles virus] | AAF85681.1 |
| hemagglutinin | Hemagglutinin [Measles virus] | CAB94927.1 |
| hemagglutinin | Hemagglutinin [Measles virus] | CAB94925.1 |
| hemagglutinin | hemagglutinin protein [Measles virus] | BAB39835.1 |
| hemagglutinin | Hemagglutinin [Measles virus] | CAB94931.1 |
| hemagglutinin | hemagglutinin [Measles virus genotype A] | AFO84712.1 |
| hemagglutinin | hemagglutinin [Measles virus] | AAA56639.1 |
| hemagglutinin | Hemagglutinin [Measles virus] | CAB94926.1 |
| hemagglutinin | hemagglutinin protein [Measles virus] | BAB39836.1 |
| hemagglutinin | Hemagglutinin [Measles virus] | CAB94929.1 |
| hemagglutinin | RecName: Full = Hemagglutinin glycoprotein | P06830.1 |
| hemagglutinin | Hemagglutinin [Measles virus] | CAB94928.1 |
| hemagglutinin | hemagglutinin protein [Measles virus] | BAB39837.1 |
| hemagglutinin | hemagglutinin [Measles virus] | AAA74935.1 |
| hemagglutinin | hemagglutinin protein [Measles virus] | CAB43780.1 |
| hemagglutinin | hemagglutinin [Measles virus] | BAA09952.1 |
| hemagglutinin | hemagglutinin protein [Measles virus] | CAB43815.1 |
| hemagglutinin | hemagglutinin [Measles virus] | AAF28390.1 |
| hemagglutinin | Hemagglutinin [Measles virus] | CAB94923.1 |
| hemagglutinin | hemagglutinin protein [Measles virus] | CAB43785.1 |
| hemagglutinin | hemagglutinin [Measles virus] | ABD34001.1 |
| hemagglutinin | hemagglutinin protein [Measles virus] | CAB43782.1 |
| hemagglutinin | hemagglutinin protein [Measles virus] | CAB43781.1 |
| hemagglutinin | hemagglutinin [Measles virus] | BAH22353.1 |
| hemagglutinin | hemagglutinin [Measles virus] | AAC35878.2 |
| hemagglutinin | hemagglutinin protein [Measles virus] | AAL86996.1 |
| hemagglutinin | hemagglutinin [Measles virus] | CAA76066.2 |
| hemagglutinin | hemagglutinin [Measles virus] | AAA46428.1 |
| hemagglutinin | hemagglutinin protein [Measles virus] | CAB43803.1 |
| hemagglutinin | Hemagglutinin [Measles virus] | CAB94918.1 |
| hemagglutinin | hemagglutinin [Measles virus] | AAF72162.1 |
| hemagglutinin | hemagglutinin [Measles virus] | AAM70154.1 |
| hemagglutinin | hemagglutinin protein [Measles virus] | CAB43776.1 |
| hemagglutinin | hemagglutinin [Measles virus genotype D4] | ACT78395.1 |
| hemagglutinin | hemagglutinin [Measles virus genotype D7] | AAL02030.1 |
| hemagglutinin | hemagglutinin protein [Measles virus] | CAB43789.1 |
| hemagglutinin | hemagglutinin protein [Measles virus] | CAB43774.1 |
| hemagglutinin | Hemagglutinin [Measles virus] | CAB94920.1 |
| hemagglutinin | Hemagglutinin [Measles virus] | CAB94922.1 |
| hemagglutinin | hemagglutinin [Measles virus] | ABB59491.1 |
| hemagglutinin | hemagglutinin protein [Measles virus] | BAB39843.1 |
| hemagglutinin | hemagglutinin protein [Measles virus] | CAB43804.1 |
| hemagglutinin | hemagglutinin [Measles virus] | AAX52048.1 |
| hemagglutinin | Hemagglutinin [Measles virus] | CAB94930.1 |
| hemagglutinin | hemagglutinin [Measles virus] | AAA74526.1 |
| hemagglutinin | hemagglutinin protein [Measles virus] | CAB43814.1 |
| hemagglutinin | hemagglutinin [Measles virus] | ABB59493.1 |
| hemagglutinin | hemagglutinin [Measles virus genotype D4] | AAL02019.1 |
| hemagglutinin | Hemagglutinin [Measles virus] | CAB94919.1 |
| hemagglutinin | hemagglutinin protein [Measles virus] | AAL86997.1 |
| hemagglutinin | hemagglutinin [Measles virus genotype C2] | AAL02017.1 |
| hemagglutinin | hemagglutinin protein [Measles virus] | CAB43769.1 |
| hemagglutinin | hemagglutinin protein [Measles virus] | CAB43808.1 |
| hemagglutinin | hemagglutinin [Measles virus] | BAO97032.1 |
| hemagglutinin | hemagglutinin protein [Measles virus] | CAB43805.1 |
| hemagglutinin | hemagglutinin protein [Measles virus] | CAB43777.1 |
| hemagglutinin | hemagglutinin [Measles virus] | AAL67793.1 |
| hemagglutinin | hemagglutinin [Measles virus] | AAF89816.1 |
| hemagglutinin | hemagglutinin [Measles virus genotype D4] | AAL02020.1 |
| hemagglutinin | hemagglutinin protein [Measles virus] | CAB43786.1 |

TABLE 15-continued

MeV NCBI Accession Numbers (Amino Acid Sequences)

| Type | Virus Name | GenBank Accession |
|---|---|---|
| hemagglutinin | hemagglutinin protein [Measles virus strain MVi/New Jersey.USA/45.05] | AEP40452.1 |
| hemagglutinin | hemagglutinin [Measles virus] | AAA74531.1 |
| hemagglutinin | hemagglutinin [Measles virus] | AAB63800.1 |
| hemagglutinin | hemagglutinin [Measles virus] | AAO21711.1 |
| hemagglutinin | hemagglutinin [Measles virus genotype D8] | ALE27189.1 |
| hemagglutinin | hemagglutinin protein [Measles virus] | CAB43810.1 |
| hemagglutinin | hemagglutinin [Measles virus] | AAF89817.1 |
| hemagglutinin | hemagglutinin [Measles virus genotype D6] | AAL02022.1 |
| hemagglutinin | hemagglutinin protein [Measles virus] | CAB43800.1 |
| hemagglutinin | hemagglutinin protein [Measles virus genotype B3] | AGA17219.1 |
| hemagglutinin | hemagglutinin protein [Measles virus] | CAB43770.1 |
| hemagglutinin | hemagglutinin protein [Measles virus strain MVi/Texas.USA/4.07] | AEP40444.1 |
| hemagglutinin | hemagglutinin [Measles virus] | AAX52047.1 |
| hemagglutinin | hemagglutinin [Measles virus] | AAB63794.1 |
| hemagglutinin | hemagglutinin [Measles virus] | AAB63796.1 |
| hemagglutinin | hemagglutinin [Measles virus] | AAA74528.1 |
| hemagglutinin | hemagglutinin [Measles virus] | AAB63774.1 |
| hemagglutinin | hemagglutinin [Measles virus] | AAB63795.1 |
| hemagglutinin | hemagglutinin [Measles virus] | AAA74519.1 |
| hemagglutinin | hemagglutinin protein [Measles virus] | CAB43778.1 |
| fusion protein | fusion protein [Measles virus strain Moraten] | AAF85672.1 |
| fusion protein | fusion protein [Measles virus] | AAA56645.1 |
| fusion protein | fusion protein [Measles virus strain Rubeovax] | AAF85688.1 |
| fusion protein | fusion protein [Measles virus] | AAF85680.1 |
| fusion protein | fusion protein [Measles virus] | AEF30359.1 |
| fusion protein | fusion protein [Measles virus] | BAA09957.1 |
| fusion protein | fusion protein [Measles virus] | AAV84957.1 |
| fusion protein | fusion protein [Measles virus MeV-eGFP_Edm-tag] | AII16636.1 |
| fusion protein | fusion protein [Measles virus] | ABY58018.1 |
| fusion protein | fusion protein [Measles virus] | BAA19838.1 |
| fusion protein | fusion protein [Measles virus] | AAA56641.1 |
| fusion protein | F protein [Measles virus] | ABK40529.1 |
| fusion protein | fusion protein [Measles virus] | AAA56652.1 |
| fusion protein | fusion protein [Measles virus] | ABY58017.1 |
| fusion protein | fusion protein [Measles virus] | ABB71645.1 |
| fusion protein | fusion protein [Measles virus] | NP_056922.1 |
| fusion protein | fusion protein [Measles virus strain AIK-C] | AAF85664.1 |
| fusion protein | fusion protein [Measles virus] | BAB60865.1 |
| fusion protein | fusion protein [Measles virus] | BAA09950.1 |
| fusion protein | fusion protein [Measles virus strain MVi/New York.USA/26.09/3] | AEP40403.1 |
| fusion protein | fusion protein [Measles virus] | AAA74934.1 |
| fusion protein | fusion protein [Measles virus] | CAB38075.1 |
| fusion protein | fusion protein [Measles virus strain MVi/Texas.USA/4.07] | AEP40443.1 |
| fusion protein | fusion protein [Measles virus] | AAF02695.1 |
| fusion protein | fusion protein [Measles virus] | AAF02696.1 |
| fusion protein | fusion protein [Measles virus] | AAT99301.1 |
| fusion protein | fusion protein [Measles virus] | ABB71661.1 |
| fusion protein | fusion protein [Measles virus] | BAK08874.1 |
| fusion protein | fusion protein [Measles virus] | AAF02697.1 |
| fusion protein | fusion protein [Measles virus genotype D4] | AFY12704.1 |
| fusion protein | fusion protein [Measles virus strain MVi/California.USA/16.03] | AEP40467.1 |
| fusion protein | fusion protein [Measles virus genotype D8] | AHN07989.1 |
| fusion protein | fusion protein [Measles virus] | AAA46421.1 |
| fusion protein | fusion protein [Measles virus] | AAA56638.1 |
| fusion protein | fusion protein [Measles virus strain MVi/Virginia.USA/15.09] | AEP40419.1 |
| fusion protein | fusion protein [Measles virus genotype D8] | ALE27200.1 |
| fusion protein | fusion protein [Measles virus genotype D8] | AFY12695.1 |
| fusion protein | fusion protein [Measles virus genotype D8] | ALE27248.1 |
| fusion protein | fusion protein [Measles virus genotype D8] | ALE27224.1 |
| fusion protein | fusion protein [Measles virus] | AAT99300.1 |
| fusion protein | fusion protein [Measles virus] | BAH96592.1 |
| fusion protein | fusion protein [Measles virus strain MVi/California.USA/8.04] | AEP40459.1 |
| fusion protein | fusion protein [Measles virus genotype D8] | AIG94081.1 |
| fusion protein | fusion protein [Measles virus] | BAA09951.1 |
| fusion protein | fusion protein [Measles virus genotype D8] | ALE27194.1 |
| fusion protein | fusion protein [Measles virus] | BAA33871.1 |
| fusion protein | fusion protein [Measles virus strain MVi/Washington.USA/18.08/1] | AEP40427.1 |
| fusion protein | fusion protein [Measles virus] | ABY21182.1 |

TABLE 15-continued

MeV NCBI Accession Numbers (Amino Acid Sequences)

| Type | Virus Name | GenBank Accession |
|---|---|---|
| fusion protein | fusion protein [Measles virus genotype D8] | ALE27284.1 |
| fusion protein | fusion protein [Measles virus] | ACA09725.1 |
| fusion protein | fusion protein [Measles virus genotype D8] | ALE27314.1 |
| fusion protein | fusion protein [Measles virus genotype G3] | AFY12712.1 |
| fusion protein | fusion protein [Measles virus genotype D8] | ALE27368.1 |
| fusion protein | RecName: Full = Fusion glycoprotein F0; Contains: RecName: Full = Fusion glycoprotein F2; Contains: RecName: Full = Fusion glycoprotein F1; Flags: Precursor | P35973.1 |
| fusion protein | fusion protein [Measles virus genotype H1] | AIG53713.1 |
| | unnamed protein product [Measles virus] | CAA34588.1 |
| fusion protein | fusion protein [Measles virus] | CAA76888.1 |
| fusion protein | fusion protein [Measles virus genotype B3.1] | AIY55563.1 |
| fusion protein | fusion protein [Measles virus] | ADO17330.1 |
| fusion protein | fusion protein [Measles virus genotype H1] | AIG53703.1 |
| fusion protein | fusion protein [Measles virus genotype B3] | AGA17208.1 |
| fusion protein | fusion protein [Measles virus] | AAL29688.1 |
| fusion protein | fusion protein [Measles virus genotype H1] | AIG53706.1 |
| fusion protein | fusion protein [Measles virus genotype H1] | AIG53701.1 |
| fusion protein | fusion protein [Measles virus genotype B3] | ALE27092.1 |
| fusion protein | fusion protein [Measles virus genotype H1] | AIG53714.1 |
| fusion protein | fusion protein [Measles virus genotype H1] | AIG53694.1 |
| fusion protein | fusion protein [Measles virus genotype H1] | AIG53668.1 |
| fusion protein | fusion protein [Measles virus] | ACC86094.1 |
| fusion protein | fusion protein [Measles virus genotype H1] | AIG53670.1 |
| fusion protein | fusion protein [Measles virus genotype H1] | AIG53707.1 |
| fusion protein | fusion protein [Measles virus genotype B3] | AGA17216.1 |
| fusion protein | fusion protein [Measles virus genotype H1] | AIG53671.1 |
| fusion protein | fusion protein [Measles virus strain MVi/New Jersey.USA/45.05] | AEP40451.1 |
| fusion protein | fusion protein [Measles virus genotype H1] | AIG53684.1 |
| fusion protein | fusion protein [Measles virus genotype H1] | AIG53688.1 |
| fusion protein | fusion protein [Measles virus genotype B3] | AGA17214.1 |
| fusion protein | fusion protein [Measles virus genotype H1] | AIG53683.1 |
| fusion protein | fusion protein [Measles virus genotype H1] | AIG53667.1 |
| fusion protein | fusion protein [Measles virus genotype H1] | AIG53686.1 |
| fusion protein | fusion protein [Measles virus genotype H1] | AIG53685.1 |
| fusion protein | fusion protein [Measles virus genotype H1] | AIG53681.1 |
| | unnamed protein product [Measles virus] | CAA34589.1 |
| fusion protein | fusion protein [Measles virus genotype H1] | AIG53678.1 |
| fusion protein | fusion protein [Measles virus genotype H1] | AIG53710.1 |
| fusion protein | fusion protein [Measles virus genotype H1] | AIG53669.1 |
| fusion protein | fusion protein [Measles virus genotype H1] | AIG53664.1 |
| fusion protein | fusion protein [Measles virus] | AAA50547.1 |
| fusion protein | fusion protein [Measles virus genotype H1] | AIG53679.1 |
| fusion protein | fusion protein [Measles virus genotype H1] | AIG53709.1 |
| fusion protein | fusion protein [Measles virus genotype H1] | AIG53672.1 |
| fusion protein | fusion protein [Measles virus genotype H1] | AIG53697.1 |
| fusion protein | fusion protein [Measles virus genotype H1] | AIG53689.1 |
| fusion protein | fusion protein [Measles virus genotype H1] | AIG53676.1 |
| fusion protein | fusion protein [Measles virus genotype H1] | AIG53675.1 |
| fusion protein | fusion protein [Measles virus genotype H1] | AIG53663.1 |
| fusion protein | fusion protein [Measles virus] | BAA19841.1 |
| fusion protein | fusion protein [Measles virus] | AAF02701.1 |
| fusion protein | fusion protein [Measles virus genotype H1] | AIG53680.1 |
| fusion protein | fusion protein [Measles virus genotype H1] | AIG53674.1 |
| C protein | C protein [Measles virus strain Moraten] | AAF85670.1 |
| C protein | RecName: Full = Protein C | P03424.1 |
| C protein | C protein [Measles virus] | ACN54404.1 |
| C protein | C protein [Measles virus] | ACN54412.1 |
| C protein | RecName: Full = Protein C | P35977.1 |
| C protein | C protein [Measles virus] | AAF85678.1 |
| C protein | C protein [Measles virus] | ABD33998.1 |
| C protein | unnamed protein product [Measles virus] | CAA34586.1 |
| C protein | C protein [Measles virus] | BAJ51786.1 |
| C protein | C protein [Measles virus] | BAA33869.1 |
| C protein | virulence factor [Measles virus] | ABO69700.1 |
| C protein | C protein [Measles virus] | NP_056920.1 |
| C protein | C protein [Measles virus] | ADO17333.1 |
| C protein | C protein [Measles virus] | ACC86082.1 |
| C protein | C protein [Measles virus] | BAA33875.1 |
| C protein | C protein [Measles virus] | ABY21189.1 |
| C protein | C protein [Measles virus] | BAE98296.1 |
| C protein | C protein [Measles virus] | ADU17782.1 |
| C protein | C protein [Measles virus strain MVi/Virginia.USA/15.09] | AEP40417.1 |
| C protein | C protein [Measles virus] | ADU17814.1 |
| C protein | C protein [Measles virus] | ADU17798.1 |

TABLE 15-continued

MeV NCBI Accession Numbers (Amino Acid Sequences)

| Type | Virus Name | GenBank Accession |
|---|---|---|
| C protein | C protein [Measles virus genotype D4] | AFY12700.1 |
| C protein | C protein [Measles virus] | ADU17784.1 |
| C protein | C protein [Measles virus strain MVi/California.USA/16.03] | AEP40465.1 |
| C protein | C protein [Measles virus] | ABB71643.1 |
| C protein | C protein [Measles virus] | AEI91027.1 |
| C protein | C protein [Measles virus] | ADU17874.1 |
| C protein | C protein [Measles virus] | ADU17903.1 |
| C protein | C protein [Measles virus] | CAA34579.1 |
| C protein | C protein [Measles virus] | ADU17790.1 |
| C protein | C protein [Measles virus] | ADU17800.1 |
| C protein | C protein [Measles virus] | ABB71667.1 |
| C protein | unnamed protein product [Measles virus] | CAA34572.1 |
| C protein | C protein [Measles virus strain MVi/Arizona.USA/11.08/2] | AEP40433.1 |
| C protein | C protein [Measles virus] | ADU17830.1 |
| C protein | C protein [Measles virus] | ADU17947.1 |
| C protein | C protein [Measles virus] | ADU17818.1 |
| C protein | C protein [Measles virus strain MVi/New Jersey.USA/45.05] | AEP40449.1 |
| C protein | C protein [Measles virus strain MVi/Texas.USA/4.07] | AEP40441.1 |
| C protein | C protein [Measles virus] | ADU17864.1 |
| C protein | C protein [Measles virus] | ADU17838.1 |
| C protein | C protein [Measles virus] | ADU17881.1 |
| C protein | C protein [Measles virus strain MVi/Washington.USA/18.08/1] | AEP40425.1 |
| C protein | C protein [Measles virus] | ADU17927.1 |
| C protein | C protein [Measles virus] | ADU17953.1 |
| C protein | C protein [Measles virus] | ADU17889.1 |
| C protein | C protein [Measles virus] | ADU17963.1 |
| C protein | C protein [Measles virus] | ADU17893.1 |
| C protein | C protein [Measles virus] | ADU17820.1 |
| C protein | C protein [Measles virus] | ABB71651.1 |
| C protein | C protein [Measles virus] | ADU17786.1 |
| C protein | C protein [Measles virus] | ADU17862.1 |
| C protein | C protein [Measles virus] | ADU17923.1 |
| C protein | C protein [Measles virus] | ADU17959.1 |
| C protein | C protein [Measles virus] | ADU17951.1 |
| C protein | C protein [Measles virus] | ADU17916.1 |
| C protein | C protein [Measles virus] | ADU17957.1 |
| C protein | C protein [Measles virus] | ADU17925.1 |
| C protein | C protein [Measles virus] | ADU17901.1 |
| C protein | C protein [Measles virus] | ADU17887.1 |
| C protein | C protein [Measles virus] | ADU17832.1 |
| C protein | C protein [Measles virus] | ADU17891.1 |
| C protein | C protein [Measles virus] | ADU17961.1 |
| C protein | C protein [Measles virus] | ADU17872.1 |
| C protein | C protein [Measles virus] | ADU17929.1 |
| C protein | C protein [Measles virus] | ADU17908.1 |
| C protein | C protein [Measles virus] | ADU17910.1 |
| C protein | C protein [Measles virus] | ADU17921.1 |
| C protein | C protein [Measles virus] | ADU17824.1 |
| C protein | C protein [Measles virus strain MVi/Pennsylvania.USA/20.09] | AEP40473.1 |
| C protein | C protein [Measles virus] | ADU17828.1 |
| C protein | C protein [Measles virus] | ADU17812.1 |
| C protein | C protein [Measles virus genotype D8] | AFY12692.1 |
| C protein | nonstructural C protein [Measles virus] | ABA59559.1 |
| C protein | RecName: Full = Protein C | Q00794.1 |
| C protein | nonstructural C protein [Measles virus] | ADO17934.1 |
| C protein | nonstructural C protein [Measles virus] | ACJ66773.1 |
| C protein | C protein [Measles virus genotype G3] | AFY12708.1 |
| C protein | RecName: Full = Protein C | P26035.1 |
| C protein | C protein [Measles virus] | BAA84128.1 |
| nucleoprotein | RecName: Full = Nucleoprotein; AltName: Full = Nucleocapsid protein; Short = NP; Short = Protein N | Q77M43.1 |
| nucleoprotein | nucleocapsid protein [Measles virus strain Rubeovax] | AAF85683.1 |
| nucleoprotein | RecName: Full = Nucleoprotein; AltName: Full = Nucleocapsid protein; Short = NP; Short = Protein N | Q89933.1 |
| nucleoprotein | nucleocapsid protein [Measles virus strain AIK-C] | AAF85659.1 |
| nucleoprotein | nucleoprotein [Measles virus] | ABI54102.1 |
| nucleoprotein | nucleoprotein [Measles virus] | AAA56643.1 |
| nucleoprotein | nucleoprotein [Measles virus] | AAC03050.1 |
| nucleoprotein | nucleoprotein [Measles virus] | AAA18990.1 |

TABLE 15-continued

| MeV NCBI Accession Numbers (Amino Acid Sequences) | | |
|---|---|---|
| Type | Virus Name | GenBank Accession |
| nucleoprotein | nucleoprotein [Measles virus] | AAA56640.1 |
| nucleoprotein | RecName: Full = Nucleoprotein; AltName: Full = Nucleocapsid protein; Short = NP; Short = Protein N | P35972.1 |
| nucleoprotein | RecName: Full = Nucleoprotein; AltName: Full = Nucleocapsid protein; Short = NP; Short = Protein N | P10050.1 |
| nucleoprotein | N protein [Measles virus] | BAB60956.1 |
| nucleoprotein | RecName: Full = Nucleoprotein; AltName: Full = Nucleocapsid protein; Short = NP; Short = Protein N | B1AAA7.1 |
| nucleoprotein | nucleoprotein [Measles virus] | AAA18991.1 |
| nucleoprotein | nucleoprotein [Measles virus] | CAB46894.1 |
| nucleoprotein | nucleoprotein [Measles virus] | CAB46871.1 |
| nucleoprotein | nucleoprotein [Measles virus] | CAB46872.1 |
| nucleoprotein | nucleoprotein [Measles virus] | ABU49606.1 |
| nucleoprotein | nucleocapsid protein [Measles virus] | AAA75494.1 |
| nucleoprotein | nucleoprotein [Measles virus] | CAB46883.1 |
| nucleoprotein | nucleoprotein [Measles virus] | CAB46892.1 |
| nucleoprotein | unnamed protein product [Measles virus] | CAA34584.1 |
| nucleoprotein | nucleoprotein [Measles virus] | AAA18997.1 |
| nucleoprotein | nucleoprotein [Measles virus] | CAB46863.1 |
| nucleoprotein | nucleoprotein [Measles virus] | AEF30352.1 |
| nucleoprotein | nucleoprotein [Measles virus] | ABI54103.1 |
| nucleoprotein | nucleocapsid protein [Measles virus] | AAA46433.1 |
| nucleoprotein | nucleoprotein [Measles virus] | CAB46902.1 |
| nucleoprotein | nucleoprotein [Measles virus] | CAB46873.1 |
| nucleoprotein | nucleoprotein [Measles virus] | CAB46906.1 |
| nucleoprotein | nucleoprotein [Measles virus] | AAA74547.1 |
| nucleoprotein | nucleoprotein [Measles virus] | AAA74537.1 |
| nucleoprotein | nucleoprotein [Measles virus] | CAB46862.1 |
| nucleoprotein | nucleocapsid protein [Measles virus] | BAA09961.1 |
| nucleoprotein | nucleoprotein [Measles virus] | AAO15875.1 |
| nucleoprotein | nucleoprotein [Measles virus] | AAO15871.1 |
| nucleoprotein | nucleoprotein [Measles virus] | CAB46882.1 |
| nucleoprotein | nucleoprotein [Measles virus] | CAB60124.1 |
| nucleoprotein | nucleoprotein [Measles virus] | ABI54104.1 |
| nucleoprotein | nucleoprotein [Measles virus] | CAB46869.1 |
| nucleoprotein | nucleoprotein [Measles virus] | CAB46880.1 |
| nucleoprotein | nucleoprotein [Measles virus] | AAA74541.1 |
| nucleoprotein | nucleocapsid protein [Measles virus strain MVi/New Jersey.USA/45.05] | AEP40446.1 |
| nucleoprotein | nucleoprotein [Measles virus] | ABI54110.1 |
| nucleoprotein | nucleoprotein [Measles virus] | CAB46903.1 |
| nucleoprotein | nucleoprotein [Measles virus] | CAB46899.1 |
| nucleoprotein | nucleoprotein [Measles virus] | CAB46901.1 |
| nucleoprotein | nucleocapsid protein [Measles virus] | ABB71640.1 |
| nucleoprotein | nucleoprotein [Measles virus] | CAB60113.1 |
| nucleoprotein | nucleoprotein [Measles virus] | CAB60114.1 |
| nucleoprotein | nucleoprotein [Measles virus] | CAB60116.1 |
| nucleoprotein | nucleoprotein [Measles virus] | CAB46895.1 |
| nucleoprotein | nucleoprotein [Measles virus] | CAB60121.1 |
| nucleoprotein | nucleoprotein [Measles virus] | ABI54111.1 |
| nucleoprotein | nucleoprotein [Measles virus] | CAB46889.1 |
| nucleoprotein | nucleoprotein [Measles virus] | CAB46898.1 |
| nucleoprotein | nucleoprotein [Measles virus genotype B3] | ALE27083.1 |
| nucleoprotein | nucleoprotein [Measles virus] | CAB60118.1 |
| nucleoprotein | nucleocapsid protein [Measles virus] | CAA34570.1 |
| nucleoprotein | nucleoprotein [Measles virus] | AAC29443.1 |
| nucleoprotein | nucleocapsid protein [Measles virus strain MVi/Washington.USA/18.08/1] | AEP40422.1 |
| nucleoprotein | nucleoprotein [Measles virus] | AAO15872.1 |
| nucleoprotein | nucleoprotein [Measles virus] | CAB46874.1 |
| nucleoprotein | nucleoprotein [Measles virus] | AAA74550.1 |
| nucleoprotein | nucleocapsid protein [Measles virus] | ABB71648.1 |
| nucleoprotein | nucleoprotein [Measles virus] | CAB46900.1 |
| nucleoprotein | nucleoprotein [Measles virus] | BAH22440.1 |
| nucleoprotein | nucleocapsid protein [Measles virus] | AAA46432.1 |
| nucleoprotein | nucleocapsid protein [Measles virus] | BAA33867.1 |
| nucleoprotein | nucleoprotein [Measles virus] | AAA74539.1 |
| nucleoprotein | nucleoprotein [Measles virus] | CAB60115.1 |
| nucleoprotein | nucleoprotein [Measles virus] | CAB60123.1 |
| nucleoprotein | nucleocapsid protein [Measles virus] | ABB71664.1 |
| nucleoprotein | nucleoprotein [Measles virus] | CAB60125.1 |
| nucleoprotein | nucleoprotein [Measles virus] | AAA74546.1 |
| nucleoprotein | nucleoprotein [Measles virus] | CAB46886.1 |
| nucleoprotein | nucleoprotein [Measles virus] | BAH22350.1 |
| nucleoprotein | nucleoprotein [Measles virus] | CAB46867.1 |
| nucleoprotein | nucleocapsid protein [Measles virus] | BAA09954.1 |

TABLE 15-continued

MeV NCBI Accession Numbers (Amino Acid Sequences)

| Type | Virus Name | GenBank Accession |
|---|---|---|
| nucleoprotein | nucleoprotein [Measles virus] | AAO15873.1 |
| nucleoprotein | nucleocapsid protein [Measles virus] | AEP95735.1 |
| nucleoprotein | nucleoprotein [Measles virus] | AAL37726.1 |
| nucleoprotein | nucleoprotein [Measles virus] | AAA74549.1 |
| nucleoprotein | RecName: Full = Nucleoprotein; AltName: Full = Nucleocapsid protein; Short = NP; Short = Protein N | P26030.1 |
| nucleoprotein | nucleoprotein [Measles virus ETH55/99] | AAK07777.1 |
| nucleoprotein | nucleoprotein [Measles virus genotype B3] | AGA17238.1 |
| nucleoprotein | nucleoprotein [Measles virus] | AEF30351.1 |
| nucleoprotein | nucleoprotein [Measles virus genotype B3] | AGA17242.1 |
| nucleoprotein | nucleoprotein [Measles virus ETH54/98] | AAK07776.1 |
| nucleoprotein | nucleoprotein [Measles virus] | AAA74548.1 |
| nucleoprotein | nucleoprotein [Measles virus] | AAA19221.1 |
| nucleoprotein | nucleoprotein [Measles virus] | AAC03039.1 |
| nucleoprotein | nucleoprotein [Measles virus] | AAA19223.1 |
| nucleoprotein | nucleoprotein [Measles virus genotype B3] | AGA17241.1 |
| nucleoprotein | nucleoprotein [Measles virus] | CAB60122.1 |
| nucleoprotein | nucleoprotein [Measles virus] | CAC34599.1 |
| nucleoprotein | nucleoprotein [Measles virus] | AAC03042.1 |
| nucleoprotein | nucleoprotein [Measles virus] | CAC34604.1 |
| nucleoprotein | nucleoprotein [Measles virus] | AAA74544.1 |
| nucleoprotein | nucleocapsid protein [Measles virus] | NP_056918.1 |
| V Protein | RecName: Full = Non-structural protein V | Q9IC37.1 |
| V Protein | RecName: Full = Non-structural protein V | Q9EMA9.1 |
| V Protein | V protein [Measles virus] | ACN54411.1 |
| V Protein | V protein [Measles virus] | ACN54403.1 |
| V Protein | V protein [Measles virus] | AEP95742.1 |
| V Protein | V protein [Measles virus strain MVi/Virginia.USA/15.09] | AEP40416.1 |
| V Protein | V protein [Measles virus] | ADU17801.1 |
| V Protein | V protein [Measles virus] | ADU17849.1 |
| V Protein | V protein [Measles virus] | ABB71642.1 |
| V Protein | V protein [Measles virus genotype D8] | AFY12693.1 |
| V Protein | V protein [Measles virus] | YP_003873249.2 |
| V Protein | V protein [Measles virus strain MVi/Arizona.USA/11.08/2] | AEP40432.1 |
| V Protein | RecName: Full = Non-structural protein V | P26036.1 |
| V Protein | V protein [Measles virus strain MVi/California.USA/16.03] | AEP40464.1 |
| V Protein | V protein [Measles virus strain MVi/California.USA/8.04] | AEP40456.1 |
| V Protein | V protein [Measles virus] | ABY21188.1 |
| V Protein | V protein [Measles virus strain MVi/Washington.USA/18.08/1] | AEP40424.1 |
| V Protein | V protein [Measles virus] | BAH96581.1 |
| V Protein | V protein [Measles virus] | ABB71666.1 |
| V Protein | RecName: Full = Non-structural protein V | P60168.1 |
| V Protein | V protein [Measles virus] | BAH96589.1 |
| V Protein | V protein [Measles virus] | ADU17954.1 |
| V Protein | V protein [Measles virus strain MVi/New York.USA/26.09/3] | AEP40400.1 |
| V Protein | V protein [Measles virus] | ABY21196.1 |
| V Protein | virulence factor [Measles virus] | ABO69701.1 |
| V Protein | V protein [Measles virus] | ABB71650.1 |
| V Protein | V protein [Measles virus] | ACC86086.1 |
| V Protein | V protein [Measles virus genotype D4] | AFY12702.1 |
| V Protein | V protein [Measles virus strain MVi/New Jersey.USA/45.05] | AEP40448.1 |
| V Protein | V protein [Measles virus] | BAE98295.1 |
| V Protein | V protein [Measles virus] | ACC86083.1 |
| V Protein | V protein [Measles virus] | ACU57139.1 |
| V Protein | V protein [Measles virus] | ADO17334.1 |
| V Protein | V protein [Measles virus] | ADU17930.1 |
| V Protein | V protein [Measles virus genotype G3] | AFY12710.1 |
| V Protein | V protein [Measles virus strain MVi/Pennsylvania.USA/20.09] | AEP40472.1 |
| V Protein | phosphoprotein [Measles virus] | ADU17839.1 |
| V Protein | V protein [Measles virus] | ADU17894.1 |
| V Protein | V protein [Measles virus] | ACN50010.1 |
| V Protein | V protein [Measles virus] | ADU17892.1 |
| | unnamed protein product [Measles virus] | CAA34585.1 |
| V Protein | V protein [Measles virus] | ABD33997.1 |

TABLE 16

| Name | Sequence | SEQ ID NO: |
|---|---|---|
| | Flagellin Nucleic Acid Sequences | |
| NT (5' UTR, ORF, 3' UTR) | TCAAGCTTTTGGACCCTCGTACAGAAGCTAATACGACTCACTAT<br>AGGGAAATAAGAGAGAAAAGAAGAGTAAGAAGAAATATAAG<br>AGCCACCATGGCACAAGTCATTAATACAAACAGCCTGTCGCTG<br>TTGACCCAGAATAACCTGAACAAATCCCAGTCCGCACTGGGCA<br>CTGCTATCGAGCGTTTGTCTTCCGGTCTGCGTATCAACAGCGCG<br>AAAGACGATGCGGCAGGACAGGCGATTGCTAACCGTTTTACCG<br>CGAACATCAAAGGTCTGACTCAGGCTTCCCGTAACGCTAACGA<br>CGGTATCTCCATTGCGCAGACCACTGAAGGCGCGCTGAACGAA<br>ATCAACAACAACCTGCAGCGTGTGCGTGAACTGGCGGTTCAGT<br>CTGCGAATGGTACTAACTCCCAGTCTGACCTCGACTCCATCCAG<br>GCTGAAATCACCCAGCGCCTGAACGAAATCGACCGTGTATCCG<br>GCCAGACTCAGTTCAACGGCGTGAAAGTCCTGGCGCAGGACAA<br>CACCCTGACCATCCAGGTTGGTGCCAACGACGGTGAAACTATC<br>GATATTGATTTAAAAGAAATCAGCTCTAAAACACTGGGACTTG<br>ATAAGCTTAATGTCCAAGATGCCTACACCCCGAAAGAAACTGC<br>TGTAACCGTTGATAAAACTACCTATAAAAATGGTACAGATCCT<br>ATTACAGCCCAGAGCAATACTGATATCCAAACTGCAATTGGCG<br>GTGGTGCAACGGGGGTTACTGGGGCTGATATCAAATTTAAAGA<br>TGGTCAATACTATTTAGATGTTAAAGGCGGTGCTTCTGCTGGTG<br>TTTATAAAGCCACTTATGATGAAACTACAAAGAAAGTTAATAT<br>TGATACGACTGATAAAACTCCGTTGGCAACTGCGGAAGCTACA<br>GCTATTCGGGGAACGGCCACTATAACCCACAACCAAATTGCTG<br>AAGTAACAAAAGAGGGTGTTGATACGACCACAGTTGCGGCTCA<br>ACTTGCTGCAGCAGGGGTTACTGGCGCCGATAAGGACAATACT<br>AGCCTTGTAAAACTATCGTTTGAGGATAAAAACGGTAAGGTTA<br>TTGATGGTGGCTATGCAGTGAAAATGGGCGACGATTTCTATGC<br>CGCTACATATGATGAGAAAACAGGTGCAATTACTGCTAAAACC<br>ACTACTTATACAGATGGTACTGGCGTTGCTCAAACTGGAGCTGT<br>GAAATTTGGTGGCGCAAATGGTAAATCTGAAGTTGTTACTGCT<br>ACCGATGGTAAGACTTACTTAGCAAGCGACCTTGACAAACATA<br>ACTTCAGAACAGGCGGTGAGCTTAAAGAGGTTAATACAGATAA<br>GACTGAAAACCCACTGCAGAAAATTGATGCTGCCTTGGCACAG<br>GTTGATACACTTCGTTCTGACCTGGGTGCGGTTCAGAACCGTTT<br>CAACTCCGCTATCACCAACCTGGGCAATACCGTAAATAACCTG<br>TCTTCTGCCCGTAGCCGTATCGAAGATTCCGACTACGCAACCGA<br>AGTCTCCAACATGTCTCGCGCGCAGATTCTGCAGCAGGCCGGT<br>ACCTCCGTTCTGGCGCAGGCGAACCAGGTTCCGCAAAACGTCC<br>TCTCTTTACTGCGTTGATAATAGGCTGGAGCCTCGGTGGCCATG<br>CTTCTTGCCCCTTGGGCCTCCCCCCAGCCCCTCCTCCCCTTCCTG<br>CACCCGTACCCCCGTGGTCTTTGAATAAAGTCTGAGTGGGCGG<br>C | 51 |
| ORF Sequence, NT | ATGGCACAAGTCATTAATACAAACAGCCTGTCGCTGTTGACCC<br>AGAATAACCTGAACAAATCCCAGTCCGCACTGGGCACTGCTAT<br>CGAGCGTTTGTCTTCCGGTCTGCGTATCAACAGCGCGAAAGAC<br>GATGCGGCAGGACAGGCGATTGCTAACCGTTTTACCGCGAACA<br>TCAAAGGTCTGACTCAGGCTTCCCGTAACGCTAACGACGGTAT<br>CTCCATTGCGCAGACCACTGAAGGCGCGCTGAACGAAATCAAC<br>AACAACCTGCAGCGTGTGCGTGAACTGGCGGTTCAGTCTGCGA<br>ATGGTACTAACTCCCAGTCTGACCTCGACTCCATCCAGGCTGAA<br>ATCACCCAGCGCCTGAACGAAATCGACCGTGTATCCGGCCAGA<br>CTCAGTTCAACGGCGTGAAAGTCCTGGCGCAGGACAACACCCT<br>GACCATCCAGGTTGGTGCCAACGACGGTGAAACTATCGATATT<br>GATTTAAAAGAAATCAGCTCTAAAACACTGGGACTTGATAAGC<br>TTAATGTCCAAGATGCCTACACCCCGAAAGAAACTGCTGTAAC<br>CGTTGATAAAACTACCTATAAAAATGGTACAGATCCTATTACA<br>GCCCAGAGCAATACTGATATCCAAACTGCAATTGGCGGTGGTG<br>CAACGGGGGTTACTGGGGCTGATATCAAATTTAAAGATGGTCA<br>ATACTATTTAGATGTTAAAGGCGGTGCTTCTGCTGGTGTTTATA<br>AAGCCACTTATGATGAAACTACAAAGAAAGTTAATATTGATAC<br>GACTGATAAAACTCCGTTGGCAACTGCGGAAGCTACAGCTATT<br>CGGGGAACGGCCACTATAACCCACAACCAAATTGCTGAAGTAA<br>CAAAAGAGGGTGTTGATACGACCACAGTTGCGGCTCAACTTGC<br>TGCAGCAGGGGTTACTGGCGCCGATAAGGACAATACTAGCCTT<br>GTAAAACTATCGTTTGAGGATAAAAACGGTAAGGTTATTGATG<br>GTGGCTATGCAGTGAAAATGGGCGACGATTTCTATGCCGCTAC<br>ATATGATGAGAAAACAGGTGCAATTACTGCTAAAACCACTACT<br>TATACAGATGGTACTGGCGTTGCTCAAACTGGAGCTGTGAAAT<br>TTGGTGGCGCAAATGGTAAATCTGAAGTTGTTACTGCTACCGAT<br>GGTAAGACTTACTTAGCAAGCGACCTTGACAAACATAACTTCA<br>GAACAGGCGGTGAGCTTAAAGAGGTTAATACAGATAAGACTG<br>AAAACCCACTGCAGAAAATTGATGCTGCCTTGGCACAGGTTGA<br>TACACTTCGTTCTGACCTGGGTGCGGTTCAGAACCGTTTCAACT<br>CCGCTATCACCAACCTGGGCAATACCGTAAATAACCTGTCTTCT<br>GCCCGTAGCCGTATCGAAGATTCCGACTACGCAACCGAAGTCT | 52 |

TABLE 16-continued

| Name | Sequence | SEQ ID NO: |
|---|---|---|
| | CCAACATGTCTCGCGCGCAGATTCTGCAGCAGGCCGGTACCTC<br>CGTTCTGGCGCAGGCGAACCAGGTTCCGCAAAACGTCCTCTCTT<br>TACTGCGT | |
| mRNA Sequence (assumes T100 tail) | G*GGGAAAUAAGAGAGAAAAGAAGAGUAAGAAGAAAUAUAA<br>GAGCCACCAUGGCACAAGUCAUUAAUACAAACAGCCUGUCGC<br>UGUUGACCCAGAAUAACCUGAACAAAUCCCAGUCCGCACUGG<br>GCACUGCUAUCGAGCGUUUGUCUUCCGGUCUGCGUAUCAACA<br>GCGCGAAAGACGAUGCGGCAGGACAGGCGAUUGCUAACCGUU<br>UUACCGCGAACAUCAAAGGUCUGACUCAGGCUUCCCGUAACG<br>CUAACGACGGUAUCUCCAUUGCGCAGACCACUGAAGGCGCGC<br>UGAACGAAAUCAACAACAACCUGCAGCGUGUGCGUGAACUGG<br>CGGUUCAGUCUGCGAAUGGUACUAACUCCCAGUCUGACCUCG<br>ACUCCAUCCAGGCUGAAAUCACCCAGCGCCUGAACGAAAUCG<br>ACCGUGUAUCCGGCCAGACUCAGUUCAACGGCGUGAAAGUCC<br>UGGCGCAGGACAACACCCUGACCAUCCAGGUUGGUGCCAACG<br>ACGGUGAAACUAUCGAUAUUGAUUUAAAAGAAAUCAGCUCU<br>AAAACACUGGGACUUGAUAAGCUUAAUGUCCAAGAUGCCUAC<br>ACCCCGAAAGAAACUGCUGUAACCGUUGAUAAAACUACCUAU<br>AAAAAUGGUACAGAUCCUAUUACAGCCCAGAGCAAUACUGAU<br>AUCCAAACUGCAAUUGGCGGUGGUGCAACGGGGGUUACUGG<br>GGCUGAUAUCAAAUUUAAAGAUGGUCAAUACUAUUUAGAUG<br>UUAAAGGCGGUGCUUCUGCUGGUGUUUAUAAAGCCACUUAU<br>GAUGAAACUACAAAGAAAGUUAAUAUUGAUACGACUGAUAA<br>AACUCCGUUGGCAACUGCGGAAGCUACAGCUAUUCGGGGAAC<br>GGCCACUAUAACCCACAACCAAAUUGCUGAAGUAACAAAAGA<br>GGGUGUUGAUACGACCACAGUUGCGGCUCAACUUGCUGCAGC<br>AGGGGUUACUGGCGCCGAUAAGGACAAUACUAGCCUUGUAA<br>AACUAUCGUUUGAGGAUAAAAACGGUAAGGUUAUUGAUGGU<br>GGCUAUGCAGUGAAAAUGGGCGACGAUUUCUAUGCCGCUACA<br>UAUGAUGAGAAAACAGGUGCAAUUACUGCUAAAACCACUAC<br>UUAUACAGAUGGUACUGGCGUUGCUCAAACUGGAGCUGUGA<br>AAUUUGGUGGCGCAAAUGGUAAAUCUGAAGUUGUUACUGCU<br>ACCGAUGGUAAGACUUACUUAGCAAGCGACCUUGACAAACAU<br>AACUUCAGAACAGGCGGUGAGCUUAAAGAGGUUAAUACAGA<br>UAAGACUGAAAACCCACUGCAGAAAAUUGAUGCUGCCUUGGC<br>ACAGGUUGAUACACUUCGUUCUGACCUGGGUGCGGUUCAGAA<br>CCGUUUCAACUCCGCUAUCACCAACCUGGGCAAUACCGUAAA<br>UAACCUGUCUUCUGCCCGUAGCCGUAUCGAAGAUUCCGACUA<br>CGCAACCGAAGUCUCCAACAUGUCUCGCGCGCAGAUUCUGCA<br>GCAGGCCGGUACCUCCGUUCUGGCGCAGGCGAACCAGGUUCC<br>GCAAAACGUCCUCUCUUUACUGCGUUGAUAAUAGGCUGGAGC<br>CUCGGUGGCCAUGCUUCUUGCCCCUUGGGCCUCCCCCCAGCC<br>CCUCCUCCCCUUCCUGCACCCGUACCCCCGUGGUCUUUGAAU<br>AAAGUCUGAGUGGGCGGCAAAAAAAAAAAAAAAAAAAAAAA<br>AAAAAAAAAAAAAAAAAAAAAAAAAAAAAAAAAAAAAAAAA<br>AAAAAAAAAAAAAAAAAAAAAAAAAAAAAAAAAAAAAUCUAG | 53 |
| | Flagellin mRNA Sequences | |
| NT (5' UTR, ORF, 3' UTR) | UCAAGCUUUUGGACCCUCGUACAGAAGCUAAUACGACUCACU<br>AUAGGGAAAUAAGAGAGAAAAGAAGAGUAAGAAGAAAUAUA<br>AGAGCCACCAUGGCACAAGUCAUUAAUACAAACAGCCUGUCG<br>CUGUUGACCCAGAAUAACCUGAACAAAUCCCAGUCCGCACUG<br>GGCACUGCUAUCGAGCGUUUGUCUUCCGGUCUGCGUAUCAAC<br>AGCGCGAAAGACGAUGCGGCAGGACAGGCGAUUGCUAACCGU<br>UUUACCGCGAACAUCAAAGGUCUGACUCAGGCUUCCCGUAAC<br>GCUAACGACGGUAUCUCCAUUGCGCAGACCACUGAAGGCGCG<br>CUGAACGAAAUCAACAACAACCUGCAGCGUGUGCGUGAACUG<br>GCGGUUCAGUCUGCGAAUGGUACUAACUCCCAGUCUGACCUC<br>GACUCCAUCCAGGCUGAAAUCACCCAGCGCCUGAACGAAAUC<br>GACCGUGUAUCCGGCCAGACUCAGUUCAACGGCGUGAAAGUC<br>CUGGCGCAGGACAACACCCUGACCAUCCAGGUUGGUGCCAAC<br>GACGGUGAAACUAUCGAUAUUGAUUUAAAAGAAAUCAGCUC<br>UAAAACACUGGGACUUGAUAAGCUUAAUGUCCAAGAUGCCU<br>ACACCCCGAAAGAAACUGCUGUAACCGUUGAUAAAACUACCU<br>AUAAAAAUGGUACAGAUCCUAUUACAGCCCAGAGCAAUACUG<br>AUAUCCAAACUGCAAUUGGCGGUGGUGCAACGGGGGUUACU<br>GGGGCUGAUAUCAAAUUUAAAGAUGGUCAAUACUAUUUAGA<br>UGUUAAAGGCGGUGCUUCUGCUGGUGUUUAUAAAGCCACUU<br>AUGAUGAAACUACAAAGAAAGUUAAUAUUGAUACGACUGAU<br>AAAACUCCGUUGGCAACUGCGGAAGCUACAGCUAUUCGGGGA<br>ACGGCCACUAUAACCCACAACCAAAUUGCUGAAGUAACAAAA<br>GAGGGUGUUGAUACGACCACAGUUGCGGCUCAACUUGCUGCA<br>GCAGGGGUUACUGGCGCCGAUAAGGACAAUACUAGCCUUGUA<br>AAACUAUCGUUUGAGGAUAAAAACGGUAAGGUUAUUGAUGG<br>UGGCUAUGCAGUGAAAAUGGGCGACGAUUUCUAUGCCGCUAC | 81 |

TABLE 16-continued

| Name | Sequence | SEQ ID NO: |
|---|---|---|
| | AUAUGAUGAGAAAACAGGUGCAAUUACUGCUAAAACCACUA<br>CUUAUACAGAUGGUACUGGCGUUGCUCAAACUGGAGCUGUG<br>AAAUUUGGUGGCGCAAAUGGUAAAUCUGAAGUUGUUACUGC<br>UACCGAUGGUAAGACUUACUUAGCAAGCGACCUUGACAAACA<br>UAACUUCAGAACAGGCGGUGAGCUUAAAGAGGUUAAUACAG<br>AUAAGACUGAAAACCCACUGCAGAAAAUUGAUGCUGCCUUGG<br>CACAGGUUGAUACACUUCGUUCUGACCUGGGUGCGGUUCAGA<br>ACCGUUUCAACUCCGCUAUCACCAACCUGGGCAAUACCGUAA<br>AUAACCUGUCUUCUGCCCGUAGCCGUAUCGAAGAUUCCGACU<br>ACGCAACCGAAGUCUCCAACAUGUCUCGCGCGCAGAUUCUGC<br>AGCAGGCCGGUACCUCCGUUCUGGCGCAGGCGAACCAGGUUC<br>CGCAAAACGUCCUCUCUUUACUGCGUUGAUAAUAGGCUGGAG<br>CCUCGGUGGCCAUGCUUCUUGCCCCUUGGGCCUCCCCCCAGC<br>CCCUCCUCCCCUUCCUGCACCCGUACCCCCGUGGUCUUUGAA<br>UAAAGUCUGAGUGGGCGGC | |
| ORF Sequence, NT | AUGGCACAAGUCAUUAAUACAAACAGCCUGUCGCUGUUGACC<br>CAGAAUAACCUGAACAAAUCCCAGUCCGCACUGGGCACUGCU<br>AUCGAGCGUUUGUCUUCCGGUCUGCGUAUCAACAGCGCGAAA<br>GACGAUGCGGCAGGACAGGCGAUUGCUAACCGUUUUACCGCG<br>AACAUCAAAGGUCUGACUCAGGCUUCCCGUAACGCUAACGAC<br>GGUAUCUCCAUUGCGCAGACCACUGAAGGCGCGCUGAACGAA<br>AUCAACAACAACCUGCAGCGUGUGCGUGAACUGGCGGUUCAG<br>UCUGCGAAUGGUACUAACUCCCAGUCUGACCUCGACUCCAUC<br>CAGGCUGAAAUCACCCAGCGCCUGAACGAAAUCGACCGUGUA<br>UCCGGCCAGACUCAGUUCAACGGCGUGAAAGUCCUGGCGCAG<br>GACAACACCCUGACCAUCCAGGUUGGUGCCAACGACGGUGAA<br>ACUAUCGAUAUUGAUUUAAAAGAAAUCAGCUCUAAAACACU<br>GGGACUUGAUAAGCUUAAUGUCCAAGAUGCCUACACCCCGAA<br>AGAAACUGCUGUAACCGUUGAUAAAACUACCUAUAAAAAUG<br>GUACAGAUCCUAUUACAGCCCAGAGCAAUACUGAUAUCCAAA<br>CUGCAAUUGGCGGUGGUGCAACGGGGGUUACUGGGGCUGAU<br>AUCAAAUUUAAAGAUGGUCAAUACUAUUUAGAUGUUAAAGG<br>CGGUGCUUCUGCUGGUGUUUAUAAAGCCACUUAUGAUGAAA<br>CUACAAAGAAAGUUAAUAUUGAUACGACUGAUAAAACUCCG<br>UUGGCAACUGCGGAAGCUACAGCUAUUCGGGGAACGGCCACU<br>AUAACCCACAACCAAAUUGCUGAAGUAACAAAAGAGGGUGU<br>UGAUACGACCACAGUUGCGGCUCAACUUGCUGCAGCAGGGGU<br>UACUGGCGCCGAUAAGGACAAUACUAGCCUUGUAAAACUAUC<br>GUUUGAGGAUAAAAACGGUAAGGUUAUUGAUGGUGGCUAUG<br>CAGUGAAAAUGGGCGACGAUUUCUAUGCCGCUACAUAUGAU<br>GAGAAAACAGGUGCAAUUACUGCUAAAACCACUACUUAUACA<br>GAUGGUACUGGCGUUGCUCAAACUGGAGCUGUGAAAUUUGG<br>UGGCGCAAAUGGUAAAUCUGAAGUUGUUACUGCUACCGAUG<br>GUAAGACUUACUUAGCAAGCGACCUUGACAAACAUAACUUCA<br>GAACAGGCGGUGAGCUUAAAGAGGUUAAUACAGAUAAGACU<br>GAAAACCCACUGCAGAAAAUUGAUGCUGCCUUGGCACAGGUU<br>GAUACACUUCGUUCUGACCUGGGUGCGGUUCAGAACCGUUUC<br>AACUCCGCUAUCACCAACCUGGGCAAUACCGUAAAUAACCUG<br>UCUUCUGCCCGUAGCCGUAUCGAAGAUUCCGACUACGCAACC<br>GAAGUCUCCAACAUGUCUCGCGCGCAGAUUCUGCAGCAGGCC<br>GGUACCUCCGUUCUGGCGCAGGCGAACCAGGUUCCGCAAAAC<br>GUCCUCUCUUUACUGCGU | 82 |
| mRNA Sequence (assumes T100 tail) | G*GGGAAAUAAGAGAGAAAAGAAGAGUAAGAAGAAAUAUAA<br>GAGCCACCAUGGCACAAGUCAUUAAUACAAACAGCCUGUCGC<br>UGUUGACCCAGAAUAACCUGAACAAAUCCCAGUCCGCACUGG<br>GCACUGCUAUCGAGCGUUUGUCUUCCGGUCUGCGUAUCAACA<br>GCGCGAAAGACGAUGCGGCAGGACAGGCGAUUGCUAACCGUU<br>UUACCGCGAACAUCAAAGGUCUGACUCAGGCUUCCCGUAACG<br>CUAACGACGGUAUCUCCAUUGCGCAGACCACUGAAGGCGCGC<br>UGAACGAAAUCAACAACAACCUGCAGCGUGUGCGUGAACUGG<br>CGGUUCAGUCUGCGAAUGGUACUAACUCCCAGUCUGACCUCG<br>ACUCCAUCCAGGCUGAAAUCACCCAGCGCCUGAACGAAAUCG<br>ACCGUGUAUCCGGCCAGACUCAGUUCAACGGCGUGAAAGUCC<br>UGGCGCAGGACAACACCCUGACCAUCCAGGUUGGUGCCAACG<br>ACGGUGAAACUAUCGAUAUUGAUUUAAAAGAAAUCAGCUCU<br>AAAACACUGGGACUUGAUAAGCUUAAUGUCCAAGAUGCCUAC<br>ACCCCGAAAGAAACUGCUGUAACCGUUGAUAAAACUACCUAU<br>AAAAAUGGUACAGAUCCUAUUACAGCCCAGAGCAAUACUGAU<br>AUCCAAACUGCAAUUGGCGGUGGUGCAACGGGGGUUACUGG<br>GGCUGAUAUCAAAUUUAAAGAUGGUCAAUACUAUUUAGAUG<br>UUAAAGGCGGUGCUUCUGCUGGUGUUUAUAAAGCCACUUAU<br>GAUGAAACUACAAAGAAAGUUAAUAUUGAUACGACUGAUAA<br>AACUCCGUUGGCAACUGCGGAAGCUACAGCUAUUCGGGGAAC<br>GGCCACUAUAACCCACAACCAAAUUGCUGAAGUAACAAAAGA<br>GGGUGUUGAUACGACCACAGUUGCGGCUCAACUUGCUGCAGC | 83 |

TABLE 16-continued

| Name | Sequence | SEQ ID NO: |
|---|---|---|
| | AGGGGUUACUGGCGCCGAUAAGGACAAUACUAGCCUUGUAA<br>AACUAUCGUUUGAGGAUAAAAACGGUAAGGUUAUUGAUGGU<br>GGCUAUGCAGUGAAAAUGGGCGACGAUUUCUAUGCCGCUACA<br>UAUGAUGAGAAAACAGGUGCAAUUACUGCUAAAACCACUAC<br>UUAUACAGAUGGUACUGGCGUUGCUCAAACUGGAGCUGUGA<br>AAUUUGGUGGCGCAAAUGGUAAAUCUGAAGUUGUUACUGCU<br>ACCGAUGGUAAGACUUACUUAGCAAGCGACCUUGACAAACAU<br>AACUUCAGAACAGGCGGUGAGCUUAAAGAGGUUAAUACAGA<br>UAAGACUGAAAACCCACUGCAGAAAAUUGAUGCUGCCUUGGC<br>ACAGGUUGAUACACUUCGUUCUGACCUGGGUGCGGUUCAGAA<br>CCGUUUCAACUCCGCUAUCACCAACCUGGGCAAUACCGUAAA<br>UAACCUGUCUUCUGCCCGUAGCCGUAUCGAAGAUUCCGACUA<br>CGCAACCGAAGUCUCCAACAUGUCUCGCGCGCAGAUUCUGCA<br>GCAGGCCGGUACCUCCGUUCUGGCGCAGGCGAACCAGGUUCC<br>GCAAAACGUCCUCUCUUUACUGCGUUGAUAAUAGGCUGGAGC<br>CUCGGUGGCCAUGCUUCUUGCCCCUUGGGCCUCCCCCCAGCC<br>CCUCCUCCCCUUCCUGCACCCGUACCCCCGUGGUCUUUGAAU<br>AAAGUCUGAGUGGGCGGCAAAAAAAAAAAAAAAAAAAAAAA<br>AAAAAAAAAAAAAAAAAAAAAAAAAAAAAAAAAAAAAAAAA<br>AAAAAAAAAAAAAAAAAAAAAAAAAAAAAAAAAAAAAUCUAG | |

TABLE 17

| Name | Sequence | SEQ ID NO: |
|---|---|---|
| | Flagellin Amino Acid Sequences | |
| ORF Sequence, AA | MAQVINTNSLSLLTQNNLNKSQSALGTAIERLSSGLRINSAKDDAA<br>GQAIANRFTANIKGLTQASRNANDGISIAQTTEGALNEINNNLQRV<br>RELAVQSANGTNSQSDLDSIQAEITQRLNEIDRVSGQTQFNGVKVL<br>AQDNTLTIQVGANDGETIDIDLKEISSKTLGLDKLNVQDAYTPKET<br>AVTVDKTTYKNGTDPITAQSNTDIQTAIGGGATGVTGADIKFKDG<br>QYYLDVKGGASAGVYKATYDETTKKVNIDTTDKTPLATAEATAI<br>RGTATITHNQIAEVTKEGVDTTTVAAQLAAAGVTGADKDNTSLV<br>KLSFEDKNGKVIDGGYAVKMGDDFYAATYDEKTGAITAKTTTYT<br>DGTGVAQTGAVKFGGANGKSEVVTATDGKTYLASDLDKHNFRT<br>GGELKEVNTDKTENPLQKIDAALAQVDTLRSDLGAVQNRFNSAIT<br>NLGNTVNNLSSARSRIEDSDYATEVSNMSRAQILQQAGTSVLAQA<br>NQVPQNVLSLLR | 54 |
| Flagellin-GS linker-circum-sporozoite protein (CSP) | MAQVINTNSLSLLTQNNLNKSQSALGTAIERLSSGLRINSAKDDAA<br>GQAIANRFTANIKGLTQASRNANDGISIAQTTEGALNEINNNLQRV<br>RELAVQSANSTNSQSDLDSIQAEITQRLNEIDRVSGQTQFNGVKVL<br>AQDNTLTIQVGANDGETIDIDLKQINSQTLGLDTLNVQQKYKVSD<br>TAATVTGYADTTIALDNSTFKASATGLGGTDQKIDGDLKFDDTTG<br>KYYAKVTVTGGTGKDGYYEVSVDKTNGEVTLAGGATSPLTGGLP<br>ATATEDVKNVQVANADLTEAKAALTAAGVTGTASVVKMSYTDN<br>NGKTIDGGLAVKVGDDYYSATQNKDGSISINTTKYTADDGTSKTA<br>LNKLGGADGKTEVVSIGGKTYAASKAEGHNFKAQPDLAEAAATT<br>TENPLQKIDAALAQVDTLRSDLGAVQNRFNSAITNLGNTVNNLTS<br>ARSRIEDSDYATEVSNMSRAQILQQAGTSVLAQANQVPQNVLSLL<br>RGGGGSGGGGSMMAPDPNANPNANPNANPNANPNANPNANPNA<br>NPNANPNANPNANPNANPNANPNANPNANPNANPNANPNANPN<br>ANPNANPNKNNQGNGQGHNMPNDPNRNVDENANANNAVKNNN<br>NEEPSDKHIEQYLKKIKNSISTEWSPCSVTCGNGIQVRIKPGSANKP<br>KDELDYENDIEKKICKMEKCSSVFNVVNS | 55 |
| Flagellin-RPVT linker-circum-sporozoite protein (CSP) | MMAPDPNANPNANPNANPNANPNANPNANPNANPNANPNANPN<br>ANPNANPNANPNANPNANPNANPNANPNANPNANPNANPNKNN<br>QGNGQGHNMPNDPNRNVDENANANNAVKNNNNEEPSDKHIEQY<br>LKKIKNSISTEWSPCSVTCGNGIQVRIKPGSANKPKDELDYENDIEK<br>KICKMEKCSSVFNVVNSRPVTMAQVINTNSLSLLTQNNLNKSQSA<br>LGTAIERLSSGLRINSAKDDAAGQAIANRFTANIKGLTQASRNAND<br>GISIAQTTEGALNEINNNLQRVRELAVQSANSTNSQSDLDSIQAEIT<br>QRLNEIDRVSGQTQFNGVKVLAQDNTLTIQVGANDGETIDIDLKQI<br>NSQTLGLDTLNVQQKYKVSDTAATVTGYADTTIALDNSTFKASAT<br>GLGGTDQKIDGDLKFDDTTGKYYAKVTVTGGTGKDGYYEVSVD<br>KTNGEVTLAGGATSPLTGGLPATATEDVKNVQVANADLTEAKAA<br>LTAAGVTGTASVVKMSYTDNNGKTIDGGLAVKVGDDYYSATQN | 56 |

TABLE 17-continued

| Name | Sequence | SEQ ID NO: |
|---|---|---|
| | KDGSISINTTKYTADDGTSKTALNKLGGADGKTEVVSIGGKTYAA<br>SKAEGHNFKAQPDLAEAAATTTENPLQKIDAALAQVDTLRSDLG<br>AVQNRFNSAITNLGNTVNNLTSARSRIEDSDYATEVSNMSRAQILQ<br>QAGTSVLAQANQVPQNVLSLLR | |

TABLE 18

Human Metapneumovirus Mutant Amino Acid Sequences

| Strain | Sequence | SEQ ID NO: |
|---|---|---|
| HMPV_SC_<br>DSCAV1_<br>4MMV | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAICKTIRLESEVTAINNALKKTNEAVSTLGNGVRV<br>LAFAVRELKDFVSKNLTRALNKNKCDIDDLKMAVSFSQFNRRFLNVVRQFS<br>DNAGITPAISLDLMTDAELARAVPNMPTSAGQIKLMLENRAMVRRKGFGIL<br>CGVYGSSVIYMVQLPIFGVIDTPCWIVKAAPSCSEKKGNYACLLREDQGWY<br>CQNAGSTVYYPNEKDCETRGDHVFCDTAAGINVAEQSKECNINISTTNYPC<br>KVSTGRHPISMVALSPLGALVACYKGVSCSIGSNRVGIIKQLNKGCSYITNQ<br>DADTVTIDNTVYQLSKVEGEQHVIKGRPVSSSFDPIKFPEDQFNVALDQVFE<br>NIENSQALVDQSNRILSSAEKGNTGFIIVIILIAVLGSSMILVSIFIIIKKTKKPTG<br>APPELSGVTNNGFIPHN | 85 |
| HMPV_SC_<br>DSTRIC_<br>4MMV | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAICKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGIL<br>CGVYGSSVIYMVQLPIFGVIDTPCWIVKAAPSCSEKKGNYACLLREDQGWY<br>CQNAGSTVYYPNEKDCETRGDHVFCDTAAGINVAEQSKECNINISTTNYPC<br>KVSTGRHPISMVALSPLGALVACYKGVSCSIGSNRVGIIKQLNKGCSYITNQ<br>DADTVTIDNTVYQLSKVEGEQHVIKGRPVSSSFDPIKFPEHQWHVALDQVFE<br>NIENSQALVDQSNRILSSAEKGNTGFIIVIILIAVLGSSMILVSIFIIIKKTKKPTG<br>APPELSGVTNNGFIPHN | 86 |
| HMPV_SC_<br>DM_Krarup_<br>T74LD185P | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 87 |
| HMPV_SC_<br>TM_Krarup_<br>T74LD185PD454N | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPENQFQVALDQVFENI<br>ENSQALVDQSNRILSSAEKGNTGFIIVIILIAVLGSSMILVSIFIIIKKTKKPTGA<br>PPELSGVTNNGFIPHN | 88 |
| HMPV_SC_<br>4M_Krarup_<br>T74LS170LD185P | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVLKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 89 |

TABLE 18-continued

Human Metapneumovirus Mutant Amino Acid Sequences

| Strain | Sequence | SEQ ID NO: |
|---|---|---|
| HMPV_SC_<br>5M_Krarup_<br>T74LS170LD185PD454N | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVLKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPENQFQVALDQVFENI<br>ENSQALVDQSNRILSSAEKGNTGFIIVIILIAVLGSSMILVSIFIIIKKTKKPTGA<br>PPELSGVTNNGFIPHN | 90 |
| HMPV_SC_<br>DM_Krarup_<br>E51PT74L | MSWKVVIIFSLLITPQHGLKESYLEESCSTITEGYLSVLRTGWYTNVFTLPVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 91 |
| HMPV_SC_<br>TM_Krarup_<br>E51PT74LD454N | MSWKVVIIFSLLITPQHGLKESYLEESCSTITEGYLSVLRTGWYTNVFTLPVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPENQFQVALDQVFENI<br>ENSQALVDQSNRILSSAEKGNTGFIIVIILIAVLGSSMILVSIFIIIKKTKKPTGA<br>PPELSGVTNNGFIPHN | 92 |
| HMPV_SC_<br>StabilizeAlpha_<br>T74L | MSWKVVIIFSLLITPQHGLKESYLEESCSTITEGYLSVLRTGWYTNVFTLEVG<br>DVENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 93 |
| HMPV_<br>SC_<br>StabilizeAlpha_<br>V55L | MSWKVVIIFSLLITPQHGLKESYLEESCSTITEGYLSVLRTGWYTNVFTLEVG<br>DLENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 94 |
| HMPV_<br>SC_<br>StabilizeAlpha_<br>S170L | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVLKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 95 |

TABLE 18-continued

| Human Metapneumovirus Mutant Amino Acid Sequences | | |
|---|---|---|
| Strain | Sequence | SEQ ID NO: |
| HMPV_<br>SC_<br>StabilizeAlpha_<br>T174W | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLWRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 96 |
| HMPV_SC_<br>4M_<br>StabilizeAlpha_<br>V55LT74LS170LT174W | MSWKVVIIFSLLITPQHGLKESYLEESCSTITEGYLSVLRTGWYTNVFTLEVG<br>DLENLTCSDGPSLIKTELDLLKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVLKNLWRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 97 |
| HMPV_<br>ProlineStab_<br>E51P | MSWKVVIIFSLLITPQHGLKESYLEESCSTITEGYLSVLRTGWYTNVFTLPVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 98 |
| HMPV_<br>ProlineStab_<br>D185P | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIPDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 99 |
| HMPV_<br>ProlineStab_<br>D183P | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCPIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 100 |
| HMPV_<br>ProlineStab_<br>E131P | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLPSEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 101 |

TABLE 18-continued

| Strain | Sequence | SEQ ID NO: |
|---|---|---|
| Human Metapneumovirus Mutant Amino Acid Sequences | | |
| HMPV_ ProlineStab_ D447P | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFPPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 102 |
| HMPV_Trimer Repulsion D454N | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPENQFQVALDQVFENI<br>ENSQALVDQSNRILSSAEKGNTGFIIVIILIAVLGSSMILVSIFIIIKKTKKPTGA<br>PPELSGVTNNGFIPHN | 103 |
| HMPV_Trimer Repulsion E453N | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQFNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPQDQFQVALDQVFENI<br>ENSQALVDQSNRILSSAEKGNTGFIIVIILIAVLGSSMILVSIFIIIKKTKKPTGA<br>PPELSGVTNNGFIPHN | 104 |
| HMPV_Stabilize AlphaF196W | MSWKVVIIFSLLITPQHGLKESYLEESCSTITEGYLSVLRTGWYTNVFTLEVG<br>DVENLTCSDGPSLIKTELDLTKSALRELKTVSADQLAREEQIENPGSGSFVLG<br>AIALGVAAAAAVTAGVAIAKTIRLESEVTAINNALKKTNEAVSTLGNGVRV<br>LATAVRELKDFVSKNLTRAINKNKCDIDDLKMAVSFSQWNRRFLNVVRQFS<br>DNAGITPAISLDLMTDAELARAVPNMPTSAGQIKLMLENRAMVRRKGFGILI<br>GVYGSSVIYMVQLPIFGVIDTPCWIVKAAPSCSEKKGNYACLLREDQGWYC<br>QNAGSTVYYPNEKDCETRGDHVFCDTAAGINVAEQSKECNINISTTNYPCK<br>VSTGRHPISMVALSPLGALVACYKGVSCSIGSNRVGIIKQLNKGCSYITNQD<br>ADTVTIDNTVYQLSKVEGEQHVIKGRPVSSSFDPIKFPEDQFQVALDQVFENI<br>ENSQALVDQSNRILSSAEKGNTGFIIVIILIAVLGSSMILVSIFIIIKKTKKPTGA<br>PPELSGVTNNGFIPHN | 105 |

TABLE 19

| Strain | Nucleic Acid Sequence | SEQ ID NO: |
|---|---|---|
| Human Metapneumovirus Mutant Nucleic Acid Sequences | | |
| HMPV_SC_ DSCAV1_4MMV | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCTGCAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CTTTGCCGTGCGCGAGCTGAAGGACTTCGTGTCCAAGAAC<br>CTGACACGGGCCCTGAACAAGAACAAGTGCGACATCGAC<br>GACCTGAAGATGGCCGTGTCCTTTAGCCAGTTCAACCGGC<br>GGTTTCTGAACGTCGTGCGGCAGTTTAGCGACAACGCCGG | 106 |

TABLE 19-continued

| Strain | Nucleic Acid Sequence | SEQ ID NO: |
|---|---|---|
| | AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGTGTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCAACGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| HMPV_SC_ DSTRIC_4MMV | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCTGCAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGTGTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGCACCAGTGGCATGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | 107 |
| HMPV_SC_DM_ Krarup_ T74LD185P | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC | 108 |

TABLE 19-continued

| Strain | Nucleic Acid Sequence | SEQ ID NO: |
|---|---|---|
| | AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCCCTGA<br>CCTGAAGATGGCCGTGTCCTTTAGCCAGTTCAACCGGCGG<br>TTTCTGAACGTCGTGCGGCAGTTTAGCGACAACGCCGGAA<br>TCACACCAGCCATCAGCCTGGACCTGATGACAGATGCTGA<br>GCTGGCTAGAGCCGTGCCTAACATGCCTACATCTGCCGGC<br>CAGATCAAGCTGATGCTCGAGAATAGAGCCATGGTCCGAC<br>GGAAAGGCTTCGGCATTCTGATTGGCGTGTACGGCAGCAG<br>CGTGATCTATATGGTGCAGCTGCCTATCTTCGGCGTGATCG<br>ACACACCCTGCTGGATTGTGAAGGCCGCTCCTAGCTGTAG<br>CGAGAAGAAGGGCAATTACGCCTGCCTGCTGAGAGAGGA<br>CCAAGGCTGGTATTGTCAGAACGCCGGCAGCACCGTGTAC<br>TACCCTAACGAGAAGGACTGCGAGACAAGAGGCGACCAC<br>GTGTTCTGTGATACCGCCGCTGGAATCAATGTGGCCGAGC<br>AGAGCAAAGAGTGCAACATCAACATCAGCACCACCAACT<br>ATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | |
| HMPV_SC_TM_<br>Krarup_<br>T74LD185PD454N | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCCCTGA<br>CCTGAAGATGGCCGTGTCCTTTAGCCAGTTCAACCGGCGG<br>TTTCTGAACGTCGTGCGGCAGTTTAGCGACAACGCCGGAA<br>TCACACCAGCCATCAGCCTGGACCTGATGACAGATGCTGA<br>GCTGGCTAGAGCCGTGCCTAACATGCCTACATCTGCCGGC<br>CAGATCAAGCTGATGCTCGAGAATAGAGCCATGGTCCGAC<br>GGAAAGGCTTCGGCATTCTGATTGGCGTGTACGGCAGCAG<br>CGTGATCTATATGGTGCAGCTGCCTATCTTCGGCGTGATCG<br>ACACACCCTGCTGGATTGTGAAGGCCGCTCCTAGCTGTAG<br>CGAGAAGAAGGGCAATTACGCCTGCCTGCTGAGAGAGGA<br>CCAAGGCTGGTATTGTCAGAACGCCGGCAGCACCGTGTAC<br>TACCCTAACGAGAAGGACTGCGAGACAAGAGGCGACCAC<br>GTGTTCTGTGATACCGCCGCTGGAATCAATGTGGCCGAGC<br>AGAGCAAAGAGTGCAACATCAACATCAGCACCACCAACT<br>ATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGAACCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 109 |

TABLE 19-continued

| Strain | Nucleic Acid Sequence | SEQ ID NO: |
|---|---|---|
| HMPV_SC_4M_ Krarup_ T74LS170LD185P | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC AGGCGTGGCCATCGCTAAGACCATCAGACTGGAAAGCGA AGTGACCGCCATCAACAACGCCCTGAAGAAGACAAACGA GGCCGTCAGCACACTCGGCAATGGCGTTAGAGTGCTGGCC ACAGCCGTGCGCGAGCTGAAGGACTTCGTGCTTAAGAACC TGACACGGGCCATTAACAAGAACAAGTGCGACATCCCTGA CCTGAAGATGGCCGTGTCCTTTAGCCAGTTCAACCGGCGG TTTCTGAACGTCGTGCGGCAGTTTAGCGACAACGCCGGAA TCACACCAGCCATCAGCCTGGACCTGATGACAGATGCTGA GCTGGCTAGAGCCGTGCCTAACATGCCTACATCTGCCGGC CAGATCAAGCTGATGCTCGAGAATAGAGCCATGGTCCGAC GGAAAGGCTTCGGCATTCTGATTGGCGTGTACGGCAGCAG CGTGATCTATATGGTGCAGCTGCCTATCTTCGGCGTGATCG ACACACCCTGCTGGATTGTGAAGGCCGCTCCTAGCTGTAG CGAGAAGAAGGGCAATTACGCCTGCCTGCTGAGAGAGGA CCAAGGCTGGTATTGTCAGAACGCCGGCAGCACCGTGTAC TACCCTAACGAGAAGGACTGCGAGACAAGAGGCGACCAC GTGTTCTGTGATACCGCCGCTGGAATCAATGTGGCCGAGC AGAGCAAAGAGTGCAACATCAACATCAGCACCACCAACT ATCCCTGCAAGGTGTCCACCGGCAGGCACCCTATTTCTAT GGTGGCTCTGTCTCCTCTGGGAGCCCTGGTGGCTTGTTATA AGGGCGTGTCCTGTAGCATCGGCAGCAACAGAGTGGGCAT CATCAAGCAGCTGAACAAGGGCTGCAGCTACATCACCAAC CAGGACGCCGATACCGTGACCATCGACAACACCGTGTATC AGCTGAGCAAGGTGGAAGGCGAACAGCACGTGATCAAGG GCAGACCTGTGTCCAGCAGCTTCGACCCTATCAAGTTCCC TGAGGATCAGTTCCAGGTGGCCCTGGACCAGGTGTTCGAG AACATCGAGAATTCCCAGGCTCTGGTGGACCAGTCCAACA GAATCCTGTCTAGCGCCGAGAAGGGAAACACCGGCTTCAT CATCGTGATCATCCTGATCGCCGTGCTGGGCAGCTCCATG ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | 110 |
| HMPV_SC_5M_ Krarup_ T74LS170LD185PD454N | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC AGGCGTGGCCATCGCTAAGACCATCAGACTGGAAAGCGA AGTGACCGCCATCAACAACGCCCTGAAGAAGACAAACGA GGCCGTCAGCACACTCGGCAATGGCGTTAGAGTGCTGGCC ACAGCCGTGCGCGAGCTGAAGGACTTCGTGCTTAAGAACC TGACACGGGCCATTAACAAGAACAAGTGCGACATCCCTGA CCTGAAGATGGCCGTGTCCTTTAGCCAGTTCAACCGGCGG TTTCTGAACGTCGTGCGGCAGTTTAGCGACAACGCCGGAA TCACACCAGCCATCAGCCTGGACCTGATGACAGATGCTGA GCTGGCTAGAGCCGTGCCTAACATGCCTACATCTGCCGGC CAGATCAAGCTGATGCTCGAGAATAGAGCCATGGTCCGAC GGAAAGGCTTCGGCATTCTGATTGGCGTGTACGGCAGCAG CGTGATCTATATGGTGCAGCTGCCTATCTTCGGCGTGATCG ACACACCCTGCTGGATTGTGAAGGCCGCTCCTAGCTGTAG CGAGAAGAAGGGCAATTACGCCTGCCTGCTGAGAGAGGA CCAAGGCTGGTATTGTCAGAACGCCGGCAGCACCGTGTAC TACCCTAACGAGAAGGACTGCGAGACAAGAGGCGACCAC GTGTTCTGTGATACCGCCGCTGGAATCAATGTGGCCGAGC AGAGCAAAGAGTGCAACATCAACATCAGCACCACCAACT ATCCCTGCAAGGTGTCCACCGGCAGGCACCCTATTTCTAT GGTGGCTCTGTCTCCTCTGGGAGCCCTGGTGGCTTGTTATA AGGGCGTGTCCTGTAGCATCGGCAGCAACAGAGTGGGCAT CATCAAGCAGCTGAACAAGGGCTGCAGCTACATCACCAAC CAGGACGCCGATACCGTGACCATCGACAACACCGTGTATC AGCTGAGCAAGGTGGAAGGCGAACAGCACGTGATCAAGG GCAGACCTGTGTCCAGCAGCTTCGACCCTATCAAGTTCCC | 111 |

TABLE 19-continued

| Strain | Nucleic Acid Sequence | SEQ ID NO: |
|---|---|---|
| | TGAGAACCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | |
| HMPV_SC_DM_<br>Krarup_<br>E51PT74L | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGCCTGTGGGC<br>GACGTCGAGAATCTGACATGCTCTGATGGCCCTAGCCTGA<br>TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 112 |
| HMPV_SC_TM_<br>Krarup_<br>E51PT74LD454N | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGCCTGTGGGC<br>GACGTCGAGAATCTGACATGCTCTGATGGCCCTAGCCTGA<br>TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC | 113 |

TABLE 19-continued

| Strain | Nucleic Acid Sequence | SEQ ID NO: |
|---|---|---|
| | TATCCCTGCAAGGTGTCCACCGGCAGGCACCCTATTTCTAT GGTGGCTCTGTCTCCTCTGGGAGCCCTGGTGGCTTGTTATA AGGGCGTGTCCTGTAGCATCGGCAGCAACAGAGTGGGCAT CATCAAGCAGCTGAACAAGGGCTGCAGCTACATCACCAAC CAGGACGCCGATACCGTGACCATCGACAACACCGTGTATC AGCTGAGCAAGGTGGAAGGCGAACAGCACGTGATCAAGG GCAGACCTGTGTCCAGCAGCTTCGACCCTATCAAGTTCCC TGAGAACCAGTTCCAGGTGGCCCTGGACCAGGTGTTCGAG AACATCGAGAATTCCCAGGCTCTGGTGGACCAGTCCAACA GAATCCTGTCTAGCGCCGAGAAGGGAAACACCGGCTTCAT CATCGTGATCATCCTGATCGCCGTGCTGGGCAGCTCCATG ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | |
| HMPV_SC_ StabilizeAlpha_ T74L | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGCTCAAGAGCGCCCTGAGAGA ACTCAAGACCGTGTCTGCCGATCAGCTGGCCAGAGAGGAA CAGATCGAGAATCCTGGCAGCGGCAGCTTTGTGCTGGGAG CCATTGCTCTTGGAGTGGCTGCTGCTGCAGCTGTTACAGC AGGCGTGGCCATCGCTAAGACCATCAGACTGGAAAGCGA AGTGACCGCCATCAACAACGCCCTGAAGAAGACAAACGA GGCCGTCAGCACACTCGGCAATGGCGTTAGAGTGCTGGCC ACAGCCGTGCGCGAGCTGAAGGACTTCGTGTCCAAGAACC TGACACGGGCCATTAACAAGAACAAGTGCGACATCGACG ACCTGAAGATGGCCGTGTCCTTTAGCCAGTTCAACCGGCG GTTTCTGAACGTCGTGCGGCAGTTTAGCGACAACGCCGGA ATCACACCAGCCATCAGCCTGGACCTGATGACAGATGCTG AGCTGGCTAGAGCCGTGCCTAACATGCCTACATCTGCCGG CCAGATCAAGCTGATGCTCGAGAATAGAGCCATGGTCCGA CGGAAAGGCTTCGGCATTCTGATTGGCGTGTACGGCAGCA GCGTGATCTATATGGTGCAGCTGCCTATCTTCGGCGTGATC GACACACCCTGCTGGATTGTGAAGGCCGCTCCTAGCTGTA GCGAGAAGAAGGGCAATTACGCCTGCCTGCTGAGAGAGG ACCAAGGCTGGTATTGTCAGAACGCCGGCAGCACCGTGTA CTACCCTAACGAGAAGGACTGCGAGACAAGAGGCGACCA CGTGTTCTGTGATACCGCCGCTGGAATCAATGTGGCCGAG CAGAGCAAAGAGTGCAACATCAACATCAGCACCACCAAC TATCCCTGCAAGGTGTCCACCGGCAGGCACCCTATTTCTAT GGTGGCTCTGTCTCCTCTGGGAGCCCTGGTGGCTTGTTATA AGGGCGTGTCCTGTAGCATCGGCAGCAACAGAGTGGGCAT CATCAAGCAGCTGAACAAGGGCTGCAGCTACATCACCAAC CAGGACGCCGATACCGTGACCATCGACAACACCGTGTATC AGCTGAGCAAGGTGGAAGGCGAACAGCACGTGATCAAGG GCAGACCTGTGTCCAGCAGCTTCGACCCTATCAAGTTCCC TGAGGATCAGTTCCAGGTGGCCCTGGACCAGGTGTTCGAG AACATCGAGAATTCCCAGGCTCTGGTGGACCAGTCCAACA GAATCCTGTCTAGCGCCGAGAAGGGAAACACCGGCTTCAT CATCGTGATCATCCTGATCGCCGTGCTGGGCAGCTCCATG ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | 114 |
| HMPV_ SC_ StabilizeAlpha_ V55L | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACCTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC | 115 |

TABLE 19-continued

| Strain | Nucleic Acid Sequence | SEQ ID NO: |
|---|---|---|
| | AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| HMPV_SC_ StabilizeAlpha_ S170L | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGCTTAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | 116 |
| HMPV_SC_ StabilizeAlpha_ T174W | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC | 117 |

TABLE 19-continued

| Strain | Nucleic Acid Sequence | SEQ ID NO: |
|---|---|---|
| | CTGTGGCGGGCCATTAACAAGAACAAGTGCGACATCGAC<br>GACCTGAAGATGGCCGTGTCCTTTAGCCAGTTCAACCGGC<br>GGTTTCTGAACGTCGTGCGGCAGTTTAGCGACAACGCCGG<br>AATCACACCAGCCATCAGCCTGGACCTGATGACAGATGCT<br>GAGCTGGCTAGAGCCGTGCCTAACATGCCTACATCTGCCG<br>GCCAGATCAAGCTGATGCTCGAGAATAGAGCCATGGTCCG<br>ACGGAAAGGCTTCGGCATTCTGATTGGCGTGTACGGCAGC<br>AGCGTGATCTATATGGTGCAGCTGCCTATCTTCGGCGTGA<br>TCGACACACCCTGCTGGATTGTGAAGGCCGCTCCTAGCTG<br>TAGCGAGAAGAAGGGCAATTACGCCTGCCTGCTGAGAGA<br>GGACCAAGGCTGGTATTGTCAGAACGCCGGCAGCACCGTG<br>TACTACCCTAACGAGAAGGACTGCGAGACAAGAGGCGAC<br>CACGTGTTCTGTGATACCGCCGCTGGAATCAATGTGGCCG<br>AGCAGAGCAAAGAGTGCAACATCAACATCAGCACCACCA<br>ACTATCCCTGCAAGGTGTCCACCGGCAGGCACCCTATTTC<br>TATGGTGGCTCTGTCTCCTCTGGGAGCCCTGGTGGCTTGTT<br>ATAAGGGCGTGTCCTGTAGCATCGGCAGCAACAGAGTGG<br>GCATCATCAAGCAGCTGAACAAGGGCTGCAGCTACATCAC<br>CAACCAGGACGCCGATACCGTGACCATCGACAACACCGTG<br>TATCAGCTGAGCAAGGTGGAAGGCGAACAGCACGTGATC<br>AAGGGCAGACCTGTGTCCAGCAGCTTCGACCCTATCAAGT<br>TCCCTGAGGATCAGTTCCAGGTGGCCCTGGACCAGGTGTT<br>CGAGAACATCGAGAATTCCCAGGCTCTGGTGGACCAGTCC<br>AACAGAATCCTGTCTAGCGCCGAGAAGGGAAACACCGGC<br>TTCATCATCGTGATCATCCTGATCGCCGTGCTGGGCAGCTC<br>CATGATCCTGGTGTCCATCTTCATCATTATCAAGAAGACC<br>AAGAAGCCCACCGGCGCTCCTCCAGAACTGAGCGGAGTG<br>ACCAACAATGGCTTCATCCCTCACAAC | |
| HMPV_SC_4M_<br>StabalizeAlpha_<br>V55LT74LS170LT174W | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACCTCGAGAATCTGACATGCTCTGATGGCCCTAGCCTGA<br>TCAAGACCGAGCTGGATCTGCTCAAGAGCGCCCTGAGAGA<br>ACTCAAGACCGTGTCTGCCGATCAGCTGGCCAGAGAGGAA<br>CAGATCGAGAATCCTGGCAGCGGCAGCTTTGTGCTGGGAG<br>CCATTGCTCTTGGAGTGGCTGCTGCTGCAGCTGTTACAGC<br>AGGCGTGGCCATCGCTAAGACCATCAGACTGGAAAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGCTTAAGAACC<br>TGTGGCGGGCCATTAACAAGAACAAGTGCGACATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 118 |
| HMPV_<br>ProlineStab_<br>E51P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGCCTGTGGGC<br>GACGTCGAGAATCTGACATGCTCTGATGGCCCTAGCCTGA<br>TCAAGACCGAGCTGGATCTGACCAAGAGCGCCCTGAGAG | 119 |

TABLE 19-continued

| Strain | Nucleic Acid Sequence | SEQ ID NO: |
|---|---|---|
| | AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCGACATCGAC<br>GACCTGAAGATGGCCGTGTCCTTTAGCCAGTTCAACCGGC<br>GGTTTCTGAACGTCGTGCGGCAGTTTAGCGACAACGCCGG<br>AATCACACCAGCCATCAGCCTGGACCTGATGACAGATGCT<br>GAGCTGGCTAGAGCCGTGCCTAACATGCCTACATCTGCCG<br>GCCAGATCAAGCTGATGCTCGAGAATAGAGCCATGGTCCG<br>ACGGAAAGGCTTCGGCATTCTGATTGGCGTGTACGGCAGC<br>AGCGTGATCTATATGGTGCAGCTGCCTATCTTCGGCGTGA<br>TCGACACACCCTGCTGGATTGTGAAGGCCGCTCCTAGCTG<br>TAGCGAGAAGAAGGGCAATTACGCCTGCCTGCTGAGAGA<br>GGACCAAGGCTGGTATTGTCAGAACGCCGGCAGCACCGTG<br>TACTACCCTAACGAGAAGGACTGCGAGACAAGAGGCGAC<br>CACGTGTTCTGTGATACCGCCGCTGGAATCAATGTGGCCG<br>AGCAGAGCAAAGAGTGCAACATCAACATCAGCACCACCA<br>ACTATCCCTGCAAGGTGTCCACCGGCAGGCACCCTATTTC<br>TATGGTGGCTCTGTCTCCTCTGGGAGCCCTGGTGGCTTGTT<br>ATAAGGGCGTGTCCTGTAGCATCGGCAGCAACAGAGTGG<br>GCATCATCAAGCAGCTGAACAAGGGCTGCAGCTACATCAC<br>CAACCAGGACGCCGATACCGTGACCATCGACAACACCGTG<br>TATCAGCTGAGCAAGGTGGAAGGCGAACAGCACGTGATC<br>AAGGGCAGACCTGTGTCCAGCAGCTTCGACCCTATCAAGT<br>TCCCTGAGGATCAGTTCCAGGTGGCCCTGGACCAGGTGTT<br>CGAGAACATCGAGAATTCCCAGGCTCTGGTGGACCAGTCC<br>AACAGAATCCTGTCTAGCGCCGAGAAGGGAAACACCGGC<br>TTCATCATCGTGATCATCCTGATCGCCGTGCTGGGCAGCTC<br>CATGATCCTGGTGTCCATCTTCATCATTATCAAGAAGACC<br>AAGAAGCCCACCGGCGCTCCTCCAGAACTGAGCGGAGTG<br>ACCAACAATGGCTTCATCCCTCACAAC | |
| HMPV_<br>ProlineStab_<br>D185P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCGACATCCCTG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 120 |

TABLE 19-continued

| Strain | Nucleic Acid Sequence | SEQ ID NO: |
|---|---|---|
| HMPV_ ProlineStab_ D183P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGGAAAGCG<br>AAGTGACCGCCATCAACAACGCCCTGAAGAAGACAAACG<br>AGGCCGTCAGCACACTCGGCAATGGCGTTAGAGTGCTGGC<br>CACAGCCGTGCGCGAGCTGAAGGACTTCGTGTCCAAGAAC<br>CTGACACGGGCCATTAACAAGAACAAGTGCCCTATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC<br>TGAGGATCAGTTCCAGGTGGCCCTGGACCAGGTGTTCGAG<br>AACATCGAGAATTCCCAGGCTCTGGTGGACCAGTCCAACA<br>GAATCCTGTCTAGCGCCGAGAAGGGAAACACCGGCTTCAT<br>CATCGTGATCATCCTGATCGCCGTGCTGGGCAGCTCCATG<br>ATCCTGGTGTCCATCTTCATCATTATCAAGAAGACCAAGA<br>AGCCCACCGGCGCTCCTCCAGAACTGAGCGGAGTGACCAA<br>CAATGGCTTCATCCCTCACAAC | 121 |
| HMPV_ ProlineStab_ E131P | ATGAGCTGGAAGGTGGTCATCATCTTCAGCCTGCTGATCA<br>CACCTCAGCACGGCCTGAAAGAGAGCTACCTGGAAGAGT<br>CCTGCAGCACCATCACAGAGGGCTACCTGTCTGTGCTGAG<br>AACCGGCTGGTACACCAACGTGTTCACACTGGAAGTGGGC<br>GACGTCGAGAATCTGACATGCTCTGATGGCCCTAGCCTGA<br>TCAAGACCGAGCTGGATCTGACCAAGAGCGCCCTGAGAG<br>AACTCAAGACCGTGTCTGCCGATCAGCTGGCCAGAGAGGA<br>ACAGATCGAGAATCCTGGCAGCGGCAGCTTTGTGCTGGGA<br>GCCATTGCTCTTGGAGTGGCTGCTGCTGCAGCTGTTACAG<br>CAGGCGTGGCCATCGCTAAGACCATCAGACTGCCTAGCGA<br>AGTGACCGCCATCAACAACGCCCTGAAGAAGACAAACGA<br>GGCCGTCAGCACACTCGGCAATGGCGTTAGAGTGCTGGCC<br>ACAGCCGTGCGCGAGCTGAAGGACTTCGTGTCCAAGAACC<br>TGACACGGGCCATTAACAAGAACAAGTGCGACATCGACG<br>ACCTGAAGATGGCCGTGTCCTTTAGCCAGTTCAACCGGCG<br>GTTTCTGAACGTCGTGCGGCAGTTTAGCGACAACGCCGGA<br>ATCACACCAGCCATCAGCCTGGACCTGATGACAGATGCTG<br>AGCTGGCTAGAGCCGTGCCTAACATGCCTACATCTGCCGG<br>CCAGATCAAGCTGATGCTCGAGAATAGAGCCATGGTCCGA<br>CGGAAAGGCTTCGGCATTCTGATTGGCGTGTACGGCAGCA<br>GCGTGATCTATATGGTGCAGCTGCCTATCTTCGGCGTGATC<br>GACACACCCTGCTGGATTGTGAAGGCCGCTCCTAGCTGTA<br>GCGAGAAGAAGGGCAATTACGCCTGCCTGCTGAGAGAGG<br>ACCAAGGCTGGTATTGTCAGAACGCCGGCAGCACCGTGTA<br>CTACCCTAACGAGAAGGACTGCGAGACAAGAGGCGACCA<br>CGTGTTCTGTGATACCGCCGCTGGAATCAATGTGGCCGAG<br>CAGAGCAAAGAGTGCAACATCAACATCAGCACCACCAAC<br>TATCCCTGCAAGGTGTCCACCGGCAGGCACCCTATTTCTAT<br>GGTGGCTCTGTCTCCTCTGGGAGCCCTGGTGGCTTGTTATA<br>AGGGCGTGTCCTGTAGCATCGGCAGCAACAGAGTGGGCAT<br>CATCAAGCAGCTGAACAAGGGCTGCAGCTACATCACCAAC<br>CAGGACGCCGATACCGTGACCATCGACAACACCGTGTATC<br>AGCTGAGCAAGGTGGAAGGCGAACAGCACGTGATCAAGG<br>GCAGACCTGTGTCCAGCAGCTTCGACCCTATCAAGTTCCC | 122 |

TABLE 19-continued

| Strain | Nucleic Acid Sequence | SEQ ID NO: |
|---|---|---|
| | TGAGGATCAGTTCCAGGTGGCCCTGGACCAGGTGTTCGAG AACATCGAGAATTCCCAGGCTCTGGTGGACCAGTCCAACA GAATCCTGTCTAGCGCCGAGAAGGGAAACACCGGCTTCAT CATCGTGATCATCCTGATCGCCGTGCTGGGCAGCTCCATG ATCCTGGTGTCCATCTTCATCATTATCAAGAAGACCAAGA AGCCCACCGGCGCTCCTCCAGAACTGAGCGGAGTGACCAA CAATGGCTTCATCCCTCACAAC | |
| HMPV_ ProlineStab_ D447P | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCCCACCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | 123 |
| HMPV_Trimer- RepulsionD454N | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA | 124 |

TABLE 19-continued

| Strain | Nucleic Acid Sequence | SEQ ID NO: |
|---|---|---|
| | ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGAACCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| HMPV_Trimer-RepulsionE453N | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTTCAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTCAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | 125 |
| HMPV_Stabilize AlphaF196W | ATGAGCTGGAAGGTGGTCATCATCTTCAGCCTGCTGATCA CACCTCAGCACGGCCTGAAAGAGAGCTACCTGGAAGAGT CCTGCAGCACCATCACAGAGGGCTACCTGTCTGTGCTGAG AACCGGCTGGTACACCAACGTGTTCACACTGGAAGTGGGC GACGTCGAGAATCTGACATGCTCTGATGGCCCTAGCCTGA TCAAGACCGAGCTGGATCTGACCAAGAGCGCCCTGAGAG AACTCAAGACCGTGTCTGCCGATCAGCTGGCCAGAGAGGA ACAGATCGAGAATCCTGGCAGCGGCAGCTTTGTGCTGGGA GCCATTGCTCTTGGAGTGGCTGCTGCTGCAGCTGTTACAG CAGGCGTGGCCATCGCTAAGACCATCAGACTGGAAAGCG AAGTGACCGCCATCAACAACGCCCTGAAGAAGACAAACG AGGCCGTCAGCACACTCGGCAATGGCGTTAGAGTGCTGGC CACAGCCGTGCGCGAGCTGAAGGACTTCGTGTCCAAGAAC CTGACACGGGCCATTAACAAGAACAAGTGCGACATCGAC GACCTGAAGATGGCCGTGTCCTTTAGCCAGTGGAACCGGC GGTTTCTGAACGTCGTGCGGCAGTTTAGCGACAACGCCGG AATCACACCAGCCATCAGCCTGGACCTGATGACAGATGCT GAGCTGGCTAGAGCCGTGCCTAACATGCCTACATCTGCCG GCCAGATCAAGCTGATGCTCGAGAATAGAGCCATGGTCCG ACGGAAAGGCTTCGGCATTCTGATTGGCGTGTACGGCAGC | 126 |

TABLE 19-continued

| Strain | Nucleic Acid Sequence | SEQ ID NO: |
|---|---|---|
| | AGCGTGATCTATATGGTGCAGCTGCCTATCTTCGGCGTGA TCGACACACCCTGCTGGATTGTGAAGGCCGCTCCTAGCTG TAGCGAGAAGAAGGGCAATTACGCCTGCCTGCTGAGAGA GGACCAAGGCTGGTATTGTCAGAACGCCGGCAGCACCGTG TACTACCCTAACGAGAAGGACTGCGAGACAAGAGGCGAC CACGTGTTCTGTGATACCGCCGCTGGAATCAATGTGGCCG AGCAGAGCAAAGAGTGCAACATCAACATCAGCACCACCA ACTATCCCTGCAAGGTGTCCACCGGCAGGCACCCTATTTC TATGGTGGCTCTGTCTCCTCTGGGAGCCCTGGTGGCTTGTT ATAAGGGCGTGTCCTGTAGCATCGGCAGCAACAGAGTGG GCATCATCAAGCAGCTGAACAAGGGCTGCAGCTACATCAC CAACCAGGACGCCGATACCGTGACCATCGACAACACCGTG TATCAGCTGAGCAAGGTGGAAGGCGAACAGCACGTGATC AAGGGCAGACCTGTGTCCAGCAGCTTCGACCCTATCAAGT TCCCTGAGGATCAGTTCCAGGTGGCCCTGGACCAGGTGTT CGAGAACATCGAGAATTCCCAGGCTCTGGTGGACCAGTCC AACAGAATCCTGTCTAGCGCCGAGAAGGGAAACACCGGC TTCATCATCGTGATCATCCTGATCGCCGTGCTGGGCAGCTC CATGATCCTGGTGTCCATCTTCATCATTATCAAGAAGACC AAGAAGCCCACCGGCGCTCCTCCAGAACTGAGCGGAGTG ACCAACAATGGCTTCATCCCTCACAAC | |
| | Human Metapneumovirus mRNA Sequences | |
| HMPV_SC_ DSCAV1_4MMV | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCUGCAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCUUUGCCGUGCGCGAGCUGAAGGACUUC GUGUCCAAGAACCUGACACGGGCCCUGAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GUGUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCAACGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | 127 |
| HMPV_SC_ DSURIC_4MMV | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCUGCAAGACCAUCAGA | 128 |

TABLE 19-continued

| Strain | Nucleic Acid Sequence | SEQ ID NO: |
|---|---|---|
| | CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCGACGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GUGUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGCACCAGUGGCAUGUGGCCCUGGACCAGGUGUUCGA<br>GAACAUCGAGAAUUCCCAGGCUCUGGUGGACCAGUCCAA<br>CAGAAUCCUGUCUAGCGCCGAGAAGGGAAACACCGGCUU<br>CAUCAUCGUGAUCAUCCUGAUCGCCGUGCUGGGCAGCUC<br>CAUGAUCCUGGUGUCCAUCUUCAUCAUUAUCAAGAAGAC<br>CAAGAAGCCCACCGGCGCUCCUCCAGAACUGAGCGGAGU<br>GACCAACAAUGGCUUCAUCCCUCACAAC | |
| HMPV_SC_DM_<br>Krarup_<br>U74LD185P | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCCCUGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | 129 |

TABLE 19-continued

| Strain | Nucleic Acid Sequence | SEQ ID NO: |
|---|---|---|
| HMPV_SC_UM_ Krarup_ U74LD185PD454N | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCCCUGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGAACCAGUUCCAGGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | 130 |
| HMPV_SC_4M_ Krarup_ U74LS170LD185P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGCUUAAGAACCUGACACGGGCCAUUAACAAGAACAA GUGCGACAUCCCUGACCUGAAGAUGGCCGUGUCCUUUAG CCAGUUCAACCGGCGGUUUCUGAACGUCGUGCGGCAGUU UAGCGACAACGCCGGAAUCACACCAGCCAUCAGCCUGGA CCUGAUGACAGAUGCUGAGCUGGCUAGAGCCGUGCCUAA CAUGCCUACAUCUGCCGGCCAGAUCAAGCUGAUGCUCGA GAAUAGAGCCAUGGUCCGACGGAAAGGCUUCGGCAUUC UGAUUGGCGUGUACGGCAGCAGCGUGAUCUAUAUGGUG CAGCUGCCUAUCUUCGGCGUGAUCGACACACCCUGCUGG AUUGUGAAGGCCGCUCCUAGCUGUAGCGAGAAGAAGGG CAAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG | 131 |

TABLE 19-continued

| Strain | Nucleic Acid Sequence | SEQ ID NO: |
|---|---|---|
| | CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | |
| HMPV_SC_5M_<br>Krarup_<br>U74LS170LD185PD454N | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGCUUAAGAACCUGACACGGGCCAUUAACAAGAACAA<br>GUGCGACAUCCCUGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGAACCAGUUCCAGGUGGCCCUGGACCAGGUGUUCGA<br>GAACAUCGAGAAUUCCCAGGCUCUGGUGGACCAGUCCAA<br>CAGAAUCCUGUCUAGCGCCGAGAAGGGAAACACCGGCUU<br>CAUCAUCGUGAUCAUCCUGAUCGCCGUGCUGGGCAGCUC<br>CAUGAUCCUGGUGUCCAUCUUCAUCAUUAUCAAGAAGAC<br>CAAGAAGCCCACCGGCGCUCCUCCAGAACUGAGCGGAGU<br>GACCAACAAUGGCUUCAUCCCUCACAAC | 132 |
| HMPV_SC_DM_<br>Krarup_<br>E51PU74L | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGCCUGU<br>GGGCGACGUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCGACGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA | 133 |

TABLE 19-continued

| Strain | Nucleic Acid Sequence | SEQ ID NO: |
| --- | --- | --- |
| | UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_SC_UM_ Krarup_ E51PU74LD454N | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGCCUGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGAACCAGUUCCAGGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | 134 |
| HMPV_SC_ SUabilizeAlpha_ U74L | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGCUCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC | 135 |

TABLE 19-continued

| Strain | Nucleic Acid Sequence | SEQ ID NO: |
|---|---|---|
| | CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_ SC_ SUabilizeAlpha_ V55L | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACCUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | 136 |
| HMPV_SC_ SUabilizeAlpha_ S170L | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU | 137 |

TABLE 19-continued

| Strain | Nucleic Acid Sequence | SEQ ID NO: |
| --- | --- | --- |
| | GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGCUUAAGAACCUGACACGGGCCAUUAACAAGAACAA<br>GUGCGACAUCGACGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | |
| HMPV_SC_<br>SUabilizeAlpha_<br>U174W | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGUGGCGGGCCAUUAACAAGAACAA<br>GUGCGACAUCGACGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA | 138 |

TABLE 19-continued

| Strain | Nucleic Acid Sequence | SEQ ID NO: |
|---|---|---|
| | CCAAGAAGCCCACCGGCGCUCCUCCAGAACUGAGCGGAG<br>UGACCAACAAUGGCUUCAUCCCUCACAAC | |
| HMPV_SC_4M_<br>SUabilizeAlpha_<br>V55LU74LS170LU174W | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACCUCGAGAAUCUGACAUGCUCUGAUGGCCCUAG<br>CCUGAUCAAGACCGAGCUGGAUCUGCUCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGCUUAAGAACCUGUGGCGGGCCAUUAACAAGAACAA<br>GUGCGACAUCGACGACCUGAAGAUGGCCGUGUCCUUUAG<br>CCAGUUCAACCGGCGGUUUCUGAACGUCGUGCGGCAGUU<br>UAGCGACAACGCCGGAAUCACACCAGCCAUCAGCCUGGA<br>CCUGAUGACAGAUGCUGAGCUGGCUAGAGCCGUGCCUAA<br>CAUGCCUACAUCUGCCGGCCAGAUCAAGCUGAUGCUCGA<br>GAAUAGAGCCAUGGUCCGACGGAAAGGCUUCGGCAUUC<br>UGAUUGGCGUGUACGGCAGCAGCGUGAUCUAUAUGGUG<br>CAGCUGCCUAUCUUCGGCGUGAUCGACACACCCUGCUGG<br>AUUGUGAAGGCCGCUCCUAGCUGUAGCGAGAAGAAGGG<br>CAAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | 139 |
| HMPV_<br>ProlineSUab_<br>E51P | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGCCUGU<br>GGGCGACGUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCGACGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCCUCUGGGAGCCCUGGUGGCUUGUUAUAAGGGC<br>GUGUCCUGUAGCAUCGGCAGCAACAGAGUGGGCAUCAUC | 140 |

TABLE 19-continued

| Strain | Nucleic Acid Sequence | SEQ ID NO: |
| --- | --- | --- |
| | AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_ ProlineSUab_ D185P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCCCUGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | 141 |
| HMPV_ ProlineSUab_ D183P | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCCCUAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA | 142 |

TABLE 19-continued

| Strain | Nucleic Acid Sequence | SEQ ID NO: |
|---|---|---|
| | UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | |
| HMPV_<br>ProlineSUab_<br>E131P | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGCCUAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC<br>GUGUCCAAGAACCUGACACGGGCCAUUAACAAGAACAAG<br>UGCGACAUCGACGACCUGAAGAUGGCCGUGUCCUUUAGC<br>CAGUUCAACCGGCGGUUUCUGAACGUCGUGCGGCAGUUU<br>AGCGACAACGCCGGAAUCACACCAGCCAUCAGCCUGGAC<br>CUGAUGACAGAUGCUGAGCUGGCUAGAGCCGUGCCUAAC<br>AUGCCUACAUCUGCCGGCCAGAUCAAGCUGAUGCUCGAG<br>AAUAGAGCCAUGGUCCGACGGAAAGGCUUCGGCAUUCU<br>GAUUGGCGUGUACGGCAGCAGCGUGAUCUAUAUGGUGC<br>AGCUGCCUAUCUUCGGCGUGAUCGACACACCCUGCUGGA<br>UUGUGAAGGCCGCUCCUAGCUGUAGCGAGAAGAAGGGC<br>AAUUACGCCUGCCUGCUGAGAGAGGACCAAGGCUGGUA<br>UUGUCAGAACGCCGGCAGCACCGUGUACUACCCUAACGA<br>GAAGGACUGCGAGACAAGAGGCGACCACGUGUUCUGUG<br>AUACCGCCGCUGGAAUCAAUGUGGCCGAGCAGAGCAAAG<br>AGUGCAACAUCAACAUCAGCACCACCAACUAUCCCUGCA<br>AGGUGUCCACCGGCAGGCACCCUAUUUCUAUGGUGGCUC<br>UGUCUCCUCUGGGAGCCCUGGUGGCUUGUUAUAAGGGC<br>GUGUCCUGUAGCAUCGGCAGCAACAGAGUGGGCAUCAUC<br>AAGCAGCUGAACAAGGGCUGCAGCUACAUCACCAACCAG<br>GACGCCGAUACCGUGACCAUCGACAACACCGUGUAUCAG<br>CUGAGCAAGGUGGAAGGCGAACAGCACGUGAUCAAGGG<br>CAGACCUGUGUCCAGCAGCUUCGACCCUAUCAAGUUCCC<br>UGAGGAUCAGUUCCAGGUGGCCCUGGACCAGGUGUUCG<br>AGAACAUCGAGAAUUCCCAGGCUCUGGUGGACCAGUCCA<br>ACAGAAUCCUGUCUAGCGCCGAGAAGGGAAACACCGGCU<br>UCAUCAUCGUGAUCAUCCUGAUCGCCGUGCUGGGCAGCU<br>CCAUGAUCCUGGUGUCCAUCUUCAUCAUUAUCAAGAAGA<br>CCAAGAAGCCCACCGGCGCUCCUCCAGAACUGAGCGGAG<br>UGACCAACAAUGGCUUCAUCCCUCACAAC | 143 |
| HMPV_<br>ProlineSUab_<br>D447P | AUGAGCUGGAAGGUGGUCAUCAUCUUCAGCCUGCUGAU<br>CACACCUCAGCACGGCCUGAAAGAGAGCUACCUGGAAGA<br>GUCCUGCAGCACCAUCACAGAGGGCUACCUGUCUGUGCU<br>GAGAACCGGCUGGUACACCAACGUGUUCACACUGGAAGU<br>GGGCGACGUCGAGAAUCUGACAUGCUCUGAUGGCCCUAG<br>CCUGAUCAAGACCGAGCUGGAUCUGACCAAGAGCGCCCU<br>GAGAGAACUCAAGACCGUGUCUGCCGAUCAGCUGGCCAG<br>AGAGGAACAGAUCGAGAAUCCUGGCAGCGGCAGCUUUG<br>UGCUGGGAGCCAUUGCUCUUGGAGUGGCUGCUGCUGCA<br>GCUGUUACAGCAGGCGUGGCCAUCGCUAAGACCAUCAGA<br>CUGGAAAGCGAAGUGACCGCCAUCAACAACGCCCUGAAG<br>AAGACAAACGAGGCCGUCAGCACACUCGGCAAUGGCGUU<br>AGAGUGCUGGCCACAGCCGUGCGCGAGCUGAAGGACUUC | 144 |

TABLE 19-continued

| Strain | Nucleic Acid Sequence | SEQ ID NO: |
|---|---|---|
| | GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCCCACCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |
| HMPV_Urimer-RepulsionD454N | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGAACCAGUUCCAGGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | 145 |
| HMPV_Urimer-RepulsionE453N | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU | 146 |

TABLE 19-continued

| Strain | Nucleic Acid Sequence | SEQ ID NO: |
|---|---|---|
| | GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUUCAACCGGCGGUUUCUGAACGUCGUGCGGCAGUUU AGCGACAACGCCGGAAUCACACCAGCCAUCAGCCUGGAC CUGAUGACAGAUGCUGAGCUGGCUAGAGCCGUGCCUAAC AUGCCUACAUCUGCCGGCCAGAUCAAGCUGAUGCUCGAG AAUAGAGCCAUGGUCCGACGGAAAGGCUUCGGCAUUCU GAUUGGCGUGUACGGCAGCAGCGUGAUCUAUAUGGUGC AGCUGCCUAUCUUCGGCGUGAUCGACACACCCUGCUGGA UUGUGAAGGCCGCUCCUAGCUGUAGCGAGAAGAAGGGC AAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UCAGGAUCAGUUCCAGGUGGCCCUGGACCAGGUGUUCGA GAACAUCGAGAAUUCCCAGGCUCUGGUGGACCAGUCCAA CAGAAUCCUGUCUAGCGCCGAGAAGGGAAACACCGGCUU CAUCAUCGUGAUCAUCCUGAUCGCCGUGCUGGGCAGCUC CAUGAUCCUGGUGUCCAUCUUCAUCAUUAUCAAGAAGAC CAAGAAGCCCACCGGCGCUCCUCCAGAACUGAGCGGAGU GACCAACAAUGGCUUCAUCCCUCACAAC | |
| HMPV_SUabilize AlphaF196W | AUGAGCUGGAAGGUGGUCAUCAUCUUCAGCCUGCUGAU CACACCUCAGCACGGCCUGAAAGAGAGCUACCUGGAAGA GUCCUGCAGCACCAUCACAGAGGGCUACCUGUCUGUGCU GAGAACCGGCUGGUACACCAACGUGUUCACACUGGAAGU GGGCGACGUCGAGAAUCUGACAUGCUCUGAUGGCCCUAG CCUGAUCAAGACCGAGCUGGAUCUGACCAAGAGCGCCCU GAGAGAACUCAAGACCGUGUCUGCCGAUCAGCUGGCCAG AGAGGAACAGAUCGAGAAUCCUGGCAGCGGCAGCUUUG UGCUGGGAGCCAUUGCUCUUGGAGUGGCUGCUGCUGCA GCUGUUACAGCAGGCGUGGCCAUCGCUAAGACCAUCAGA CUGGAAAGCGAAGUGACCGCCAUCAACAACGCCCUGAAG AAGACAAACGAGGCCGUCAGCACACUCGGCAAUGGCGUU AGAGUGCUGGCCACAGCCGUGCGCGAGCUGAAGGACUUC GUGUCCAAGAACCUGACACGGGCCAUUAACAAGAACAAG UGCGACAUCGACGACCUGAAGAUGGCCGUGUCCUUUAGC CAGUGGAACCGGCGGUUUCUGAACGUCGUGCGGCAGUU UAGCGACAACGCCGGAAUCACACCAGCCAUCAGCCUGGA CCUGAUGACAGAUGCUGAGCUGGCUAGAGCCGUGCCUAA CAUGCCUACAUCUGCCGGCCAGAUCAAGCUGAUGCUCGA GAAUAGAGCCAUGGUCCGACGGAAAGGCUUCGGCAUUC UGAUUGGCGUGUACGGCAGCAGCGUGAUCUAUAUGGUG CAGCUGCCUAUCUUCGGCGUGAUCGACACACCCUGCUGG AUUGUGAAGGCCGCUCCUAGCUGUAGCGAGAAGAAGGG CAAUUACGCCUGCCUGCUGAGAGAGGACCAAGGCUGGUA UUGUCAGAACGCCGGCAGCACCGUGUACUACCCUAACGA GAAGGACUGCGAGACAAGAGGCGACCACGUGUUCUGUG AUACCGCCGCUGGAAUCAAUGUGGCCGAGCAGAGCAAAG AGUGCAACAUCAACAUCAGCACCACCAACUAUCCCUGCA AGGUGUCCACCGGCAGGCACCCUAUUUCUAUGGUGGCUC UGUCUCCCUCUGGGAGCCCUGGUGGCUUGUUAUAAGGGC GUGUCCUGUAGCAUCGGCAGCAACAGAGUGGGCAUCAUC AAGCAGCUGAACAAGGGCUGCAGCUACAUCACCAACCAG GACGCCGAUACCGUGACCAUCGACAACACCGUGUAUCAG CUGAGCAAGGUGGAAGGCGAACAGCACGUGAUCAAGGG CAGACCUGUGUCCAGCAGCUUCGACCCUAUCAAGUUCCC UGAGGAUCAGUUCCAGGUGGCCCUGGACCAGGUGUUCG AGAACAUCGAGAAUUCCCAGGCUCUGGUGGACCAGUCCA ACAGAAUCCUGUCUAGCGCCGAGAAGGGAAACACCGGCU | 147 |

TABLE 19-continued

| Strain | Nucleic Acid Sequence | SEQ ID NO: |
|---|---|---|
| | UCAUCAUCGUGAUCAUCCUGAUCGCCGUGCUGGGCAGCU CCAUGAUCCUGGUGUCCAUCUUCAUCAUUAUCAAGAAGA CCAAGAAGCCCACCGGCGCUCCUCCAGAACUGAGCGGAG UGACCAACAAUGGCUUCAUCCCUCACAAC | |

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A betacoronavirus vaccine for a human subject, comprising a messenger ribonucleic acid (mRNA) formulated in a lipid nanoparticle comprising 20-60 mol % ionizable cationic lipid, 5-25 mol % neutral lipid, 25-55 mol % cholesterol, and 0.5-15 mol % PEG-modified lipid, wherein the mRNA comprises an open reading frame encoding a full-length betacoronavirus spike protein, wherein the open reading frame comprises nucleosides consisting of N1-methylpseudouridine, adenosine, guanosine, and cytidine, and wherein the vaccine is formulated for intramuscular injection to a human subject at a dose that comprises from 20-50 μg of the mRNA.

2. The vaccine of claim 1, wherein the dose comprises 25 μg of the mRNA.

3. The vaccine of claim 1, wherein the dose comprises 30 μg of the mRNA.

4. The vaccine of claim 1, wherein the dose comprises 50 μg of the mRNA.

5. A betacoronavirus vaccine for a human subject, comprising a messenger ribonucleic acid (mRNA) formulated in a lipid nanoparticle comprising 20-60 mol % ionizable cationic lipid, 5-25 mol % neutral lipid, 25-55 mol % cholesterol, and 0.5-15 mol % PEG-modified lipid, wherein the mRNA comprises an open reading frame encoding a full-length betacoronavirus spike protein, wherein the open reading frame comprises nucleosides consisting of N1-methylpseudouridine, adenosine, guanosine, and cytidine, and wherein the vaccine is formulated for intramuscular injection to a human subject at a dose that comprises from 10-15 μg of the mRNA.

6. A betacoronavirus vaccine for a human subject, comprising a messenger ribonucleic acid (mRNA) formulated in a lipid nanoparticle comprising 20-60 mol % ionizable cationic lipid, 5-25 mol % neutral lipid, 25-55 mol % cholesterol, and 0.5-15 mol % PEG-modified lipid, wherein the mRNA comprises an open reading frame encoding a full-length betacoronavirus Spike protein, wherein the open reading frame comprises nucleosides consisting of N1-methyl-pseudouridine, adenosine, guanosine, and cytidine, and wherein the vaccine is formulated for intramuscular injection to a human subject at a dose that comprises from 10-100 μg of the mRNA.

7. The vaccine of claim 6, wherein the dose comprises 100 μg of the mRNA.

8. The vaccine of claim 5, wherein the dose comprises 10 μg of the mRNA.

* * * * *